(12) United States Patent
Venkatesan et al.

(10) Patent No.: US 11,925,629 B2
(45) Date of Patent: *Mar. 12, 2024

(54) HETEROCYCLIC INHIBITORS OF ERK1 AND ERK2 AND THEIR USE IN THE TREATMENT OF CANCER

(71) Applicant: Asana Biosciences, LLC, Bridgeville, NJ (US)

(72) Inventors: Aranapakam M. Venkatesan, Rego Park, NY (US); Scott K. Thompson, Phoenixville, PA (US); Roger A. Smith, Chester Springs, PA (US); Sanjeeva P. Reddy, Chester Springs, PA (US); Raghava Reddy Kethiri, Bangalore (IN); Purushottam M. Dewang, Bangalore (IN); Gurulingappa Hallur, Bangalore (IN); Chandrika Mulakala, Bangalore (IN)

(73) Assignee: ASANA BIOSCIENCES, LLC, Bridgewater, NJ (US)

( * ) Notice: Subject to any disclaimer, the term of this patent is extended or adjusted under 35 U.S.C. 154(b) by 151 days.

This patent is subject to a terminal disclaimer.

(21) Appl. No.: 17/368,559

(22) Filed: Jul. 6, 2021

(65) Prior Publication Data

US 2023/0051842 A1 Feb. 16, 2023

Related U.S. Application Data

(63) Continuation of application No. 16/790,082, filed on Feb. 13, 2020, now Pat. No. 11,103,491, which is a continuation of application No. 15/183,504, filed on Jun. 15, 2016, now Pat. No. 10,751,332.

(60) Provisional application No. 62/175,756, filed on Jun. 15, 2015.

(51) Int. Cl.
| | |
|---|---|
| A61K 31/443 | (2006.01) |
| A61K 31/4439 | (2006.01) |
| A61K 31/444 | (2006.01) |
| A61K 31/506 | (2006.01) |
| A61K 31/5377 | (2006.01) |
| C07D 401/04 | (2006.01) |

(52) U.S. Cl.
CPC ........ *A61K 31/443* (2013.01); *A61K 31/4439* (2013.01); *A61K 31/444* (2013.01); *A61K 31/506* (2013.01); *A61K 31/5377* (2013.01); *C07D 401/04* (2013.01)

(58) Field of Classification Search
CPC ............. A61K 31/443; A61K 31/4439; A61K 31/444; A61K 31/506; A61K 31/5377; A61P 35/00; C07D 401/04; C07D 405/14
See application file for complete search history.

(56) References Cited

U.S. PATENT DOCUMENTS

| | | | |
|---|---|---|---|
| 6,743,941 | B2 | 6/2004 | Schroeder et al. |
| 8,546,404 | B2 | 10/2013 | Cooper et al. |
| 8,629,132 | B2 | 1/2014 | Lee et al. |
| 9,896,445 | B2 | 2/2018 | Venkatesan et al. |
| 10,471,051 | B2 | 11/2019 | Venkatesan et al. |
| 10,751,332 | B2 | 8/2020 | Venkatesan et al. |
| 11,103,491 | B2 | 8/2021 | Venkatesan et al. |
| 2004/0176395 | A1 | 9/2004 | Flynn et al. |
| 2005/0288286 | A1 | 12/2005 | Flynn et al. |
| 2006/0160807 | A1 | 7/2006 | Aronov et al. |
| 2007/0191336 | A1 | 8/2007 | Flynn et al. |
| 2011/0281841 | A1 | 11/2011 | Lee et al. |

(Continued)

FOREIGN PATENT DOCUMENTS

| | | |
|---|---|---|
| WO | WO-02064586 A2 | 8/2002 |
| WO | WO-2006071644 A1 | 7/2006 |

(Continued)

OTHER PUBLICATIONS

Berge (J of Pharmaceutical Sciences, Jan. 1977, 66, 1). (Year: 1977).*
Alexander et al. (Acyloxy)alkyl carbamate prodrugs of norfloxacin. J. Med. Chem. 34:78-81 (1991).
Alexander et al. (Acyloxy)alkyl carbamates as novel bioreversible prodrugs for amines: increased permeation through biological membranes. J. Med. Chem. 31:318-322 (1988).
Alexander et al. Investigation of (Oxodioxolenyl)methyl carbamates as nonchiral bioreversible prodrug moieties for chiral amines. J. Med. Chem. 39:480-486 (1996).

(Continued)

*Primary Examiner* — Umamaheswari Ramachandran
(74) *Attorney, Agent, or Firm* — WILSON SONSINI GOODRICH & ROSATI

(57) ABSTRACT

The present application provides novel heterocyclic compounds and pharmaceutically acceptable salts thereof. Also provided are methods for preparing these compounds. These compounds are useful for inhibiting ERK1/2. By administering to a patient in need a therapeutically effective amount of one or more of the compounds of formula (I), wherein X, Y, Z, J, M, and $R^1$ to $R^8$ are defined herein, these compounds are effective in treating conditions associated with dysregulation of the RAS/RAF/MEK/ERK pathway. A variety of conditions can be treated using these compounds and include diseases which are characterized by abnormal cellular proliferation. In one embodiment, the disease is cancer.

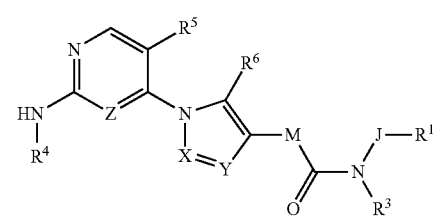

14 Claims, No Drawings

(56) References Cited

U.S. PATENT DOCUMENTS

| | | |
|---|---|---|
| 2012/0264798 A1 | 10/2012 | Sinha et al. |
| 2016/0362406 A1 | 12/2016 | Venkatesan et al. |
| 2023/0027072 A1 | 1/2023 | Reddy et al. |

FOREIGN PATENT DOCUMENTS

| | | |
|---|---|---|
| WO | WO-2011060295 A1 | 5/2011 |
| WO | WO-2016205418 A1 | 12/2016 |
| WO | WO-2017222958 A1 | 12/2017 |
| WO | WO-2020046966 A1 | 3/2020 |
| WO | WO-2021086726 A1 | 5/2021 |
| WO | WO-2022221547 A1 | 10/2022 |

OTHER PUBLICATIONS

Anderson. The process of structure-based drug design. Chem and Biol 10:787-797 (2003).
Bissery et al. Docetaxel (Taxotere): a review of preclinical and clinical experience. Part I: Preclinical experience. Anti Cancer Drugs 6(3):339-368 (1995).
Bundgaard. Design of Prodrugs: Bioreversible Derivatives for Various Functional Groups and Chemical Entities. Elsevier (pp. 1-92) (1985).
Edelman et al. Promising new agents in the treatment of non-small cell lung cancer. Cancer Chemother. Pharmacol. 37(5):385-393 (1996).
Hatzivassiliou et al. ERK Inhibition Overcomes Acquired Resistance to MEK Inhibition. Mal. Cancer Ther. 11:1143-1154 (2012).
Li et al. Synthesis of (alkoxycarbonyloxy)methyl, (acyloxy)methyl and (oxodioxolenyl)methyl carbamates as bioreversible prodrug moieties for amines. Bioorg. Med. Chem. Lett., 7:2909-2912 (1997).
Mebratu et al. How ERK1/2 activation controls cell proliferation and cell death: Is subcellular localization the answer? Cell Cycle 8(8):1168-1175 (2009).
PCT/US2016/037697 International Preliminary Report on Patentability dated Dec. 28, 2017.
PCT/US2016/037697 International Search Report dated Sep. 5, 2016.
PCT/US2020/056936 International Search Report and Written Opinion dated Feb. 11, 2021.
Portelinha et al. ASN007 is a selective ERK1/2 inhibitor with preferential activity against RAS-and RAF-mutant tumors. Cell Rep Med 2(7):100350 (2021).
Rautio et al. Prodrugs: design and clinical applications. Nat Rev Drug Discov 7(3):255-270 (2008).
Ren et al. Discovery of Highly Potent, Selective and Efficacious Small Molecule Inhibitors of ERKI/2, J. Med. Chem. 58(4):1976-1991 (2015).
Silverman. Chapter 8: Prodrugs and Drug Delivery Systems. The Organic Chemistry of Drug Design and Drug Action, Academic Press, Inc., San Diego (pp. 352-401) (1992).
Silvestrini et al. In vitro cytotoxic activity of Taxol and Taxotere on primary cultures and established cell lines of human ovarian cancer. Stem Cells 11(6):528-535 (1993).
Simplício et al. Prodrugs for amines. Molecules 13:519-547 (2008).
Thiel. Structure-aided drug design's next generation. Nat Biotechnol 22(5):513-319 (2004).
U.S. Appl. No. 15/183,486 Office Action dated Oct. 21, 2016.
U.S. Appl. No. 15/183,504 Office Action dated Apr. 16, 2018.
U.S. Appl. No. 15/183,504 Office Action dated Jan. 17, 2019.
U.S. Appl. No. 15/183,504 Office Action dated Jun. 19, 2019.
U.S. Appl. No. 15/183,504 Office Action dated Nov. 21, 2019.
U.S. Appl. No. 15/183,504 Office Action dated Sep. 20, 2017.
U.S. Appl. No. 15/694,124 Office Action dated Dec. 31, 2018.
U.S. Appl. No. 15/694,124 Office Action dated Jan. 11, 2018.
U.S. Appl. No. 15/694,124 Office Action dated Jul. 12, 2018.
U.S. Appl. No. 16/790,082 Office Action dated Mar. 31, 2021.
Wolff. Burger's Medicinal Chemistry and Drug Discovery. 5th Ed. Part 1, pp. 975-977 (1995).
Asana Biosciences. A Study of ASN007 in Patients With Advanced Solid Tumors. ClinicalTrials.gov, NCT03415126 version 9, Jul. 7, 2020, <url: <a=""href="https://clinicaltrials.gov/ct2/show/NCT03415126?term=ASN007&draw=2&rank=1">https://clinicaltrials.gov/ct2/show/NCT03415126?term=ASN007&draw=2&rank=1 [retrieved online May 20, 2022].</url:>.
PCT/US2022/024841 International Search Report and Written Opinion dated Jun. 2, 2022.
Tolcher et al. Abstract PR09: Phase 1 clinical safety and efficacy ofASN007, a novel oral ERK1/2 inhibitor, in patients with RAS, RAF or MEK mutant advanced solid tumors. Mol Cancer Ther 8(suppl. 12): Abstract No. PR09 (2019).

* cited by examiner

HETEROCYCLIC INHIBITORS OF ERK1 AND ERK2 AND THEIR USE IN THE TREATMENT OF CANCER

CROSS-REFERENCE TO RELATED APPLICATIONS

This application is a continuation of U.S. application Ser. No. 16/790,082, filed Feb. 13, 2020, which is a continuation of U.S. application Ser. No. 15/183,504, filed Jun. 15, 2016, now U.S. Pat. No. 10,751,332, issued Aug. 25, 2020, which claims priority from U.S. Provisional Application No. 62/175,756, filed Jun. 15, 2015, the disclosures of which are hereby incorporated herein by reference in their entirety.

FIELD OF THE INVENTION

The present invention relates to novel heterocyclic compounds useful as inhibitors of ERK1 and ERK2. The present invention further relates to compositions containing such compounds, and methods of use thereof.

BACKGROUND OF THE INVENTION

ERK1 and ERK2 (collectively "ERK1/2") are related protein-serine/threonine kinases that participate in, amongst others, the Ras-Raf-MEK-ERK signal transduction pathway, which is sometimes denoted as the mitogen-activated protein kinase (MAPK) pathway. This pathway is thought to play a central role in regulating a number of fundamental cellular processes including one or more of cell proliferation, survival, adhesion, cycle progression, migration, differentiation, metabolism, and transcription. The activation of the MAPK pathway has been reported in numerous tumor types including lung, colon, pancreatic, renal, and ovarian cancers. Accordingly, substances that could reduce activation could be of interest for possible treatments.

ERK1/2 appear to be activated by MEK through phosphorylation of both a threonine and a tyrosine residue, namely at Tyr204/187 and Thr202/185. Once activated, ERK1/2 catalyze the phosphorylation of serine/threonine residues of more than 100 substrates and activate both cytosolic and nuclear proteins that are linked to cell growth, proliferation, survival, angiogenesis and differentiation, all hallmarks of the cancer phenotype. Thus it may be beneficial to target ERK to develop and use ERK1/2 inhibitors as a way to inhibit tumor growth.

Furthermore, an ERK inhibitor may have utility in combination with other MAPK inhibitors. Recently, researchers reported that dual inhibition of MEK and ERK by small molecule inhibitors was synergistic and acted to overcome acquired resistance to MEK inhibitors. See Hatzivassiliou et al., ERK Inhibition Overcomes Acquired Resistance to MEK Inhibition, *Mol. Cancer Ther.* 2012, 11, 1143-1154.

Small molecular ERK inhibitors have been reported in the literature including U.S. Pat. Nos. 6,743,941, 8,546,404, and Ren et al., Discovery of Highly Potent, Selective and Efficacious Small Molecule Inhibitors of ERK1/2, *J. Med. Chem.*, 2015, 58(4), 1976-1991. A small number of ERK inhibitors (e.g., BVD-523 and GDC-0994) are in early clinical development. However, no ERK inhibitor has been reported to advance into late stage clinical trials. Therefore, there is a continuing need for the development of improved and efficacious ERK1/2 inhibitors for the treatment of cancer.

SUMMARY OF THE INVENTION

The present invention addresses a compound of formula (I):

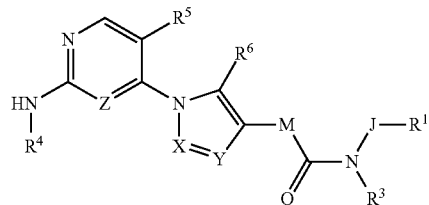

and a pharmaceutically acceptable salt, prodrug, solvate, hydrate, or stereoisomer thereof, wherein:
  $R^1$ is unsubstituted or substituted $C_{6-12}$aryl or unsubstituted or substituted 5- to 10-membered heteroaryl;
  J is a linker group selected from $-C(R^2)(R^8)(CH_2)_n-$;
  $R^2$ and $R^8$ are each independently H, $C_{1-6}$alkyl, hydroxy$C_{1-6}$alkyl, amino$C_{1-6}$alkyl, $-C_{1-6}$alkyl-O-$C_{1-6}$alkyl, $-C_{1-6}$alkyl-NH-$C_{1-6}$alkyl, $-C_{1-6}$alkyl-N-$(C_{1-6}$alkyl$)_2$, $-C_{1-6}$alkyl-NH-$C_{1-6}$alkyl-OH, $-C_{1-6}$alkyl-NH-$C_{1-6}$alkyl-$C_{3-10}$cycloalkyl, $-C_{1-6}$alkyl-NH-$C_{1-6}$alkyl-NH-$C_{1-6}$alkyl, $-C_{1-6}$alkyl-NH-C(O)-$C_{1-6}$alkyl, $-C_{1-6}$alkyl-O-C(O)-$C_{1-6}$alkyl, $-C_{1-6}$alkyl-NH-$C_{0-6}$alkyl-(4- to 6-membered heterocyclyl), $-C(O)-NH_2$, $-C(O)-NH-C_{1-6}$alkyl, $-C(O)-N-(C_{1-6}$alkyl$)_2$, or $-C_{1-6}$alkyl-NH-$C_{0-6}$alkyl-(5- to 6-membered heteroaryl), wherein the $C_{1-6}$alkyl, cycloalkyl, heterocyclyl, or heteroaryl is unsubstituted or substituted;
  or $R^2$, $R^8$, and the C atom that both $R^2$ and $R^8$ are attached join together to form a 3- to 10-membered cycloalkyl or 4- to 10-membered heterocyclyl ring, wherein the cycloalkyl or heterocyclyl ring is unsubstituted or substituted;
  n is 0 to 6;
  $R^3$ is H or $C_{1-6}$alkyl, wherein the $C_{1-6}$alkyl is unsubstituted or substituted with 1-5 halogens;
  M is a bond or NH;
  X and Y are each independently CH, C—$R^7$, or N;
  Z is CH or N,
  $R^5$ is H, halogen, $C_{1-6}$alkyl, or $-O-C_{1-6}$alkyl, wherein the $C_{1-6}$alkyl is unsubstituted or substituted with 1-5 halogens;
  $R^6$ is H or $C_{1-6}$alkyl, wherein the $C_{1-6}$alkyl is unsubstituted or substituted with 1-5 halogens;
  $R^7$ is $C_{1-6}$alkyl, wherein the $C_{1-6}$alkyl is unsubstituted or substituted with 1-5 halogens; and
  $R^4$ is unsubstituted or substituted $C_{1-6}$alkyl, unsubstituted or substituted $C_{3-10}$cycloalkyl, unsubstituted or substituted $C_{4-10}$cycloalkenyl, unsubstituted or substituted 4- to 10-membered heterocyclyl, unsubstituted or substituted phenyl, unsubstituted or substituted 5- to 10-membered heteroaryl, unsubstituted or substituted $-C_{1-6}$alkyl-(4- to 6-membered heterocycly), unsubstituted or substituted $-C_{1-6}$alkyl-(5- to 6-membered heteroaryl), or unsubstituted or substituted $-C_{1-6}$alkyl-phenyl.

The present invention further addresses a compound of formula (I), and a pharmaceutically acceptable salt, prodrug, solvate, hydrate, or stereoisomer thereof, wherein:
  $R^1$ is phenyl or 5- to 10-membered heteroaryl, which is unsubstituted or substituted with 1-3 substituents selected from halogen, $C_{1-6}$alkyl, CN, hydroxy$C_{1-6}$alkyl, amino$C_{1-6}$alkyl, $-C_{1-6}$alkyl-O-$C_{1-6}$alkyl, $-C_{1-6}$alkyl-NH-$C_{1-6}$alkyl, $-C_{1-6}$alkyl-N-$(C_{1-6}$alkyl$)_2$, $-C_{1-6}$alkyl-NH-$C_{1-6}$alkyl-OH, $-C_{1-6}$alkyl-NH-$C_{1-6}$alkyl-$C_{3-10}$cycloalkyl, $-C_{1-6}$alkyl-NH-$C_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl;

J is —C(R$^2$)(R$^8$)(CH$_2$)$_n$—

R$^2$ and R$^8$ are each independently H, C$_{1-6}$alkyl, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), —C(O)—NH$_2$, —C(O)—NH—C$_{1-6}$alkyl, —C(O)—N—(C$_{1-6}$alkyl)$_2$, or —C$_{1-6}$alkyl-NH—C$_{0-6}$alkyl-(5- to 6-membered heteroaryl), wherein the C$_{1-6}$alkyl, cycloalkyl, heterocyclyl, or heteroaryl is unsubstituted or substituted with 1-3 substituents selected from halogen, C$_{1-6}$alkyl, NH$_2$, hydroxyC$_{1-6}$alkyl, or amino C$_{1-6}$alkyl;

or R$^2$, R$^8$, and the C atom that both R$^2$ and R$^8$ are attached join together to form a 3- to 10-membered cycloalkyl or 4- to 10-membered heterocyclyl ring, wherein the cycloalkyl or heterocyclyl is unsubstituted or substituted with 1-3 substituents selected from hydroxyl, halogen, or C$_{1-6}$alkyl;

n is 0 to 6;

R$^3$ is H or C$_{1-6}$alkyl, wherein the C$_{1-6}$alkyl is unsubstituted or substituted with 1-5 halogens;

M is a bond or NH;

X and Y are each independently CH, C—R$^7$, or N;

R$^7$ is C$_{1-6}$alkyl, wherein the C$_{1-6}$alkyl is unsubstituted or substituted with 1-5 halogens;

Z is CH or N;

R$^5$ is H, halogen, C$_{1-6}$alkyl, or OC$_{1-6}$alkyl, wherein the C$_{1-6}$alkyl is unsubstituted or substituted with 1-5 halogens;

R$^6$ is H or C$_{1-6}$alkyl, wherein the C$_{1-6}$alkyl is unsubstituted or substituted with 1-5 halogens; and R$^4$ is C$_{1-6}$alkyl, C$_{3-10}$cycloalkyl, C$_{4-10}$cycloalkenyl, —C$_{1-6}$alkyl-phenyl, —C$_{1-6}$alkyl-(5- to 6-membered heteroaryl), —C$_{1-6}$alkyl-(4- to 6-membered heterocyclyl), 5- to 10-membered heteroaryl, 4- to 10-membered heterocyclyl, or phenyl, wherein the alkyl, cycloalkyl, cycloalkenyl, phenyl, heteroaryl, or heterocyclyl is unsubstituted or substituted with 1-3 substituents selected from halogen, CN, —C(O)—NH$_2$, —C(O)—NH—C$_{1-6}$alkyl, —C(O)—N—(C$_{1-6}$alkyl)$_2$, —O—C$_{1-6}$ alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, C$_{2-6}$alknyl, hydroxyl, C$_{1-6}$alkoxyl, or hydroxyC$_{1-6}$alkyl, and the heterocyclyl or heteroaryl is unsubstituted or substituted with 1-3 substituents selected from halogen, C$_{1-6}$alkyl, —C(O)—C$_{1-6}$alkyl, or 4- to 6-membered heterocyclyl.

The present invention further addresses a compound of formula (I), and a pharmaceutically acceptable salt, prodrug, solvate, hydrate, or stereoisomer thereof, wherein:

R$^1$ is phenyl or thienyl which can be unsubstituted or substituted with 1-3 substituents selected from halogen, C$_{1-6}$alkyl, or hydroxyC$_{1-6}$alkyl, aminoC$_{1-6}$alkyl, or CN, wherein C$_{1-6}$alkyl is unsubstituted or substituted with 1-3 halogens;

J is —CH(R$^2$)—;

R$^2$ is H, hydroxyC$_{1-6}$alkyl, aminoC$_{1-6}$alkyl, —C$_{1-6}$alkyl-NH—C$_{1-6}$alkyl, —C$_{1-6}$alkyl-NH—C$_{1-6}$alkyl-OH, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl);

R$^3$ is H;

M is a bond;

X is CH;

Y is CH or N;

Z is N;

R$^5$ is H, halogen, or C$_{1-6}$alkyl;

R$^6$ is H; and

R$^4$ is hydroxyC$_{1-6}$alkyl,

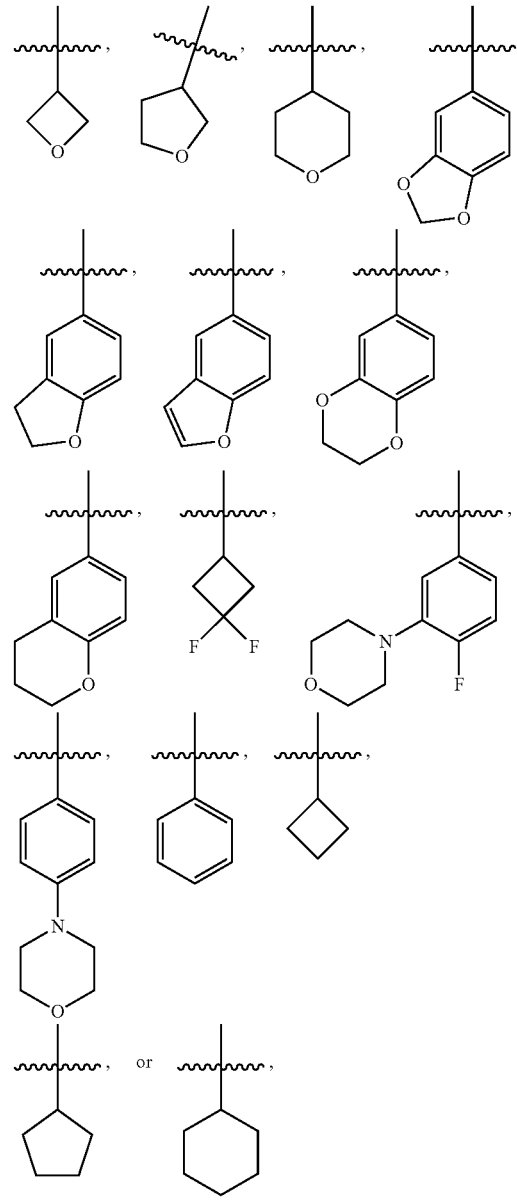

which can be unsubstituted or substituted with 1-3 substituents selected from halogen or C$_{1-6}$alkoxy.

The present invention further addresses a compound selected from:

(S)-1-(2-(benzo[d][1,3]dioxol-5-ylamino)-5-methylpyrimidin-4-yl)-N-(2-hydroxy-1-phenylethyl)-1H-pyrrole-3-carboxamide;
1-(2-(benzofuran-5-ylamino)-5-methylpyrimidin-4-yl)-N-(2-hydroxy-1-phenylethyl)-1H-pyrrole-3-carboxamide;
1-(2-(benzofuran-5-ylamino)-5-methylpyrimidin-4-yl)-N-(1-(3-chlorophenyl)-2-hydroxyethyl)-1H-pyrrole-3-carboxamide;
N-(3-chloro-2-(hydroxymethyl)benzyl)-1-(5-methyl-2-((tetrahydro-2H-pyran-4-yl)amino)-pyrimidin-4-yl)-1H-imidazole-4-carboxamide;
(S)—N-(1-(3-chloro-4-fluorophenyl)-2-hydroxyethyl)-1-(5-methyl-2-((3,4,5-trimethoxyphenyl)amino)pyrimidin-4-yl)-1H-pyrrole-3-carboxamide;
1-(2-((2,3-dihydrobenzofuran-5-yl)amino)-5-methylpyrimidin-4-yl)-N-(2-hydroxy-1-phenylethyl)-1H-pyrrole-3-carboxamide;
N-(1-(3-chlorophenyl)-2-hydroxyethyl)-1-(2-((2,3-dihydrobenzo[b][1,4]dioxin-6-yl)amino)-5-methylpyrimidin-4-yl)-1H-pyrrole-3-carboxamide;
N—(S)-1-(3-chlorophenyl)-2-hydroxyethyl)-1-(5-methyl-2-((tetrahydrofuran-3-yl)amino)pyrimidin-4-yl)-1H-pyrrole-3-carboxamide;
N—((S)-1-(3-chlorophenyl)-2-hydroxyethyl)-1-(5-methyl-2-(((S)-tetrahydrofuran-3-yl)amino)pyrimidin-4-yl)-1H-pyrrole-3-carboxamide;
N—((S)-1-(3-chlorophenyl)-2-hydroxyethyl)-1-(5-methyl-2-(((R)-tetrahydrofuran-3-yl)amino)pyrimidin-4-yl)-1H-pyrrole-3-carboxamide;
1-(2-(chroman-6-ylamino)-5-methylpyrimidin-4-yl)-N-(2-hydroxy-1-phenylethyl)-1H-pyrrole-3-carboxamide;
N-(1-(3-chlorophenyl)-2-hydroxyethyl)-1-(2-((4-fluoro-3-morpholinophenyl)amino)-5-methyl-pyrimidin-4-yl)-1H-pyrrole-3-carboxamide;
(S)—N-(2-amino-1-(3-chlorophenyl)ethyl)-1-(2-((4-fluorophenyl)amino)-5-methylpyrimidin-4-yl)-1H-imidazole-4-carboxamide;
N-(1-(3-chlorophenyl)-2-hydroxyethyl)-1-(5-methyl-2-((tetrahydro-2H-pyran-4-yl)-amino)pyrimidin-4-yl)-1H-imidazole-4-carboxamide;
N-(1-(3-chlorophenyl)-2-hydroxyethyl)-1-(5-methyl-2-((4-morpholinophenyl)amino)pyrimidin-4-yl)-1H-pyrrole-3-carboxamide;
(S)—N-(1-(3-chlorophenyl)-2-hydroxyethyl)-1-(5-methyl-2-((tetrahydro-2H-pyran-4-yl)amino)-pyrimidin-4-yl)-1H-imidazole-4-carboxamide;
(R)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;
(S)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;
(S)—N-(1-(3-chlorophenyl)-2-hydroxyethyl)-1-(5-fluoro-2-((tetrahydro-2H-pyran-4-yl)amino)-pyrimidin-4-yl)-1H-pyrrole-3-carboxamide;
N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide;
(S)—N-(2-amino-1-(3-chlorophenyl)ethyl)-1-(2-((3,3-difluorocyclobutyl)amino)-5-methyl-pyrimidin-4-yl)-1H-imidazole-4-carboxamide;
(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide;
(S)—N-(2-(((1H-pyrrol-2-yl)methyl)amino)-1-(3-chlorophenyl)ethyl)-1-(5-methyl-2-((tetrahydro-2H-pyran-4-yl)amino)pyrimidin-4-yl)-1H-imidazole-4-carboxamide;
(S)—N-(3-chloro-2-(hydroxymethyl)benzyl)-1-(5-methyl-2-(tetrahydrofuran-3-yl)amino)-pyrimidin-4-yl)-1H-imidazole-4-carboxamide;
(S)—N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide;
(S)—N-(1-(3-chlorophenyl)-2-((2-hydroxyethyl)amino)ethyl)-1-(5-methyl-2-((tetrahydro-2H-pyran-4-yl)amino)pyrimidin-4-yl)-1H-imidazole-4-carboxamide; and
N-(3-chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide, or a pharmaceutically acceptable salt, prodrug, solvate, hydrate, or stereoisomer thereof.

The present invention further addresses a pharmaceutically acceptable salt of the compound of claim 1, which is selected from:

(S)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide benzenesulfonic acid salt;
(S)—N-(2-amino-1-(3-chlorophenyl)ethyl)-1-(2-((3,3-difluorocyclobutyl)amino)-5-methyl-pyrimidin-4-yl)-1H-imidazole-4-carboxamide benzenesulfonic acid salt; and
(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide benzenesulfonic acid salt.

The present invention further relates to compositions containing such compounds, and methods of use thereof in treating a condition treatable by inhibiting ERK1/2.

In one embodiment, the condition is a cancer of prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma.

DETAILED DESCRIPTION OF THE INVENTION

The present invention provides novel inhibitors of ERK1 and ERK2 of formula (I)

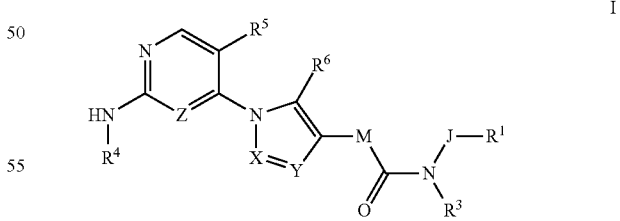

or a pharmaceutically acceptable salt, prodrug, solvate, hydrate, or stereoisomer thereof, wherein:

$R^1$ is phenyl or 5- to 10-membered heteroaryl, which is unsubstituted or substituted with 1-3 substituents selected from halogen, $C_{1-6}$alkyl, CN, hydroxy$C_{1-6}$alkyl, amino$C_{1-6}$alkyl, —$C_{1-6}$alkyl-O—$C_{1-6}$alkyl, —$C_{1-6}$alkyl-NH—$C_{1-6}$alkyl, —$C_{1-6}$alkyl-N—$(C_{1-6}$alkyl$)_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl;

J is a linker group selected from —C(R$^2$)(R$^8$)(CH$_2$)$_n$—;

R$^2$ and R are each independently H, C$_{1-6}$alkyl, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), —C(O)—NH$_2$, —C(O)—NH—C$_{1-6}$alkyl, —C(O)—N—(C$_{1-6}$alkyl)$_2$, or —C$_{1-6}$alkyl-NH—C$_{0-6}$alkyl-(5- to 6-membered heteroaryl), wherein the C$_{1-6}$alkyl, cycloalkyl, heterocyclyl, or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl;

or R$^2$, R$^8$, and the C atom that both R$^2$ and R$^8$ are attached join together to form a 3- to 10-membered cycloalkyl or 4- to 10-membered heterocyclyl ring, wherein the cycloalkyl or heterocyclyl ring is unsubstituted or substituted with 1-3 substituents selected from hydroxyl, halogen, or C$_{1-6}$alkyl;

n is 0 to 6;

R$^3$ is H or C$_{1-6}$alkyl, wherein the C$_{1-6}$alkyl is unsubstituted or substituted with 1-5 halogens;

M is a bond or NH;

X and Y are each independently CH, C—R$^7$, or N;

Z is CH or N,

R$^5$ is H, halogen, C$_{1-6}$alkyl, or OC$_{1-6}$alkyl, wherein C$_{1-6}$alkyl is unsubstituted or substituted with 1-5 halogens;

R$^6$ is H or C$_{1-6}$alkyl, wherein the C$_{1-6}$alkyl is unsubstituted or substituted with 1-5 halogens;

R$^7$ is C$_{1-6}$alkyl, wherein the C$_{1-6}$alkyl is unsubstituted or substituted with 1-5 halogens; and R$^4$ is C$_{1-6}$alkyl, C$_{3-10}$cycloalkyl, C$_{4-10}$cycloalkenyl, —C$_{1-6}$alkyl-phenyl, —C$_{1-6}$alkyl-(5- to 6-membered heteroaryl), C$_{1-6}$alkyl-(4- to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—NH$_2$, —C(O)—NH—C$_{1-6}$alkyl, —C(O)—N—(C$_{1-6}$alkyl)$_2$, —O—C$_{1-6}$ alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, C$_{2-6}$alknyl, hydroxyl, C$_{1-6}$alkoxyl, or hydroxyC$_{1-6}$alkyl, and the heterocyclyl or heteroaryl is unsubstituted or substituted with 1-3 substituents selected from halogen, C$_{1-6}$alkyl, —C(O)—C$_{1-6}$alkyl, or 4- to 6-membered heterocyclyl.

In one aspect, the present invention provides novel inhibitors of ERK1 and ERK2 of formula (II)

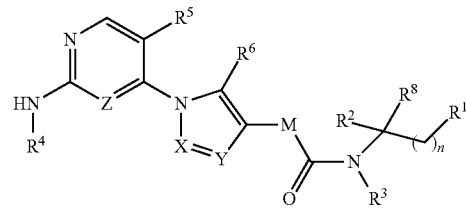

or a pharmaceutically acceptable salt, prodrug, solvate, hydrate, or stereoisomer thereof, wherein:

R$^1$ is phenyl or 5- to 10-membered heteroaryl, which is unsubstituted or substituted with 1-3 substituents selected from halogen, C$_{1-6}$alkyl, CN, hydroxyC$_{1-6}$alkyl, aminoC$_{1-6}$alkyl, —C$_{1-6}$alkyl-O—C$_{1-6}$alkyl, —C$_{1-6}$ alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl;

n is 0 to 6;

R$^2$ is C$_{1-6}$alkyl, hydroxyC$_{1-6}$alkyl, aminoC$_{1-6}$alkyl, —C$_{1-6}$ alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), —C(O)—NH$_2$, —C(O)—NH—C$_{1-6}$alkyl, —C(O)—N(C$_{1-6}$alkyl)$_2$, or —C$_{1-6}$alkyl-NH—C$_{0-6}$alkyl-(5- to 6-membered heteroaryl), wherein the C$_{1-6}$alkyl, cycloalkyl, heterocyclyl, or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl; and R$^8$ is H or C$_{1-6}$alkyl;

alternatively, R$^2$, R$^8$, and the C atom that both R$^2$ and R$^8$ are attached join together to form a 3- to 10-membered cycloalkyl or 4- to 10-membered heterocyclyl ring, wherein the cycloalkyl or heterocyclyl is unsubstituted or substituted with 1-3 substituents selected from hydroxyl, halogen, or C$_{1-6}$alkyl;

R$^3$ is H or C$_{1-6}$alkyl, wherein the C$_{1-6}$alkyl is unsubstituted or substituted with 1-5 halogens;

M is a bond or NH;

X and Y are each independently CH, C—R$^7$, or N;

Z is CH or N,

R$^5$ is H, halogen, C$_{1-6}$alkyl, or O—C$_{1-6}$alkyl, wherein C$_{1-6}$alkyl is unsubstituted or substituted with 1-5 halogens;

R$^6$ is H or C$_{1-6}$alkyl, wherein the C$_{1-6}$alkyl is unsubstituted or substituted with 1-5 halogens;

R$^7$ is C$_{1-6}$alkyl, wherein the C$_{1-6}$alkyl is unsubstituted or substituted with 1-5 halogens; and R$^4$ is C$_{1-6}$alkyl, C$_{3-10}$cycloalkyl, C$_{4-10}$cycloalkenyl, —C$_{1-6}$ alkyl-phenyl, —C$_{1-6}$alkyl-(5 to 6-membered heteroaryl), —C$_{1-6}$alkyl-(4 to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—NH$_2$, —C(O)—NH—C$_{1-6}$alkyl, —C(O)—N—(C$_{1-6}$alkyl)$_2$, —O—C$_{1-6}$ alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, C$_{2-6}$alknyl, hydroxyl, C$_{1-6}$alkoxyl, or hydroxyC$_{1-6}$alkyl, and the heterocyclyl or heteroaryl is unsubstituted or substituted with 1-3 substituents selected from halogen, C$_{1-6}$alkyl, —C(O)—C$_{1-6}$alkyl, or 4- to 6-membered heterocyclyl.

In one embodiment, a compound of formula (II) or a pharmaceutically acceptable salt, solvate, hydrate, or stereoisomer, wherein:

R$^1$ is phenyl, pyridyl, thienyl, or thiazolyl, which is unsubstituted or substituted with 1-3 substituents selected from halogen, C$_{1-6}$alkyl, CN, hydroxyC$_{1-6}$alkyl, or aminoC$_{1-6}$alkyl, wherein the C$_{1-6}$alkyl is unsubstituted or substituted with 1-3 substituents selected from halogen;

n is 0 to 1;

R$^2$ is C$_{1-6}$alkyl, hydroxyC$_{1-6}$alkyl, aminoC$_{1-6}$alkyl, —C$_{1-6}$ alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), —C(O)—NH$_2$, —C(O)—NH—C$_{1-6}$alkyl, —C(O)—N(C$_{1-6}$alkyl)$_2$, or —C$_{1-6}$alkyl-NH—C$_{0-6}$alkyl-(5- to 6-membered heteroaryl), wherein the C$_{1-6}$alkyl, cycloalkyl, heterocyclyl, or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl; and R$^8$ is H or C$_{1-6}$alkyl;

alternatively, R$^2$, R$^8$, and the C atom that both R$^2$ and R$^8$ are attached join together to form a 3- to 6-membered cycloalkyl or 4- to 6-membered heterocyclyl ring, wherein the cycloalkyl or heterocyclyl is unsubstituted or substituted with 1-3 substituents selected from hydroxyl, halogen, or C$_{1-6}$alkyl;

R$^3$ is H or C$_{1-6}$alkyl, wherein the C$_{1-6}$alkyl is unsubstituted or substituted with 1-3 halogens;

M is a bond or NH;

X and Y are each independently CH, C—R$^7$, or N;

Z is CH or N,

R$^5$ is H, halogen, C$_{1-6}$alkyl, or O—C$_{1-6}$alkyl, wherein C$_{1-6}$alkyl is unsubstituted or substituted with 1-3 halogens;

R$^6$ is H or C$_{1-6}$alkyl, wherein the C$_{1-6}$alkyl is unsubstituted or substituted with 1-3 halogens;

R$^7$ is C$_{1-6}$alkyl, wherein the C$_{1-6}$alkyl is unsubstituted or substituted with 1-3 halogens; and R$^4$ is C$_{1-6}$alkyl, C$_{3-10}$cycloalkyl, C$_{4-10}$cycloalkenyl, —C$_{1-6}$ alkyl-phenyl, —C$_{1-6}$alkyl-(5 to 6-membered heteroaryl), —C$_{1-6}$alkyl-(4 to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—NH$_2$, —C(O)—NH—C$_{1-6}$alkyl, —C(O)—N—(C$_{1-6}$alkyl)$_2$, —O—C$_{1-6}$ alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, C$_{2-6}$alknyl, hydroxyl, C$_{1-6}$alkoxyl, or hydroxyC$_{1-6}$alkyl, and the heterocyclyl or heteroaryl is unsubstituted or substituted with 1-3 substituents selected from halogen, C$_{1-6}$alkyl, —C(O)—C$_{1-6}$alkyl, or 4- to 6-membered heterocyclyl.

In one embodiment, R$^1$ is unsubstituted or substituted C$_{6-12}$aryl or unsubstituted or substituted 5- to 10-membered heteroaryl. In one embodiment, R$^1$ is phenyl or 5- to 6-membered heteroaryl containing 1-2 ring heteroatoms selected from O, N or S, wherein the phenyl or heteroaryl is unsubstituted or substituted with 1-3 substituents selected from halogen, C$_{1-6}$alkyl, CN, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl. In one embodiment, R$^1$ is phenyl, pyridyl, thienyl, or thiazolyl, which is unsubstituted or substituted with 1-3 substituents selected from halogen, C$_{1-6}$alkyl, CN, hydroxyC$_{1-6}$alkyl, or aminoC$_{1-6}$alkyl, wherein the C$_{1-6}$alkyl is unsubstituted or substituted with 1-3 substituents selected from halogen. In one embodiment, R$^1$ is phenyl, pyridyl, thienyl, or thiazolyl, which is unsubstituted or substituted with 1-3 substituents selected from F, Cl, C$_{1-3}$alkyl, CN, hydroxyC$_{1-3}$alkyl, or aminoC$_{1-3}$alkyl, wherein the C$_{1-3}$alkyl is unsubstituted or substituted with 1-3 substituents selected from F. In one embodiment, R$^1$ is phenyl, pyridyl, thienyl, or thiazolyl, which is unsubstituted or substituted with 1-3 substituents selected from F, Cl, CH$_3$, —C(CH$_3$)$_3$, CF$_3$, —CH$_2$OH, —CH$_2$CH$_2$OH, CH$_2$NH$_2$, CN, or —C(CH$_3$)$_2$OH. In one embodiment, R$^1$ is phenyl, which is unsubstituted or substituted with 1-3 substituents selected from F, Cl, CH$_3$, —C(CH$_3$)$_3$, CF$_3$, —CH$_2$OH, —CH$_2$CH$_2$OH, CH$_2$NH$_2$, CN, or —C(CH$_3$)$_2$OH.

In one embodiment, n is 0 to 6. In one embodiment, n is 0 to 2. In one embodiment, n is 0 to 1. In one embodiment, n is 0.

In one embodiment, R$^2$ is C$_{1-6}$alkyl, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), —C(O)—NH$_2$, —C(O)—NH—C$_{1-6}$alkyl, —C(O)—N(C$_{1-6}$alkyl)$_2$, or —C$_{1-6}$alkyl-NH—C$_{0-6}$alkyl-(5- to 6-membered heteroaryl), wherein the C$_{1-6}$alkyl, cycloalkyl, heterocyclyl, or heteroaryl is unsubstituted or substituted with 1-3 substituents selected from halogen, C$_{1-6}$alkyl, NH$_2$, hydroxyC$_{1-6}$alkyl, or aminoC$_{1-6}$alkyl; and R$^8$ is H or C$_{1-6}$alkyl. In one embodiment, R$^2$ is C$_{1-3}$alkyl, hydroxyC$_{1-3}$alkyl, aminoC$_{1-3}$alkyl, —C$_{1-3}$alkyl-O—C$_{1-3}$alkyl, —C$_{1-3}$alkyl-NH—C$_{1-3}$alkyl, —C$_{1-3}$alkyl-N—(C$_{1-3}$alkyl)$_2$, —C$_{1-3}$alkyl-NH—C$_{1-3}$alkyl-OH, —C$_{1-3}$alkyl-NH—C$_{1-3}$alkyl-C$_{3-6}$cycloalkyl, —C$_{1-3}$alkyl-NH—C$_{1-3}$alkyl-NH—C$_{1-3}$alkyl, —C$_{1-3}$alkyl-NH—C(O)—C$_{1-3}$alkyl, —C$_{1-3}$alkyl-O—C(O)—C$_{1-3}$alkyl, —C$_{1-3}$alkyl-NH—C$_{0-3}$alkyl-(4- to 6-membered heterocyclyl), —C(O)—NH$_2$, —C(O)—NH—C$_{1-3}$alkyl, —C(O)—N(C$_{1-3}$alkyl)$_2$, or —C$_{1-3}$alkyl- NH—$C_{0-3}$alkyl-(5- to 6-membered heteroaryl), wherein the $C_{1-3}$alkyl, cycloalkyl, heterocyclyl, or heteroaryl is unsubstituted or substituted with 1-3 substituents selected from halogen, $C_{1-3}$alkyl, $NH_2$, hydroxy$C_{1-3}$alkyl, or amino$C_{1-3}$alkyl; and $R^8$ is H or $C_{1-3}$alkyl. In one embodiment, $R^2$ is $C_{1-3}$alkyl, hydroxy$C_{1-3}$alkyl, amino$C_{1-3}$alkyl, —$C_{1-3}$alkyl-NH—$C_{1-3}$alkyl, —$C_{1-3}$alkyl-NH—$C_{1-3}$alkyl-OH, —$C_{1-3}$alkyl-NH—$C_{0-3}$alkyl-(4- to 6-membered heterocyclyl), or —$C_{1-3}$alkyl-NH—$C_{0-3}$alkyl-(5- to 6-membered heteroaryl); and $R^8$ is H. In one embodiment, $R^2$ is $CH_3$, —$CH_2OH$, —$CH_2NH_2$, —$CH_2OCH_3$, —$CH_2N(CH_3)_2$, —$CH_2NH(CH_3)$, —$CH_2NHCH_2CH_2OH$, —$CH_2NHC(O)CH_3$, —$CH_2OC(O)CH(NH_2)CH_2CH(CH_3)_2$, —$C(O)NH_2$, —$CH_2NH$-(tetrahydro-2H-pyran), or —$CH_2NHCH_2$-(pyrrole); and $R^8$ is H. In one embodiment, $R^2$ is $CH_3$, —$CH_2OH$, —$CH_2NH_2$, —$CH_2NH(CH_3)$, —$CH_2NHCH_2CH_2OH$, —$CH_2NH$-(tetrahydro-2H-pyran), or —$CH_2NHCH_2$-(pyrrole); and $R^8$ is H. In one embodiment, $R^2$ is —$CH_2OH$ or —$CH_2NH_2$; and $R^8$ is H.

In another embodiment, $R^2$, $R^8$, and the C atom that both $R^2$ and Rare attached join together to form a 3- to 6-membered cycloalkyl or 4- to 6-membered heterocyclyl ring, wherein the cycloalkyl or heterocyclyl is unsubstituted or substituted with 1-3 substituents selected from hydroxyl, halogen, or $C_{1-6}$alkyl. In one embodiment, $R^2$, $R^8$, and the C atom that both $R^2$ and Rare attached join together to form a 3- to 6-membered cycloalkyl, which is unsubstituted or substituted with 1-3 substituents selected from hydroxyl. In one embodiment, $R^2$, $R^8$, and the C atom that both $R^2$ and Rare attached join together to form cyclobutyl, which is unsubstituted or substituted with hydroxyl.

In one embodiment, $R^3$ is H or $C_{1-6}$alkyl, wherein the $C_{1-6}$alkyl is unsubstituted or substituted with 1-5 halogens. In one embodiment, $R^3$ is H or $C_{1-3}$alkyl, wherein the $C_{1-6}$alkyl is unsubstituted or substituted with 1-3 halogens. In one embodiment, $R^3$ is H or $CH_3$.

In one embodiment, M is a bond or NH. In one embodiment, M is a bond.

In one embodiment, X and Y are each independently CH, C—$R^7$, or N. In one embodiment, X is CH, C—$CH_3$ or N. In one embodiment, X is CH. In one embodiment, Y is CH, C—$CH_3$ or N. In one embodiment, Y is N.

In one embodiment, $R^7$ is $C_{1-6}$alkyl, wherein the $C_{1-6}$alkyl is unsubstituted or substituted with 1-5 halogens. In one embodiment, $R^7$ is $C_{1-6}$alkyl. In one embodiment, $R^7$ is $CH_3$.

In one embodiment, Z is CH or N. In one embodiment, Z is N.

In one embodiment, R is H, halogen, $C_{1-6}$alkyl, or O—$C_{1-6}$ alkyl, wherein $C_{1-6}$alkyl is unsubstituted or substituted with 1-5 halogens. In one embodiment, $R^5$ is H, Cl, F, $C_{1-3}$alkyl, or —O—$C_{1-3}$alkyl, wherein $C_{1-3}$alkyl is unsubstituted or substituted with 1-3 halogens. In one embodiment, $R^5$ is H, Cl, F, $CH_3$, or —$OCH_3$.

In one embodiment, $R^6$ is H or $C_{1-6}$alkyl, wherein the $C_{1-6}$alkyl is unsubstituted or substituted with 1-5 halogens. In one embodiment, $R^6$ is H or $CH_3$. In one embodiment, $R^6$ is H.

In one embodiment, $R^4$ is $C_{1-6}$alkyl, $C_{3-10}$cycloalkyl, $C_{4-10}$cycloalkenyl, —$C_{1-6}$alkyl-phenyl, —$C_{1-6}$alkyl-(5 to 6-membered heteroaryl), —$C_{1-6}$alkyl-(4 to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—$NH_2$, —C(O)—NH—$C_{1-6}$alkyl, —C(O)—N—$(C_{1-6}$alkyl$)_2$, —O—$C_{1-6}$alkyl-$NH_2$, —O—$C_{1-6}$alkyl-NH—$(C_{1-6}$alkyl), —O—$C_{1-6}$alkyl-N($C_{1-6}$alkyl$)_2$, 4- to 6-membered heterocyclyl, —C(O)-(4- to 6-membered heterocyclyl), —O-phenyl, —O—$C_{1-6}$alkyl-(4- to 6-membered heterocyclyl), $C_{1-6}$alkyl, $C_{2-6}$alknyl, hydroxyl, $C_{1-6}$alkoxyl, or hydroxy$C_{1-6}$alkyl, and the heterocyclyl or heteroaryl is unsubstituted or substituted with 1-3 substituents selected from halogen, $C_{1-6}$alkyl, —C(O)—$C_{1-6}$alkyl, or 4- to 6-membered heterocyclyl.

In one embodiment, $R^4$ is

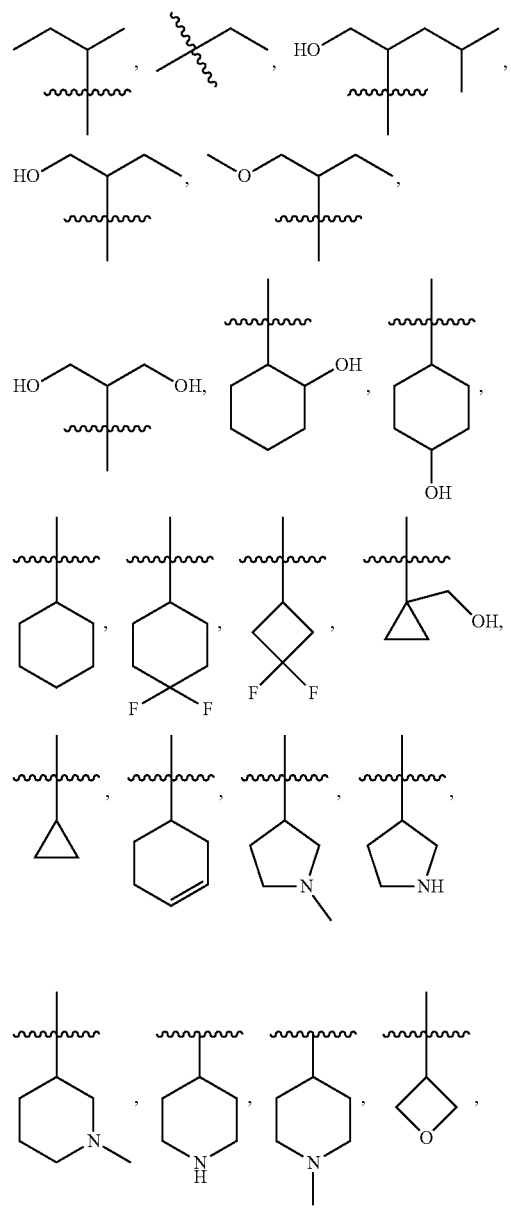

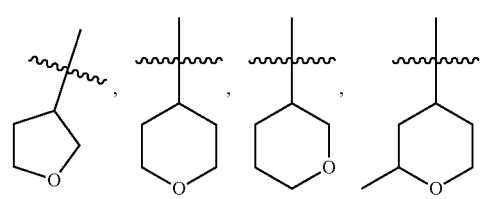

-continued
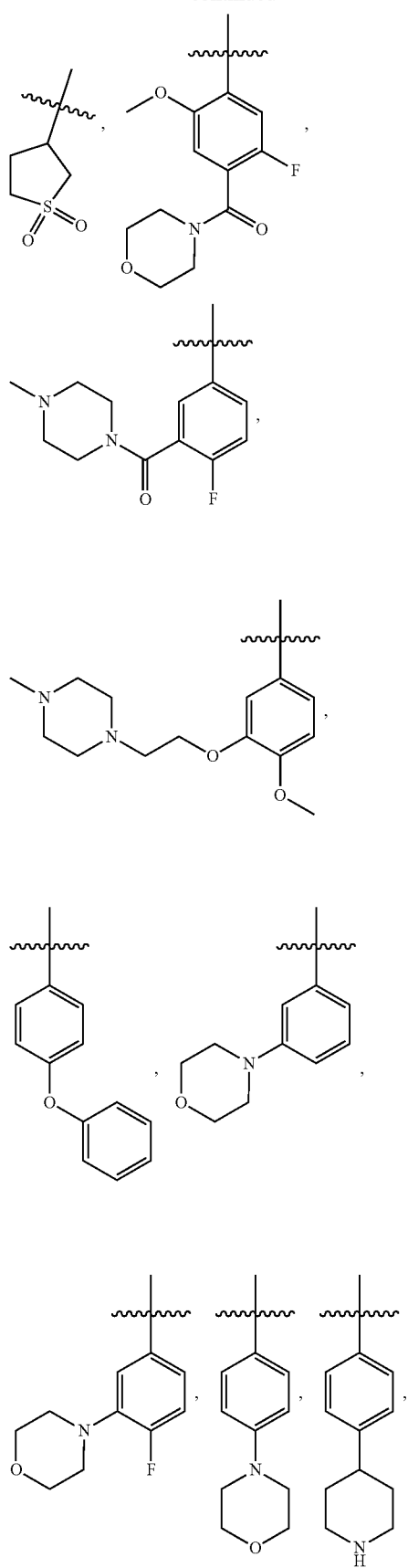
-continued
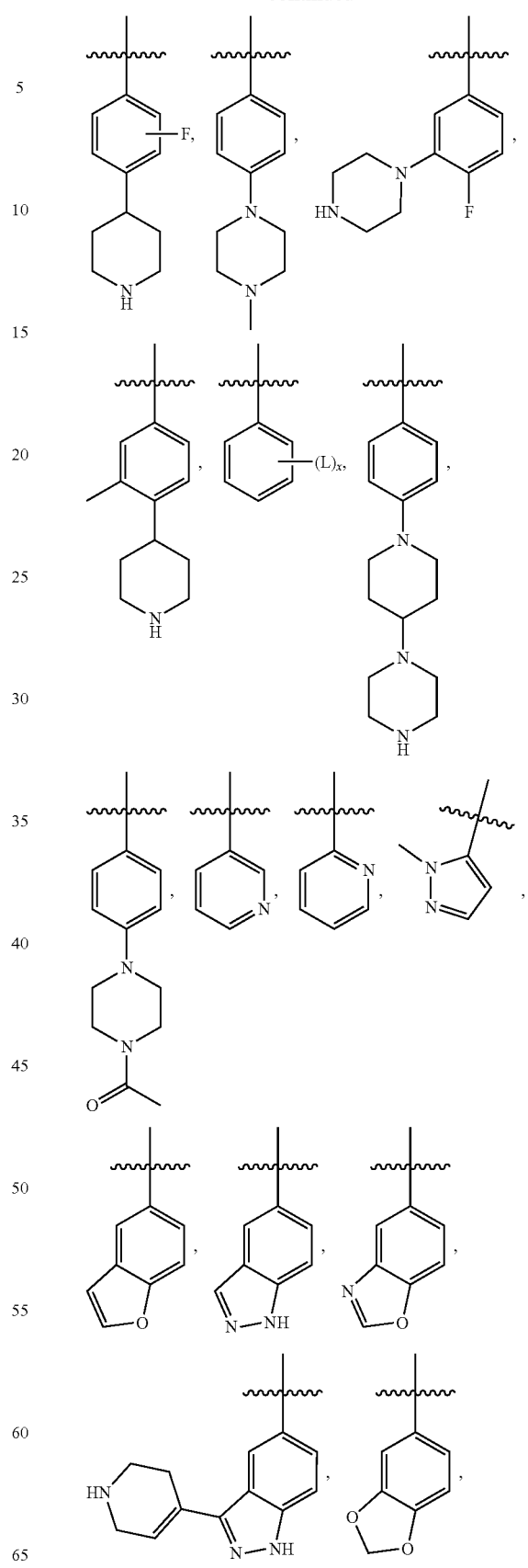

-continued

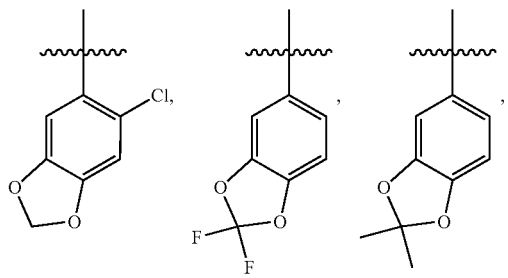

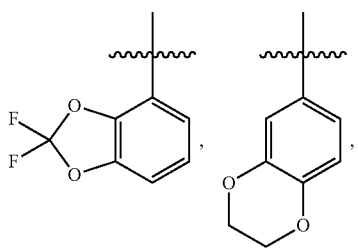

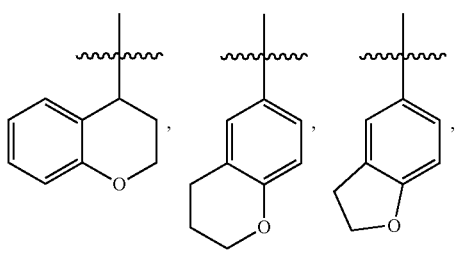

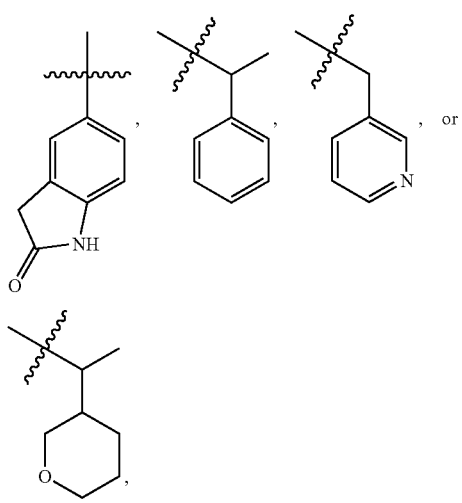

wherein each L is independently selected from halogen, CN, $C_{2-6}$alknyl, $C_{1-6}$alkoxy, —C(O)NH$C_{1-6}$alkyl, —C(O)NH($C_{1-6}$alkyl)$_2$, —O—$C_{1-6}$alkyl-NH$C_{1-6}$alkyl, or —O—$C_{1-6}$alkyl-N($C_{1-6}$alkyl)$_2$, and x is 0, 1, 2, or 3.

In one embodiment, $R^4$ is $C_{1-6}$alkyl, which is unsubstituted or substituted with 1-3 substituents selected from hydroxyl, or $C_{1-6}$alkoxyl. In one embodiment, $R^4$ is

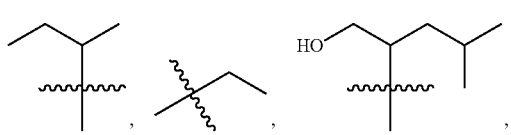

-continued

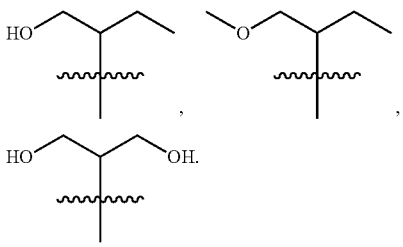

In one embodiment, $R^4$ is $C_{3-10}$cycloalkyl or $C_{4-10}$cycloalkenyl, which is unsubstituted or substituted with 1-3 substituents selected from hydroxyl, halogen, or hydroxy$C_{1-6}$ alkyl. In one embodiment, $R^4$ is $C_{3-6}$cycloalkyl or $C_{4-6}$cycloalkenyl, which is unsubstituted or substituted with 1-3 substituents selected from hydroxyl, F, Cl, or hydroxy$C_{1-3}$alkyl. In one embodiment, $R^4$ is

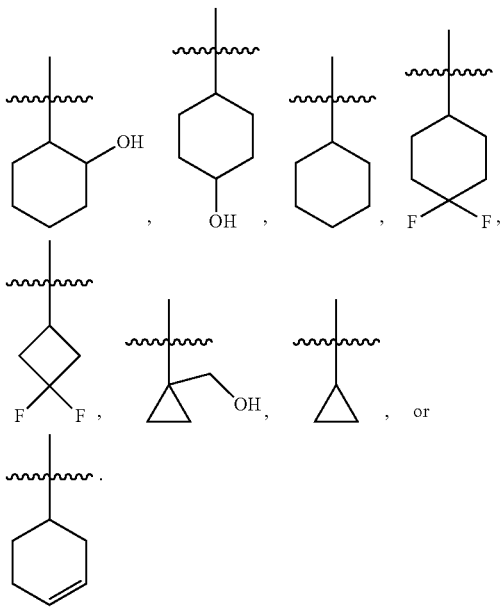

In one embodiment, $R^4$ is 4- to 10-membered monocyclic or bicyclic heterocyclyl containing 1-2 ring heteroatoms or hetero groups selected from O, N, S, S(=O), S(=O)$_2$, or C(=O), which is unsubstituted or substituted with 1-2 substituents selected from $C_{1-6}$alkyl. In one embodiment, $R^4$ is 4- to 6-membered monocyclic heterocyclyl containing 1-2 ring heteroatoms or hetero groups selected from O, N or S(=O)$_2$, which is unsubstituted or substituted with 1-2 substituents selected from $C_{1-3}$alkyl. In one embodiment, $R^4$ is

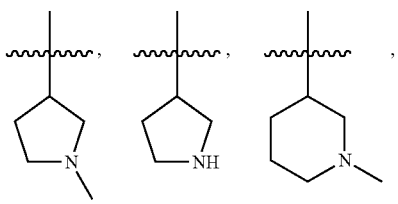

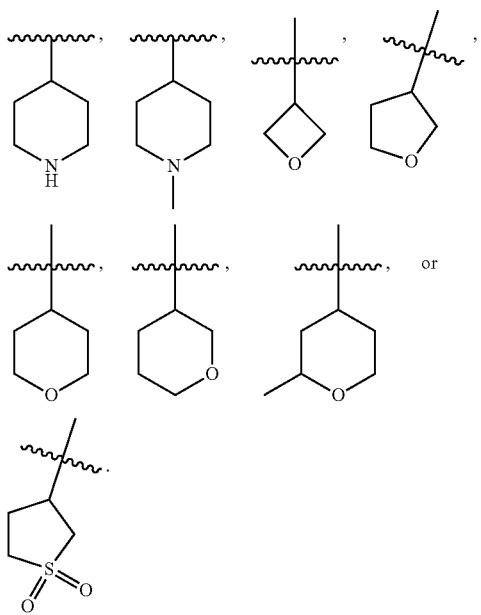

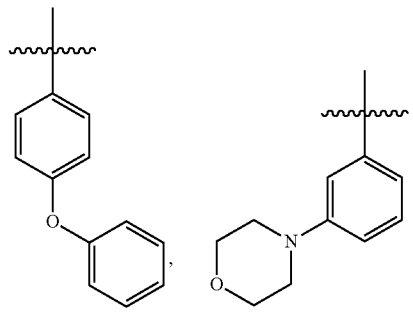

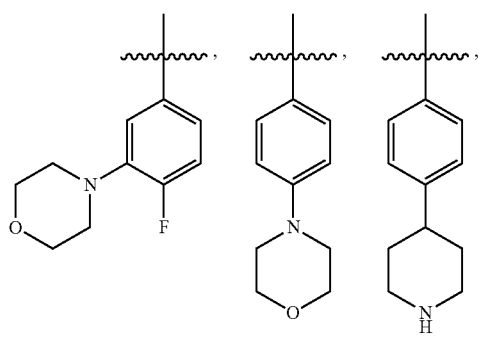

In one embodiment, R⁴ is phenyl, which is unsubstituted or substituted with 1-3 substituents selected from halogen, CN, $C_{2-6}$alknyl, —C(O)—NH$_2$, —C(O)—NH—$C_{1-6}$alkyl, —C(O)—N—($C_{1-6}$alkyl)$_2$, —O—$C_{1-6}$alkyl-NH$_2$, —O—$C_{1-6}$alkyl-NH—($C_{1-6}$alkyl), —O—$C_{1-6}$alkyl-N($C_{1-6}$alkyl)$_2$, 4- to 6-membered heterocyclyl, —C(O)-(4- to 6-membered heterocyclyl), —O-phenyl, —O—$C_{1-6}$alkyl-(4- to 6-membered heterocyclyl), $C_{1-6}$alkyl, hydroxyl, $C_{1-6}$alkoxyl, or hydroxy$C_{1-6}$alkyl, and the heterocyclyl or heteroaryl is unsubstituted or substituted with 1-3 substituents selected from halogen, $C_{1-6}$alkyl, —C(O)—$C_{1-6}$alkyl, or 4- to 6-membered heterocyclyl. In one embodiment, R⁴ is

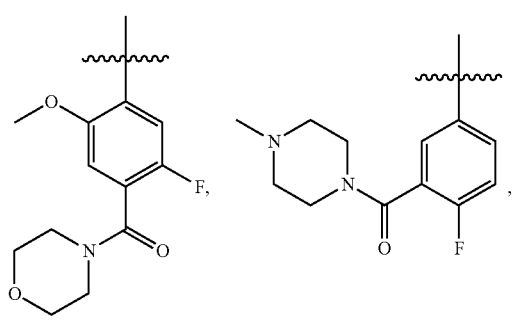

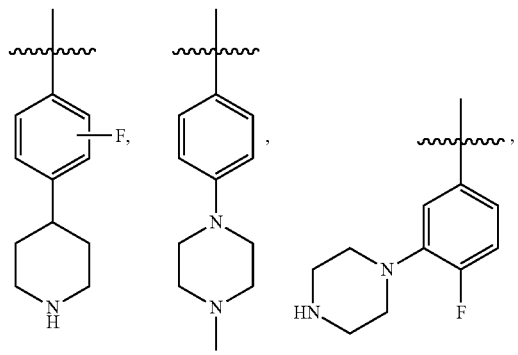

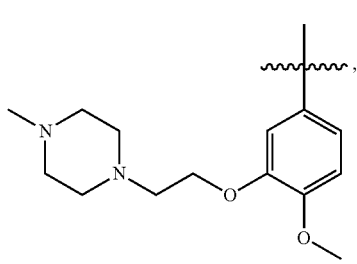

-continued

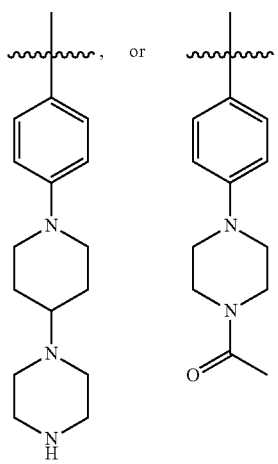

wherein each L is independently selected from halogen, CN, $C_{2-6}$alknyl, $C_{1-6}$alkoxy, $C(O)NHC_{1-6}$alkyl, or $C(O)NH(C_{1-6}\text{alkyl})_2$, and n is 0, 1, 2, or 3. In one embodiment, each L is independently selected from F, Cl, CN, $C_{1-3}$alkoxy, $-C(O)N(CH_3)_2$, and x is 0, 1, 2, or 3.

In one embodiment, $R^4$ is 5- to 10-membered monocyclic or bicyclic heteroaryl containing 1-2 ring heteroatoms or hetero groups selected from N, O, C(=O), or S, which is unsubstituted or substituted with 1-3 substituents selected from halogen, $C_{1-6}$alkyl or $C_{4-6}$cycloalkenyl. In one embodiment, $R^4$ is 5- or 6-membered monocyclic heteroaryl containing 1-2 ring heteroatoms selected from N or O, which is unsubstituted or substituted with 1-3 substituents selected from halogen or $CH_3$. In one embodiment, $R^4$ is

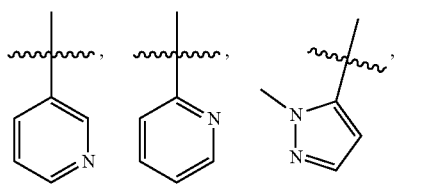

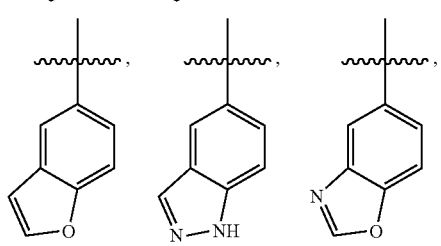

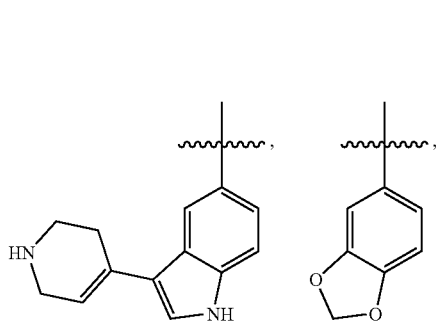

-continued

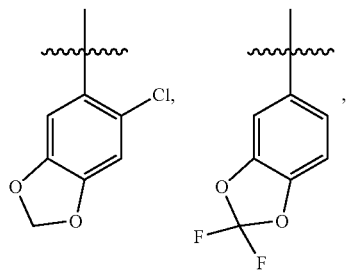

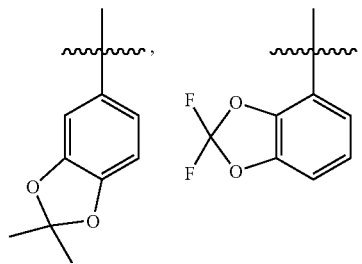

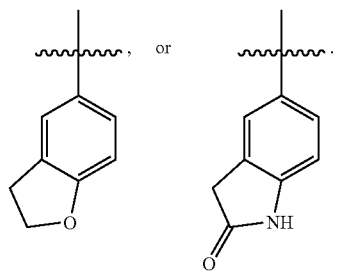

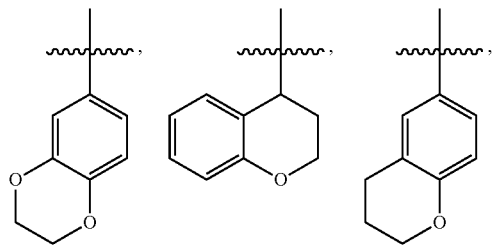

In one embodiment, $R^4$ is $-C_{1-6}$alkyl-(5- to 6-membered heteroaryl), which is unsubstituted or substituted with 1-3 substituents selected from halogen or $C_{1-6}$alkyl. In one embodiment, $R^4$ is

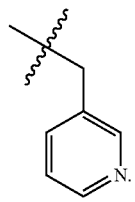 [SMILES: *Cc1cccnc1]

In one embodiment, $R^4$ is $-C_{1-6}$alkyl-phenyl, which is unsubstituted or substituted with 1-3 substituents selected from halogen or $C_{1-6}$alkyl. In one embodiment, $R^4$ is $-CH_2$-phenyl, which is unsubstituted or substituted with $CH_3$. In one embodiment, $R^4$ is

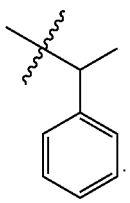 [SMILES: *C(C)c1ccccc1]

In one embodiment, $R^4$ is-$C_{1-6}$alkyl-(4- to 6-membered heterocyclyl), which is unsubstituted or substituted with 1-3 substituents selected from halogen or $C_{1-6}$alkyl. In one embodiment, $R^4$ is

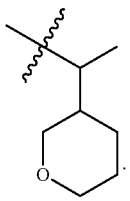 [SMILES: *C(C)C1CCCOC1]

In one embodiment, $R^4$ is

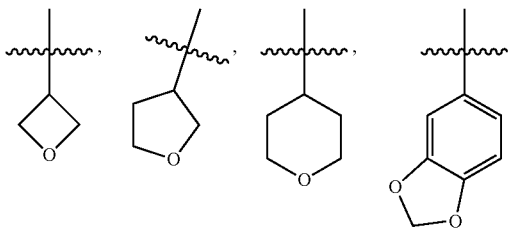

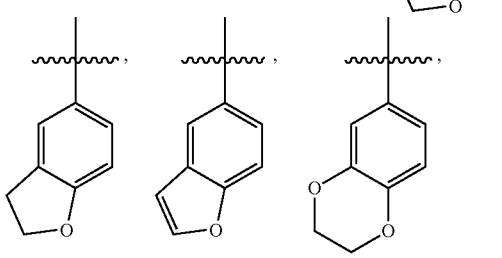

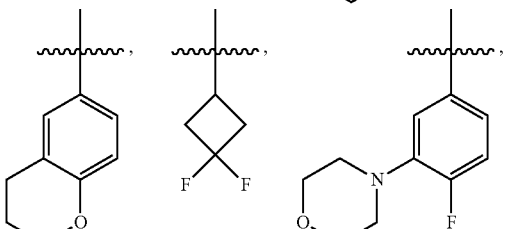

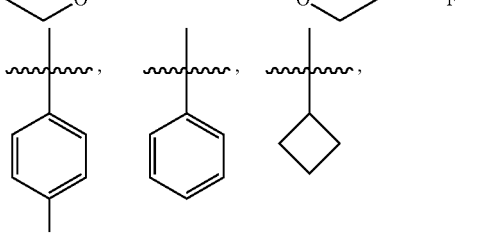

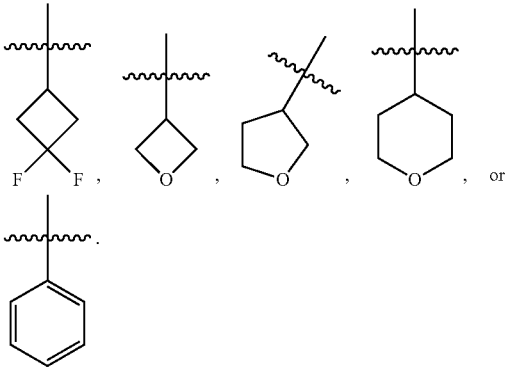

In one embodiment, $R^4$ is

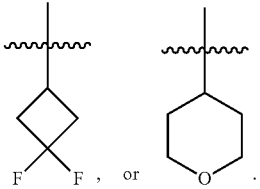 [SMILES: *C1CC(F)(F)C1 ; *C1CCOCC1]

In one embodiment, a compound of formula (II) or a pharmaceutically acceptable salt, solvate, hydrate, or stereoisomer, wherein:
$R^1$ is phenyl, pyridyl, thienyl, orthiazolyl, which is unsubstituted or substituted with 1-3 substituents selected from halogen, $C_{1-6}$alkyl, CN, hydroxy$C_{1-6}$alkyl, or amino$C_{1-6}$alkyl, wherein the $C_{1-6}$alkyl is unsubstituted or substituted with 1-3 substituents selected from halogen;
n is 0;
$R^2$ is $C_{1-6}$alkyl, hydroxy$C_{1-6}$alkyl, amino$C_{1-6}$alkyl, —$C_{1-6}$ alkyl-NH—$C_{0-6}$alkyl-(4- to 6-membered heterocyclyl), —C(O)—NH$_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—$C_{1-6}$alkyl, —C(O)—NH—$C_{1-6}$alkyl, —C(O)—N($C_{1-6}$alkyl)$_2$, or —$C_{1-6}$alkyl-NH—$C_{0-6}$alkyl-(5- to 6-membered heteroaryl), wherein the $C_{1-6}$alkyl, cycloalkyl, heterocyclyl, or heteroaryl is unsubstituted or substituted with 1-3 substituents selected from halogen, $C_{1-6}$alkyl, NH$_2$, hydroxy$C_{1-6}$alkyl, or amino$C_{1-6}$alkyl; and
$R^8$ is H;
$R^3$ is H;
M is a bond;
X is CH;
Y is CH or N;
Z is N;

R[5] is H, halogen, or $C_{1-6}$alkyl;
R[6] is H; and
R[4] is

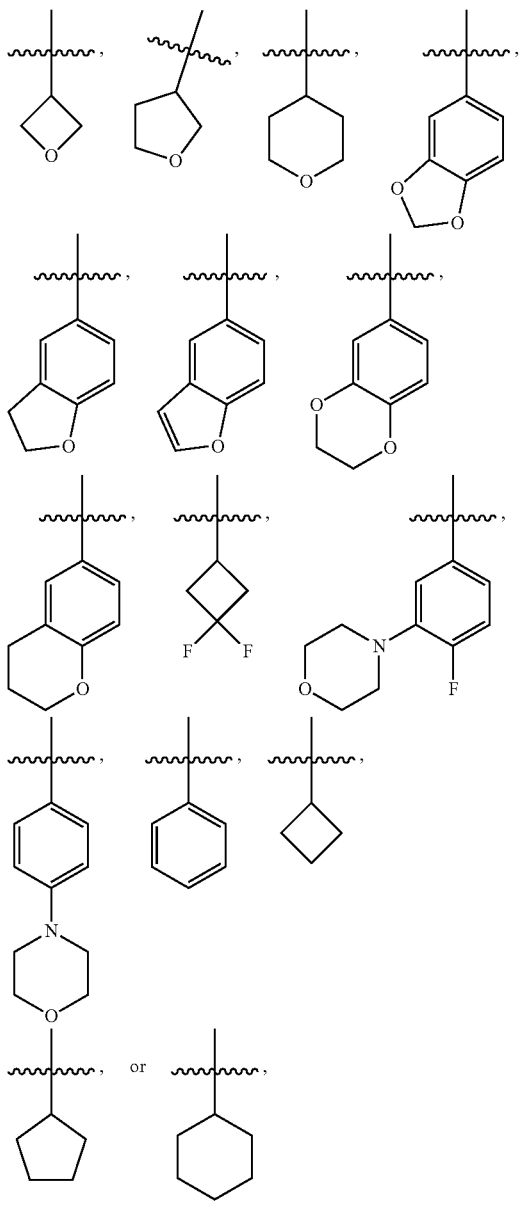

which can be unsubstituted or substituted with 1-3 substituents selected from halogen or $C_{1-6}$alkoxy.

In one embodiment, a compound of formula (II) or a pharmaceutically acceptable salt, solvate, hydrate, or stereoisomer, wherein:
R[1] is phenyl, or thienyl, which is unsubstituted or substituted with 1-3 substituents selected from halogen, $C_{1-6}$alkyl, CN, hydroxy$C_{1-6}$alkyl, or amino$C_{1-6}$alkyl, wherein the $C_{1-6}$alkyl is unsubstituted or substituted with 1-3 substituents selected from halogen;
n is 0;
R[2] is $C_{1-6}$alkyl, hydroxy$C_{1-6}$alkyl, amino$C_{1-6}$alkyl, —$C_{1-6}$alkyl-NH—$C_{0-6}$alkyl-(4- to 6-membered heterocyclyl), —C(O)—NH$_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—$C_{1-6}$alkyl, —C(O)—NH—$C_{1-6}$alkyl, —C(O)—N($C_{1-6}$alkyl)$_2$, or —$C_{1-6}$alkyl-NH—$C_{0-6}$alkyl-(5- to 6-membered heteroaryl), wherein the $C_{1-6}$alkyl, cycloalkyl, heterocyclyl, or heteroaryl is unsubstituted or substituted with 1-3 substituents selected from halogen, $C_{1-6}$alkyl, NH$_2$, hydroxy$C_{1-6}$alkyl, or amino$C_{1-6}$alkyl; and
R[8] is H;
R[3] is H;
M is a bond;
X is CH;
Y is CH or N;
Z is N;
R[5] is H, halogen, or $C_{1-6}$alkyl;
R[6] is H; and
R[4] is

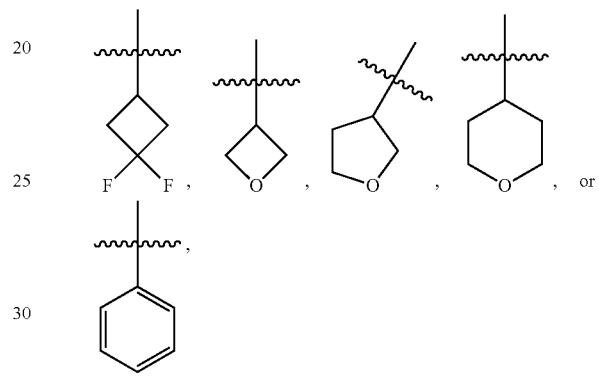

which can be unsubstituted or substituted with 1-3 substituents selected from halogen or $C_{1-6}$alkoxy.

In one embodiment, a compound of formula (II) or a pharmaceutically acceptable salt, solvate, hydrate, or stereoisomer, wherein:
R[1] is phenyl, which is unsubstituted or substituted with 1-3 substituents selected from F or Cl;
n is 0;
R[2] is CH$_2$OH, CH$_2$NH$_2$, —CH$_2$NH(CH$_3$), —CH$_2$NHCH$_2$CH$_2$OH, —C(O)NH$_2$, —CH$_2$NH-(tetrahydro-2H-pyran), or —CH$_2$NH—CH$_2$-(1H-pyrrole); and
R[8] is H;
R[3] is H;
M is a bond;
X is CH;
Y is N;
Z is N;
R is CH$_3$;
R[6] is H; and
R[4] is

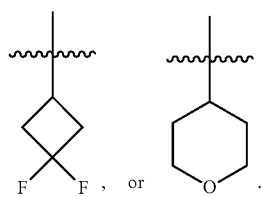 [SMILES: *C1CC(F)(F)C1 ; *C1CCOCC1]

In one aspect, the present invention provides novel inhibitors of ERK1 and ERK2 of formula (III)

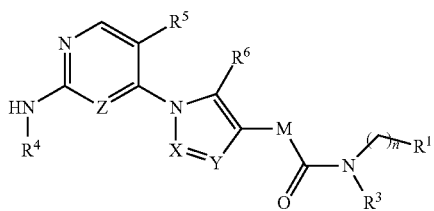

III or a pharmaceutically acceptable salt, prodrug, solvate, hydrate, or stereoisomer thereof, wherein:

$R^1$ is phenyl or 5- to 10-membered heteroaryl, wherein the phenyl or heteroaryl is unsubstituted or substituted with 1-3 substituents selected from halogen, $C_{1-6}$alkyl, CN, hydroxy$C_{1-6}$alkyl, amino$C_{1-6}$alkyl, —$C_{1-6}$alkyl-O—$C_{1-6}$alkyl, —$C_{1-6}$alkyl-NH—$C_{1-6}$alkyl, —$C_{1-6}$alkyl-N—$(C_{1-6}$alkyl$)_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—$C_{1-6}$alkyl, —$C_{1-6}$alkyl-NH—C(O)—$C_{1-6}$alkyl, —$C_{1-6}$alkyl-O—C(O)—$C_{1-6}$alkyl, —$C_{1-6}$alkyl-NH—$C_{0-6}$alkyl-(4- to 6-membered heterocyclyl), —$C_{1-6}$alkyl-NH—$C_{0-6}$alkyl-(5- to 6-membered heteroaryl), —C(O)—$NH_2$, —C(O)—NH—$C_{1-6}$alkyl, or —C(O)—N($C_{1-6}$alkyl$)_2$, wherein the $C_{1-6}$alkyl, cycloalkyl, heterocyclyl, and/or heteroaryl is unsubstituted or substituted with 1-3 substituents selected from halogens, $C_{1-6}$alkyl, hydroxy$C_{1-6}$ alkyl, or amino$C_{1-6}$alkyl;

n is 0 to 6;

$R^3$ is H or $C_{1-6}$alkyl, wherein $C_{1-6}$alkyl is unsubstituted or substituted with 1-5 halogens;

M is a bond or NH;

X and Y are each independently CH, C—$R^7$, or N;

Z is CH or N, $R^5$ is H, halogen, $C_{1-6}$alkyl, or O—$C_{1-6}$alkyl, wherein $C_{1-6}$alkyl is unsubstituted or substituted with 1-5 halogens;

$R^6$ is H or $C_{1-6}$alkyl, wherein the $C_{1-6}$alkyl is unsubstituted or substituted with 1-5 halogens;

$R^7$ is $C_{1-6}$alkyl, wherein $C_{1-6}$alkyl is unsubstituted or substituted with 1-5 halogens; and $R^4$ is $C_{1-6}$alkyl, $C_{3-10}$cycloalkyl, $C_{4-10}$cycloalkenyl, —$C_{1-6}$ alkyl-phenyl, —$C_{1-6}$alkyl-(5 to 6-membered heteroaryl), —$C_{1-6}$alkyl-(4- to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—$NH_2$, —C(O)—NH—$C_{1-6}$alkyl, —C(O)—N—$(C_{1-6}$alkyl$)_2$, —O—$C_{1-6}$ alkyl-$NH_2$, —O—$C_{1-6}$alkyl-NH—$(C_{1-6}$alkyl), —O—$C_{1-6}$alkyl-N$(C_{1-6}$alkyl$)_2$, 4- to 6-membered heterocyclyl, —C(O)-(4- to 6-membered heterocyclyl), —O-phenyl, —O—$C_{1-6}$alkyl-(4- to 6-membered heterocyclyl), $C_{1-6}$alkyl, $C_{2-6}$alknyl, hydroxyl, $C_{1-6}$alkoxyl, or hydroxy$C_{1-6}$alkyl, and the heterocyclyl or heteroaryl is unsubstituted or substituted with 1-3 substituents selected from halogen, $C_{1-6}$alkyl, —C(O)—$C_{1-6}$alkyl, or 4- to 6-membered heterocyclyl.

In one embodiment, $R^1$ is unsubstituted or substituted $C_{6-12}$aryl or unsubstituted or substituted 5- to 10-membered heteroaryl. In one embodiment, $R^1$ is phenyl or 5- to 6-membered heteroaryl containing 1-2 ring heteroatoms selected from O, N or S, wherein the phenyl or heteroaryl is unsubstituted or substituted with 1-3 substituents selected from halogen, $C_{1-6}$alkyl, CN, hydroxy$C_{1-6}$alkyl, amino$C_{1-6}$alkyl, —$C_{1-6}$alkyl-O—$C_{1-6}$alkyl, —$C_{1-6}$alkyl-NH—$C_{1-6}$alkyl, —$C_{1-6}$alkyl-N—$(C_{1-6}$alkyl$)_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—$C_{1-6}$alkyl, —$C_{1-6}$alkyl-NH—C(O)—$C_{1-6}$alkyl, —$C_{1-6}$alkyl-O—C(O)—$C_{1-6}$alkyl, —$C_{1-6}$alkyl-NH—$C_{0-6}$alkyl-(4- to 6-membered heterocyclyl), —$C_{1-6}$alkyl-NH—$C_{0-6}$alkyl-(5- to 6-membered heteroaryl), C(O)—$NH_2$, —C(O)—NH—$C_{1-6}$alkyl, or —C(O)—N($C_{1-6}$alkyl$)_2$, wherein the $C_{1-6}$alkyl, cycloalkyl, heterocyclyl, and/or heteroaryl is unsubstituted or substituted with 1-3 substituents selected from halogen, $C_{1-6}$alkyl, $NH_2$, hydroxy$C_{1-6}$ alkyl, or amino$C_{1-6}$alkyl. In one embodiment, $R^1$ is phenyl, pyridyl, thienyl, orthiazolyl, which is unsubstituted or substituted with 1-3 substituents selected from halogen, $C_{1-6}$alkyl, CN, hydroxy$C_{1-6}$alkyl, or amino$C_{1-6}$alkyl, wherein the $C_{1-6}$alkyl is unsubstituted or substituted with 1-3 substituents selected from halogen. In one embodiment, $R^1$ is phenyl, pyridyl, thienyl, or thiazolyl, which is unsubstituted or substituted with 1-3 substituents selected from F, Cl, $C_{1-3}$alkyl, CN, hydroxy$C_{1-3}$alkyl, or amino$C_{1-3}$alkyl, wherein the $C_{1-3}$alkyl is unsubstituted or substituted with 1-3 substituents selected from F. In one embodiment, $R^1$ is phenyl, pyridyl, thienyl, or thiazolyl, which is unsubstituted or substituted with 1-3 substituents selected from F, Cl, $CH_3$, —$C(CH_3)_3$, $CF_3$, —$CH_2OH$, —$CH_2CH_2OH$, $CH_2NH_2$, CN, or —$C(CH_3)_2OH$. In one embodiment, $R^1$ is phenyl, which is unsubstituted or substituted with 1-3 substituents selected from F, Cl, CH₃, —C(CH₃)₃, CF₃, —CH₂OH, —CH₂CH₂OH, CH₂NH₂, CN, or —C(CH₃)₂OH.

In one embodiment, n is 0 to 6. In one embodiment, n is 1 to 2. In one embodiment, n is 1.

In one embodiment, $R^3$ is H or $C_{1-6}$alkyl, wherein the $C_{1-6}$alkyl is unsubstituted or substituted with 1-5 halogens. In one embodiment, $R^3$ is H or $C_{1-3}$alkyl, wherein the $C_{1-6}$alkyl is unsubstituted or substituted with 1-3 halogens. In one embodiment, $R^3$ is H or CH₃.

In one embodiment, M is a bond or NH. In one embodiment, M is a bond.

In one embodiment, X and Y are each independently CH, C—$R^7$, or N. In one embodiment, X is CH, C—CH₃ or N. In one embodiment, X is CH. In one embodiment, Y is CH, C—CH₃ or N. In one embodiment, Y is N.

In one embodiment, $R^7$ is $C_{1-6}$alkyl, wherein the $C_{1-6}$alkyl is unsubstituted or substituted with 1-5 halogens. In one embodiment, $R^7$ is $C_{1-6}$alkyl. In one embodiment, $R^7$ is CH₃.

In one embodiment, Z is CH or N. In one embodiment, Z is N.

In one embodiment, R is H, halogen, $C_{1-6}$alkyl, or O—$C_{1-6}$ alkyl, wherein $C_{1-6}$alkyl is unsubstituted or substituted with 1-5 halogens. In one embodiment, $R^5$ is H, Cl, F, $C_{1-3}$alkyl, or —O—$C_{1-3}$alkyl, wherein $C_{1-3}$alkyl is unsubstituted or substituted with 1-3 halogens. In one embodiment, $R^5$ is H, Cl, F, CH₃, or —OCH₃.

In one embodiment, $R^6$ is H or $C_{1-6}$alkyl, wherein the $C_{1-6}$alkyl is unsubstituted or substituted with 1-5 halogens. In one embodiment, $R^6$ is H or CH₃. In one embodiment, $R^6$ is H.

In one embodiment, $R^4$ is $C_{1-6}$alkyl, $C_{3-10}$cycloalkyl, $C_{4-10}$cycloalkenyl, —$C_{1-6}$alkyl-phenyl, —$C_{1-6}$alkyl-(5 to 6-membered heteroaryl), —$C_{1-6}$alkyl-(4 to 6-membered heterocyclyl), 4- to 10-membered heterocyclyl, phenyl, or 5- to 10-membered heteroaryl, wherein the alkyl, cycloalkyl, cycloalkenyl, phenyl, heteroaryl, or heterocyclyl is unsubstituted or substituted with 1-3 substituents selected from halogen, CN, —C(O)—NH₂, —C(O)—NH—$C_{1-6}$alkyl, —C(O)—N—($C_{1-6}$alkyl)₂, —O—$C_{1-6}$alkyl-NH₂, —O—$C_{1-6}$alkyl-NH—($C_{1-6}$alkyl), —O—$C_{1-6}$alkyl-N($C_{1-6}$alkyl)₂, 4- to 6-membered heterocyclyl, —C(O)-(4- to 6-membered heterocyclyl), —O-phenyl, —O—$C_{1-6}$alkyl-(4- to 6-membered heterocyclyl), $C_{1-6}$alkyl, $C_{2-6}$alknyl, hydroxyl, $C_{1-6}$alkoxyl, or hydroxy$C_{1-6}$alkyl, and the heterocyclyl or heteroaryl is unsubstituted or substituted with 1-3 substituents selected from halogen, $C_{1-6}$alkyl, —C(O)—$C_{1-6}$alkyl, or 4- to 6-membered heterocyclyl.

In one embodiment $R^4$ is

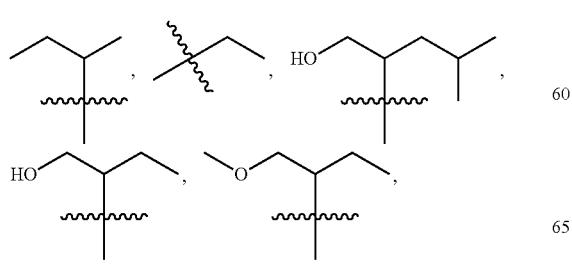

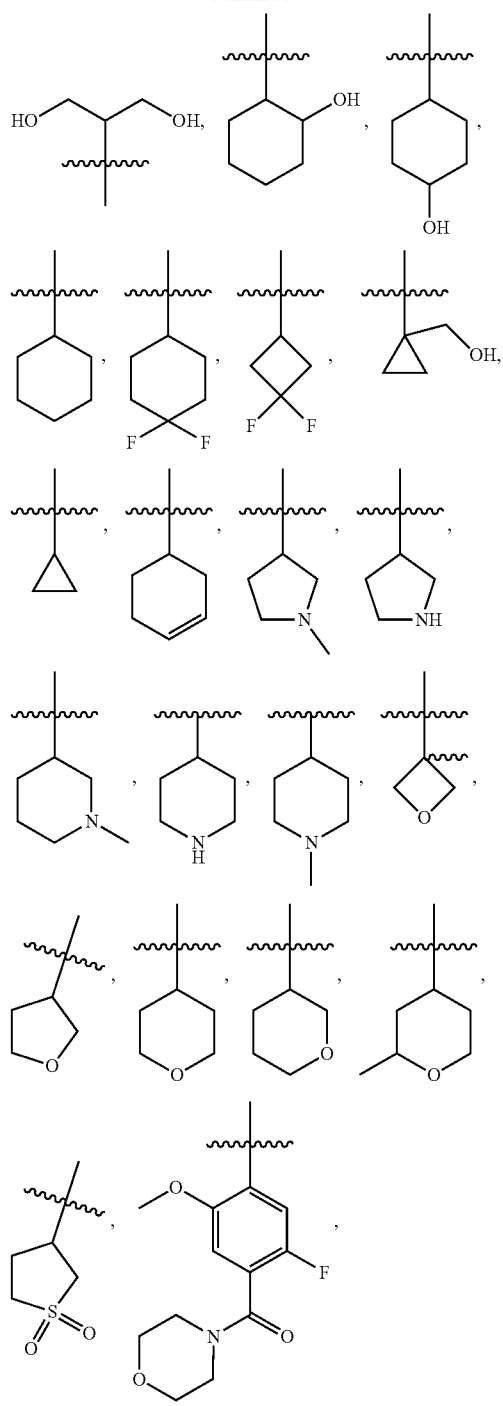

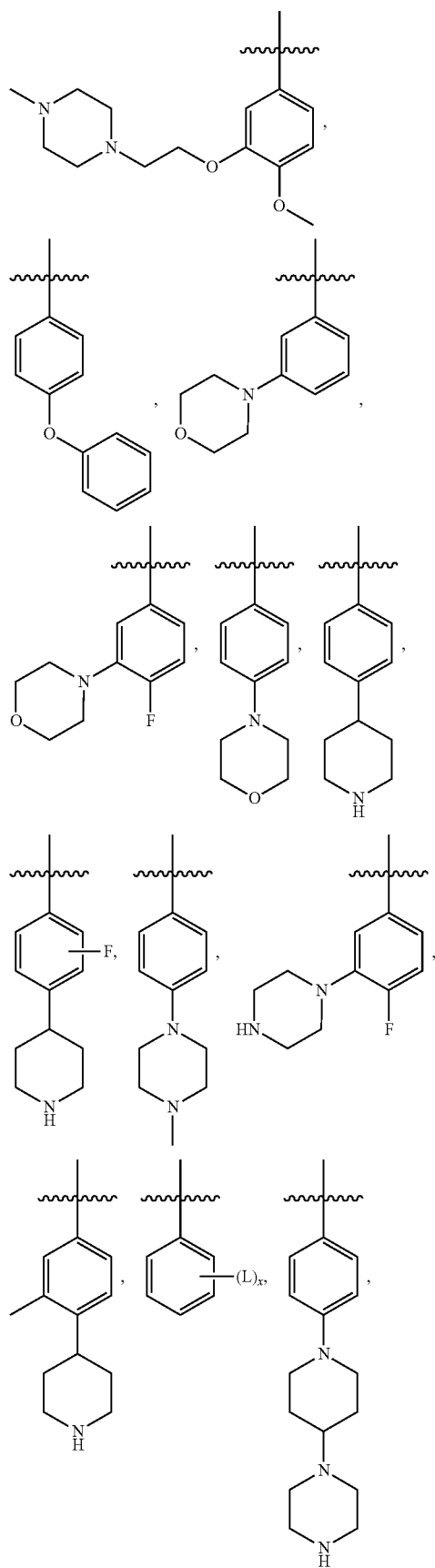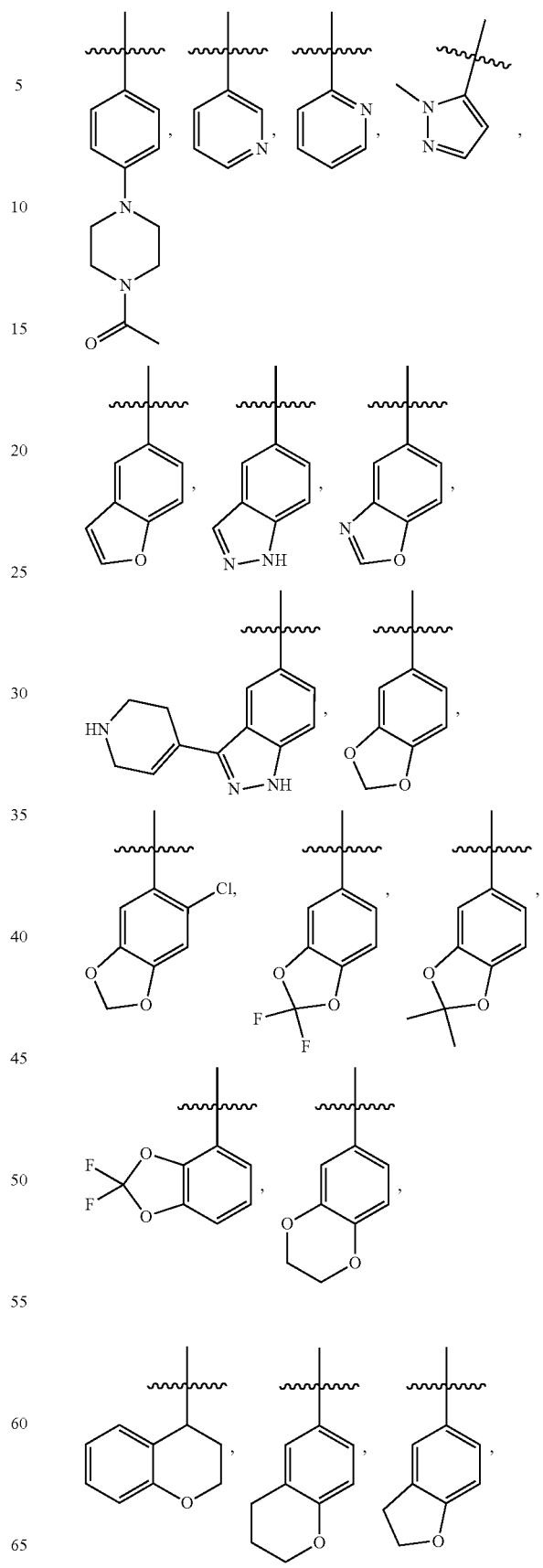

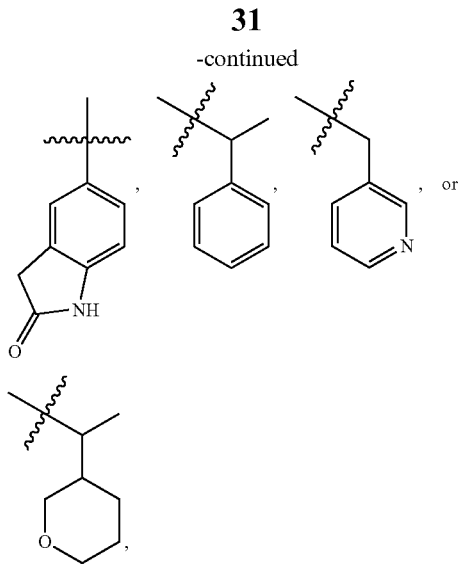

wherein each L is independently selected from halogen, CN, $C_{2-6}$alknyl, $C_{1-6}$alkoxy, —C(O)NH$C_{1-6}$alkyl, —C(O)NH($C_{1-6}$alkyl)$_2$, —O—$C_{1-6}$alkyl-NH$C_{1-6}$alkyl, or —O—$C_{1-6}$alkyl-N($C_{1-6}$alkyl)$_2$, and x is 0, 1, 2, or 3.

In one embodiment, $R^4$ is $C_{1-6}$alkyl, which is unsubstituted or substituted with 1-3 substituents selected from hydroxyl, or $C_{1-6}$alkoxyl. In one embodiment, $R^4$ is

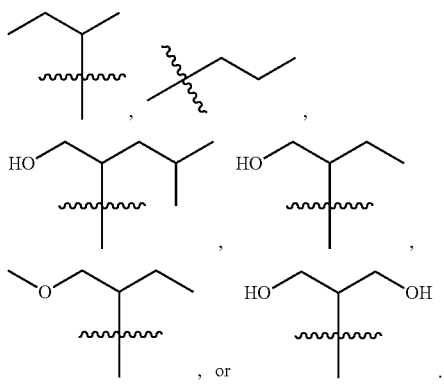

In one embodiment, $R^4$ is $C_{3-10}$cycloalkyl or $C_{4-10}$cycloalkenyl, which is unsubstituted or substituted with 1-3 substituents selected from hydroxyl, halogen, or hydroxy$C_{1-6}$ alkyl. In one embodiment, $R^4$ is $C_{3-6}$cycloalkyl or $C_{4-6}$cycloalkenyl, which is unsubstituted or substituted with 1-3 substituents selected from hydroxyl, F, Cl, or hydroxy$C_{1-3}$alkyl. In one embodiment, $R^4$ is

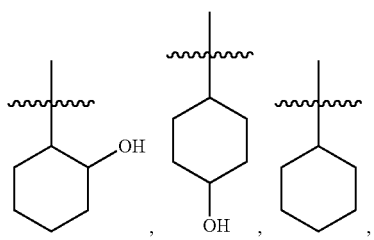

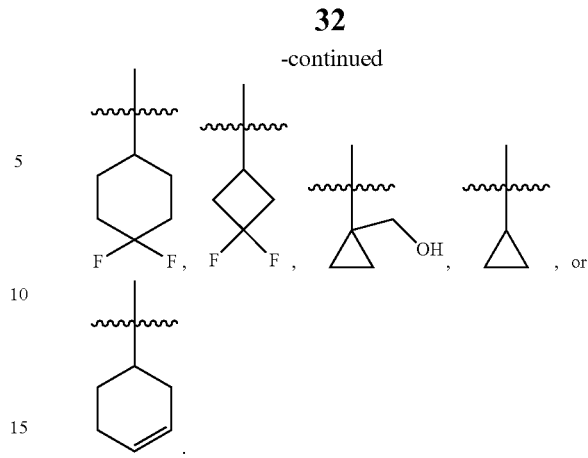

In one embodiment, $R^4$ is 4- to 10-membered heterocyclyl containing 1-2 ring heteroatoms or hetero groups selected from O, N, S, S(=O), S(=O)$_2$, or C(=O), which is unsubstituted or substituted with 1-2 substituents selected from $C_{1-6}$alkyl. In one embodiment, $R^4$ is 4- to 6-membered monocyclic heterocyclyl containing 1-2 ring heteroatoms or hetero groups selected from O, N or S(O)$_2$, which is unsubstituted or substituted with 1-2 substituents selected from $C_{1-3}$alkyl. In one embodiment, $R^4$ is

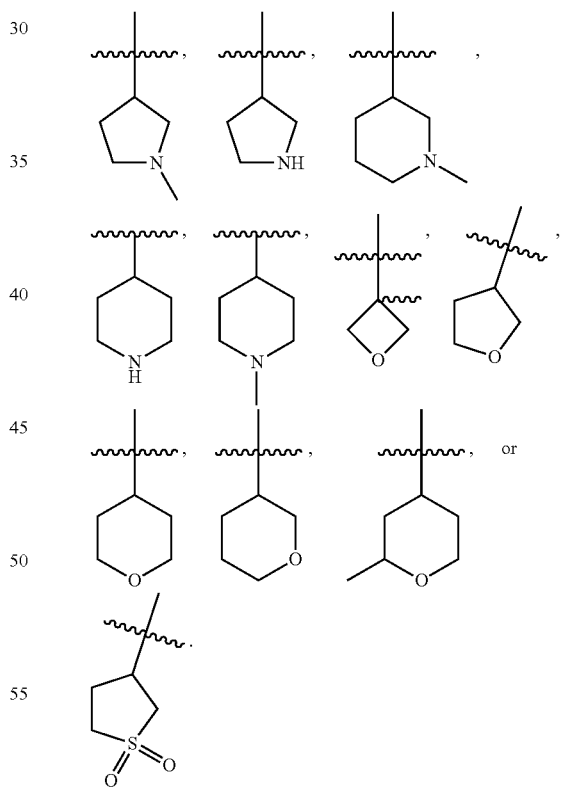

In one embodiment, $R^4$ is phenyl, which is unsubstituted or substituted with 1-3 substituents selected from halogen, $C_{2-6}$alknyl, CN, —C(O)—NH$_2$, —C(O)—NH—$C_{1-6}$alkyl, —C(O)—N—($C_{1-6}$alkyl)$_2$, —O—$C_{1-6}$alkyl-NH$_2$, —O—$C_{1-6}$alkyl-NH—($C_{1-6}$alkyl), —O—$C_{1-6}$alkyl-N($C_{1-6}$alkyl)$_2$, 4- to 6-membered heterocyclyl, —C(O)-(4- to 6-membered heterocyclyl), —O-phenyl, —O—$C_{1-6}$alkyl- (4- to 6-membered heterocyclyl), $C_{1-6}$alkyl, hydroxyl, $C_{1-6}$alkoxyl, or hydroxy$C_{1-6}$alkyl, and the heterocyclyl or heteroaryl is unsubstituted or substituted with 1-3 substituents selected from halogen, $C_{1-6}$alkyl, —C(O)—$C_{1-6}$alkyl, or 4- to 6-membered heterocyclyl. In one embodiment $R^4$ is

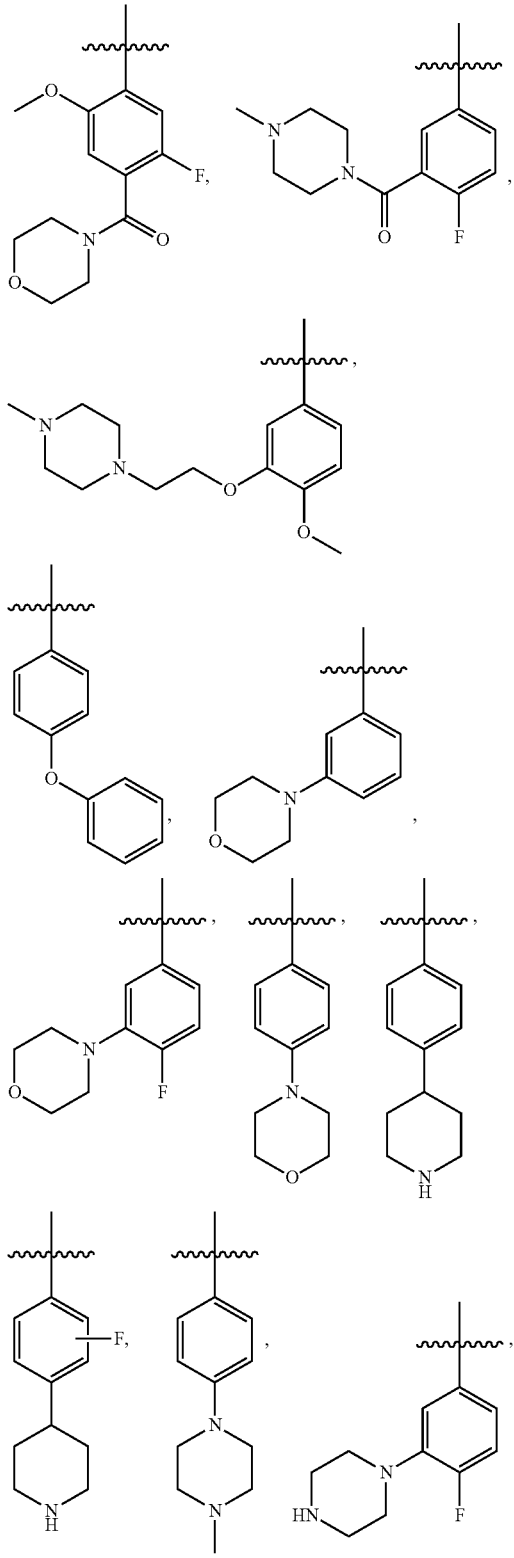

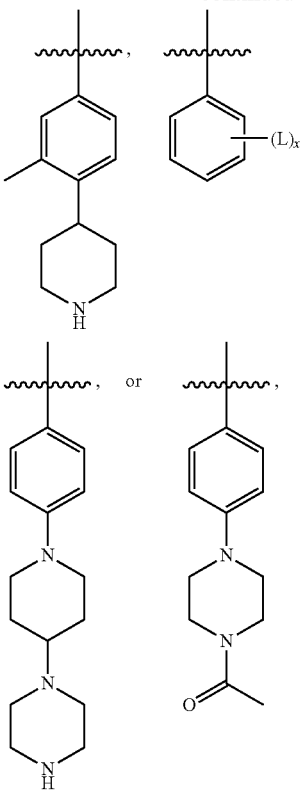

wherein each L is independently selected from halogen, CN, $C_{2-6}$alknyl, $C_{1-6}$alkoxy, C(O)NH$C_{1-6}$alkyl, or C(O)NH($C_{1-6}$alkyl)$_2$, and n is 0, 1, 2, or 3. In one embodiment, each L is independently selected from F, Cl, CN, $C_{1-3}$alkoxy, —C(O)N(CH$_3$)$_2$, and x is 0, 1, 2, or 3.

In one embodiment, $R^4$ is 5- to 10-membered monocyclic or bicyclic heteroaryl containing 1-2 ring heteroatoms or hetero groups selected from O, N, S, S(=O), S(=O)$_2$, or C(=O), which is unsubstituted or substituted with 1-3 substituents selected from halogen, $C_{1-6}$alkyl or $C_{4-6}$cycloalkenyl. In one embodiment, $R^4$ is 5- or 6-membered monocyclic heteroaryl containing 1-2 ring heteroatoms selected from N or O, which is unsubstituted or substituted with 1-3 substituents selected from halogen or CH$_3$. In one embodiment, $R^4$ is

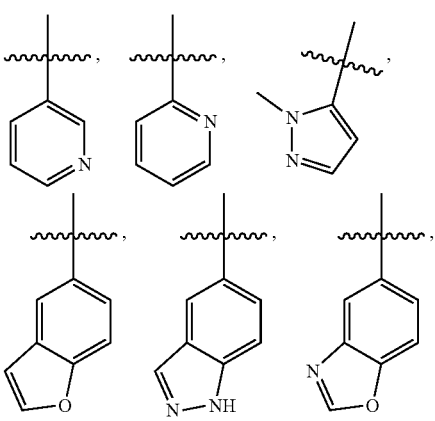

-continued

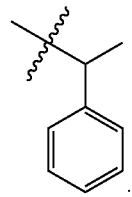 [SMILES: *C(C)c1ccccc1]

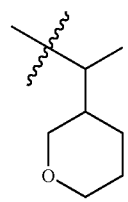

In one embodiment, R⁴ is —$C_{1-6}$alkyl-(5- to 6-membered heteroaryl), which is unsubstituted or substituted with 1-3 substituents selected from halogen or $C_{1-6}$alkyl. In one embodiment, R⁴ is In one embodiment, R⁴ is —$C_{1-6}$alkyl-phenyl, which is unsubstituted or substituted with 1-3 substituents selected from halogen or $C_{1-6}$alkyl. In one embodiment, R⁴ is —CH₂-phenyl, which is unsubstituted or substituted with CH₃. In one embodiment, R⁴ is In one embodiment, R⁴ is-$C_{1-6}$alkyl-(4- to 6-membered heterocyclyl), which is unsubstituted or substituted with 1-3 substituents selected from halogen or $C_{1-6}$alkyl. In one embodiment, R⁴ is In one embodiment, R⁴ is

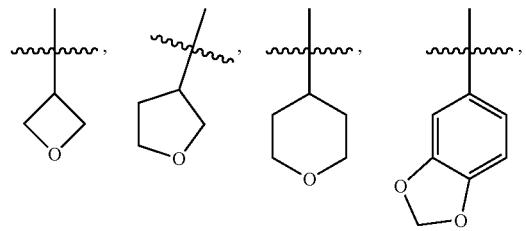

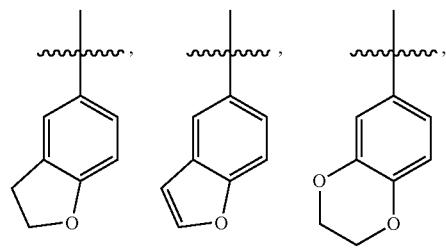

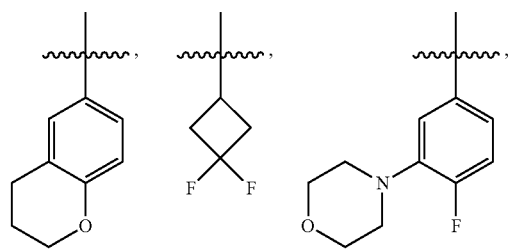

-continued

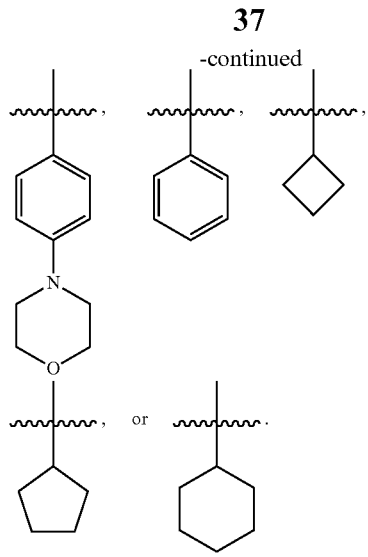

In one embodiment, R⁴ is

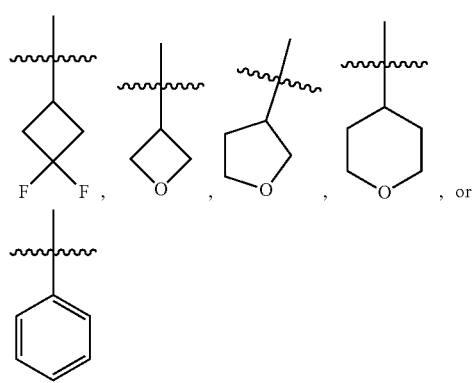

In one embodiment, R⁴ is

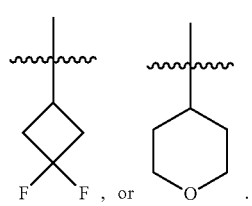 [SMILES: *C1CC(F)(F)C1 ; *C1CCOCC1]

In one embodiment, a compound of formula (III) or a pharmaceutically acceptable salt, solvate, hydrate, or stereoisomer, wherein:
  R¹ is phenyl, or thienyl, which is unsubstituted or substituted with 1-3 substituents selected from halogen, $C_{1-6}$alkyl, CN, hydroxy$C_{1-6}$alkyl, or amino$C_{1-6}$alkyl, wherein the $C_{1-6}$alkyl is unsubstituted or substituted with 1-3 substituents selected from halogen;
  n is 1;
  R³ is H;
  M is a bond;
  X is CH;
  Y is N;
  Z is N,
  R⁵ is H, halogen, or $C_{1-6}$alkyl;
  R⁶ is H; and
  R⁴ is

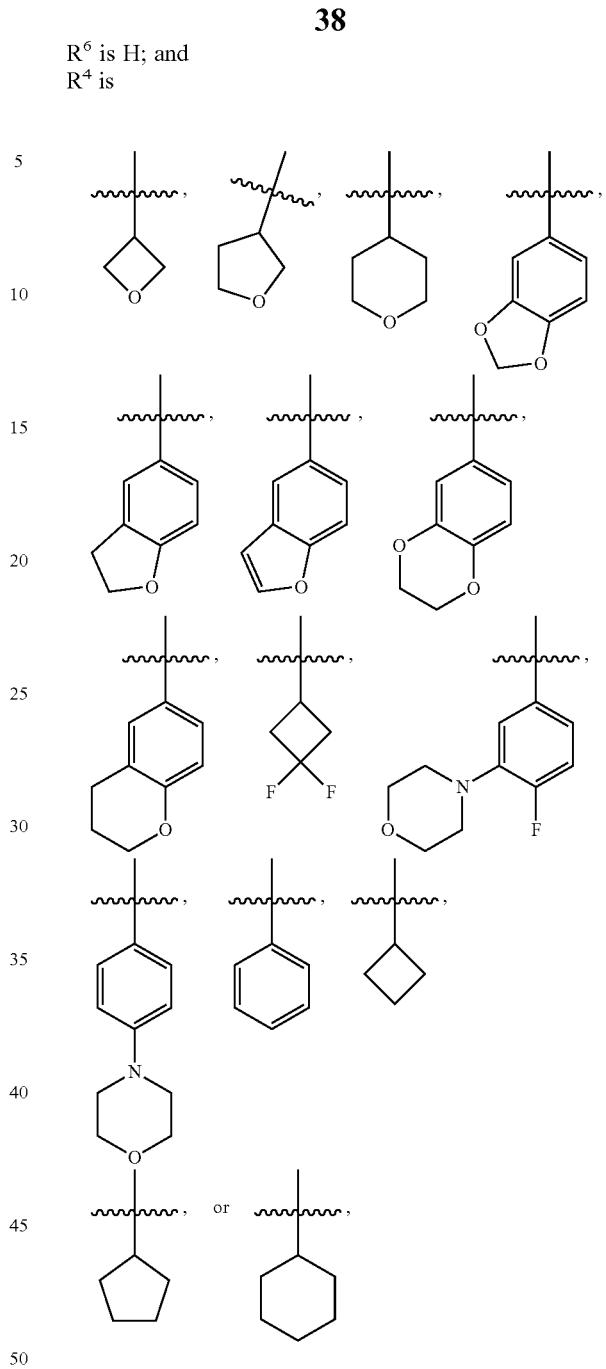

which can be unsubstituted or substituted with 1-3 substituents selected from halogen or $C_{1-6}$alkoxy.

In one embodiment, a compound of formula (III) or a pharmaceutically acceptable salt, solvate, hydrate, or stereoisomer, wherein:
  R¹ is phenyl, which is unsubstituted or substituted with 1-3 substituents selected from halogen, $C_{1-6}$alkyl, CN, hydroxy$C_{1-6}$alkyl, or amino$C_{1-6}$alkyl, wherein the $C_{1-6}$alkyl is unsubstituted or substituted with 1-3 substituents selected from halogen;
  n is 1;
  R³ is H;
  M is a bond;
  X is CH;
  Y is N;
  Z is N, R⁵ is CH₃;
R⁶ is H; and
R⁴ is

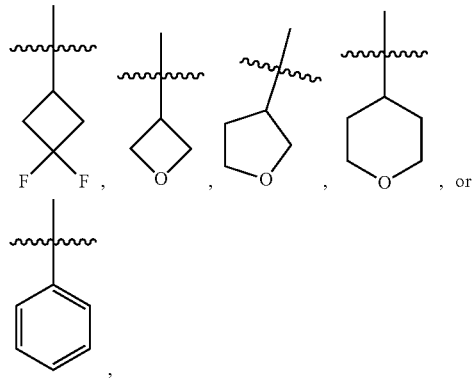

which can be unsubstituted or substituted with 1-3 substituents selected from halogen or C$_{1-6}$alkoxy.

In one embodiment, a compound of formula (III) or a pharmaceutically acceptable salt, solvate, hydrate, or stereoisomer, wherein:
R¹ is phenyl, which is unsubstituted or substituted with 1-3 substituents selected from halogen, CH₂OH, or CH₂NH₂;
n is 1;
R³ is H;
M is a bond;
X is CH;
Y is N;
Z is N,
R⁵ is CH₃;
R⁶ is H; and
R⁴ is

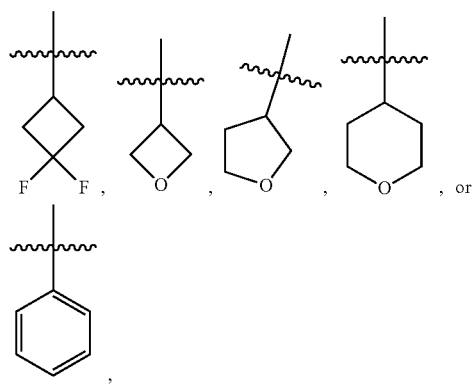

which can be unsubstituted or substituted with 1-3 substituents selected from halogen or C$_{1-6}$alkoxy.

In one embodiment, a compound of formula (III) or a pharmaceutically acceptable salt, solvate, hydrate, or stereoisomer, wherein:
R¹ is phenyl, which is substituted with 1-3 substituents selected from F, Cl, CH₂OH, or CH₂NH₂, and at least one ortho position is substituted;
n is 1;
R³ is H;
M is a bond;
X is CH;
Y is N;
Z is N,
R⁵ is CH₃;
R⁶ is H; and

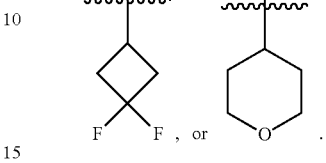

In one embodiment, a compound of formula (III) or a pharmaceutically acceptable salt, solvate, hydrate, or stereoisomer, wherein:
R¹ is phenyl, which is substituted with 1-3 substituents selected from F, Cl, CH₂OH, or CH₂NH₂, and at least one ortho position is substituted with CH₂OH or CH₂NH₂;
n is 1;
R³ is H;
M is a bond;
X is CH;
Y is N;
Z is N,
R⁵ is CH₃;
R⁶ is H; and
R⁴ is

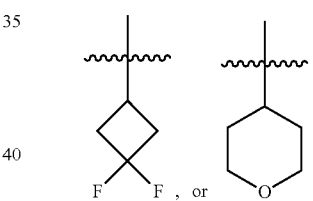

In one embodiment, the compound is one selected from:
(S)-1-(2-(benzo[d][1,3]dioxol-5-ylamino)-5-methylpyrimidin-4-yl)-N-(2-hydroxy-1-phenylethyl)-1H-pyrrole-3-carboxamide;
1-(2-(benzofuran-5-ylamino)-5-methylpyrimidin-4-yl)-N-(2-hydroxy-1-phenylethyl)-1H-pyrrole-3-carboxamide;
1-(2-(benzofuran-5-ylamino)-5-methylpyrimidin-4-yl)-N-(1-(3-chlorophenyl)-2-hydroxyethyl)-1H-pyrrole-3-carboxamide;
N-(3-chloro-2-(hydroxymethyl)benzyl)-1-(5-methyl-2-((tetrahydro-2H-pyran-4-yl)amino)pyrimidin-4-yl)-1H-imidazole-4-carboxamide;
(S)—N-(1-(3-chloro-4-fluorophenyl)-2-hydroxyethyl)-1-(5-methyl-2-((3,4,5-trimethoxyphenyl)amino)pyrimidin-4-yl)-1H-pyrrole-3-carboxamide;
1-(2-((2,3-dihydrobenzofuran-5-yl)amino)-5-methylpyrimidin-4-yl)-N-(2-hydroxy-1-phenylethyl)-1H-pyrrole-3-carboxamide;
N-(1-(3-chlorophenyl)-2-hydroxyethyl)-1-(2-((2,3-dihydrobenzo[b][1,4]dioxin-6-yl)amino)-5-methylpyrimidin-4-yl)-1H-pyrrole-3-carboxamide;
N—((S)-1-(3-chlorophenyl)-2-hydroxyethyl)-1-(5-methyl-2-((tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((S)-tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((R)-tetrahydrofuran-3-yl)amino)pyrimidin-4-yl)-1H-pyrrole-3-carboxamide;

1-(2-(chroman-6-ylamino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((4-fluoro-3-morpholinophenyl)amino)-5-methylpyrimidin-4-yl)-1H-pyrrole-3-carboxamide;

N-(2-amino-1-(3-chlorophenyl)ethyl)-1-(2-((4-fluorophenyl)amino)-5-methylpyrimidin-4-yl)-1H-imidazole-4-carboxamide;

N-(1-(3-chlorophenyl)-2-hydroxyethyl)-1-(5-methyl-2-((tetrahydro-2H-pyran-4-yl)-amino)pyrimidin-4-yl)-1H-imidazole-4-carboxamide;

N-(1-(3-chlorophenyl)-2-hydroxyethyl)-1-(5-methyl-2-((4-morpholinophenyl)-amino)pyrimidin-4-yl)-1H-pyrrole-3-carboxamide;

(S)—N-(1-(3-chlorophenyl)-2-hydroxyethyl)-1-(5-methyl-2-((tetrahydro-2H-pyran-4-yl)amino)pyrimidin-4-yl)-1H-imidazole-4-carboxamide;

(R)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-hydroxyethyl)-1-(5-fluoro-2-((tetrahydro-2H-pyran-4-yl)amino)pyrimidin-4-yl)-1H-pyrrole-3-carboxamide;

N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(2-((3,3-difluorocyclobutyl)amino)-5-methylpyrimidin-4-yl)-1H-imidazole-4-carboxamide;

(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide;

(S)—N-(2-(((1H-pyrrol-2-yl)methyl)amino)-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(3-chloro-2-(hydroxymethyl)benzyl)-1-(5-methyl-2-(tetrahydrofuran-3-yl)amino)-pyrimidin-4-yl)-1H-imidazole-4-carboxamide;

(S)—N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-((2-hydroxyethyl)amino)ethyl)-1-(5-methyl-2-((tetrahydro-2H-pyran-4-yl)amino)pyrimidin-4-yl)-1H-imidazole-4-carboxamide; and N-(3-chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide, or a pharmaceutically acceptable salt, prodrug, solvate, hydrate, or stereoisomer thereof.

The compounds of formulae (I-III) are limited to those that are chemically feasible and stable. Therefore, a combination of substituents or variables in the compounds described above is permissible only if such a compound results in a stable or chemically feasible compound. A stable compound or chemically feasible compound is one in which the chemical structure is not substantially altered when kept at a temperature of 40° C. or less, in the absence of moisture or other chemically reactive conditions, for at least for a week.

The compounds of formulae (I-III) and each of the species thereof, alone or in combination, also are salts, prodrugs, solvates, hydrates, racemic forms, enantiomers, diastereomers, metabolites and mixtures thereof, to the extent practicable, unless otherwise stated or inconsistent from the context.

Representative "pharmaceutically acceptable salts" include, but are not limited to, water-soluble and water-insoluble salts. In one embodiment, the salt is of a base. The salt can be of a base selected from, e.g., alkali metal salt bases such as sodium, lithium, or potassium salt bases and organic bases, such as ammonium, mono-, di-, and trimethylammonium, mono-, di- and triethylammonium, mono-, di- and tripropylammonium, ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanol-ammonium, ethyl diethanolammonium, n-butyl-monoethanolammonium, tris(hydroxymethyl)methyl-ammonium, phenylmonoethanolammonium bases, among others. In another embodiment, the salt is of an acid. The salt can be of an acid selected from, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, camphorsulfonic, among others. Optionally, a composition of the invention may contain both a pharmaceutically acceptable salt and the free base form of a compound of the invention.

Prodrugs of compounds of formulae (I-III) may be used to modulate the pharmacokinetic properties, using various methods known to those skilled in the art. See, e.g., Jarkko Rautio et al., Nature Reviews Drug Discovery, 7:255-270 (2008), which is hereby incorporated by reference. In the case of drugs containing an amine moiety such as when $R^2$ is $CH_2NH_2$, a variety of prodrug approaches have been reviewed by A. L. Simplicio, Molecules, 13:519-547 (2008), which is hereby incorporated by reference. More specifically, (alkoxycarbonyloxy)alkyl carbamates, (acyloxy)alkyl carbamates, and (oxodioxolenyl)alkyl carbamates have been reported as effective prodrug strategies for amines by Zhong Li, Bioorg. Med. Chem. Lett., 7:2909-2912 (1997); J. Alexander, J. Med. Chem., 34:78-81 (1991); J. Alexander, J. Med. Chem., 31:318-322 (1988); and J. Alexander, J. Med. Chem., 39:480-486 (1996), all of which are incorporated by reference herein. In one embodiment, the prodrug is an amide of formulae (I-III). In one embodiment, when $R^2$ is $CH_2NH_2$, the amide is $\sim\sim\sim C(O)(C_{1-6}alkyl)$, wherein $C_{1-6}alkyl$ can be optionally substituted. In another embodiment, the prodrug is an ester of formulae (I-III). In one embodiment, when $R^2$ is $CH_2OH$, the ester of it is $\sim\sim\sim C(O)(C_{1-6}alkyl)$, wherein $C_{1-6}alkyl$ can be optionally substituted.

In a further embodiment, a compound of the invention may be a solvate. As used herein, "solvate" does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A hydrate is a special form of solvate which includes water combined in a definite ratio as water of crystallization.

Compounds described herein may contain an asymmetric center and may thus exist as enantiomers. Where the compounds according to the invention possess two or more asymmetric centers, they may exist as diastereomers. When bonds to the chiral center are depicted as straight lines in the formula of the invention, it is understood that both the (R) and (S) configurations, and hence both enantiomers and mixtures thereof, are embraced. The present invention includes all such possible stereoisomers, unless the specific stereochemistry is specifically indicated. It is well known in the art how to prepare substantially pure stereoisomer, such as by resolution of racemic forms or by synthesis from optically active starting materials. In one embodiment, the compound of formulae (I-III) is a substantially pure stereoisomer. "Substantially pure stereoisomer" refers to a stereoisomer form is at least 95% pure with respect to other stereoisomers of otherwise the same structure.

The following definitions are used in connection with the compounds described herein. In general, the number of carbon atoms present in a given group is designated "$C_{x-y}$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least one hydrogen atom on the designated atom such as carbon or nitrogen atom is optionally replaced by other substituents, provided that the normal valence of the designated atom is not exceeded, and that the substitution results in a stable compound. When more than one substituent is present on an atom or group, the chosen substituents are independent of each other (i.e., same or different).

"Alkyl" refers to a hydrocarbon chain that may be linear or branched alkyl radical. In one embodiment, "$C_{1-7}$alkyl" means an alkyl that contains 1 to 7 (inclusive) carbon atoms. In another embodiment, "$C_{1-6}$alkyl" means an alkyl that contains 1 to 6 (inclusive) carbon atoms. In yet another embodiment, "$C_{1-4}$alkyl" means an alkyl containing 1 to 4 (inclusive) carbon atoms. Examples of alkyl groups that are hydrocarbon chains include, but are not limited to, methyl, ethyl, propyl, butyl, pentyl, hexyl, and heptyl, where all isomers of these examples are contemplated.

"Substituted alkyl" refers to an alkyl group, as defined above, that is substituted with the groups including, without limitation, one or more F, one or two Cl, one or two OH, one amino group, one ($C_{1-6}$alkyl)amino group (i.e., $C_{1-6}$alkyl-NH—), one (di-$C_{1-6}$alkyl)amino group (i.e., (alkyl)$_2$N—), one or two $C_{1-6}$alkoxy groups, one —NH—C(O)—$C_{1-6}$alkyl group, one —C(O)—NH$_2$ group, one —C(O)—NH—($C_{1-6}$alkyl) group, one —C(O)—N—($C_{1-6}$alkyl)$_2$ group, or one cyano group, or any combination of these substituents. "Substituted" means that one or more of the alkyl group's hydrogen atoms is replaced with a substituent group as listed above.

"Hydroxyalkyl" refers to -(alkyl)OH, where the alkyl is optionally substituted and is defined above. The OH moiety of the hydroxyalkyl may be bound to any carbon atom, for example, any one of the internal carbon atoms or the terminal carbon atom of a hydrocarbon alkyl chain. Examples of hydroxyalkyl include, but are not limited to, —CH$_2$OH, —CH$_2$CH$_2$OH, —CH(OH)CH$_3$, —CH$_2$CH$_2$CH$_2$OH, —CH$_2$CH(OH)CH$_3$, —CH(OH)CH$_2$CH$_3$, —C(OH)(CH$_3$)$_2$, -(2-hydroxy)-cyclopentyl, (3-hydroxy)-cyclobutyl, and the like.

"$C_{3-10}$cycloalkyl" refers to a saturated cyclic alkyl group which may be monocyclic, bicyclic, polycyclic, or a fused/bridged ring system having 3 to 10 carbon atoms. Exemplary cycloalkyl groups include, but not limited to, cyclopropyl, cyclobutyl, cyclopentyl, cyclohexyl, cycloheptyl, cyclooctyl, and the like. Typical bridged cycloalkyls include, but are not limited to adamantyl, noradamantyl, bicyclo[1.1.0]butanyl, norbornyl(bicyclo[2.2.1]heptanyl), and the like. $C_{3-10}$cycloalkyl can be unsubstituted or substituted with one or more of groups including, without limitation, hydroxyl, halogen, or $C_{1-6}$alkyl.

"$C_{4-10}$cycloalkenyl" refers to an unsaturated or partially saturated non-aromatic cyclic alkyl group which may be monocyclic, bicyclic, polycyclic, or a fused/bridged ring system having 4 to 10 carbon atoms. Exemplary cycloalkyl groups include, but not limited to cyclobutene, cyclopentene, cyclohexene, cyclohexa-1,4-diene, and the like.

"$C_{2-6}$alkenl" refers to a linear monovalent hydrocarbon radical or a branched monovalent hydrocarbon radical of two to six carbon atoms containing at least one double bond. Exemplary cycloalkenyl groups include, but not limited to ethenyl, propenyl, and the like.

"$C_{2-6}$alkynl" refers to a linear monovalent hydrocarbon radical or a branched monovalent hydrocarbon radical of two to six carbon atoms containing at least one triple bond. Exemplary cycloalkyl groups include, but not limited to ethynyl, propynyl, and the like.

"Alkoxy" refers to (alkyl)O, where the alkyl is optionally substituted and is defined above. Examples of alkoxy include, but are not limited to, methoxy, ethoxy, propoxy, and butoxy. The alkyl radical of an alkoxy group can be unsubstituted or substituted as defined above.

"Aryl" refers to a monocyclic, bicyclic or polycyclic aromatic hydrocarbon group containing carbon atoms. In one embodiment, aryl contains 6-12 carbon atoms. In one embodiment, the aryl is phenyl. In one embodiment, the aryl is an aromatic or partly aromatic bicyclic group. In another embodiment, the aryl is naphthyl (such as α-naphthyl or β-naphthyl), 1,2,3,4-tetrahydronaphthyl, or indanyl. An aryl group can be unsubstituted or substituted with one or more of groups including, without limitation, halogen, $C_{1-6}$alkyl, $C_{2-6}$alkynyl, CN, hydroxy$C_{1-6}$alkyl, amino$C_{1-6}$alkyl, —$C_{1-6}$alkyl-O—$C_{1-6}$alkyl, —$C_{1-6}$alkyl-NH—$C_{1-6}$alkyl, $C_{1-6}$alkyl-N—($C_{1-6}$alkyl)$_2$, —$C_{1-6}$alkyl-NH—$C_{1-6}$alkyl-OH, —$C_{1-6}$alkyl-NH—$C_{1-6}$alkyl-$C_{3-10}$cycloalkyl, —$C_{1-6}$alkyl-NH—$C_{1-6}$alkyl-NH—$C_{1-6}$alkyl, —$C_{1-6}$alkyl-NH—C(O)—$C_{1-6}$alkyl, —$C_{1-6}$alkyl-O—C(O)—$C_{1-6}$alkyl, —$C_{1-6}$alkyl-NH—$C_{0-6}$alkyl-(4- to 6-membered heterocyclyl), or —$C_{1-6}$alkyl-NH—$C_{0-6}$alkyl-(5- to 6-membered heteroaryl), wherein the $C_{1-6}$alkyl, cycloalkyl, heterocyclyl, and/or heteroaryl is unsubstituted or substituted with 1-3 substituents selected from halogens, $C_{1-6}$alkyl, hydroxy$C_{1-6}$alkyl, or amino$C_{1-6}$alkyl. In one embodiment, an aryl group can be substituted with one or more of groups including, without limitation, halogen, CN, —C(O)—NH$_2$, —C(O)—NH—$C_{1-6}$alkyl, —C(O)—N—($C_{1-6}$alkyl)$_2$, —O—$C_{1-6}$alkyl-NH$_2$, —O—$C_{1-6}$alkyl-NH—($C_{1-6}$alkyl), —O—$C_{1-6}$alkyl-N($C_{1-6}$ alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, C$_{2-6}$alknyl, hydroxyl, C$_{1-6}$alkoxyl, or hydroxyC$_{1-6}$alkyl, wherein the heterocyclyl or heteroaryl is unsubstituted or substituted with 1-3 substituents selected from halogen, C$_{1-6}$alkyl, C(O)—C$_{1-6}$alkyl, or 4- to 6-membered heterocyclyl.

"Substituted phenyl" refers to a phenyl group that is substituted with one or more of groups including, without limitation, halogen, C$_{1-6}$alkyl, C$_{2-6}$alkenyl, C$_{2-6}$alkynyl, CN, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogens, C$_{1-6}$alkyl, hydroxyC$_{1-6}$alkyl, or aminoC$_{1-6}$alkyl. In one embodiment, a phenyl group can be substituted with one or more of groups including, without limitation, halogen, CN, C$_{2-6}$alknyl, —C(O)—NH$_2$, —C(O)—NH—C$_{1-6}$alkyl, —C(O)—N—(C$_{1-6}$alkyl)$_2$, —O—C$_{1-6}$alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, hydroxyl, C$_{1-6}$alkoxyl, or hydroxyC$_{1-6}$alkyl, wherein the heterocyclyl or heteroaryl is unsubstituted or substituted with 1-3 substituents selected from halogen, C$_{1-6}$alkyl, C(O)—C$_{1-6}$alkyl, or 4- to 6-membered heterocyclyl.

"Halogen" refers to F, Cl, Br or I.

"Heteroaryl" refers to a monocyclic, bicyclic or polycyclic aromatic or partially aromatic ring system having one to three heteroatoms or heterogroups selected from O, N, S, S(=O), S(=O)$_2$, or C(=O). "Partially aromatic" refers to multi-cyclic fused ring groups where at least one but not all rings are aromatic, such as a benzodioxole group. In one embodiment, heteroaryl is a 5- to 10-membered ring system. In another embodiment, heteroaryl is a 5- to 6-membered ring system. Exemplary heteroaryl ring groups include, but not limited to, furanyl, oxazolyl, isoxazolyl, isothiazolyl, imidazolyl, triazolyl, thiophenyl, thiazolyl, pyridinyl, pyrimidinyl, thiazinyl, pyrazinyl, pyrazolyl, pyrrolyl, tetrazolyl, imidazothiazolyl, oxadiazolyl, indolizidinyl, indolinyl, indazolyl, chromanyl, oxoindolinyl, indolyl, oxoindolyl, quinolinyl, 3,4-dihydroisoquinolin-2(1H)-yl, quinoxalinyl, benzofuranyl, benzoxazolyl, benzo[d]isoxazolyl, benzo[d]thiazolyl, benzo[d][1,3]dioxolyl, 1H-benzo[d][1,2,3]triazolyl, 2H-indazolyl, 1H-indazolyl, quinoxalin-2-yl, 1H-benzo[d]imidazolyl, pyrazolo[1,5-a]pyridinyl, dihydrobenzo[b][1,4]dioxinyl, (5,6,7,8-tetrahydroimidazo[1,2-a]pyridin-7-yl), 4,5,6,7-tetrahydropyrazolo[1,5-a]pyrazinyl, 5,6-dihydroimidazo[1,2-a]pyrazin-7(8H)-yl), 5,6,7,8-tetrahydroimidazo[1,2-a]pyrazinyl, Hexahydropyrrolo[1,2-a]pyrazin-2(1H)-yl, 5,6-dihydro-[1,2,4]triazolo[4,3-a]pyrazinyl, pyrazolo[1,5a]pyridinyl and the like.

"Substituted heteroaryl" refers to a heteroaryl group, as defined above, that is substituted with one or more of groups including, without limitation, halogen, C$_{1-6}$alkyl, CN, hydroxyC$_{1-6}$alkyl, aminoC$_{1-6}$alkyl, —C$_{1-6}$alkyl-O—C$_{1-6}$alkyl, —C$_{1-6}$alkyl-NH—C$_{1-6}$alkyl, —C$_{1-6}$alkyl-N—(C$_{1-6}$alkyl)$_2$, —C$_{1-6}$alkyl-NH—C$_{1-6}$alkyl-OH, —C$_{1-6}$alkyl-NH—C$_{1-6}$alkyl-C$_{3-10}$cycloalkyl, —C$_{1-6}$alkyl-NH—C$_{1-6}$alkyl-NH—C$_{1-6}$alkyl, —C$_{1-6}$alkyl-NH—C(O)—C$_{1-6}$alkyl, —C$_{1-6}$alkyl-O—C(O)—C$_{1-6}$alkyl, —C$_{1-6}$alkyl-NH—C$_{0-6}$alkyl-(4- to 6-membered heterocyclyl), or —C$_{1-6}$alkyl-NH—C$_{0-6}$alkyl-(5- to 6-membered heteroaryl), wherein the C$_{1-6}$alkyl, cycloalkyl, heterocyclyl, and/or heteroaryl is unsubstituted or substituted with 1-3 substituents selected from halogen, C$_{1-6}$alkyl, hydroxyC$_{1-6}$alkyl, or aminoC$_{1-6}$alkyl. In one embodiment, a heteroaryl group can be substituted with one or more of groups including, without limitation, halogen, C$_{1-6}$alkyl, NH$_2$, hydroxyC$_{1-6}$alkyl, or aminoC$_{1-6}$alkyl. In one embodiment, a heteroaryl group can be substituted with one or more of groups including, without limitation, halogen, CN, —C(O)—NH$_2$, —C(O)—NH—C$_{1-6}$alkyl, —C(O)—N—(C$_{1-6}$alkyl)$_2$, —O—C$_{1-6}$alkyl-NH$_2$, —O—C$_{1-6}$alkyl-NH—(C$_{1-6}$alkyl), —O—C$_{1-6}$alkyl-N(C$_{1-6}$alkyl)$_2$, 4- to 6-membered heterocyclyl, —C(O)-(4- to 6-membered heterocyclyl), —O-phenyl, —O—C$_{1-6}$alkyl-(4- to 6-membered heterocyclyl), C$_{1-6}$alkyl, hydroxyl, C$_{1-6}$alkoxyl, or hydroxyC$_{1-6}$alkyl, wherein the heterocyclyl or heteroaryl is unsubstituted or substituted with 1-3 substituents selected from halogen, C$_{1-6}$alkyl, C(O)—C$_{1-6}$alkyl, or 4- to 6-membered heterocyclyl.

"Heterocycle" or "heterocyclyl" refers to a monocyclic, bicyclic or polycyclic saturated ring system having one to three heteroatoms or heterogroups selected from O, N, S, S(=O), S(=O)$_2$, or C(=O). A monocyclic heterocycle can be a 4- to 10-membered ring, whereas a bicyclic heterocycle contains two fused or bridged 4- to 6-membered rings having 5 to 10 ring atoms. Exemplary heterocyclyl groups include, but are not limited to, azetidinyl, azepanyl, oxetanyl, pyrrolidinyl, tetrahydrofuranyl, tetrahydrothiophenyl (thiolanyl), piperidinyl, piperazinyl, tetrahydropyranyl, tetrahydro-2H-pyranyl, morpholinyl, thiomorpholinyl, dioxanyl, 2,5-diazabicyclo[2.2.1]heptane, 2,5-diazabicyclo[2.2.2]octane, and the like.

"Substituted heterocycle" or "substituted heterocyclyl" refers to a heterocycle or heterocyclyl group that is substituted with one or more of groups including, without limitation, halogen, CN, —C(O)—NH$_2$, —C(O)—NH—C$_{1-6}$alkyl, —C(O)—N—(C$_{1-6}$alkyl)$_2$, —O—C$_{1-6}$alkyl-NH$_2$, —O—C$_{1-6}$alkyl-NH—(C$_{1-6}$alkyl), —O—C$_{1-6}$alkyl-N—(C$_{1-6}$alkyl)$_2$, 4- to 6-membered heterocyclyl, —C(O)-heterocyclyl, —O-phenyl, —O—C$_{1-6}$alkyl-(4- to 6-membered heterocyclyl), C$_{1-6}$alkyl, hydroxyl, C$_{1-6}$alkoxyl, or hydroxyC$_{1-6}$alkyl, wherein the heterocyclyl or heteroaryl is unsubstituted or substituted with 1-3 substituents selected from halogen, C$_{1-6}$alkyl, C(O)—C$_{1-6}$alkyl, or 4- to 6-membered heterocyclyl. In one embodiment, a heterocyclyl group can be substituted with one or more of groups including, without limitation, halogen, C$_{1-6}$alkyl, NH$_2$, hydroxyC$_{1-6}$alkyl, or aminoC$_{1-6}$alkyl. In one embodiment, a heterocyclyl group can be substituted with one or more of groups including, without limitation, hydroxyl, halogen, or C$_{1-6}$alkyl.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term "treating" or "treatment" is meant to encompass administering to a subject a compound of the present invention for the purposes of amelioration of one or more symptoms of a disease or disorder, including palliative care. A "therapeutically effective amount" refers to the minimum amount of the active compound which effects treatment.

Pharmaceutical compositions useful herein contain at least one or more of compounds of formulae (I)-(III), or pharmaceutically acceptable salts, prodrugs, solvates, hydrates, or stereoisomers thereof in a pharmaceutically acceptable carrier optionally with other pharmaceutically inert or inactive ingredients. In another embodiment, a compound of formulae (I-III) is present in a single composition. In a further embodiment, a compound of formulae (I-III) is combined with one or more excipients and/or other therapeutic agents as described below.

The pharmaceutical compositions of the invention comprise an amount of at least one or more of compounds of formulae (I-III) or pharmaceutically acceptable salts, prodrugs, solvates, hydrates, or stereoisomers thereof that is effective for treating a condition treatable by inhibiting ERK1/2 in a subject in need thereof. Specifically, the dosage of the compound of formulae (I-III) to achieve a therapeutic effect will depend on the formulation, age, weight and sex of the patient and route of delivery. It is also contemplated that the treatment and dosage of the compound of formulae (I-III) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be vaned by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formulae (I-III) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formulae (I-III) or a pharmaceutically acceptable salt, prodrug or solvate thereof is administered, the therapeutically effective amounts correspond to the total amount administered.

The pharmaceutical compositions containing a compound of formulae (I-III) may be formulated neat or with one or more pharmaceutical carriers for administration. The amount of the pharmaceutical carrier(s) is determined by the solubility and chemical nature of the compound of formulae (I-III), chosen route of administration and standard pharmacological practice. The pharmaceutical carrier(s) may be solid or liquid and may incorporate both solid and liquid carriers. A variety of suitable liquid carriers is known and may be readily selected by one of skill in the art. Such carriers may include, e.g., DMSO, saline, buffered saline, hydroxypropylcyclodextrin, and mixtures thereof. Similarly, a variety of solid carriers and excipients are known to those of skill in the art. The compounds of formulae (I-III) may be administered by any route, taking into consideration the specific condition for which it has been selected. The compounds of formulae (I-III) may, be delivered orally, by injection, inhalation (including orally, intranasally and intratracheally), ocularly, transdermally, intravascularly, subcutaneously, intramuscularly, sublingually, intracranially, epidurally, rectally, and vaginally, among others.

Although the compound of formulae (I-III) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formulae (I-III) is dissolved a liquid carrier. In another embodiment, the compound of formulae (I-III) is suspended in a liquid carrier. One of skill in the art of formulations would be able to select a suitable liquid carrier, depending on the route of administration. The compound of formulae (I-III) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formulae (I-III). For example, the unit dosage can be packaged compositions, e.g., packeted powders, vials, ampoules, prefilled syringes or sachets containing liquids.

Examples of excipients which may be combined with one or more compound of formulae (I-III) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", $5^{th}$ Edition, Eds.: Rowe, Sheskey, and Owen, APhA Publications (Washington, DC), Dec. 14, 2005, which is incorporated herein by reference.

In one embodiment, the compositions may be utilized as inhalants. For this route of administration, compositions may be prepared as fluid unit doses using a compound of formulae (I-III) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formulae (I-III) which is delayed or otherwise controlled. Those of skill in the art know suitable sustained delivery devices. For use in such sustained delivery devices, the compound of formulae (I-III) is formulated as described herein.

In addition to the components described above for use in the composition and the compound of formulae (I-III), the compositions and kits described herein may contain one or more medications or therapeutic agents. In one embodiment, the compositions and kits described herein may contain one or more medications or therapeutic agents which are used to treat cancers, including, e.g., cancers characterized by tumors, including solid tumors, and "liquid" or non-solid tumor cancers (e.g., lymphoma). In one embodiment, the medication is a chemotherapeutic. Examples of chemotherapeutics include those recited in the "Physician's Desk Reference", 64$^{th}$ Edition, Thomson Reuters, 2010, which is hereby incorporated by reference. Therapeutically effective amounts of the additional medication(s) or therapeutic agents are well known to those skilled in the art. However, it is well within the attending physician to determine the amount of other medication to be delivered.

The compounds of formulae (I-III) and/or other medication(s) or therapeutic agent(s) may be administered in a single composition. However, the present invention is not so limited. In other embodiments, the compounds of formulae (I-III) may be administered in one or more separate formulations from other compounds of formulae (I-III), chemotherapeutic agents, or other agents as is desired.

Also provided herein are kits or packages of pharmaceutical formulations containing the compounds of formulae (I-III) or compositions described herein. The kits may be organized to indicate a single formulation or combination of formulations to be taken at each desired time.

Suitably, the kit contains packaging or a container with the compound of formulae (I-III) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formulae (I-III) or compositions described herein can be a single dose or for continuous or periodic discontinuous administration. For continuous administration, a package or kit can include the compound of formulae (I-III) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formulae (I-III) is to be delivered periodically in a discontinuous fashion, a package or kit can include placebos during periods when the compound of formulae (I-III) is not delivered. When varying concentrations of a composition, of the components of the composition, or the relative ratios of the compounds of formulae (I-III) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forceps, measuring spoon, eye dropper or any such medically approved delivery means.

In one embodiment, a kit is provided and contains a compound of formulae (I-III). The compound of formulae (I-III) may be in the presence or absence of one or more of the carriers or excipients described above. The kit may optionally contain instructions for administering the medication and the compound of formulae (I-III) to a subject having a disease characterized by the dysregulation of the RAS/RAF/MEK/ERK pathway.

In a further embodiment, a kit is provided and contains a compound of formulae (I-III) in a second dosage unit, and one or more of the carriers or excipients described above in a third dosage unit. The kit may optionally contain instructions for administering the medication and the compound of formulae (I-III) to a subject having a disease characterized by the dysregulation of the RAS/RAF/MEK/ERK pathway.

The compounds described herein are useful in regulating conditions which are associated with the RAS/RAF/MEK/ERK pathways. In one embodiment, such a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma. In one embodiment, the disease characterized by abnormal cellular proliferation is melanoma skin cancer or cancer of the lung, colon, breast or prostate. In another embodiment, the abnormal cellular proliferation is associated with either solid tumor or hematological cancer.

The term "regulation" or variations thereof as used herein refers to the ability of a compound of formulae (I-III) to inhibit one or more components of a biological pathway. In one embodiment, "regulation" refers to inhibition ERK1/2 activity. In yet another embodiment, regulation includes inhibition of the RAS/RAF/MEK/ERK pathway.

The activity of compounds of formulae (I-III) was established in multiple in vitro and in vivo assays. For example, compounds of the invention were demonstrated to cause inhibition of ERK1 and ERK2 enzymatic activities in biochemical assays using a homogeneous time resolved fluorescence (HTRF) technique; representative data are provided in Table 2. Furthermore, compounds of the invention were found to be active in a cell-based mechanistic assay; that is, compounds of the invention were demonstrated to inhibit phosphorylation of RSK1(S380) (the downstream protein target of ERK1/2) by an enzyme-linked immunosorbent assay (ELISA) method. Representative data are provided in Table 2. The functional utility of compounds of formulae (I-III) was demonstrated by their activity in in vitro tumor cell proliferation assays in a panel of tumor cell lines with mutations in the RAS/BRAF/MEK/ERK pathway; representative data are again provided in Table 2. The compounds of formulae (I-III) exhibit ERK1/2 inhibitory activity, and therefore can be utilized in order to inhibit abnormal cell growth in which the RAS/RAF/MEK/ERK pathway plays a role. Thus, the compounds of formulae (I-III) are effective in the treatment of disorders with which abnormal cell growth actions of RAS/RAF/MEK/ERK dysregulation are associated, such as cancer. One of skill in the art would recognize that there is an established link between activity in tumor cell proliferation assays in vitro and anti-tumor activity in the clinical setting. For example, the therapeutic utility of a variety of pharmaceutical agents, e.g, taxol (Silvestrini, Stem Cells, 1993, 11(6):528-535), taxotere (Bissery, Anti Cancer Drugs, 1995, 6(3):330) and topoisomerase inhibitors (Edelman, Cancer Chemother. Pharmacol., 1996, 37(5): 385-39), has been demonstrated by using in vitro tumor proliferation assays.

Finally, compounds of formulae (I-III) were demonstrated to inhibit in vivo tumor growth upon dosing the compounds in human tumor xenograft models, such as the A375 human melanoma xenograft model harboring B-RAF V600E mutation, the HT-29 human colon cancer xenograft model harboring B-RAF V600E mutation, the HCT116 human colon cancer xenograft model harboring KRAS mutation, the A549 human lung carcinoma xenograft model harboring KRAS mutation, and the BxPC3 human pancreatic carcinoma xenograft model. The compounds were also demonstrated to inhibit the level of phospho-RSK in the tumors in the A375 xenograft model, upon treatment with compounds; this indicates effective inhibition of the target proteins ERK1/2 in vivo by compounds of the invention. One of skill in the art would recognize that there is an established link between activity in human tumor xenograft models and anti-tumor activity in the clinical setting.

Compounds of formulae (I-III) that have particularly promising utility can be identified by using the assays as described herein. For example, compounds of formulae (I-III) that are found to exhibit $IC_{50}$ values less than 100 nM in the ERK1/2 biochemical assays, and $IC_{50}$ values less than 500 nM in the phospho-RSK1 and cell proliferation assays, and causing 40% or greater tumor growth inhibition in one or more human tumor xenograft models, would be identified as particularly useful compounds of the invention.

In one embodiment, methods for regulating the RAS/RAF/MEK/ERK pathway are provided and include administering a therapeutically effective amount of a compound of formulae (I-III) to a patient in need thereof.

In a further embodiment, methods for inhibiting ERK1/2 are provided and include administering a therapeutically effective amount of a compound of formulae (I-III) to a patient in need thereof.

In another desirable embodiment, methods for treating a disease characterized by an abnormal cellular growth resulting from a dysregulated RAS/RAF/MEK/ERK pathway are provided and include administering of a therapeutically effective amount of a compound of formulae (I-III) to a patient in need thereof.

In a further desirable embodiment, methods for treating a condition treatable by inhibiting ERK1/2 are provided and include administering a therapeutically effective amount of a compound of formulae (I-III) to a patient in need thereof.

As described herein, "a therapeutically effective amount" of a compound when used for the treatment of a condition is an amount that at least slows the progression of the condition. "A therapeutically effective amount" of a compound when used for the treatment of cancer is an amount which may slow the progression of cancer, reduce the number of cancer cells in fluids (e.g., blood, peripheral cells or lymphatic fluids), reduce tumor size, inhibit metastasis, inhibit tumor growth and/or ameliorate one or more of the symptoms of the cancer. For cancer therapy, efficacy can be measured for example, by assessing the time to disease progression and/or determining the response rate.

Process for Preparing the Compounds

Methods useful for preparing the compounds of formulae (I-III) are set forth in the Examples and generalized in the Schemes below. One of skill in the art will recognize that the schemes can be adapted to produce other compounds and their pharmaceutically acceptable salts, prodrugs, solvates, hydrates, or stereoisomers of formulae (I-III).

In the following reactions described to prepare compounds described herein, it can be necessary to protect reactive functional groups, for example hydroxyl, amino, imino, thio or carboxyl groups, which are desired in the final product, to avoid their unwanted participation in the reactions. Conventional protecting groups can be used in accordance with standard practices, for example, see Green et al., Protective Groups in Organic Chemistry, John Wiley & Sons, 1991.

The below schemes outline the syntheses of the compounds of formulae (I-III). The examples following those are illustrated as representatives prepared in each scheme, and should not be construed as limiting the scope of the present invention.

The following abbreviations are used and have the indicated definitions: MHz is megahertz (frequency), m is multiplet, t is triplet, d is doublet, s is singlet, br is broad, $CDCl_3$ is deutero chloroform, calcd is calculated, min is minutes, h is hours, g is grams, mmol is millimoles, mL is milliliters, N is Normal (concentration), M is molarity (concentration), M is micromolar, ee is enantiomeric excess, ° C. is degree centigrade, HPLC is High Performance Liquid Chromatography, LC-MS is Liquid Chromatography-Mass Spectroscopy, mp is melting point, NMR is Nuclear Magnetic Resonance, TLC is thin layer chromatography, THF is tetrahydrofuran, MeOH is methanol, DCM is dichloromethane, DMF is N,N-dimethyl formamide, DMSO is dimethyl sulfoxide, EtOH is ethyl alcohol, EtOAc is ethyl acetate, MeOH is methanol, RT is room temperature, HCl is hydrogen chloride or hydrochloric acid, TFA is trifluoroacetic acid, EtMgBr is ethyl magnesium bromide, n-BuLi is n-butyl lithium, NaHCO$_3$ is sodium bicarbonate, Na$_2$CO$_3$ is sodium carbonate, Na$_2$SO$_4$ is sodium sulfate, NMP is N-methyl-2-pyrrolidone, EDC or EDC.HCl is N-(3-dimethylaminopropyl)-N-ethylcarbodiimide hydrochloride, TEA is triethylamine, DIPEA is diisopropylethylamine, HOBt is N-hydroxy-benzotriazole or N-hydroxy-benzotriazole hydrate, and T3P is propylphosphonic anhydride.

Scheme 1 depicts one synthesis method to prepare compounds of formula (I) where M is NH, Z=N, X=N, J=—CH(R$^2$)— or —CH(R$^2$)CH$_2$—, R$^2$=H, C$_{1-4}$alkyl, CH$_2$OH, CH$_2$OC$_{1-6}$alkyl, or CH$_2$N(C$_{1-6}$alkyl)$_2$, and Y=CH. In one embodiment, a 4-nitropyrazole [A] is reacted with a 2,4-dichloropyrimidine [B] to provide a pyrazolyl-pyrimidine [C]. This reaction is performed in the presence of a base, such as potassium carbonate, in a suitable solvent such as acetone or dioxane. The reaction may be performed at elevated temperatures up to the reflux temperature of the solvent. Intermediate [C] is then reacted with an amine R$^4$—NH$_2$ to provide the intermediate [D]. This coupling reaction may be performed in the presence of a palladium catalyst such as Pd$_2$(dba)$_3$ [tris(dibenzylideneacetone)dipalladium(0)], BINAP (2,2'-bis(diphenylphosphino)-1,1'-binaphthyl), and potassium carbonate, in a suitable solvent such as dioxane. The reaction may be performed at elevated temperatures, for example in dioxane at 90° C. in a sealed glass tube. Reduction of the nitro moiety in [D] then provides the amino-pyrazolyl intermediate [E]. This reduction process can be carried out by reaction with zinc powder and ammonium chloride in a solvent such as THF:methanol (2:1), at a temperature such as 0° C. to 25° C. The amine intermediate [E] is then reacted with an amine [F] to form a compound of the invention, namely the urea (I-A). This coupling reaction can be performed using CDI (1,1'-carbonyldiimidazole) in a solvent such as THF. The reaction may be performed at elevated temperatures, for example in THF at 85° C. to 120° C. with microwave radiation. This coupling reaction can also be carried out by using 4-nitrophenyl chloroformate, pyridine and DIPEA (diisopropylethylamine) instead of CDI.

Schemes

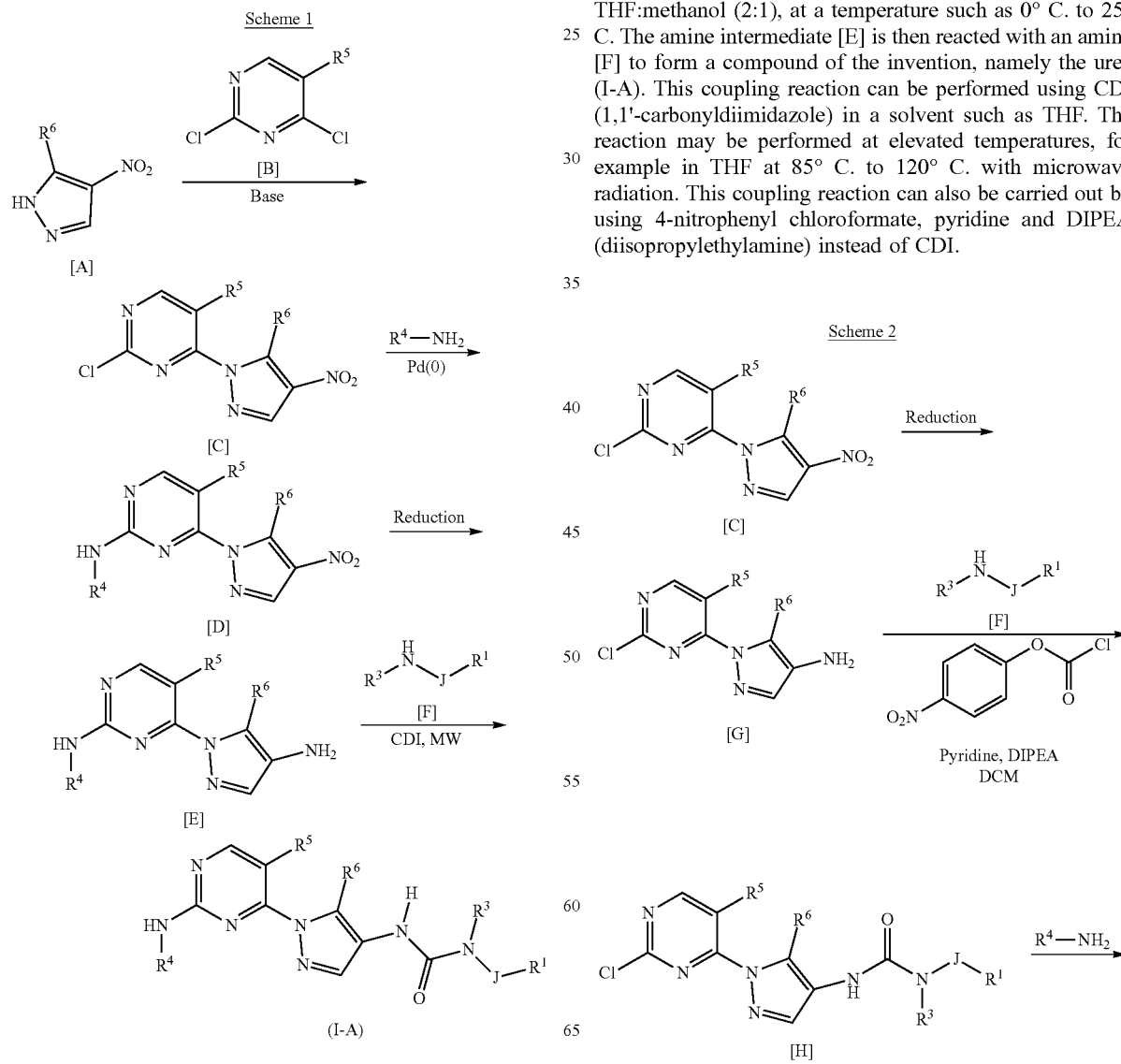

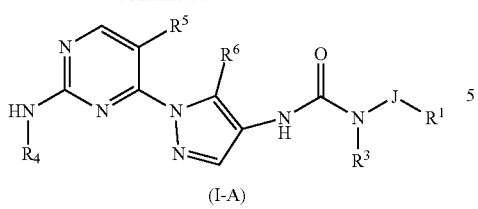

(I-A)

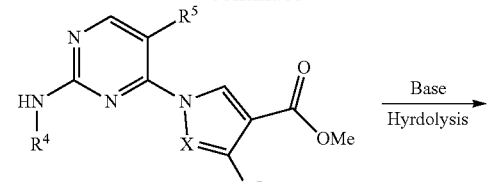

Scheme 2 depicts another synthesis method to prepare compounds of formula (I), where in this example M is NH, Z=N, X=N, J=—CH($R^2$)— or —CH($R^2$)$CH_2$—, $R^2$=H, $C_{1-4}$alkyl, $CH_2OH$, $CH_2OC_{1-6}$alkyl, or $CH_2N(C_{1-6}alkyl)_2$, and Y=CH. In this method, intermediate [C] is prepared as described in Scheme 1, and then a reduction process is carried out to provide amino-pyrazole [G]. This reduction process can be carried out by reaction with zinc powder and ammonium chloride in a solvent such as THF:methanol (2:1), at a temperature such as 0° C. to 25° C. The amine intermediate [G] is then reacted with an amine [F] to form a urea intermediate [H]. This reaction can be carried out by using 4-nitrophenyl chloroformate, pyridine and DIPEA (diisopropylethylamine) in a suitable solvent such as DCM (dichloromethane), at a temperature such as 0° C. to 25° C. The intermediate [H] is then reacted with an amine $R^4$—$NH_2$ to provide a compound of the invention (I-A). This coupling reaction may be performed in the presence of a palladium catalyst such as $Pd_2(dba)_3$, BINAP, and potassium carbonate, in a suitable solvent such as dioxane. The reaction may be performed at elevated temperatures, for example in dioxane at 90° C. in a sealed glass tube. An alternative method for the last step is to react the intermediate [H] with an amine $R^4$—$NH_2$ in ethanol or isopropanol, optionally in the presence of DIPEA, with heating in a sealed glass tube.

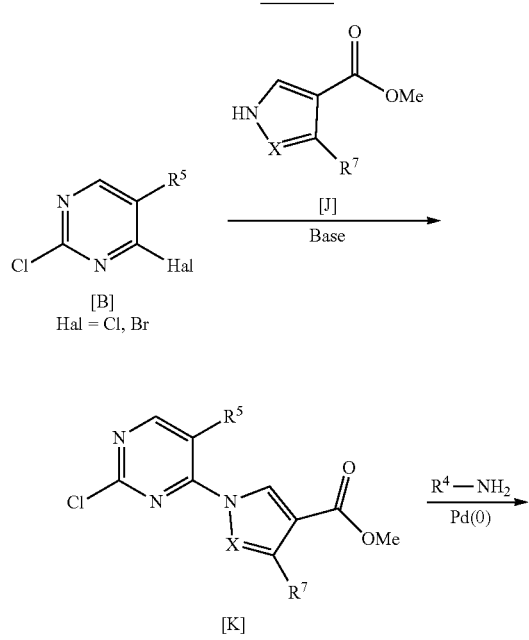

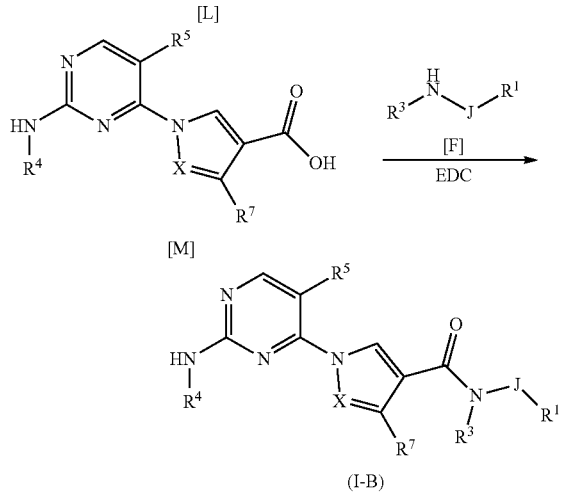

(I-B)

Scheme 3 depicts one synthesis method to prepare compounds of formula (I), where in this example M is a bond, Z=N, J=—CH($R^2$)— or —CH($R^2$)$CH_2$—, $R^2$=H, $C_{1-4}$alkyl, $CH_2OH$, $CH_2OC_{1-6}$alkyl, or $CH_2N(C_{1-6}alkyl)_2$, and Y=$CR^7$. In this method, a 2, 4-dichloropyrimidine or 2-chloro-4-bromopyrimidine [B] is reacted with a heterocyclic ester [J] to form the intermediate [K]. The reaction can be carried out in the presence of a base, for example potassium carbonate, in a suitable solvent such as acetonitrile. The reaction may be performed at elevated temperatures up to the reflux temperature of the solvent. The intermediate [K] is then reacted with an amine $R^4$—$NH_2$ to provide the intermediate [L]. This coupling reaction may be performed in the presence of a palladium catalyst such as $Pd_2(dba)_3$, BINAP, and potassium carbonate, in a suitable solvent such as dioxane. The reaction may be performed at elevated temperatures, for example in dioxane at 90° C. to 100° C. in a sealed glass tube. An alternative method to form the intermediate [L] is to react the intermediate [K] with an amine $R^4$—$NH_2$ in ethanol or isopropanol, optionally in the presence of DIPEA, with heating in a sealed glass tube. The ester moiety in intermediate [L] is hydrolyzed to provide the corresponding carboxylic acid [M], for example by treatment with aqueous sodium hydroxide or aqueous lithium hydroxide in a solvent such as methanol or THF, at a temperature such as 0° C. to 50° C. The intermediate [M] is then coupled with an amine [F] to form a compound of the invention, namely the amide (I-B). This amide-coupling reaction can be carried out by using the amide-coupling reagent EDC [1-ethyl-3-(3-dimethylaminopropyl)carbodiimide], optionally in the presence of HOBt (1-hydroxybenzotriazole) and triethylamine, in a suitable solvent such as NMP (N-methyl-2-pyrrolidone). The reaction may be performed at a temperature such as 0° C. to 25° C. This coupling reaction can alternatively be carried out by using any of several other amide-coupling reagents that are known to those skilled in the art, for example T3P (propylphosphonic anhydride).

Scheme 3a

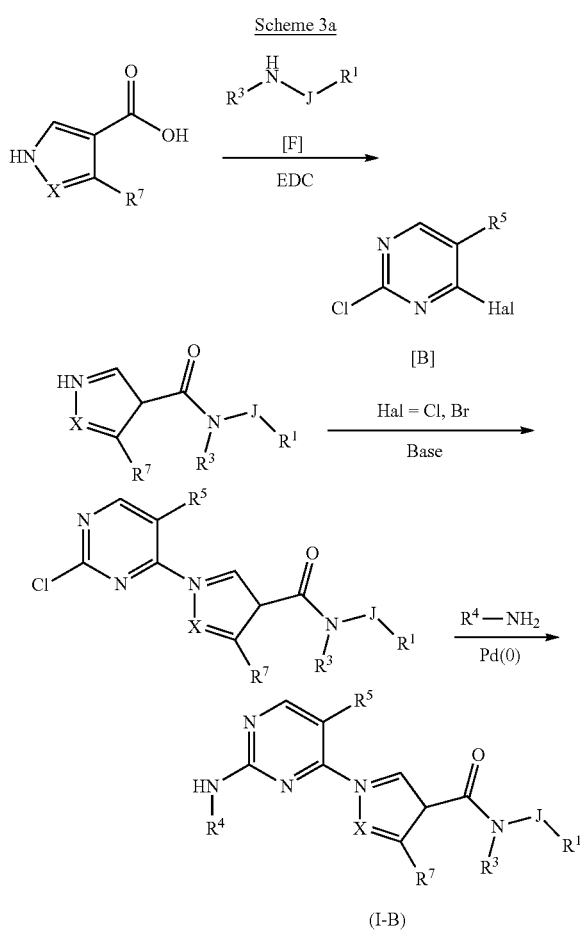

(I-B)

Scheme 3a depicts a variation of Scheme 3, wherein the amide-coupling reaction with amine [F] is carried out first, followed by reaction with the pyrimidine [B], and then reaction with the amine $R^4$—$NH_2$ to provide a compound of the invention, namely the amide (I-B).

Scheme 4

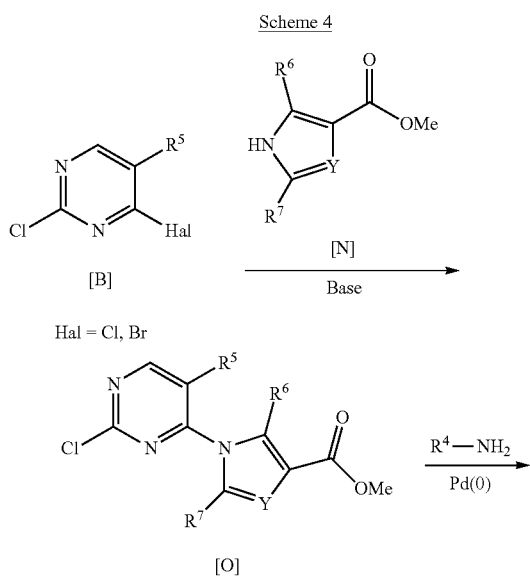

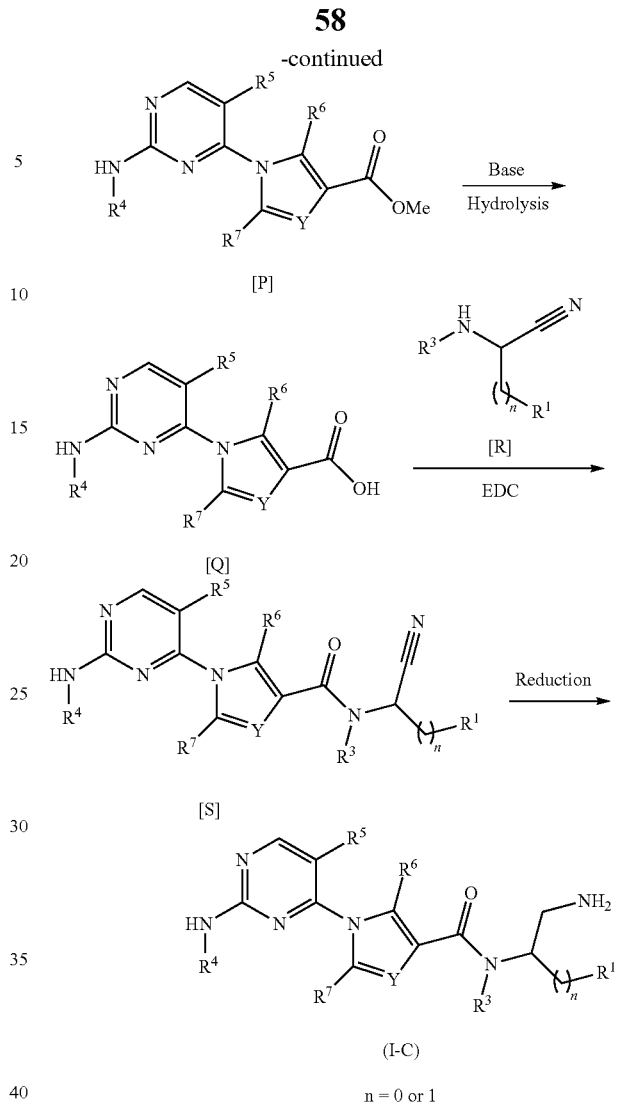

(I-C)

n = 0 or 1

Scheme 4 depicts a synthesis method to prepare compounds of formula (I) where M is a bond, $R^2$ =$CH_2NH_2$, Z=N, and X=$CR^7$. In this method, a 2, 4-dichloropyrimidine or 2-chloro-4-bromopyrimidine [B] is coupled with a heterocyclic ester [N] to form the intermediate [O], by a method similar to that described in Scheme 3 for the preparation of [K]. Reaction of compound [O] with an amine $R^4$—$NH_2$ to form intermediate [P] is carried out by methods similar to those described in Scheme 3 for the preparation of [L]. Hydrolysis of the ester moiety in [P] to form the corresponding carboxylic acid [Q] is achieved by methods similar to those described in Scheme 3 for the preparation of [M]. The intermediate [Q] is then coupled with an amine [R] to form the amide [S], by using amide-coupling methods such as those described for the preparation of (I-B) in Scheme 3. As an alternative, the ester intermediate [P] can be converted directly to (S) by reaction with an amine [R], in the presence of trimethylaluminum in a suitable solvent such as toluene. The reaction is carried out at a temperature such as 0° C. to 100° C., optionally using microwave radiation. Reduction of the nitrile moiety in [S] is carried out to provide the corresponding amine (I-C), a compound of the invention, by hydrogenation using Raney nickel in methanolic ammonia. The reaction is performed, for example, at 25 psi hydrogen for 16 hours at about room temperature.

Scheme 5

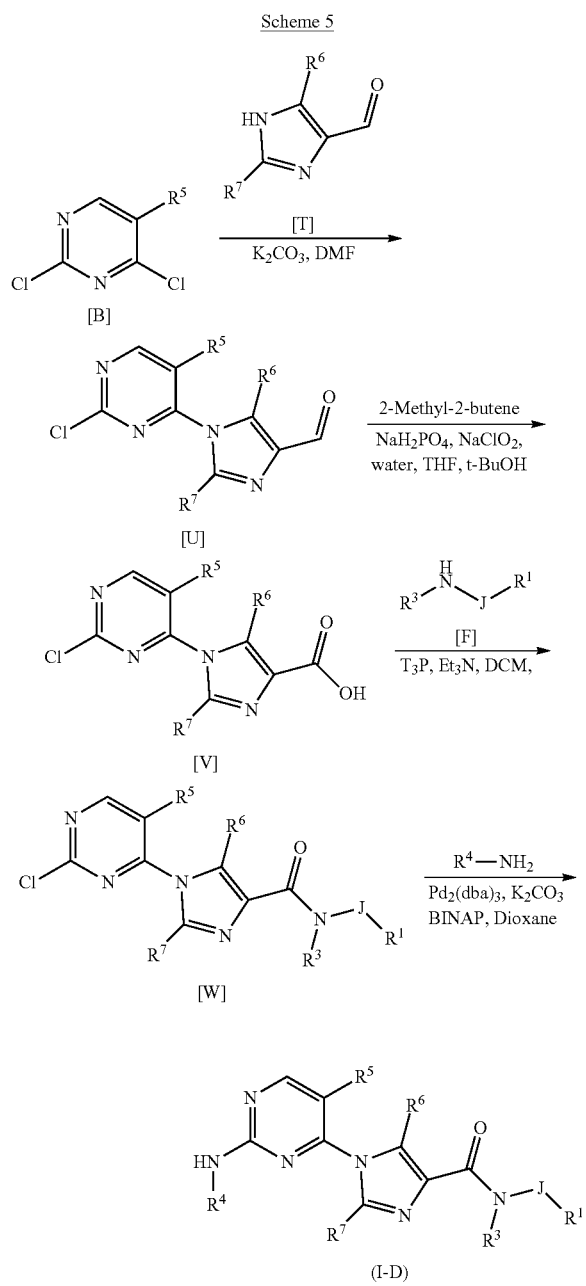

Scheme 6

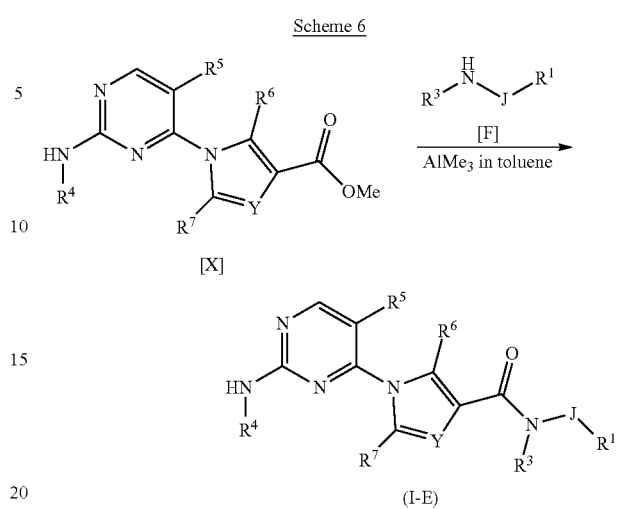

Scheme 5 depicts another method to synthesize compounds of formula (I), in this example where M is a bond, Z=N, J=—CH($R^2$)— or —CH($R^2$)$CH_2$—, $R^2$=H, $C_{1-4}$alkyl, $CH_2OH$, $CH_2OC_{1-6}$alkyl, or $CH_2N(C_{1-6}$alkyl$)_2$, Y=N, and X=C—$R^7$. In this method, an aldehyde building block [T] is reacted with a 2,4-dichloropyrimidine (or a 2-chloro-4-bromopyrimidine) to prepare the aldehyde intermediate [U], which is then converted to the corresponding carboxylic acid intermediate [V] by methods known in the art. The intermediate [V] is then coupled with an amine [F] by an amide-coupling method such as described in Scheme 3, to form the amide intermediate [W]. Reaction of [W] with an amine $R^4$—$NH_2$, by methods such as those described for the formation of [L] in Scheme 3, provides a compound of the invention (I-D).

Scheme 6 depicts another method to synthesize compounds of formula (I), where M is a bond, Z=N, J=—CH($R^2$)— or —CH($R^2$)$CH_2$—, $R^2$=H, $C_{1-4}$alkyl, $CH_2OH$, $CH_2OC_{1-6}$alkyl, or $CH_2N(C_{1-6}$alkyl$)_2$, and X=C—$R^7$. In this method, the intermediate [X] is prepared by methods similar to those used to prepare intermediate [P] in Scheme 4. The ester intermediate [X] is then reacted with an amine [F], in the presence of trimethylaluminum in a suitable solvent such as toluene. The reaction is carried out at a temperature such as 0° C. to 100° C., optionally using microwave radiation, to provide a compound of the invention (I-E). This method has particular utility when $R^4$ is optionally substituted alkyl.

Scheme 7

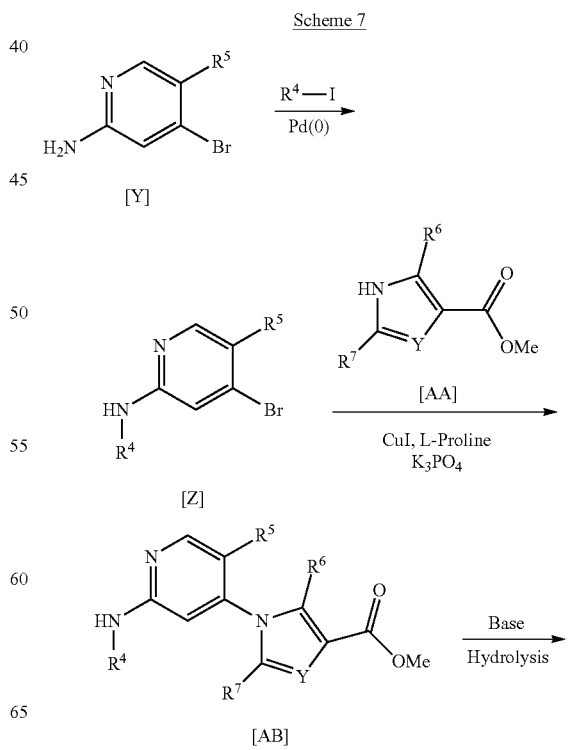

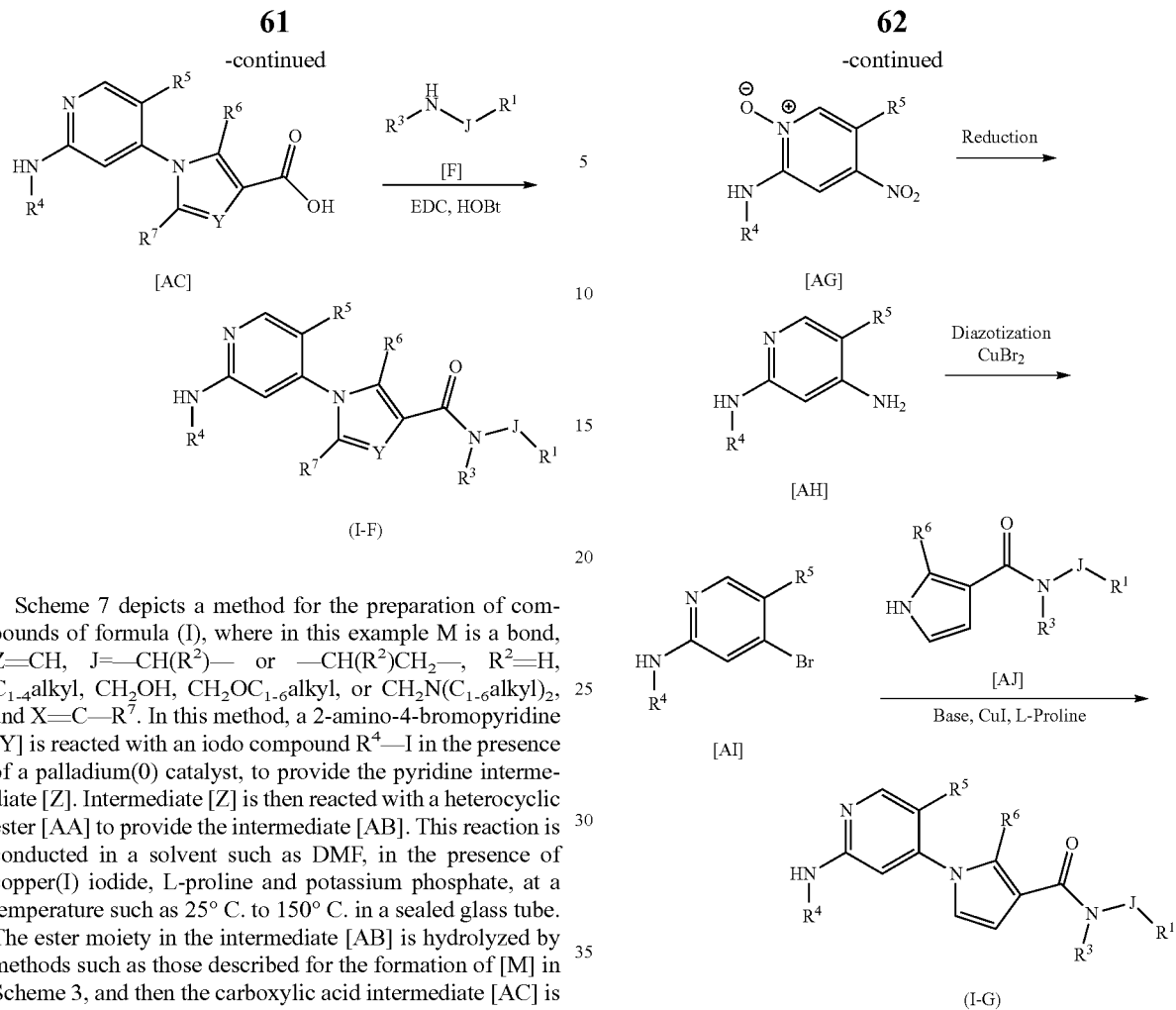

Scheme 7 depicts a method for the preparation of compounds of formula (I), where in this example M is a bond, Z=CH, J=—CH($R^2$)— or —CH($R^2$)CH$_2$—, $R^2$=H, $C_{1-4}$alkyl, CH$_2$OH, CH$_2$OC$_{1-6}$alkyl, or CH$_2$N(C$_{1-6}$alkyl)$_2$, and X=C—$R^7$. In this method, a 2-amino-4-bromopyridine [Y] is reacted with an iodo compound $R^4$—I in the presence of a palladium(0) catalyst, to provide the pyridine intermediate [Z]. Intermediate [Z] is then reacted with a heterocyclic ester [AA] to provide the intermediate [AB]. This reaction is conducted in a solvent such as DMF, in the presence of copper(I) iodide, L-proline and potassium phosphate, at a temperature such as 25° C. to 150° C. in a sealed glass tube. The ester moiety in the intermediate [AB] is hydrolyzed by methods such as those described for the formation of [M] in Scheme 3, and then the carboxylic acid intermediate [AC] is reacted with [F] using an amide-coupling method such as those described in Scheme 3, to provide a compound of the invention (I-F). Alternatively, the ester intermediate [AB] can be converted directly to (I-F) by using trimethylaluminum in a suitable solvent such as toluene, using the method as described in Scheme 6.

Scheme 8

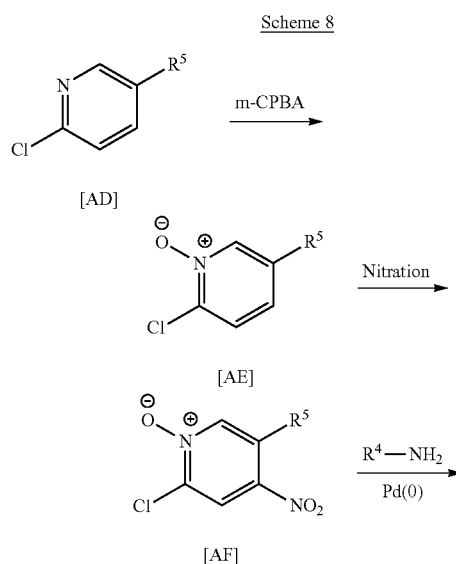

Scheme 8 depicts a further method for the preparation of compounds of formula (I), where in this case M is a bond, Z=CH, J=—CH($R^2$)— or —CH($R^2$)CH$_2$—, $R^2$=H, $C_{1-4}$alkyl, CH$_2$OH, CH$_2$OC$_{1-6}$alkyl, or CH$_2$N(C$_{1-6}$alkyl)$_2$, X=CH, and Y=CH. In this method, a 2-chloro-pyridine [AD] is oxidized, nitrated and then reacted with an amine $R^4$—NH$_2$ to provide the 4-nitro-pyridine N-oxide intermediate [AG]. The N-oxide and nitro moieties in [AG] are reduced and the resulting 4-amino group in [AH] is converted to a bromide moiety. The 4-bromo-pyridine intermediate [AI] is then reacted with an appropriate heterocycle such as the pyrrole derivative [AJ], to provide a compound of the invention (I-G).

Scheme 9

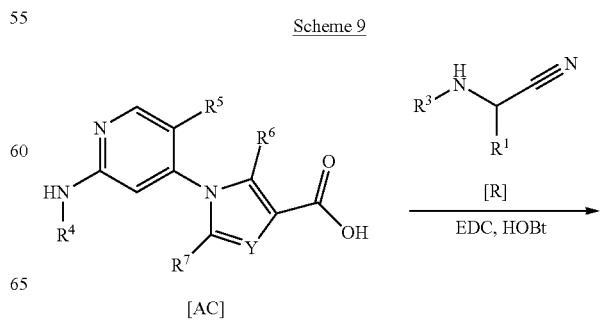

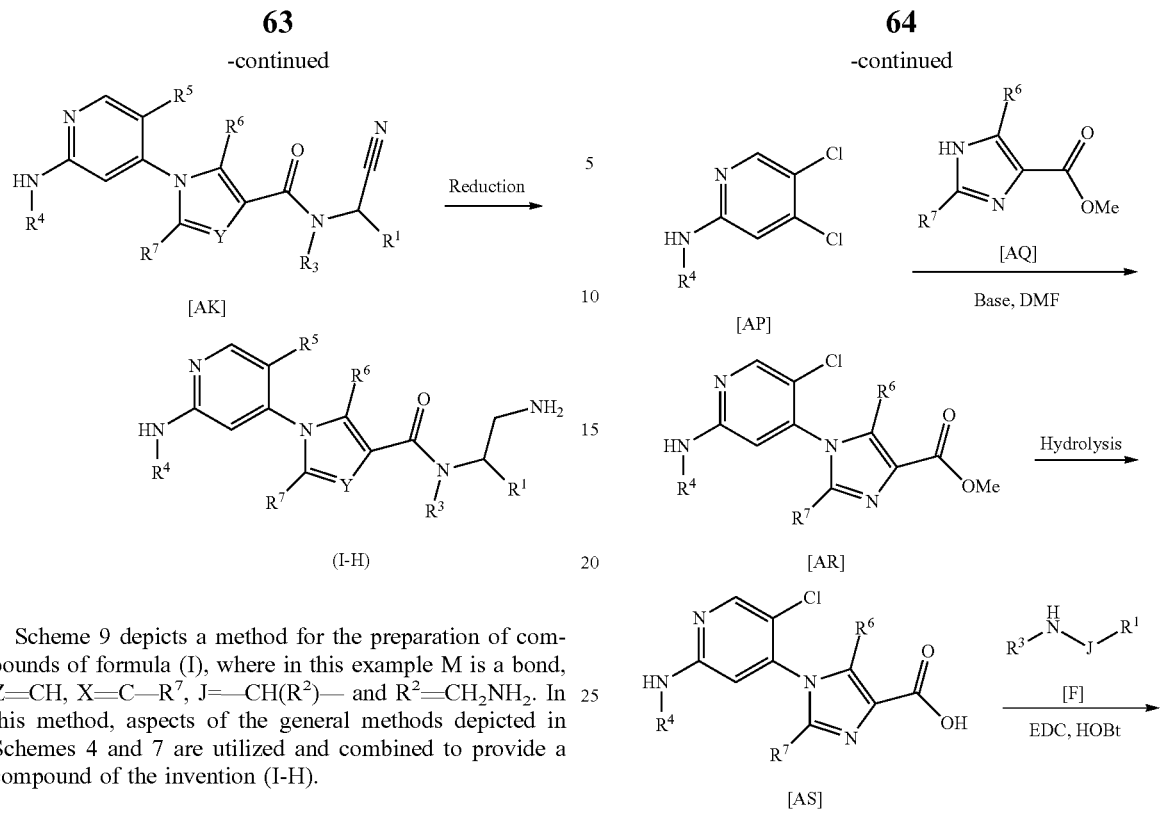

Scheme 9 depicts a method for the preparation of compounds of formula (I), where in this example M is a bond, Z=CH, X=C—R$^7$, J=—CH(R$^2$)— and R$^2$=CH$_2$NH$_2$. In this method, aspects of the general methods depicted in Schemes 4 and 7 are utilized and combined to provide a compound of the invention (I-H).

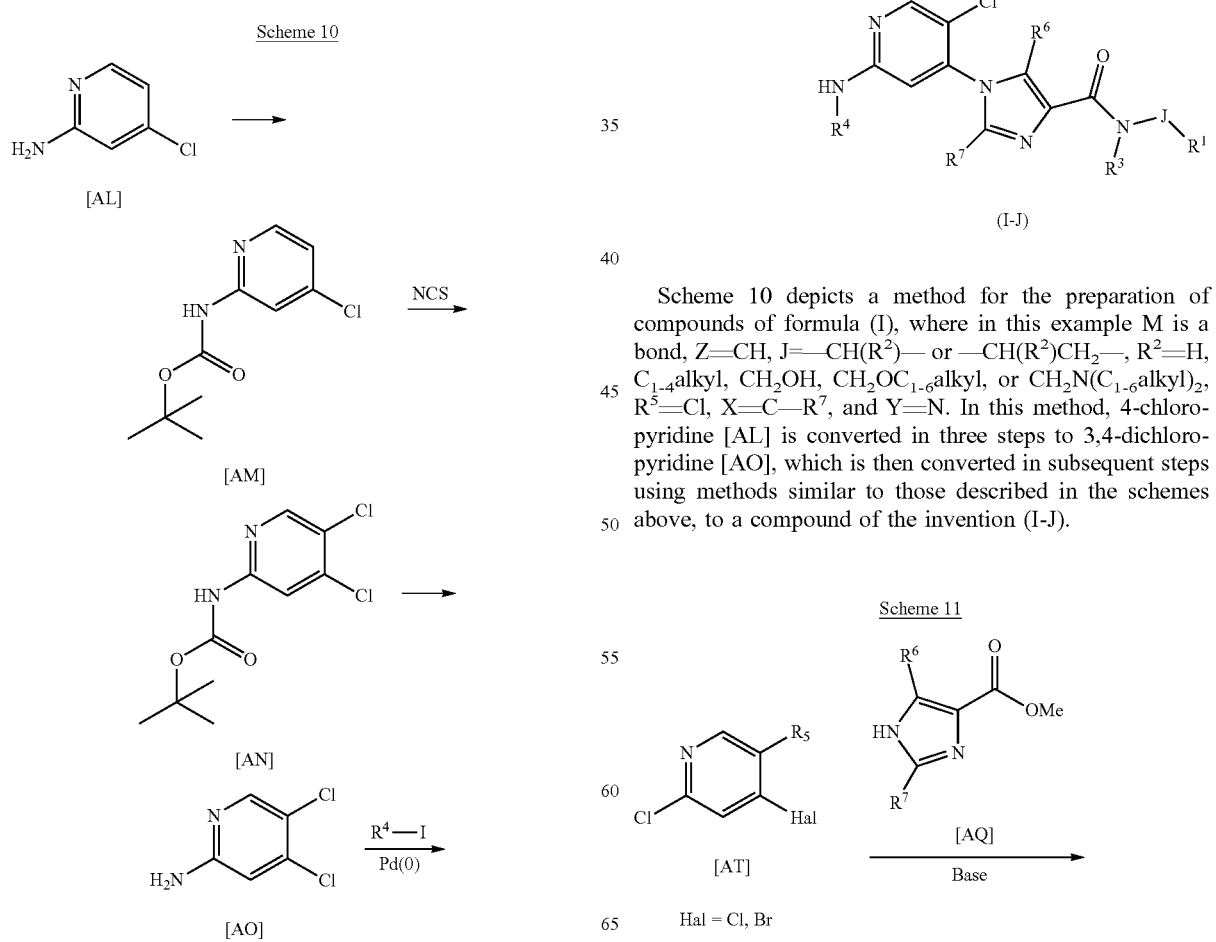

Scheme 10 depicts a method for the preparation of compounds of formula (I), where in this example M is a bond, Z=CH, J=—CH(R$^2$)— or —CH(R$^2$)CH$_2$—, R$^2$=H, C$_{1-4}$alkyl, CH$_2$OH, CH$_2$OC$_{1-6}$alkyl, or CH$_2$N(C$_{1-6}$alkyl)$_2$, R$^5$=Cl, X=C—R$^7$, and Y=N. In this method, 4-chloropyridine [AL] is converted in three steps to 3,4-dichloropyridine [AO], which is then converted in subsequent steps using methods similar to those described in the schemes above, to a compound of the invention (I-J).

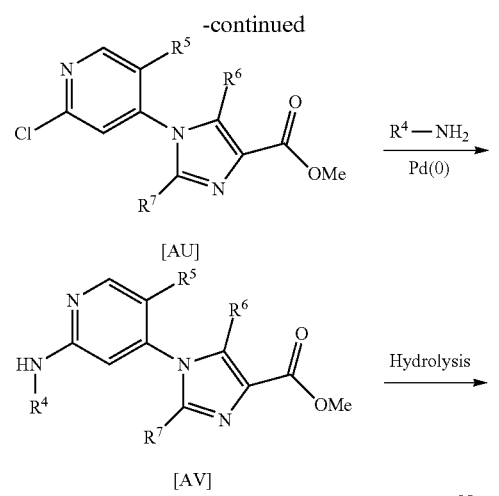

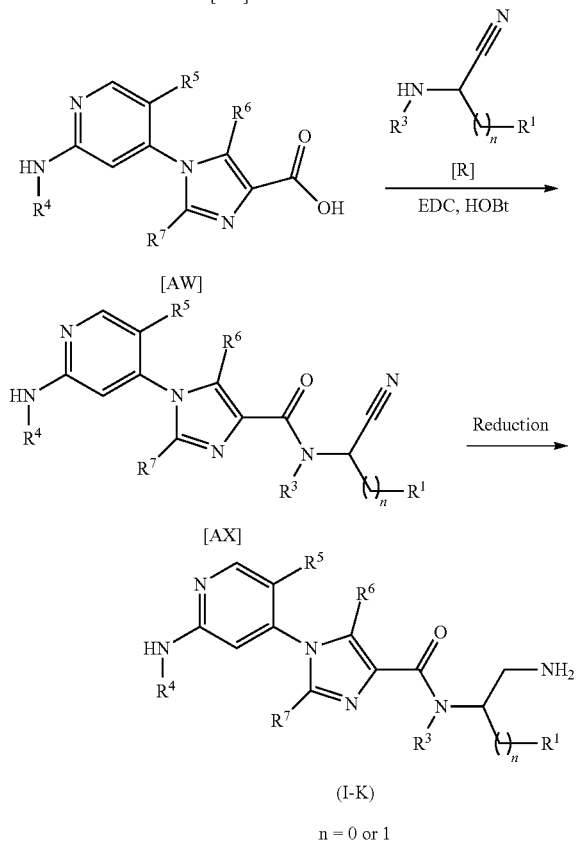

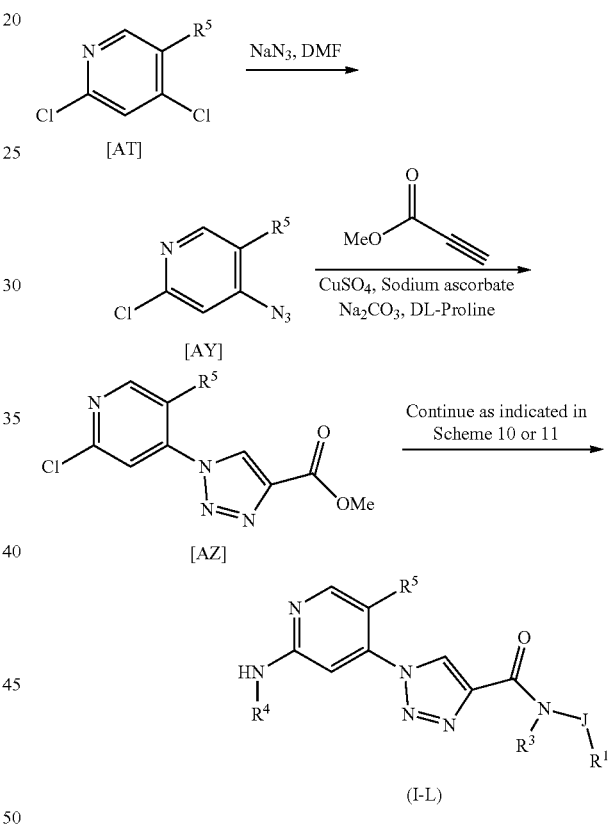

dioxane at 90° C. in a sealed glass tube, or using microwave radiation at 100° C. The ester moiety of intermediate [AV] is then hydrolyzed to provide the corresponding carboxylic acid [AW], for example by treatment with aqueous sodium hydroxide or aqueous lithium hydroxide in a solvent such as methanol or THF, at a temperature such as 0° C. to 50° C. The carboxylic acid [AW] is then coupled with an amine [R] to form the amide [AX], by using amide-coupling methods such as those described for the preparation of (I-B) in Scheme 3. Reduction of the nitrile moiety in [AX] is carried out to provide the corresponding amine (I-K), a compound of the invention, by hydrogenation using Raney nickel in methanolic ammonia. The reaction is performed, for example, at 15 psi to 25 psi hydrogen for about 6 to 16 hours at about room temperature.

Scheme 11 depicts a method for the preparation of compounds of formula (I), where in this example M is a bond, Z=CH, $R^2$=$CH_2NH_2$, X=C—$R^7$, and Y=N. In this method, a 2,4-dichloro-pyridine or 2-chloro-4-bromopyridine [AT] is reacted with a heterocyclic ester [AQ], in the presence of a base such as potassium carbonate, in a suitable solvent such as DMF. The reaction may be performed at room temperature to elevated temperatures such as 100° C. or the reflux temperature of the solvent. The 2-chloro-pyridine intermediate [AU] is then reacted with an amine $R^4$—$NH_2$ to provide the intermediate [AV]. This coupling reaction may be performed in the presence of a palladium catalyst such as $Pd_2(dba)_3$, BINAP, and potassium carbonate, in a suitable solvent such as dioxane. The reaction may be performed at elevated temperatures, for example in Scheme 12 depicts a method for the preparation of compounds of formula (I), where in this example M is a bond, Z=CH, X=N, and Y=N. In this method, a 2,4-dichloro-pyridine (or 2-chloro-4-bromopyridine) [AT] is reacted with sodium azide to provide the 4-azido-pyridine [AY], which is then condensed with methyl propiolate to produce the triazole intermediate [AZ]. The ester moiety in intermediate [AZ] is hydrolyzed by methods such as those described in Scheme 11 to give the corresponding carboxylic acid, which is then reacted with an amine such as [F] by using amide-coupling methods such as described in Scheme 10, or reacted with an amine such as [R] by using amide-coupling methods and then reduced such as described in Scheme 11, to provide a compound of the invention (I-L).

Scheme 13

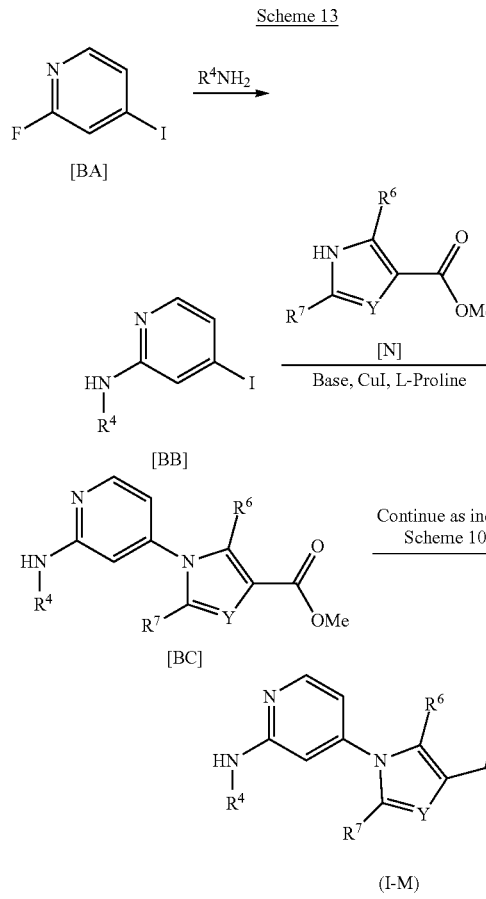

Scheme 14

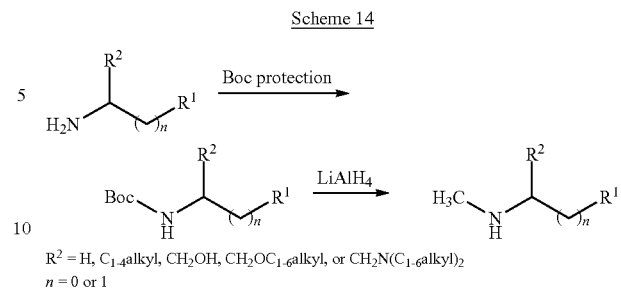

$R^2 = H$, $C_{1-4}alkyl$, $CH_2OH$, $CH_2OC_{1-6}alkyl$, or $CH_2N(C_{1-6}alkyl)_2$
$n = 0$ or $1$ Scheme 15

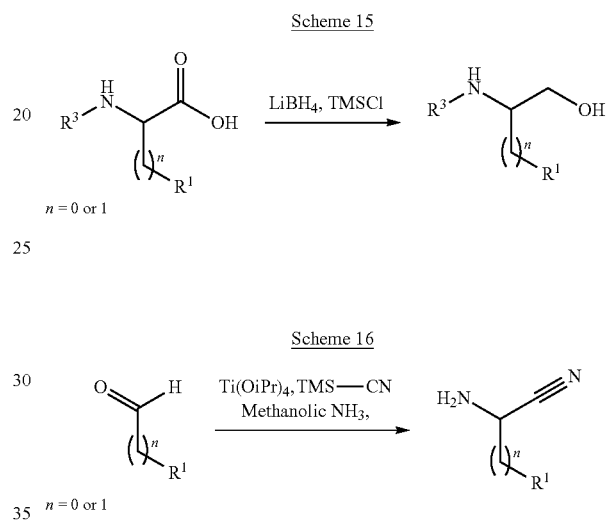

$n = 0$ or $1$

Scheme 16

Scheme 17

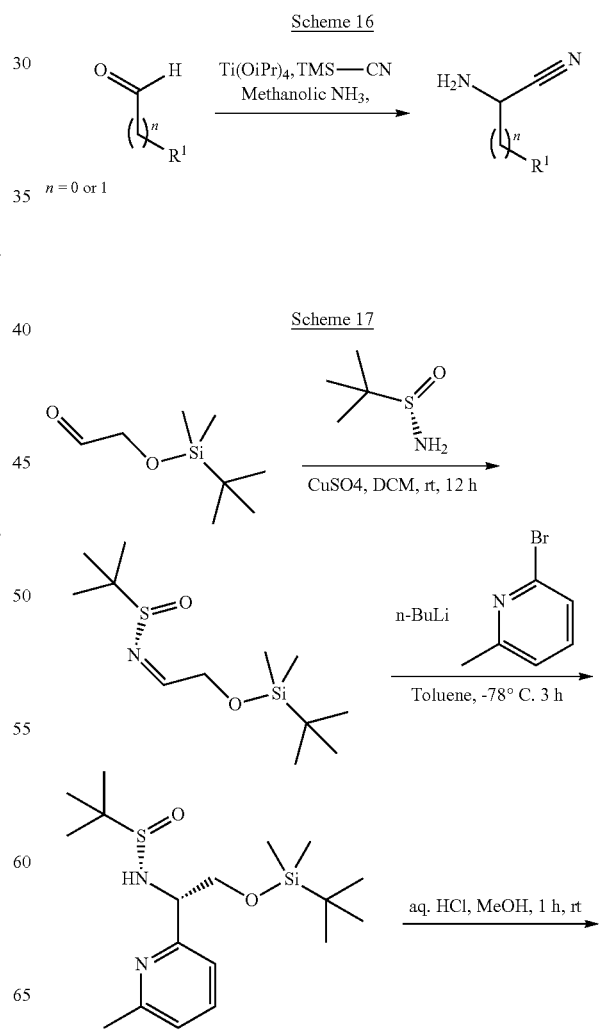

$n = 0$ or $1$

Scheme 13 depicts a method for the preparation of compounds of formula (I), where in this example M is a bond, Z=CH, $R^5$=H, and X=CR$^7$. In this method, 2-fluoro-4-iodo-pyridine [BA] is reacted with an amine $R^4$—NH$_2$ to provide the intermediate [BB]. The reaction is carried out in a suitable solvent such as DMF or NMP, and may be performed at elevated temperatures, for example at 90° C. to 100° C. in a sealed glass tube. The intermediate [BB] is then reacted with a heterocyclic ester [N] to provide the intermediate [BC]. The reaction is conducted in a suitable solvent such as DMF or NMP in the presence of L-proline, copper(I) iodide, and a base such as potassium carbonate, at a temperature ranging from 25° C. to elevated temperatures such as 100° C. to 150° C. in a sealed glass tube. The ester moiety in the intermediate [BC] is hydrolyzed by methods such as those described in Scheme 11 to give the corresponding carboxylic acid, which is then reacted with an amine such as [F] by using amide-coupling methods such as described in Scheme 10, or reacted with an amine such as [R] by using amide-coupling methods and then reduced such as described in Scheme 11, to provide a compound of the invention (I-M).

Methods useful for the preparation of synthesis building blocks used in the synthesis of compounds of formula (I) are set forth in the schemes below. One of skill in the art will recognize that the schemes can be adapted to produce the other compounds of formula (I) and pharmaceutically acceptable salts, prodrugs, solvates, hydrates, or stereoisomers of compounds of formula (I).

69
-continued
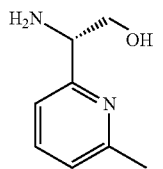
Examples of methods useful for the preparation of compounds such as (I-N) and (I-O) that may act as prodrugs of compounds of formula (I) are set forth in the Schemes 18 and 19 below. One of skill in the art will recognize that these schemes can be adapted to produce additional compounds that may act as prodrugs of compounds of formula (I).
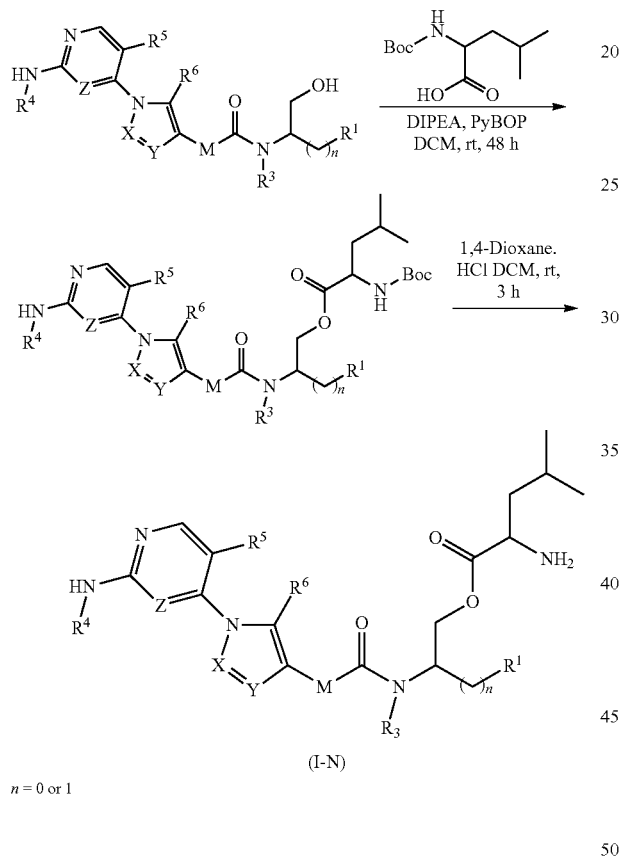
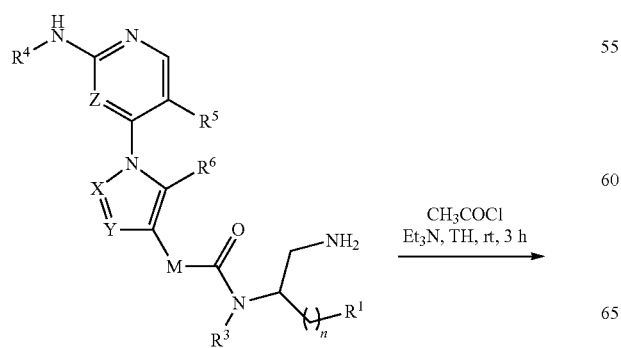
70
-continued
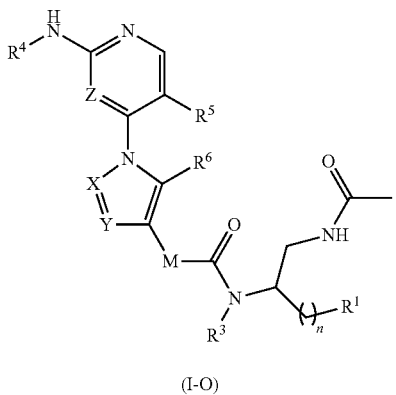
(I-O)
n = 0 or 1
Scheme 20
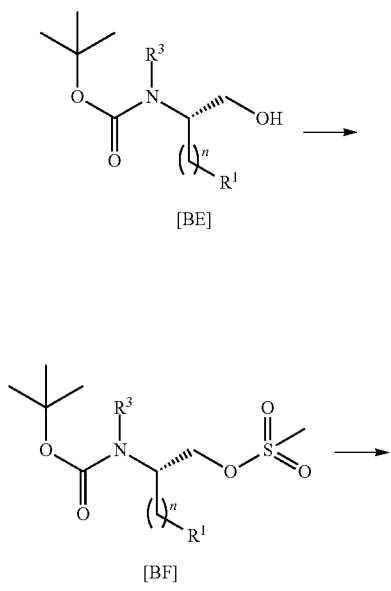

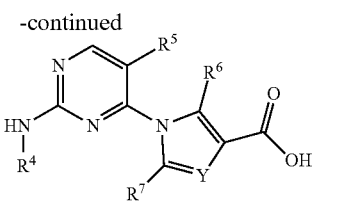

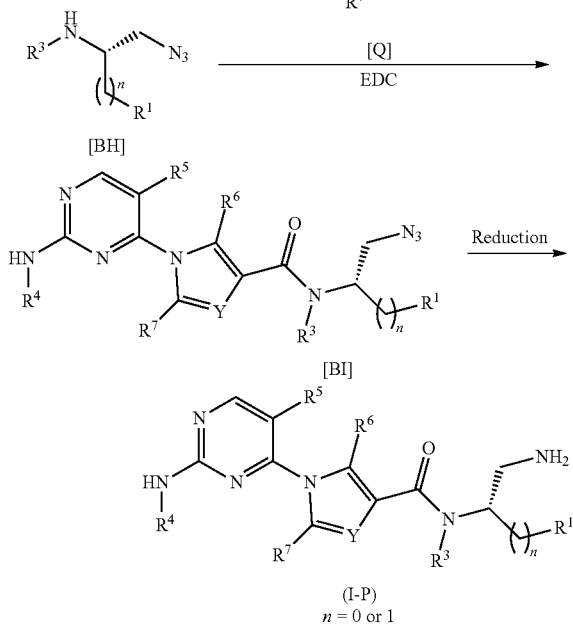

(I-P)
n = 0 or 1

Scheme 20 depicts a further method for the preparation of compounds of formula (I), where in this example M is a bond, $R^2=CH_2NH_2$, $Z=N$, and $X=CR^7$. This method provides an alternative to the method described in Scheme 4. In this method, an amino-alcohol (in this example, a single enantiomer) [BD] is converted by standard methods to the N-Boc protected analog [BE], and then the hydroxyl moiety is converted to the corresponding methanesulfonate ester, for example by reaction with methanesulfonyl chloride and triethylamine in a solvent such as dichloromethane. This methanesulfonate compound [BF] is then reacted with sodium azide to form the corresponding azide derivative [BG]. The azide reaction is carried out in a suitable solvent such as DMF or NMP, and may be performed at elevated temperatures, for example at about 50° C. The N-Boc group is then removed by standard methods, for example by treatment with 4 M HCl in dioxane. The resulting amino azide compound [BH] is then coupled with intermediate [Q] to form the amide [BI], by using amide-coupling methods such as those described for the preparation of (I-B) in Scheme 3. The azide moiety is reduced, for example by reaction with zinc dust and ammonium chloride in a solvent such as methanol, to provide a compound of the invention (I-P), in this example as a single enantiomer.

EXAMPLES

All reactions were carried out under dry nitrogen and or argon atmosphere unless otherwise specified. Unless otherwise stated, all the raw starting materials, solvents and reagents were purchased from commercial sources (e.g., Avocado Research Chemicals, Apollo Scientific Limited, Bepharma Ltd., Combi-Blocks Inc., Sigma Aldrich Chemicals Pvt. Ltd., Ultra Labs, Toronto Research Chemicals Inc., Chemical House, RFCL Limited, Spectro Chem Pvt. Ltd., Leonid Chemicals, Loba Chemie, Changzhou Yangyuan, NeoSynth., Rankem, etc.) and used as such without further purification or reagents can be synthesized by procedures known in the art. Typically, the progress of each reaction was monitored by TLC analysis.

Biotage Isolera® One and CombiFlash® (Teledyne Isco) Automated Flash Purification System were commonly used for the purification of crude products, using the eluent combination mentioned in the respective procedures. Flash Chromatography was performed using silica gel (60-100, 100-200 and 230-400 mesh) from ChemLabs, with nitrogen and/or compressed air to enable pressurized eluent flow. Preparative thin-layer chromatography (preparative TLC) was carried out using silica gel (GF 1500 μM 20×20 cm and GF 2000 μM 20×20 cm Prep-scored plates from Analtech, Inc. Delaware, USA). Analytical thin-layer chromatography (TLC) was carried out using pre-coated silica gel sheets (Merck 60 $F_{254}$). Visual detection was performed with ultraviolet light, p-anisaldehyde stain, ninhydrin stain, dinitrophenyl hydrazine stain, potassium permanganate stain, or iodine. Reactions at lower temperature were performed by using cold baths, e.g., $H_2O$/ice at 0° C., and acetone/dry ice at −78° C. Reactions under microwave conditions were conducted in a CEM Discover SP 909155 microwave oven. Melting points were determined by using a LabIndia MR-VIS visual melting range apparatus. $^1$H NMR spectra were recorded at 400 MHz with a Varian V400 spectrometer, Bruker 400 (unless otherwise noted) at ambient temperature, using tetramethylsilane as internal reference. The chemical shift values are quoted in δ (parts per million). Mass spectra of all the intermediates and final compounds were recorded using Acquity® UPLC-SQD (Waters) & Agilent 1290 Infinity® UHPLC with 6150 SQD machines. HPLC spectra were recorded using Agilent 1290 Infinity® UHPLC and Alliance (Waters) systems. LCMS spectra were recorded using Agilent 1200® LCMS, Agilent 1290® UHPLC-SQD with diode array detector (DAD) detection LC-MS instruments using a BEH C18 column and Zorbax® HD C18 column (50 mm×2.1 mm×1.7 μm) & (50 mm×2.1 mm×1.8 m), a mobile phase of 0.01% of formic acid and acetonitrile or 0.01% of trifluoroacetic acid and acetonitrile, and a flow rate of 0.3 mL/min, a column temperature of 70 or 50° C., and a run time of 3 to 5 min. The purity of each of the final compounds was determined using Waters® PDA with SQD and Agilent® DAD with 6150 SQD instruments and the following conditions:

Condition 1: Column: BEH C18 (Waters); mobile phase: 0.01% acetic acid with acetonitrile & 0.01% acetic acid with methanol; gradient: (B/% T): 0/0, 1.2/100, 2.5/100, 2.8/0, 3.0/0; flow: 0.3 mL/min; temperature: 70° C.; run time: 3.0 min.

Condition 2: Column: Zorbax® HD C18; mobile phase: 0.01% acetic acid with acetonitrile & 0.01% acetic acid with methanol; gradient: (B/% T): 0/0, 2.5/100, 4.5/100, 4.8/0, 5.0/0; flow: 0.3 mL/min; temperature: 50° C.; run time: 5.0 min For use in the preparation of certain compounds of the invention, the following intermediates were produced as follows.

Preparation 1: 2-Amino-2-(3-chlorophenyl)acetonitrile

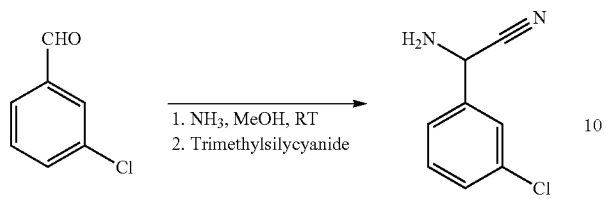

A solution of 3-chlorobenzaldehyde (5 g, 35.0 mmol) in methanol (100 mL) was purged with ammonia gas for 2 h at RT. The mixture was cooled to 0° C., and trimethylsilylcyanide (5.293 g, 53.0 mmol) was added. The mixture was stirred at RT for 2 h. The mixture was concentrated under reduced pressure and the residue was purified by gradient column chromatography using ethyl acetate in hexane as eluent to afford 2-amino-2-(3-chlorophenyl)acetonitrile as a yellow solid (4.8 g, 81% yield). 1HNMR (400 MHz, DMSO-$d_6$): δ 7.57 (s, 1H), 7.47-7.40 (m, 3H), 5.06 (s, 1H), 2.92 (s, 2H).

Preparation 2: 2-Amino-3-phenylpropanenitrile

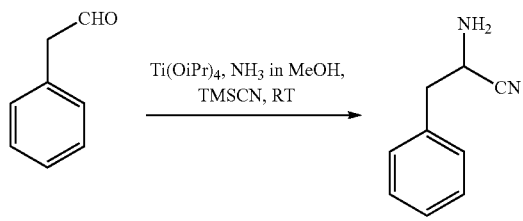 [SMILES: O=CCc1ccccc1 ; N#CC(N)Cc1ccccc1]

To a stirred solution of 2-phenylacetaldehyde (10.0 g, 83.33 mmol) in MeOH (50 mL), was added $NH_3$ in MeOH (80.0 mL) and Ti(OiPr)$_4$ (30.7 g, 108.33 mmol), and the resulting solution was stirred at RT for 2 h. To the reaction mixture was then added trimethylsilylcyanide (TMSCN) (14.88 g, 149.9 mmol), then the reaction mixture was stirred at RT for 20 h. Reaction mixture was quenched with water, and the resulting white precipitate was filtered. The filtrate was concentrated under reduced pressure, combined with ethyl acetate and washed with brine (2×15 mL). The organic layer was dried over $Na_2SO_4$, filtered and concentrated under reduced pressure, and the residue was purified by Combiflash, eluting with MeOH in DCM, to give 2-amino-3-phenylpropanenitrile (5.4 g, 45%). 1HNMR (400 MHz, DMSO-$d_6$): δ 7.37-7.21 (m, 5H), 3.93 (t, J=7.2 Hz, 1H), 3.33-3.23 (m, 2H), 2.36 (br s, 2H). LC-MS calcd exact mass 146.08, found m/z 147.04 [M+H]$^+$.

Representative Example for Scheme 1

Example 1: (S)-1-(1-(3-chlorophenyl)-2-hydroxyethyl)-3-(1-(2-(2-chlorophenyl)amino)-5-methylpyrimidin-4-yl)-1H-pyrazol-4-yl)urea (Compound #2)

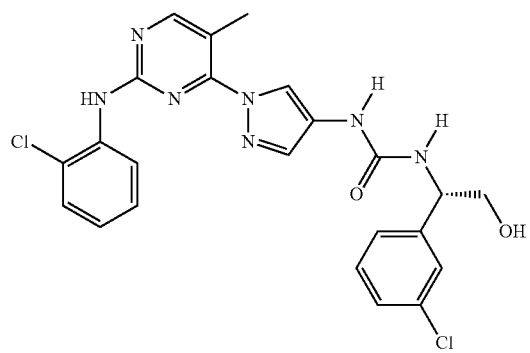 [SMILES: Cc1cnc(Nc2ccccc2Cl)nc1-n1cc(NC(=O)N[C@H](CO)c2cccc(Cl)c2)cn1]

Step 1: 2-Chloro-5-methyl-4-(4-nitro-1H-pyrazol-1-yl)pyrimidine

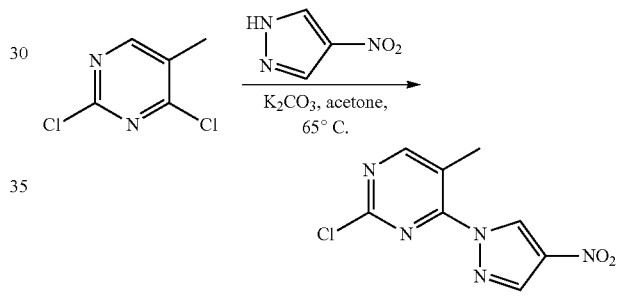

A reaction mixture of 4-nitro-1H-pyrazole (1.0 g, 8.8 mmol), 2,4-dichloro-5-methylpyrimidine (1.18 g, 7.96 mmol), potassium carbonate (3.6 g, 26.4 mmol) and acetone (30 mL) was heated at 65° C. for 6 h. The reaction mixture was evaporated; residue was suspended in water, and extracted with ethyl acetate. Organic layer was dried over sodium sulfate, evaporated, and the residue was purified by column chromatography over silica gel using ethyl acetate in hexanes as eluent to give 2-chloro-5-methyl-4-(4-nitro-1H-pyrazol-1-yl)pyrimidine (0.73 g, 56%). 1HNMR (400 MHz, CDCl$_3$): 9.32 (s, 1H), 8.62 (s, 1H), 8.31 (s, 1H), 2.69 (s, 3H). LC-MS calcd exact mass 239.02, found m/z 240.1 [M+H]$^+$.

Step 2: N-(2-Chlorophenyl)-5-methyl-4-(4-nitro-1H-pyrazol-1-yl)pyrimidin-2-amine

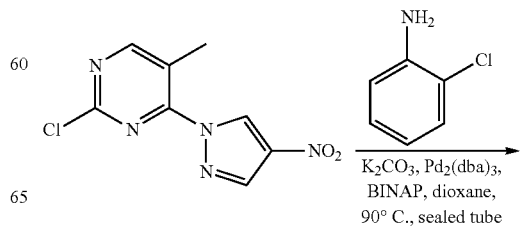

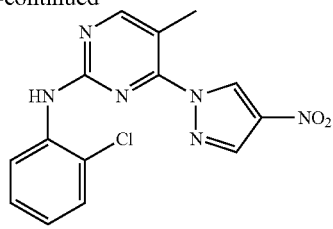

A reaction mixture of 2-chloro-5-methyl-4-(4-nitro-1H-pyrazol-1-yl)pyrimidine (0.4 g, 1.67 mmol), 2-chloroaniline (0.19 mL, 1.84 mmol), potassium carbonate (0.34 g, 2.5 mmol), and dioxane (15 mL) in a glass tube was purged with nitrogen gas for 20 min. Tris(dibenzylideneacetone)dipalladium(0) (0.076 g, 0.083 mmol) and BINAP (0.103 g, 0.167 mmol) were added to the reaction mixture, which was purged with nitrogen gas for another 15 min, and then the tube was sealed and heated at 90° C. for 4 hours. Reaction mixture was filtered through Celite, and the filtrate was evaporated; residue was suspended in water, and extracted with ethyl acetate. Organic layer was dried over sodium sulfate, evaporated, and the residue was purified by column chromatography over silica gel using 20% ethyl acetate in hexanes as eluent to give N-(2-chlorophenyl)-5-methyl-4-(4-nitro-1H-pyrazol-1-yl)pyrimidin-2-amine (0.33 g, 60%). 1HNMR (400 MHz, DMSO-$d_6$): 9.23 (s, 1H), 9.17 (s, 1H), 8.61 (s, 1H), 8.54 (s, 1H), 7.78 (d, J=8 Hz, 1H), 7.51 (d, J=8 Hz, 1H), 7.35 (t, J=8 Hz, 1H), 7.18 (t, 1H, J=8 Hz), 2.38 (s, 3H). LC-MS calcd exact mass 330.06, found m/z 331.1 [M+H]$^+$.

Step 3: 4-(4-Amino-1H-pyrazol-1-yl)-N-(2-chlorophenyl)-5-methylpyrimidin-2-amine

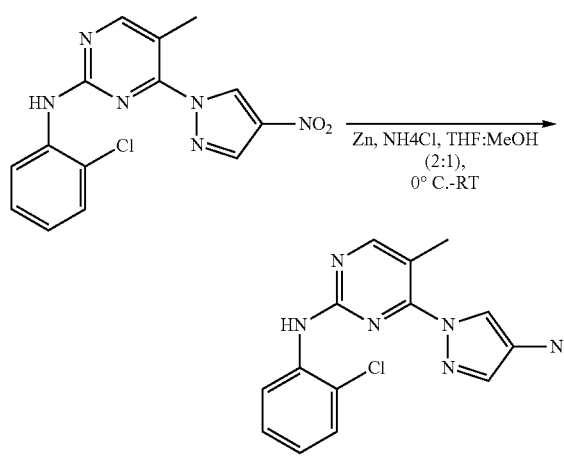

To a solution of compound N-(2-chlorophenyl)-5-methyl-4-(4-nitro-1H-pyrazol-1-yl)pyrimidin-2-amine (0.33 g, 1.0 mmol) in THF:methanol (2:1) (10 mL) which was cooled to 0° C., zinc powder (0.39 g, 6.0 mmol) and ammonium chloride (0.43 g, 8.0 mmol) were added. The mixture was stirred at RT for 30 min. Reaction mixture was filtered through Celite, and filtrate was evaporated; residue was suspended in water, and extracted with DCM. Organic layer was dried over sodium sulfate, and evaporated to give 4-(4-amino-1H-pyrazol-1-yl)-N-(2-chlorophenyl)-5-methylpyrimidin-2-amine (0.24 g, 80%). This product was used in the next step without further purification. 1HNMR (400 MHz, DMSO-$d_6$): 8.63 (s, 1H), 8.26 (s, 1H), 7.83 (t, J=8 Hz, 1H), 7.72 (s, 1H), 7.48 (d, J=7.6 Hz, 1H), 7.42 (s, 1H), 7.38-7.32 (m, 1H), 7.13-7.11 (m, 1H), 4.39 (s, 2H), 2.40 (s, 3H). LC-MS calcd exact mass 300.09, found m/z 301.1 [M+H]$^+$.

Step 4: (S)-1-(1-(3-Chlorophenyl)-2-hydroxyethyl)-3-(1-(2-(2-chlorophenyl)amino)-5-methylpyrimidin-4-yl)-1H-pyrazol-4-yl)urea

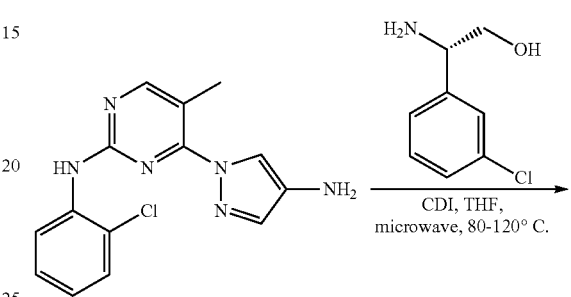

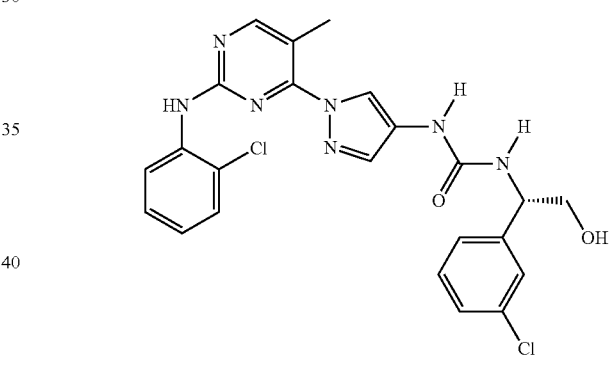

A reaction mixture of 4-(4-amino-1H-pyrazol-1-yl)-N-(2-chlorophenyl)-5-methylpyrimidin-2-amine (0.15 g, 0.5 mmol), 1,1'-carbonyldiimidazole (0.32 g, 2.0 mmol), and THF (5 mL) in a CEM microwave vial was stirred at 85° C. for 20 min in CEM microwave. (S)-2-amino-2-(3-chlorophenyl)ethanol (0.25 g, 1.5 mmol) was added to the reaction mixture and was stirred at 120° C. for 20 min in CEM microwave. The reaction mixture was evaporated; residue was suspended in water, and extracted with ethyl acetate. Organic layer was dried over sodium sulfate, evaporated, and the residue was purified by preparative thin layer chromatography using methanol in DCM as eluent to give (S)-1-(1-(3-chlorophenyl)-2-hydroxyethyl)-3-(1-(2-(2-chlorophenyl)amino)-5-methylpyrimidin-4-yl)-1H-pyrazol-4-yl)urea (0.02 g, 8%). 1HNMR (400 MHz, DMSO-$d_6$): δ 8.79 (s, 1H), 8.63 (s, 1H), 8.46 (s, 1H), 8.31 (s, 1H), 7.79 (s, 1H), 7.78 (s, 1H), 7.47 (d, J=7.6 Hz, 1H), 7.35-7.26 (m, 4H), 7.13 (t, J=7.8 Hz, 1H), 6.79 (d, J=8 Hz, 1H), 4.99-4.91 (m, 1H), 4.74-4.72 (m, 1H), 3.65-3.55 (m, 2H), 2.41 (s, 3H). LC-MS m/z calcd exact mass 497.11, found m/z 498.3 [M+H]$^+$; HPLC purity 99.17%.

Representative Examples for Scheme 2

Example 2: (S)—N-(1-(3-Chlorophenyl)-2-hydroxyethyl)-4-(5-methoxy-1H-indazol-3-yl)-1H-pyrrole-2-carboxamide (Compound #20)

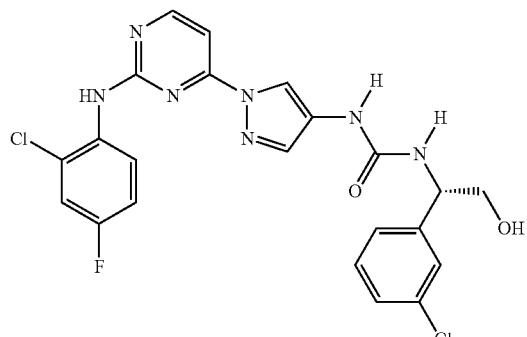

Step 1:
2-Chloro-4-(4-nitro-1H-pyrazol-1-yl)pyrimidine

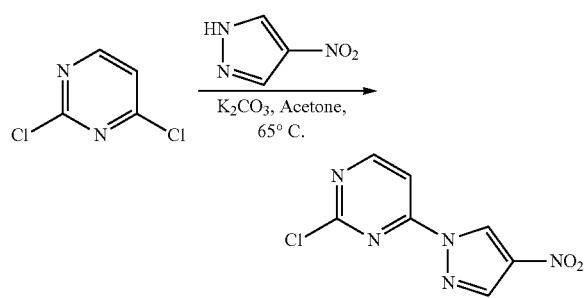

A reaction mixture of 4-nitro-1H-pyrazole (4.0 g, 35.3 mmol), 2,4-dichloropyrimidine (5.23 g, 35.3 mmol), potassium carbonate (14.6 g, 106 mmol) and acetone (200 mL) was heated at 65° C. for 4 h. The reaction mixture was evaporated; residue was suspended in water, and extracted with ethyl acetate. Organic layer was dried over sodium sulfate, evaporated, and the residue was purified by column chromatography over silica gel using ethyl acetate in hexanes as eluent to give 2-chloro-4-(4-nitro-1H-pyrazol-1-yl)pyrimidine (1.7 g, 21%). 1HNMR (400 MHz, CDCl$_3$): 9.30 (s, 1H), 8.78 (d, J=5.6 Hz, 1H) 8.32 (s, 1H), 7.74 (d, J=5.2 Hz, 1H).

Step 2:
1-(2-Chloropyrimidin-4-yl)-1H-pyrazol-4-amine

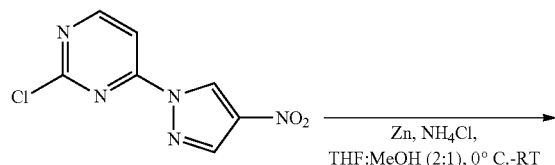

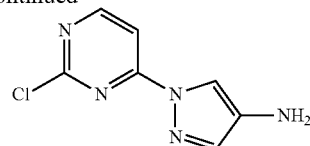

To a solution of 2-chloro-4-(4-nitro-1H-pyrazol-1-yl)pyrimidine (0.4 g, 1.77 mmol) in THF:methanol (2:1) (20 mL) which was cooled to 0° C., zinc powder (0.7 g, 10.6 mmol) and ammonium chloride (0.75 g, 14.16 mmol) were added. The mixture was stirred at RT for 30 min. Reaction mixture was filtered through Celite, and filtrate was evaporated; residue was suspended in water, and extracted with DCM. The organic layer was dried over sodium sulfate, and evaporated to give 1-(2-chloropyrimidin-4-yl)-1H-pyrazol-4-amine (0.33 g, 97%). This product was used in the next step without further purification. 1HNMR (400 MHz, DMSO-d$_6$): 8.60 (d, J=5.6 Hz, 1H), 7.76 (s, 1H), 7.71 (d, J=8 Hz, 1H), 7.58 (s, 1H), 5.21 (br s, 2H). LC-MS calcd exact mass 195.03, found m/z 196.1 [M+H]$^+$.

Step 3: (S)-1-(1-(3-Chlorophenyl)-2-hydroxyethyl)-3-(1-(2-chloropyrimidin-4-yl)-1H-pyrazol-4-yl)urea

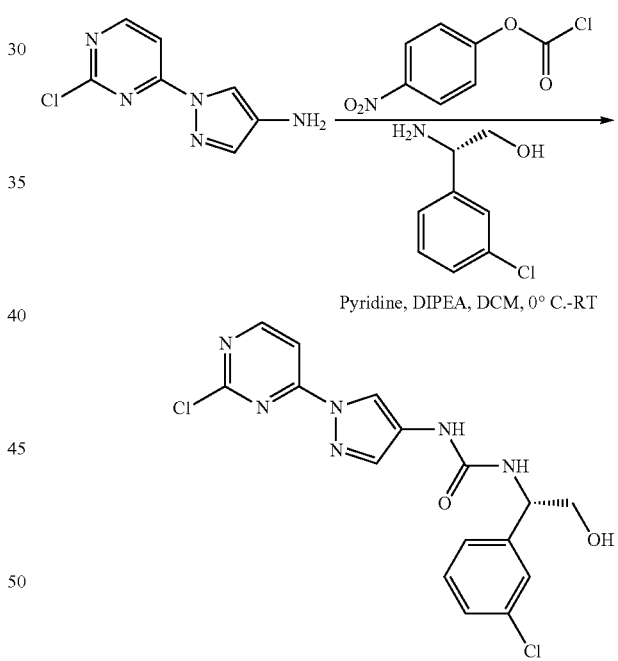

A mixture of 1-(2-chloropyrimidin-4-yl)-1H-pyrazol-4-amine (0.1 g, 0.51 mmol), pyridine (0.041 mL, 0.51 mmol) in DCM (6 mL) was cooled to 0° C., then 4-nitrophenyl carbonochloridate (0.102 g, 0.51 mmol) was added and the mixture was stirred at RT for 1.5 hours. The reaction mixture was cooled to 0° C., and DIPEA (0.28 mL, 1.53 mmol) and (S)-2-amino-2-(3-chlorophenyl)ethanol (0.088 g, 0.51 mmol) were added. The reaction mixture was stirred at RT for 16 hours. The reaction mixture was diluted with DCM and washed with water and brine. Organic layer was dried over sodium sulfate, evaporated, and the residue was purified by column chromatography over silica gel using 60% ethyl acetate in hexanes as eluent to give (S)-1-(1-(3- chlorophenyl)-2-hydroxyethyl)-3-(1-(2-chloropyrimidin-4-yl)-1H-pyrazol-4-yl)urea (0.045 g, 23%). 1HNMR (400 MHz, DMSO-d$_6$): 8.74 (s, 1H), 8.68 (d, J=5.6 Hz, 1H), 8.45 (s, 1H), 7.92 (s, 1H), 7.80 (d, J=5.6 Hz, 1H), 7.36-7.32 (m, 2H), 7.28 (d, J=7.6 Hz, 2H), 6.96 (d, J=8 Hz, 1H), 5.00-4.98 (m, 1H), 4.76-4.72 (m, 1H), 3.65-3.58 (m, 2H). LC-MS calcd exact mass 392.06, found m/z 393.1 [M+H]$^+$.

Step 4: (S)-1-(1-(2-(2-Chloro-4-fluorophenyl)amino)pyrimidin-4-yl)-1H-pyrazol-4-yl)-3-(1-(3-chlorophenyl)-2-hydroxyethyl)urea

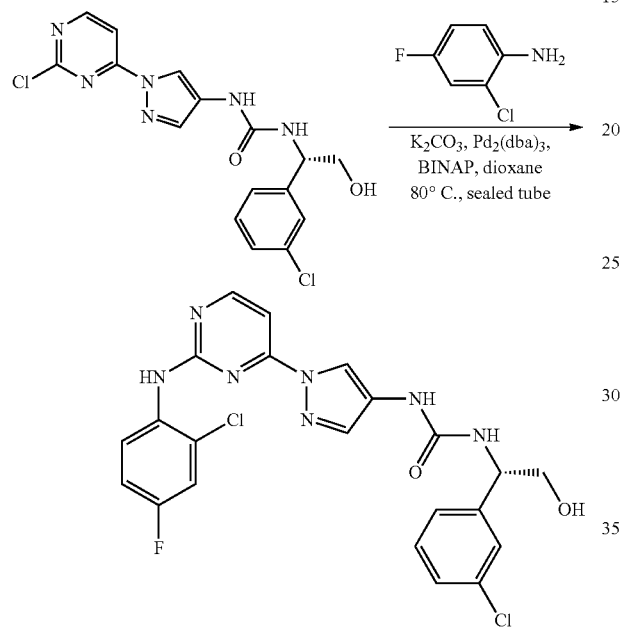

A mixture of (S)-1-(1-(3-chlorophenyl)-2-hydroxyethyl)-3-(1-(2-chloropyrimidin-4-yl)-1H-pyrazol-4-yl)urea (0.02 g, 0.05 mmol), 2-chloro-4-fluoroaniline (0.009 g, 0.6 mmol), potassium carbonate (0.01 g, 0.075 mmol), and dioxane (2 mL) in a glass tube was purged with nitrogen gas for 20 min. Tris(dibenzylideneacetone)dipalladium(0) (0.002 g, 0.0025 mmol) and BINAP (0.003 g, 0.005 mmol) were added to the reaction mixture, which was purged with nitrogen gas for another 15 min. The tube was sealed and heated at 90° C. for 4 hours. Reaction mixture was filtered through Celite, and filtrate was evaporated; residue was suspended in water, and extracted with ethyl acetate. Organic layer was dried over sodium sulfate, evaporated, and the residue was purified by column chromatography over silica gel using 60% ethyl acetate in hexanes as eluent to give (S)-1-(1-(2-((2-chloro-4-fluorophenyl)amino)pyrimidin-4-yl)-1H-pyrazol-4-yl)-3-(1-(3-chlorophenyl)-2-hydroxyethyl)urea (0.003 g, 12%). 1HNMR (400 MHz, CDCl$_3$, plus a few drops MeOD): 8.50 (s, 1H), 8.33 (d, J=5.2 Hz, 1H), 8.27-8.25 (m, 1H), 7.51 (s, 1H), 7.28-7.19 (m, 1H), 7.23-7.12 (m, 3H), 7.12-7.10 (m, 1H) 7.04-6.99 (m, 1H), 6.23 (d, J=6.8 Hz, 1H) 4.87-4.84 (m, 1H), 3.81-3.77 (m, 1H), 3.64-3.61 (m, 1H). LC-MS calcd exact mass 501.09, found m/z 502.3 [M+H]$^+$. HPLC purity 98.17%.

Example 3: (S)-1-(1-(2-(benzo[d][1,3]dioxol-5-ylamino)-5-methylpyrimidin-4-yl)-1H-pyrazol-4-yl)-3-(2-hydroxy-1-phenylethyl)urea (Compound #55)

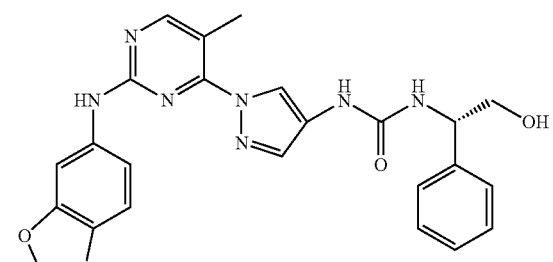

Step 1: 2-chloro-5-methyl-4-(4-nitro-1H-pyrazol-1-yl)pyrimidine

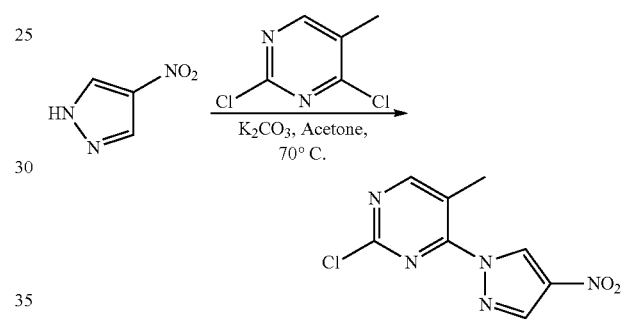

To a stirred solution of 4-nitro-1H-pyrazole (4.0 g, 35.36 mmol) in acetone (100 mL) was added potassium carbonate (14.66 g, 106.1 mmol). The mixture was stirred for 15 min at RT, followed by the addition of 2,4-dichloro-5-methylpyrimidine (5.76 g, 35.36 mmol), then the mixture was stirred for 8 h at 70° C. The reaction was quenched with water (100 mL), extracted with ethyl acetate (3×100 mL), followed by washing with brine (30 mL). The combined organic layers were dried over sodium sulfate, and concentrated under reduced pressure. The residue was purified by gradient column chromatography eluting with 8% ethyl acetate in n-hexane to afford 2-chloro-5-methyl-4-(4-nitro-1H-pyrazol-1-yl)pyrimidine, as colorless solid (4.2 g, 50% yield). 1HNMR (400 MHz CDCl$_3$): δ 9.31 (s, 1H), 8.61 (s, 1H), 8.31 (s, 1H), 2.68 (s, 3H). LC-MS calcd exact mass 239.02, found m/z 240.2 [M+H]$^+$.

Step 2: 1-(2-chloro-5-methylpyrimidin-4-yl)-1H-pyrazol-4-amine

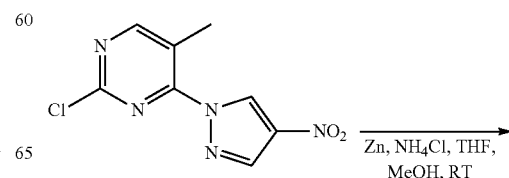

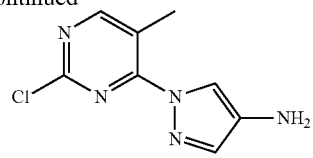

To a stirred solution of 2-chloro-5-methyl-4-(4-nitro-1H-pyrazol-1-yl)pyrimidine (4.2 g, 17.2 mmol) in THF:methanol (50:25 mL) was added ammonium chloride (6.85 g, 172.0 mmol) and zinc (5.28 g, 87.4 mmol), and then the reaction mixture was stirred at RT for 30 min. Then the reaction mixture was filtered through Celite using methanol (50 mL), and the filtrate was evaporated under reduced pressure. It was then combined with water (100 mL), and extracted with ethyl acetate (3×100 mL), followed by brine (50 mL). The combined organic layers were dried over sodium sulfate and concentrated under reduced pressure to give 1-(2-chloro-5-methylpyrimidin-4-yl)-1H-pyrazol-4-amine as an off-white solid (3.0 g, 82% yield). 1HNMR (400 MHz CDCl$_3$): δ 8.36 (s, 1H), 8.11 (s, 1H), 7.49 (d, J=8 Hz, 1H), 3.19 (s, 2H), 2.62 (s, 3H). LC-MS calcd exact mass 209.04, found m/z 210.2 [M+H]$^+$.

Step 3: (S)-1-(1-(2-chloro-5-methylpyrimidin-4-yl)-1H-pyrazol-4-yl)-3-(2-hydroxy-1-phenylethyl)urea

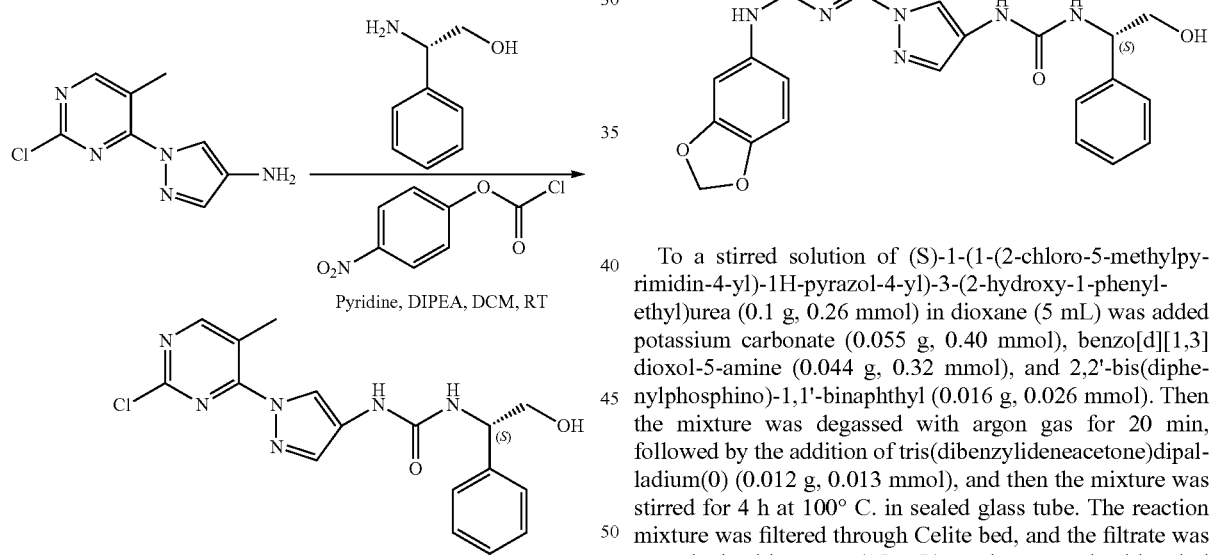

To a stirred solution of 1-(2-chloro-5-methylpyrimidin-4-yl)-1H-pyrazol-4-amine (0.2 g, 0.95 mmol) in DCM (15 mL) was added 4-nitrophenyl carbonochloridate (0.23 g, 0.11 mmol) at 0° C., and then the mixture was stirred for 2 h at RT. Then, to the mixture was added DIPEA (0.5 mL, 2.86 mmol), (S)-2-amino-2-phenylethanol (0.13 g, 0.95 mmol) in DCM (3 mL), and pyridine (0.08 mL, 0.95 mmol), and the reaction mixture was stirred at RT overnight. The reaction mixture was quenched by the addition of water (25 mL), and extracted with ethyl acetate (3×50 mL). The combined organic layers were dried over sodium sulfate, filtered and concentrated under reduced pressure, washed with ether and then dried under high vacuum, to give (S)-1-(1-(2-chloro-5-methylpyrimidin-4-yl)-1H-pyrazol-4-yl)-3-(2-hydroxy-1-phenylethyl)urea, as an off-white solid (0.1 g, 28%). 1HNMR (400 MHz DMSO-d$_6$): δ 8.68 (s, 1H), 8.61 (s, 1H), 8.52 (s, 1H), 7.89 (s, 1H), 7.3 (d, J=4.4 Hz, 4H), 7.24-7.19 (m, 1H), 6.83 (d, J=7.6 Hz, 1H), 4.93 (t, J=5.2 Hz, 1H), 4.75-4.71 (m, 1H), 3.65-3.55 (m, 2H), 2.48 (s, 3H). LC-MS calcd exact mass 372.11, found m/z 373.1 [M+H]$^+$.

Step 4: (S)-1-(1-(2-(benzo[d][1,3]dioxol-5-ylamino)-5-methylpyrimidin-4-yl)-1H-pyrazol-4-yl)-3-(2-hydroxy-1-phenylethyl)urea

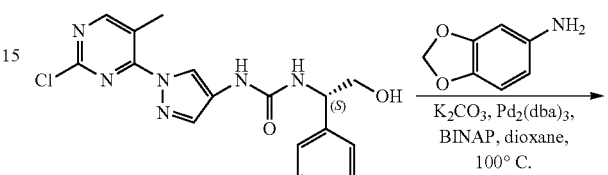

To a stirred solution of (S)-1-(1-(2-chloro-5-methylpyrimidin-4-yl)-1H-pyrazol-4-yl)-3-(2-hydroxy-1-phenylethyl)urea (0.1 g, 0.26 mmol) in dioxane (5 mL) was added potassium carbonate (0.055 g, 0.40 mmol), benzo[d][1,3]dioxol-5-amine (0.044 g, 0.32 mmol), and 2,2'-bis(diphenylphosphino)-1,1'-binaphthyl (0.016 g, 0.026 mmol). Then the mixture was degassed with argon gas for 20 min, followed by the addition of tris(dibenzylideneacetone)dipalladium(0) (0.012 g, 0.013 mmol), and then the mixture was stirred for 4 h at 100° C. in sealed glass tube. The reaction mixture was filtered through Celite bed, and the filtrate was quenched with water (15 mL), and extracted with ethyl acetate (3×20 mL). The combined organic layers were dried over sodium sulfate, filtered and evaporated under reduced pressure. The residue was purified by gradient column chromatography eluting with 3.5% methanol in DCM, to afford (S)-1-(1-(2-(benzo[d][1,3]dioxol-5-ylamino)-5-methylpyrimidin-4-yl)-1H-pyrazol-4-yl)-3-(2-hydroxy-1-phenylethyl)urea, as an off-white solid (4 mg, 4%). 1HNMR (400 MHz, DMSO-d$_6$): δ 9.44 (s, 1H), 8.81 (s, 1H), 8.56 (s, 1H), 8.34 (d, J=12.4 Hz, 1H), 7.77 (s, 1H), 7.37 (d, J=1.6 Hz, 1H), 7.31-7.29 (m, 4H), 7.23-7.19 (m, 1H) 7.12-7.09 (m, 1H), 6.9 (d, J=7.6 Hz, 1H), 6.8 (d, J=8 Hz, 1H), 5.97 (s, 2H), 4.95 (s, 1H), 4.74-4.69 (m, 1H), 3.63-3.55 (m, 2H), 2.45 (s, 3H). LC-MS calcd exact mass 473.18, found m/z 474.5 [M+H]$^+$; HPLC Purity 98.33%, Chiral HPLC Purity 99.01%, mp 208.3° C.

83

Representative Example for General Scheme 3

Example 4: (S)-1-(2-((2-Chloro-4-fluorophenyl)amino)-5-methylpyrimidin-4-yl)-N-(1-(3-chlorophenyl)-2-hydroxyethyl)-1H-pyrrole-3-carboxamide (Compound #29)

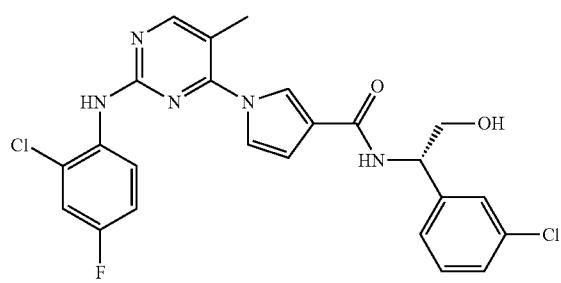 [SMILES: Cc1cnc(Nc2ccc(F)cc2Cl)nc1-n1ccc(C(=O)N[C@H](CO)c2cccc(Cl)c2)c1]

Step 1: Methyl 1-(2-chloro-5-methylpyrimidin-4-yl)-1H-pyrrole-3-carboxylate

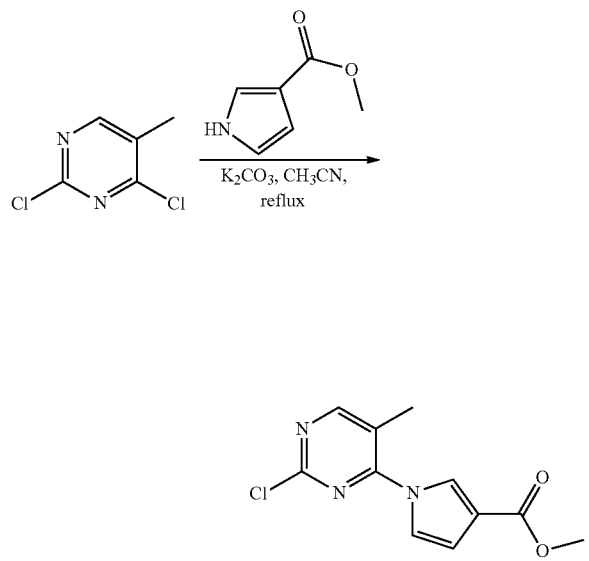

To a solution of methyl 1H-pyrrole-3-carboxylate (3.0 g, 24 mmol) in acetonitrile (100 mL) were added 2,4-dichloro-5-methylpyrimidine (5.9 g, 36 mmol) and potassium carbonate (6.6 g, 48 mmol). The reaction was stirred at reflux for 12 h. The reaction mixture was diluted with ethyl acetate (500 mL) and then washed with water and brine. The ethyl acetate layer was dried over sodium sulfate, filtered and evaporated under reduced pressure. The residue was purified by gradient column chromatography using ethyl acetate in hexane as eluent to afford methyl 1-(2-chloro-5-methylpyrimidin-4-yl)-1H-pyrrole-3-carboxylate as an off-white solid (3.2 g, 53%). $^1$HNMR (400 MHz, CDCl$_3$): δ 8.51 (s, 1H), 8.0 (s, 1H), 7.41 (d, J=2.4 Hz, 1H), 6.79 (t, J=1.2 Hz, 1H), 3.85 (s, 3H), 2.51 (s, 3H). LC-MS calcd exact mass 251.05, found m/z 252.2 [M+H]$^+$.

84

Step 2: Methyl 1-(2-((2-chloro-4-fluorophenyl)amino)-5-methylpyrimidin-4-yl)-1H-pyrrole-3-carboxylate

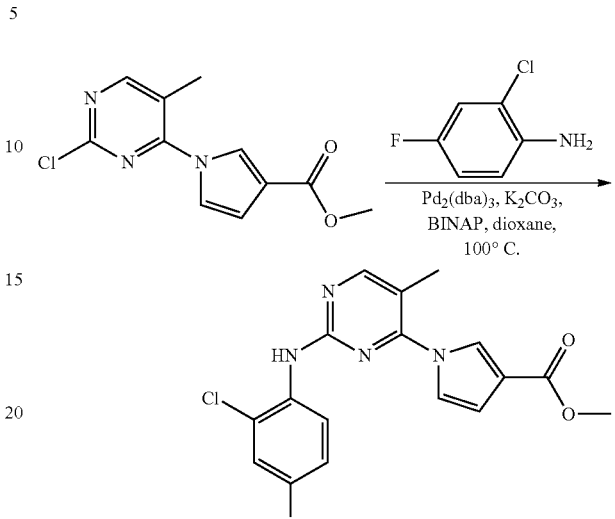

To a solution of methyl 1-(2-chloro-5-methylpyrimidin-4-yl)-1H-pyrrole-3-carboxylate (0.3 g, 0.1195 mmol) in dioxane (10 mL) were added 2-chloro-4-fluoroaniline (0.17 g, 0.1195 mmol) and potassium carbonate (0.24 g, 1.17 mmol). The resulting reaction mixture was purged with nitrogen gas for min, then 2,2'-bis(diphenylphosphino)-1,1'-binaphthyl(0.074 g, 0.119 mmol) and palladium(dibenzylidineacetone)dipalladium(0) (0.054 g, 0.059 mmol) were added. The reaction mixture was stirred at 100° C. for 12 h. The reaction mixture was diluted with ethyl acetate (200 mL) and filtered through Celite bed. The bed was washed with ethyl acetate (2×50 mL). The filtrate was washed several times with cold water and then with brine. The organic layer was dried over sodium sulfate, filtered and evaporated under reduced pressure. The residue was purified by gradient column chromatography using ethyl acetate in hexane as eluent to afford methyl 1-(2-((2-chloro-4-fluorophenyl)amino)-5-methylpyrimidin-4-yl)-1H-pyrrole-3-carboxylate as an off-white solid (0.25 g, 58%). $^1$HNMR (400 MHz, CDCl$_3$): δ 8.40-8.36 (m, 2H), 7.95 (s, 1H), 7.51 (s, 1H), 7.40-7.34 (m, 1H), 7.19-7.16 (m, 1H), 7.07-6.99 (m, 1H), 6.77-6.76 (m, 1H), 3.86 (s, 3H), 2.40 (s, 3H). LC-MS calcd exact mass 360.08, found m/z 361.3 [M+H]$^+$.

Step 3: 1-(2-((2-Chloro-4-fluorophenyl)amino)-5-methylpyrimidin-4-yl)-1H-pyrrole-3-carboxylic acid

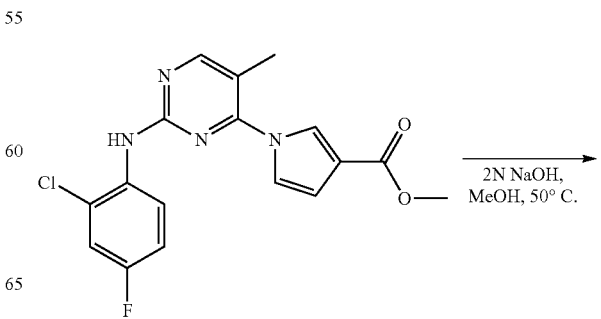

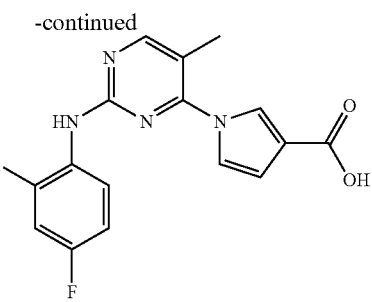

To a solution of methyl 1-(2-((2-chloro-4-fluorophenyl)amino)-5-methylpyrimidin-4-yl)-1H-pyrrole-3-carboxylate (0.25 g, 0.833 mmol) in methanol (20.0 mL) was added 2N-sodium hydroxide solution (10 mL). The reaction mixture was stirred at 50° C. for 2 h. Methanol was removed under reduced pressure and the pH was adjusted to pH-6.5-7 by addition of dilute hydrochloric acid. The aqueous layer was extracted with ethyl acetate (3×50 mL) and the combined organic layer was dried over sodium sulfate, filtered, and evaporated under reduced pressure to afford 1-(2-((2-chloro-4-fluorophenyl)amino)-5-methylpyrimidin-4-yl)-1H-pyrrole-3-carboxylic acid as an off-white solid (0.17 g, 71%). $^1$HNMR (400 MHz, DMSO-$d_6$): δ 12.14 (s, 1H), 9.06 (s, 1H), 8.39 (s, 1H), 7.86 (s, 1H), 7.67-7.64 (m, 1H), 7.50-7.48 (m, 1H), 7.36 (t, J=2.8 Hz, 1H), 7.24-7.19 (m, 1H), 6.57 (t, J=2.0 Hz, 2H), 2.27 (s, 3H). LC-MS calcd exact mass 346.06, found m/z 347.3 [M+H]$^+$.

Step 4: (S)-1-(2-((2-Chloro-4-fluorophenyl)amino)-5-methylpyrimidin-4-yl)-N-(1-(3-chlorophenyl)-2-hydroxyethyl)-1H-pyrrole-3-carboxamide

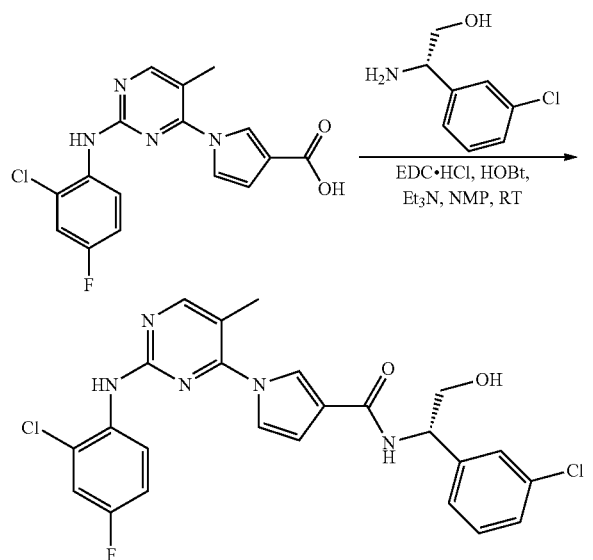

To a solution of 1-(2-(2-chloro-4-fluorophenyl)amino)-5-methylpyrimidin-4-yl)-1H-pyrrole-3-carboxylic acid (0.05 g, 0.144 mmol) in NMP (2.0 mL) were added (S)-2-amino-2-(3-chlorophenyl)ethanol (0.029 g, 0.173 mmol), EDC (0.055 g, 0.288 mmol) and HOBt (0.005 g, 0.043 mmol). To the resulting reaction mixture was added triethylamine (0.04 g, 0.432 mmol) dropwise at RT. The reaction mixture was stirred at RT for 15 h. The reaction mixture was poured into cold water (10 mL) and then extracted with ethyl acetate (3×50 mL). The combined organic layer was dried over sodium sulfate, filtered and evaporated under reduced pressure. The residue was dissolved in a small volume of DCM and then diluted with ether. The solvent was decanted. The solid that had formed was washed with ether and n-pentane to afford (S)-1-(2-((2-chloro-4-fluorophenyl)amino)-5-methylpyrimidin-4-yl)-N-(1-(3-chlorophenyl)-2-hydroxyethyl)-1H-pyrrole-3-carboxamide as an off-white solid (0.022 g, 31%). 1HNMR (400 MHz, DMSO-$d_6$): δ 8.99 (s, 1H), 8.37 (s, 1H), 8.25 (d, J=8.4 Hz, 1H), 7.95 (s, 1H), 7.69-7.65 (m, 1H), 7.49-7.41 (m, 1H), 7.37-7.18 (m, 6H), 6.75 (s, 1H), 5.04-4.99 (m, 1H), 4.92 (br s, 1H), 3.65-3.64 (m, 2H), 2.28 (s, 3H). LC-MS calcd exact mass 499.10, found m/z 500.3 [M+H]$^+$; HPLC Purity: 99.03%, chiral HPLC: 99.66%.

Example 5: (S)—N-(1-(3-chlorophenyl)-2-hydroxyethyl)-1-(2-(cyclopropylamino)-5-methylpyrimidin-4-yl)-1H-pyrazole-4-carboxamide (Compound #39)

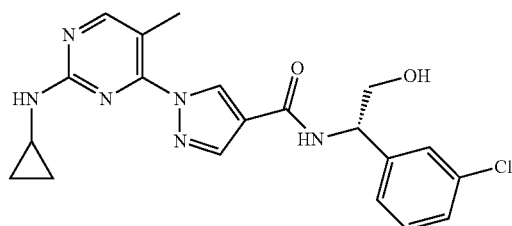

Step 1: Methyl 1-(2-chloro-5-methylpyrimidin-4-yl)-1H-pyrazole-4-carboxylate

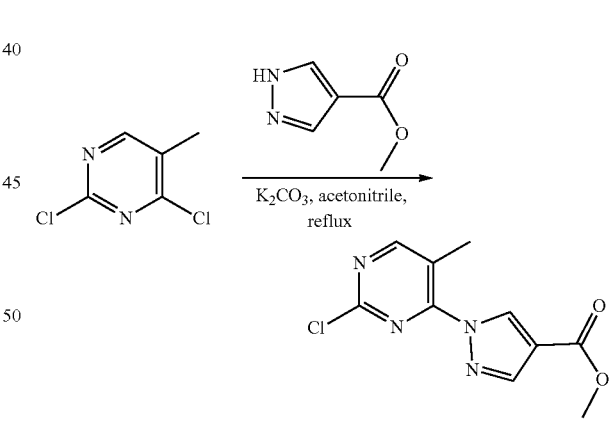

To a stirred solution of methyl-1H-pyrazole-4-carboxylate (1.00 g, 6.134 mmol) in acetonitrile (20 mL) was added potassium carbonate (2.543 g, 18.40 mmol), and the mixture was stirred for 5 min at RT. To this mixture was added 2,4-dichloro-5-methylpyrimidine (0.773 g, 6.134 mmol), and the mixture was stirred at 80° C. overnight. The mixture was cooled and water (15 mL) was added, and the mixture was extracted with ethyl acetate (3×50 mL). The combined organic layer was dried over sodium sulfate, then evaporated under reduced pressure and the residue was purified by gradient column chromatography using ethyl acetate in n-hexane as eluent to give methyl 1-(2-chloro-5-methylpyrimidin-4-yl)-1H-pyrazole-4-carboxylate as a colorless solid (0.65 g, 42%). 1HNMR (400 MHz, CDCl₃): δ 9.08 (s, 1H), 8.54 (s, 1H), 8.15 (s, 1H), 3.89 (s, 3H), 2.67 (s, 3H).

Step 2: Methyl 1-(2-(cyclopropylamino)-5-methylpyrimidin-4-yl)-1H-pyrazole-4-carboxylate

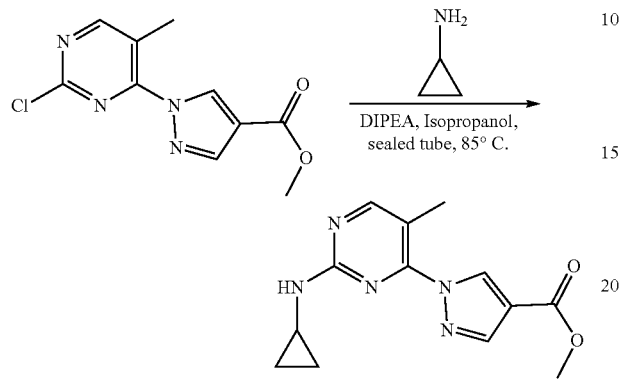

To a solution of methyl-1-(2-chloro-5-methylpyrimidin-4-yl)-1H-pyrazole-4-carboxylate (0.3 g, 1.18 mmol) in isopropanol (7 mL) was added DIPEA (0.43 mL, 2.47 mmol) and cyclopropylamine (0.09 mL, 1.3 mmol). The reaction mixture was stirred in a sealed glass tube at 85° C. overnight. The reaction mixture was cooled and quenched with water (10 mL), and extracted with ethyl acetate (3×10 mL). The organic layer was dried over sodium sulfate, filtered and evaporated under reduced pressure, and the residue was purified by gradient column chromatography using ethyl acetate in n-hexane as eluent to afford methyl 1-(2-(cyclopropylamino)-5-methylpyrimidin-4-yl)-1H-pyrazole-4-carboxylate as a colorless solid (0.17 g, 52%). 11HNMR (400 MHz, CDCl₃): δ 8.97 (s, 1H), 8.27 (s, 1H), 8.09 (s, 1H), 5.26 (s, 1H), 3.87 (s, 3H), 2.80-2.76 (m, 1H), 2.47 (s, 3H), 0.87-0.83 (m, 2H), 0.56 (t, J=7.2 Hz, 2H). LC-MS calcd exact mass 273.12, found m/z 274.6 [M+H]⁺.

Step 3: 1-(2-(cyclopropylamino)-5-methylpyrimidin-4-yl)-1H-pyrazole-4-carboxylic acid

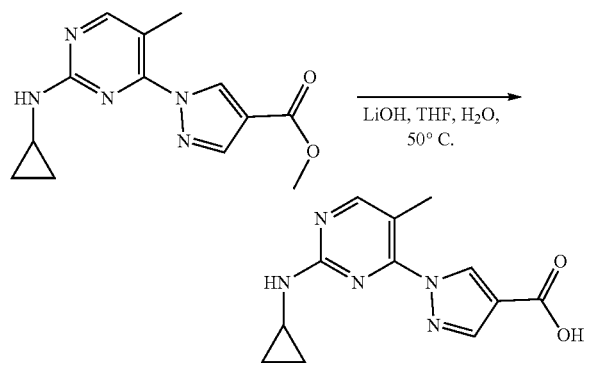

To a stirred solution of methyl 1-(2-(cyclopropylamino)-5-methylpyrimidin-4-yl)-1H-pyrazole-4-carboxylate (0.2 g, 0.72 mmol) in THF (7 mL) and water (1 mL) was added lithium hydroxide monohydrate (0.306 g, 7.29 mmol). The reaction mixture was stirred at 50° C. for 4 h. The mixture was cooled and concentrated under reduced pressure, and neutralized (pH~7) by addition of 1N HCl. The solid that formed was filtered to give 1-(2-(cyclopropylamino)-5-methylpyrimidin-4-yl)-1H-pyrazole-4-carboxylic acid as a colorless solid (0.122 g, 65%). 1HNMR (400 MHz, DMSO-d₆): δ 12.0 (br s, 1H), 8.82 (s, 1H), 8.31 (s, 1H), 8.09 (s, 1H), 7.48 (s, 1H), 2.74-2.71 (m, 1H), 2.30 (s, 3H), 0.69-0.65 (m, 2H), 0.48-0.44 (m, 2H). LC-MS calcd exact mass 259.11, found m/z 260.2 [M+H]⁺.

Step 4: (S)—N-(1-(3-chlorophenyl)-2-hydroxyethyl)-1-(2-(cyclopropylamino)-5-methylpyrimidin-4-yl)-1H-pyrazole-4-carboxamide

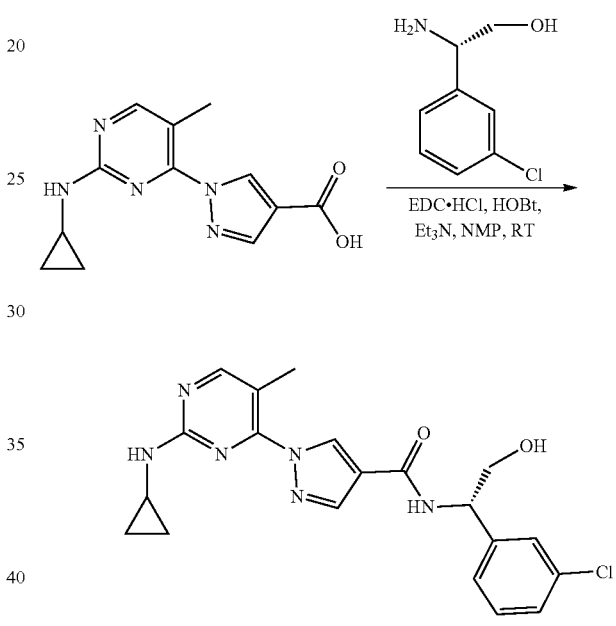

To a stirred solution of 1-(2-(cyclopropylamino)-5-methylpyrimidin-4-yl)-1H-pyrazole-4-carboxylic acid (0.035 g, 0.134 mmol) in NMP (0.8 mL) was added EDC (0.051 g, 0.26 mmol), HOBt (0.005 g, 0.04 mmol), and triethylamine (0.05 mL, 0.4 mmol), and the mixture was then stirred at RT for 10 min. To this mixture was added (S)-2-amino-2-(3-chlorophenyl)ethanol (0.027 g, 0.16 mmol). The reaction mixture was stirred at RT overnight. The mixture was diluted with water (10 mL) and extracted with ethyl acetate (2×20 mL). Combined organic layers were washed with brine, dried over sodium sulfate, and evaporated under reduced pressure. The residue was purified by column chromatography using methanol in DCM as eluent to afford (S)—N-(1-(3-chlorophenyl)-2-hydroxyethyl)-1-(2-(cyclopropylamino)-5-methylpyrimidin-4-yl)-1H-pyrazole-4-carboxamide as a colorless solid (0.011 g, 20%). 1HNMR (400 MHz, DMSO-d₆): δ 9.00 (s, 1H), 8.61 (d, J=8 Hz, 1H), 8.32 (s, 1H), 8.22 (s, 1H), 7.44 (d, J=11.2 Hz, 2H), 7.36-7.27 (m, 3H), 5.07-5.01 (m, 1H), 4.98-4.95 (m, 1H), 3.66-3.65 (m, 2H), 2.76-2.73 (m, 1H), 2.34 (s, 3H), 0.68 (d, J=5.2 Hz, 2H), 0.48 (d, J=2.4 Hz, 2H). LC-MS calcd exact mass 412.14, found m/z 413.2 [M+H]⁺; HPLC Purity 99.32%, Chiral HPLC Purity 99.76%.

Representative Example for General Scheme 4

Example 6: N-(2-amino-1-(3-chlorophenyl)ethyl)-1-(2-(2,2-difluorobenzo[d][1,3]dioxol-5-yl)amino)-5-methylpyrimidin-4-yl)-1H-pyrrole-3-carboxamide (Compound #136)

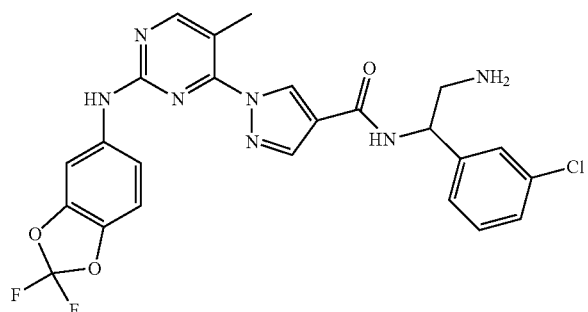

Step 1: Methyl 1H-pyrrole-3-carboxylate

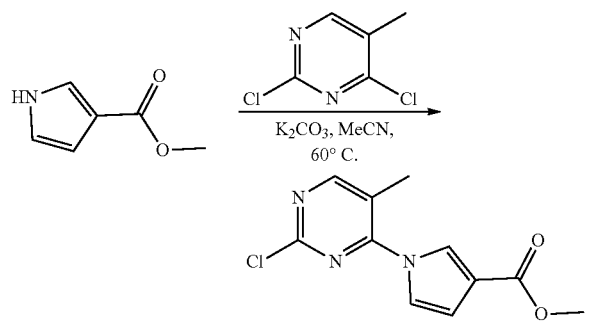

To a solution of 1H-pyrrole-3-carboxylic acid (4.3 g, 38.7 mmol) in methanol (40 mL) that was cooled to 0-5° C. was added 6N HCl (9 mL). The mixture was stirred at RT for 5 min, and then heated at reflux overnight. The reaction mixture was cooled and concentrated under reduced pressure, then cooled to 0° C. and adjusted to pH~7 by the addition of saturated sodium bicarbonate. The mixture was extracted with ethyl acetate, and the organic layer was dried over sodium sulfate, filtered and evaporated under reduced pressure to afford methyl 1H-pyrrole-3-carboxylate as a brown solid (4 g, 83%). $^1$HNMR (400 MHz, CDCl$_3$): δ 8.56 (br s, 1H), 7.43 (s, 1H), 6.75 (s, 1H), 6.65 (s, 1H), 3.92 (s, 3H). LC-MS calcd exact mass 125.05, found m/z 126.2 [M+H]$^+$.

Step 2: Methyl 1-(2-chloro-5-methylpyrimidin-4-yl)-1H-pyrrole-3-carboxylate

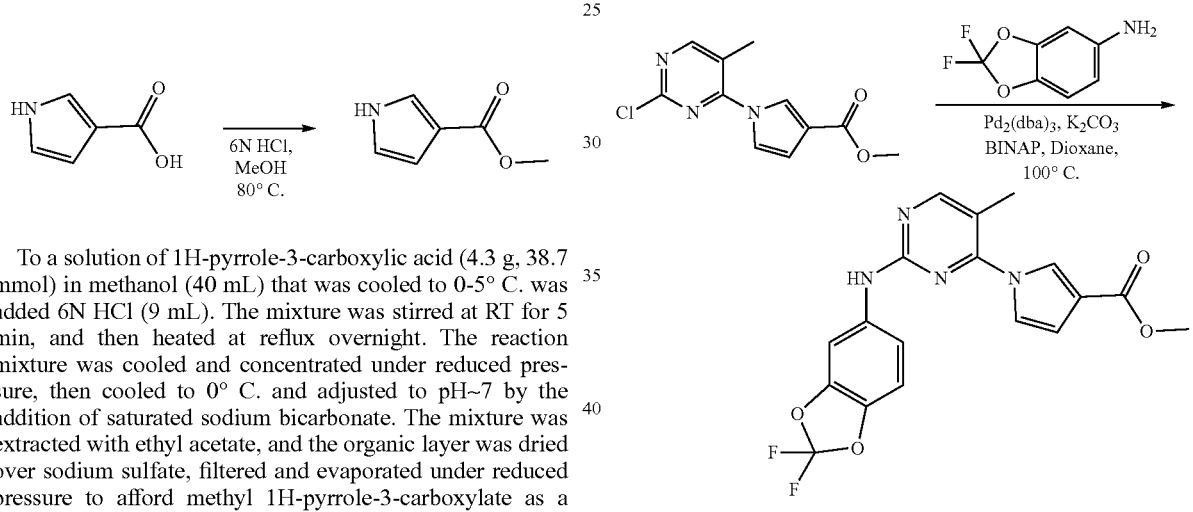

To a solution of methyl-1H-pyrrole-3-carboxylate (1.4 g, 11.2 mmol) in acetonitrile (50 mL) was added potassium carbonate (3.09 g, 22.4 mmol). The mixture was stirred at RT for 15 min and then 2,4-dichloro-5-methylpyrimidine (2.738 g, 16.8 mmol) was added. The resulting mixture was heated at reflux overnight. The reaction mixture was cooled and then evaporated under reduced pressure, combined with water and extracted with ethyl acetate. The combined organic layer was dried over sodium sulfate, filtered and evaporated under reduced pressure. The residue was purified by gradient column chromatography using ethyl acetate in n-hexane as eluent to afford methyl 1-(2-chloro-5-methylpyrimidin-4-yl)-1H-pyrrole-3-carboxylate as a white solid (1.2 g, 43%). $^1$HNMR (400 MHz, CDCl$_3$): δ 8.50 (s, 1H), 7.99 (s, 1H), 7.40-7.39 (m, 1H), 6.78-6.77 (m, 1H), 3.85 (s, 3H), 2.51 (s, 3H). LC-MS calcd exact mass 251.05, found m/z 252.3 [M+H]$^+$.

Step 3: Methyl 1-(2-((2,2-difluorobenzo[d][1,3]dioxol-5-yl)amino)-5-methylpyrimidin-4-yl)-1H-pyrrole-3-carboxylate To a solution of methyl-1-(2-chloro-5-methylpyrimidin-4-yl)-1H-pyrrole-3-carboxylate (3.1 g 12.31 mmol) in dioxane (20 mL) was added potassium carbonate (2.549 g, 18.47 mmol), 2,2'-bis(diphenylphosphino)-1,1'-binaphthalene (0.766 g, 1.231 mmol) and 2,2-difluorobenzo[d][1,3]dioxol-5-amine (2.23 g, 12.92 mmol). The reaction mixture was degassed with argon for 15 min, followed by the addition of tris(dibenzylideneacetone)-dipalladium(0) (0.563 g, 0.615 mmol). The resulting mixture was stirred in a sealed glass tube at 100° C. for 9 h. The reaction mixture was filtered on Celite, and the filtrate was concentrated under reduced pressure. The residue was dissolved in water, extracted with ethyl acetate, and the combined organic phase was washed with water and brine. The combined organic phase was dried over sodium sulfate, filtered and evaporated under reduced pressure. The residue was purified by gradient column chromatography using ethyl acetate in n-hexane as eluent to afford methyl 1-(2-((2,2-difluorobenzo[d][1,3]dioxol-5-yl)amino)-5-methylpyrimidin-4-yl)-1H-pyrrole-3-carboxylate as an off-white solid (2.3 g, 48%). $^1$HNMR (400 MHz, CDCl$_3$): δ 8.34 (s, 1H), 7.95 (s, 1H), 7.69 (d, J=1.6 Hz, 1H), 7.34 (t, J=2.8 Hz, 1H), 7.23 (s, merged with CDCl$_3$ peak, 1H), 7.06-6.99 (m, 2H), 6.78-6.77 (m, 1H), 3.86 (s, 3H), 2.40 (s, 3H). LC-MS calcd exact mass 388.10, found m/z 389.3 [M+H]⁺.

Step 4: 1-(2-((2,2-difluorobenzo[d][1,3]dioxol-5-yl)amino)-5-methylpyrimidin-4-yl)-1H-pyrrole-3-carboxylic acid

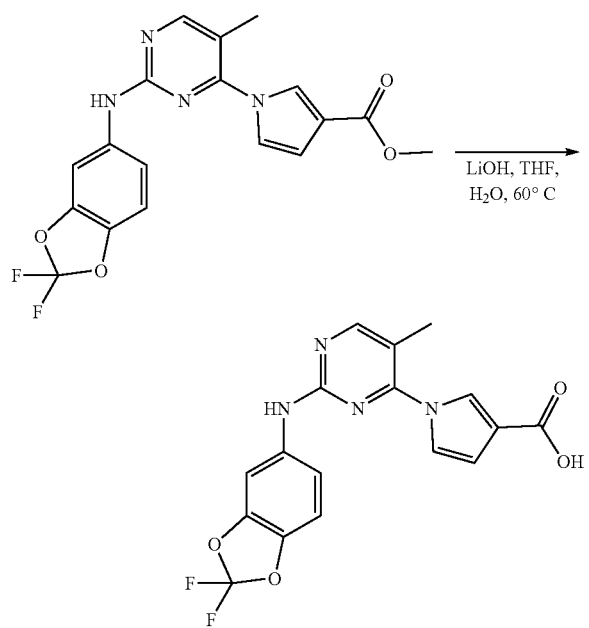

To a solution of methyl 1-(2-((2,2-difluorobenzo[d][1,3]dioxol-5-yl)amino)-5-methylpyrimidin-4-yl)-1H-pyrrole-3-carboxylate (1.0 g, 2.5 mmol) in THF (40 mL) and water (20 mL) was added lithium hydroxide monohydrate (0.648 g, 15.4 mmol). The resulting mixture was heated to reflux at 70° C. for 12 h. The reaction mixture was cooled and then concentrated under reduced pressure, and adjusted to pH~6 by the addition of 1N HCl. The solid was filtered and washed with n-pentane and diethyl ether to afford 1-(2-((2,2-difluorobenzo[d][1,3]dioxol-5-yl)amino)-5-methylpyrimidin-4-yl)-1H-pyrrole-3-carboxylic acid as a white solid (0.85 g, 88%). ¹HNMR (400 MHz, DMSO-d₆): δ 11.98 (br s, 1H), 9.58 (s, 1H), 8.38 (s, 1H), 7.94-7.82 (m, 2H), 7.36 (d, 2H J=8 Hz), 7.0 (d, 1H J=8.4 Hz), 6.69 (s, 1H), 2.38 (s, 3H). LC-MS calcd exact mass 374.08, found m/z 375.1 [M+H]⁺.

Step 5: N-((3-Chlorophenyl)(cyano)methyl)-1-(2-((2,2-difluorobenzo[d][1,3]dioxol-5-yl)amino)-5-methylpyrimidin-4-yl)-1H-pyrrole-3-carboxamide

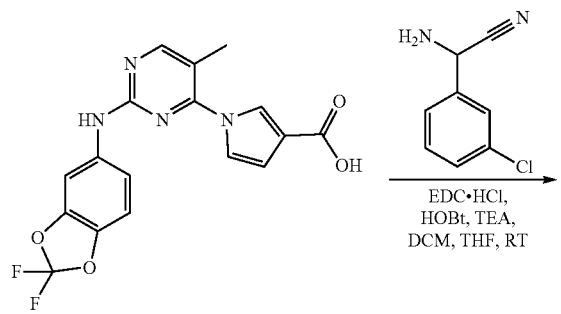

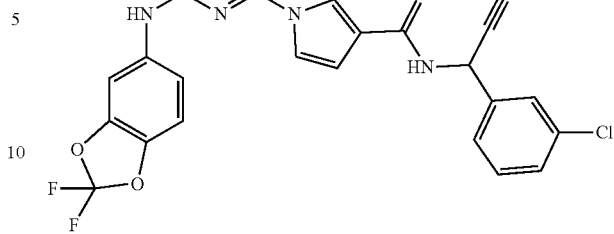

To a solution of 1-(2-((2,2-difluorobenzo[d][1,3]dioxol-5-yl)amino)-5-methylpyrimidin-4-yl)-1H-pyrrole-3-carboxylic acid (0.2 g, 0.53 mmol) in DCM (15 mL) and THF (3 mL) was added triethylamine (0.2 mL, 1.6 mmol), and the mixture was stirred for 5 min under nitrogen atmosphere. Then, to the mixture was added 2-amino-2-(3-chlorophenyl)acetonitrile (0.1 g, 0.64 mmol), EDC (0.2 g, 1.06 mmol), and HOBt (0.021 g, 0.16 mmol). The resulting mixture was stirred at RT overnight. The reaction mixture was quenched with water, and extracted with DCM. The combined organic layer was washed with water and brine, dried over sodium sulfate, filtered and evaporated under reduced pressure. The residue was purified by gradient column chromatography using ethyl acetate in n-hexane as eluent to afford N-((3-chlorophenyl)(cyano)methyl)-1-(2-((2,2-difluorobenzo[d][1,3]dioxol-5-yl)amino)-5-methylpyrimidin-4-yl)-1H-pyrrole-3-carboxamide as a white solid (0.1 g, 36%). 1HNMR (400 MHz, CDCl₃): δ 8.35 (s, 1H), 7.95 (s, 1H), 7.6 (s, 1H), 7.56 (s, 1H), 7.4 (d, J 6.8 Hz, 1H), 7.41-7.38 (m, 3H), 7.0-6.99 (m, 2H), 6.6 (s, 1H), 6.4 (d, J 8.8 Hz, 2H), 6.34 (d, J 8.8 Hz, 2H), 2.4 (s, 3H). LC-MS calcd exact mass 522.10, found m/z 523.2 [M+H]⁺, HPLC purity 98.03%.

Step 6: N-(2-Amino-1-(3-chlorophenyl)ethyl)-1-(2-((2,2-difluorobenzo[I][1,3]dioxol-5-yl)amino)-5-methylpyrimidin-4-yl)-1H-pyrrole-3-carboxamide

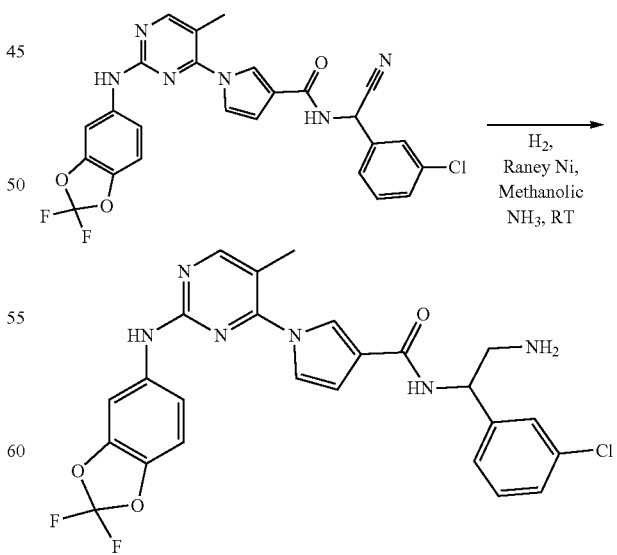

To a solution of N-(3-chlorophenyl)(cyano)methyl)-1-(2-((2,2-difluorobenzo[d][1,3]dioxol-5-yl)amino)-5-methylpyrimidin-4-yl)-1H-pyrrole-3-carboxamide (0.1 g, 0.191 mmol) in methanol (10 mL) was added methanolic ammonia (20 mL) at 0° C., followed by the addition of Raney nickel (0.05 g). The resulting reaction mixture was stirred overnight at RT under a hydrogen atmosphere using a bladder. The reaction mixture was filtered on Celite, and the filtrate was evaporated under reduced pressure. The residue was purified by gradient column chromatography using methanol in DCM as eluent to afford N-(2-amino-1-(3-chlorophenyl)ethyl)-1-(2-((2,2-difluorobenzo[d][1,3]dioxol-5-yl)amino)-5-methylpyrimidin-4-yl)-1H-pyrrole-3-carboxamide as an off-white solid (0.03 g, 30%). 1HNMR (400 MHz, CDCl3): δ 8.34 (s, 1H), 7.95 (s, 1H), 7.69 (d, J=1.6 Hz, 1H), 7.34 (t, J=2.8 Hz, 1H), 7.23 (s, merged with CDCl3 peak, 1H), 7.06-6.99 (m, 2H), 6.78-6.77 (m, 1H), 3.86 (s, 3H), 2.40 (s, 3H). LC-MS calcd exact mass 526.13, found m/z 527.5 [M+H]+.

Example 7: N-(2-Amino-1-(3-chlorophenyl)ethyl)-1-(5-methyl-2-((tetrahydro-2H-pyran-4-yl)amino)pyrimidin-4-yl)-1H-imidazole-4-carboxamide (Compound #225)

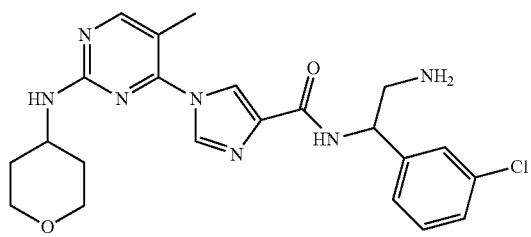 [SMILES: Cc1cnc(NC2CCOCC2)nc1-n1cnc(C(=O)NC(CN)c2cccc(Cl)c2)c1]

Step 1: Methyl 1-(2-chloro-5-methylpyrimidin-4-yl)-1H-imidazole-4-carboxylate

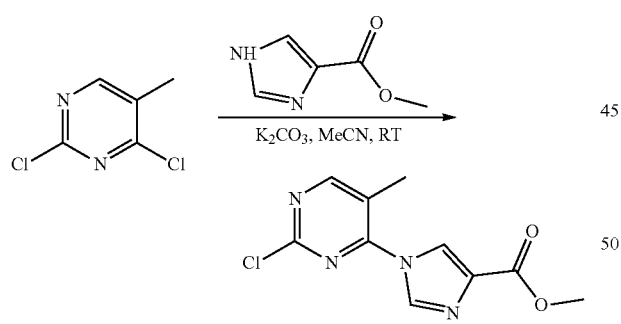

To a solution of methyl-1H-imidazole-4-carboxylate (10.37 g, 74.0 mmol) in acetonitrile (200 mL) was added 2,4-dichloro-5-methylpyrimidine (10 g, 61.7 mmol) and potassium carbonate (25.5 g, 185.2 mmol), and then the mixture was stirred at RT for 16 h under an inert atmosphere. The reaction mixture was quenched with water, and extracted with ethyl acetate. The organic layer was washed with water, dried over sodium sulfate, filtered and evaporated under reduced pressure. The residue was purified by gradient column chromatography using ethyl acetate in hexane as eluent to afford methyl 1-(2-chloro-5-methylpyrimidin-4-yl)-1H-imidazole-4-carboxylate as a white solid (11 g, 75%). 1HNMR (400 MHz, DMSO-d6): δ 8.88 (s, 1H), 8.38 (s, 2H), 3.80 (s, 3H), 2.41 (s, 3H). LC-MS exact mass calcd 252.04, found m/z 253.2 [M+H]+.

Step 2: Methyl 1-(5-methyl-2-((tetrahydro-2H-pyran-4-yl)amino)pyrimidin-4-yl)-1H-imidazole-4-carboxylate

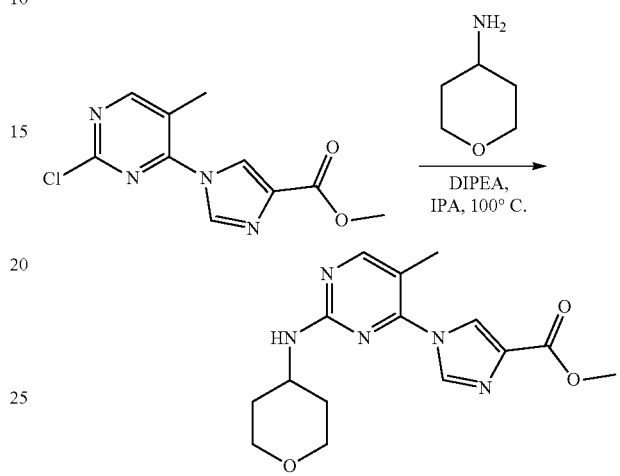

To a solution of 1-(2-chloro-5-methylpyrimidin-4-yl)-1H-imidazole-4-carboxylate (5 g, 19.7 mmol) in isopropanol (30 mL) was added DIPEA (7.658 g, 59.0 mmol) and tetrahydro-2H-pyran-4-amine (2.402 g, 23.0 mmol). The resulting mixture was stirred in a sealed glass tube at 100° C. for 17 h. The reaction mixture was cooled to RT, and allowed to form crystals. The crystals were filtered, washed with hexane, and dried under vacuum to afford methyl 1-(5-methyl-2-((tetrahydro-2H-pyran-4-yl)amino)-pyrimidin-4-yl)-1H-imidazole-4-carboxylate as an off-white solid (5.2 g, 83%). 1HNMR (400 MHz, DMSO-d6): δ 8.36 (s, 1H), 8.30 (s, 1H), 8.27 (s, 1H), 7.39 (d, J=7.6 Hz, 1H), 3.90-3.83 (m, 3H), 3.78 (s, 3H), 3.37 (t, J=11.6 Hz, 2H), 2.16 (s, 3H), 1.82 (d, J 12 Hz, 2H), 1.54-1.45 (m, 2H), LC-MS exact mass calcd 317.15, found m/z 318.2 [M+H]+.

Step 3: N-((3-Chlorophenyl)(cyano)methyl)-1-(5-methyl-2-((tetrahydro-2H-pyran-4-yl)amino)-pyrimidin-4-yl)-1H-imidazole-4-carboxamide

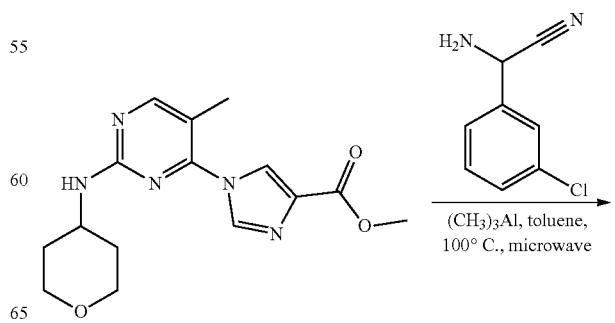

-continued

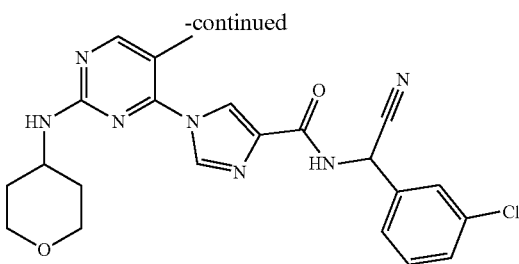

To a solution of methyl 1-(5-methyl-2-((tetrahydro-2H-pyran-4-yl)amino)pyrimidin-4-yl)-1H-imidazole-4-carboxylate (0.500 g, 1.57 mmol) in toluene (20 mL) was added 2-amino-2-(3-chlorophenyl)acetonitrile (0.392 g, 2.3 mmol) and trimethylaluminium (2M solution in toluene; 1.96 mL, 2.5 eq). The resulting mixture was stirred in CEM microwave at 100° C. for 1 h. The reaction mixture was quenched with water, and extracted with ethyl acetate. The organic layer was washed with cold water, dried over sodium sulfate, filtered and evaporated under reduced pressure. The residue was purified by gradient column chromatography twice using methanol in DCM as eluent to give N-((3-chlorophenyl)(cyano)methyl)-1-(5-methyl-2-((tetrahydro-2H-pyran-4-yl)amino)pyrimidin-4-yl)-1H-imidazole-4-carboxamide as a yellow solid (0.29 g). LC-MS exact mass calcd 451.15, found m/z 452.2 [M+H]$^+$.

Step 4: N-(2-Amino-1-(3-chlorophenyl)ethyl)-1-(5-methyl-2-((tetrahydro-2H-pyran-4-yl)amino)pyrimidin-4-yl)-1H-imidazole-4-carboxamide

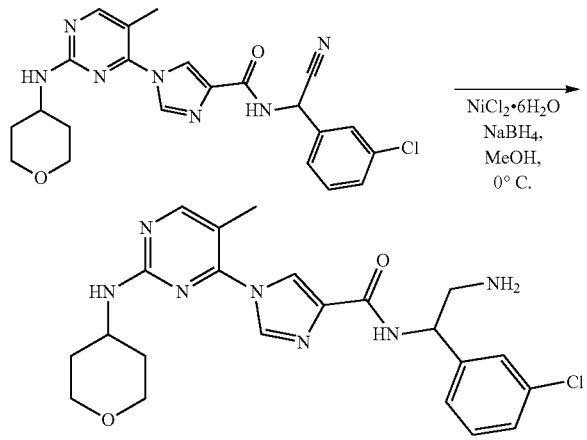

To a solution of N-((3-chlorophenyl)(cyano)methyl)-1-(5-methyl-2-((tetrahydro-2H-pyran-4-yl)amino)pyrimidin-4-yl)-1H-imidazole-4-carboxamide (0.700 g, 1.54 mmol) in methanol (15 mL) was added nickel dichloride hexahydrate (0.552 g, 2.3 mmol) at 0° C. under an inert atmosphere, and then the mixture was stirred to obtain a clear solution. To the reaction mixture was slowly added sodium borohydride (0.175 g, 4.6 mmol) at 0° C. and then the mixture was stirred for 10 min at 0° C. The reaction mixture was filtered through Celite and the filtrate was evaporated under reduced pressure. The residue was purified by gradient column chromatography using methanol in dichloromethane as eluent to afford N-(2-amino-1-(3-chlorophenyl)ethyl)-1-(5-methyl-2-((tetrahydro-2H-pyran-4-yl)amino)pyrimidin-4-yl)-1H-imidazole-4-carboxamide (racemic mixture) as an off-white solid (0.050 g, 7%), which was used directly in the chiral HPLC separation. Data obtained for a separate batch that was prepared in a similar manner: 1HNMR (400 MHz, DMSO-d6): δ 8.53 (d, J=8 Hz 1H), 8.32 (s, 1H), 8.25 (s, 1H), 8.06 (s, 1H), 7.40 (s, 1H), 7.32-7.27 (m, 4H), 4.98-4.88 (m, 1H), 3.83-3.81 (m, 3H), 3.37-3.35 (m, 2H), 2.95-2.88 (m, 2H), 2.16 (s, 3H), 1.79 (d, J=11.2 Hz, 2H), 1.50-1.40 (m, 2H). LC-MS exact mass calcd 455.18, found m/z 456.5 [M+H]$^+$.

Example 8a: Enantiomer #1, (S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide; and Example 8b: Enantiomer, (R)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide (Compound #225a and Compound #225b, respectively)

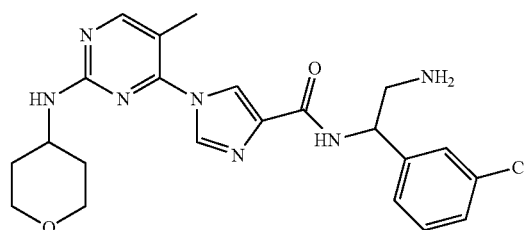

Racemic N-(2-amino-1-(3-chlorophenyl)ethyl)-1-(5-methyl-2-((tetrahydro-2H-pyran-4-yl)-amino)pyrimidin-4-yl)-1H-imidazole-4-carboxamide (50 mg) was dissolved in 1 mL 50:50 methanol/DCM, and subjected to chiral HPLC purification using Chiralpak® IA column [250 mm×4.6 mm×5 µm], with mobile phase as isopropyl alcohol with 0.01% diethylamine (100%); flow rate 1 mL/min. Eluted fractions of the two enantiomers were separately collected and these fractions were separately evaporated to afford 12 mg (48% recovery) of Enantiomer #1 ((S), Compound #225a) as the first eluting enantiomer, and 10 mg (40% recovery) of Enantiomer #2 ((R), Compound #225b) as the second eluting enantiomer, with >98.1% ee and >98.7% ee, respectively.

Example 8a, Compound #225a (Enantiomer #1, (S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide): 1HNMR (400 MHz, DMSO-d$_6$): δ 8.58 (d, J=6.8 Hz, 1H), 8.33 (s, 1H), 8.27 (s, 1H), 8.07 (s, 1H), 7.41 (s, 1H), 7.36-7.28 (m, 4H), 4.97 (br s, 1H), 3.84-3.82 (m, 3H), 3.38-3.33 (m, 2H), 3.01-2.94 (m, 2H), 2.16 (s, 3H), 1.80 (d, J=11.6 Hz, 2H), 1.52-1.44 (m, 2H). LC-MS exact mass calcd 455.18, found m/z 456.2 [M+H]$^+$.

Example 8b, Compound #225b (Enantiomer #2, (R)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide): 1HNMR (400 MHz, DMSO-d$_6$): δ 8.58 (d, J=8 Hz, 1H), 8.33 (s, 1H), 8.27 (s, 1H), 8.07 (s, 1H), 7.42 (s, 1H), 7.36-7.27 (m, 4H), 5.02-4.91 (m, 1H), 3.84-3.82 (m, 3H), 3.35 (m, 2H), 3.05-2.91 (m, 2H), 2.16 (s, 3H), 1.79 (d, J=11.6 Hz, 2H), 1.51-1.4 (m, 2H). LC-MS exact mass calcd 455.18, found m/z 456.2 [M+H]$^+$.

Representative Example for General Scheme 5

Example 9: 1-(2-((4-Fluorophenyl)amino)-5-methylpyrimidin-4-yl)-N-(2-hydroxy-1-phenylethyl)-2-methyl-1H-imidazole-4-carboxamide (Compound #153)

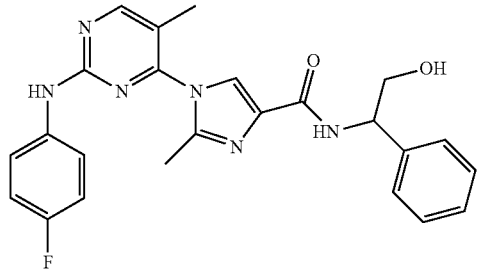 [SMILES: Cc1cnc(Nc2ccc(F)cc2)nc1-n1cc(C(=O)NC(CO)c2ccccc2)nc1C]

Step 1: 1-(2-Chloro-5-methylpyrimidin-4-yl)-2-methyl-1H-imidazole-4-carbaldehyde

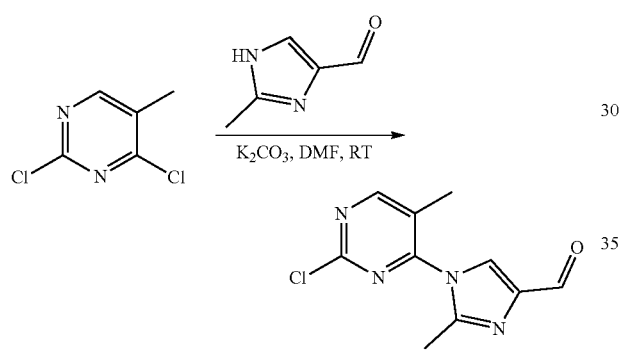

A mixture of 2,4-dichloro-5-methylpyrimidine (2.50 g, 15.33 mmol), 2-methyl-1H-imidazole-4-carbaldehyde (1.85 g, 16.87 mmol), and potassium carbonate (4.65 g, 33.74 mmol) in DMF (30 mL) was stirred at RT for 18 h. The mixture was diluted with water (100 mL) and extracted with ethyl acetate (3×100 mL). The organic layer was dried over sodium sulfate and evaporated under reduced pressure, and the residue was purified by column chromatography over silica gel (100-200 mesh) using 80-90% ethyl acetate in hexanes as eluent to obtain 1-(2-chloro-5-methylpyrimidin-4-yl)-2-methyl-1H-imidazole-4-carbaldehyde (0.5 g, 15%). 1HNMR (400 MHz, DMSO-$d_6$): δ 9.76 (s, 1H), 8.99 (s, 1H), 8.40 (s, 1H), 2.35 (s, 1H), 2.22 (s, 3H). LC-MS: exact mass calcd 236.05, found m/z 237.07 [M+H]$^+$, purity: 99.23%.

Step 2: 1-(2-Chloro-5-methylpyrimidin-4-yl)-2-methyl-1H-imidazole-4-carboxylic acid

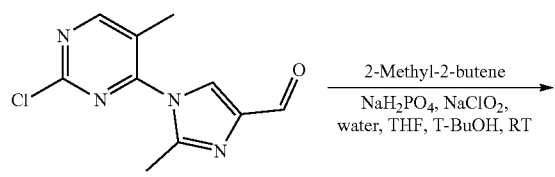

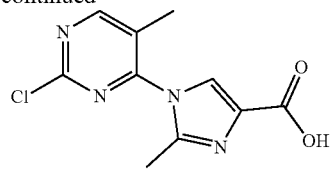

To a solution of 1-(2-chloro-5-methylpyrimidin-4-yl)-2-methyl-1H-imidazole-4-carbaldehyde (0.5 g, 2.11 mmol) in t-butanol (1.5 mL) and THF (7 mL) at RT was added 2-methyl-2-butene. To this mixture, a solution of sodium chlorite (1.87 g, 20.7 mmol) and sodium dihydrogenphosphate (1.5 g, 12.28 mmol) in water (5 mL) was added slowly. After TLC showed complete reaction, the mixture was diluted with water (25 mL) and washed with ethyl acetate (2×10 mL). The aqueous layer was concentrated under vacuum and extracted with 10% methanol in DCM (3×50 mL). The organic layer was concentrated under reduced pressure to obtain 1-(2-chloro-5-methylpyrimidin-4-yl)-2-methyl-1H-imidazole-4-carboxylic acid (0.70 g) as a white solid. LC-MS exact mass calcd 252.04, found m/z 253.0 [M+H]$^+$.

Step 3: 1-(2-Chloro-5-methylpyrimidin-4-yl)-N-(2-hydroxy-1-phenylethyl)-2-methyl-1H-imidazole-4-carboxamide

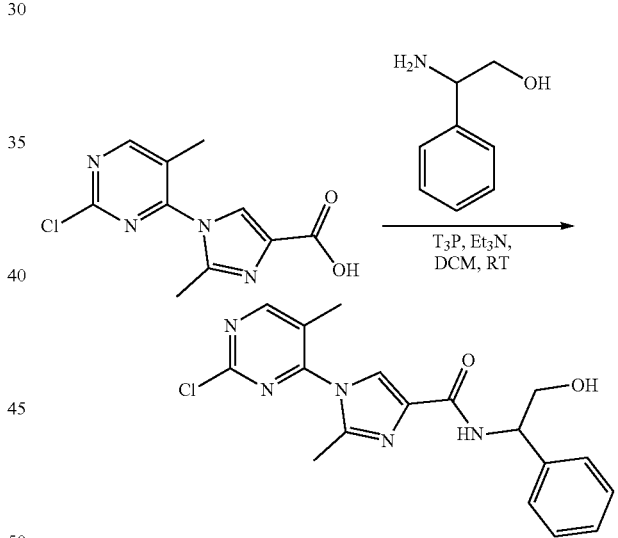

To a solution of 1-(2-chloro-5-methylpyrimidin-4-yl)-2-methyl-1H-imidazole-4-carboxylic acid (0.5 g, 1.98 mmol) and triethylamine (0.5 mL, 3.96 mmol) in DCM was added slowly (DL)-2-amino-2-phenylethan-1-ol (0.288 g, 2.18 mmol). To this mixture, T3P (2.5 mL, 3.96 mmol, 50% solution in ethyl acetate) was added and the mixture was stirred at RT for 18 h. After TLC showed reaction was complete, the mixture was quenched by the addition of water (30 mL). The mixture was extracted with DCM (3×30 mL), and the organic layer was washed with brine, dried over sodium sulfate and evaporated under reduced pressure. The residue was purified by flash chromatography on silica gel (230-400 mesh) using 5% MeOH in DCM as eluent to obtain 1-(2-chloro-5-methylpyrimidin-4-yl)-N-(2-hydroxy-1-phenylethyl)-2-methyl-1H-imidazole-4-carboxamide (0.580 g, 79%) as an off-white solid. 1HNMR (400 MHz, DMSO-$d_6$):

δ 8.95 (s, 1H), 8.26 (d, J=8.4 Hz, 1H), 7.98 (s, 1H), 7.36-7.35 (m, 2H), 7.33-7.34 (m, 3H), 7.22-7.21 (m, 1H), 5.02-4.98 (m, 2H), 3.74-3.69 (m, 2H), 2.36 (s, 3H), 2.21 (s, 3H). LC-MS Exact mass calcd 371.11, found m/z 372.0 [M+H]$^+$.

Step 4: 1-(2-((4-Fluorophenyl)amino)-5-methylpyrimidin-4-yl)-N-(2-hydroxy-1-phenylethyl)-2-methyl-1H-imidazole-4-carboxamide

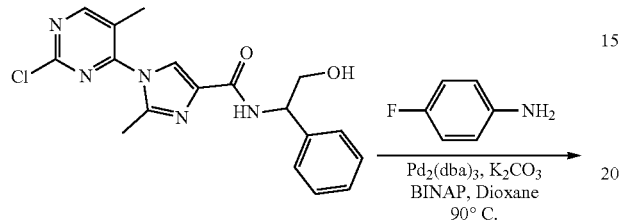

A mixture of 1-(2-chloro-5-methylpyrimidin-4-yl)-N-(2-hydroxy-1-phenylethyl)-2-methyl-1H-imidazole-4-carboxamide (0.5 g, 1.42 mmol), 4-fluoroaniline (0.173 g, 1.56 mmol), and potassium carbonate (0.39 g, 2.84 mmol) in dioxane (20 mL) in a glass tube was purged with argon gas for 10 min. Tris(dibenzylideneacetone)dipalladium(0) (0.130 g, 0.142 mmol) and BINAP (0.0.089 g, 0.142 mmol) were added to the reaction mixture which was purged with argon gas for another 10 min. The mixture was heated at 90° C. in a sealed glass tube for 6 hours. After reaction was complete, the reaction mixture was cooled, diluted with water and extracted with ethyl acetate (3×100 mL). The organic layer was dried over sodium sulfate and evaporated, and the residue was purified by flash column chromatography over silica gel (230-400 mesh) using 80% ethyl acetate in hexanes as eluent to give 1-(2-((4-fluorophenyl)amino)-5-methylpyrimidin-4-yl)-N-(2-hydroxy-1-phenylethyl)-2-methyl-1H-imidazole-4-carboxamide (0.109 g, 17%) as a white solid. 1HNMR (400 MHz, DMSO-d$_6$): δ 9.89 (s, 1H), 8.60 (s, 1H), 8.21 (d, J=8.4 Hz, 1H), 7.92 (s, 1H), 7.70-7.67 (m, 2H), 7.37 (d, J=7.2 Hz, 2H), 7.31 (t, J=7.2 Hz, 2H), 7.24 (d, J=7.2 Hz, 1H), 7.16 (t, J=8.8 Hz, 2H), 5.02 (d, J=4.8 Hz, 2H), 3.77-3.69 (m, 2H), 2.35 (s, 3H), 2.03 (s, 3H). LC-MS calcd exact mass 446.19, found m/z 447.52 [M+H]$^+$, purity: 96.12%.

Representative Examples for General Scheme 6

Example 10: N—((S)-1-(3-Chlorophenyl)-2-hydroxyethyl)-1-(5-methyl-2-(((S)-tetrahydrofuran-3-yl)amino)pyrimidin-4-yl)-1H-imidazole-4-carboxamide (Compound #192)

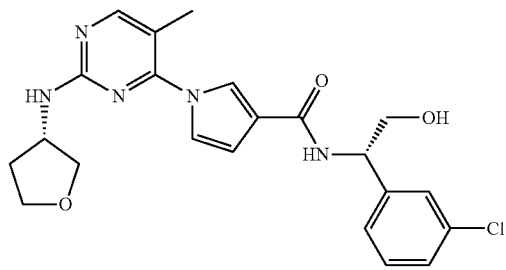 [SMILES: Cc1cnc(N[C@H]2CCOC2)nc1-n1ccc(C(=O)N[C@H](CO)c2cccc(Cl)c2)c1]

Step 1: Methyl 1-(2-chloro-5-methylpyrimidin-4-yl)-1H-imidazole-4-carboxylate

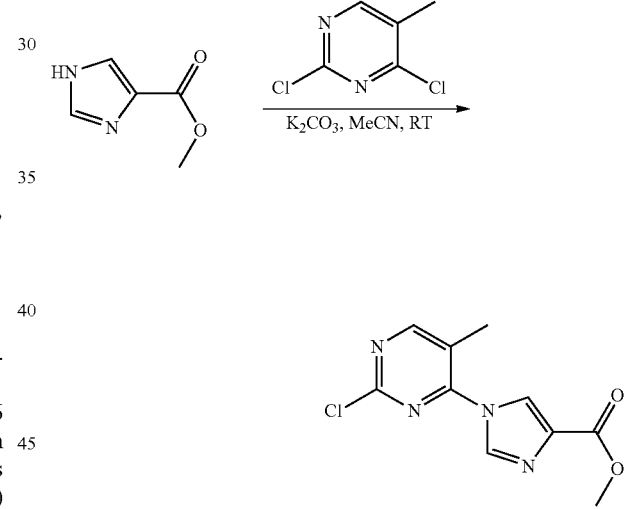

To a stirred solution of methyl-1H-imidazole-4-carboxylate (7 g, 42.9 mmol) in acetonitrile (50 mL), was added potassium carbonate (11.87 g, 85.88 mmol). The mixture was stirred at RT and then 2,4-dichloro-5-methylpyrimidine (5.41 g, 42.9 mmol) was added, and the mixture was stirred at RT overnight. The mixture was combined with water (50 mL) and extracted with ethyl acetate (3×150 mL). The combined organic layer was washed with brine (20 mL), dried over anhydrous sodium sulfate, filtered and evaporated under reduced pressure and the residue was purified by gradient column chromatography using ethyl acetate in n-hexane as eluent to afford methyl 1-(2-chloro-5-methylpyrimidin-4-yl)-1H-imidazole-4-carboxylate as a white solid (4.5 g, 41%). 1HNMR (400 MHz, DMSO-d$_6$): δ 8.88 (s, 1H), 8.38 (s, 1H), 3.8 (s, 3H), 2.41 (s, 3H). LC-MS calcd exact mass 252.04, found m/z 253.2 [M+H]$^+$.

Step 2: (S)-Methyl 1-(5-methyl-2-((tetrahydrofuran-3-yl)amino)pyrimidin-4-yl)-1H-imidazole-4-carboxylate

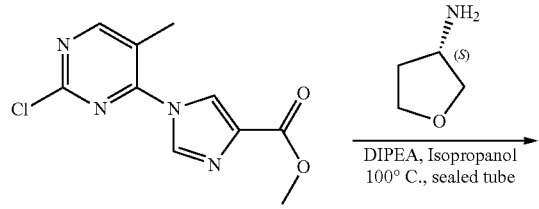

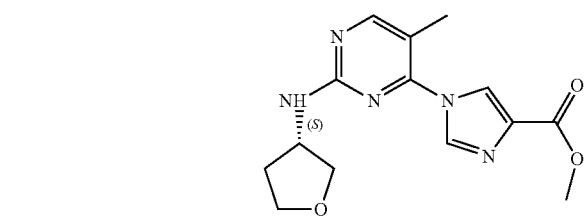

To a solution of methyl 1-(2-chloro-5-methylpyrimidin-4-yl)-1H-imidazole-4-carboxylate (0.6 g, 2.37 mmol) in isopropanol (30 mL) was added (S)-tetrahydrofuran-3-amine (0.310 g, 3.56 mmol) and DIPEA (1.53 g, 11.8 mmol), and the mixture was stirred in a sealed glass tube for 36 h at 100° C. The mixture was cooled and then concentrated under reduced pressure, diluted with water (50 mL) and extracted with ethyl acetate (2×100 mL). The organic layer was washed with brine (5 mL), dried over anhydrous sodium sulfate, filtered and evaporated under reduced pressure. The residue was purified by gradient column chromatography using ethyl acetate in hexane as eluent to afford (S)-methyl 1-(5-methyl-2-((tetrahydrofuran-3-yl)amino)pyrimidin-4-yl)-1H-imidazole-4-carboxylate as a white solid (0.45 g, 63% yield). 1HNMR (400 MHz, CDCl₃): δ 8.28 (s, 1H), 8.16 (d, J=2.4 Hz, 2H), 5.47 (s, 1H), 4.56 (s, 1H), 4.0-3.88 (m, 5H), 3.87-3.85 (m, 1H), 3.75-3.71 (m, 1H), 2.31 (s, 3H), 2.36-2.33 (m, 1H), 1.92-1.85 (m, 2H), LC-MS calcd exact mass 303.13, found m/z 304.4 [M+H]⁺.

Step 3: N—((S)-1-(3-Chlorophenyl)-2-hydroxyethyl)-1-(5-methyl-2-(((S)-tetrahydrofuran-3-yl)amino)pyrimidin-4-yl)-1H-imidazole-4-carboxamide

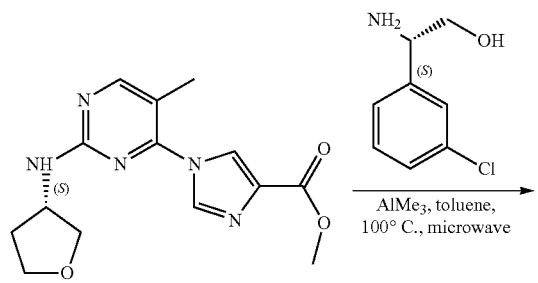

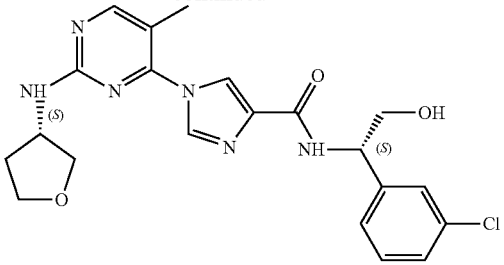

To a stirred solution of (S)-methyl-1-(5-methyl-2-(tetrahydrofuran-3-yl)amino)pyrimidin-4-yl)-1H-imidazole-4-carboxylate (0.45 g, 1.48 mmol) in toluene (25 mL) was added (S)-2-amino-2-(3-chlorophenyl)ethanol (0.509 g, 2.96 mmol) and trimethylaluminum (2M solution in toluene; 2.2 mL, 4.45 mmol) at 0° C. in CEM microwave vial. The vial was sealed and the reaction mixture was stirred at 100° C. for 2 h in CEM microwave. The mixture was cooled, quenched with water and extracted with ethyl acetate (3×200 mL). The combined organic layer was washed with brine (10 mL), dried over anhydrous sodium sulfate, filtered and evaporated under reduced pressure. The residue was purified by gradient column chromatography using methanol in DCM as eluent to afford N—(S)-1-(3-chlorophenyl)-2-hydroxyethyl)-1-(5-methyl-2-(S)-tetrahydrofuran-3-yl)amino)pyrimidin-4-yl)-1H-imidazole-4-carboxamide as a white solid (0.23 g, 35%). 1HNMR (400 MHz, DMSO-d₆): δ 8.38 (t, J=8.4 Hz, 2H) 8.29 (s, 1H), 8.11 (s, 1H), 7.60 (d, J=5.2 Hz, 1H), 7.43 (s, 1H), 7.31 (d, J=15.6 Hz, 3H), 5.02 (d, J=5.2 Hz, 2H), 4.34 (s, 1H), 3.87-3.78 (m, 2H), 3.72-3.67 (m, 3H), 3.55-3.28 (m, 1H), 2.19 (s, 3H), 2.19-2.08 (m, 1H), 1.89-1.85 (m, 1H). LC-MS calcd exact mass 442.15, found m/z 443.5 [M+H]⁺. HPLC Purity 99.2%, chiral HPLC Purity 99.7%; mp 117° C.

Example 11: N-(1-(3-chlorophenyl)-2-hydroxyethyl)-1-(5-methyl-2-((tetrahydro-2H-pyran-4-yl)amino)pyrimidin-4-yl)-1H-imidazole-4-carboxamide (Compound #201)

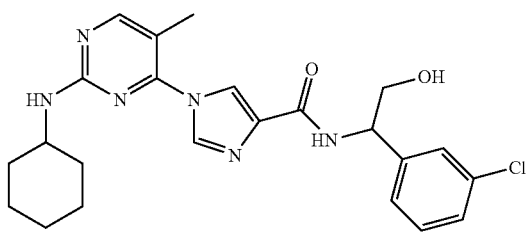 [SMILES: Cc1cnc(NC2CCCCC2)nc1-n1cnc(C(=O)NC(CO)c2cccc(Cl)c2)c1]

Step 1: Methyl 1-(2-chloro-5-methylpyrimidin-4-yl)-1H-imidazole-4-carboxylate

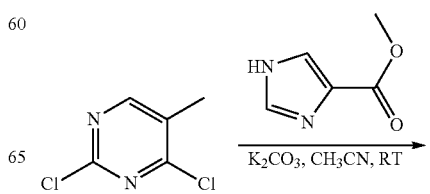

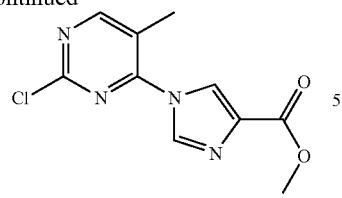

To a stirred solution of methyl 1H-imidazole-4-carboxylate (2.32 g, 18.4 mmol) in acetonitrile (75 mL) was added potassium carbonate (5.08 g, 36.8 mmol). The reaction mixture was stirred at RT for 5 min, then 2,4-dichloro-5-methylpyrimidine (2 g, 18.4 mmol) was added. The resulting mixture was stirred at RT overnight. The mixture was quenched with water (50 mL) and extracted with ethyl acetate (3×150 mL). The combined organic layer was dried over sodium sulfate, filtered and evaporated under reduced pressure. The residue was purified by gradient column chromatography using ethyl acetate in n-hexane as eluent to afford methyl 1-(2-chloro-5-methylpyrimidin-4-yl)-1H-imidazole-4-carboxylate as an off-white solid (53.7%)._$^1$HNMR (400 MHz, CDCl$_3$): δ 8.63 (s, 1H), 8.25 (d, J=5.2 Hz, 2H), 3.95 (s, 3H), 2.52 (s, 3H). LC-MS calcd exact mass 252.04, found m/z 253.1 [M+H]$^+$.

Step 2: Methyl 1-(5-methyl-2-((tetrahydro-2H-pyran-4-yl)amino)pyrimidin-4-yl)-1H-imidazole-4-carboxylate

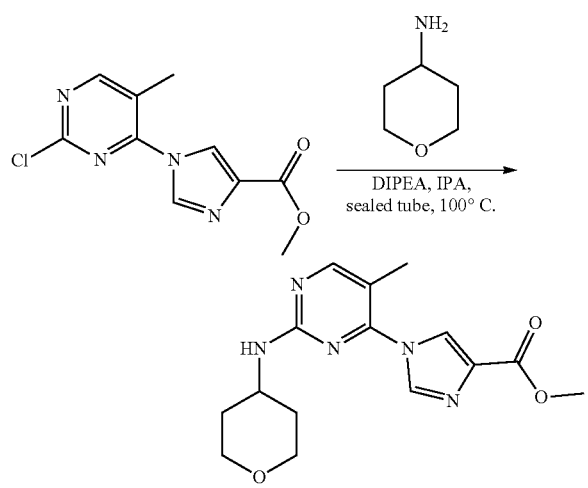

To a solution of 1-(2-chloro-5-methylpyrimidin-4-yl)-1H-imidazole-4-carboxylate (0.27 g, 1.07 mmol) in isopropanol (5 mL) was added DIPEA (0.58 mL, 3.21 mmol) and tetrahydro-2H-pyran-4-amine (0.16 mL, 1.60 mmol). The resulting mixture was stirred in a sealed glass tube at 100° C. for 20 h. The reaction mixture was quenched with water (10 mL), and extracted with ethyl acetate (50 mL). The organic layer was dried over sodium sulfate, filtered and evaporated under reduced pressure. The residue was purified by gradient column chromatography using methanol in DCM as eluent to afford methyl 1-(5-methyl-2-(tetrahydro-2H-pyran-4-yl)amino)pyrimidin-4-yl)-1H-imidazole-4-carboxylate as an off-white solid (0.25 g, 76%). 1HNMR (400 MHz, DMSO-d$_6$): δ 8.35 (s, 1H), 8.29 (s, 1H), 8.26 (s, 1H), 7.38 (d, J=7.6 Hz, 1H), 3.85-3.82 (m, 3H), 3.77 (s, 3H), 3.37 (t, J=10 Hz, 2H), 2.15 (s, 3H), 1.80 (d, J=10.4 Hz, 2H), 1.50-1.46 (m, 2H). LC-MS calcd exact mass 317.15, found m/z 318.4 [M+H]$^+$.

Step 3: N-(1-(3-Chlorophenyl)-2-hydroxyethyl)-1-(5-methyl-2-((tetrahydro-2H-pyran-4-yl)amino)pyrimidin-4-yl)-1H-imidazole-4-carboxamide

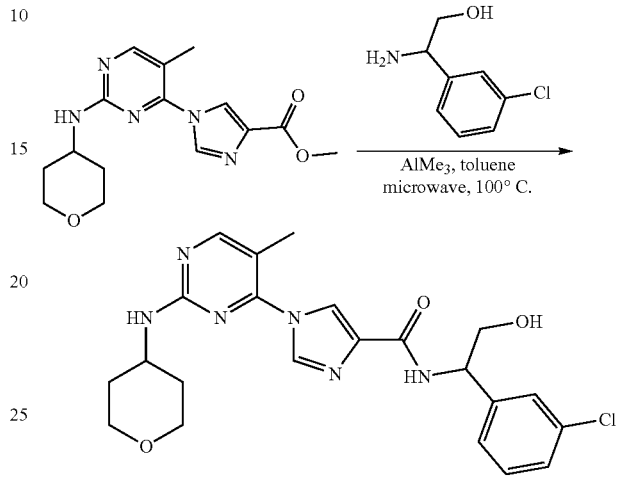

To a solution of methyl-1-(5-methyl-2-(tetrahydro-2H-pyran-4-yl)amino)pyrimidin-4-yl)-1H-imidazole-4-carboxylate (0.1 g, 0.315 mmol) in toluene (10 mL) was added 2-amino-2-(3-chlorophenyl)ethanol (0.10 g, 0.63 mmol) and trimethylaluminum (2M solution in toluene; 0.78 mL, 1.57 mmol). The resulting mixture was stirred in CEM microwave at 100° C. for 1.5 h. The mixture was cooled, and then quenched with water (10 mL) and extracted with ethyl acetate (50 mL). The organic layer was washed with water (10 mL), dried over sodium sulfate, filtered and evaporated under reduced pressure. The residue was purified by gradient column chromatography using methanol in DCM as eluent to afford N-(1-(3-chlorophenyl)-2-hydroxyethyl)-1-(5-methyl-2-((tetrahydro-2H-pyran-4-yl)amino)-pyrimidin-4-yl)-1H-imidazole-4-carboxamide as an off-white solid (0.12 g, 86%). 1HNMR (400 MHz, DMSO-d$_6$): δ 8.41 (d, J=7.8 Hz, 1H), 8.34 (s, 1H), 8.28 (s, 1H), 8.09 (s, 1H), 7.42 (s, 1H), 7.38 (d, J=9.6 Hz, 1H), 7.32-7.27 (m, 3H), 5.05-4.98 (m, 2H), 3.85-3.77 (m, 3H), 3.71 (t, J=4 Hz, 2H), 3.38 (t, J=8 Hz, 2H), 2.16 (s, 3H), 1.80 (d, J=11.2 Hz, 2H), 1.51-1.44 (m, 2H). LC-MS calcd exact mass 456.17, found m/z 457.5 [M+H]$^+$; HPLC purity 99.53%.

Example 12: (S)—N-(1-(3-chlorophenyl)-2-hydroxyethyl)-1-(5-methyl-2-((tetrahydro-2H-pyran-4-yl)amino)pyrimidin-4-yl)-1H-imidazole-4-carboxamide (Compound #211)

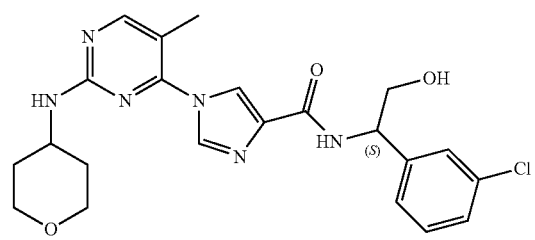

Step 1 and Step 2: The Procedure Followed was Similar to that Described in Example 11

Step 3: (S)—N-(1-(3-Chlorophenyl)-2-hydroxyethyl)-1-(5-methyl-2-(tetrahydro-2H-pyran-4-yl)amino)pyrimidin-4-yl)-1H-imidazole-4-carboxamide

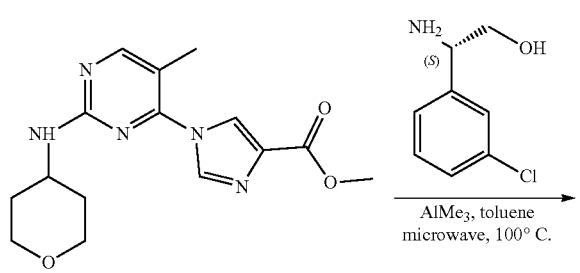

To a solution of methyl 1-(5-methyl-2-((tetrahydro-2H-pyran-4-yl)amino)pyrimidin-4-yl)-1H-imidazole-4-carboxylate (0.07 g, 0.22 mmol) in toluene (2 mL) was added (S)-2-amino-2-(3-chlorophenyl)ethanol (0.075 g, 0.44 mmol) and trimethylaluminum (2M solution in toluene; 0.22 mL, 0.44 mmol). The resulting mixture was stirred in CEM microwave at 100° C. for 1.5 h. The mixture was cooled, quenched with water (10 mL), and extracted with ethyl acetate (50 mL). The organic layer was washed with water (10 mL), dried over sodium sulfate, filtered and evaporated under reduced pressure. The residue was purified by gradient column chromatography using methanol in DCM as eluent and the isolated product was then washed with n-pentane to afford (S)—N-(1-(3-chlorophenyl)-2-hydroxyethyl)-1-(5-methyl-2-((tetrahydro-2H-pyran-4-yl)amino)pyrimidin-4-yl)-1H-imidazole-4-carboxamide as an off-white solid (0.060 g, 60%). 1HNMR (400 MHz, DMSO-$d_6$): δ 8.39 (d, J=8 Hz, 1H), 8.34 (s, 1H), 8.28 (s, 1H), 8.09 (s, 1H), 7.43 (s, 1H), 7.37-7.32 (m, 3H), 7.29 (br s, 1H), 5.02 (d, J=8 Hz, 2H), 3.85-3.82 (m, 3H), 3.72 (t, J=8 Hz, 2H), 3.39-3.26 (m, 2H), 2.17 (s, 3H), 1.81 (d, J=8 Hz, 2H), 1.48 (d, J=8 Hz, 2H). LC-MS calcd exact mass 456.17, found m/z 457.2 [M+H]$^+$; HPLC purity 99.81%, Chiral HPLC purity 99.92%; mp 145° C.

Representative Example for a Combination of Methods Used in Schemes 4 and 3

Example 13: N-(3-chloro-2-(hydroxymethyl) benzyl)-1-(5-methyl-2-((tetrahydro-2H-pyran-4-yl)amino) pyrimidin-4-yl)-1H-imidazole-4-carboxamide (Compound #93)

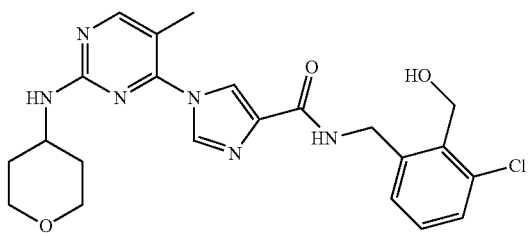 [SMILES: Cc1cnc(NC2CCOCC2)nc1-n1cnc(C(=O)NCc2cccc(Cl)c2CO)c1]

Step 1 and Step 2: The Procedure Followed was Similar to that Described in Example 11

Step 3: 1-(5-Methyl-2-((tetrahydro-2H-pyran-4-yl)amino)pyrimidin-4-yl)-1H-imidazole-4-carboxylic acid To a stirred solution of methyl 1-(5-methyl-2-((tetrahydro-2H-pyran-4-yl)amino)pyrimidin-4-yl)-1H-imidazole-4-carboxylate (1.5 g, 4.731 mmol) in tetrahydrofuran (30 mL) was added potassium trimethylsilanolate (1.82 g, 14.18 mmol) at 0° C. The reaction mixture was stirred at 45° C. for 1.5 h. Then the reaction mixture was quenched with water (25 mL), and washed with ethyl acetate (2×10 mL). The aqueous layer was adjusted to pH~5-6 by addition of 4N HCl solution. The aqueous layer was then extracted with ethyl acetate (3×60 mL), and the combined organic layer was concentrated under reduced pressure, to afford 1-(5-methyl-2-((tetrahydro-2H-pyran-4-yl)amino)pyrimidin-4-yl)-1H-imidazole-4-carboxylic acid, as an off-white solid, (1.2 g, 84%). $^1$HNMR (400 MHz, DMSO-$d_6$): δ 12.47 (br s, 1H), 8.33 (s, 1H), 8.23 (br s, 1H), 8.20 (s, 1H), 7.36 (d, J=7.6 Hz, 1H), 3.88 (br s, 1H), 3.83 (d, J=11.6 Hz, 2H), 3.36 (t, J=10.8 Hz, 2H), 2.15 (s, 3H), 1.80 (d, J=10.4 Hz, 2H), 1.52-1.42 (m, 2H). LC-MS calcd exact mass 303.13, found m/z 304.4 [M+H]$^+$.

Step 4: Methyl 2-(bromomethyl)-6-chlorobenzoate

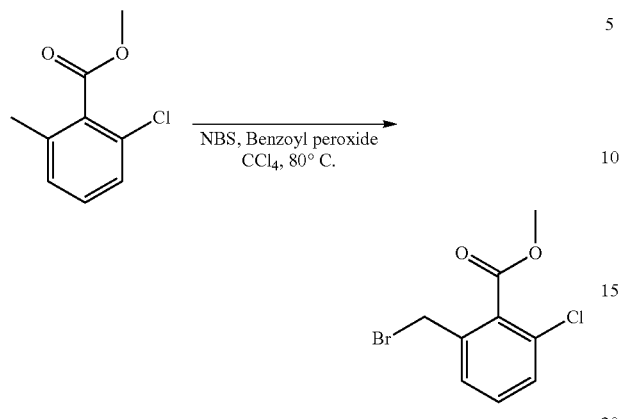

To a solution of methyl 2-chloro-6-methylbenzoate (1 g, 5.4 mmol) in carbon tetrachloride (50 mL) was added N-bromosuccinimide (1 g, 5.9 mmol) and benzoyl peroxide (0.131 g, 0.5 mmol). The resulting mixture was stirred for 10 h at 80° C. The reaction mixture was filtered through Celite, and the filtrate was evaporated under reduced pressure to afford methyl 2-(bromomethyl)-6-chlorobenzoate (1.2 g). LC-MS calcd exact mass 261.94, found m/z 263.0 [M+H]$^+$.

Step 5: Methyl 2-(azidomethyl)-6-chlorobenzoate

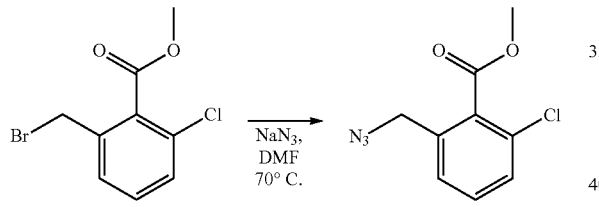

To a solution of methyl 2-(bromomethyl)-6-chlorobenzoate (1 g, 3.8 mmol) in DMF (10 mL) was added sodium azide (0.494 g, 7.6 mmol) at 0° C. The resulting mixture was stirred for 12 h at 70° C. The reaction mixture was diluted with ice cold water (100 mL), and extracted with ethyl acetate (2×100 mL). The combined organic layer was washed with brine (10 mL), dried over sodium sulfate, filtered and evaporated under reduced pressure to afford methyl 2-(azidomethyl)-6-chlorobenzoate (1.2 g). LC-MS calcd exact mass 225.03, found m/z 198.1 [M+H-N$_2$].

Step 6: (2-(Aminomethyl)-6-chlorophenyl) methanol

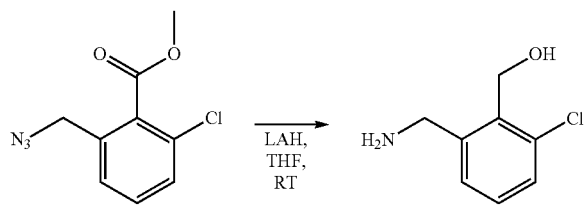

To a solution of methyl 2-(azidomethyl)-6-chlorobenzoate (0.5 g, 2.2 mmol) in tetrahydrofuran (10 mL) was slowly added lithium aluminum hydride (0.337 g, 8.8 mmol) at 0° C. The resulting mixture was stirred for 12 h at room temperature. The reaction mixture was diluted with ice cold water (50 mL), and extracted with ethyl acetate (2×100 mL). The combined organic layer was washed with brine (10 mL), dried over sodium sulfate, filtered and evaporated under reduced pressure to afford (2-(aminomethyl)-6-chlorophenyl) methanol (0.4 g). LC-MS calcd exact mass 171.05, found m/z 172.1 [M+H]$^+$.

Step 7: N-(3-chloro-2-(hydroxymethyl) benzyl)-1-(5-methyl-2-((tetrahydro-2H-pyran-4-yl) amino) pyrimidin-4-yl)-1H-imidazole-4-carboxamide

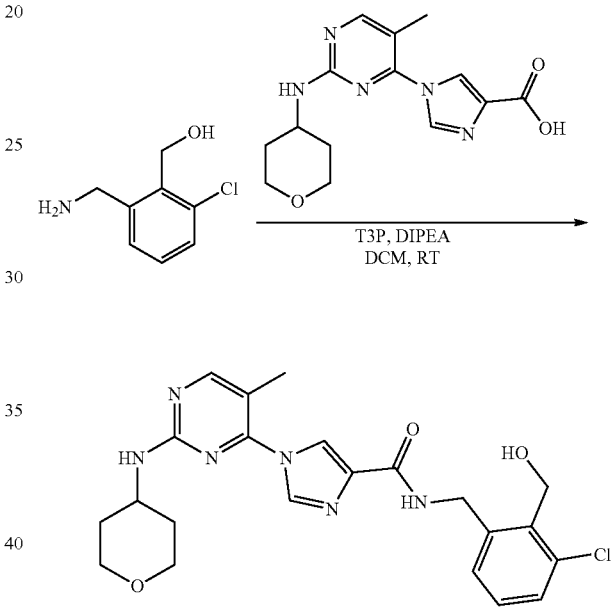

To a solution of 1-(5-methyl-2-((tetrahydro-2H-pyran-4-yl)amino)pyrimidin-4-yl)-1H-imidazole-4-carboxylic acid (0.1 g, 0.3 mmol) in DCM (10 mL) was added (2-(aminomethyl)-6-chlorophenyl) methanol (0.84 g, 0.4 mmol) and DIPEA (0.17 mL, 0.9 mmol) followed by T3P (0.24 mL, 0.8 mmol). The resulting mixture was stirred for 6 h at room temperature. The reaction mixture was diluted with ice cold water (50 mL), and extracted with DCM (2×100 mL). The combined organic layer was washed with brine (10 mL), dried over sodium sulfate, filtered and evaporated under reduced pressure. The residue was purified by Biotage Isolera using methanol in DCM as eluent to afford N-(3-chloro-2-(hydroxymethyl) benzyl)-1-(5-methyl-2-((tetrahydro-2H-pyran-4-yl) amino) pyrimidin-4-yl)-1H-imidazole-4-carboxamide as an off-white solid (0.43 g, 29%). HNMR (400 MHz, DMSO-d$_6$): δ 8.62 (t, J=6 Hz, 1H), 8.33 (s, 1H), 8.25 (s, 1H), 8.10 (s, 1H), 7.36-7.23 (m, 4H), 5.24 (t, J=5.0 Hz, 1H), 4.76 (d, J=5.2 Hz, 2H), 4.61 (d, J=6 Hz, 2H), 3.9 (br s, 1H), 3.83 (d, J=11.2 Hz, 2H), 3.36 (t, J=11.0 Hz, 2H), 2.17 (s, 3H), 1.80 (d, J=11.6 Hz, 2H), 1.52-1.43 (m, 2H). LC-MS calcd exact mass 456.17, found m/z 457.0 [M+H]$^+$; HPLC purity 99.05%.

Representative Example for General Scheme 7

Example 14: N-(1-(3-chlorophenyl)-2-hydroxy-ethyl)-1-(2-(phenylamino)pyridin-4-yl)-1H-imidazole-4-carboxamide (Compound #77)

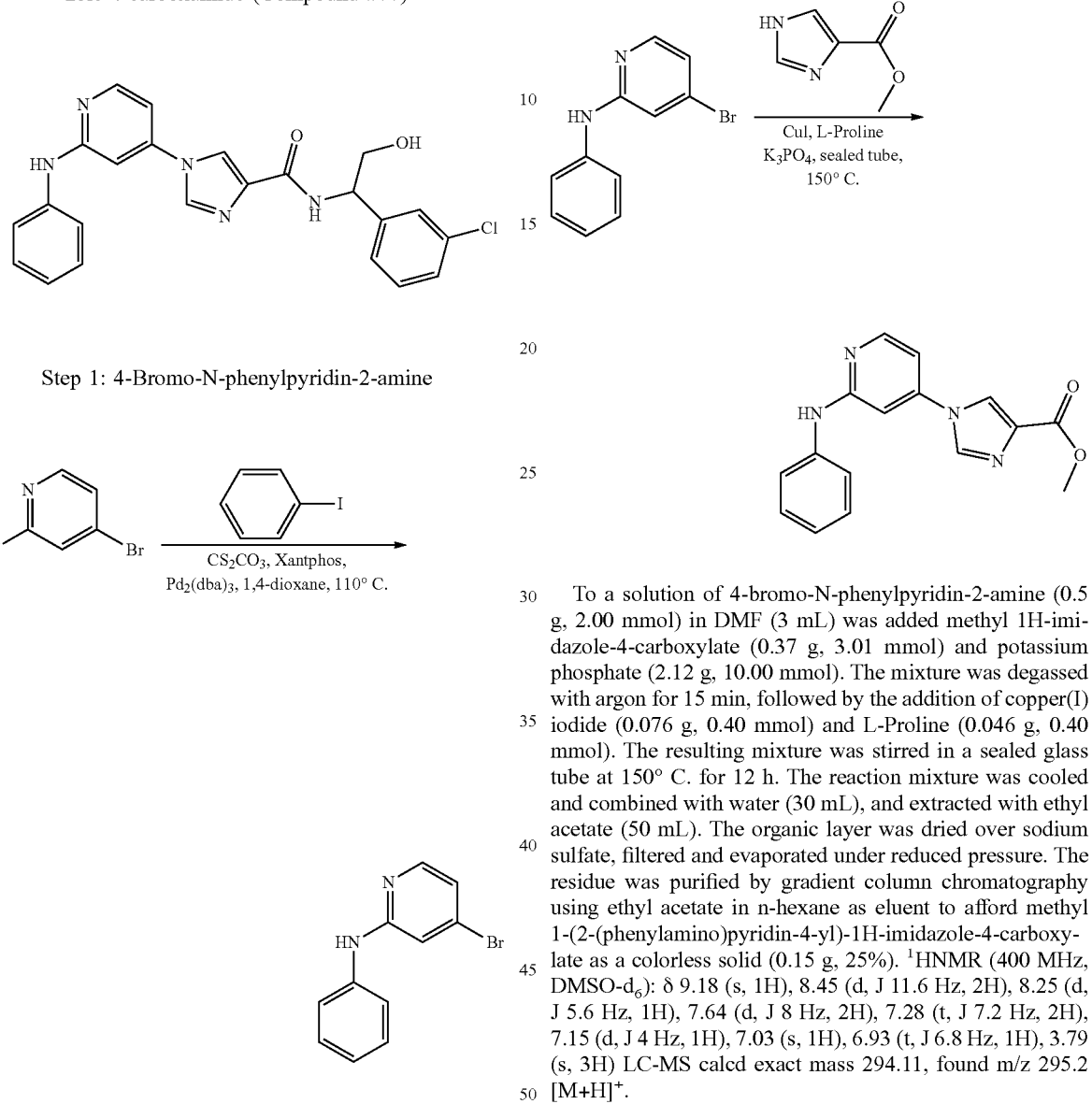

Step 1: 4-Bromo-N-phenylpyridin-2-amine

A solution of 4-bromopyridin-2-amine (1.0 g, 5.7 mmol), iodobenzene (2.35 g, 11.56 mmol) and cesium carbonate (8.82 g, 24.855 mmol) in 1,4-dioxane was degassed with argon for 30 min, followed by the addition of Xantphos (0.66 g, 1.156 mmol) and tris(dibenzylideneacetone)dipalladium(0)-chloroform adduct (0.528 g, 0.578 mmol). The resulting mixture was stirred in sealed glass tube at 150° C. for 12 h. The reaction mixture was cooled, combined with water (50 mL), and extracted with ethyl acetate (3×200 mL). Combined organic layer was washed with water (100 mL) and brine (50 mL), dried over sodium sulfate, filtered and evaporated under reduced pressure. The residue was purified by gradient column chromatography using ethyl acetate in n-hexane as eluent to afford 4-bromo-N-phenylpyridin-2-amine as a yellow solid (0.81 g, 56%). LC-MS calcd exact mass 247.99 and 249.99, found m/z 251.1 [M+H]$^+$.

Step 2: Methyl 1-(2-(phenylamino)pyridin-4-yl)-1H-imidazole-4-carboxylate

To a solution of 4-bromo-N-phenylpyridin-2-amine (0.5 g, 2.00 mmol) in DMF (3 mL) was added methyl 1H-imidazole-4-carboxylate (0.37 g, 3.01 mmol) and potassium phosphate (2.12 g, 10.00 mmol). The mixture was degassed with argon for 15 min, followed by the addition of copper(I) iodide (0.076 g, 0.40 mmol) and L-Proline (0.046 g, 0.40 mmol). The resulting mixture was stirred in a sealed glass tube at 150° C. for 12 h. The reaction mixture was cooled and combined with water (30 mL), and extracted with ethyl acetate (50 mL). The organic layer was dried over sodium sulfate, filtered and evaporated under reduced pressure. The residue was purified by gradient column chromatography using ethyl acetate in n-hexane as eluent to afford methyl 1-(2-(phenylamino)pyridin-4-yl)-1H-imidazole-4-carboxylate as a colorless solid (0.15 g, 25%). $^1$HNMR (400 MHz, DMSO-d$_6$): δ 9.18 (s, 1H), 8.45 (d, J 11.6 Hz, 2H), 8.25 (d, J 5.6 Hz, 1H), 7.64 (d, J 8 Hz, 2H), 7.28 (t, J 7.2 Hz, 2H), 7.15 (d, J 4 Hz, 1H), 7.03 (s, 1H), 6.93 (t, J 6.8 Hz, 1H), 3.79 (s, 3H) LC-MS calcd exact mass 294.11, found m/z 295.2 [M+H]$^+$.

Step 3: 1-(2-(Phenylamino)pyridin-4-yl)-1H-imidazole-4-carboxylic acid

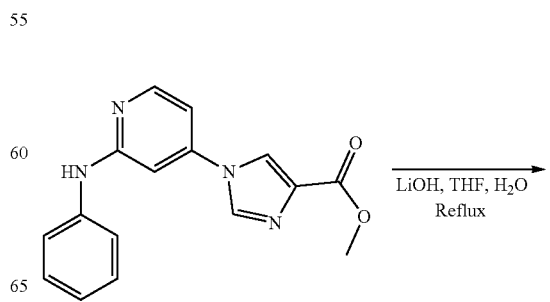

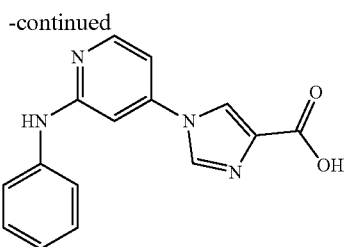

To a solution of methyl 1-(2-(phenylamino)pyridin-4-yl)-1H-imidazole-4-carboxylate (0.1 g, 0.77 mmol) in THF (6 mL) and water (6 mL) was added lithium hydroxide monohydrate (0.057 g, 1.36 mmol). The resulting mixture was stirred at RT for 6 h. The mixture was evaporated under reduced pressure, and adjusted to pH~6 by the addition of 1N HCl. The solid that formed was removed by filtration, washing with water (5 mL), and then dried under reduced pressure to afford 1-(2-(phenylamino)pyridin-4-yl)-1H-imidazole-4-carboxylic acid as a colorless solid (0.08 g, 88%). 1HNMR (400 MHz, DMSO-$d_6$): δ 12 (br s, 1H), 9.30 (s, 1H), 8.42 (s, 1H), 8.37 (s, 1H), 8.24 (d, J 5.6 Hz, 1H), 7.64 (d, J 8 Hz, 2H), 7.28 (t, J 7.6 Hz, 2H), 7.17 (d, J 1.6 Hz, 1H), 7.06 (s, 1H), 6.94 (t, J 7.2 Hz, 1H). LC-MS calcd exact mass 280.10, found m/z 281.1 [M+H]$^+$.

Step 4: N-(1-(3-Chlorophenyl)-2-hydroxyethyl)-1-(2-(phenylamino)pyridin-4-yl)-1H-imidazole-4-carboxamide

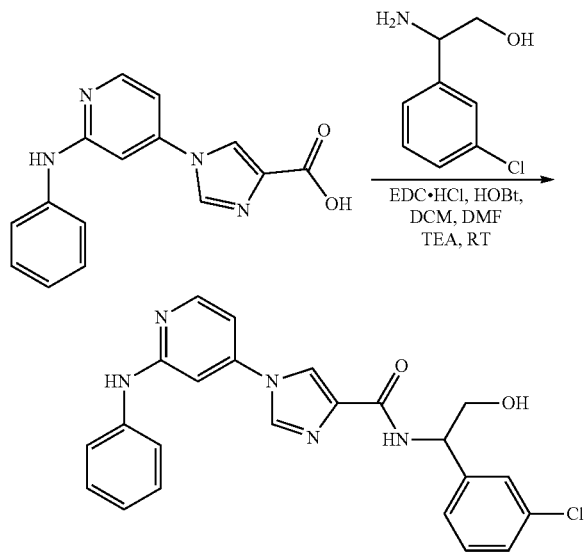

To a solution of 1-(2-(phenylamino)pyridin-4-yl)-1H-imidazole-4-carboxylic acid (0.04 g, 0.178 mmol) in DCM (6 mL) and DMF (0.2 mL) was added triethylamine (0.053 mL, 0.534 mmol), EDC (0.068 g, 0.356 mmol) and HOBt (0.007 g, 0.053 mmol). The reaction mixture was stirred at RT for 15 min and then 2-amino-2-(3-chlorophenyl)ethanol (0.036 g, 0.213 mmol) was added. The mixture was stirred at RT for 12 h. The reaction mixture was combined with water and extracted with ethyl acetate. The organic layer was dried over sodium sulfate, filtered and evaporated under reduced pressure. The residue was purified by gradient column chromatography using methanol in DCM as eluent to afford N-(1-(3-chlorophenyl)-2-hydroxyethyl)-1-(2-(phenylamino)pyridin-4-yl)-1H-imidazole-4-carboxamide as a colorless solid (0.015 g, 24%). 1HNMR (400 MHz, DMSO-$d_6$): δ 9.17 (s, 1H), 8.45 (s, 1H), 8.40 (d, J=8.4 Hz, 1H), 8.24 (d, J=7.6 Hz, 2H), 7.64 (d, J=7.6 Hz, 2H), 7.42 (s, 1H), 7.32-7.28 (m, 2H), 7.27-7.25 (m, 3H), 7.15 (d, J=5.6 Hz, 1H), 7.02 (s, 1H), 6.92 (t, J=7.2 Hz, 1H), 5.04-4.99 (m, 2H), 3.73 (t, J=5.6 Hz, 2H). LC-MS calcd exact mass 433.13, found m/z 434.2 [M+H]$^+$. HPLC purity 99.52%; mp 130.0° C.

Representative Example for General Scheme 8

Example 15: 1-(2-(Benzo[d][1,3]dioxol-5-ylamino)-5-methylpyrimidin-4-yl)-N-(1-(3,5-dichloro-phenyl)-2-hydroxyethyl)-1H-pyrrole-3-carboxamide (Compound #74)

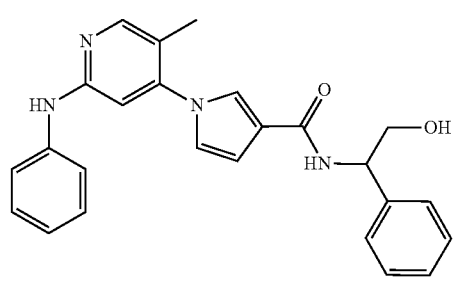 [SMILES: Cc1cnc(Nc2ccccc2)cc1-n1ccc(C(=O)NC(CO)c2ccccc2)c1]

Step 1: 2-chloro-5-methylpyridine 1-oxide

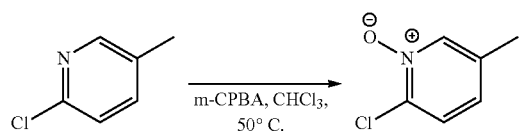

To a solution of 2-chloro-5-methylpyridine (2.0 g, 15.7 mmol) in CHCl$_3$ (20 mL) was added meta-chloroperoxybenzoic acid (3.2 g, 18.89 mmol) portion-wise, then the mixture was heated at 50° C. for 16 h. The reaction mixture was cooled to −10° C., and the solid was filtered through Celite. The filtrate was evaporated and purified by column chromatography over silica gel using 80% ethyl acetate in hexanes as eluent to give 2-chloro-5-methylpyridine 1-oxide (1.9 g, 84%). 1HNMR (400 MHz, DMSO-$d_6$): δ 8.33 (s, 1H), 7.64 (d, J=8.4 Hz, 1H), 7.18 (d, J=8.4 Hz, 1H), 2.22 (s, 3H). LC-MS calcd exact mass 143.01, found m/z 144.1 [M+H]$^+$.

Step 2: 2-Chloro-5-methyl-4-nitropyridine 1-oxide

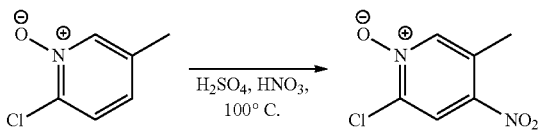

To a mixture of fuming nitric acid (4.5 mL) and sulfuric acid (6 mL) was slowly added 2-chloro-5-methylpyridine-1-oxide (1.4 g, 9.7 mmol). The mixture was then heated at 100° C. for 2 h. The mixture was cooled to RT, poured into crushed ice, and then neutralized by the addition of solid sodium carbonate. The mixture was extracted with ethyl acetate, and the organic layer was dried over sodium sulfate, and evaporated under reduced pressure to give 2-chloro-5-methyl-4-nitropyridine 1-oxide (1.3 g, 72%). 1HNMR (400 MHz, CDCl₃): δ 8.27 (s, 1H), 8.26 (s, 1H), 2.60 (s, 3H). LC-MS calcd exact mass 188.00, found m/z 189.1 [M+H]⁺.

Step 3: 5-Methyl-4-nitro-2-(phenylamino)pyridine 1-oxide

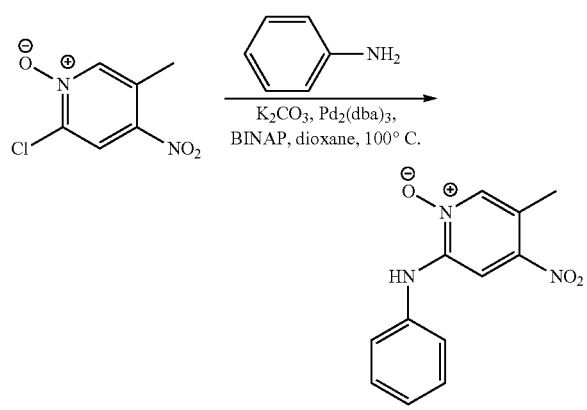

A mixture of 2-chloro-5-methyl-4-nitropyridine 1-oxide (0.5 g, 2.6 mmol), aniline (0.5 g, 5.3 mmol), potassium carbonate (0.73 g, 5.3 mmol) in dioxane (10 mL) was purged with nitrogen gas for 30 min. Tris(dibenzylideneacetone)dipalladium(0) (0.12 g, 0.13 mmol) and BINAP (0.16 g, 0.26 mmol) were added to the mixture, which was purged with nitrogen gas for another 20 min, and then was heated at 100° C. for 16 h. The mixture was filtered through Celite, and the filtrate was evaporated under reduced pressure. The residue was suspended in water, and extracted with ethyl acetate. The organic layer was dried over sodium sulfate, and evaporated under reduced pressure, and the residue was purified by column chromatography over silica gel using 60% ethyl acetate in hexane as eluent to give 5-methyl-4-nitro-2-(phenylamino)pyridine 1-oxide. (0.4 g, 56%). 1HNMR (400 MHz, CDCl₃): δ 8.48 (s, 1H), 8.17 (s, 1H), 7.73 (s, 1H), 7.45 (t, J=8.4 Hz, 2H), 7.29-7.25 (m, 3H), 2.50 (s, 3H). LC-MS calcd exact mass 245.08, found m/z 246.1 [M+H]⁺.

Step 4: 5-Methyl-N-2-phenylpyridine-2,4-diamine

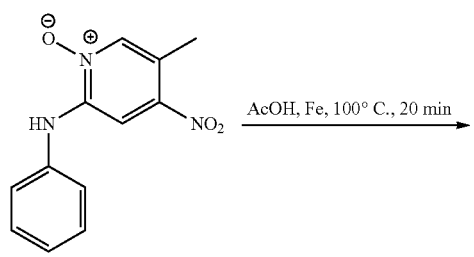

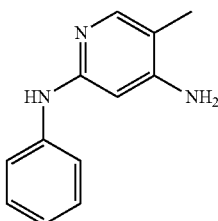

Iron powder (0.53 g, 9.57 mmol) was added to a solution of 5-methyl-4-nitro-2-(phenyl-amino)pyridine-1-oxide (0.35 g, 1.42 mmol) in acetic acid (7 mL), and the mixture was heated at 100° C. for 20 min. The mixture was cooled and then poured into 1M NaOH solution and extracted with DCM. The organic layer was washed with water and brine, dried over sodium sulfate, and evaporated under reduced pressure to give 5-methyl-N-2-phenylpyridine-2,4-diamine (0.26 g, 93%). 1HNMR (400 MHz, DMSO-d₆): 8.75 (s, 1H), 7.52 (s, 1H), 7.38 (d, J=8 Hz, 2H), 7.25 (t, J=7.6 Hz, 2H), 6.92 (t, J=7.2 Hz, 1H), 6.26 (br s, 2H), 6.07 (s, 1H), 1.93 (s, 3H). LC-MS calcd exact mass 199.11, found m/z 200.2 [M+H]⁺.

Step 5: 4-Bromo-5-methyl-N-phenylpyridin-2-amine

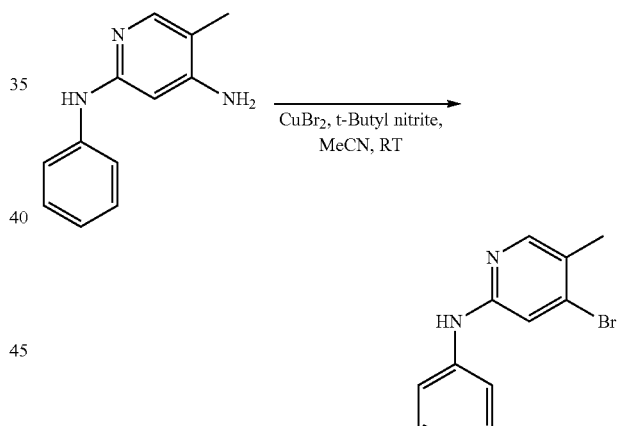

A mixture of copper(II) bromide (0.56 g, 2.51 mmol) and tert-butyl nitrite (0.25 mL, 3.12 mmol) in acetonitrile (5 mL) was stirred at RT for 30 min, cooled to 0° C., and then 5-methyl-N-2-phenylpyridine-2,4-diamine (0.25 g, 1.25 mmol) was added. The mixture was stirred at RT for 1 h. The mixture was poured into water, and extracted with ethyl acetate. The organic later was washed with aqueous ammonium hydroxide solution (until blue color disappeared), water and brine. The organic layer was dried over sodium sulfate, evaporated under reduced pressure, and the residue was purified by column chromatography over silica gel using 6% ethyl acetate in hexane as eluent to give 4-bromo-5-methyl-N-phenylpyridin-2-amine (0.07 g, 18%). 1HNMR (400 MHz, CDCl₃): 8.21 (s, 1H), 8.15 (s, 1H), 7.53-7.39 (m, 4H), 7.04 (d, J=7.2 Hz, 2H), 2.39 (s, 3H). LC-MS calcd exact mass 262.01 and 264.01, found m/z 265.1 [M+H]⁺.

Step 6: N-(2-hydroxy-1-phenylethyl)-1-(5-methyl-2-(phenylamino)pyridin-4-yl)-1H-pyrrole-3-carboxamide

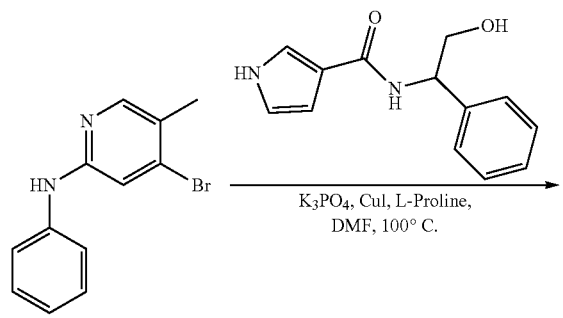

A mixture of 4-bromo-5-methyl-N-phenylpyridin-2-amine (0.07 g, 0.26 mmol), N-(2-hydroxy-1-phenylethyl)-1H-pyrrole-3-carboxamide (0.07 g, 0.29 mmol), potassium phosphate (0.16 g, 0.79 mmol) in DMF (2 mL) was purged with nitrogen gas for 15 min. L-proline (0.006 g, 0.053 mmol) and copper iodide (0.01 g, 0.053 mmol) were added to the reaction mixture, which was purged with nitrogen gas for another 10 min, and was then heated in a sealed glass tube at 100° C. for 16 h. The mixture was cooled and suspended in water, and extracted with ethyl acetate. Organic layer was dried over sodium sulfate and evaporated under reduced pressure, and the residue was purified by column chromatography over silica gel using 2% methanol in DCM as eluent to give N-(2-hydroxy-1-phenylethyl)-1-(5-methyl-2-(phenylamino)pyridin-4-yl)-1H-pyrrole-3-carboxamide (0.04 g, 40%). 1HNMR (400 MHz, DMSO-$d_6$): 9.04 (s, 1H), 8.13 (s, 1H), 8.09 (d, J=8.4 Hz, 1H), 7.66 (s, 1H), 7.61 (d, J=8 Hz, 2H), 7.31 (t, J=7.2 Hz, 2H) 7.29-7.22 (m, 5H), 7.19-7.08 (m, 1H), 6.87 (t, J=7.6 Hz, 1H), 6.74 (d, J=7.6 Hz, 2H), 5.06-5.01 (m, 1H), 4.85 (t, J=5.6 Hz, 1H), 3.66-3.63 (m, 2H), 2.14 (s, 3H). LC-MS calcd exact mass 412.19, found m/z 413.3 [M+H]$^+$. HPLC purity 99.39%.

Representative Example for General Scheme 9

Example 16: N-(2-Amino-1-(3-chlorophenyl)ethyl)-1-(2-((4-fluorophenyl)amino)-5-methylpyridin-4-yl)-1H-pyrrole-3-carboxamide (Compound #159)

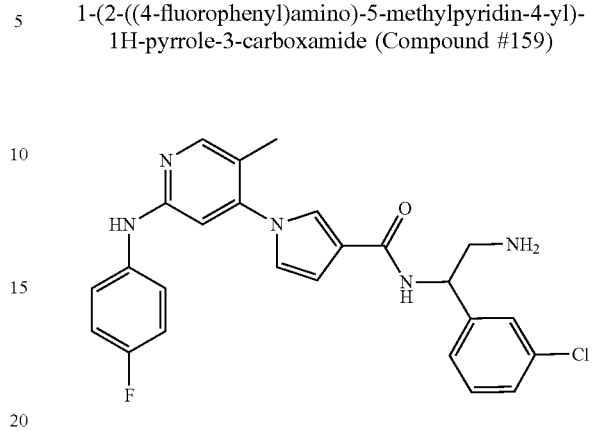

Step 1: Methyl 1-(2-chloro-5-methylpyridin-4-yl)-1H-pyrrole-3-carboxylate

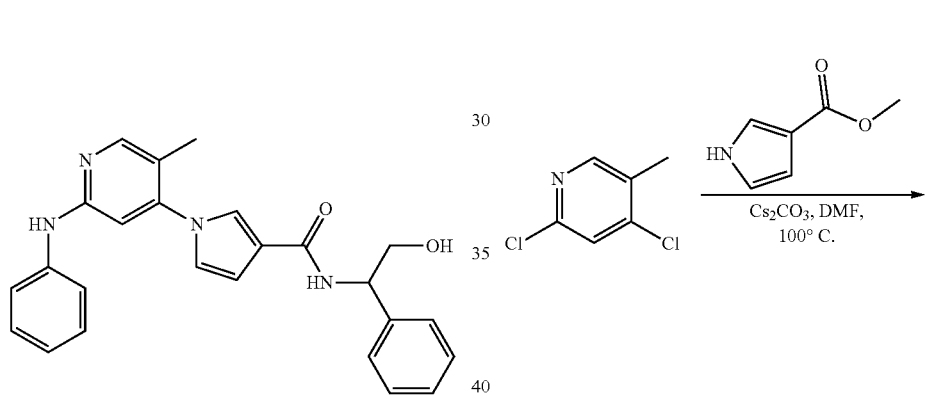

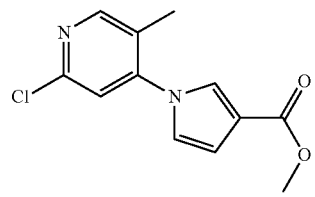

To a stirred solution of methyl 1H-pyrrole-3-carboxylate (1.24 g, 9.97 mmol) in DMF (15 mL) was added cesium carbonate (1.22 g, 3.72 mmol). The reaction mixture was stirred at RT for 15 min, then 2,4-dichloro-5-methylpyridine (2 g, 1.24 mmol) was added. The resulting mixture was heated at 100° C. for 10 h. The mixture was combined with water (200 mL), and extracted with ethyl acetate (800 mL). The organic layer was dried over sodium sulfate, filtered and evaporated under reduced pressure. The residue was purified by gradient column chromatography using ethyl acetate in n-hexane as eluent to afford methyl 1-(2-chloro-5-methylpyridin-4-yl)-1H-pyrrole-3-carboxylate as a colorless solid (1.3 g, 43%). $^1$HNMR (400 MHz, DMSO-$d_6$): δ 8.44 (s, 1H), 7.80 (s, 1H), 7.59 (s, 1H), 7.22 (t, J=2.0 Hz, 1H), 6.66-6.65 (m, 1H), 3.73 (s, 3H), 2.25 (s, 3H). LC-MS calcd exact mass 250.05, found m/z 251.1 [M+H]$^+$.

Step 2: Methyl 1-(2-((4-fluorophenyl)amino)-5-methylpyridin-4-yl)-1H-pyrrole-3-carboxylate

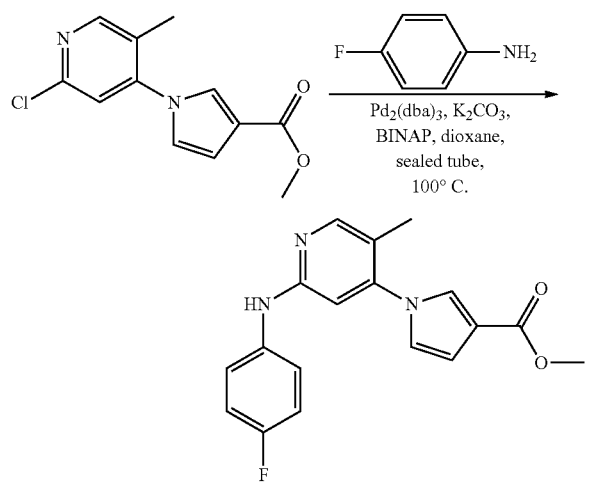

To a solution of methyl 1-(2-chloro-5-methylpyridin-4-yl)-1H-pyrrole-3-carboxylate (0.4 g, 1.60 mmol) in dioxane (10 mL) was added potassium carbonate (0.66 g, 4.8 mmol) and 4-fluoroaniline (0.26 g, 2.40 mmol). The mixture was degassed with argon for 15 min, followed by the addition of tris(dibenzylideneacetone)dipalladium(0) (0.073 g, 0.08 mmol) and 2-(dicyclohexylphosphino)-2',4',6'-triisopropyl-biphenyl (0.09 g, 0.16 mmol). The resulting mixture was stirred in a sealed glass tube at 100° C. for 12 h. The mixture was cooled and quenched with water (50 mL), and extracted with ethyl acetate (200 mL). The organic layer was dried over sodium sulfate, filtered and evaporated under reduced pressure. The residue was purified by gradient column chromatography using ethyl acetate in n-hexane as eluent to afford methyl 1-(2-((4-fluorophenyl)amino)-5-methylpyridin-4-yl)-1H-pyrrole-3-carboxylate as an off-white solid (0.4 g, 76%). 1HNMR (400 MHz, DMSO-$d_6$): δ 9.06 (s, 1H), 8.12 (s, 1H), 7.69 (s, 1H), 7.64-7.60 (m, 2H), 7.14-7.07 (m, 3H), 6.69 (s, 1H), 6.64-6.63 (m, 1H), 3.73 (s, 3H), 2.10 (s, 3H). LC-MS calcd exact mass 325.12, found m/z 326.2 [M+H]$^+$.

Step 3: 1-(2-((4-Fluorophenyl)amino)-5-methylpyridin-4-yl)-1H-pyrrole-3-carboxylic acid

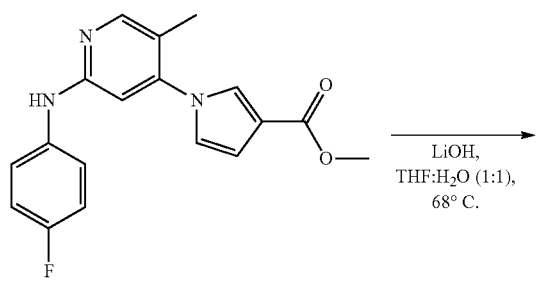

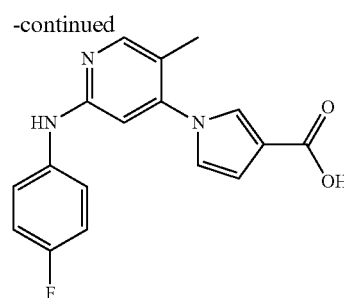

To a mixture of methyl 1-(2-(4-fluorophenyl)amino)-5-methylpyridin-4-yl)-1H-pyrrole-3-carboxylate (0.5 g, 1.33 mmol) in THF (10 mL) and water (10 mL) was added lithium hydroxide monohydrate (0.25 g, 6.15 mmol). The resulting mixture was heated to reflux for 12 h. The mixture was cooled and concentrated under reduced pressure, and adjusted to pH~6 by addition of 1N HCl. The solid was removed by filtration, washing with water, and dried under vacuum to afford 1-(2-(4-fluorophenyl)amino)-5-methylpyridin-4-yl)-1H-pyrrole-3-carboxylic acid as an off-white solid (0.45 g, 94%). $^1$HNMR (400 MHz, DMSO-$d_6$): δ 9.16 (s, 1H), 8.11 (s, 1H), 7.62 (t, J 7.6 Hz, 3H), 7.11 (t, J 8.4 Hz, 3H), 6.71 (s, 1H), 6.59 (s, 1H), 2.12 (s, 3H). LC-MS calcd exact mass 311.11, found m/z 312.2 [M+H]$^+$.

Step 4: N-((3-chlorophenyl)(cyano)methyl)-1-(2-((4-fluorophenyl)amino)-5-methylpyridin-4-yl)-1H-pyrrole-3-carboxamide

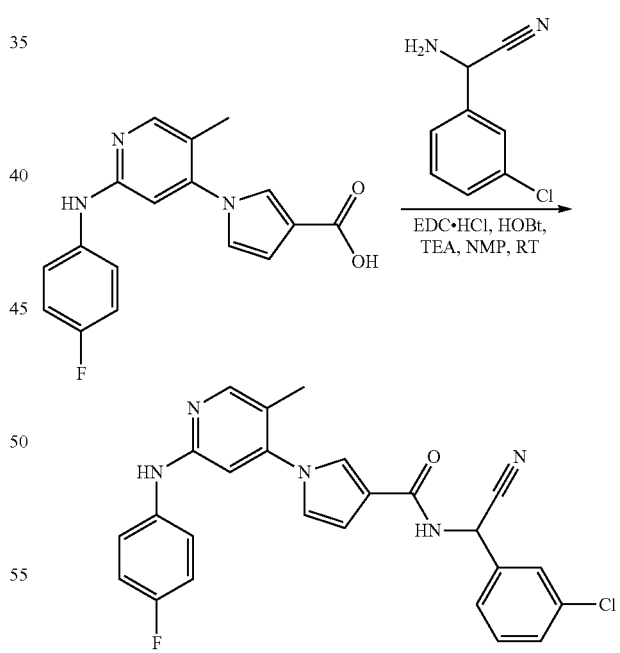

To a solution of 1-(2-(4-fluorophenyl)amino)-5-methylpyridin-4-yl)-1H-pyrrole-3-carboxylic acid (0.1 g, 0.32 mmol) in NMP (5 mL) was added triethylamine (0.09 g, 0.96 mmol), EDC (0.12 g, 0.69 mmol) and HOBt (0.013 g, 0.096 mmol). The reaction mixture was stirred at RT for 15 min, and then 2-amino-2-(3-chlorophenyl)acetonitrile (0.064 g, 0.38 mmol) was added. The resulting mixture was stirred at RT for 12 h. The reaction mixture was quenched with water (100 mL), and extracted with ethyl acetate (100 mL). The organic layer was dried over sodium sulfate, filtered and evaporated under reduced pressure. The residue was purified by gradient column chromatography using methanol in DCM as eluent to afford N-(3-chlorophenyl)(cyano) methyl)-1-(2-((4-fluorophenyl)amino)-5-methylpyridin-4-yl)-1H-pyrrole-3-carboxamide as a colorless solid (0.03 g, 20%). 1HNMR (400 MHz, DMSO-d$_6$): δ 9.21 (d, J=8 Hz, 1H), 9.07 (s, 1H), 8.12 (s, 1H), 7.71 (s, 1H), 7.64-7.60 (m, 2H), 7.54 (s, 1H), 7.49 (s, 3H), 7.13 (s, 1H), 7.10 (t, J=8.8 Hz, 2H), 6.75 (s, 1H), 6.68 (s, 1H), 6.40 (d, J=7.6 Hz, 1H), 2.13 (s, 3H). LC-MS calcd exact mass 459.13, found m/z 460.2 [M+H]$^+$.

Step 5: N-(2-Amino-1-(3-chlorophenyl)ethyl)-1-(2-((4-fluorophenyl)amino)-5-methylpyridin-4-yl)-1H-pyrrole-3-carboxamide

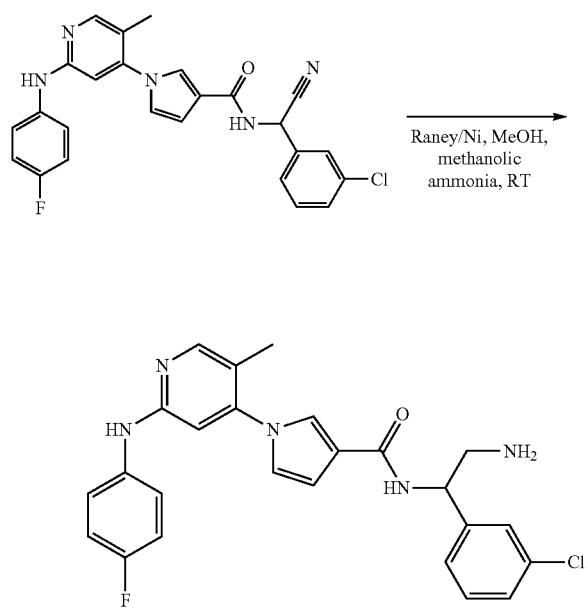

To a solution of N-(3-chlorophenyl)(cyano)methyl)-1-(2-(4-fluorophenyl)amino)-5-methylpyridin-4-yl)-1H-pyrrole-3-carboxamide (0.03 g, 0.065 mmol) in methanol (15 mL) was added Raney nickel (~0.05 g) under an argon atmosphere, and then methanolic ammonia (10 mL) was added.

The resulting mixture was stirred under an atmosphere of H$_2$ using a bladder, at RT for 12 h. The reaction mixture was filtered through Celite, washed with methanol (100 mL), and the filtrate was evaporated under reduced pressure. The residue was purified by gradient column chromatography using methanol in DCM as eluent to afford N-(2-amino-1-(3-chlorophenyl)ethyl)-1-(2-((4-fluorophenyl)amino)-5-methylpyridin-4-yl)-1H-pyrrole-3-carboxamide as a colorless solid (0.015 g, 50%). 1HNMR (400 MHz, DMSO-d$_6$): δ 9.07 (s, 1H), 8.15-8.12 (m, 2H), 7.67-7.61 (m, 3H), 7.39 (s, 1H), 7.36-7.26 (m, 3H), 7.09-7.06 (m, 3H), 6.75 (s, 1H), 6.69 (s, 1H), 4.90 (d, J=6.8 Hz, 1H), 2.84 (d, J=7.2 Hz, 2H), 1.88 (br s, 2H), 2.14 (s, 3H). LC-MS calcd exact mass 463.16, found m/z 464.5 [M+H]$^+$, HPLC purity 99.71%, mp 118.1° C.

Representative Example for General Scheme 10

Example 17: 1-(5-Chloro-2-(phenylamino)pyridin-4-yl)-N-(1-(3-chlorophenyl)-2-hydroxyethyl)-1H-imidazole-4-carboxamide (Compound #106)

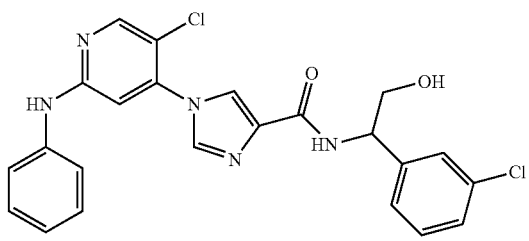 [SMILES: O=C(NC(CO)c1cccc(Cl)c1)c1cn(-c2cc(Nc3ccccc3)ncc2Cl)cn1]

Step 1: Tert-butyl (4-chloropyridin-2yl)carbamate

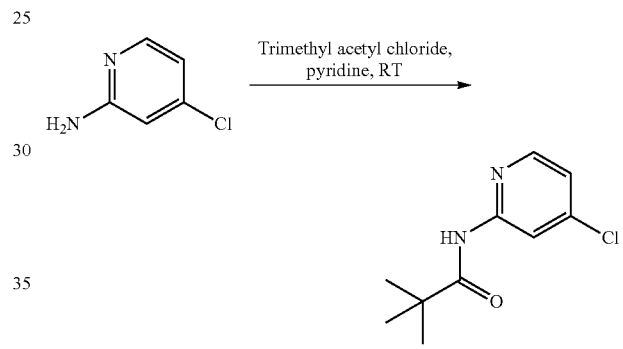

To a stirred solution of 4-chloropyridin-2-amine (1.5 g, 1.16 mmol) in pyridine (15 mL), was added trimethylacetyl chloride (1.688 g, 1.4 mmol). The mixture was stirred at RT overnight. The mixture was combined with water (20 mL) and extracted with ethyl acetate (3×40 ml). The combined organic layers were dried over sodium sulfate, then evaporated under reduced pressure and purified by gradient column chromatography basic alumina using ethyl acetate in n-hexane as eluent to afford tert-N-(4-chloropyridin-2-yl) pivalamide as a white solid (1.7 g, 69%). $^1$HNMR (400 MHz, CDCl$_3$): δ 8.35 (s, 1H), 8.14 (d, J=5.6 Hz, 1H), 8.02 (br s, 1H), 7.04-7.02 (m, 1H), 1.32 (s, 9H).

Step 2: Tert-butyl (4,5-dichloropyridin-2-yl)carbamate

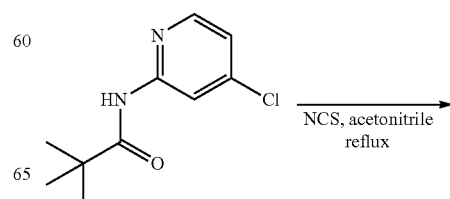

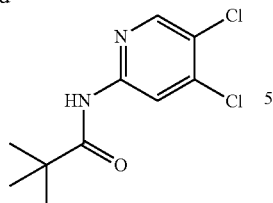

To a stirred solution of N-(4-chloropyridin-2-yl)pivalamide (1.6 g, 7.5 mmol) in acetonitrile (40 mL) was added N-chlorosuccinimide (5.02 g, 3.76 mmol). The mixture was stirred at reflux overnight. The mixture was cooled, combined with water (10 mL), and extracted with ethyl acetate (3×50 mL). The combined organic layers were dried over sodium sulfate, then evaporated under reduced pressure and purified by gradient column chromatography using ethyl acetate in n-hexane as eluent to afford N-(4,5-dichloropyridin-2-yl)pivalamide as a white solid (1.3 g, 70%). $^1$HNMR (400 MHz, CDCl$_3$): δ 8.48 (s, 1H), 8.25 (s, 1H), 7.98 (br s, 1H), 1.32 (s, 9H).

Step 3: 4,5-Dichloropyridin-2-amine

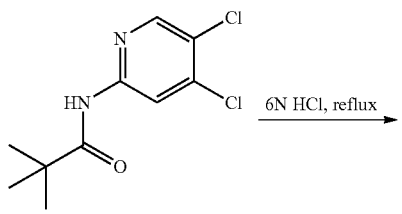

A mixture of N-(4,5-dichloropyridin-2-yl)pivalamide (1.25 g, 5.04 mmol) in 6N HCl (20 mL) was stirred at 100° C. for 10 h. The mixture was cooled, combined with water (20 mL), and basified by the addition of sodium bicarbonate solution (20 mL). The mixture was extracted with ethyl acetate (3×40 mL), and the combined organic layers were dried over sodium sulfate, then evaporated under reduced pressure and purified by gradient column chromatography using ethyl acetate in n-hexane as eluent to afford 4,5-dichloropyridin-2-amine as a white solid (0.7 g, 85%). $^1$HNMR (400 MHz, CDCl$_3$): δ 8.06 (s, 1H), 6.60 (s, 1H), 4.48 (br s, 2H). LC-MS calcd exact mass 161.98, found m/z 162.8 [M+H]$^+$.

Step 4: 4, 5-Dichloro-N-phenylpyridin-2-amine

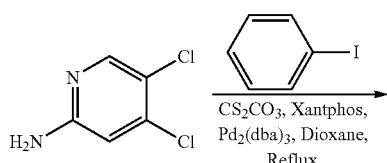

To a stirred solution of (4,5-dichloropyridin-2-amine (0.1 g, 0.61 mmol) in dioxane (5 mL) was added iodobenzene (0.25 g, 1.22 mmol), cesium carbonate (0.597 g, 1.83 mmol), and Xantphos (4,5-bis(diphenylphosphino)-9,9-dimethylxanthene; 0.035 g, 0.06 mmol). The mixture was degassed with argon for 10 min, then tris(dibenzylideneacetone)dipalladium(0) (0.029 g, 0.03 mmol) was added, and the mixture was degassed again with argon for 10 min. The mixture was stirred for 3 h at 100° C. The mixture was cooled, concentrated under reduced pressure, diluted with water (10 mL) and extracted with ethyl acetate (3×50 mL). The combined organic layer was washed with brine (10 mL), dried over anhydrous sodium sulfate, filtered and evaporated under reduced pressure. The residue was purified by gradient column chromatography using ethyl acetate in hexane as eluent to afford 4,5-dichloro-N-phenylpyridin-2-amine as an off-white solid (82 mg, 56% yield). 1HNMR (400 MHz, CDCl$_3$): δ 8.17 (s, 1H), 7.36 (t, J=7.2 Hz, 2H), 7.28 (s, 2H), 7.12 (t, J=7.6 Hz, 1H), 6.92 (s, 1H), 6.51 (br s, 1H). LC-MS calcd exact mass 238.01, found m/z 239.1 [M+H]$^+$.

Step 5: Methyl 1-(5-chloro-2-(phenylamino)pyridin-4-yl)-1H-imidazole-4-carboxylate

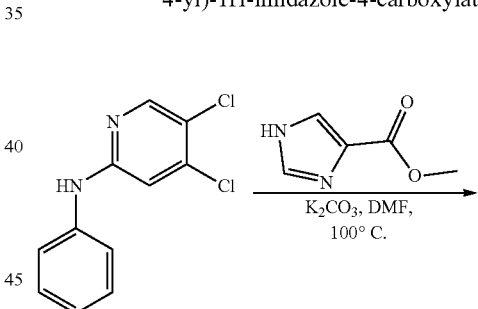

To a stirred solution of 4,5-dichloro-N-phenylpyridin-2-amine (0.3 g, 1.25 mmol) in DMF (7 mL) was added potassium carbonate (0.867 g, 6.2 mmol). The mixture was stirred at RT for 15 min, then methyl 1H-imidazole-4-carboxylate (0.159 g, 1.25 mmol) was added, and the mixture was stirred at 100° C. for 10 h. The mixture was cooled, combined with water (40 mL) and extracted with ethyl acetate (3×100 mL). The combined organic layers were dried over sodium sulfate, then evaporated under reduced pressure, and the residue was purified by gradient column chromatography using ethyl acetate in n-hexane as eluent to afford methyl 1-(5-chloro-2-(phenylamino)pyridin-4-yl)-1H-imidazole-4-carboxylate as an off-white solid (103 mg, 25% yield). 1HNMR (400 MHz, DMSO-d₆): δ 9.44 (s, 1H), 8.39 (s, 1H), 8.26 (d, J=1.6 Hz, 1H), 8.14 (d, J=1.2 Hz, 1H), 7.62-7.59 (m, 2H), 7.3 (t, J=5.2 Hz, 2H), 6.96 (t, J=8 Hz, 2H), 3.78 (s, 3H). LC-MS calcd exact mass 328.07, found m/z 329.1 [M+H]⁺.

Step 4: 1-(5-Chloro-2-(phenylamino)pyridin-4-yl)-1H-imidazole-4-carboxylic acid

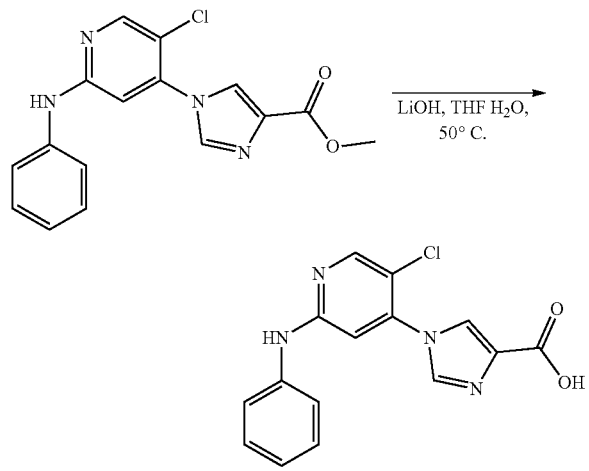

To a stirred mixture of methyl 1-(5-chloro-2-(phenylamino)pyridin-4-yl)-1H-imidazole-4-carboxylate (0.075 g, 0.22 mmol) in THF (14 mL) and water (4 mL) was added lithium hydroxide monohydrate (0.039 g, 0.91 mmol). The reaction mixture was stirred at 50° C. overnight. The mixture was concentrated under reduced pressure, and neutralized to pH~7 by the addition of 1N HCl. The solid that formed was removed by filtration to afford 1-(5-chloro-2-(phenylamino)pyridin-4-yl)-1H-imidazole-4-carboxylic acid as a grey solid (35 mg, 49% yield). 1HNMR (400 MHz, DMSO): δ 9.45 (s, 1H), 8.38 (s, 1H), 8.16 (s, 1H), 8.11 (s, 1H), 7.61 (d, J=8 Hz, 2H), 7.29 (t, J=7.6 Hz, 2H), 6.97-6.93 (m, 2H). LC-MS calcd exact mass 314.06, found m/z 315.1 [M+H]⁺.

Step 7: 1-(5-Chloro-2-(phenylamino)pyridin-4-yl)-N-(1-(3-chlorophenyl)-2-hydroxyethyl)-1H-imidazole-4-carboxamide

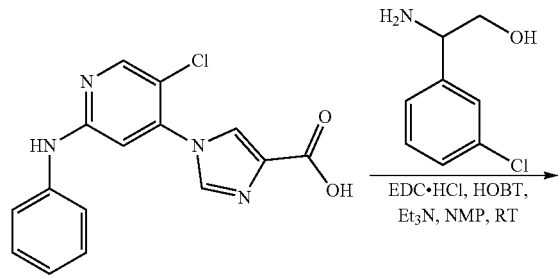

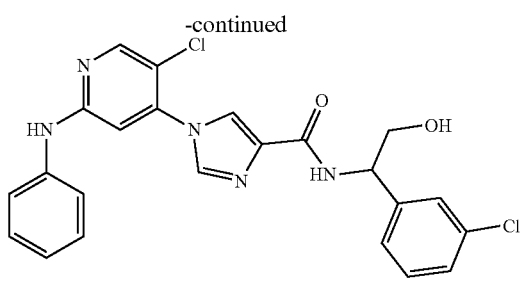

To a stirred solution of 1-(5-chloro-2-(phenylamino)pyridin-4-yl)-1H-imidazole-4-carboxylic acid (0.035 g, 0.11 mmol) in NMP (1.5 mL) was added EDC (0.065 g, 0.33 mmol), HOBt (0.005 g, 0.033 mmol), triethylamine (0.02 mL, 0.22 mmol), and 2-amino-2-(3-chlorophenyl)ethanol (0.022 g, 0.13 mmol). The reaction mixture was stirred at RT overnight. The mixture was diluted with water (10 mL) and extracted with ethyl acetate (3×15 mL). The combined organic layers were washed with brine (10 mL), dried over sodium sulfate, and evaporated under reduced pressure. The crude residue was purified by preparative TLC using methanol in DCM as eluent to afford 1-(5-chloro-2-(phenylamino)pyridin-4-yl)-N-(1-(3-chlorophenyl)-2-hydroxyethyl)-1H-imidazole-4-carboxamide as an off-white solid (19 mg, 36% yield). 1HNMR (400 MHz, DMSO-d₆): δ 9.44 (s, 1H), 8.41 (s, 1H), 8.38 (d, J=4.0 Hz, 1H), 8.16 (s, 1H), 8.02 (s, 1H), 7.61 (d, J=7.6 Hz, 2H), 7.44 (s, 1H), 7.33-7.30 (m, 2H), 7.29-7.27 (m, 3H), 6.93 (s, 2H), 5.02-5.01 (m, 2H), 3.72 (t, J=5.6 Hz, 2H). LC-MS calcd exact mass 467.09, found m/z 468.1 [M+H]⁺; HPLC purity 99.88%.

Representative Example for General Scheme 11

Example 18: N-(2-amino-1-phenylethyl)-1-(2-((4-fluorophenyl)amino)-5-methylpyridin-4-yl)-1H-imidazole-4-carboxamide (Compound #191)

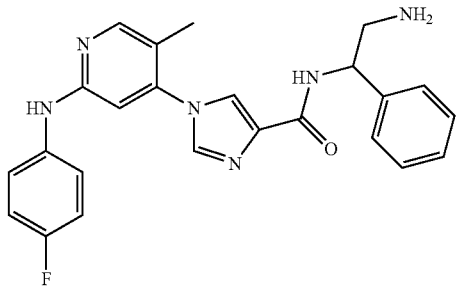 [SMILES: Cc1cnc(Nc2ccc(F)cc2)cc1-n1cnc(C(=O)NC(CN)c2ccccc2)c1]

Step 1: Methyl 1-(2-chloro-5-methylpyridin-4-yl)-1H-imidazole-4-carboxylate

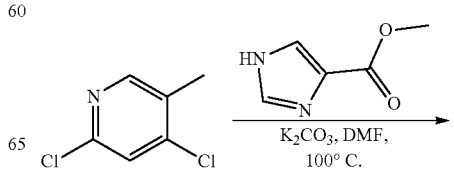

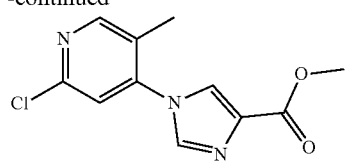

To a solution of 2,4-dichloro-5-methylpyridine (1.285 g, 7.93 mmol) in DMF (15 mL) were added methyl 1H-imidazole-4-carboxylate (1 g, 7.93 mmol) and K$_2$CO$_3$ (5.476 g, 39.68 mmol), and then the mixture was stirred at 100° C. for 6 h. The mixture was cooled and diluted with water, and the solid that formed was removed by filtration and dried to obtain crude product. The crude product was purified by Biotage Isolera (using 50% ethyl acetate in hexane as eluent) to obtain methyl 1-(2-chloro-5-methylpyridin-4-yl)-1H-imidazole-4-carboxylate (0.670 g, 34%). 1HNMR (400 MHz, CDCl$_3$): δ 8.44 (s, 1H), 7.79 (s, 1H), 7.69 (s, 1H), 7.27 (s, 1H), 3.94 (s, 3H), 2.28 (s, 3H). LC-MS calcd exact mass 251.05, found m/z 252.1 [M+H]$^+$.

Step 2: Methyl 1-(2-((4-fluorophenyl)amino)-5-methylpyridin-4-yl)-1H-imidazole-4-carboxylate

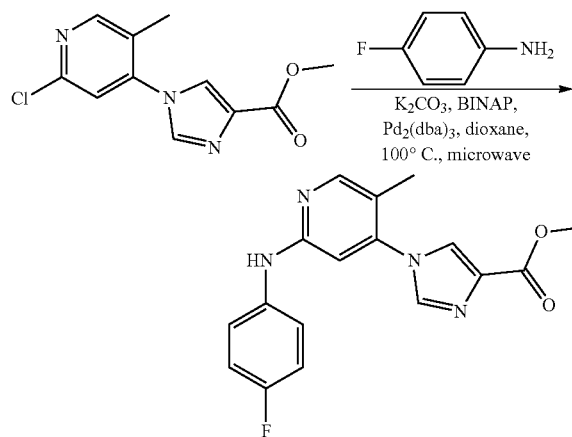

To a solution of methyl 1-(2-chloro-5-methylpyridin-4-yl)-1H-imidazole-4-carboxylate (0.4 g, 1.59 mmol) in dioxane (10 mL) were added 4-fluoroaniline (0.353 g, 3.18 mmol) and K$_2$CO$_3$ (0.439 g, 3.18 mmol). The reaction mixture was degassed with argon, then tris(dibenzylideneacetone)dipalladium(0) (0.072 g, 0.079 mmol) and BINAP (0.099 g, 0.15 mmol) were added, and then the mixture was heated at 100° C. for 1 h in the CEM microwave system. The mixture was cooled, diluted with water, and extracted with ethyl acetate. The combined organic phases were washed with water and brine, dried over sodium sulfate, filtered and evaporated under reduced pressure. The residue was purified by column chromatography (using 4% methanol in DCM as eluent) to obtain methyl 1-(2-((4-fluorophenyl) amino)-5-methylpyridin-4-yl)-1H-imidazole-4-carboxylate (0.4 g, 77%). 1HNMR (400 MHz, CDCl$_3$): δ 8.18 (s, 1H), 7.74 (s, 1H), 7.61 (s, 1H), 7.29-7.25 (m, 2H), 7.06 (t, J=8 Hz, 2H), 6.55 (s, 1H), 5.29 (s, 1H), 3.92 (s, 3H), 2.14 (s, 3H). LC-MS calcd exact mass 326.12, found m/z 327.2 [M+H]$^+$.

Step 3: 1-(2-((4-Fluorophenyl)amino)-5-methylpyridin-4-yl)-1H-imidazole-4-carboxylic acid

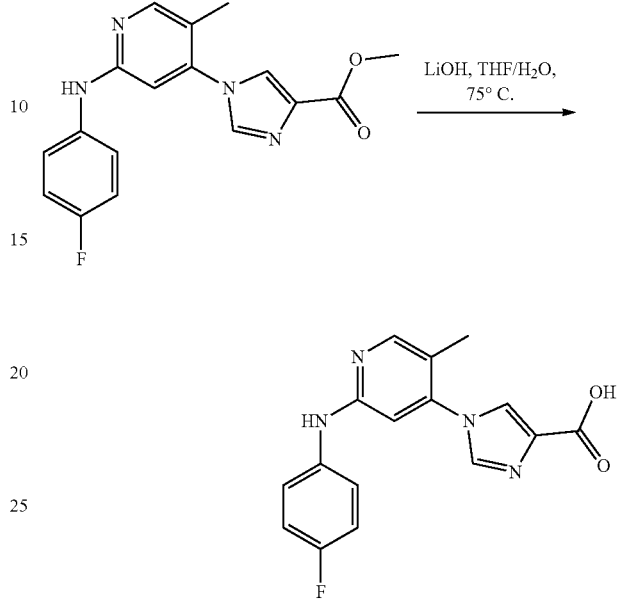

To a solution of methyl 1-(2-((4-fluorophenyl)amino)-5-methylpyridin-4-yl)-1H-imidazole-4-carboxylate (0.450 g, 1.38 mmol) in THF (12 mL) was added LiOH (0.289 g, 6.90 mmol) in water (8 mL). The mixture was stirred at reflux overnight, and the mixture was cooled, concentrated under reduced pressure, and neutralized by the addition of 2N HCl. The reaction mixture was diluted with water and extracted with ethyl acetate. The combined organic phases were dried over with sodium sulfate, filtered and evaporated under reduced pressure to obtain 1-(2-((4-fluorophenyl)amino)-5-methylpyridin-4-yl)-1H-imidazole-4-carboxylic acid (0.210 g, 49%). 1HNMR (400 MHz, CDCl$_3$): δ 12.0 (br s, 1H), 9.15 (s, 1H), 8.15 (d, J=11.2 Hz, 2H), 8.04 (s, 1H), 7.64-7.60 (m, 2H), 7.09 (t, J=17.2 Hz, 2H), 6.73 (s, 1H), 2.08 (s, 3H), LC-MS calcd exact mass 312.10, found m/z 313.1 [M+H]$^+$.

Step 4: N—(Cyano(phenyl)methyl)-1-(2-((4-fluorophenyl)amino)-5-methylpyridin-4-yl)-1H-imidazole-4-carboxamide

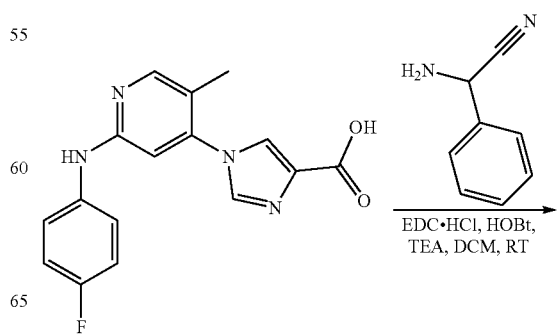

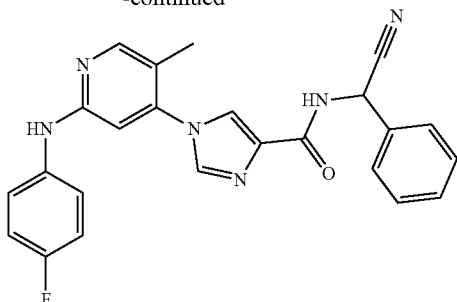

To a solution of 1-(2-((4-fluorophenyl)amino)-5-methylpyridin-4-yl)-1H-imidazole-4-carboxylic acid (0.2 g, 0.0641 mmol) in DCM (16 mL) were added 2-amino-2-phenylacetonitrile (0.151 g, 0.0769 mmol), EDC (0.345 g, 0.128 mmol), HOBt (0.040 g, 0.019 mmol), and TEA (0.194 g, 0.192 mmol).

The reaction mixture was stirred at RT for 24 h. Reaction mixture was quenched with water and extracted with ethyl acetate. The organic phase was dried over sodium sulfate, filtered and evaporated under reduced pressure to obtain crude product. The crude product was purified by Biotage Isolera (using 6% methanol in DCM as eluent) to give N-(cyano(phenyl)methyl)-1-(2-((4-fluorophenyl)amino)-5-methylpyridin-4-yl)-1H-imidazole-4-carboxamide (0.040 g, 15%). 1HNMR (400 MHz, CDCl$_3$): δ 8.36 (s, 1H), 8.12 (d, J=14.4 Hz, 2H), 7.63-7.60 (m, 3H), 7.52 (d, J=12 Hz, 2H), 7.45-7.34 (m, 4H), 7.09 (t, J=8 Hz, 2H), 6.73 (s, 1H), 6.34 (d, J=8 Hz, 1H), 2.87 (s, 1H), 2.08 (s, 3H). LC-MS calcd exact mass 426.16, found m/z 427.2 [M+H]$^+$.

Step 5: N-(2-amino-1-phenylethyl)-1-(2-((4-fluorophenyl)amino)-5-methylpyridin-4-yl)-1H-imidazole-4-carboxamide

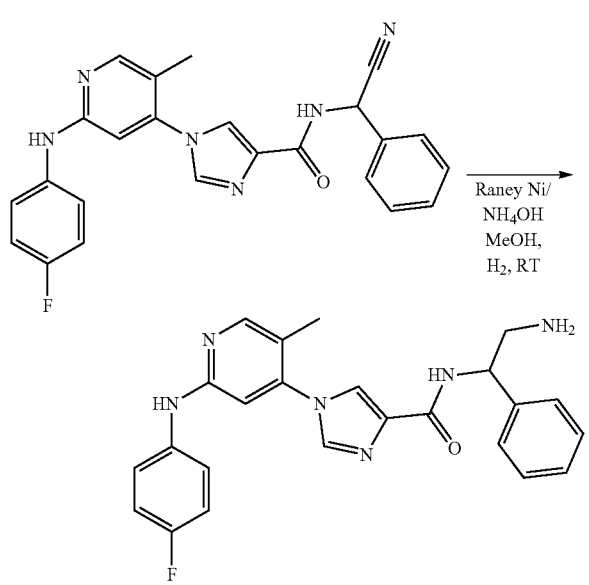

To a solution of N-(cyano(phenyl)methyl)-1-(2-(4-fluorophenyl)amino)-5-methylpyridin-4-yl)-1H-imidazole-4-carboxamide (0.04 g, 0.0094 mmol) in methanol (5 mL) was added Raney nickel (0.060 g) and ammonium hydroxide (5 mL). The resulting reaction mixture was stirred under hydrogen atmosphere using bladder for 6 h at RT. The reaction mixture was filtered through Celite bed and washed with methanol, and the filtrate was evaporated under reduced pressure. The residue was purified by preparative TLC (using 3.5% methanol in DCM as eluent) to obtain desired product (0.010 g, 25%). 1HNMR (400 MHz, DMSO-d$_6$): δ 9.14 (s, 1H), 8.45 (d, J=8.4 Hz, 8.15 (s, 1H), 8.08 (s, 1H), 7.97 (s, 1H), 7.61 (t, J=8.4 Hz, 2H), 7.37-7.29 (m, 4H), 7.24-7.22 (m, 1H), 7.11-7.06 (m, 2H), 6.72 (s, 1H), 4.98 (d, J=5.2 Hz, 1H), 3.06-2.93 (m, 2H), 2.09 (s, 3H). LC-MS calcd exact mass 430.19, found m/z 431.5 [M+H]$^+$, HPLC purity 98.54%, mp 154.7° C.

Representative Example for General Scheme 12

Example 19: N-(1-cyano-2-phenylethyl)-1-(2-((2,2-difluorobenzo[d][1,3]dioxol-5-yl)amino)-5-methylpyridin-4-yl)-1H-1,2,3-triazole-4-carboxamide (Compound #134)

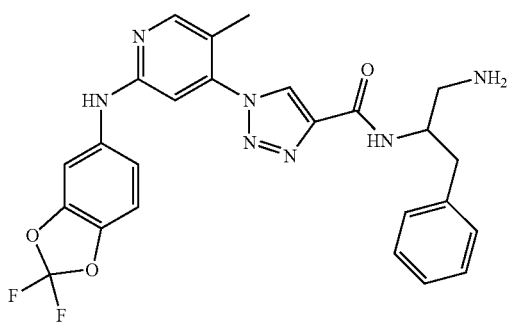

Step 1: 4-Azido-2-chloro-5-methylpyridine

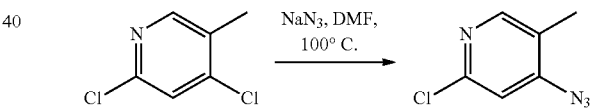

To a stirred solution of 2,4-dichloro-5-methylpyridine (1.0 g, 6.7 mmol) in DMF (15 mL) was added sodium azide (0.52 g, 8.1 mmol), and the resulting solution was then stirred at 100° C. for 4 h. Then the mixture was cooled to 0° C., quenched with water (35 mL), and extracted with ethyl acetate (3×25 mL). The combined organic layers were dried over Na$_2$SO$_4$, filtered and concentrated under reduced pressure, and the residue (crude product, 1.2 g) was used in the next step without purification.

Step 2: Methyl 1-(2-chloro-5-methylpyridin-4-yl)-1H-1,2,3-triazole-4-carboxylate

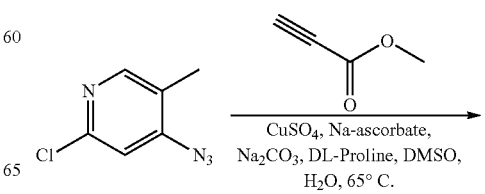

-continued

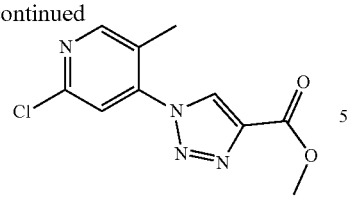

To a stirred solution of 4-azido-2-chloro-5-methylpyridine (1.0 g, 5.93 mmol, crude) in DMSO (10 mL) plus H₂O (2 mL) was added CuSO$_4$.5H$_2$O (0.074 g, 0.0297 mmol), methyl propiolate (0.499 g, 5.95 mmol), sodium ascorbate (0.117 g, 0.595 mmol), sodium carbonate (0.126 g, 1.19 mmol), and DL-proline (0.126 g, 1.19 mmol) at RT. The resulting mixture was stirred at 65° C. for 18 h. Then the reaction mixture was cooled to 0° C., quenched with water (35 mL), and extracted with ethyl acetate (3×25 mL). The combined organic layers were dried over Na$_2$SO$_4$, filtered and concentrated under reduced pressure, and the residue was purified by column chromatography using 40% ethyl acetate in n-hexane as eluent, to give desired product as a white solid (0.87 g, 56%). LC-MS calcd exact mass 252.04, found m/z 253.06 [M+H]⁺.

Step 3: Methyl 1-(2-((2, 2-difluorobenzo[d][1,3]dioxol-5-yl)amino)-5-methylpyridin-4-yl)-1H-1,2,3-triazole-4-carboxylate

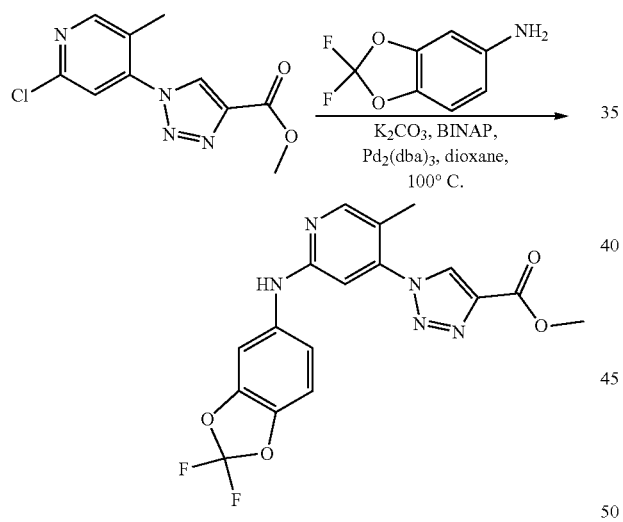

To a stirred solution of methyl 1-(2-chloro-5-methylpyridin-4-yl)-1H-1,2,3-triazole-4-carboxylate (0.4 g, 1.58 mmol) in dioxane (20 mL) was added K$_2$CO$_3$ (0.438 g, 3.17 mmol), BINAP (0.098 g, 0.158 mmol), and 2,2-difluorobenzo[d][1,3]dioxol-5-amine (0.549 g, 3.17 mmol) at RT. The resulting solution was degassed with argon gas for 20 min, then Pd$_2$(dba)$_3$ (0.145 g, 0.18 mmol) was added, and the reaction mixture was stirred at 100° C. for 8 h in a sealed glass tube. Then the reaction mixture was cooled to 0° C., quenched with water (35 mL), and extracted with ethyl acetate (3×25 mL). The combined organic layers were dried over Na$_2$SO$_4$, filtered and concentrated under reduced pressure, and the crude product residue was purified by column chromatography using ethyl acetate in n-hexane as eluent to give desired product as a white solid (0.43 g, 70%). LC-MS calcd exact mass 389.09, found m/z 388.19 [M−H]⁻.

Step 4: 1-(2-((2, 2-Difluorobenzo[d][1,3]dioxol-5-yl)amino)-5-methylpyridin-4-yl)-1H-1,2,3-triazole-4-carboxylic acid

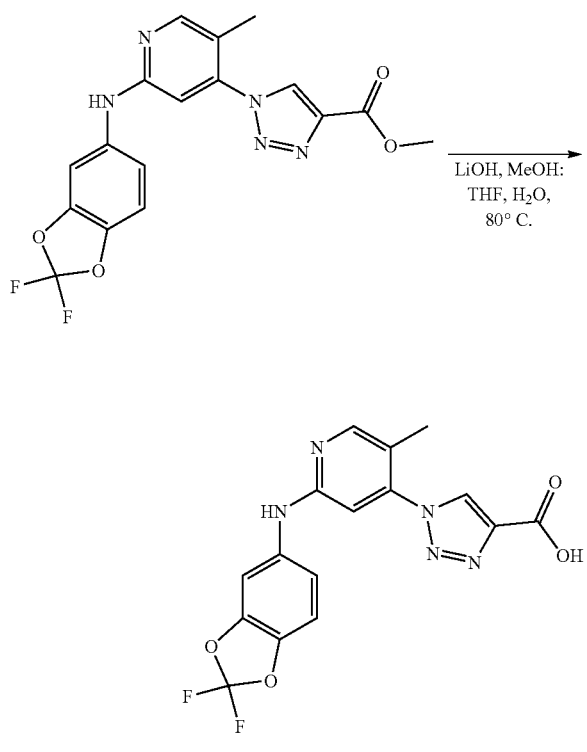

To a stirred solution of methyl 1-(2-((2,2-difluorobenzo[d][1,3]dioxol-5-yl)amino)-5-methylpyridin-4-yl)-1H-1,2,3-triazole-4-carboxylate (0.24 g, 1.02 mmol) in THF:H$_2$O (5 mL:2 mL) was added LiOH (0.215 g, 5.14 mmol), and then the reaction mixture was stirred at 80° C. for 4 h. The mixture was cooled to 0° C., acidified by the addition of 2 N HCl solution (10 mL), and then extracted with ethyl acetate (3×20 mL). The combined organic layers were dried over Na$_2$SO$_4$, filtered and concentrated under reduced pressure, to give desired product as a yellowish solid (0.21 g, 91%). LC-MS calcd exact mass 375.08, found m/z 376.0 [M+H]⁺.

Step 5: N-(1-cyano-2-phenylethyl)-1-(2-((2,2-difluorobenzo[d][1,3]dioxol-5-yl)amino)-5-methylpyridin-4-yl)-1H-1,2,3-triazole-4-carboxamide

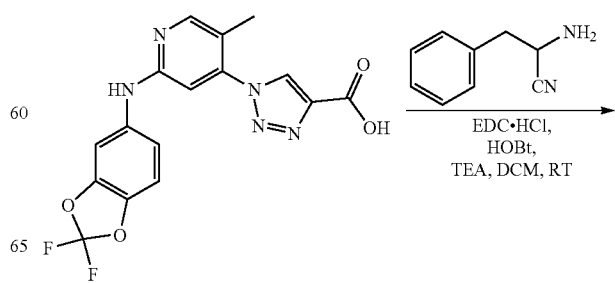

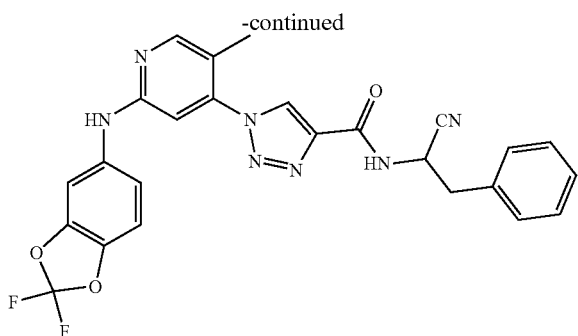

To a stirred solution of 1-(2-(2,2-difluorobenzo[d][1,3]dioxol-5-yl)amino)-5-methylpyridin-4-yl)-1H-1,2,3-triazole-4-carboxylic acid (0.2 g, 0.533 mmol) in DCM (10 mL) was added EDC (0.2 g, 1.06 mmol), triethylamine (0.18 mL, 1.33 mmol), and HOBt (0.1 g, 0.799 mmol). Then, 2-amino-3-phenylpropanenitrile (0.155 g, 1.066 mmol) was added and the resulting mixture was stirred at RT for 18 h. The mixture was quenched with water (20 mL), and extracted with ethyl acetate (3×20 mL). The combined organic layers were dried over Na$_2$SO$_4$, filtered and concentrated under reduced pressure, and the residue was purified by gradient chromatography using 60-120 mesh silica gel, eluting with 25% ethyl acetate in n-hexane, to give desired product as a yellowish solid (0.15 g, 56%).

Step 6: N-(1-amino-3-phenylpropan-2-yl)-1-(2-((2,2-difluorobenzo[d][1,3]dioxol-5-yl)amino)-5-methylpyridin-4-yl)-1H-1,2,3-triazole-4-carboxamide

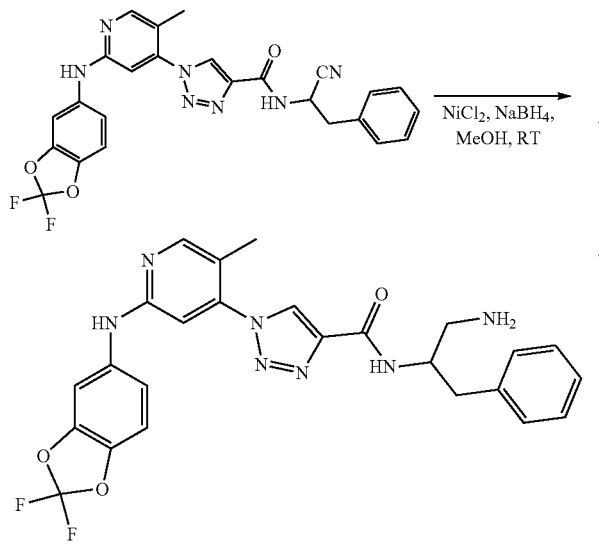

To a stirred solution of N-(1-cyano-2-phenylethyl)-1-(2-((2,2-difluorobenzo[d][1,3]dioxol-5-yl)amino)-5-methylpyridin-4-yl)-1H-1,2,3-triazole-4-carboxamide (0.13 g, 0.258 mmol) in methanol (10 mL) was added DCM (2 mL) to form a clear solution. To the solution was then added NiCl$_2$ (0.006 g, 0.051 mmol) and NaBH$_4$ (0.049 g, 1.29 mmol), and the mixture was stirred at RT for 14 h. The reaction mixture was quenched with water (20 mL), filtered through Celite, and extracted with DCM (3×20 mL). The combined organic layers were dried over Na$_2$SO$_4$, filtered and concentrated under reduced pressure, and the crude product residue was purified by gradient chromatography using 60-120 mesh silica gel, eluting with 8% MeOH in DCM, to give desired product as a yellowish solid (0.03 g, 23%). 1HNMR (400 MHz, DMSO-d$_6$): δ 11.29 (s, 1H), 9.49 (s, 1H), 9.04 (s, 1H), 8.59 (d, J=8.8 Hz, 1H), 8.28 (s, 1H), 7.93 (d, J=1.6 Hz, 1H), 7.33-7.14 (m, 8H), 6.94 (d, J=9.6 Hz, 1H), 4.29 (s, 1H), 3.50 (s, 1H), 3.16-2.83 (m, 3H), 1.97 (s, 3H). LC-MS calcd exact mass 507.18, found m/z 508.22 [M+H]$^+$; HPLC purity 97.94%.

Representative Example for General Scheme 13

Example 20: N-(1-(3-chlorophenyl)-2-hydroxyethyl)-1-(2-(((S)-1-hydroxybutan-2-yl)amino)pyridin-4-yl)-1H-imidazole-4-carboxamide (Compound #105)

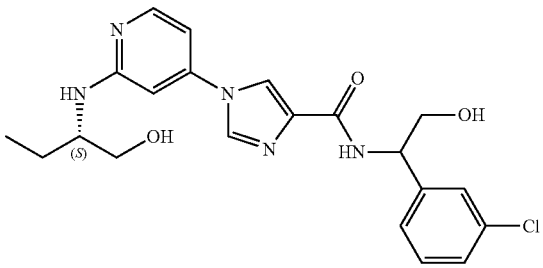

Step 1: (S)-2-((4-Iodopyridin-2-yl)amino)butan-1-ol

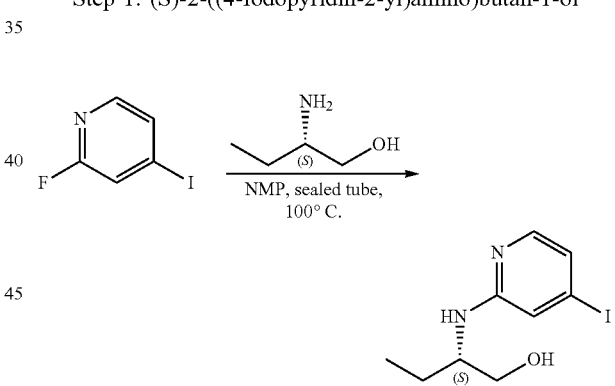

To a stirred solution of 2-fluoro-4-iodopyridine (2.0 g, 8.97 mmol), in NMP (10 mL) was added (S)-2-aminobutan-1-ol (1.197 g, 13.45 mmol), then the mixture was stirred for 12 h at 100° C. in a sealed glass tube. Then the reaction mixture was cooled, quenched with water (50 mL), and extracted with ethyl acetate (3×80 mL). The combined organic layers were dried over sodium sulfate, filtered and concentrated under reduced pressure, and the residue was purified by gradient column chromatography eluting with 20% ethyl acetate in n-hexane to give (S)-2-((4-iodopyridin-2-yl)amino)butan-1-ol, as an off-white solid, (0.8 g, 30%). 1HNMR (400 MHz, DMSO-d$_6$): δ 7.61 (d, J=5.6 Hz, 1H), 6.91 (s, 1H), 6.74-6.72 (m, 1H), 6.34 (d, J=8 Hz, 1H), 4.57 (t, J=6 Hz, 1H), 3.73 (d, J=5.2 Hz, 1H), 3.42-3.38 (m, 1H), 3.31 (s, 1H), 1.60 (t, J=6 Hz, 1H), 1.36 (t, J=7.2 Hz, 1H), 0.84 (t, J=7.6 Hz, 3H). LC-MS calcd exact mass 292.01, found m/z 293.0 [M+H]$^+$.

Step 2: (S)-Methyl 1-(2-((1-hydroxybutan-2-yl)amino)pyridin-4-yl)-1H-imidazole-4-carboxylate

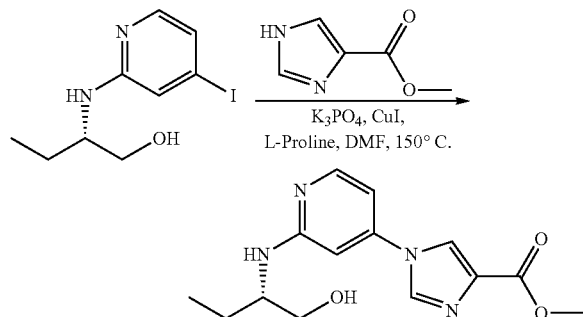

To a stirred solution of (S)-2-((4-iodopyridin-2-yl)amino)butan-1-ol (0.8 g, 1.71 mmol), in DMF (5 mL) was added potassium phosphate (0.32 g, 2.57 mmol), methyl 1H-imidazole-4-carboxylate (0.323 g, 2.57 mmol), and L-proline (0.039 g, 0.34 mmol). The mixture was degassed with argon gas for 20 min, then copper(I) iodide (0.065 g, 0.34 mmol) was added, and then the mixture was stirred for 12 h at 150° C. in a sealed glass tube. Then the reaction mixture was cooled and quenched with water (35 mL), and extracted with ethyl acetate (3×60 mL). The combined organic layers were dried over sodium sulfate, filtered and concentrated under reduced pressure, and the residue was purified by gradient column chromatography eluting with 80% ethyl acetate in n-hexane to give (S)-methyl 1-(2-((1-hydroxybutan-2-yl)amino)pyridin-4-yl)-1H-imidazole-4-carboxylate as an off-white semi-solid, (0.25 g, 32% yield). $^1$HNMR (400 MHz, DMSO-$d_6$): δ 8.42 (s, 1H), 8.38 (s, 1H), 8.02 (d, J=6 Hz, 1H), 7.67 (m, 1H), 6.85 (m, 1H), 6.75 (s, 1H), 6.36 (d, J=8.4 Hz, 1H), 5.72 (s, 1H), 4.61 (s, 1H), 4.12 (m, 1H), 3.81 (d, J=4 Hz, 1H), 3.78 (s, 3H), 3.46 (t, J=5.6 Hz, 1H), 3.34 (t, J=5.6 Hz, 2H), 1.60-1.44 (m, 1H), 1.33-1.24 (m, 1H), 0.89-0.83 (m, 3H). LC-MS calcd exact mass 290.14, found m/z 291.2 [M+H]$^+$.

Step 3: (S)-1-(2-((1-Hydroxybutan-2-yl)amino)pyridin-4-yl)-1H-imidazole-4-carboxylic acid

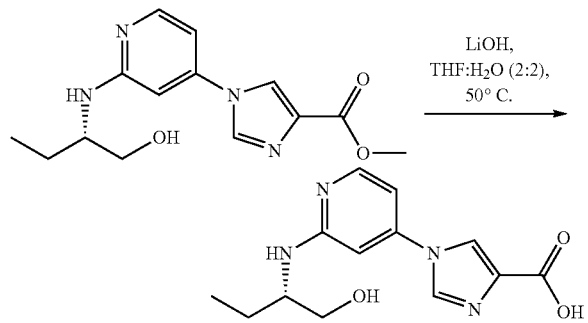

To a stirred solution of (S)-methyl 1-(2-((1-hydroxybutan-2-yl)amino)pyridin-4-yl)-1H-imidazole-4-carboxylate (0.25 g, 0.86 mmol) in THF:water (5 mL:5 mL) was added lithium hydroxide monohydrate (0.179 g, 4.29 mmol), and then the mixture was stirred for 12 h at 50° C. The mixture was cooled and concentrated under reduced pressure, combined with water (15 mL), and washed with ethyl acetate (2×5 mL). The aqueous layer was adjusted to pH~6-6.5 by the addition of 4N HCl, then the solid that formed was removed by filtration and dried under high vacuum, to give desired product as an off-white solid (0.15 g, 63% yield). $^1$HNMR (400 MHz, DMSO-$d_6$): δ 12.5 (br s, 1H), 8.32 (d, J=12 Hz, 2H), 8.02 (d, J=5.2 Hz, 1H), 6.84-6.82 (m, 1H), 6.74 (s, 1H), 6.37 (d, J=8.4 Hz, 1H), 3.81 (d, J=5.6 Hz, 1H), 3.48-3.44 (m, 1H), 1.67-1.60 (m, 1H), 1.46-1.40 (m, 1H), 1.37-1.31 (m, 1H), 1.26-1.24 (m, 1H), 0.89-0.86 (m, 3H). LC-MS calcd exact mass 276.12, found m/z 277.2 [M+H]$^+$.

Step 4: N-(1-(3-Chlorophenyl)-2-hydroxyethyl)-1-(2-(((S)-1-hydroxybutan-2-yl)amino)pyridin-4-yl)-1H-imidazole-4-carboxamide

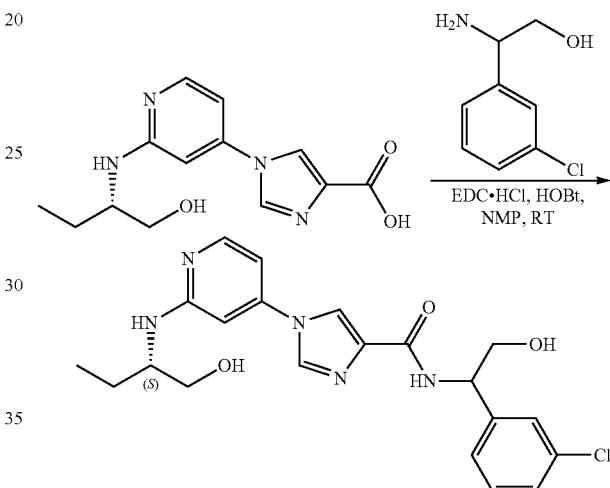

To a stirred solution of (S)-1-(2-((1-hydroxybutan-2-yl)amino)pyridin-4-yl)-1H-imidazole-4-carboxylic acid (0.07 g, 0.25 mmol) in NMP (3 mL), was added triethylamine (0.076 g, 0.76 mmol), followed by EDC (0.097 g, 0.51 mmol) and HOBt (0.01 g, 0.075 mmol). The mixture was stirred for 20 min at RT, and then 2-amino-2-(3-chlorophenyl)ethanol (0.052 g, 0.30 mmol) was added, and then the reaction mixture was stirred for 12 h at RT. The reaction mixture was quenched with water (25 mL), and extracted with ethyl acetate (3×50 mL). The combined organic layers were washed with brine (10 mL), dried over sodium sulfate, filtered and evaporated under reduced pressure and the residue was purified by gradient column chromatography, eluting with 3% methanol in DCM, to give N-(1-(3-chlorophenyl)-2-hydroxyethyl)-1-(2-(((S)-1-hydroxybutan-2-yl)amino)pyridin-4-yl)-1H-imidazole-4-carboxamide, as an off-white solid, (15 mg, 14%). $^1$HNMR (400 MHz, DMSO-$d_6$): δ 8.38 (t, J=7.2 Hz, 2H), 8.18 (s, 1H), 8.01 (d, J=5.6 Hz, 1H), 7.42 (s, 1H), 7.32-7.26 (m, 3H), 6.84 (d, J=5.6 Hz, 1H), 6.74 (s, 1H), 6.36 (d, J=7.6 Hz, 1H), 5.02-4.99 (m, 2H), 4.61 (d, J=5.6 Hz, 1H), 3.81 (s, 1H), 3.71 (t, J=5.6 Hz, 1H), 3.47-3.44 (m, 1H), 3.34-3.27 (m, 1H), 1.67-1.65 (m, 1H), 1.63-1.61 (m, 1H), 1.07 (t, J=7.2 Hz, 1H), 0.87 (t, J=6.8 Hz, 3H). LC-MS calcd exact mass 429.16, found m/z 430.2 [M+H]$^+$; HPLC Purity 99.46%.

Example 21: N-(1-(3-chlorophenyl)-2-hydroxy-ethyl)-1-(2-((2,3-dihydrobenzofuran-5-yl)amino)pyridin-4-yl)-1H-imidazole-4-carboxamide (Compound #163)

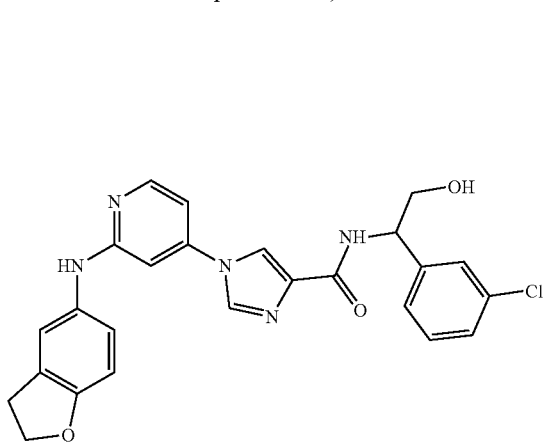

Step 1: N-(2,3-Dihydrobenzofuran-5-yl)-4-iodopyridin-2-amine

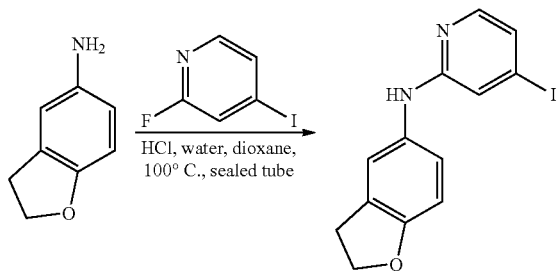

To a suspension of 2,3-dihydrobenzofuran-5-amine (1 g, 7.4 mmol) in 1:1 dioxane:water (200 mL) was added 2-fluoro-4-iodopyridine (1.982 g, 8.8 mmol) and aqueous HCl (2 mL, 35%). The mixture was stirred for 15 h at 100° C. in a sealed glass tube. Reaction mixture was cooled and basified by the addition of saturated aqueous sodium bicarbonate, and extracted with ethyl acetate. The combined organic layers were dried over Na$_2$SO$_4$, filtered and evaporated to give crude product residue, which was purified by gradient column chromatography using ethyl acetate in n-hexane as eluent to afford N-(2,3-dihydrobenzofuran-5-yl)-4-iodopyridin-2-amine as yellow solid, (600 mg, 24%). 1HNMR (400 MHz, CDCl$_3$): δ 7.76 (d, J=4.8 Hz, 1H), 7.13 (s, 1H), 7.00-6.97 (m, 3H), 6.77 (d, J=8.4 Hz, 1H), 6.48 (s, 1H), 4.60 (t, J=8.8 Hz, 2H), 3.23 (t, J=8.8 Hz, 2H). LC-MS calcd exact mass 337.99, found m/z 339.0 [M+H]$^+$.

Step 2: Methyl 1-(2-((2,3-dihydrobenzofuran-5-yl)amino)pyridin-4-yl)-1H-imidazole-4-carboxylate

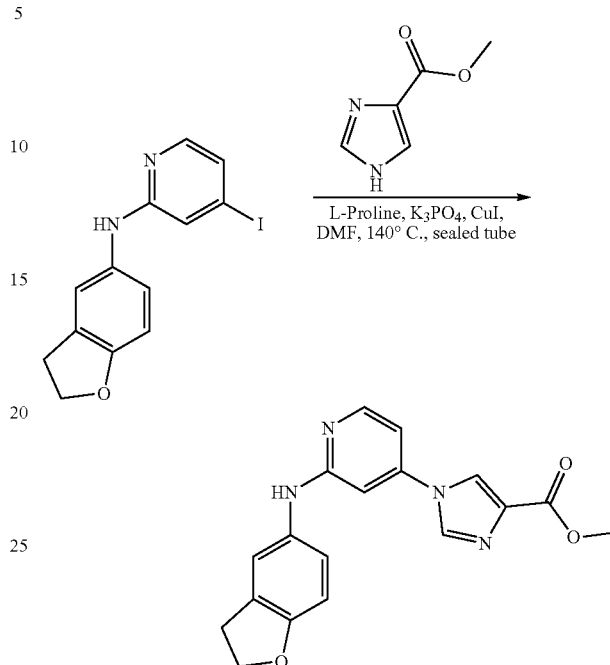

To a solution of N-(2,3-dihydrobenzofuran-5-yl)-4-iodopyridin-2-amine (300 mg, 0.88 mmol) in DMF (3 mL) was added methyl 1H-imidazole-4-carboxylate (167 mg, 1.3 mmol), potassium phosphate (564 mg, 2.6 mmol) and L-Proline (20 mg, 0.17 mmol) under a nitrogen atmosphere. The reaction mixture was purged with nitrogen for 10 min, then copper iodide (33 mg, 0.17 mmol) was added, and then the reaction mixture was stirred for 15 h at 140° C. in a sealed glass tube. Reaction mixture was cooled and filtered through Celite, and the filtrate was diluted with water and extracted with ethyl acetate. The combined organic layers were dried over Na$_2$SO$_4$, filtered, and evaporated under reduced pressure, and the residue was purified by gradient column chromatography using ethyl acetate in n-hexane as eluent to afford methyl 1-(2-((2,3-dihydrobenzofuran-5-yl)amino)pyridin-4-yl)-1H-imidazole-4-carboxylate as a yellow semi-solid (0.10 g, 17%). LC-MS calcd exact mass 336.12, found m/z 337.2 [M+H]$^+$.

Step 3: N-(1-(3-Chlorophenyl)-2-hydroxyethyl)-1-(2-((2,3-dihydrobenzofuran-5-yl)amino)pyridin-4-yl)-1H-imidazole-4-carboxamide

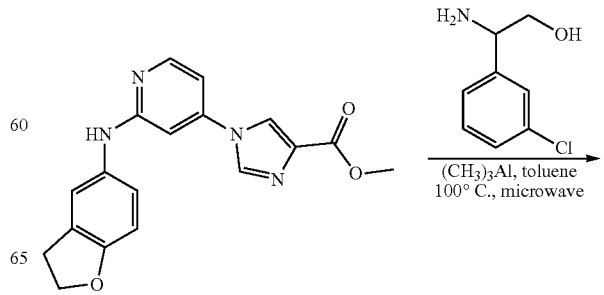

-continued

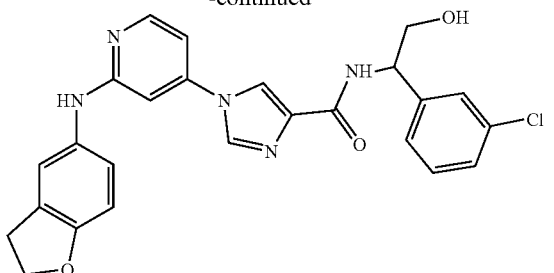

To a solution of methyl 1-(2-((2,3-dihydrobenzofuran-5-yl)amino)pyridin-4-yl)-1H-imidazole-4-carboxylate (90 mg, 0.26 mmol) in toluene (3 mL) was added 2-amino-2-(3-chlorophenyl)ethanol (91 mg, 5.3 mmol) and trimethyl-aluminum in toluene (2M, 0.26 mL, 2 eq) under a nitrogen atmosphere. The mixture was stirred for 45 min at 100° C. in the CEM microwave. The reaction mixture was poured into ice water and extracted with ethyl acetate. Combined organic layers were dried over Na$_2$SO$_4$, filtered and evaporated under reduced pressure to give a residue, which was purified by gradient column chromatography using methanol in DCM as eluent to afford N-(1-(3-chlorophenyl)-2-hydroxyethyl)-1-(2-((2,3-dihydrobenzofuran-5-yl)amino)pyridin-4-yl)-1H-imidazole-4-carboxamide as an off-white solid (20 mg, 16%). 1HNMR (400 MHz, DMSO-d$_6$): δ 8.88 (s, 1H), 8.42-8.37 (m, 2H), 8.20-8.16 (m, 2H), 7.51 (s, 1H), 7.42 (s, 1H), 7.32-7.28 (m, 4H), 7.21 (d, J=8.4 Hz, 1H), 7.05 (d, J=4.8 Hz, 1H), 6.88 (s, 1H), 6.8 (d, J=8.4 Hz, 2H), 5.02 (br s, 2H), 4.47 (t, J=8.8 Hz, 2H), 3.72 (s, 2H), 3.15 (t, J=8.4 Hz, 2H). LC-MS calcd exact mass 475.14, found m/z 476.1 [M+H]$^+$.

Representative Example for General Scheme 20

Example 22: (S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide (Alternative Synthesis for Compound #225a)

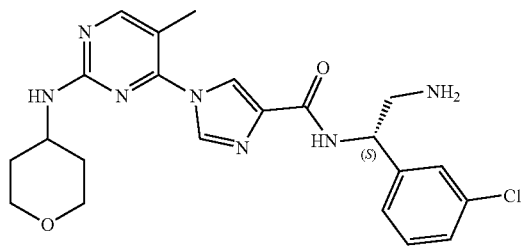

Step 1: (S)-tert-butyl (1-(3-chlorophenyl)-2-hydroxyethyl)carbamate

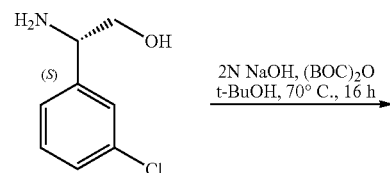

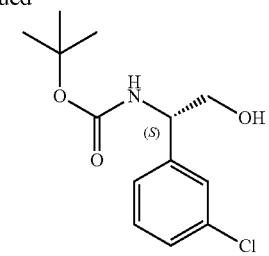

To a stirred solution of (S)-2-amino-2-(3-chlorophenyl)ethanol (1.0 g, 5.83 mmol) in t-butanol (15 mL) was added 2M sodium hydroxide solution (0.29 g, 7.28 mmol) and di-tert-butyl-dicarbonate (1.92 mL, 8.16 mmol). The reaction mixture was stirred at 70° C. for 16.0 h. The progress of the reaction was monitored by TLC (30% ethyl acetate in n-hexane, KMnO$_4$ active). The reaction mixture was quenched with water (40 mL), extracted with ethyl acetate (3×40 mL), and combined organic layers were concentrated under reduced pressure. The residue was purified by gradient chromatography, using 60-120 mesh silica gel, eluting with 20% ethyl acetate in in-hexane, collect the fractions and concentrated under reduced pressure, to afford (S)-tert-butyl (1-(3-chlorophenyl)-2-hydroxyethyl)carbamate, as a white solid (1.0 g, 63%). $^1$HNMR (400 MHz, DMSO-d$_6$): δ 7.32-7.21 (m, 5H), 4.78 (t, J=5.6 Hz, 1H), 4.49 (d, J=5.6 Hz, 1H), 3.51-3.41 (m, 2H), 1.34 (s, 9H).

Step 2: (S)-2-((tert-butoxycarbonyl)amino)-2-(3-chlorophenyl) ethyl methanesulfonate

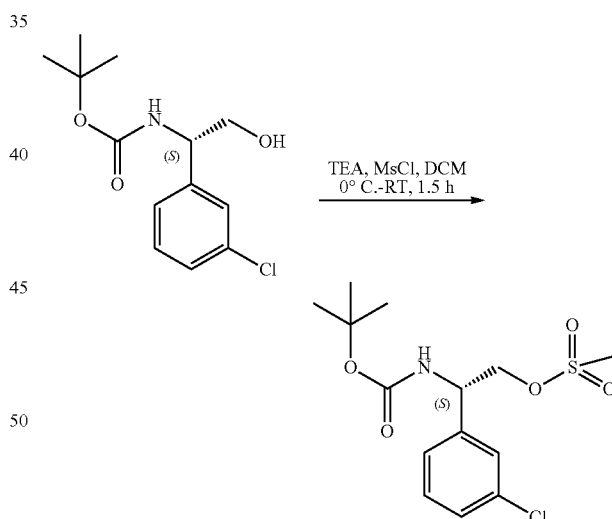

To a stirred solution of (S)-tert-butyl (1-(3-chlorophenyl)-2-hydroxyethyl)carbamate (1.0 g, 3.68 mmol) in dichloromethane (15 mL) was added triethyl amine (0.62 mL, 4.42 mmol), the mixture was cooled to 0° C. Methanesulfonyl chloride (0.313 mL, 4.049 mmol) was added at 0° C., then the mixture was stirred at room temperature for 1.5 h. The progress of the reaction was monitored by TLC (25% ethyl acetate in n-hexane). The reaction mixture was quenched with saturated ammonium chloride (20 mL), extracted with dichloromethane (3×30 mL), and the combined organic layers were dried over sodium sulphate, filtered and concentrated under reduced pressure, washed with n-pentane and dried under vacuum, to afford (S)-2-((tert-butoxycarbonyl)amino)-2-(3-chlorophenyl)ethyl methanesulfonate, as a yellow oil, (0.65 g, 51%).

Step 3: (S)-tert-butyl (2-azido-1-(3-chlorophenyl)ethyl)carbamate

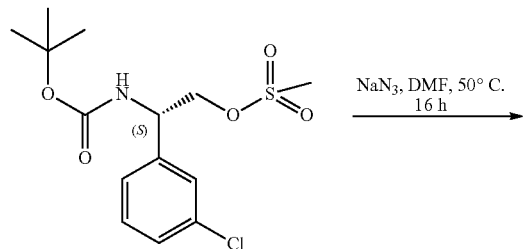

To a stirred solution of (S)-2-((tert-butoxycarbonyl)amino)-2-(3-chlorophenyl)ethyl methanesulfonate (0.65 g, 1.86 mmol), in N,N-dimethyl formamide (10 mL) was added sodium azide (0.242 g, 3.72 mmol) and the mixture was stirred at 50° C. for 16 h. The progress of the reaction was monitored by TLC (20% ethyl acetate in n-hexane). The reaction mixture was quenched with saturated ammonium chloride (15 mL), followed by water (30 mL), extracted with ethyl acetate (3×30 mL), and combined organic layers were concentrated under reduced pressure. The residue was purified by gradient chromatography using 60-120 mesh silica gel, eluting with 8% ethyl acetate in n-hexane. The appropriate fractions were collected and concentrated under reduced pressure, to afford (S)-tert-butyl (2-azido-1-(3-chlorophenyl)ethyl)carbamate, as a colorless oil, (0.5 g, 91%). $^1$HNMR (400 MHz, DMSO-d$_6$): δ 7.67-7.58 (m, 1H), 7.42 (br s, 1H), 7.37-7.31 (m, 3H), 4.73 (br s, 1H), 3.44 (t, J=8.4 Hz, 2H), 1.35 (s, 9H).

Step 4: (S)-2-azido-1-(3-chlorophenyl)ethanamine hydrochloride

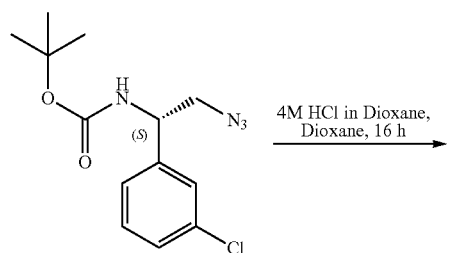

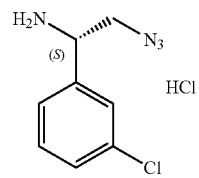

To a stirred solution of (S)-tert-butyl (2-azido-1-(3-chlorophenyl)ethyl) carbamate (0.5 g, 1.69 mmol) in dioxane (5 mL) was added 4M HCl in dioxane (10 mL) at 0° C. and the mixture was stirred at room temperature for 16 h. The reaction mixture was concentrated under reduced pressure, triturated with n-pentane and dried under vacuum, to afford (S)-2-azido-1-(3-chlorophenyl)ethanamine hydrochloride, as an off white solid, (0.43 g, HCl salt), LCMS calcd exact mass 196.05, m z found 197.1 [M+H]$^+$.

Step 5: 1-(5-methyl-2-((tetrahydro-2H-pyran-4-yl)amino)pyrimidin-4-yl)-1H-imidazole-4-carboxylic acid

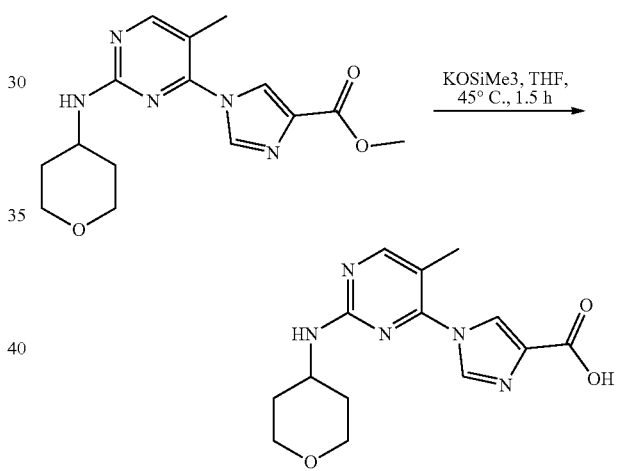

To a stirred solution of methyl 1-(5-methyl-2-((tetrahydro-2H-pyran-4-yl)amino)pyrimidin-4-yl)-1H-imidazole-4-carboxylate (10.0 g, 31.53 mmol) in tetrahydrofuran (450 mL), was added potassium trimethyl silanolate (12.13 g, 94.60 mmol) at 0° C., and the resulting mixture was stirred at 45° C. for 1.5 h. The progress of reaction was monitored by TLC (5% methanol in dichloromethane). The reaction mixture was quenched with water (250 mL), washed with ethyl acetate (3×50 mL), then the aqueous layer was adjusted to pH 4-5 by addition of 4N HCl solution, extracted with 10% methanol in dichloromethane (8×250 mL), and combined organic layers were concentrated under reduced pressure, to afford 1-(5-methyl-2-((tetrahydro-2H-pyran-4-yl)amino)pyrimidin-4-yl)-1H-imidazole-4-carboxylic acid, as an off white solid, (7.0 g, 73%). $^1$HNMR (400 MHz, DMSO-d$_6$): δ 12.46 (br s, 1H), 8.34 (s, 1H), 8.23 (br s, 1H), 8.20 (s, 1H), 7.36 (d, J=7.6 Hz, 1H), 3.89 (br s, 1H), 3.83 (d, J=11.6 Hz, 2H), 3.39-3.33 (m, 2H), 2.16 (s, 3H), 1.80 (d, J=10.4 Hz, 2H), 1.52-1.42 (m, 2H). LCMS calcd exact mass 303.13, found m z 304.1 [M+H]$^+$.

Step 6: (S)—N-(2-azido-1-(3-chlorophenyl)ethyl)-1-(5-methyl-2-((tetrahydro-2H-pyran-4-yl)amino)pyrimidin-4-yl)-1H-imidazole-4-carboxamide

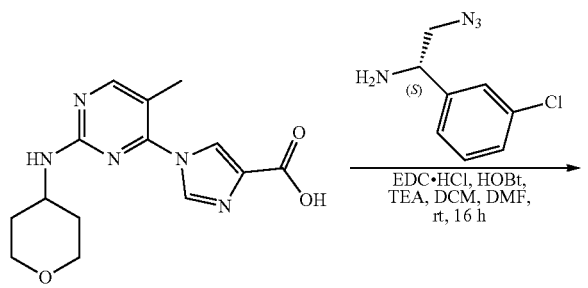

To a stirred solution of 1-(5-methyl-2-((tetrahydro-2H-pyran-4-yl)amino)pyrimidin-4-yl)-1H-imidazole-4-carboxylic acid (6.0 g, 19.80 mmol) in dichloromethane (150 mL) and N,N-dimethyl formamide (50 mL) was added triethylamine (13.81 mL, 98.97 mmol), 1-ethyl-3-(3-dimethylaminopropyl)carbodiimide (5.99 g, 59.40 mmol), hydroxybenzotriazole (0.605 g, 3.96 mmol) and (S)-2-azido-1-(3-chlorophenyl)ethanamine hydrochloride (4.65 g, 19.80 mmol) under nitrogen atmosphere. The reaction mixture was stirred at room temperature for 16 h. The progress of the reaction was monitored by TLC (5% methanol in dichloromethane). Then the reaction mixture was quenched with saturated sodium bicarbonate solution (50 mL) and extracted with dichloromethane (3×50 mL), washed with water (100 mL) and brine (50 mL). The combined organic layers were concentrated under reduced pressure. The residue was purified by gradient chromatography using 60-120 mesh silica gel, eluting with 4% methanol in dichloromethane. The appropriate fractions were collected and concentrated under reduced pressure to afford (S)—N-(2-azido-1-(3-chlorophenyl)ethyl)-1-(5-methyl-2-((tetrahydro-2H-pyran-4-yl)amino)pyrimidin-4-yl)-1H-imidazole-4-carboxamide as an off white solid (5.65 g, 59%). LCMS calcd exact mass 481.17, found m z 482.1 [M+H]$^+$.

Step 7: (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide

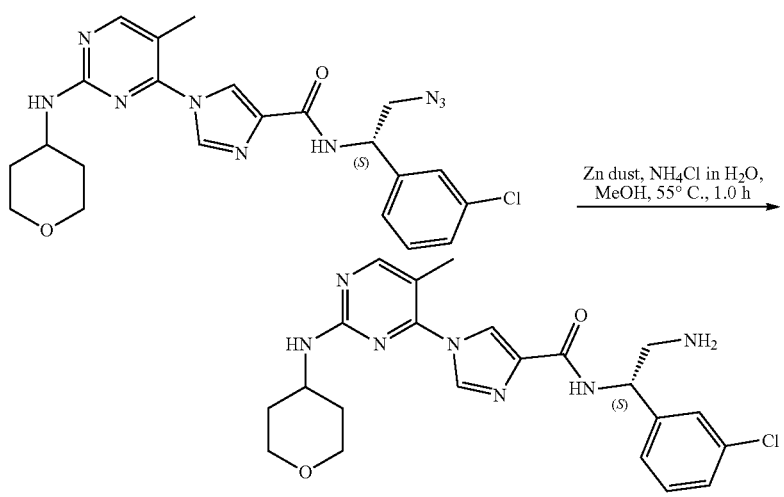

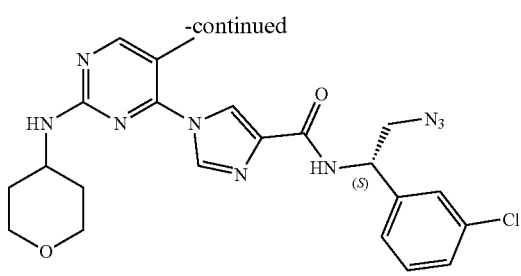

To a stirred solution of (S)—N-(2-azido-1-(3-chlorophenyl)ethyl)-1-(5-methyl-2-((tetrahydro-2H-pyran-4-yl)amino)pyrimidin-4-yl)-1H-imidazole-4-carboxamide (7.12 g, 14.77 mmol) in methanol (75 mL) was added zinc dust (4.82 g, 73.87 mmol), the resulting solution was stirred at room temperature for 10 min, then added ammonium chloride (3.95 g, 73.87 mmol) in water (15 mL). The reaction mixture was stirred at 55° C. for 1 h. The progress of the reaction was monitored by TLC (5% methanol in dichloro methane). The reaction mixture was quenched with saturated sodium bicarbonate solution (50 mL) and filtered through celite, then washed with 10% methanol in dichloromethane. The organic layer was washed with water (2×25 mL), and the combined organic layers were concentrated under reduced pressure. The residue was purified by Biotage chromatography system using 60-120 mesh silica gel, eluting with 13% (methanol/isopropylamine) in dichloromethane. The appropriate fractions were collected and concentrated under reduced pressure, to afford (S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide, as an off white solid, (4.38 g, 65%). $^1$HNMR (400 MHz, DMSO-d$_6$): δ 8.52 (d, J=8.0 Hz, 1H), 8.33 (s, 1H), 8.26 (s, 1H), 8.07 (s, 1H), 7.40 (s, 1H), 7.36-7.25 (m, 4H), 4.92-4.87 (m, 1H), 3.86 (br s, 1H), 3.84-3.81 (d, J=11.2 Hz, 2H), 3.33 (t, J=11.6 Hz, 2H), 2.97-2.92 (m, 1H), 2.88-2.85 (m, 1H), 2.17 (s, 3H), 1.80 (d, J=11.6 Hz, 2H), 1.51-1.44 (m, 4H). LCMS calcd exact mass 455.18, found m/z 456.1 [M+H]+. HPLC purity: 99.47%, Chiral HPLC purity: 99.68%.

The following examples illustrate the preparation of some of the compounds:

Example 23: (S)—N-(2-Amino-1-(3-chlorophenyl)ethyl)-1-(2-((3,3-difluorocyclobutyl)amino)-5-methylpyrimidin-4-yl)-1H-imidazole-4-carboxamide (Compound #259)

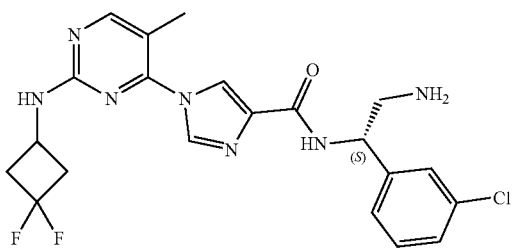

Step 1: Methyl 1-(2-((3,3-difluorocyclobutyl)amino)-5-methylpyrimidin-4-yl)-1H-imidazole-4-carboxylate

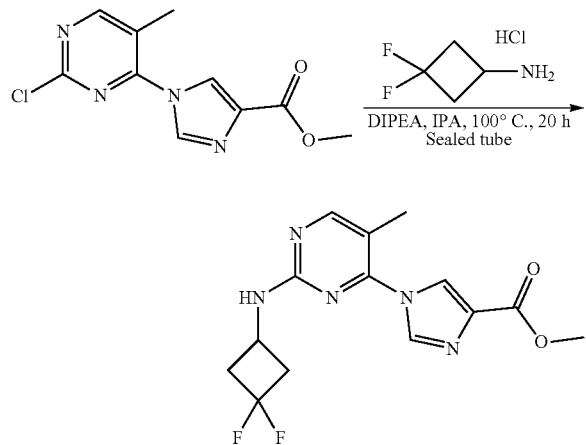

To a stirred solution of methyl 1-(2-chloro-5-methylpyrimidin-4-yl)-1H-imidazole-4-carboxylate (10.0 g, 39.59 mmol) in isopropanol (60 mL) was added N,N-diisopropylethylamine (28.36 mL) and 3,3-difluorocyclobutanamine hydrochloride (6.81 g, 47.50 mmol). The reaction mixture was stirred at 100° C. for 20 h in a sealed tube. The progress of the reaction was monitored by TLC (5% methanol in dichloromethane). The reaction mixture was cooled to 0° C. and the crystals that formed were filtered and dried under reduced pressure to afford compound methyl 1-(2-((3,3-difluorocyclobutyl)amino)-5-methylpyrimidin-4-yl)-1H-imidazole-4-carboxylate, as an off-white solid, (23.0 g, 89%). LCMS calcd exact mass 323.12, found m z 324.2 [M+H]+.

Step 2: 1-(2-((3,3-Difluorocyclobutyl)amino)-5-methylpyrimidin-4-yl)-1H-imidazole-4-carboxylic acid

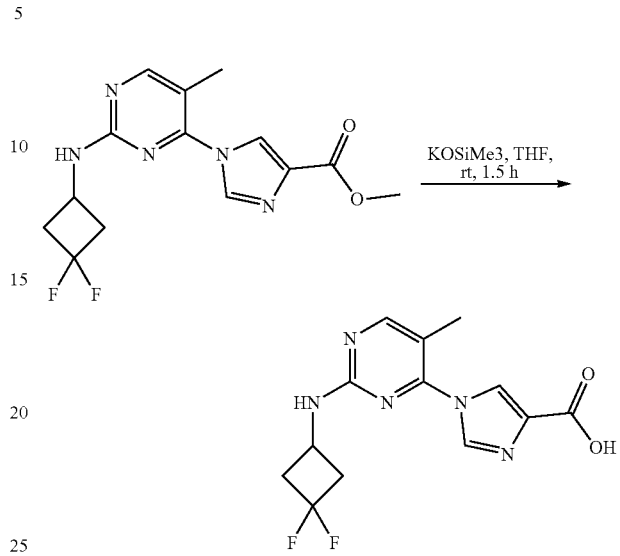

To a stirred solution of methyl 1-(2-((3,3-difluorocyclobutyl)amino)-5-methylpyrimidin-4-yl)-1H-imidazole-4-carboxylate (30.5 g, 94.3 mmol) in THF (1.0 L) was added potassium trimethyl silanolate (48.38 g, 377.4 mmol) at 0° C., and the resulting reaction mixture was then stirred at room temperature for 1.5 h, using a mechanical stirrer. The progress of the reaction was monitored by TLC (5% methanol in dichloromethane). The reaction mixture was quenched with water (1.0 L), and washed with ethyl acetate (3×200 mL). The aqueous phase was adjusted to pH~3-4 by gradual addition of concentrated HCl, and the mixture was extracted with 10% methanol in dichloromethane (8×1.5 L). The combined organic layers were concentrated under reduced pressure, to afford 1-(2-((3,3-difluorocyclobutyl)amino)-5-methylpyrimidin-4-yl)-1H-imidazole-4-carboxylic acid, as an off white solid, (27.0 g, 93%). $^1$HNMR (400 MHz, DMSO-$d_6$): δ 12.50 (br s, 1H), 8.38 (s, 1H), 8.26 (s, 1H), 8.22 (s, 1H), 7.88 (d, J=6.0 Hz, 1H), 4.17 (t, J=6.4 Hz, 1H), 2.98-2.88 (m, 2H), 2.68-2.57 (m, 2H), 2.18 (s, 3H). LCMS calcd exact mass 309.10, found m z 310.1 [M+H]+.

Step 3: (S)—N-(2-Azido-1-(3-chlorophenyl)ethyl)-1-(2-((3,3-difluorocyclobutyl)amino)-5-methyl-pyrimidin-4-yl)-1H-imidazole-4-carboxamide

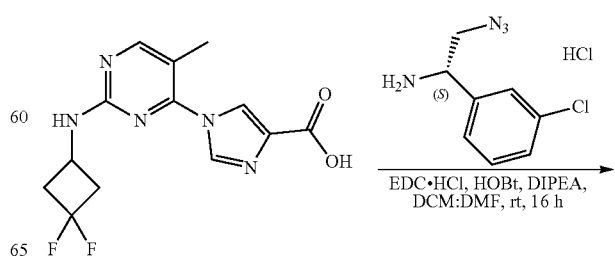

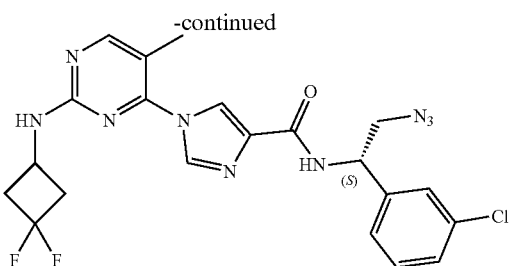

To a stirred solution of 1-(2-((3,3-difluorocyclobutyl)amino)-5-methylpyrimidin-4-yl)-1H-imidazole-4-carboxylic acid (5.5 g, 17.79 mmol) in dichloromethane: N,N-dimethylformamide (150 mL: 50 mL), was added N,N-diisopropylethylamine (15.49 mL, 88.98 mmol), 1-ethyl-3-(3-dimethylaminopropyl) carbodiimide (6.82 g, 35.54 mmol), hydroxybenzotriazole (1.399 g, 88.99 mmol), and (S)-2-azido-1-(3-chlorophenyl)ethanamine hydrochloride (4.950 g, 19.41 mmol), and then the mixture was stirred at room temperature for 16 h. The progress of the reaction was monitored by TLC (5% methanol in dichloromethane). The reaction mixture was quenched with water (500 mL), followed by addition of saturated sodium bicarbonate solution (50 mL), then extracted with ethyl acetate (3×250 mL). The combined organic layers were dried over sodium sulfate, and concentrated under reduced pressure. The residue was purified by gradient chromatography using 60-120 mesh silica gel, eluting at 3% methanol in dichloromethane. The collected fractions were concentrated under reduced pressure, to afford (S)—N-(2-azido-1-(3-chlorophenyl)ethyl)-1-(2-((3,3-difluorocyclobutyl)amino)-5-methyl-pyrimidin-4-yl)-1H-imidazole-4-carboxamide, as a yellow gummy oil (6.0 g, 69%). $^1$HNMR (400 MHz, DMSO-$d_6$): δ 8.87 (d, J=9.2 Hz, 1H), 8.38 (s, 1H), 8.30 (s, 1H), 8.13 (s, 1H), 7.86 (d, J=6.0 Hz, 1H), 7.55 (s, 1H), 7.42 (d, J=7.2 Hz, 1H), 7.36-7.28 (m, 2H), 5.25 (d, J=5.2 Hz, 1H), 4.17 (t, J=6.4 Hz, 1H), 3.86 (t, J=12.0 Hz, 1H), 3.65-3.60 (m, 1H), 2.95-2.90 (m, 2H), 2.67-2.60 (m, 2H), 2.20 (s, 3H). LCMS calcd exact mass 487.14, found m z 488.1 [M+H]$^+$.

Step 4: (S)—N-(2-Amino-1-(3-chlorophenyl)ethyl)-1-(2-((3,3-difluoro cyclo butyl) amino)-5-methylpyrimidin-4-yl)-1H-imidazole-4-carboxamide

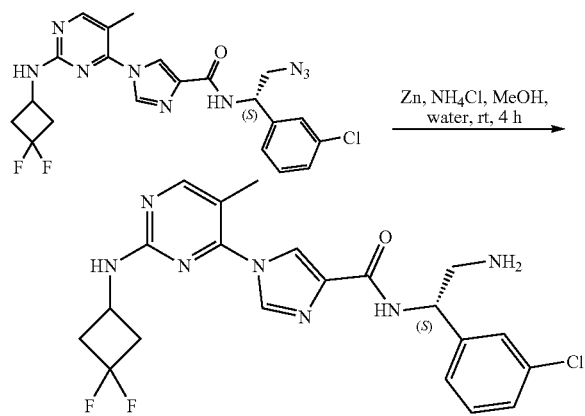

To a stirred solution of (S)—N-(2-azido-1-(3-chlorophenyl)ethyl)-1-(2-((3,3-difluorocyclobutyl) amino)-5-methyl pyrimidin-4-yl)-1H-imidazole-4-carboxamide (6.0 g, 12.30 mmol) in methanol (100 mL), was added zinc dust (6.43 g, 98.38 mmol) and ammonium chloride (5.35 g, 98.38 mmol) in water (25 mL), and then the mixture was stirred at room temperature for 4 h. The progress of the reaction was monitored by TLC (5% methanol in dichloromethane). The reaction mixture was quenched with ammonia solution (50 mL), filtered through celite, washed with 5% methanol in dichloromethane (25 mL), and the organic layer was separated. The aqueous layer was extracted with 5% methanol in dichloromethane (3×80 mL), and the combined organic layers were concentrated under reduced pressure. The residue was purified by gradient chromatography using 60-120 mesh silica gel, eluting with 8% (methanol/isopropylamine) in dichloromethane. Fractions were collected and concentrated under reduced pressure, to afford (S)—N-(2-amino-1-(3-chlorophenyl)ethyl)-1-(2-((3,3-difluorocyclobutyl) amino)-5-methylpyrimidin-4-yl)-1H-imidazole-4-carboxamide, as a white solid (4.1 g, 72%). $^1$HNMR (400 MHz, DMSO-$d_6$): δ 8.54 (d, J=8.0 Hz, 1H), 8.38 (s, 1H), 8.29 (s, 1H), 8.10 (s, 1H), 7.86 (d, J=5.6 Hz, 1H), 7.40 (s, 1H), 7.35-7.25 (m, 3H), 4.93-4.88 (m, 1H), 4.17 (d, J=6.0 Hz, 1H), 2.90-2.84 (m, 4H), 2.68-2.55 (m, 2H), 2.20 (s, 3H), 1.54 (br s, 2H). LCMS calcd exact mass 461.15, found m z 462.1 [M+H]$^+$. HPLC purity: 99.98%, Chiral HPLC: 99.97%, mp 104.3° C.

Example 24: (S)—N-(2-Amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide (Compound #275)

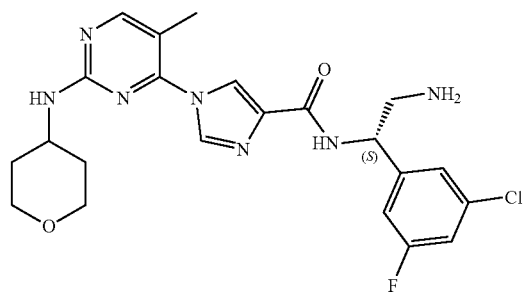

Step 1: (S)-tert-Butyl (1-(3-chloro-5-fluorophenyl)-2-hydroxyethyl) carbamate

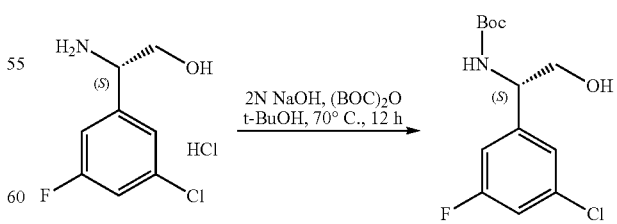

To a stirred solution of (S)-2-amino-2-(3-chloro-5-fluorophenyl)ethanol hydrochloride (10 g, 44.44 mmol) in t-butanol (100 mL) was added 2N NaOH (2.22 g, 55.55 mmol, in 111 mL water) and di-tert-butyl dicarbonate (13.56 g, 62.22 mmol). The resulting mixture was stirred at 70° C. for 12 h. The progress of the reaction was monitored by TLC. Then the reaction was quenched with water (2×100 mL) and extracted with ethyl acetate (2×100 mL), and the combined organic layers were washed with water (30 mL) followed by brine (30 mL), dried over sodium sulfate, filtered and evaporated under reduced pressure to provide 13 g of crude product. The crude product was combined with two additional crude product batches that were prepared in a similar manner, and the combined material was purified by gradient column chromatography using ethyl acetate in n-hexane as eluent to afford (S)-tert-butyl (1-(3-chloro-5-fluorophenyl)-2-hydroxyethyl)carbamate as an off white solid (94% yield). ¹HNMR (400 MHz, DMSO-d₆): δ 7.26-7.23 (m, 2H), 7.20 (s, 1H), 7.11 (d, J=8 Hz, 1H), 4.83 (t, J=4 Hz, 1H), 4.52-4.50 (m, 1H), 3.50-3.43 (m, 2H), 1.34 (s, 9H). LC-MS calcd exact mass 289.74, found m z 190.0 [M+H-Boc]+.

Step 2: (S)-2-((tert-Butoxycarbonyl)amino)-2-(3-chloro-5-fluorophenyl)ethylmethanesulfonate

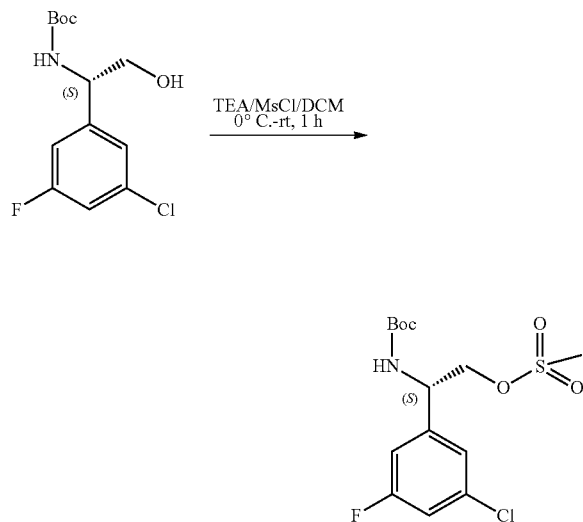

To a stirred solution of (S)-tert-butyl (1-(3-chloro-5-fluorophenyl)-2-hydroxyethyl) carbamate (12 g, 41.52 mmol) in dichloromethane (100 mL) at 0° C. was added triethylamine (6.93 mL, 49.83 mmol) and the mixture was stirred for 10 min at 0° C. Then methane sulfonyl chloride (3.73 mL, 45.674 mmol) was added, and the mixture was stirred at room temperature for 1 h. The progress of the reaction was monitored by TLC. The reaction was quenched with water (100 mL) and extracted with dichloromethane (3×100 mL), and the combined organic layers were washed with saturated ammonium chloride solution (100 mL) and brine (50 mL). The organic layer was dried over sodium sulfate, filtered and evaporated under reduced pressure to afford (S)-2-((tert-butoxycarbonyl)amino)-2-(3-chloro-5-fluorophenyl)ethyl methanesulfonate (15.25 g) as a light yellow solid, which was used for the next step without further purification. ¹HNMR (400 MHz, DMSO-d₆): δ 7.68 (d, J=8.4 Hz, 1H), 7.36 (s, 1H), 7.33 (s, 1H), 7.29 (d, J=9.6 Hz, 1H), 4.28-4.19 (m, 2H), 3.15 (s, 3H), 1.36 (s, 9H). LC-MS calcd exact mass 367.07, found m z 268.0 [M+H-Boc]+.

Step 3: (S)-tert-Butyl (2-azido-1-(3-chloro-5-fluoro-phenyl)ethyl)carbamate

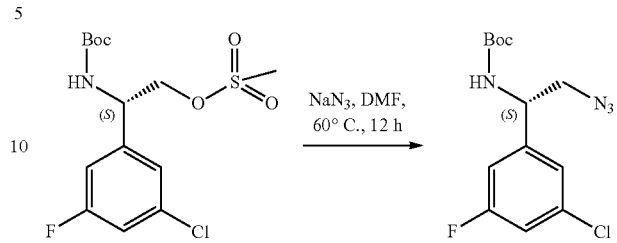

To a stirred solution of (S)-2-((tert-butoxycarbonyl) amino)-2-(3-chloro-5-fluorophenyl)ethyl methanesulfonate (15.25 g, 41.55 mmol) in N,N,-dimethylformamide (100 mL) at room temperature was added sodium azide (5.4 g, 83.11 mmol). The reaction mixture was heated at 60° C. for 12 h. The progress of the reaction was monitored by TLC, then the reaction mixture was cooled to room temperature, diluted with water (100 mL) and extracted with ethyl acetate (3×100 mL). The combined organic layers were washed with water (100 mL) followed by brine (100 mL), and dried over sodium sulfate, filtered and evaporated under reduced pressure. The crude product was combined with two additional crude product batches that were prepared in a similar manner, and the combined material was purified by gradient column chromatography using ethyl acetate in n-hexane as eluent to afford (S)-tert-butyl (2-azido-1-(3-chloro-5-fluorophenyl)ethyl)carbamate as an off white solid (83% yield). ¹HNMR (400 MHz, DMSO-d₆): δ 7.66 (d, J=8.0 Hz, 1H), 7.31 (bs, 2H), 7.21 (d, J=12.0 Hz, 1H), 4.77-4.75 (m, 1H), 4.44 (d, J=8.0 Hz, 2H), 1.36 (s, 9H). LC-MS calcd exact mass 314.09, found m z 259 [M+H-tBu]+.

Step 4: (S)-2-Azido-1-(3-chloro-5-fluorophenyl) ethanamine hydrochloride

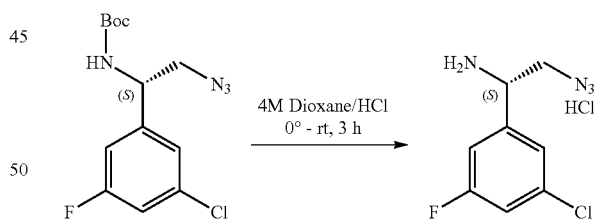

To a stirred solution of (S)-tert-butyl (2-azido-1-(3-chloro-5-fluoro phenyl)ethyl)carbamate (10 g, 31.85 mmol) in 1,4-dioxane (100 mL) was added drop wise 4M HCl in 1,4-dioxane (100 mL) at 0° C. The reaction mixture was stirred at room temperature for 3 h. Excess solvent was evaporated under reduced pressure to obtain a solid residue. The solid was washed with pentane (2×50 mL) and dried to give (S)-2-azido-1-(3-chloro-5-fluorophenyl) ethanamine hydrochloride (7.87 g, 98.8%) as an off-white solid. ¹HNMR (400 MHz, DMSO-d₆): δ 8.94 (br s, 3H), 7.56 (s, 1H), 7.49 (d, J=4.8 Hz, 2H), 4.55 (t, J=6.4 Hz, 1H), 3.92-3.81 (m, 2H). LC-MS calcd exact mass 214.04, found m z 215.1 [M+H]⁺.

Step 5: (S)—N-(2-Azido-1-(3-chloro-5-fluorophenyl)ethyl)-1-(5-methyl-2-((tetrahydro-2H-pyran-4-yl)amino)pyrimidin-4-yl)-1H-imidazole-4-carboxamide

Step 6: (S)—N-(2-Amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide

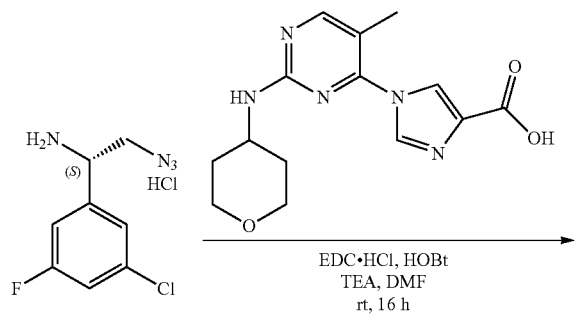

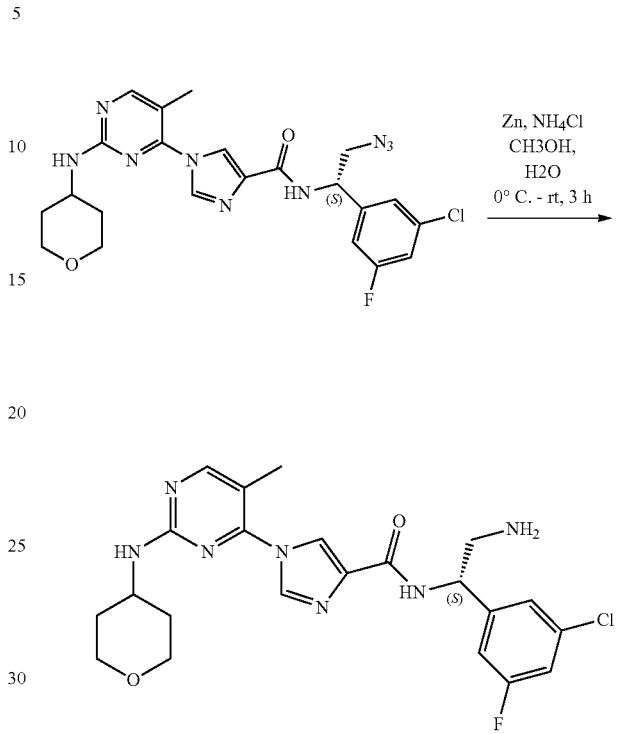

To a stirred solution of 1-(5-methyl-2-((tetrahydro-2H-pyran-4-yl)amino)pyrimidin-4-yl)-1H-imidazole-4-carboxylic acid (12.2 g, 40.26 mmol) in N,N'-dimethylformamide (120 mL) was added triethylamine (16.8 mL, 120.79 mmol), 1-ethyl-3-(3-dimethylaminopropyl)carbodiimide (15.44 g, 80.53 mmol), hydroxybenzotriazole (3.08 g, 20.13 mmol) and (S)-2-azido-1-(3-chloro-5-fluorophenyl)ethanamine hydrochloride (8.01 g, 32.21 mmol) under nitrogen atmosphere. The resulting mixture was stirred at room temperature for 16 h. The progress of the reaction was monitored by TLC (8% methanol in dichloromethane). The reaction mixture was diluted with water (2×100 mL) and extracted with ethyl acetate (2×100 mL). The combined organic layers were washed with saturated ammonium chloride solution (1×200 mL), followed by saturated sodium bicarbonate solution (1×200 mL) and brine (1×50 mL). The organic layer was dried over sodium sulfate, filtered and concentrated under reduced pressure to give the desired crude product. The crude product was combined with two additional crude product batches that were prepared in a similar manner, and the combined material was purified by gradient column chromatography using methanol in dichloromethane as eluent to afford (S)—N-(2-azido-1-(3-chloro-5-fluorophenyl)ethyl)-1-(5-methyl-2-((tetrahydro-2H-pyran-4-yl)amino)pyrimidin-4-yl)-1H-imidazole-4-carboxamide (69%) as an off-white solid. $^1$HNMR (400 MHz, DMSO-$d_6$): δ 8.90 (d, J=8.8 Hz, 1H), 8.34 (s, 1H), 8.28 (s, 1H), 8.11 (s, 1H), 7.42 (s, 1H), 7.34-7.31 (m, 3H), 5.29-5.23 (m, 1H), 3.86 (br s, 1H), 3.85-3.84 (m, 3H), 3.66-3.62 (m, 1H), 3.36 (t, J=10.8 Hz, 2H), 2.17 (s, 3H), 1.80 (d, J=10.8 Hz, 2H), 1.51-1.44 (m, 2H). LCMS calcd exact mass 499.16, found m z 500.1 [M+H]$^+$.

To a stirred solution of (S)—N-(2-azido-1-(3-chloro-5-fluorophenyl)ethyl)-1-(5-methyl-2-((tetrahydro-2H-pyran-4-yl)amino)pyrimidin-4-yl)-1H-imidazole-4-carboxamide (9.0 g, 18.04 mmol) in methanol (100 mL) was added zinc dust (5.89 g, 90.18 mmol), followed by ammonium chloride (4.823 g, 90.18 mmol) in water (20 mL) at 0° C., then the mixture was stirred at room temperature for 3 h. The progress of the reaction was monitored by TLC (8% methanol in dichloromethane). The reaction mixture was quenched with saturated sodium bicarbonate solution (100 mL) and methanol (100 mL), then filtered through celite, washing with methanol. The filtrate was evaporated and diluted with 50 mL sodium bicarbonate, and extracted with DCM (3×100 mL). The combined organic layers were dried over sodium sulfate, filtered and evaporated to give the crude product. The crude product was combined with two additional crude product batches that were prepared in a similar manner, and the combined material was purified by gradient column chromatography using methanol in dichloromethane with 0.1% isopropylamine as eluent, to afford (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide (18.5 g, 55%) as an off-white solid. $^1$HNMR (400 MHz, DMSO-$d_6$): δ 8.58 (d, J=8 Hz, 1H), 8.34 (s, 1H), 8.27 (s, 1H), 8.08 (s, 1H), 7.35 (d, J=7.2 Hz, 1H), 7.28-7.25 (m, 2H), 7.19 (d, J=9.2 Hz, 1H), 4.93-4.90 (m, 1H), 3.90 (br s, 1H), 3.83 (d, J=11.6 Hz, 2H), 3.36 (t, J=10.8 Hz, 2H), 2.95-2.95 (m, 1H), 2.91-2.88 (m, 1H), 2.17 (s, 3H), 1.98-1.9 (br s, 2H), 1.80 (d, J=12 Hz, 2H), 1.50-1.46 (m, 2H), LCMS calcd exact mass 473.17, found m z 474.2 [M+H]$^+$. HPLC purity: 99.79%, Chiral HPLC purity: 99.92%.

Example 25: N-(3-Chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide (Compound #297)

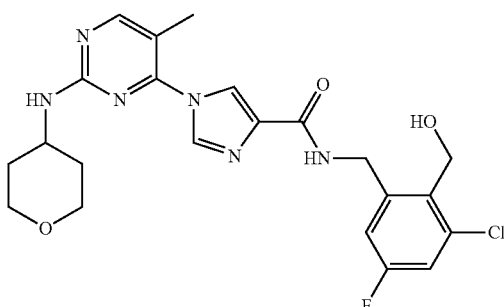

Step 1: 2-Chloro-4-fluoro-6-methylbenzoic acid

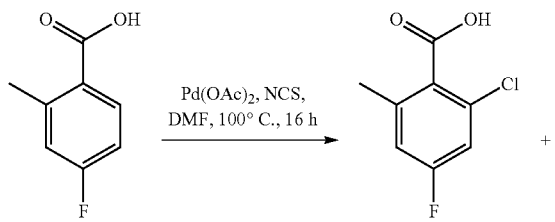

To a stirred solution of 4-fluoro-2-methylbenzoic acid (5.0 g, 32.46 mmol) in N,N-dimethyl-formamide (20 mL) was added palladium acetate (1.74 g, 2.59 mmol), and N-chlorosuccinimide (6.4 g, 48.70 mmol) then the mixture was stirred at 100° C. for 16 h. The reaction mixture was cooled and diluted with saturated sodium thiosulfate solution (200 mL), extracted with ethyl acetate (2×500 mL), and the combined organic layers were washed with brine (50 mL), concentrated under reduced pressure, and dried under vacuum to afford a mixture of 2-chloro-4-fluoro-6-methylbenzoic acid and 4-fluoro-6-methylbenzoic acid, as a brown solid (5 g, crude product mixture) that was used in the next step without purification. LC-MS calcd exact mass for 2-chloro-4-fluoro-6-methylbenzoic acid 188.0, found m z 189.1 [M+H]+.

Step 2: 2-Chloro-4-fluoro-6-methylbenzoic acid

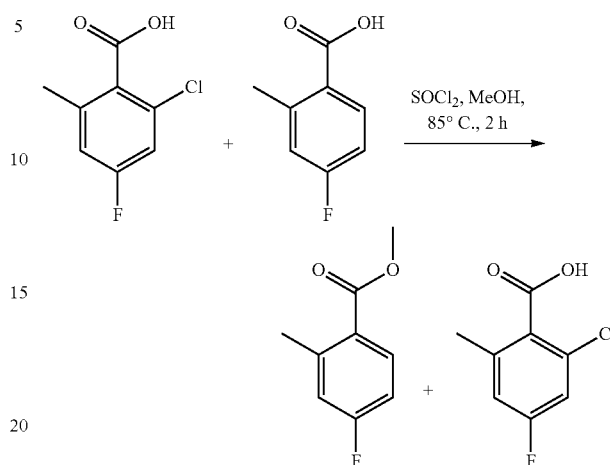

To a stirred solution of 2-chloro-4-fluoro-6-methylbenzoic acid and 4-fluoro-6-methylbenzoic acid (5 g) in methanol (100 mL) was slowly added dropwise thionyl chloride (11.6 mL, 159.5 mmol) at 0° C., then the reaction mixture was stirred at 85° C. for 2 h. The reaction mixture was evaporated and quenched with saturated sodium bicarbonate solution (100 mL), extracted with ethyl acetate (2×300 mL), then aqueous layer was adjusted to pH~6-7 by addition of concentrated HCl, then the compound was extracted with ethyl acetate (2×300 mL), combined organic layers were washed with brine (20 mL), dried over $Na_2SO_4$, concentrated under reduced pressure to afford 2-chloro-4-fluoro-6-methylbenzoic acid as a brown solid (2 g), which was used without further purification. LC-MS calcd exact mass 188.0, found m z 189.0 [M+H]+.

Step 3: Methyl 2-chloro-4-fluoro-6-methylbenzoate

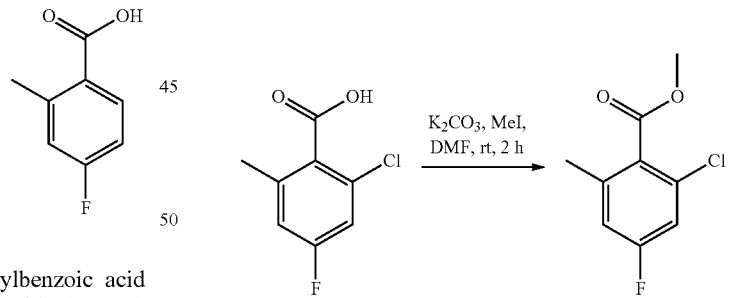

To a stirred solution of 2-chloro-4-fluoro-6-methylbenzoic acid (2 g, 10.63 mmol) in N,N-dimethylformamide (15 mL) was added potassium carbonate (2.9 g, 21.27 mmol) and methyl iodide (3.3 mL, 53.19 mmol) at 0° C., and the mixture was stirred at room temperature for 2 h. The progress of the reaction was monitored by TLC. The reaction mixture was quenched with water (50 mL), extracted with ethyl acetate (2×100 mL), and the combined organic layers were washed with brine (20 mL), dried over sodium sulfate and concentrated under reduced pressure to afford methyl 2-chloro-4-fluoro-6-methylbenzoate as a colorless oil (2 g), which was used without further purification. LC-MS calcd exact mass 202.02, found m z 203.0 [M+H]+.

Step 4: Methyl 2-(bromomethyl)-6-chloro-4-fluorobenzoate

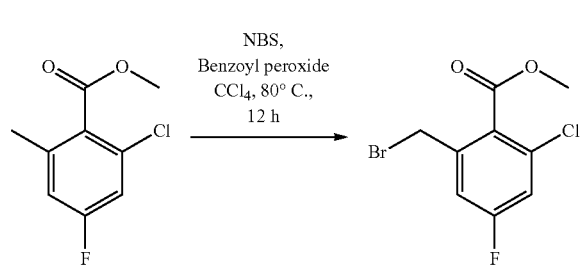

To a stirred solution of methyl 2-chloro-4-fluoro-6-methylbenzoate (2 g, 9.9 mmol) in carbon tetrachloride (5 mL) was added N-bromosuccinimide (1.9 g, 10.8 mmol) and benzoyl peroxide (0.239 g, 0.99 mmol). The resulting mixture was stirred for 12 h at 80° C. The progress of the reaction was monitored by TLC. The reaction mixture was quenched with 1% sodium hydroxide solution (50 mL), extracted with ethyl acetate (2×200 mL), and the combined organic layers were washed with brine (20 mL), dried over sodium sulfate and concentrated under reduced pressure to afford methyl 2-(bromomethyl)-6-chloro-4-fluorobenzoate as a brown liquid (2 g, crude product). LC-MS calcd exact mass 279.93, found m z 281.0 [M+H]$^+$.

Step 5: Methyl 2-(azidomethyl)-6-chloro-4-fluorobenzoate

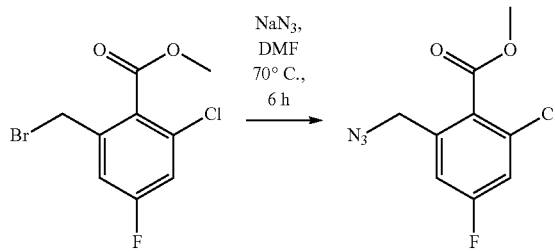

To a stirred solution of methyl 2-(bromomethyl)-6-chloro-4-fluorobenzoate (2 g, 7.16 mmol) in N,N-dimethylformamide (10 mL) was added sodium azide (0.931 g, 14.33 mmol) at 0° C. The resulting mixture was stirred for 6 h at 70° C. The progress of the reaction was monitored by TLC. The reaction mixture was diluted with ice cold water (100 mL), and extracted with ethyl acetate (2×200 mL). The combined organic layer was washed with brine (10 mL), dried over anhydrous sodium sulfate, filtered and evaporated under reduced pressure to afford methyl 2-(azidomethyl)-6-chloro-4-fluorobenzoate as a brown solid (1.5 g, crude product). LC-MS calcd exact mass 243.02, found m z 218.0 for [M−N$_2$+H$_3$].

Step 6: (2-(Aminomethyl)-6-chloro-4-fluorophenyl)methanol

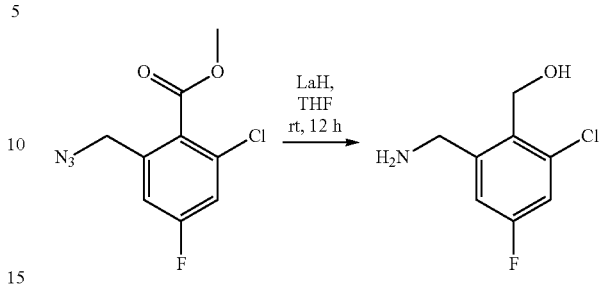

To a stirred solution of methyl 2-(azidomethyl)-6-chloro-4-fluorobenzoate (0.2 g, 0.823 mmol) in THF (10 mL) was added lithium aluminum hydride (0.108 g, 3.29 mmol) at 0° C. slowly. The resulting mixture was stirred for 12 h at room temperature. The progress of reaction was monitored by TLC. The reaction mixture was diluted with ice cold water (50 mL), and extracted with ethyl acetate (2×200 mL). The combined organic layer was washed with brine (10 mL), dried over anhydrous sodium sulfate, filtered and evaporated under reduced pressure to afford (2-(aminomethyl)-6-chloro-4-fluorophenyl)methanol (0.2 g, crude product). LC-MS calcd exact mass 189.04, found m z 190.1 [M+H]$^+$.

Step 7: N-(3-Chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide

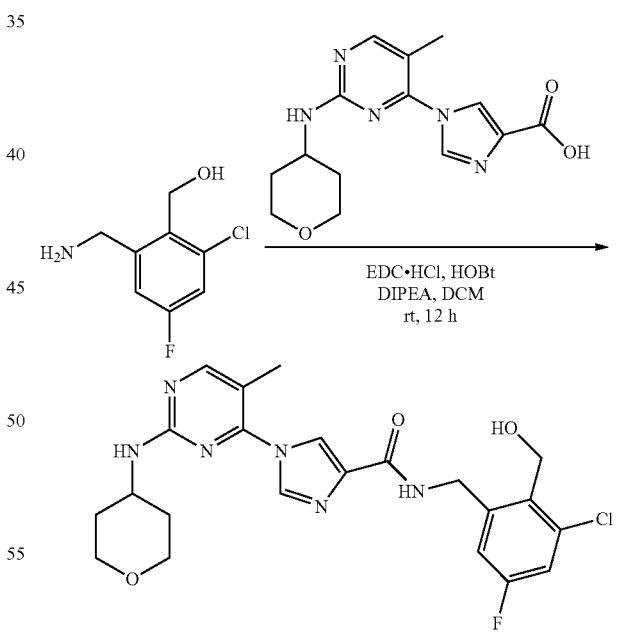

To a stirred solution of 1-(5-methyl-2-((tetrahydro-2H-pyran-4-yl)amino)pyrimidin-4-yl)-1H-imidazole-4-carboxylic acid (0.1 g, 0.33 mmol) in dichloromethane (10 mL) was added (2-(aminomethyl)-6-chloro-4-fluorophenyl)methanol (0.093 g, 0.495 mmol), N,N-diisopropylethylamine (0.16 mL, 0.9 mmol) followed by 1-ethyl-3-(3-dimethylaminopropyl)carbodiimide (0.075 g, 0.396 mmol) and hydroxybenzotriazole (0.06 g, 0.396 mmol). The resulting mixture was stirred for 12 h at room temperature. The progress of the reaction was monitored by TLC. The reaction mixture was diluted with ice cold water (50 mL), and extracted with dichloromethane (2×200 mL). The combined organic layer was washed with brine (10 mL), dried over anhydrous sodium sulfate, filtered and evaporated under reduced pressure. The residue was purified by using a Biotage Isolera system using methanol in dichloromethane as eluent to afford N-(3-chloro-5-fluoro-2-(hydroxymethyl) benzyl)-1-(5-methyl-2-((tetrahydro-2H-pyran-4-yl)amino) pyrimidin-4-yl)-1H-imidazole-4-carboxamide as an off-white solid (0.015 g, 9.5%). $^1$HNMR (400 MHz, DMSO-$d_6$): δ 8.73 (t, 1H), 8.33 (s, 1H), 8.26 (s, 1H), 8.11 (s, 1H), 7.35 (d, J=7.6 Hz, 1H), 7.30-7.28 (m, 1H), 7.10-7.07 (m, 1H), 5.22 (t, 1H), 4.71 (d, J=5.2 Hz, 2H), 4.60 (d, J=6 Hz, 2H), 3.89 (s, 1H), 3.83 (d, J=10.8 Hz, 2H), 3.39-3.32 (m, 2H), 2.17 (s, 3H), 1.82 (t, 2H), 1.53-1.44 (m, 2H). LC-MS calcd exact mass 474.16, found m z 475.1 [M+H]$^+$. HPLC purity 98.2%.

Example 26: (S)—N-(2-Amino-1-(3-chlorophenyl) ethyl)-1-(5-methyl-2-((tetrahydro-2H-pyran-4-yl) amino) pyrimidin-4-yl)-1H-imidazole-4-carboxamide hydrochloride salt (Compound #298)

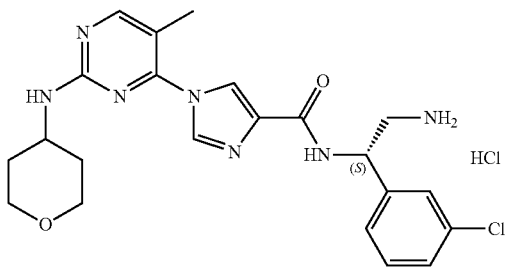

To a solution of (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide (0.1 g, 0.21 mmol) in 1,4-dioxane (10 mL) was slowly added 4M HCl in 1,4-dioxane (0.05 mL, 0.22 mmol) at 0° C. The reaction mixture was stirred for 1.0 h at room temperature. The reaction mixture was evaporated, washed with diethyl ether and dried to afford (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide hydrochloride salt as an off-white solid (0.1 g, 93%). $^1$HNMR (400 MHz, DMSO-$d_6$): δ 8.90 (d, J=9.2 Hz, 1H), 8.35 (s, 1H), 8.29 (s, 1H), 8.14 (s, 1H), 7.97 (br s, 3H), 7.51 (s, 1H), 7.42-7.37 (m, 4H), 5.32 (d, J=4.4 Hz, 1H), 3.83 (d, J=11.6 Hz, 3H), 3.38-3.35 (m, 2H), 3.31-3.23 (m, 2H), 2.16 (s, 3H), 1.80 (d, J=12.8 Hz, 2H), 1.49 (t, 2H). LC-MS calcd exact mass 455.18, found m z 456.2 for [M+H]$^+$. HPLC purity 98.79%, Melting point: 193-195° C.

Example 27: (S)—N-(2-Amino-1-(3-chlorophenyl) ethyl)-1-(5-methyl-2-((tetrahydro-2H-pyran-4-yl) amino)pyrimidin-4-yl)-1H-imidazole-4-carboxamide p-toluenesulfonic acid salt (Compound #299)

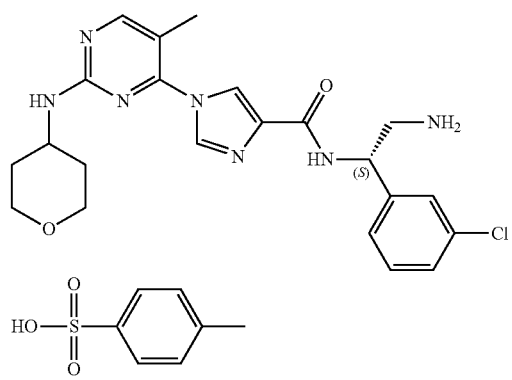

To a solution of (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide (0.1 g, 0.21 mmol) in 1,4-dioxane (6 mL) was added p-toluenesulfonic acid monohydrate (0.041 g, 0.22 mmol) slowly at 0° C. The reaction mixture was stirred for 1 h at room temperature. The reaction mixture was evaporated, washed with diethyl ether and dried to afford (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide p-toluenesulfonic acid as an off-white solid (0.104 g, 74%). $^1$HNMR (400 MHz, DMSO-$d_6$): δ 8.81 (d, J=8.8 Hz, 1H), 8.35 (s, 1H), 8.29 (s, 1H), 8.11 (s, 1H), 7.46 (t, 2H), 7.41-7.35 (m, 4H), 7.09-7.07 (br s, 3H), 5.24 (d, J=4 Hz, 1H), 3.85-3.82 (m, 3H), 3.38-3.27 (m, 3H), 3.18-3.13 (m, 1H), 2.30 (s, 3H), 2.16 (s, 2H), 1.80 (d, J=11.6 Hz, 2H), 1.52-1.44 (m, 2H). LC-MS calcd exact mass 455.18, found m z 456.2 for [M+H]$^+$. HPLC purity 99.32%.

Example 28: (S)—N-(2-Amino-1-(3-chlorophenyl) ethyl)-1-(5-methyl-2-((tetrahydro-2H-pyran-4-yl) amino)pyrimidin-4-yl)-1H-imidazole-4-carboxamide benzenesulfonic acid salt (Compound #300)

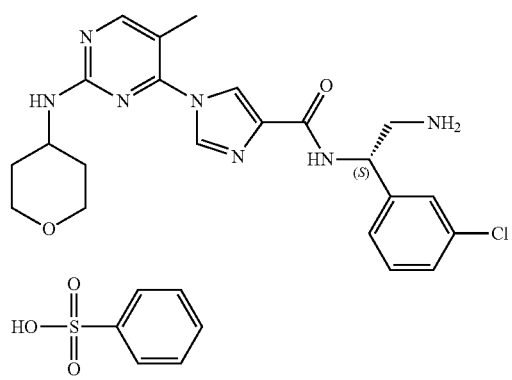

To a solution of (S)—N-(2-amino-1-(3-chlorophenyl) ethyl)-1-(5-methyl-2-((tetrahydro-2H-pyran-4-yl)amino)pyrimidin-4-yl)-1H-imidazole-4-carboxamide (6 g, 13.18 mmol) in 1,4-dioxane (360 mL) was slowly added benzenesulfonic acid (2.08 g, 13.18 mmol) at 0° C. The reaction mixture was stirred for 1 h at room temperature. The reaction mixture was evaporated, washed with diethyl ether and dried to afford (S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide benzenesulfonic acid salt as an off-white solid (6 g, 74%). Melting point: 141-142.5° C. $^1$HNMR (400 MHz, DMSO-d$_6$): δ 8.89 (d, J=9.2 Hz, 1H), 8.35 (s, 1H), 8.29 (s, 1H), 8.12 (s, 1H), 7.91 (br s, 3H), 7.58 (d, J=5.6 Hz, 2H), 7.51 (s, 1H), 7.42-7.35 (m, 4H), 7.28 (d, J=6 Hz, 3H), 5.34-5.31 (m, 1H), 3.85-3.82 (m, 3H), 3.41-3.32 (m, 3H), 3.28 (s, 1H), 2.16 (s, 3H), 1.80 (d, J=11.6 Hz, 2H), 1.49 (t, 2H). LC-MS calcd exact mass 455.18, found m z 456.2 for [M+H]$^+$. HPLC purity 98.63%.

Example 29: (S)—N-(2-Amino-1-(3-chlorophenyl)ethyl)-1-(2-((3,3-difluorocyclobutyl)amino)-5-methylpyrimidin-4-yl)-1H-imidazole-4-carboxamide hydrochloride salt (Compound #301)

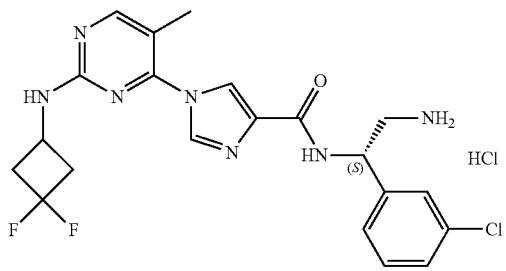

To a stirred solution of (S)—N-(2-amino-1-(3-chlorophenyl)ethyl)-1-(2-((3,3-difluorocyclobutyl)-amino)-5-methylpyrimidin-4-yl)-1H-imidazole-4-carboxamide (1 g, 2.16 mmol) in 1,4-dioxane (20 mL) was slowly added 4M HCl in dioxane (0.54 mL, 2.16 mmol) at 0° C. The reaction mixture was stirred for 1 h at room temperature. The reaction mixture was evaporated, washed with diethyl ether and dried to afford (S)—N-(2-amino-1-(3-chlorophenyl)ethyl)-1-(2-((3,3-difluorocyclobutyl)amino)-5-methyl-pyrimidin-4-yl)-1H-imidazole-4-carboxamide hydrochloride salt as an off-white solid (1 g, 93%). $^1$HNMR (400 MHz, DMSO-d$_6$): δ 8.90 (d, J=8.8 Hz, 1H), 8.39 (s, 1H), 8.31 (s, 1H), 8.18 (s, 1H), 7.88 (d, J=4.8 Hz, 1H), 7.62 (br s, 3H), 7.50 (s, 1H), 7.38-7.35 (m, 3H), 5.29 (d, J=4 Hz, 1H), 4.16 (s, 1H), 3.39-3.28 (m, 1H), 3.18-3.14 (m, 1H), 2.92 (t, 2H), 2.61 (t, 2H), 2.19 (s, 3H). LC-MS calcd exact mass 461.15, found m z 462.1 for [M+H]$^+$. HPLC purity 99.81%, Melting point: 213-216° C.

Example 30: (S)—N-(2-Amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide benzenesulfonic acid salt (Compound #302)

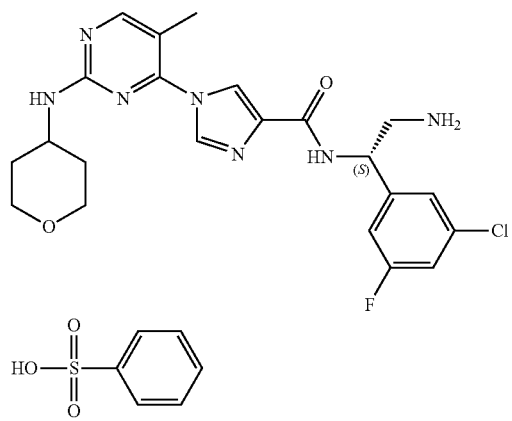

To a stirred solution of (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide (0.2 g, 0.422 mmol) in 1,4-dioxane (10 mL) was slowly added benzenesulfonic acid (0.066 g, 0.422 mmol) at 0° C. The reaction mixture was stirred for 1 h at room temperature. The reaction mixture was evaporated, washed with diethyl ether and dried to afford (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamidebenzenesulfonic acid salt as an off-white solid (0.22 g, 83%). $^1$HNMR (400 MHz, DMSO-d$_6$): δ 8.92 (d, J=8.8 Hz, 1H), 8.35 (s, 1H), 8.30 (s, 1H), 8.13 (s, 1H), 7.83 (br s, 3H), 7.57 (d, J=6.4 Hz, 2H), 7.37 (s, 3H), 7.28 (d, J=6.4 Hz, 4H), 5.32 (d, J=4.4 Hz, 1H), 3.83 (d, J=11.6 Hz, 3H), 3.41-3.27 (m, 3H), 3.18-3.14 (m, 1H), 2.16 (s, 3H), 1.80 (d, J=12 Hz, 2H), 1.52-1.44 (m, 2H). LC-MS calcd exact mass 473.17, found m z 474.2 [M+H]$^+$. HPLC purity 99.85%, Melting point: 161-162° C.

Example 31: (S)—N-(2-Amino-1-(3-chlorophenyl)ethyl)-1-(2-((3,3-difluorocyclobutyl)amino)-5-methylpyrimidin-4-yl)-1H-imidazole-4-carboxamide p-toluenesulfonic acid salt (Compound #303)

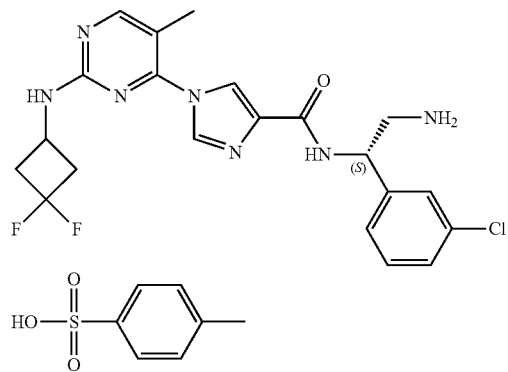

To a stirred solution of (S)—N-(2-amino-1-(3-chlorophenyl)ethyl)-1-(2-((3,3-difluorocyclobutyl)-amino)-5-methylpyrimidin-4-yl)-1H-imidazole-4-carboxamide (0.1 g, 2.16 mmol) in 1,4-dioxane (6 mL) was slowly added p-toluenesulfonic acid monohydrate (0.041 g, 2.16 mmol) at 0° C. The reaction mixture was stirred for 1 h at room temperature. The reaction mixture was evaporated, washed with diethyl ether and dried to afford (S)—N-(2-amino-1-(3-chlorophenyl)ethyl)-1-(2-((3,3-difluorocyclobutyl)amino)-5-methylpyrimidin-4-yl)-1H-imidazole-4-carboxamide p-toluenesulfonic acid salt as an off-white solid (0.11 g, 78%). $^1$HNMR (400 MHz, DMSO-$d_6$): δ 8.88 (d, J=9.2 Hz, 1H), 8.39 (s, 1H), 8.32 (s, 1H), 8.14 (s, 1H), 7.87 (d, J=5.2 Hz, 2H), 7.75 (br s, 3H), 7.51 (s, 1H), 7.46-7.42 (m, 2H), 7.40-7.35 (m, 3H), 7.08 (d, J=7.6 Hz, 2H), 5.31 (d, J=4.4 Hz, 1H), 4.16 (s, 1H), 3.40-3.27 (m, 1H), 3.24-3.19 (m, 1H), 2.92 (t, 2H), 2.61 (t, 2H), 2.26 (s, 3H), 2.19 (s, 3H). LC-MS calcd exact mass 461.15, found m/z 462.1 for [M+H]$^+$. HPLC purity 98.11%, Melting point: 150-151° C.

Example 32: (S)—N-(2-Amino-1-(3-chlorophenyl)ethyl)-1-(2-((3,3-difluorocyclobutyl)amino)-5-methylpyrimidin-4-yl)-1H-imidazole-4-carboxamide benzenesulfonic acid salt (Compound #304)

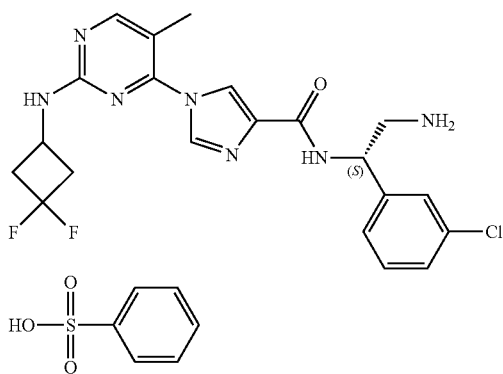

To a stirred solution of (S)—N-(2-amino-1-(3-chlorophenyl)ethyl)-1-(2-((3,3-difluorocyclo-butyl)amino)-5-methylpyrimidin-4-yl)-1H-imidazole-4-carboxamide (0.25 g, 0.541 mmol) in 1,4-dioxane (12 mL) was slowly added benzenesulfonic acid (0.085 g, 0.541 mmol) at 0° C. The reaction mixture was stirred for 1.0 h at room temperature. The reaction mixture was evaporated, washed with diethyl ether and dried to afford (S)—N-(2-amino-1-(3-chlorophenyl)ethyl)-1-(2-((3,3-difluorocyclobutyl)amino)-5-methylpyrimidin-4-yl)-1H-imidazole-4-carboxamide benzenesulfonic acid salt as an off-white solid (0.28 g, 83%). $^1$HNMR (400 MHz, DMSO-$d_6$): δ 8.88 (d, J=8.8 Hz, 1H), 8.39 (s, 1H), 8.32 (s, 1H), 8.14 (s, 1H), 7.87 (d, J=4.8 Hz, 1H), 7.72 (br s, 3H), 7.57 (d, J=6 Hz, 2H), 7.51 (s, 1H), 7.42-7.37 (m, 3H), 7.28 (d, J=6.4 Hz, 3H), 5.31 (d, J=4.4 Hz, 1H), 4.16 (s, 1H), 3.39-3.27 (m, 1H), 3.23 (d, J=4.8 Hz, 1H), 2.92 (t, 2H), 2.63 (d, J=12 Hz, 2H), 2.19 (s, 3H). LC-MS calcd exact mass 461.15, found m z 462.1 for [M+H]$^+$. HPLC purity 99.82%, Melting point: 155-156° C.

Example 33: (S)—N-(2-Amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide hydrochloride salt (Compound #305)

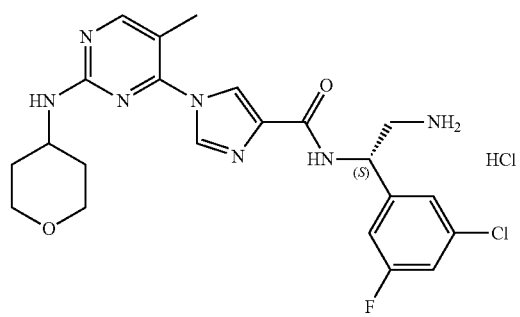

To a stirred solution of (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide (0.05 g, 0.105 mmol) in 1,4-dioxane (3 mL) was slowly added 4M HCl in dioxane (0.02 mL, 0.105 mmol) at 0° C. The reaction mixture was stirred for 1.0 h at room temperature. The reaction mixture was evaporated, washed with diethyl ether and dried to afford (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide hydrochloride salt as an off white solid (0.05 g, 94%). $^1$HNMR (400 MHz, DMSO-$d_6$): δ 8.95 (d, J=8.8 Hz, 1H), 8.35 (s, 1H), 8.30 (s, 1H), 8.15 (s, 1H), 8.00 (br s, 3H), 7.37 (br s, 3H), 7.28 (d, J=9.6 Hz, 1H), 5.33 (t, 1H), 3.85-3.82 (m, 3H), 3.37-3.33 (m, 3H), 3.25 (t, 1H), 2.16 (s, 3H), 1.80 (d, J=11.6 Hz, 2H), 1.52-1.44 (m, 2H). LC-MS calcd exact mass 473.17, found m z 474.2 for [M+H]$^+$. HPLC purity 99.86%, Melting point: 210-211° C.

The following Table 1 provides a summary of the synthetic methods utilized to prepare the compounds of the present invention identified therein, by reference to the Schemes described above, and data obtained and utilized in the characterization of the prepared compounds. In some cases, the synthetic method used was a combination of two different methods, as indicated in the Table by reference to two Scheme numbers. In certain other cases, the method utilized was a slight variation of the method referenced by the Scheme number; such variation would be apparent to one skilled in the art. In certain other cases, the synthetic method was as indicated by the Scheme number in the Table, followed by further slight chemical modification using methodology well known to those skilled in the art.

TABLE 1

| Cmpd # | Structure | Name | NMR data | Scheme # |
|---|---|---|---|---|
| 1 | 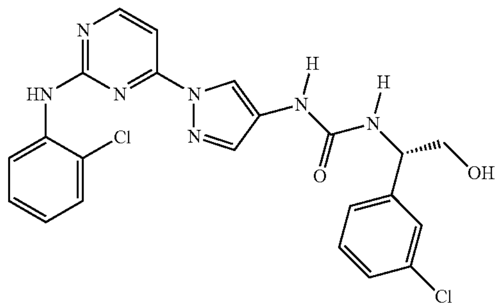 [SMILES: O=C(Nc1cnn(-c2ccnc(Nc3ccccc3Cl)n2)c1)N[C@H](CO)c1cccc(Cl)c1] | (S)-1-(1-(3-chlorophenyl)-2-hydroxyethyl)-3-(1-(2-((2-chlorophenyl)amino)pyrimidin-4-yl)-1H-pyrazol-4-yl)urea | 1HNMR (400 MHz, DMSO-d$_6$): δ 9.02 (s, 1H), 8.66 (s, 1H), 8.39 (s 1H), 8.38 (s, 1H), 7.79 (s, 1H), 7.74 (d, J = 8 Hz, 1H), 7.49 (d, J = 7.99 Hz, 1H), 7.52-7.34 (m, 2H), 7.31-7.26 (m, 2H), 7.19-7.15 (m, 2H), 6.83 (d, J = 7.59 Hz, 1H), 4.98 (s, 1H), 4.74-4.72 (m, 1H), 3.64-3.56 (m, 2H) | 1 |
| 2 | 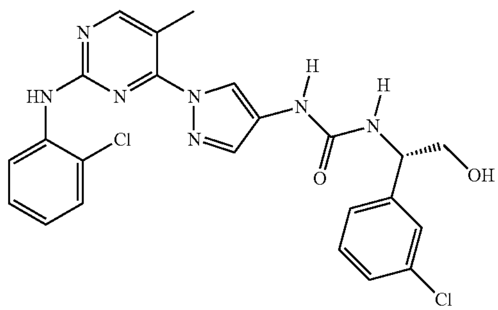 [SMILES: Cc1cnc(Nc2ccccc2Cl)nc1-n1cc(NC(=O)N[C@H](CO)c2cccc(Cl)c2)cn1] | (S)-1-(1-(3-chlorophenyl)-2-hydroxyethyl)-3-(1-(2-((2-chlorophenyl)amino)-5-methylpyrimidin-4-yl)-1H-pyrazol-4-yl)urea | 1HNMR (400 MHz, DMSO-d$_6$): δ 8.79 (s, 1H), 8.63 (s, 1H), 8.46 (s, 1H), 8.31 (s, 1H), 7.79 (s, 1H), 7.78 (s, 1H), 7.47 (d, J = 7.6 Hz, 1H), 7.35-7.26 (m, 4H), 7.13 (t, J = 7.8 Hz, 1H), 6.79 (d, J = 8 Hz, 1H), 4.99-4.91 (m, 1H), 4.74-4.72 (m, 1H), 3.65-3.55 (m, 2H), 2.41 (s, 3H) | 1 |
| 3 | 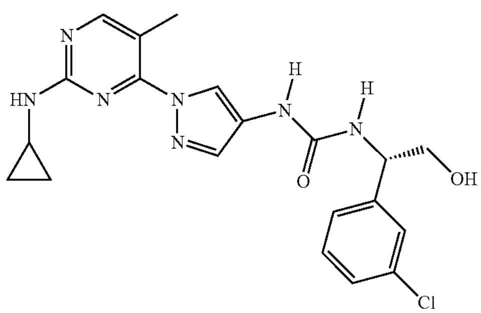 [SMILES: Cc1cnc(NC2CC2)nc1-n1cc(NC(=O)N[C@H](CO)c2cccc(Cl)c2)cn1] | (S)-1-(1-(3-chlorophenyl)-2-hydroxyethyl)-3-(1-(2-(cyclopropyl-amino)-5-methyl-pyrimidin-4-yl)-1H-pyrazol-4-yl)urea | 1HNMR (400 MHz, DMSO-d$_6$): δ 8.61 (s, 1H), 8.55 (s, 1H), 8.18 (s, 1H), 7.72 (s, 1H), 7.34-7.26 (m, 4H), 6.77 (d, J = 7.6 Hz, 1H), 4.97 (s, 1H), 4.73-4.71 (m, 1H), 3.62-3.57 (m, 2H), 2.67-2.66 (m, 1H), 2.34 (s, 3H), 0.63 (d, J = 5.2 Hz, 2H), 0.44 (s, 2H) | 1 |
| 4 | 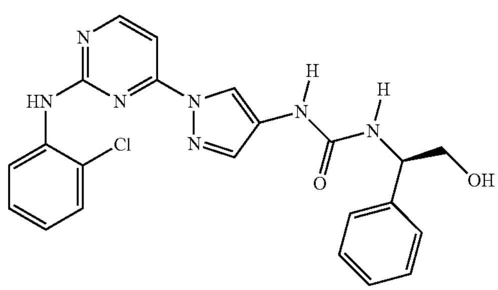 [SMILES: O=C(Nc1cnn(-c2ccnc(Nc3ccccc3Cl)n2)c1)N[C@@H](CO)c1ccccc1] | (R)-1-(1-(2-((2-chlorophenyl)amino)pyrimidin-4-yl)-1H-pyrazol-4-yl)-3-(2-hydroxy-1-phenylethyl)urea | 1HNMR (400 MHz, DMSO-d$_6$): 9.01 (s, 1H), 8.63 (s, 1H), 8.38 (d, J = 6.4 Hz, 2H), 7.78 (s, 1H), 7.74 (d, J = 8 Hz, 1H), 7.49 (d, J = 8 Hz, 1H), 7.34-7.29 (m, 4H), 7.22-7.15 (m, 3H), 6.73 (d, J = 8 Hz, 1H), 4.92 (s, 1H), 4.73-4.70 (m, 1H), 3.63-3.54 (m, 2H) | 1 |
| 5 | 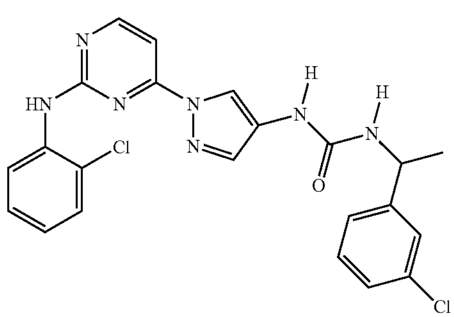 [SMILES: CC(NC(=O)Nc1cnn(-c2ccnc(Nc3ccccc3Cl)n2)c1)c1cccc(Cl)c1] | 1-(1-(2-((2-chlorophenyl)amino)pyrimidin-4-yl)-1H-pyrazol-4-yl)-3-(1-(3-chlorophenyl)ethyl)urea | 1HNMR (400 MHz, DMSO-d$_6$): δ 9.02 (s, 1H), 8.45 (s, 1H), 8.45-8.39 (m, 2H), 7.79 (s, 1H), 7.74 (d, J = 7.99 Hz, 1H), 7.49 (d, J = 7.59 Hz, 1H), 7.37-7.26 (m, 4H), 7.19-7.16 (m, 2H), 6.83 (d, J = 7.99 Hz, 1H), 4.79 (t, J = 6.79 Hz, 1H,), 1.36 (d, J = 6.79 Hz, 3H), 1.2 (s, 1H) | 1 |

TABLE 1-continued

| Cmpd # | Structure | Name | NMR data | Scheme # |
|---|---|---|---|---|
| 6 | 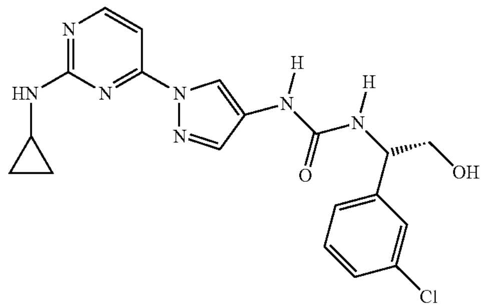 | (S)-1-(1-(3-chlorophenyl)-2-hydroxyethyl)-3-(1-(2-(cyclopropyl-amino)pyrimidin-4-yl)-1H-pyrazol-4-yl)urea | 1HNMR (400 MHz, DMSO-d$_6$): δ 8.64 (s, 1H), 8.51 (s, 1H), 8.29 (d, J = 4.8 Hz, 1H), 7.73 (s, 1H), 7.50 (br s, 1H), 7.35-7.31 (m, 2H), 7.27-7.25 (m, 2H), 6.97 (d, J = 8 Hz, 1H), 6.82 (d, J = 8 Hz, 1H), 5.015-4.94 (m, 1H), 4.73-4.71 (m, 1H), 3.64-3.58 (m, 2H), 2.73-2.72 (m, 1H), 0.67-0.66 (m, 2H), 0.47 (s, 2H) | 1 |
| 7 | 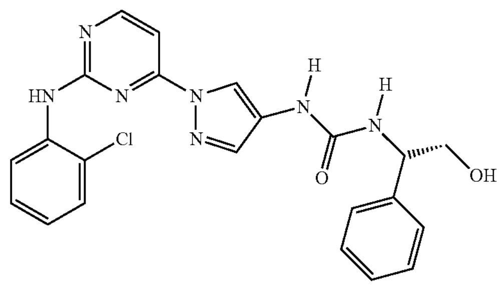 | (S)-1-(1-(2-((2-chlorophenyl)amino)pyrimidin-4-yl)-1H-pyrazol-4-yl)-3-(2-hydroxy-1-phenylethyl)urea | 1HNMR (400 MHz, DMSO-d$_6$): δ 9.01 (s, 1H), 8.63 (s, 1H), 8.39 (d, J = 5.59 Hz, 2H), 7.78 (s, 1H), 7.74 (d, J = 3.04 Hz, 1H), 7.49 (d, J = 7.99 Hz, 1H), 7.34-7.29 (m, 4H), 7.22-7.15 (m, 3H), 6.73 (d, J = 7.6 Hz, 1H), 4.91 (br s, 1H), 4.73-7.71 (m, 1H), 3.63-3.56 (m, 2H) | 1 |
| 9 | 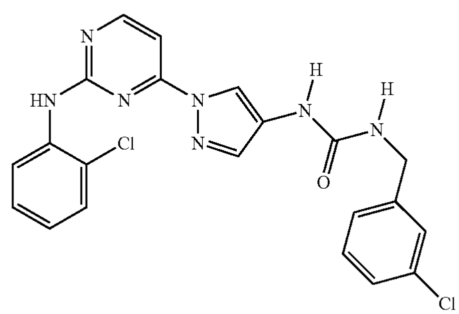 [SMILES: O=C(NCc1cccc(Cl)c1)Nc1cnn(-c2ccnc(Nc3ccccc3Cl)n2)c1] | 1-(3-chlorobenzyl)-3-(1-(2-((2-chlorophenyl)amino)pyrimidin-4-yl)-1H-pyrazol-4-yl)urea | 1HNMR (400 MHz, DMSO-d$_6$): δ 9.04 (s, 1H), 8.71 (s, 1H), 8.43 (s, 1H), 8.39 (d, J = 5.6 Hz, 1H), 7.80 (s, 1H), 7.75 (d, J = 8 Hz, 1H), 7.49 (d, J = 7.6 Hz, 1H), 7.35-7.23 (m, 5H), 7.20-7.16 (m, 2H), 6.85 (br s, 1H), 4.28 (d, J = 5.6 Hz, 2H) | 1 |
| 10 | 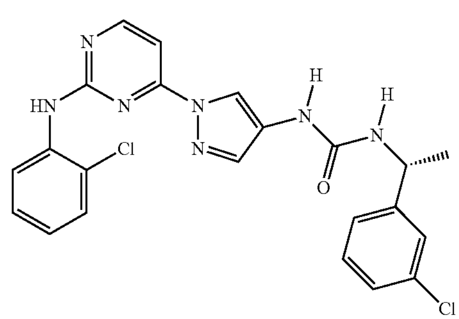 [SMILES: C[C@@H](NC(=O)Nc1cnn(-c2ccnc(Nc3ccccc3Cl)n2)c1)c1cccc(Cl)c1] | (R)-1-(1-(2-(2-chlorophenyl)amino)pyrimidin-4-yl)-1H-pyrazol-4-yl)-3-(1-(3-chlorophenyl)ethyl)urea | 1HNMR (400 MHz, DMSO-d$_6$): δ 9.02 (s, 1H), 8.45 (s, 1H), 8.39 (t, J = 5.2 Hz, 2H), 7.79 (s, 1H), 7.74 (d, J = 8 Hz, 1H), 7.49 (d, J = 8 Hz, 1H), 7.37-7.26 (m, 5H), 7.19-7.15 (m, 2H), 6.82 (d, J = 7.6 Hz, 1H), 4.79 (t, J = 7.2 Hz, 1H), 1.36 (d, J = 6.8 Hz, 3H) | 1 |

TABLE 1-continued

| Cmpd # | Structure | Name | NMR data | Scheme # |
|---|---|---|---|---|
| 11 | 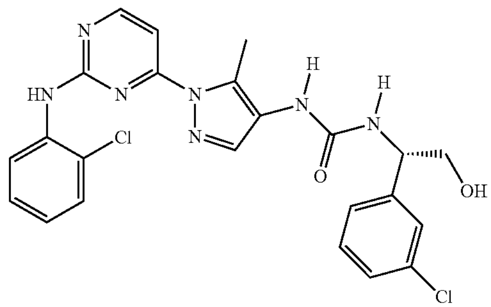 [SMILES: Cc1c(NC(=O)N[C@H](CO)c2cccc(Cl)c2)cnn1-c1ccnc(Nc2ccccc2Cl)n1] | (S)-1-(1-(3-chlorophenyl)-2-hydroxy-ethyl)-3-(1-(2-((2-chlorophenyl)amino)pyrimidin-4-yl)-5-methyl-1H-pyrazol-4-yl)urea | 1HNMR (400 MHz, DMSO-d$_6$): δ 8.91 (s, 1H), 8.47 (s, 1H), 8.33 (d, J = 4.8 Hz, 2H), 7.73 (d, J = 8 Hz, 1H), 7.47 (d, J = 8 Hz, 1H), 7.34-7.26 (m, 5H), 7.19-7.09 (m, 2H), 6.94 (d, J = 7.6 Hz, 1H), 5.01 (s, 1H), 4.73-4.70 (m, 1H), 3.65-3.61 (m, 2H), 2.22 (s, 3H) | 1 |
| 12 | 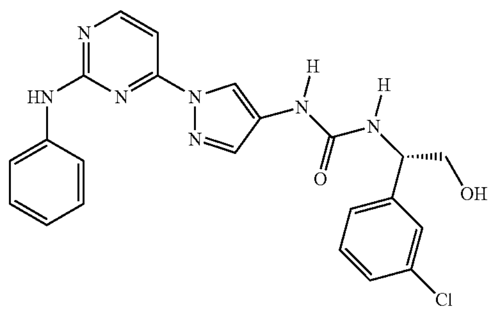 [SMILES: O=C(Nc1cnn(-c2ccnc(Nc3ccccc3)n2)c1)N[C@H](CO)c1cccc(Cl)c1] | (S)-1-(1-(3-chlorophenyl)-2-hydroxy-ethyl)-3-(1-(2-(phenyl-amino)pyrimidin-4-yl)-1H-pyrazol-4-yl)urea | 1HNMR (400 MHz, DMSO-d$_6$): δ 9.73 (s, 1H), 8.69 (s, 1H), 8.57 (s, 1H), 8.46 (d, J = 5.2 Hz, 1H), 7.79 (s, 1H), 7.73 (d, J = 8 Hz, 2H), 7.36-7.32 (m, 2H), 7.29-7.15 (m, 4H), 7.17 (d, J = 5.6 Hz, 1H), 6.96 (t, J = 6.8 Hz, 1H), 6.85 (d, J = 7.6 Hz, 1H), 4.9 (br s, 1H), 4.75-4.73 (m, 1H), 3.65-3.57 (m, 2H) | 1 |
| 13 | 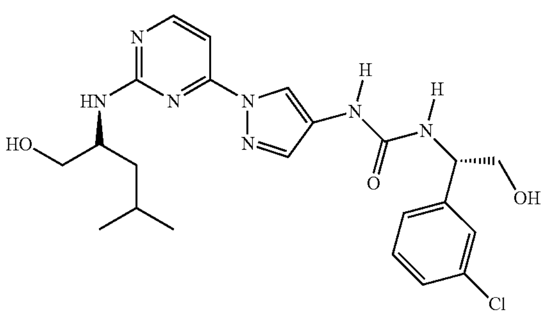 | 1-((S)-1-(3-chlorophenyl)-2-hydroxy-ethyl)-3-(1-(2-(((R)-1-hydroxy-4-methylpentan-2-yl)amino)pyrimidin-4-yl)-1H-pyrazol-4-yl)urea | 1HNMR (400 MHz, DMSO-d$_6$): δ 8.63 (s, 1H), 8.48 (br s, 1H), 8.23 (br s, 1H), 7.72 (s, 1H), 7.35-7.32 (m, 2H), 7.28-7.26 (m, 2H), 6.93-6.87 (m, 2H), 6.81 (d, J = 7.6 Hz, 1H), 4.98 (t, J = 5.2 Hz, 1H), 4.73-4.72 (m, 1H), 4.59 (s, 1H), 4.05 (br s, 1H), 3.65-3.55 (m, 2H), 3.43-3.38 (m, 1H), 1.66-1.59 (m, 1H), 1.39-1.36 (m, 2H), 0.88-0.86 (m, 6 H) | 2 |
| 14 | 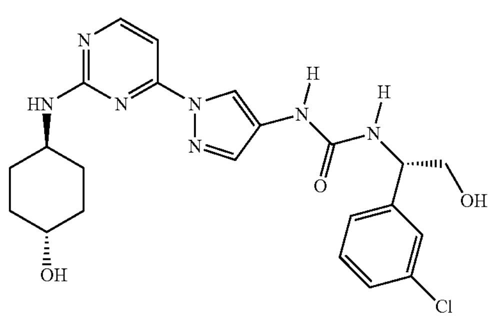 [SMILES: O=C(Nc1cnn(-c2ccnc(N[C@H]3CC[C@H](O)CC3)n2)c1)N[C@H](CO)c1cccc(Cl)c1] | 1-((S)-1-(3-chlorophenyl)-2-hydroxy-ethyl)-3-(1-(2-((trans-4-hydroxycyclohexyl)amino)pyrimidin-4-yl)-1H-pyrazol-4-yl)urea | 1HNMR (400 MHz, DMSO-d$_6$): δ 8.64 (s, 1H), 8.49 (s, 1H), 8.25 (s, 1H), 7.20-7.66 (m, 2H), 7.53 (s, 1H), 7.35-7.23 (m, 4H), 6.91 (d, J = 5.2 Hz, 1H), 6.83 (d, J = 8.4 Hz, 1H), 4.98 (s, 1H), 4.82 (s, 1H), 4.73 (s, 1H), 4.59-4.52 (m, 1H), 4.49-4.40 (m, 1H), 4.12 (s, 1H), 3.71 (s, 1H), 3.61 (s, 1H), 3.49 (s, 1H), 1.99-1.90 (m, 2H), 1.35 (m, 4H) | 1 |

TABLE 1-continued

| Cmpd # | Structure | Name | NMR data | Scheme # |
|---|---|---|---|---|
| 15 | 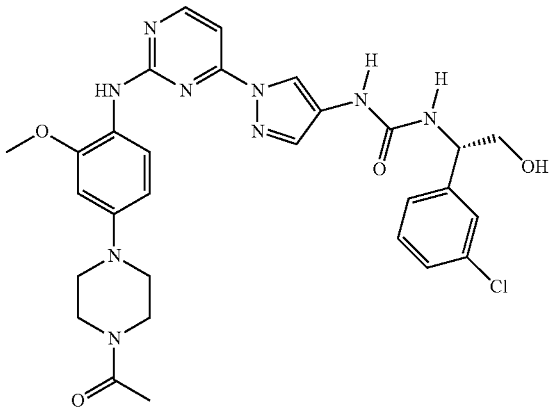 [SMILES: COc1cc(N2CCN(C(C)=O)CC2)ccc1Nc1nccc(-n2cc(NC(=O)N[C@H](CO)c3cccc(Cl)c3)cn2)n1] | (S)-1-(1-(2-((4-(4-acetyl-piperazin-1-yl)-2-methoxy-phenyl)amino)pyrimidin-4-yl)-1H-pyrazol-4-yl)-3-(1-(3-chloro-phenyl)-2-hydroxyethyl)urea | 1HNMR (400 MHz, DMSO-d$_6$): δ 8.65 (s, 1H), 8.42 (s, 1H), 8.34 (d, J = 5.2 Hz, 1H), 8.19 (s, 1H), 7.78 (s, 1H), 7.62 (d, J = 8.8 Hz, 1H), 7.36-7.27 (m, 4H), 7.05 (d, J = 4.8 Hz, 1H), 6.84 (d, J = 7.6 Hz, 1H), 6.63 (s, 1H), 6.50 (d, J = 7.6 Hz, 1H), 4.98 (s, 1H), 4.74 (d, J = 6 Hz, 1H), 3.79 (s, 3H), 3.58 (br s, 6H), 3.10 (d, J = 24.8 Hz, 4H), 2.03 (s, 3H) | 1 |
| 16 | 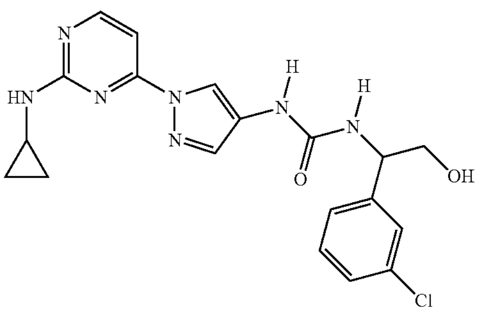 [SMILES: O=C(Nc1cnn(-c2ccnc(NC3CC3)n2)c1)NC(CO)c1cccc(Cl)c1] | 1-(1-(3-chlorophenyl)-2-hydroxy-ethyl)-3-(1-(2-(cyclopropylamino)pyrimidin-4-yl)-1H-pyrazol-4-yl)urea | 1HNMR (400 MHz, DMSO-d$_6$): δ 8.63 (s, 1H), 8.51 (s, 1H), 8.29 (d, J = 4.8 Hz, 1H), 7.72 (s, 1H), 7.51 (s, 1H), 7.35-7.32 (m, 2H), 7.28 (d, J = 7.6 Hz, 2H), 6.96 (t, J = 5.2 Hz, 1H), 6.81 (d, J = 7.6 Hz, 1H), 4.99-4.96 (m, 1H), 4.74-4.70 (m, 1H), 3.65-3.57 (m, 2H), 2.74-2.72 (m, 1H), 0.68-0.66 (d, J = 6.4 Hz, 2H), 0.46 (s, 2H) | 1 |
| 18 | 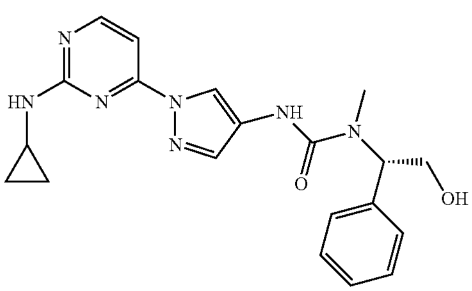 [SMILES: CN(C(=O)Nc1cnn(-c2ccnc(NC3CC3)n2)c1)[C@H](CO)c1ccccc1] | (S)-3-(1-(2-(cyclopropyl-amino)pyrimidin-4-yl)-1H-pyrazol-4-yl)-1-(2-hydroxy-1-phenylethyl)-1-methylurea | 1HNMR (400 MHz, DMSO-d$_6$): 8.69 (s, 1H), 8.33 (d, J = 5.6 Hz, 1H), 7.75 (s, 1H), 7.38-7.26 (m, 4H), 7.14 (d, J = 5.6 Hz, 1H), 6.66 (s, 1H), 5.55-5.52 (m, 1H), 5.34 (s, 1H), 4.68 (br s, 1H), 4.23-4.11 (m, 2H), 2.80 (s, 3H), 0.87-0.83 (m, 2H), 0.57 (br s, 2H) | 2 |
| 20 | 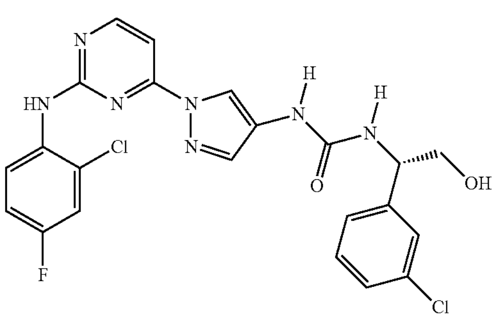 [SMILES: O=C(Nc1cnn(-c2ccnc(Nc3ccc(F)cc3Cl)n2)c1)N[C@H](CO)c1cccc(Cl)c1] | (S)-1-(1-(2-((2-chloro-4-fluoro-phenyl)amino)pyrimidin-4-yl)-1H-pyrazol-4-yl)-3-(1-(3-chloro-phenyl)-2-hydroxyethyl)urea | 1HNMR (400 MHz, CDCl$_3$, few drops MeOD): 8.50 (s, 1H), 8.33 (d, J = 5.2 Hz, 1H), 8.27-8.25 (m, 1H), 7.51 (s, 1H), 7.28-7.19 (m, 1H), 7.23-7.12 (m, 3H), 7.12-7.10 (m, 1H) 7.04-6.99 (m, 1H), 6.23 (d, J = 6.8 Hz, 1H) 4.87-4.84 (m, 1H), 3.81-3.77 (m, 1H), 3.64-3.61 (m, 1H) | 2 |

TABLE 1-continued

| Cmpd # | Structure | Name | NMR data | Scheme # |
|---|---|---|---|---|
| 21 | 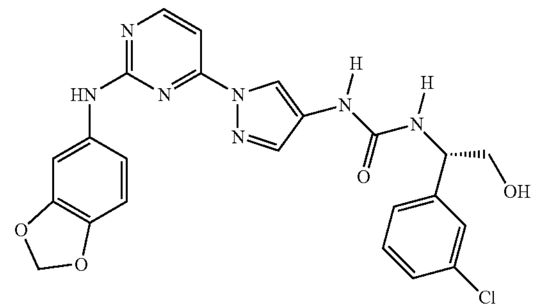 [SMILES: O=C(Nc1cnn(-c2ccnc(Nc3ccc4c(c3)OCO4)n2)c1)N[C@H](CO)c1cccc(Cl)c1] | (S)-1-(1-(2-(benzo[d][1,3]dioxol-5-ylamino)-pyrimidin-4-yl)-1H-pyrazol-4-yl)-3-(1-(3-chlorophenyl)-2-hydroxyethyl)urea | 1HNMR (400 MHz, DMSO-$d_6$): δ 9.60 (s, 1H), 8.68 (s, 1H), 8.53 (s, 1H), 8.42 (d, J = 5.6 Hz, 1H), 7.78 (s, 1H), 7.41 (d, J = 2 Hz, 1H), 7.36-7.34 (m, 2H), 7.32-7.27 (m, 2H), 7.13-7.09 (m, 2H), 6.83 (t, J = 6 Hz, 2H), 5.95 (s, 2H), 4.99 (t, J = 4.1 Hz, 1H), 4.74-4.72 (m, 1H), 3.65-3.57 (m, 2H) | 1 |
| 22 | 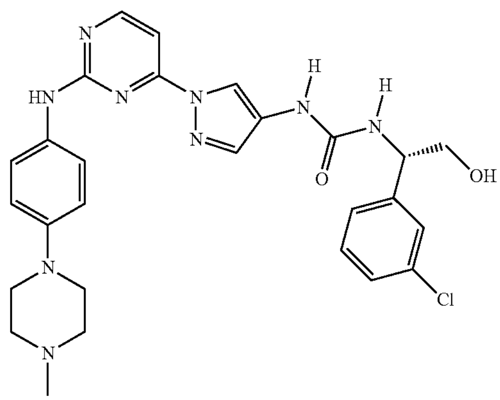 [SMILES: CN1CCN(c2ccc(Nc3nccc(-n4cc(NC(=O)N[C@H](CO)c5cccc(Cl)c5)cn4)n3)cc2)CC1] | (S)-1-(1-(3-chlorophenyl)-2-hydroxy-ethyl)-3-(1-(2-((4-(4-methyl-piperazin-1-yl)-phenyl)amino)pyrimidin-4-yl)-1H-pyrazol-4-yl)urea | 1HNMR (400 MHz, DMSO-$d_6$): δ 9.47 (s, 1H), 8.67 (s, 1H), 8.53 (s, 1H), 8.39 (d, J = 5.6 Hz, 1H), 7.78 (s, 1H), 7.54 (d, J = 9.2 Hz, 2H), 7.34 (m, 2H), 7.28 (d, J = 8.4 Hz, 2H), 7.08 (d, J = 5.6 Hz, 1H), 6.89-6.83 (m, 3H), 4.99 (t, J = 5.2 Hz, 1H), 4.73 (t, J = 7.2 Hz, 1H), 3.65-3.56 (m, 2H), 3.08 (br s, 3H), 2.31 (br s, 2H) (some aliphatic protons are merged with solvent signal) | 1 |
| 23 | 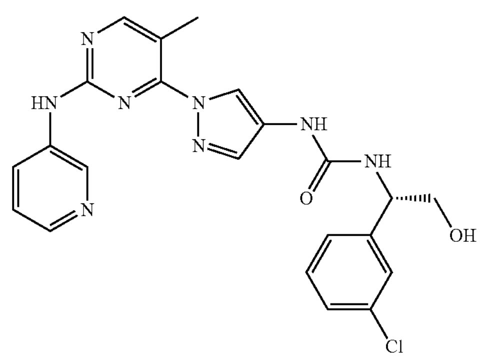 [SMILES: Cc1cnc(Nc2cccnc2)nc1-n1cc(NC(=O)N[C@H](CO)c2cccc(Cl)c2)cn1] | (S)-1-(1-(3-chlorophenyl)-2-hydroxy-ethyl)-3-(1-(5-methyl-2-(pyridin-3-yl-amino)pyrimidin-4-yl)-1H-pyrazol-4-yl)urea | 1HNMR (400 MHz, DMSO-$d_6$): δ 9.79 (s, 1H), 8.86 (s, 1H), 8.70 (s, 1H), 8.61 (s, 1H), 8.40 (s, 1H), 8.14 (d, J = 5.2 Hz, 2H), 7.80 (s, 1H), 7.34 (t, J = 7.6 Hz, 2H), 7.30-7.27 (m, 3H), 6.84 (d, J = 7.6 Hz, 1H), 5.0 (t, J = 4.8 Hz, 1H), 4.73 (t, J = 6.8 Hz, 1H), 3.65-3.56 (m, 2H), 2.44 (s, 3H) | 2 |
| 24 | 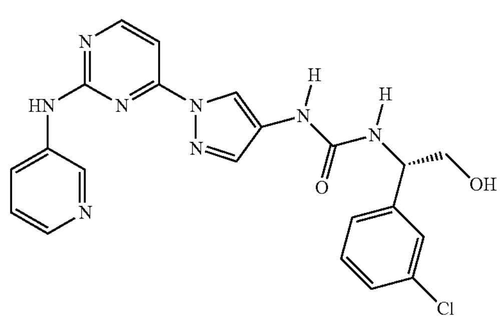 [SMILES: O=C(Nc1cnn(-c2ccnc(Nc3cccnc3)n2)c1)N[C@H](CO)c1cccc(Cl)c1] | (S)-1-(1-(3-chlorophenyl)-2-hydroxy-ethyl)-3-(1-(2-(pyridin-3-yl-amino)pyrimidin-4-yl)-1H-pyrazol-4-yl)urea | 1HNMR (400 MHz, DMSO-$d_6$): δ 10.08 (s, 1H), 8.98 (s, 1H), 8.72 (s, 1H), 8.58 (s, 1H), 8.52 (d, J = 5.2 Hz, 1H), 8.24 (d, J = 4.8 Hz, 2H), 7.81 (s, 1H), 7.46 (d, J = 7.6 Hz, 2H), 7.36-7.32 (m, 2H), 7.29-7.25 (m, 3H), 6.87 (d, J = 7.6 Hz, 1H), 4.73 (t, J = 7.2 Hz, 1H) | 2 |

TABLE 1-continued

| Cmpd # | Structure | Name | NMR data | Scheme # |
|---|---|---|---|---|
| 25 | 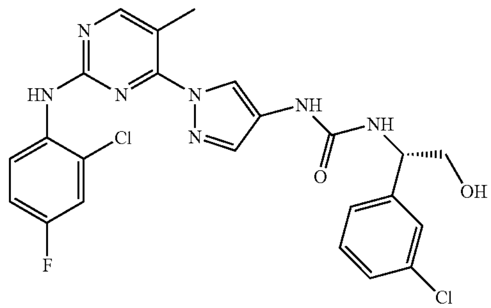 [SMILES: Cc1cnc(Nc2ccc(F)cc2Cl)nc1-n1cc(NC(=O)N[C@H](CO)c2cccc(Cl)c2)cn1] | (S)-1-(1-(2-((2-chloro-4-fluoro-phenyl)amino)-5-methyl-pyrimidin-4-yl)-1H-pyrazol-4-yl)-3-(1-(3-chloro-phenyl)-2-hydroxy-ethyl)urea | 1HNMR (400 MHz, DMSO-$d_6$): δ 8.92 (s, 1H), 8.62 (s, 1H), 8.42 (s, 1H), 8.27 (s, 1H), 7.79 (s, 1H), 7.70-7.66 (m, 1H), 7.48-7.45 (m, 1H), 7.35-7.32 (m, 2H), 7.28-7.26 (m, 2H), 7.20-7.17 (m, 1H), 6.79 (d, J = 7.2 Hz, 1H), 4.98 (s, 1H), 4.74-4.72 (m, 1H), 3.64-3.56 (m, 2H), 2.40 (s, 3H) | 2 |
| 26 | 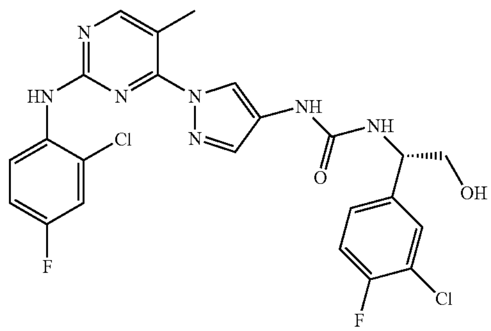 [SMILES: Cc1cnc(Nc2ccc(F)cc2Cl)nc1-n1cc(NC(=O)N[C@H](CO)c2ccc(F)c(Cl)c2)cn1] | (S)-1-(1-(3-chloro-4-fluorophenyl)-2-hydroxy-ethyl)-3-(1-(2-((2-chloro-4-fluorophenyl)amino)-5-methyl-pyrimidin-4-yl)-1H-pyrazol-4-yl)urea | 1HNMR (400 MHz, DMSO-$d_6$): δ 8.91 (s, 1H), 8.62 (s, 1H), 8.41 (s, 1H), 8.27 (s, 1H), 7.79 (s, 1H), 7.70-7.66 (m, 1H), 7.50-7.46 (m, 2H), 7.32-7.31 (m, 2H), 7.20-717 (m, 1H), 6.79 (d, J = 8 Hz, 1H), 4.98 (t, J = 4.8 Hz, 1H), 4.73-4.71 (m, 1H), 3.62-3.57 (m, 2H), 2.40 (s, 3H) | 2 |
| 27 | 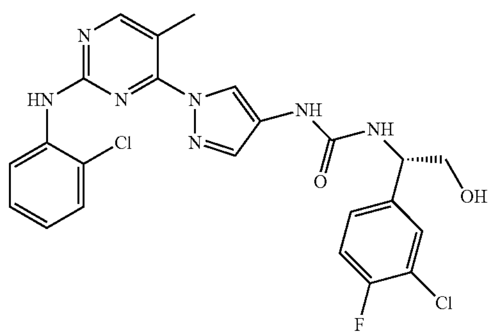 [SMILES: Cc1cnc(Nc2ccccc2Cl)nc1-n1cc(NC(=O)N[C@H](CO)c2ccc(F)c(Cl)c2)cn1] | (S)-1-(1-(3-chloro-4-fluorophenyl)-2-hydroxy-ethyl)-3-(1-(2-((2-chloro-phenyl)amino)-5-methyl-pyrimidin-4-yl)-1H-pyrazol-4-yl)urea | 1HNMR (400 MHz, DMSO-$d_6$): δ 8.79 (s, 1H), 8.63 (s, 1H), 8.45 (s, 1H), 8.31 (s, 1H), 7.80 (d, J = 4.4 Hz, 2H), 7.48 (t, J = 6 Hz, 2H), 7.37-7.27 (m, 3H), 7.15-7.12 (m, 1H), 6.79 (d, J = 8 Hz, 1H), 4.98 (t, J = 5.2 Hz, 1H), 4.74-4.72 (m, 1 Hz), 3.63-3.55 (m, 2H), 2.48 (s, 3H) | 2 |
| 28 | 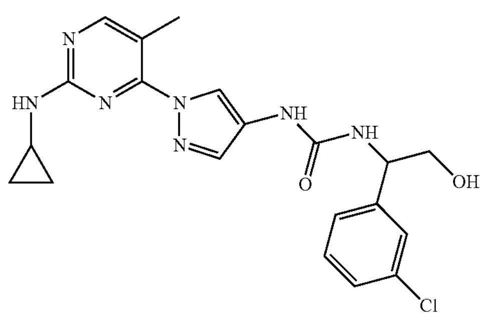 [SMILES: Cc1cnc(NC2CC2)nc1-n1cc(NC(=O)NC(CO)c2cccc(Cl)c2)cn1] | 1-(1-(3-chloro-phenyl)-2-hydroxy-ethyl)-3-(1-(2-(cyclopropyl-amino)-5-methyl-pyrimidin-4-yl)-1H-pyrazol-4-yl)urea | 1HNMR (400 MHz, DMSO-$d_6$): δ 8.60 (s, 1H), 8.55 (s, 1H), 8.17 (s, 1H), 7.72 (s, 1H), 7.34-7.25 (m, 5H), 6.77 (d, J = 7.2 Hz, 1H), 4.97 (t, J = 7.2 Hz, 1H), 4.72 (d, J = 6.8 Hz, 1H), 3.63-3.54 (m, 2H), 2.67-2.64 (m, 1H), 2.34 (s, 3H), 0.64-0.62 (m, 2H), 0.43 (br s, 2H) | 2 |
| 29 | 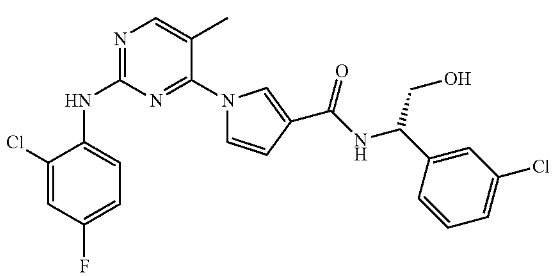 | (S)-1-(2-((2-chloro-4-fluorophenyl)amino)-5-methyl-pyrimidin-4-yl)-N-(1-(3-chlorophenyl)-2-hydroxy-ethyl)-1H-pyrrole-3-carboxamide | 1HNMR (400 MHz, DMSO-$d_6$): δ 8.99 (s, 1H), 8.37 (s, 1H), 8.25 (d, J = 8.4 Hz, 1H), 7.95 (s, 1H), 7.69-7.65 (m, 1H), 7.49-7.41 (m, 1H), 7.37-7.18 (m, 6H), 6.75 (s, 1H), 5.04-4.99 (m, 1H), 4.92 (br s, 1H), 3.65-3.64 (m, 2H), 2.28 (s, 3H). | 3 |

TABLE 1-continued

| Cmpd # | Structure | Name | NMR data | Scheme # |
|---|---|---|---|---|
| 30 | 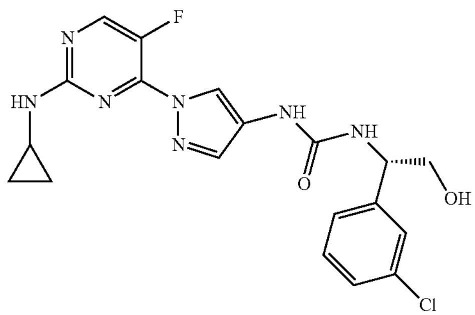 [SMILES: O=C(Nc1cnn(-c2nc(NC3CC3)ncc2F)c1)N[C@H](CO)c1cccc(Cl)c1] | (S)-1-(1-(3-chlorophenyl)-2-hydroxy-ethyl)-3-(1-(2-(cyclo-propyl-amino)-5-fluoro-pyrimidin-4-yl)-1H-pyrazol-4-yl)urea | 1HNMR (400 MHz, DMSO-d$_6$): δ 8.68 (s, 1H), 8.49 (s, 1H), 8.42 (s, 1H), 7.79 (s, 1H), 7.57 (s, 1H), 7.35-7.32 (m, 2H), 7.28 (br s, 2H), 6.84 (d, J = 7.2 Hz, 1H), 4.98 (s, 1H), 4.73 (s, 1H), 3.60 (t, J = 4.8 Hz, 2H), 1.34 (s, 1H), 0.65 (d, J = 6 Hz, 2H), 0.45 (s, 2H) | 1 |
| 31 | 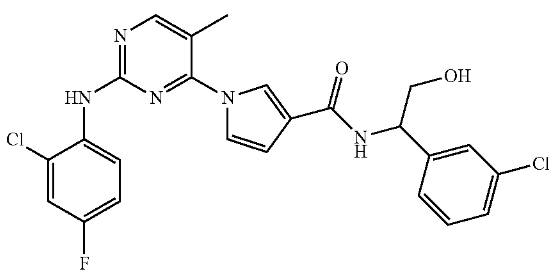 [SMILES: Cc1cnc(Nc2ccc(F)cc2Cl)nc1-n1ccc(C(=O)NC(CO)c2cccc(Cl)c2)c1] | 1-(2-((2-chloro-4-fluorophenyl)amino)-5-methyl-pyrimidin-4-yl)-N-(1-(3-chlorophenyl)-2-hydroxy-ethyl)-1H-pyrrole-3-carboxamide | 1HNMR (400 MHz, DMSO-d$_6$): δ 8.99 (s, 1H), 8.38 (s, 1H), 8.25 (d, J = 8.4 Hz, 1H), 7.69 (s, 1H), 7.69-7.65 (m, 1H), 7.49-7.41 (m, 1H), 7.37-7.18 (m, 6H), 6.75 (s, 1H), 5.04-4.99 (m, 1H), 4.92 (t, J = 5.6 Hz, 1H), 3.66-3.62 (m, 2H), 2.28 (s, 3H) | 3 |
| 32 | 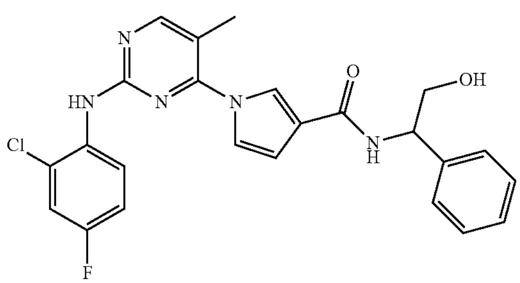 [SMILES: Cc1cnc(Nc2ccc(F)cc2Cl)nc1-n1ccc(C(=O)NC(CO)c2ccccc2)c1] | 1-(2-((2-chloro-4-fluorophenyl)amino)-5-methyl-pyrimidin-4-yl)-N-(2-hydroxy-1-phenylethyl)-1H-pyrrole-3-carboxamide | 1HNMR (400 MHz, DMSO-d$_6$): δ 8.99 (s, 1H), 8.38 (s, 1H), 8.22 (d, J = 7.6 Hz, 1H), 7.95 (s, 1H), 7.68 (br s, 1H), 7.47 (d, J = 8.0 Hz, 1H), 7.35 (d, J = 8.4 Hz, 3H), 7.31-7.21 (m, 4H), 6.76 (s, 1H), 5.04 (s, 1H), 4.86 (br s, 1H), 3.64 (s, 2H), 2.29 (s, 3H) | 3 |
| 33 | 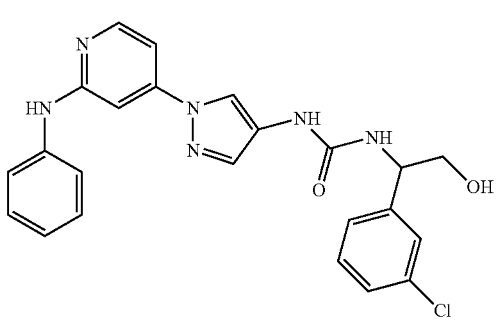 [SMILES: O=C(Nc1cnn(-c2ccnc(Nc3ccccc3)c2)c1)NC(CO)c1cccc(Cl)c1] | 1-(1-(3-chlorophenyl)-2-hydroxy-ethyl)-3-(1-(2-(phenyl-amino)-pyridin-4-yl)-1H-pyrazol-4-yl)urea | 1HNMR (400 MHz, DMSO-d$_6$): δ 9.08 (s, 1H), 8.57 (s, 1H), 8.30 (s, 1H), 8.13 (d, J = 5.6 Hz, 1H), 7.72 (s, 1H), 7.64 (d, J = 8 Hz, 2H), 7.33 (d, J = 8.4 Hz, 2H), 7.28-7.22 (m, 4H), 7.19 (s, 1H), 7.10 (d, J = 4.4 Hz, 1H), 6.88 (t, J = 7.2 Hz, 1H), 6.83 (d, J = 8 Hz, 1H), 4.98 (t, J = 5.2 Hz, 1H), 4.73 (d, J = 7.6 Hz, 1H), 3.66-3.56 (m, 2H) | 7, 1 |

TABLE 1-continued

| Cmpd # | Structure | Name | NMR data | Scheme # |
|---|---|---|---|---|
| 34 | 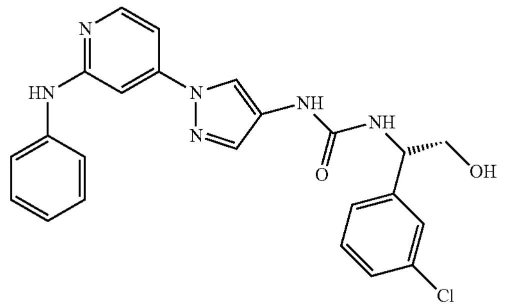 | (S)-1-(1-(3-chlorophenyl)-2-hydroxy-ethyl)-3-(1-(2-(phenyl-amino)pyridin-4-yl)-1H-pyrazol-4-yl)urea | 1HNMR (400 MHz, DMSO-$d_6$): δ 9.08 (s, 1H), 8.58 (s, 1H), 8.30 (s, 1H), 8.13 (d, J = 5.6 Hz, 1H), 7.72 (s, 1H), 7.64 (d, J = 8 Hz, 2H), 7.33 (d, J = 8.4 Hz, 2H), 7.28-7.22 (m, 4H), 7.19 (s, 1H), 7.10 (d, J = 4.4 Hz, 1H), 6.89-6.82 (m, 2H), 4.99 (br s, 1H), 4.74-4.72 (m, 1H), 3.63-3.58 (m, 2H) | 7, 1 |
| 35 | 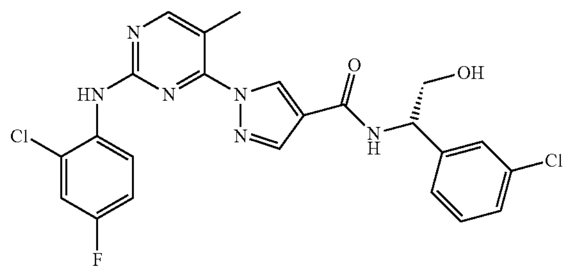 | (S)-1-(2-((2-chloro-4-fluoro-phenyl)amino)-5-methyl-pyrimidin-4-yl)-N-(1-(3-chloro-phenyl)-2-hydroxy-ethyl)-1H-pyrazole-4-carboxamide | 1HNMR (400 MHz, DMSO-$d_6$): δ 9.03 (s, 1H), 8.92 (s, 1H), 8.64 (d, J = 8.4 Hz, 1H), 8.42 (s, 1H), 8.25 (s, 1H), 7.73-7.7.66 (m, 1H), 7.50-7.47 (m, 1H), 7.43 (s, 1H), 7.35-7.28 (m, 3H), 7.25-7.20 (m, 1H), 5.06-5.01 (m, 1H), 4.96 (t, J = 5.6 Hz, 1H), 3.66-3.61 (m, 2H), 2.48 (s, 3H) | 3 |
| 36 | 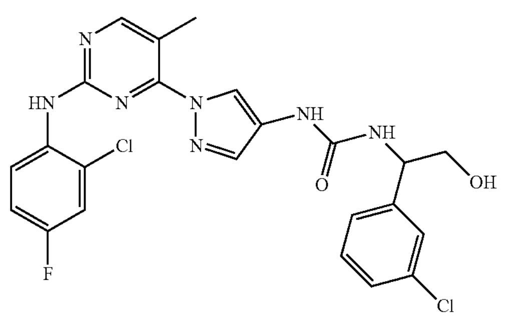 [SMILES: Cc1cnc(Nc2ccc(F)cc2Cl)nc1-n1cc(NC(=O)NC(CO)c2cccc(Cl)c2)cn1] | 1-(1-(2-((2-chloro-4-fluorophenyl)amino)-5-methyl-pyrimidin-4-yl)-1H-pyrazol-4-yl)-3-(1-(3-chlorophenyl)-2-hydroxy-ethyl)urea | 1HNMR (400 MHz, DMSO-$d_6$): δ 8.9 (s, 1H), 8.61 (s, 1H), 8.41 (s, 1H), 8.27 (s, 1H), 7.78 (s, 1H), 7.68-7.65 (m, 1H), 7.46-7.44 (m, 2H), 7.35-7.27 (m, 2H), 7.21-7.20 (m, 1H), 7.19-7.16 (m, 1H), 6.78 (d, J = 8 Hz, 1H), 4.97 (t, J = 4.8 Hz, 1H), 4.74-4.70 (m, 1H), 3.65-3.55 (m, 2H), 2.39 (s, 3H) | 2 |
| 37 | 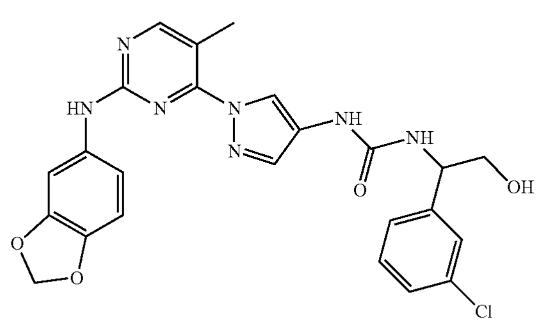 [SMILES: Cc1cnc(Nc2ccc3c(c2)OCO3)nc1-n1cc(NC(=O)NC(CO)c2cccc(Cl)c2)cn1] | 1-(1-(2-(benzo[d][1,3]dioxol-5-ylamino)-5-methyl-pyrimidin-4-yl)-1H-pyrazol-4-yl)-3-(1-(3-chlorophenyl)-2-hydroxy-ethyl)urea | 1HNMR (400 MHz, DMSO-$d_6$): δ 9.44 (s, 1H), 8.66 (s, 1H), 8.56 (s, 1H), 8.32 (s, 1H), 7.78 (s, 1H), 7.37-7.32 (m, 3H), 7.28-7.26 (m, 2H), 7.11 (d, J = 7.2 Hz, 1H), 6.80 (d, J = 8.4 Hz, 2H), 5.93 (s, 2H), 4.99 (t, J = 5.6 Hz, 1H), 4.73-4.722 (m, 1H), 3.63-3.58 (m, 2H), 2.4 (s, 3H) | 2 |

TABLE 1-continued

| Cmpd # | Structure | Name | NMR data | Scheme # |
|---|---|---|---|---|
| 38 | 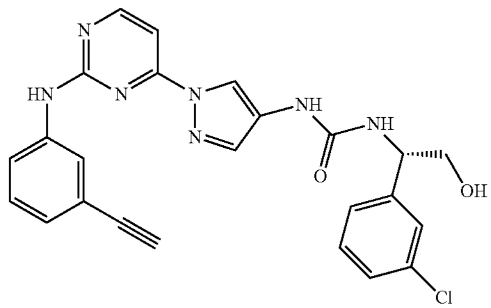 [SMILES: C#Cc1cccc(Nc2nccc(-n3cc(NC(=O)N[C@H](CO)c4cccc(Cl)c4)cn3)n2)c1] | (S)-1-(1-(3-chlorophenyl)-2-hydroxy-ethyl)-3-(1-(2-((3-ethynyl-phenyl)amino)pyrimidin-4-yl)-1H-pyrazol-4-yl)urea | 1HNMR (400 MHz, DMSO-d$_6$): δ 9.85 (s, 1H), 8.69 (s, 1H), 8.59 (s, 1H), 8.49 (d, J = 5.2 Hz, 1H), 7.87 (s, 1H), 7.80 (d, J = 8.8 Hz, 2H), 7.36-7.26 (m, 5H), 7.20 (d, J = 5.6 Hz, 1H), 7.04 (d, J = 7.2 Hz, 1H), 6.85 (d, J = 7.6 Hz, 1H), 4.99 (t, J = 4.8 Hz, 1H), 4.73 (d, J = 6.4 Hz, 1H), 4.06 (s, 1H), 3.64-3.57 (m, 2H) | 2 |
| 39 | 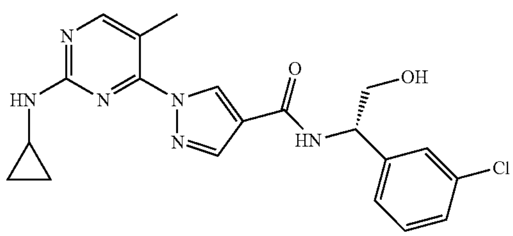 [SMILES: Cc1cnc(NC2CC2)nc1-n1cc(C(=O)N[C@H](CO)c2cccc(Cl)c2)cn1] | (S)-N-(1-(3-chlorophenyl)-2-hydroxy-ethyl)-1-(2-(cyclopropyl-amino)-5-methyl-pyrimidin-4-yl)-1H-pyrazole-4-carboxamide | 1HNMR (400 MHz, DMSO-d$_6$): δ 9.00 (s, 1H), 8.61 (d, J = 8 Hz, 1H), 8.32 (s, 1H), 8.22 (s, 1H), 7.44 (d, J = 11.2 Hz, 2H), 7.36-7.27 (m, 3H), 5.07-5.01 (m, 1H), 4.98-4.95 (m, 1H), 3.66-3.65 (m, 2H), 2.76-2.73 (m, 1H), 2.34 (s, 3H), 0.68 (d, J = 5.2 Hz, 2H), 0.48 (d, J = 2.4 Hz, 2H) | 3 |
| 40 | 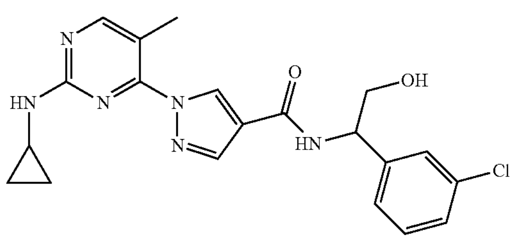 [SMILES: Cc1cnc(NC2CC2)nc1-n1cc(C(=O)NC(CO)c2cccc(Cl)c2)cn1] | N-(1-(3-chlorophenyl)-2-hydroxy-ethyl)-1-(2-(cyclopropyl-amino)-5-methyl-pyrimidin-4-yl)-1H-pyrazole-4-carboxamide | 1HNMR (400 MHz, DMSO-d$_6$): δ 8.99 (s, 1H), 8.61 (d, J = 8 Hz, 1H), 8.32 (s, 1H), 8.22 (s, 1H), 7.44 (d, J = 10.3 Hz, 2H), 7.31 (d, J = 13.6 Hz, 3H), 5.04-4.90 (m, 1H), 4.95 (d, J = 5.2 Hz, 1H), 3.65 (s, 2H), 2.65 (br s, 1H), 2.36 (s, 3H), 0.68 (d, J = 4.8 Hz, 2H), 0.47 (br s, 2H) | 3 |
| 41 | 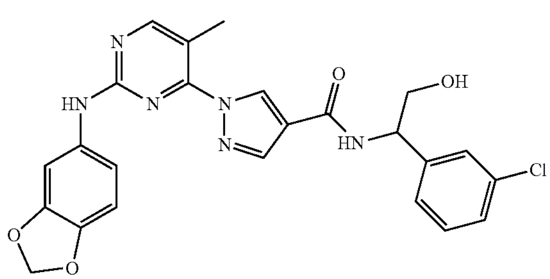 [SMILES: Cc1cnc(Nc2ccc3c(c2)OCO3)nc1-n1cc(C(=O)NC(CO)c2cccc(Cl)c2)cn1] | 1-(2-(benzo[d][1,3]dioxol-5-ylamino)-5-methyl-pyrimidin-4-yl)-N-(1-(3-chloro-phenyl)-2-hydroxy-ethyl)-1H-pyrazole-4-carboxamide | 1HNMR (400 MHz, DMSO-d$_6$): δ 9.58 (s, 1H), 9.02 (s, 1H), 8.66 (d, J = 8.0 Hz, 1H), 8.47 (s, 1H), 8.26 (s, 1H), 7.44 (s, 1H), 7.37-7.30 (m, 4H), 7.12 (d, J = 9.6 Hz, 1H), 6.84 (d, J = 8.4 Hz, 1H), 5.95 (s, 2H), 5.06-5.04 (m, 1H), 4.96 (br s, 1H), 3.65 (br s, 2H), 2.40 (s, 3H) | 3 |

TABLE 1-continued

| Cmpd # | Structure | Name | NMR data | Scheme # |
|---|---|---|---|---|
| 42 | 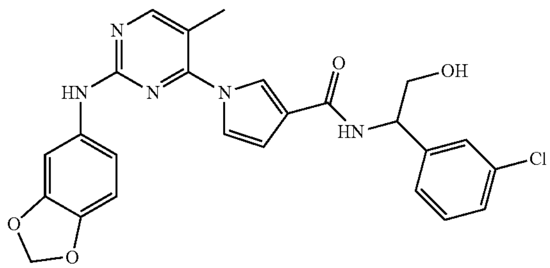 [SMILES: Cc1cnc(Nc2ccc3c(c2)OCO3)nc1-n1ccc(C(=O)NC(CO)c2cccc(Cl)c2)c1] | 1-(2-(benzo[d][1,3]dioxol-5-ylamino)-5-methyl-pyrimidin-4-yl)-N-(1-(3-chloro-phenyl)-2-hydroxy-ethyl)-1H-pyrrole-3-carboxamide | 1HNMR (400 MHz, DMSO-d$_6$): δ 9.53 (s, 1H), 8.43 (s, 1H), 8.26 (d, J = 8.0 Hz, 1H), 8.00 (s, 1H), 7.41 (d, J = 8.0 Hz, 2H), 7.32 (s, 2H), 7.28 (br s, 1H), 7.10 (d, J = 8.4 Hz, 1H), 6.83-6.78 (m, 2H), 5.94 (s, 2H), 5.04-5.01 (m, 1H), 4.92 (t, J = 5.2 Hz, 1H), 3.63 (d, J = 4.8 Hz, 2H), 2.29 (s, 3H) | 3 |
| 43 | 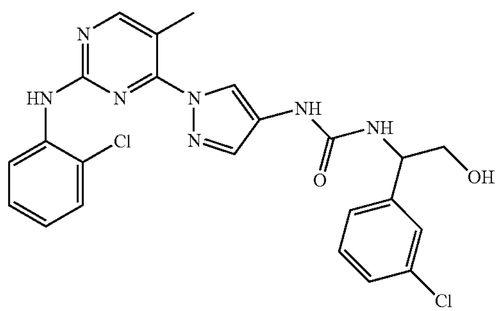 [SMILES: Cc1cnc(Nc2ccccc2Cl)nc1-n1cc(NC(=O)NC(CO)c2cccc(Cl)c2)cn1] | 1-(1-(3-chlorophenyl)-2-hydroxy-ethyl)-3-(1-(2-((2-chloro-phenyl)amino)-5-methyl-pyrimidin-4-yl)-1H-pyrazol-4-yl)urea | 1HNMR (400 MHz, DMSO-d$_6$): δ 8.78 (s, 1H), 8.63 (s, 1H), 8.45 (s, 1H), 8.30 (s, 1H), 7.79 (t, J = 3.6 Hz, 2H), 7.47 (d, J = 8 Hz, 1H), 7.39-7.25 (m, 4H), 7.13 (t, J = 6.7 Hz, 1H), 6.79 (d, J = 8 Hz, 1H), 4.98 (t, J = 5.6 Hz, 1H), 4.73 (br s, 1H), 3.65-3.55 (m, 2H), 2.47 (s, 3H) | 2 |
| 44 | 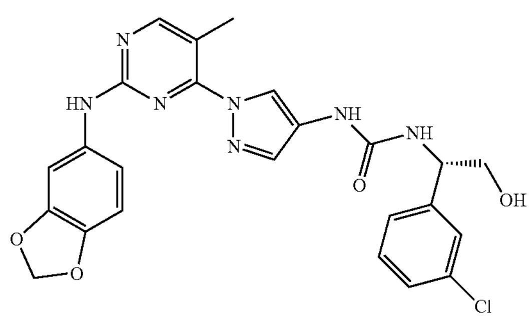 [SMILES: Cc1cnc(Nc2ccc3c(c2)OCO3)nc1-n1cc(NC(=O)N[C@H](CO)c2cccc(Cl)c2)cn1] | (S)-1-(1-(2-(benzo[d][1,3]dioxol-5-ylamino)-5-methyl-pyrimidin-4-yl)-1H-pyrazol-4-yl)-3-(1-(3-chloro-phenyl)-2-hydroxy-ethyl)urea | 1HNMR (400 MHz, DMSO-d$_6$): δ 9.44 (s, 1H), 8.66 (s, 1H), 8.57 (s, 1H), 8.32 (s, 1H), 7.78 (s, 1H), 7.37-7.32 (m, 3H), 7.27 (d, J = 7.2 Hz, 2H), 7.12-7.09 (m, 1H), 6.8-6.79 (m, 2H), 5.94 (s, 2H), 5.0 (t, J = 4.8 Hz, 1H), 4.74 (t, J = 5.2 Hz, 1H), 3.65-3.57 (m, 2H), 2.4 (s, 3H) | 2 |
| 45 | 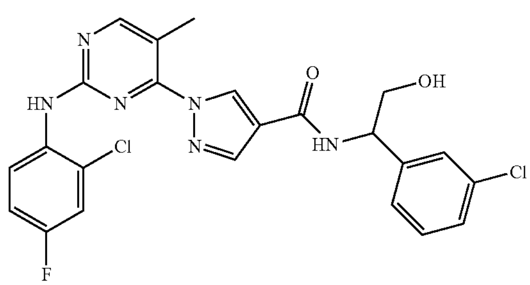 [SMILES: Cc1cnc(Nc2ccc(F)cc2Cl)nc1-n1cc(C(=O)NC(CO)c2cccc(Cl)c2)cn1] | 1-(2-((2-chloro-4-fluorophenyl)amino)-5-methyl-pyrimidin-4-yl)-N-(1-(3-chlorophenyl)-2-hydroxy-ethyl)-1H-pyrazole-4-carboxamide | 1HNMR (400 MHz, DMSO-d$_6$): δ 9.04 (s, 1H), 8.93 (s, 1H), 8.64 (d, J = 8.4 Hz, 1H), 8.42 (s, 1H), 8.25 (s, 1H), 7.73-7.50 (m, 1H), 7.49-7.43 (m, 1H), 7.35 (s, 1H), 7.33-7.28 (m, 3H), 7.25-7.20 (m, 1H), 5.06-5.01 (m, 1H), 4.97-4.94 (m, 1H), 3.65 (t, J = 6.4 Hz, 2H), 2.40 (s, 3H) | 3 |
| 46 | 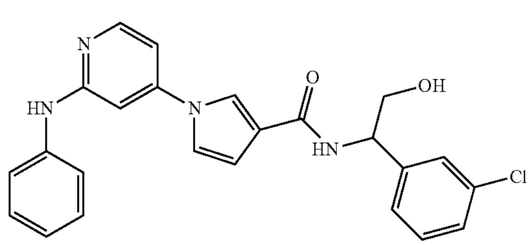 [SMILES: O=C(NC(CO)c1cccc(Cl)c1)c1ccn(-c2ccnc(Nc3ccccc3)c2)c1] | N-(1-(3-chloro-phenyl)-2-hydroxy-ethyl)-1-(2-(phenyl-amino)pyridin-4-yl)-1H-pyrrole-3-carboxamide | 1HNMR (400 MHz, DMSO-d$_6$): δ 9.13 (s, 1H), 8.35-8.1 (m, 2H), 8.0-7.9 (m, 1H), 7.8-7.55 (m, 2H), 7.5-7.11 (m, 7H), 7.11-6.71 (m, 4H), 5.1-4.90 (m, 2H), 3.65 (br s, 2H) | 7 |

TABLE 1-continued

| Cmpd # | Structure | Name | NMR data | Scheme # |
|---|---|---|---|---|
| 47 | 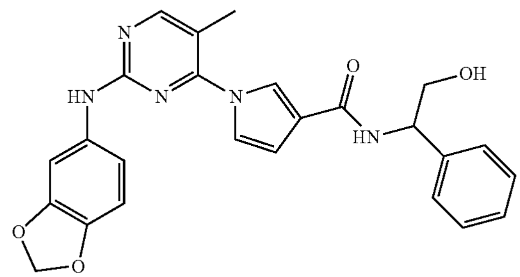 [SMILES: Cc1cnc(Nc2ccc3c(c2)OCO3)nc1-n1ccc(C(=O)NC(CO)c2ccccc2)c1] | 1-(2-(benzo[d][1,3]dioxol-5-ylamino)-5-methyl-pyrimidin-4-yl)-N-(2-hydroxy-1-phenylethyl)-1H-pyrrole-3-carboxamide | 1HNMR (400 MHz, DMSO-d$_6$): δ 9.53 (s, 1H), 8.42 (s, 1H), 8.22 (d, J = 8.0 Hz, 1H), 8.0 (s, 1H), 7.41 (s, 2H), 7.37 (d, J = 6.8 Hz, 2H), 7.28 (t, J = 7.2 Hz, 1H), 7.21 (d, J = 6.0 Hz, 1H), 7.10 (d, J = 8.4 Hz, 1H), 6.83-6.79 (m, 2H), 5.94 (s, 2H), 5.04 (d, J = 7.6 Hz, 1H), 4.86 (br s, 1H), 3.65 (br s, 2H), 2.29 (s, 3H) | 3 |
| 48 | 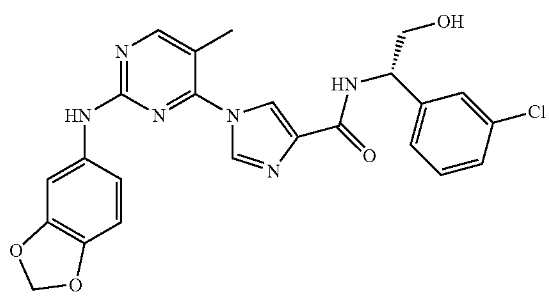 [SMILES: Cc1cnc(Nc2ccc3c(c2)OCO3)nc1-n1cnc(C(=O)N[C@H](CO)c2cccc(Cl)c2)c1] | (S)-1-(2-(benzo[d][1,3]dioxol-5-ylamino)-5-methyl-pyrimidin-4-yl)-N-(1-(3-chloro-phenyl)-2-hydroxy-ethyl)-1H-imidazole-4-carboxamide | 1HNMR (400 MHz, DMSO-d$_6$): 9.65 (s, 1H), 8.51 (s, 1H), 8.41 (d, J = 8.4 Hz, 1H), 8.33 (s, 1H), 8.15 (s, 1H), 7.43 (s, 1H), 7.38 (s, 1H), 7.34-7.32 (m, 3H), 7.06 (d, J = 1.6 Hz, 1H), 6.82 (d, J = 8.4 Hz, 1H), 5.94 (s, 2H), 5.03 (br s, 2H), 3.73-3.71 (m, 2H), 2.25 (s, 3H) | 6 |
| 49 | 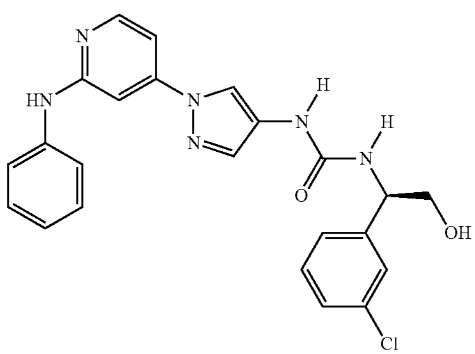 [SMILES: O=C(Nc1cnn(-c2ccnc(Nc3ccccc3)c2)c1)N[C@@H](CO)c1cccc(Cl)c1] | (R)-1-(1-(3-chloro-phenyl)-2-hydroxy-ethyl)-3-(1-(2-(phenylamino)pyridin-4-yl)-1H-pyrazol-4-yl)urea | 1HNMR (400 MHz, DMSO-d$_6$): δ 9.08 (s, 1H), 8.57 (s, 1H), 8.30 (s, 1H), 8.13 (d, J = 5.6 Hz, 1H), 7.72 (s, 1H), 7.64 (d, J = 8 Hz, 2H), 7.33 (d, J = 8.4 Hz, 2H), 7.28-7.10 (m, 6H), 7.19 (s, 1H), 7.10 (d, J = 4.4 Hz, 1H), 6.88-6.82 (m, 2H), 4.98 (t, J = 5.2 Hz, 1H), 4.73 (br s, 1H), 3.65-3.55 (m, 2H) | 7, 1 |
| 50 | 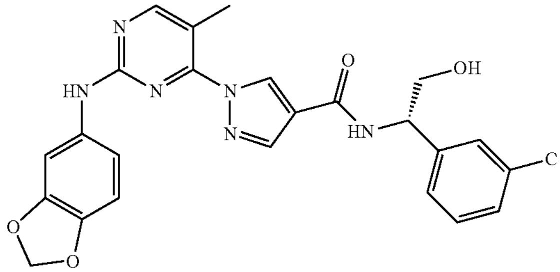 [SMILES: Cc1cccc([C@@H](CO)NC(=O)c2cnn(-c3nc(Nc4ccc5c(c4)OCO5)ncc3C)c2)c1] | (S)-1-(2-(benzo[d][1,3]dioxol-5-ylamino)-5-methyl-pyrimidin-4-yl)-N-(1-(3-chloro-phenyl)-2-hydroxy-ethyl)-1H-pyrazole-4-carboxamide | 1HNMR (400 MHz, DMSO-d$_6$): δ 9.58 (s, 1H), 9.01 (s, 1H), 8.65 (d, J = 8.0 Hz, 1H), 8.47 (s, 1H), 8.26 (s, 1H), 7.44 (s, 1H), 7.37-7.30 (m, 4H), 7.12 (d, J = 6.4 Hz, 1H), 6.84 (d, J = 8.4 Hz, 1H), 5.95 (s, 2H), 5.08-5.02 (m, 1H), 4.96 (t, J = 5.2 Hz, 1H), 3.65 (br s, 2H), 2.40 (s, 3H) | 3 |

TABLE 1-continued

| Cmpd # | Structure | Name | NMR data | Scheme # |
|---|---|---|---|---|
| 51 | 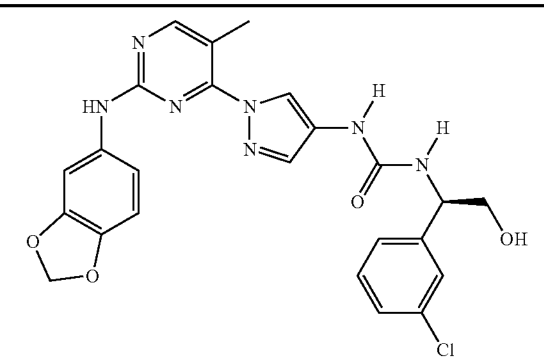 | (R)-1-(1-(2-(benzo[d][1,3]dioxol-5-ylamino)-5-methyl-pyrimidin-4-yl)-1H-pyrazol-4-yl)-3-(1-(3-chloro-phenyl)-2-hydroxy-ethyl)urea | 1HNMR (400 MHz, DMSO-d$_6$): δ 9.44 (s, 1H), 8.66 (s, 1H), 8.56 (s, 1H), 8.32 (s, 1H), 7.78 (s, 1H), 7.36-7.32 (m, 3H), 7.29-7.26 (m, 2H), 7.11-7.09 (m, 1H), 6.82-6.79 (m, 2H), 5.94 (s, 2H), 4.99 (t, J = 5.2 Hz, 1H), 4.74-4.72 (m, 1H), 3.65-3.57 (m, 2H), 2.47 (s, 3H) | 2 |
| 52 | 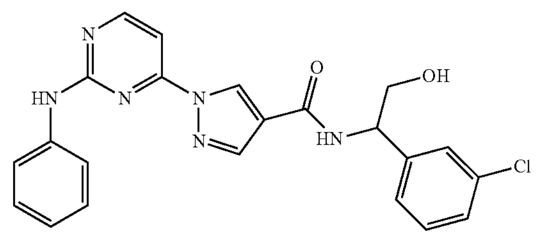 [SMILES: O=C(NC(CO)c1cccc(Cl)c1)c1cnn(-c2ccnc(Nc3ccccc3)n2)c1] | N-(1-(3-chloro-phenyl)-2-hydroxy-ethyl)-1-(2-(phenyl-amino)pyrimidin-4-yl)-1H-pyrazole-4-carboxamide | 1HNMR (400 MHz, DMSO-d$_6$): δ 9.85 (s, 1H), 9.04 (s, 1H), 8.76 (d, J = 8 Hz, 1H), 8.59 (d, J = 5.6 Hz, 1H), 8.29 (s, 1H), 7.75 (d, J = 8 Hz, 2H), 7.45 (s, 1H), 7.34-7.27 (m, 6H), 7.00-6.90 (m, 1H), 5.1-4.9 (m, 2H), 3.67-3.65 (m, 2H) | 3 |
| 53 | 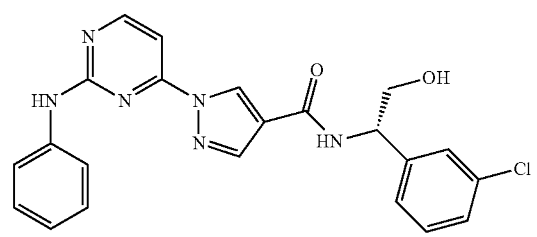 [SMILES: O=C(N[C@H](CO)c1cccc(Cl)c1)c1cnn(-c2ccnc(Nc3ccccc3)n2)c1] | (S)-N-(1-(3-chlorophenyl)-2-hydroxy-ethyl)-1-(2-(phenylamino)pyrimidin-4-yl)-1H-pyrazole-4-carboxamide | 1HNMR (400 MHz, DMSO-d$_6$): δ 9.85 (s, 1H), 9.04 (s, 1H), 8.76 (d, J = 8 Hz, 1H), 8.59 (d, J = 5.6 Hz, 1H), 8.29 (s, 1H), 7.75 (d, J = 8 Hz, 2H), 7.45 (s, 1H), 7.35-7.27 (m, 6H), 7.02-6.98 (m, 1H), 5.05-5.02 (m, 1H), 4.98 (t, J = 2 Hz, 1H), 3.67 (t, J = 5.2 Hz, 2H) | 3 |
| 54 | 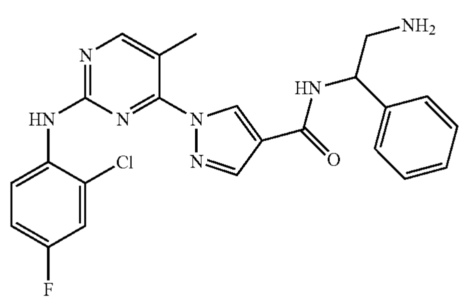 [SMILES: Cc1cnc(Nc2ccc(F)cc2Cl)nc1-n1cc(C(=O)NC(CN)c2ccccc2)cn1] | N-(2-amino-1-phenylethyl)-1-(2-((2-chloro-4-fluoro-phenyl)amino)-5-methyl-pyrimidin-4-yl)-1H-pyrazole-4-carboxamide | 1HNMR (400 MHz, DMSO-d$_6$): 9.04 (s, 1H), 8.92 (s, 1H), 8.58 (d, J = 7.6 Hz, 1H), 8.42 (s, 1H), 8.24 (s, 1H), 7.73-7.66 (m, 1H), 7.50-7.47 (m, 1H), 7.34-7.25 (m, 4H), 7.24-7.20 (m, 2H), 4.93-4.90 (m, 1H), 2.85-2.83 (d, J = 6.8 Hz, 2H), 2.40 (s, 3H) | 4 |
| 55 | 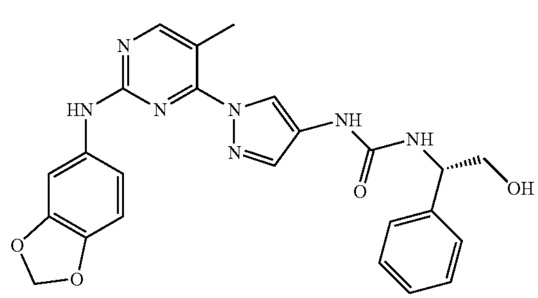 [SMILES: Cc1cnc(Nc2ccc3c(c2)OCO3)nc1-n1cc(NC(=O)N[C@H](CO)c2ccccc2)cn1] | (S)-1-(1-(2-(benzo[d][1,3]dioxol-5-ylamino)-5-methyl-pyrimidin-4-yl)-1H-pyrazol-4-yl)-3-(2-hydroxy-1-phenylethyl)urea | 1HNMR (400 MHz, DMSO-d$_6$): δ 9.44 (s, 1H), 8.81 (s, 1H), 8.56 (s, 1H), 8.32 (s, 1H), 7.77 (s, 1H), 7.37 (d, J = 1.6 Hz, 1H), 7.31-7.29 (m, 4H), 7.23-7.19 (m, 1H) 7.12-7.09 (m, 1H), 6.9 (d, J = 7.6 Hz, 1H), 6.8 (d, J = 8 Hz, 1H), 5.97 (s, 2H), 4.95 (s, 1H), 4.74-4.69 (m, 1H), 3.63-3.55 (m, 2H), 2.45 (s, 3H) | 2 |

TABLE 1-continued

| Cmpd # | Structure | Name | NMR data | Scheme # |
|---|---|---|---|---|
| 56 | 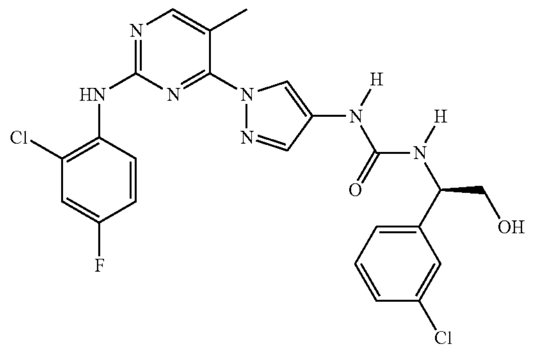 [SMILES: Cc1cnc(Nc2ccc(F)cc2Cl)nc1-n1cc(NC(=O)N[C@@H](CO)c2cccc(Cl)c2)cn1] | (R)-1-(1-(2-((2-chloro-4-fluoro-phenyl)amino)-5-methyl-pyrimidin-4-yl)-1H-pyrazol-4-yl)-3-(1-(3-chloro-phenyl)-2-hydroxy-ethyl)urea | 1HNMR (400 MHz, DMSO-d$_6$): δ 8.91 (s, 1H), 8.64 (s, 1H), 8.41 (s, 1H), 8.27 (s, 1H), 7.79 (s, 1H), 7.70-7.60 (m, 1H), 7.47-7.45 (m, 1H), 7.35-7.32 (m, 2H), 7.22 (d, J = 4 Hz, 2H), 7.19-7.17 (m, 1H), 6.8 (d, J = 8 Hz, 1H), 4.98 (t, J = 4.8 Hz, 1H), 4.73-4.72 (m, 1H), 3.64-3.65 (m, 2H), 2.40 (s, 3H) | 2 |
| 57 | 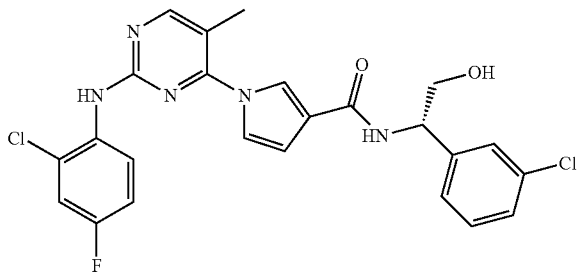 | (S)-1-(2-((2-chloro-4-fluorophenyl)amino)-5-methyl-pyrimidin-4-yl)-N-(1-(3-chlorophenyl)-2-hydroxy-ethyl)-1H-pyrrole-3-carboxamide | 1HNMR (400 MHz, DMSO-d$_6$): δ 8.99 (s, 1H), 8.38 (s, 1H), 8.27 (d, J = 8.0 Hz, 1H), 7.96 (s, 1H), 7.70-7.66 (m, 1H), 7.47-7.19 (m, 7H), 6.75 (s, 1H), 5.03-5.01 (m, 1H), 3.64 (br s, 2H), 2.29 (s, 3H) | 3 |
| 58 | 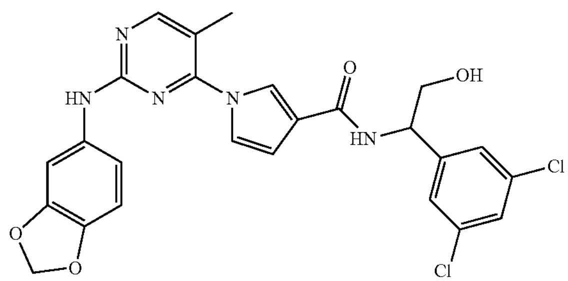 [SMILES: Cc1cnc(Nc2ccc3c(c2)OCO3)nc1-n1ccc(C(=O)NC(CO)c2cc(Cl)cc(Cl)c2)c1] | 1-(2-(benzo[d][1,3]dioxol-5-ylamino)-5-methyl-pyrimidin-4-yl)-N-(1-(3,5-dichloro-phenyl)-2-hydroxy-ethyl)-1H-pyrrole-3-carboxamide | 1HNMR (400 MHz, DMSO-d$_6$): δ 9.54 (s, 1H), 8.43 (s, 1H), 8.29 (d, J = 8.4 Hz, 1H), 8.01 (s, 1H), 7.46-7.40 (m, 5H), 7.11 (d, J = 8.4 Hz, 1H), 6.82 (d, J = 8.4 Hz, 1H), 6.77 (s, 1H), 5.94 (s, 2H), 5.04-4.98 (m, 2H), 3.66-3.65 (m, 2H), 2.29 (s, 3H) | 3 |
| 59 | 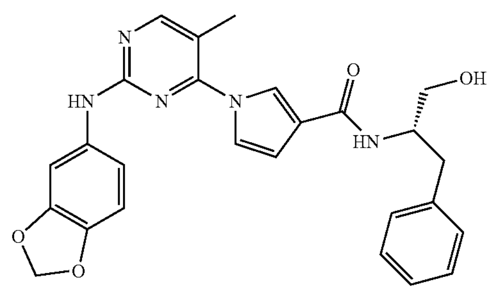 [SMILES: Cc1cnc(Nc2ccc3c(c2)OCO3)nc1-n1ccc(C(=O)N[C@H](CO)Cc2ccccc2)c1] | (S)-1-(2-(benzo[d][1,3]dioxol-5-ylamino)-5-methyl-pyrimidin-4-yl)-N-(1-hydroxy-3-phenyl-propan-2-yl)-1H-pyrrole-3-carboxamide | 1HNMR (400 MHz, DMSO-d$_6$): δ 9.52 (s, 1H), 8.41 (s, 1H), 7.89 (s, 1H), 7.73 (d, J = 8.8 Hz, 1H), 7.39-7.38 (m, 2H), 7.24-7.23 (m, 4H), 7.13-7.09 (m, 2H), 6.82 (d, J = 8.4 Hz, 1H), 6.70 (s, 1H), 5.94 (s, 2H), 4.78 (t, J = 5.2 Hz, 1H), 4.11 (s, 1H), 3.46 (t, J = 6 Hz, 1H), 3.40-3.37 (m, 1H), 2.95-2.90 (m, 1H), 2.78-2.72 (m, 1H), 2.28 (s, 3H) | 3 |
| 60 | 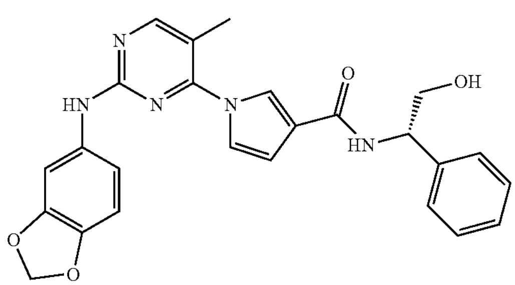 [SMILES: Cc1cnc(Nc2ccc3c(c2)OCO3)nc1-n1ccc(C(=O)N[C@H](CO)c2ccccc2)c1] | (S)-1-(2-(benzo[d][1,3]dioxol-5-ylamino)-5-methyl-pyrimidin-4-yl)-N-(2-hydroxy-1-phenylethyl)-1H-pyrrole-3-carboxamide | 1HNMR (400 MHz, DMSO-d$_6$): δ 9.54 (s, 1H), 8.43 (s, 1H), 8.29 (d, J = 8.4 Hz, 1H), 8.01 (s, 1H), 7.46-7.40 (m, 6H), 7.11 (d, J = 8.4 Hz, 1H), 6.83-6.81 (m, 2H), 6.77 (s, 1H), 5.94 (s, 2H), 5.04-4.98 (m, 2H), 3.66 (d, J = 7.2 Hz, 2H), 2.29 (s, 3H) | 3 |

| Cmpd # | Structure | Name | NMR data | Scheme # |
|---|---|---|---|---|
| 61 | 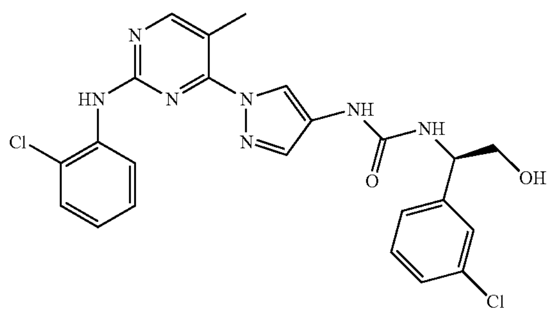 [SMILES: Cc1cnc(Nc2ccccc2Cl)nc1-n1cc(NC(=O)N[C@@H](CO)c2cccc(Cl)c2)cn1] | (R)-1-(1-(3-chlorophenyl)-2-hydroxyethyl)-3-(1-(2-((2-chlorophenyl)amino)-5-methylpyrimidin-4-yl)-1H-pyrazol-4-yl)urea | 1HNMR (400 MHz, DMSO-$d_6$): δ 8.78 (s, 1H), 8.67 (s, 1H), 8.45 (s, 1H), 8.30 (s, 1H), 7.80 (d, J = 4.0 Hz, 2H), 7.47 (d, J = 7.2 Hz, 1H), 7.35-7.31 (m, 3H), 7.28-7.26 (m, 2H), 7.13 (t, J = 8.8 Hz, 1H), 6.83 (d, J = 7.60 Hz, 1H), 4.98 (t, J = 5.2 Hz, 1H), 4.73 (d, J = 7.2 Hz, 1H), 3.63-3.58 (m, 2H), 2.48 (s, 3H) | 2 |
| 62 | 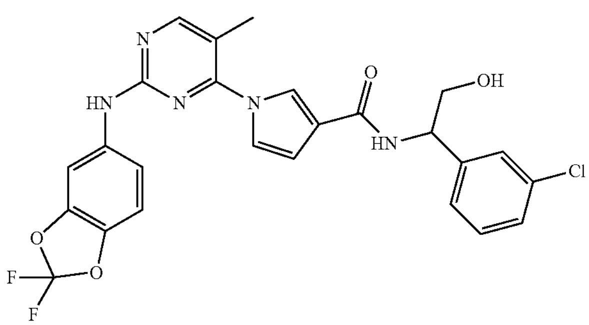 [SMILES: Cc1cnc(Nc2ccc3c(c2)OC(F)(F)O3)nc1-n1ccc(C(=O)NC(CO)c2cccc(Cl)c2)c1] | N-(1-(3-chloro-phenyl)-2-hydroxyethyl)-1-(2-((2,2-difluoro-benzo[d][1,3]dioxol-5-yl)amino)-5-methyl-pyrimidin-4-yl)-1H-pyrrole-3-carboxamide | 1HNMR (400 MHz, DMSO-$d_6$): δ 9.90 (s, 1H), 8.49 (s, 1H), 8.28 (d, J = 8 Hz, 1H), 8.04 (s, 1H), 7.91 (d, J = 2.0 Hz, 1H), 7.45-7.39 (m, 3H), 7.36-7.27 (m, 4H), 6.79 (d, J = 1.2 Hz, 1H), 5.06-5.03 (m, 1H), 4.93 (t, J = 5.6 Hz, 1H), 3.68-3.64 (m, 2H), 2.32 (s, 3H) | 3 |
| 63 | 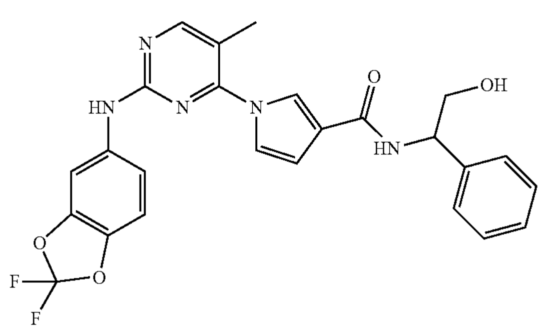 [SMILES: Cc1cnc(Nc2ccc3c(c2)OC(F)(F)O3)nc1-n1ccc(C(=O)NC(CO)c2ccccc2)c1] | 1-(2-((2,2-difluoro-benzo[d][1,3]dioxol-5-yl)amino)-5-methyl-pyrimidin-4-yl)-N-(2-hydroxy-1-phenylethyl)-1H-pyrrole-3-carboxamide | 1HNMR (400 MHz, DMSO-$d_6$): δ 9.89 (s, 1H), 8.49 (s, 1H), 8.24 (d, J = 8.0 Hz, 1H), 8.04 (s, 1H), 7.92 (s, 1H), 7.44 (s, 1H), 7.40-7.38 (m, 3H), 7.36-7.31 (m, 3H), 7.21-7.19 (m, 1H), 6.80 (s, 1H), 5.07-5.02 (m, 1H), 4.86 (t, J = 5.2 Hz, 1H), 3.65 (s, 2H), 2.32 (s, 3H) | 3 |
| 64 | 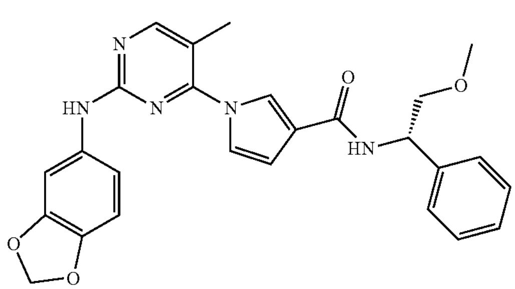 [SMILES: COC[C@@H](NC(=O)c1ccn(-c2nc(Nc3ccc4c(c3)OCO4)ncc2C)c1)c1ccccc1] | (S)-1-(2-(benzo[d][1,3]dioxol-5-ylamino)-5-methyl-pyrimidin-4-yl)-N-(2-methoxy-1-phenylethyl)-1H-pyrrole-3-carboxamide | 1HNMR (400 MHz, DMSO-$d_6$): δ 9.54 (s, 1H), 8.42 (s, 1H), 8.35 (d, J = 8.4 Hz, 1H), 8.01 (s, 1H), 7.41-7.38 (m, 4H), 7.31-7.29 (m, 2H), 7.25-7.21 (m, 1H), 7.11-7.09 (m, 1H), 6.83-6.81 (m, 2H), 5.94 (s, 2H), 5.28-5.22 (m, 1H), 3.65 (t, J = 10 Hz, 1H), 3.56-3.54 (m, 1H), 2.29 (s, 3H) | 3 |

TABLE 1-continued

| Cmpd # | Structure | Name | NMR data | Scheme # |
|---|---|---|---|---|
| 65 | 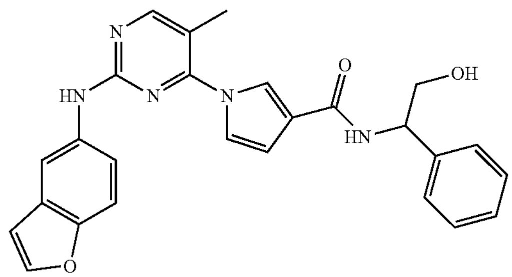 [SMILES: Cc1cnc(Nc2ccc3occc3c2)nc1-n1ccc(C(=O)NC(CO)c2ccccc2)c1] | 1-(2-(benzo-furan-5-ylamino)-5-methyl-pyrimidin-4-yl)-N-(2-hydroxy-1-phenylethyl)-1H-pyrrole-3-carboxamide | 1HNMR (400 MHz, DMSO-$d_6$): δ 9.65 (s, 1H), 8.45 (s, 1H), 8.24 (d, J = 8 Hz, 1H), 8.08-8.06 (m, 2H), 7.91 (d, J = 2 Hz, 1H), 7.54 (s, 1H), 7.52-7.45 (m, 2H), 7.44-7.38 (m, 1H), 7.36-7.32 (m, 2H), 7.30-7.28 (m, 2H), 6.90 (d, J = 2.0 Hz, 1H), 6.78 (s, 1H), 5.08-5.04 (m, 1H), 4.86 (t, J = 6.0 Hz, 1H), 3.68-3.65 (m, 2H), 2.31 (s, 3H) | 3 |
| 66 | 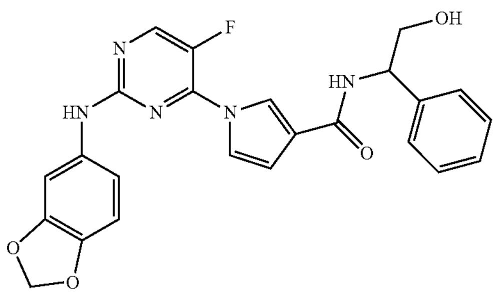 [SMILES: O=C(NC(CO)c1ccccc1)c1ccn(-c2nc(Nc3ccc4c(c3)OCO4)ncc2F)c1] | 1-(2-(benzo[d][1,3]dioxol-5-ylamino)-5-fluoro-pyrimidin-4-yl)-N-(2-hydroxy-1-phenylethyl)-1H-pyrrole-3-carboxamide | 1HNMR (400 MHz, DMSO-$d_6$): δ 9.67 (s, 1H), 8.63 (d, J = 4.0 Hz, 1H), 8.39 (d, J = 8.0 Hz, 1H), 8.18 (s, 1H) 7.57 (s, 1H), 7.37-7.30 (m, 5H), 7.22-7.19 (m, 1H), 7.08 (d, J = 8.4 Hz, 1H), 6.86 (s, 1H), 6.84 (s, 1H), 5.96 (s, 2H), 5.03 (d, J = 6.8 Hz, 1H), 4.87 (s, 1H), 3.65 (d, J = 6.8 Hz, 2H) | 3 |
| 67 | 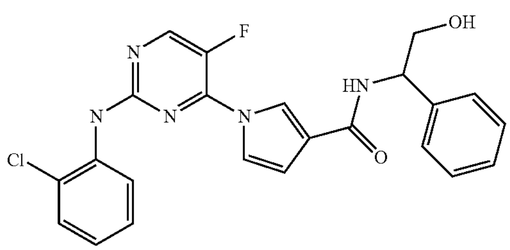 [SMILES: O=C(NC(CO)c1ccccc1)c1ccn(-c2nc(Nc3ccccc3Cl)ncc2F)c1] | 1-(2-((2-chloro-phenyl)amino)-5-fluoro-pyrimidin-4-yl)-N-(2-hydroxy-1-phenylethyl)-1H-pyrrole-3-carboxamide | 1HNMR (400 MHz, DMSO-$d_6$): δ 9.15 (s, 1H), 8.61 (d, J = 4.0 Hz, 1H), 8.38 (d, J = 7.6 Hz, 1H), 8.13 (s, 1H), 7.71 (d, J = 7.6 Hz, 1H), 7.51 (s 2H), 7.35-7.34 (m, 3H), 7.29 (t, J = 8.0 Hz, 2H), 7.22-7.17 (m, 2H), 6.83 (d, J = 1.6 Hz, 1H), 5.05-5.00 (m, 1H), 4.86 (t, J = 6 Hz, 1H), 3.69-3.61 (m, 2H). | 3 |
| 68 | 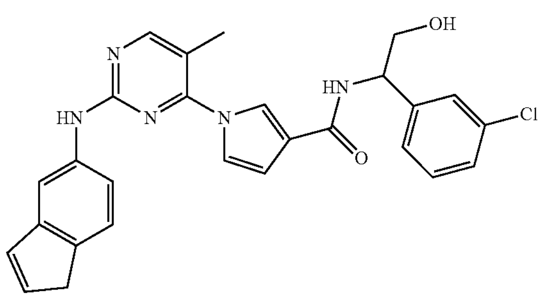 [SMILES: Cc1cnc(Nc2ccc3c(c2)C=CC3)nc1-n1ccc(C(=O)NC(CO)c2cccc(Cl)c2)c1] | 1-(2-(benzo-furan-5-ylamino)-5-methyl-pyrimidin-4-yl)-N-(1-(3-chlorophenyl)-2-hydroxy-ethyl)-1H-pyrrole-3-carboxamide | 1HNMR (400 MHz, DMSO-$d_6$): δ 9.65 (s, 1H), 8.46 (s, 1H), 8.29 (d, J = 8.00 Hz, 1H), 8.07 (d, J = 7.2 Hz, 2H), 7.91 (d, J = 2.0 Hz, 1H), 7.54-7.47 (m, 4H), 7.43 (s, 2H), 7.33 (s, 1H), 7.29 (s, 1H), 6.89 (s, 1H), 6.77 (s, 1H), 5.07-5.04 (m, 1H), 4.93 (t, J = 6.0 Hz, 1H), 3.66 (d, J = 4.0 Hz, 2H), 2.31 (s, 3H) | 3 |

TABLE 1-continued

| Cmpd # | Structure | Name | NMR data | Scheme # |
|---|---|---|---|---|
| 69 | 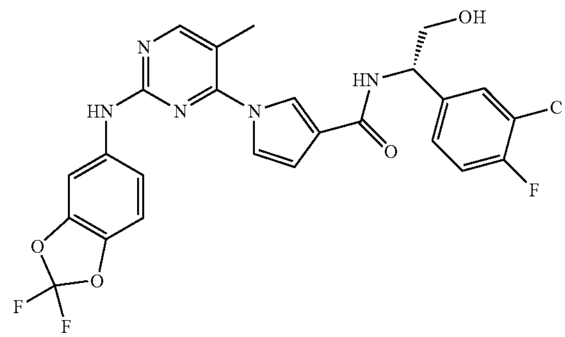 [SMILES: Cc1cc([C@@H](CO)NC(=O)c2ccn(-c3nc(Nc4ccc5c(c4)OC(F)(F)O5)ncc3C)c2)ccc1F] | (S)-N-(1-(3-chloro-4-fluoro-phenyl)-2-hydroxy-ethyl)-1-(2-((2,2-difluoro-benzo[d][1,3]dioxol-5-yl)amino)-5-methyl-pyrimidin-4-yl)-1H-pyrrole-3-carboxamide | 1HNMR (400 MHz, DMSO-d$_6$): δ 9.90 (s, 1H), 8.49 (s, 1H), 8.27 (d, J = 8 Hz, 1H), 8.03 (s, 1H), 7.91 (s, 1H), 7.56-7.46 (m, 1H), 7.44-7.41 (m, 1H), 7.40-7.29 (m, 4H), 6.79-6.78 (m, 1H), 5.07-5.01 (m, 1H), 4.93 (t, J = 5.6 Hz, 1H), 3.67-3.64 (m, 2H), 2.32 (s, 3H) | 3 |
| 70 | 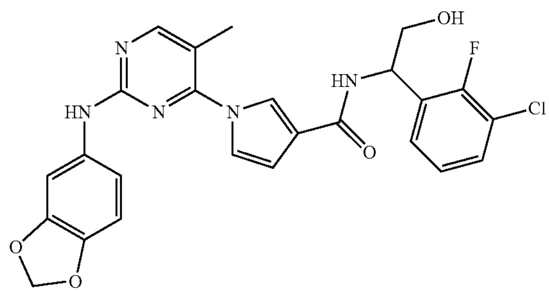 [SMILES: Cc1cnc(Nc2ccc3c(c2)OCO3)nc1-n1ccc(C(=O)NC(CO)c2cccc(Cl)c2F)c1] | 1-(2-(benzo[d][1,3]dioxol-5-ylamino)-5-methyl-pyrimidin-4-yl)-N-(1-(3-chloro-2-fluorophenyl)-2-hydroxy-ethyl)-1H-pyrrole-3-carboxamide | 1HNMR (400 MHz, DMSO-d$_6$): δ 9.54 (s, 1H), 8.43 (s, 1H), 8.34 (d, J = 6.8 Hz, 1H), 8.01 (s, 1H), 7.44-7.41 (m, 4H), 7.19 (t, J = 7.6 Hz, 1H), 7.09 (d, J = 8.0 Hz, 1H), 6.82 (d, J = 8.4 Hz, 2H), 6.77 (s, 1H), 5.94 (s, 2H), 5.33 (d, J = 6.4 Hz, 1H), 5.03 (s, 1H), 3.66 (d, J = 5.2 Hz, 2H), 2.29 (s, 3H) | 3 |
| 71 | 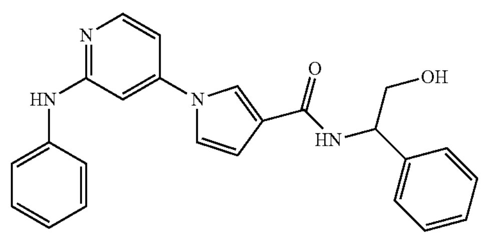 [SMILES: O=C(NC(CO)c1ccccc1)c1ccn(-c2ccnc(Nc3ccccc3)c2)c1] | N-(2-hydroxy-1-phenylethyl)-1-(2-(phenylamino)pyridin-4-yl)-1H-pyrrole-3-carboxamide | 1HNMR (400 MHz, DMSO-d$_6$): δ 9.12 (s, 1H), 8.18 (t, J = 5.2 Hz, 1H), 8.02 (s, 1H), 7.65 (d, J = 8 Hz, 2H), 7.43 (s, 1H), 7.37-7.32 (m, 2H), 7.26-7.19 (m, 5H), 7.04-7.03 (m, 1H), 6.95 (s, 1H), 6.90 (t, J = 8 Hz, 1H), 6.78 (s, 1H), 5.07-5.01 (m, 1H), 4.86 (t, J = 5.2 Hz, 1H), 3.70-306 (m, 2H) | 7 |
| 72 | 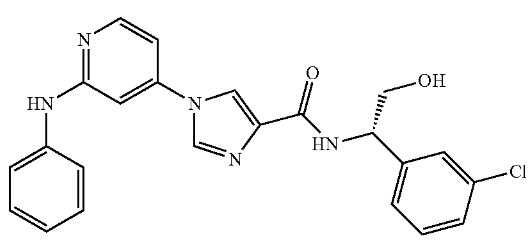 [SMILES: O=C(N[C@H](CO)c1cccc(Cl)c1)c1cn(-c2ccnc(Nc3ccccc3)c2)cn1] | (S)-N-(1-(3-chlorophenyl)-2-hydroxy-ethyl)-1-(2-(phenylamino)pyridin-4-yl)-1H-imidazole-4-carboxamide | 1HNMR (400 MHz, DMSO-d$_6$): δ 9.18 (s, 1H), 8.45 (s, 1H), 8.40 (d, J = 8.4 Hz, 1H), 8.24 (d, J = 7.2 Hz, 2H), 7.64 (d, J = 7.6 Hz, 2H) 7.42 (s, 1H), 7.32-7.28 (m, 2H), 7.27-7.25 (m, 3H), 7.16 (d, J = 5.6 Hz, 1H), 7.02 (s, 1H), 6.91 (t, J = 6.8 Hz, 1H), 5.03-4.99 (m, 2H), 3.73 (t, J = 5.6 Hz, 2H) | 13 |

TABLE 1-continued

| Cmpd # | Structure | Name | NMR data | Scheme # |
|---|---|---|---|---|
| 73 | 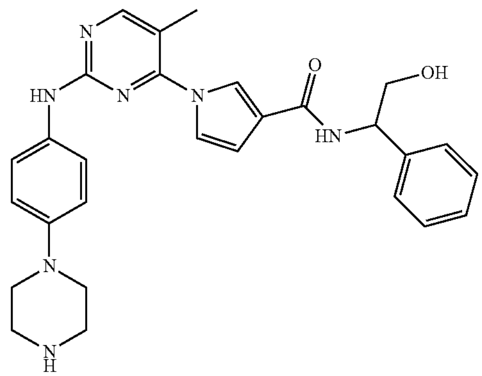 [SMILES: Cc1cnc(Nc2ccc(N3CCNCC3)cc2)nc1-n1ccc(C(=O)NC(CO)c2ccccc2)c1] | N-(2-hydroxy-1-phenylethyl)-1-(5-methyl-2-((4-(piperazin-1-yl)-phenyl)amino)pyrimidin-4-yl)-1H-pyrrole-3-carboxamide | 1HNMR (400 MHz, DMSO-d$_6$): δ 9.43 (s, 1H), 8.40 (s, 1H), 8.25 (d, J = 8.4 Hz, 1H), 8.01 (s, 1H), 7.56 (d, J = 8.8 Hz, 2H), 7.42 (s, 1H), 7.37-7.31 (m, 2H), 7.30-7.28 (m, 2 H), 7.21-7.19 (m, 1H), 6.89 (d, J = 8.8 Hz, 2H), 6.79 (s, 1H), 5.03 (t, J = 7.2 Hz, 1H), 4.88 (s, 1H), 3.65 (br s, 2H), 3.10-3.02 (m, 8H), 2.29 (s, 3H) | 3 |
| 74 | 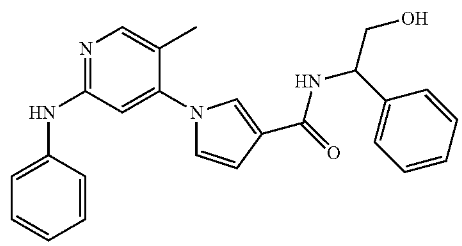 [SMILES: Cc1cnc(Nc2ccccc2)cc1-n1ccc(C(=O)NC(CO)c2ccccc2)c1] | N-(2-hydroxy-1-phenylethyl)-1-(5-methyl-2-(phenylamino)pyridin-4-yl)-1H-pyrrole-3-carboxamide | 1HNMR (400 MHz, DMSO-d$_6$): 9.04 (s, 1H), 8.13 (s, 1H), 8.09 (d, J = 8.4 Hz, 1H), 7.66 (s, 1H), 7.61 (d, J = 8 Hz, 2H), 7.31 (t, J = 7.2 Hz, 2H) 7.29-7.22 (m, 5H), 7.19-7.08 (m, 1H), 6.87 (t, J = 7.6 Hz, 1H), 6.74 (d, J = 7.6 Hz, 2H), 5.06-5.01 (m, 1H), 4.85 (t, J = 5.6 Hz, 1H), 3.66-3.63 (m, 2H), 2.14 (s, 3H) | 8 |
| 75 | 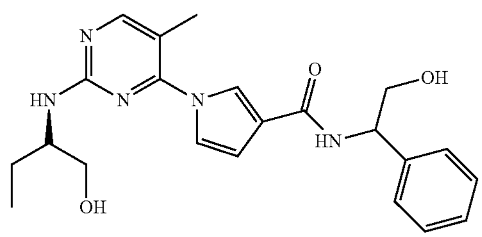 | N-(2-hydroxy-1-phenylethyl)-1-(2-(((S)-1-hydroxybutan-2-yl)amino)-5-methyl-pyrimidin-4-yl)-1H-pyrrole-3-carboxamide | 1HNMR (400 MHz, DMSO-d$_6$): δ 8.23 (s, 2H), 7.94 (s, 1H), 7.35 (d, J = 8.0 Hz, 3H), 7.29 (t, J = 7.2 Hz, 2H), 7.21 (d, J = 7.2 Hz, 1H), 6.77 (t, J = 8.4 Hz, 2H), 5.03 (d, J = 6.0 Hz, 1H), 4.90 (s, 1H), 4.56 (s, 1H), 3.81 (s, 1H), 3.64 (s, 2H), 3.32 (br s, 1H), 2.21 (s, 3H), 1.64 (br s, 2H), 1.45-1.41 (m, 1H), 0.85 (t, J = 6.8 Hz, 3H) | 3 |
| 76 | 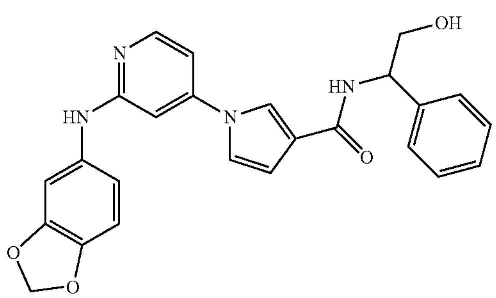 [SMILES: O=C(NC(CO)c1ccccc1)c1ccn(-c2ccnc(Nc3ccc4c(c3)OCO4)c2)c1] | 1-(2-(benzo[d][1,3]dioxol-5-ylamino)pyridin-4-yl)-N-(2-hydroxy-1-phenylethyl)-1H-pyrrole-3-carboxamide | 1HNMR (400 MHz, DMSO-d$_6$): δ 8.99 (s, 1H), 8.18-8.14 (m, 2H), 8.00 (s, 1H), 7.40 (s, 2H), 7.37-7.31 (m, 2H), 7.30-7.22 (m, 2H), 7.21-7.19 (m, 2H), 6.99-6.94 (m, 2H), 6.84-6.77 (m, 3H), 5.94 (s, 2H), 5.06-5.01 (m, 1H), 4.86 (s, 1H), 3.50 (d, J = 5.6 Hz, 2H) | 7 |

TABLE 1-continued

| Cmpd # | Structure | Name | NMR data | Scheme # |
|---|---|---|---|---|
| 77 | 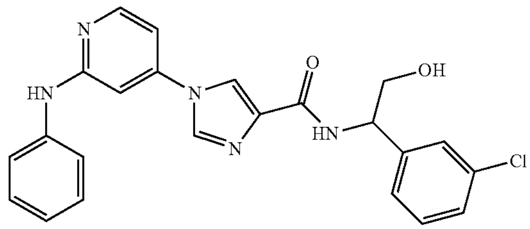 [SMILES: O=C(NC(CO)c1cccc(Cl)c1)c1cn(-c2ccnc(Nc3ccccc3)c2)cn1] | N-(1-(3-chloro-phenyl)-2-hydroxy-ethyl)-1-(2-(phenyl-amino)pyridin-4-yl)-1H-imidazole-4-carboxamide | 1HNMR (400 MHz, DMSO-d$_6$): δ 9.17 (s, 1H), 8.45 (s, 1H), 8.40 (d, J = 8.4 Hz, 1H), 8.24 (d, J = 7.6 Hz, 2H), 7.64 (d, J = 7.6 Hz, 2H), 7.42 (s, 1H), 7.32-7.28 (m, 2H), 7.27-7.25 (m, 3H), 7.15 (d, J = 5.6 Hz, 1H), 7.02 (s, 1H), 6.92 (t, J = 7.2 Hz, 1H), 5.04-4.99 (m, 2H), 3.73 (t, J = 5.6 Hz, 2H) | 7 |
| 78 | 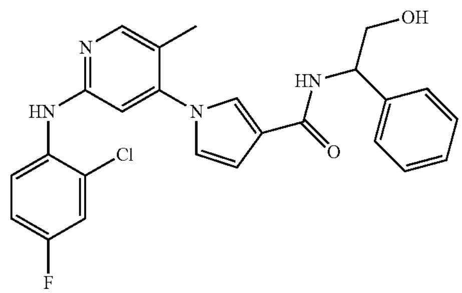 [SMILES: Cc1cnc(Nc2ccc(F)cc2Cl)cc1-n1ccc(C(=O)NC(CO)c2ccccc2)c1] | 1-(2-((2-chloro-4-fluorophenyl)amino)-5-methyl-pyridin-4-yl)-N-(2-hydroxy-1-phenylethyl)-1H-pyrrole-3-carboxamide | 1HNMR (400 MHz, DMSO-d$_6$): 8.45 (s, 1H), 8.12 (s, 1H), 8.10 (d, J = 6.4 Hz, 2H), 7.99-7.95 (m, 1H), 7.67 (s, 1H), 7.46-7.43 (m, 1H), 7.37 (d, J = 7.6 Hz, 2H), 7.33 (t, J = 7.6 Hz, 2H), 7.24-7.16 (m, 2H), 7.09 (s, 1H), 6.76 (s, 1H), 5.08-5.02 (m, 1H), 4.88 (t, J = 6.0 Hz, 1H), 3.66 (s, 2H), 2.16 (s, 3H) | 8 |
| 79 | 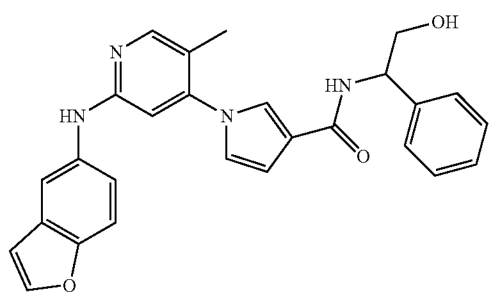 [SMILES: Cc1cnc(Nc2ccc3occc3c2)cc1-n1ccc(C(=O)NC(CO)c2ccccc2)c1] | 1-(2-(benzo-furan-5-ylamino)-5-methyl-pyridin-4-yl)-N-(2-hydroxy-1-phenylethyl)-1H-pyrrole-3-carboxamide | 1HNMR (400 MHz, DMSO-d$_6$): 9.02 (s, 1H), 8.14 (s, 1H), 8.10 (d, J = 8.0 Hz, 1H), 8.05 (s, 1H), 7.91 (d, J = 2 Hz, 1H), 7.67 (s, 1H), 7.48 (d, J = 9.2 Hz, 1H), 7.38 (d, J = 7.2 Hz, 3H), 7.33 (t, J = 7.6 Hz, 2H), 7.24-7.20 (m, 1H), 7.10 (s, 1H), 6.91 (s, 1H), 6.76 (s, 1H), 6.72 (s, 1H), 5.08-5.04 (m, 1H), 4.88 (t, J = 5.6 Hz, 1H), 3.66 (s, 2H), 2.16 (s, 3H) | 8 |
| 80 | 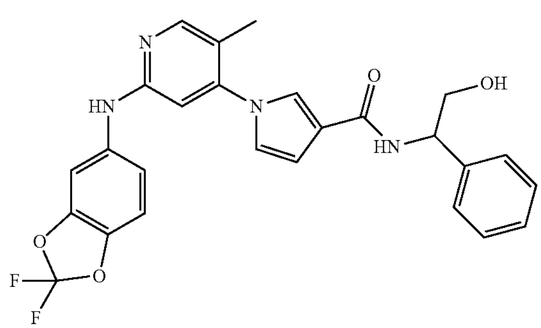 [SMILES: Cc1cnc(Nc2ccc3c(c2)OC(F)(F)O3)cc1-n1ccc(C(=O)NC(CO)c2ccccc2)c1] | 1-(2-((2,2-difluorobenzo[d][1,3]dioxol-5-yl)-amino)-5-methyl-pyridin-4-yl)-N-(2-hydroxy-1-phenyl-ethyl)-1H-pyrrole-3-carboxamide | 1HNMR (400 MHz, DMSO-d$_6$): δ 9.30 (s, 1H), 8.17 (s, 1H), 8.11 (d, J = 7.6 Hz, 1H), 7.95 (s, 1H), 7.68 (s, 1H), 7.37 (d, J = 7.6 Hz, 2H), 7.33-7.30 (m, 3H), 7.28-7.22 (m, 2H), 7.11 (s, 1H), 6.77 (s, 1H), 6.72 (s, 1H), 5.08-5.03 (m, 1H), 4.87 (t, J = 5.6 Hz, 1H), 3.66-3.65 (m, 2H), 2.17 (s, 3H) | 8 |

TABLE 1-continued

| Cmpd # | Structure | Name | NMR data | Scheme # |
|---|---|---|---|---|
| 81 | 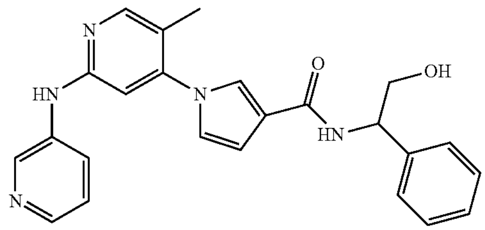 [SMILES: Cc1cnc(Nc2cccnc2)cc1-n1ccc(C(=O)NC(CO)c2ccccc2)c1] | N-(2-hydroxy-1-phenylethyl)-1-(5-methyl-2-(pyridin-3-ylamino)pyridin-4-yl)-1H-pyrrole-3-carboxamide | 1HNMR (400 MHz, DMSO-d$_6$): δ 9.29 (s, 1H), 8.77 (s, 1H), 8.19-8.10 (m, 4H), 7.69 (s, 1H), 7.38 (d, J = 7.2 Hz, 2H), 7.33-7.29 (m, 3H), 7.28-7.27 (m, 1H), 7.20 (s, 1H), 6.77 (s, 2H), 5.07-5.05 (m, 1H), 4.87 (s, 1H), 3.66 (s, 2H), 2.18 (s, 3H). | 8 |
| 82 | 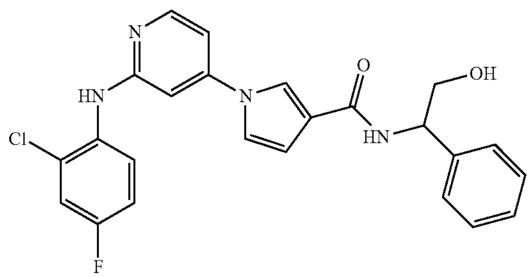 [SMILES: O=C(NC(CO)c1ccccc1)c1ccn(-c2ccnc(Nc3ccc(F)cc3Cl)c2)c1] | 1-(2-((2-chloro-4-fluorophenyl)amino)pyridin-4-yl)-N-(2-hydroxy-1-phenylethyl)-1H-pyrrole-3-carboxamide | 1HNMR (400 MHz, DMSO-d$_6$): δ 9.13 (d, J = 7.2 Hz, 1H), 8.29 (s, 1H), 8.23 (d, J = 7.2 Hz, 1H), 8.13 (d, J = 8.0 Hz, 1H), 7.86 (s, 1H), 7.79-7.77 (m, 1H), 7.76 (s, 1H), 7.48 (d, J = 7.6 Hz, 1H), 7.39-7.37 (m, 2H), 7.34-7.31 (m, 4H), 7.23 (t, J = 7.6 Hz, 1H), 6.82 (s, 1H), 5.07-5.03 (m, 1H), 4.89 (t, J = 5.6 Hz, 1H), 3.67 (t, J = 6.0 Hz, 2H). | 7 |
| 83 | 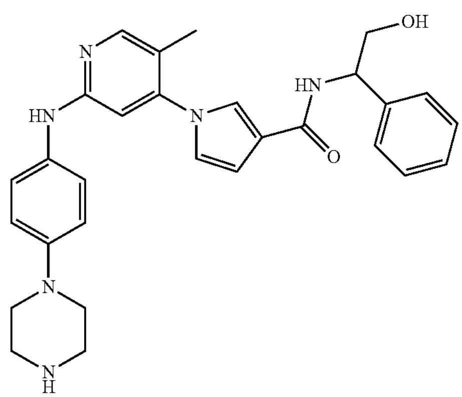 [SMILES: Cc1cnc(Nc2ccc(N3CCNCC3)cc2)cc1-n1ccc(C(=O)NC(CO)c2ccccc2)c1] | N-(2-hydroxy-1-phenylethyl)-1-(5-methyl-2-((4-(piperazin-1-yl)-phenyl)amino)-pyridin-4-yl)-1H-pyrrole-3-carboxamide | 1HNMR (400 MHz, DMSO-d$_6$): 8.76 (s, 1H), 8.09 (d, J = 14.0 Hz, 2H), 7.64 (s, 1H), 7.44 (d, J = 8.4 Hz, 2H), 7.37 (d, J = 7.6 Hz, 2H), 7.31 (t, J = 7.2 Hz, 2H), 7.24 (d, J = 6.8 Hz, 1H), 7.07 (s, 1H), 6.87 (d, J = 8.8 Hz, 2H), 6.75 (s, 1H), 6.24 (s, 1H), 5.06-5.04 (m, 1H), 4.87 (s, 1H), 3.65 (s, 2H), 2.99 (s, 4H), 2.89 (s, 4H), 2.13 (s, 3H) | 3a |
| 84 | 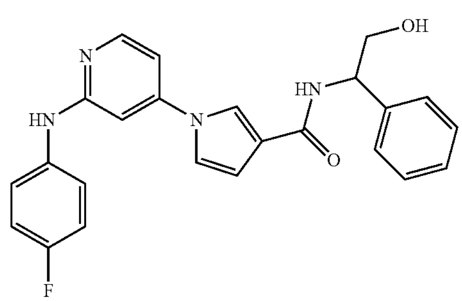 [SMILES: O=C(NC(CO)c1ccccc1)c1ccn(-c2ccnc(Nc3ccc(F)cc3)c2)c1] | 1-(2-((4-fluoro-phenyl)amino)pyridin-4-yl)-N-(2-hydroxy-1-phenyl-ethyl)-1H-pyrrole-3-carboxamide | 1HNMR (400 MHz, DMSO-d$_6$): δ 9.15 (s, 1H), 8.17 (d, J = 6.0 Hz, 2H), 8.01 (s, 1H), 7.67-7.64 (m, 2H), 7.42 (s, 1H), 7.36 (d, J = 7.6 Hz, 2H), 7.30 (t, J = 14.0 Hz, 3H), 7.21 (t, J = 7.6 Hz, 1H), 7.12 (t, J = 8.8 Hz, 1H), 7.02 (d, J = 4.0 Hz, 1H), 6.89 (s, 1H), 6.71 (s, 1H), 5.06-5.01 (m, 1H), 4.87-4.80 (m, 1H), 3.69-3.63 (m, 2H). | 7 |

TABLE 1-continued

| Cmpd # | Structure | Name | NMR data | Scheme # |
|---|---|---|---|---|
| 85 | 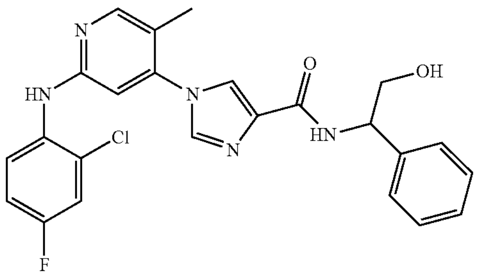 [SMILES: Cc1cnc(Nc2ccc(F)cc2Cl)cc1-n1cnc(C(=O)NC(CO)c2ccccc2)c1] | 1-(2-((2-chloro-4-fluorophenyl)amino)-5-methyl-pyridin-4-yl)-N-(2-hydroxy-1-phenylethyl)-1H-imidazole-4-carboxamide | 1HNMR (400 MHz, DMSO-d$_6$): δ 8.51 (s, 1H), 8.25 (d, J = 8.4 Hz, 1H), 8.08 (d, J = 11.6 Hz, 2H), 7.96 (s, 1H), 7.92-7.88 (m, 1H), 7.45-7.42 (m, 1H), 7.36 (d, J = 7.6 Hz, 2H), 7.30 (d, J = 7.6 Hz, 2H), 7.23-7.15 (m, 2H), 6.91 (s, 1H), 5.03-4.96 (m, 2H), 3.71 (d, J = 5.6 Hz, 2H), 2.09 (s, 3H) | 11 |
| 86 | 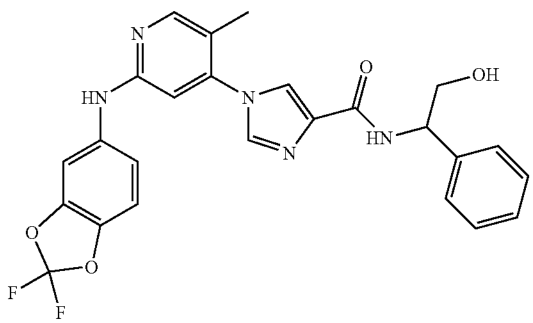 [SMILES: Cc1cnc(Nc2ccc3c(c2)OC(F)(F)O3)cc1-n1cnc(C(=O)NC(CO)c2ccccc2)c1] | 1-(2-((2,2-difluoro-benzo[d][1,3]dioxol-5-yl)-amino)-5-methyl-pyridin-4-yl)-N-(2-hydroxy-1-phenyl-ethyl)-1H-imidazole-4-carboxamide | 1HNMR (400 MHz, DMSO-d$_6$): δ 9.36 (s, 1H), 8.25 (d, J = 8.4 Hz, 1H), 8.19 (s, 1H), 8.09 (s, 1H), 7.99 (s, 1H), 7.91 (d, J = 1.6 Hz, 1H), 7.37-7.32 (m, 2H), 7.29-7.27 (m, 3H), 7.23-7.21 (m, 2H), 6.75 (s, 1H), 5.01-4.96 (m, 2H), 3.71 (d, J = 4.8 Hz, 2H), 2.10 (s, 3H) | 11 |
| 87 | 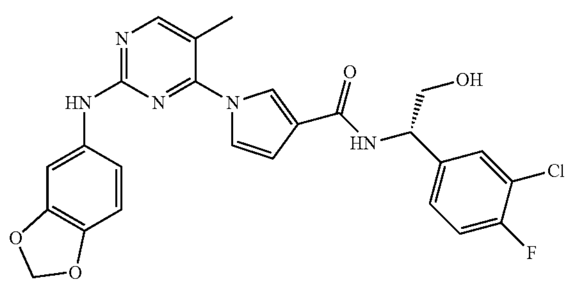 [SMILES: Cc1cnc(Nc2ccc3c(c2)OCO3)nc1-n1ccc(C(=O)N[C@H](CO)c2ccc(F)c(Cl)c2)c1] | (S)-1-(2-(benzo[d][1,3]dioxol-5-ylamino)-5-methyl-pyrimidin-4-yl)-N-(1-(3-chloro-4-fluorophenyl)-2-hydroxy-ethyl)-1H-pyrrole-3-carboxamide | 1HNMR (400 MHz, DMSO-d$_6$): δ 9.54 (s, 1H), 8.43 (s, 1H), 8.25 (d, J = 8 Hz, 1H), 8.00 (s, 1H), 7.56 (d, J = 7.2 Hz, 1H), 7.42-7.34 (m, 4H), 7.20 (d, J = 8.4 Hz, 1H), 6.82 (d, J = 8.4 Hz, 1H), 6.77 (s, 1H), 5.94 (s, 2H), 5.03 (d, J = 6.4 Hz, 1H), 4.93 (s, 1H), 3.65 (d, J = 6.0 Hz, 2H), 2.29 (s, 3H) | 3 |
| 88 | 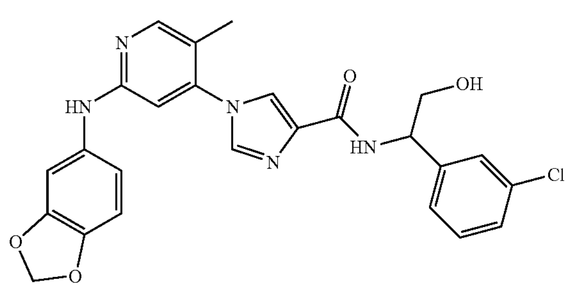 [SMILES: Cc1cnc(Nc2ccc3c(c2)OCO3)cc1-n1cnc(C(=O)NC(CO)c2cccc(Cl)c2)c1] | 1-(2-(benzo[d][1,3]dioxol-5-ylamino)-5-methyl-pyridin-4-yl)-N-(1-(3-chloro-phenyl)-2-hydroxy-ethyl)-1H-imidazole-4-carboxamide | 1HNMR (400 MHz, DMSO-d$_6$): δ 8.97 (s, 1H), 8.36 (d, J = 8.4 Hz, 1H), 8.13 (s, 1H), 8.08 (s, 1H), 7.98 (s, 1H), 7.44 (s, 1H), 7.34-7.28 (m, 4H), 6.93 (d, J = 8.4 Hz, 1H), 6.81 (d, J = 8.4 Hz, 1H), 6.67 (s, 1H), 5.93 (s, 2H), 5.03-5.01 (m, 2H), 3.72 (t, J = 5.6 Hz, 2H), 2.07 (s, 3H) | 11 |

TABLE 1-continued

| Cmpd # | Structure | Name | NMR data | Scheme # |
|---|---|---|---|---|
| 89 | 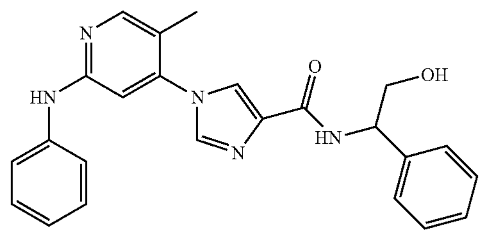 [SMILES: Cc1cnc(Nc2ccccc2)cc1-n1cnc(C(=O)NC(CO)c2ccccc2)c1] | N-(2-hydroxy-1-phenylethyl)-1-(5-methyl-2-(phenylamino)pyridin-4-yl)-1H-imidazole-4-carboxamide | 1HNMR (400 MHz, DMSO-d$_6$): δ 9.12 (s, 1H), 8.25 (d, J = 8.4 Hz, 1H), 8.17 (s, 1H), 8.08 (s, 1H), 7.98 (s, 1H), 7.61 (d, J = 8.4 Hz, 2H), 7.36 (d, J = 7.2 Hz, 2H), 7.30-7.27 (m, 2H), 7.25-7.20 (m, 4H), 6.88 (t, J = 7.2 Hz, 1H), 6.77 (s, 1H), 5.02-4.96 (m, 2H), 3.71 (d, J = 5.6 Hz, 2H), 2.09 (s, 3H). | 11 |
| 90 | 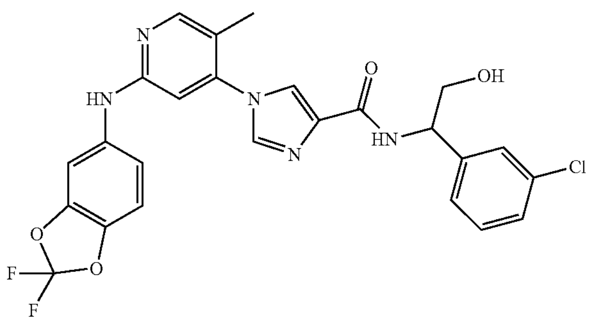 [SMILES: Cc1cnc(Nc2ccc3c(c2)OC(F)(F)O3)cc1-n1cnc(C(=O)NC(CO)c2cccc(Cl)c2)c1] | N-(1-(3-chlorophenyl)-2-hydroxy-ethyl)-1-(2-((2,2-difluoro-benzo[d][1,3]dioxol-5-yl)amino)-5-methyl-pyridin-4-yl)-1H-imidazole-4-carboxamide | 1HNMR (400 MHz, DMSO-d$_6$): δ 9.36 (s, 1H), 8.38 (d, J = 8.0 Hz, 1H), 8.19 (s, 1H), 8.10 (s, 1H), 8.00 (s, 1H), 7.91 (s, 1H), 7.44 (s, 1H), 7.34 (d J = 4.8 Hz, 2H), 7.28 (d, J = 8.8 Hz, 2H), 7.22 (d, J = 8.4 Hz, 1H), 6.76 (s, 1H), 5.04-4.99 (m, 2H), 3.72 (t, J = 5.6 Hz, 2H), 2.10 (s, 3H) | 11 |
| 91 | 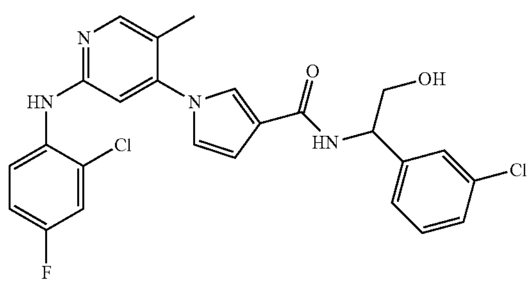 [SMILES: Cc1cnc(Nc2ccc(F)cc2Cl)cc1-n1ccc(C(=O)NC(CO)c2cccc(Cl)c2)c1] | 1-(2-((2-chloro-4-fluorophenyl)amino)-5-methyl-pyridin-4-yl)-N-(1-(3-chlorophenyl)-2-hydroxy-ethyl)-1H-pyrrole-3-carboxamide | 1HNMR (400 MHz, DMSO-d$_6$): δ 8.44 (s, 1H), 8.14 (d, J = 8.0 Hz, 1H), 8.07 (s, 1H), 7.95-7.93 (m, 1H), 7.65 (s, 1H), 7.43 (t, J = 2.8 Hz, 2H), 7.32-7.26 (m, 3H), 7.20-7.15 (m, 1H), 7.09 (s, 1H), 6.88 (s, 1H), 6.74 (s, 1H), 5.04-5.02 (m, 1H), 4.92 (t, J = 5.6 Hz, 1H), 3.65-3.62 (m, 2H), 2.14 (s, 3H) | 3a |
| 92 | 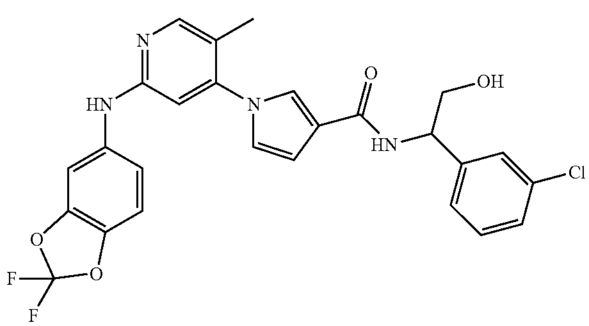 [SMILES: Cc1cnc(Nc2ccc3c(c2)OC(F)(F)O3)cc1-n1ccc(C(=O)NC(CO)c2cccc(Cl)c2)c1] | N-(1-(3-chlorophenyl)-2-hydroxy-ethyl)-1-(2-((2,2-difluoro-benzo[d][1,3]dioxol-5-yl)amino)-5-methyl-pyridin-4-yl)-1H-pyrrole-3-carboxamide | 1HNMR (400 MHz, DMSO-d$_6$): δ 9.29 (s, 1H), 8.15 (d, J = 8 Hz, 2H), 7.93 (d, J = 2 Hz, 1H), 7.67 (s, 1H), 7.42 (s, 1H), 7.35 (d, J = 7.6 Hz, 2H), 7.28-7.26 (m, 2H), 7.22-7.20 (m, 1H), 7.10 (s, 1H), 6.75 (s, 1H), 6.71 (s, 1H), 5.04-5.00 (m, 1H), 4.92 (t, J = 5.6 Hz, 1H), 3.67-3.63 (m, 2H), 2.15 (s, 3H) | 3a |

TABLE 1-continued

| Cmpd # | Structure | Name | NMR data | Scheme # |
|---|---|---|---|---|
| 93 | 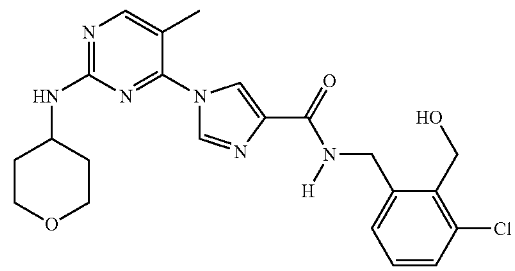 [SMILES: Cc1cnc(NC2CCOCC2)nc1-n1cnc(C(=O)NCc2cccc(Cl)c2CO)c1] | N-(3-chloro-2-(hydroxy-methyl)benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.62 (t, J = 6 Hz, 1H), 8.33 (s, 1H), 8.25 (s, 1H), 8.10 (s, 1H), 7.36-7.23 (m, 4H), 5.24 (t, J = 5.0 Hz, 1H), 4.76 (d, J = 5.2 Hz, 2H), 4.61 (d, J = 6 Hz, 2H), 3.9 (br s, 1H), 3.83 (d, J = 11.2 Hz, 2H), 3.36 (t, J = 11.0 Hz, 2H), 2.17 (s, 3H), 1.80 (d, J = 11.6 Hz, 2H), 1.52-1.43 (m, 2H) | 4, 3 |
| 94 | 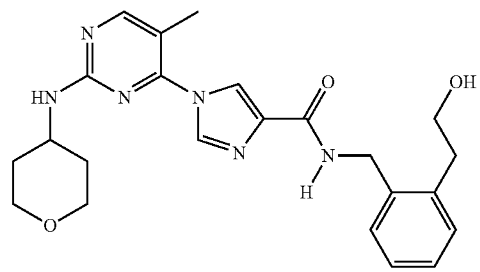 [SMILES: Cc1cnc(NC2CCOCC2)nc1-n1cnc(C(=O)NCc2ccccc2CCO)c1] | N-(2-(2-hydroxy-ethyl)benzyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.46 (t, J = 6 Hz, 1H), 8.33 (s, 1H), 8.24 (s, 1H), 8.09 (s, 1H), 7.35 (d, J = 12 Hz, 1H), 7.25 (d, J = 5.2 Hz, 1H), 7.16-7.13 (m, 3H), 4.67 (t, J = 5.2 Hz, 1H), 4.48 (d, J = 6 Hz, 2H), 3.89 (br s, 1H), 3.83 (d, J = 11.2 Hz, 2H), 3.62-3.57 (m, 2H), 3.39-3.32 (m, 2H), 2.82 (t, J = 6.8 Hz, 2H), 2.17 (s, 3H), 1.80 (d, J = 11.2 Hz, 2H), 1.52-1.44 (m, 2H) | 4, 3 |
| 95 | 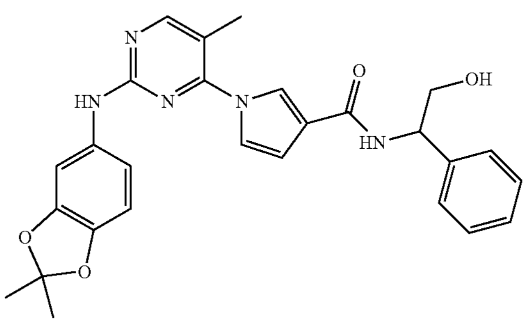 [SMILES: Cc1cnc(Nc2ccc3c(c2)OC(C)(C)O3)nc1-n1ccc(C(=O)NC(CO)c2ccccc2)c1] | 1-(2-((2,2-dimethyl-benzo[d][1,3]dioxol-5-yl)-amino)-5-methyl-pyrimidin-4-yl)-N-(2-hydroxy-1-phenylethyl)-1H-pyrrole-3-carboxamide | 1HNMR (400 MHz, DMSO-d$_6$): δ 9.46 (s, 1H), 8.41 (s, 1H), 8.23 (d, J = 8 Hz, 1H), 7.99 (s, 1H), 7.41-740 (m, 1H), 7.37-7.35 (m, 2H), 7.31-7.28 (m, 3H), 7.22-7.21 (m, 1H), 7.19-7.05 (m, 1H), 7.03-6.78 (m, 1H), 6.72-6.70 (m, 1H), 5.05-5.03 (m, 1H), 4.85 (t, J = 5.6 Hz, 1H), 3.66 (d, J = 9.6 Hz, 2H), 2.28 (s, 3H), 1.6 (s, 6H) | 3 |
| 96 | 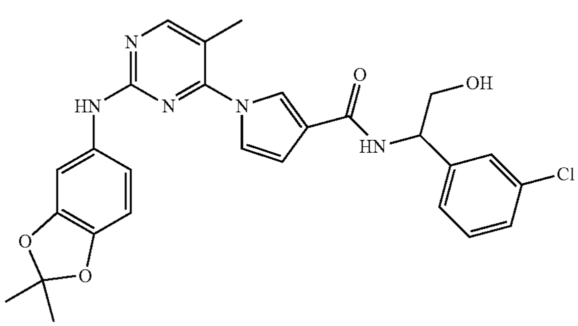 [SMILES: Cc1cnc(Nc2ccc3c(c2)OC(C)(C)O3)nc1-n1ccc(C(=O)NC(CO)c2cccc(Cl)c2)c1] | N-(1-(3-chloro-phenyl)-2-hydroxy-ethyl)-1-(2-((2,2-dimethyl-benzo[d][1,3]dioxol-5-yl)amino)-5-methyl-pyrimidin-4-yl)-1H-pyrrole-3-carboxamide | 1HNMR (400 MHz, DMSO-d$_6$): δ 8.28 (s, 1H), 7.91 (s, 1H), 7.37 (s, 2H), 7.33-7.29 (m, 3H), 7.28-7.17 (m, 1H), 6.99 (s, 1H), 6.93-6.83 (m, 1H), 6.81-6.8 (m, 1H), 6.69-6.67 (m, 1H), 6.62-6.56 (m, 1H), 5.25-5.23 (m, 1H), 4.0 (t, J = 5.2 Hz, 2H), 2.49 (d, J = 5.2 Hz, 1H), 2.35 (s, 3H), 1.67 (s, 6H) | 3 |

| Cmpd # | Structure | Name | NMR data | Scheme # |
|---|---|---|---|---|
| 97 | 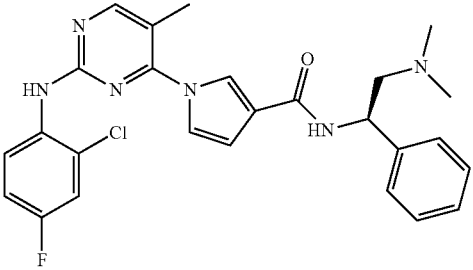 [SMILES: Cc1cnc(Nc2ccc(F)cc2Cl)nc1-n1ccc(C(=O)N[C@@H](CN(C)C)c2ccccc2)c1] | (R)-1-(2-((2-chloro-4-fluorophenyl)amino)-5-methyl-pyrimidin-4-yl)-N-(2-(dimethyl-amino)-1-phenylethyl)-1H-pyrrole-3-carboxamide | 1HNMR (400 MHz, DMSO-d$_6$): δ 8.99 (s, 1H), 8.37 (s, 1H), 8.21 (d, J = 8.0 Hz, 1H), 7.92 (s, 1H), 7.67 (t, J = 7.2 Hz, 1H), 7.48 (d, J = 6.0 Hz, 1H), 7.38-7.32 (m, 3H), 7.30 (t, J = 7.2 Hz, 2H), 7.24-7.16 (m, 2H), 6.74 (s, 1H), 5.10 (br s, 1H), 2.71-2.60 (m, 2H), 2.28 (s, 3H), 2.19 (s, 6H) | 3 |
| 98 | 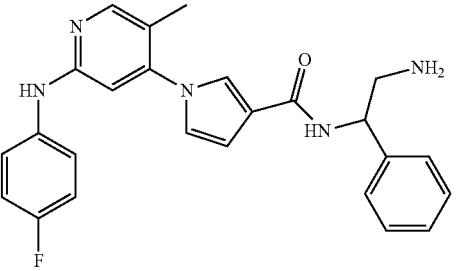 [SMILES: Cc1cnc(Nc2ccc(F)cc2)cc1-n1ccc(C(=O)NC(CN)c2ccccc2)c1] | N-(2-amino-1-phenylethyl)-1-(2-((4-fluorophenyl)amino)-5-methyl-pyridin-4-yl)-1H-pyrrole-3-carboxamide | 1HNMR (400 MHz, DMSO-d$_6$): δ 9.18 (s, 1H), 8.34 (d, J = 8.4 Hz, 1H), 8.11 (s, 1H), 7.74 (s, 1H), 7.66-7.63 (m, 2H), 7.37-7.29 (m, 2H), 7.22 (t, J = 6.8 Hz, 1H), 7.08 (t, J = 8.8 Hz, 3H), 6.77 (s, 1H), 6.72 (s, 1H), 5.60 (br s, 2H), 5.02 (t, J = 5.6 Hz, 1H), 3.02-2.89 (m, 2H), 2.14 (s, 3H) | 9 |
| 99 | 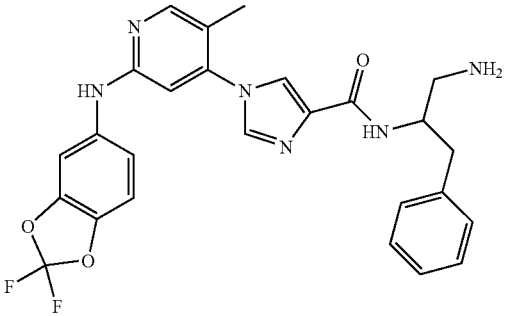 | N-(1-amino-3-phenyl-propan-2-yl)-1-(2-((2,2-difluoro-benzo[d][1,3]dioxol-5-yl)amino)-5-methyl-pyridin-4-yl)-1H-imidazole-4-carboxamide | 1HNMR (400 MHz, DMSO-d$_6$): δ 9.36 (s, 1H), 8.19 (s, 1H), 8.04 (s, 1H), 7.90 (t, J = 1.6 Hz, 3 H), 7.29-7.20 (m, 6H), 7.15 (s, 1H), 6.74 (s, 1H), 4.12 (s, 1H), 2.85 (d, J = 5.6 Hz, 2H), 2.65 (br s, 2H), 2.09 (s, 3H) | 9 |
| 100 | 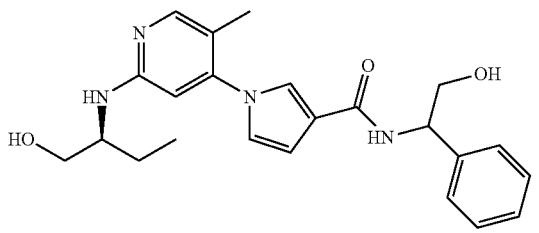 [SMILES: CC[C@@H](CO)Nc1cc(-n2ccc(C(=O)NC(CO)c3ccccc3)c2)c(C)cn1] | N-(2-hydroxy-1-phenyl-ethyl)-1-(2-(((S)-1-hydroxy-butan-2-yl)amino)-5-methyl-pyridin-4-yl)-1H-pyrrole-3-carboxamide | 1HNMR (400 MHz, DMSO-d$_6$): δ 8.06 (d, J = 8 Hz, 1H), 7.89 (s, 1H), 7.57 (s, 1H), 7.36-7.34 (m, 2H), 7.31-7.29 (m, 2H), 7.22-7.20 (m, 1H), 6.99 (s, 1H), 6.70 (s, 1H), 6.40 (s, 1H), 6.23 (d, J = 7.6 Hz, 1H), 5.03-5.02 (m, 1H), 4.84 (s, 1H), 4.58 (s, 1H), 3.76 (s, 1H), 3.46 (s, 2H), 3.44 (m, 1H), 2.02 (s, 3H), 1.66-1.65 (m, 1H), 1.42-1.38 (m, 1H), 0.81 (t, J = 12.8 Hz, 3H) | 8 |

TABLE 1-continued

| Cmpd # | Structure | Name | NMR data | Scheme # |
|---|---|---|---|---|
| 101 | 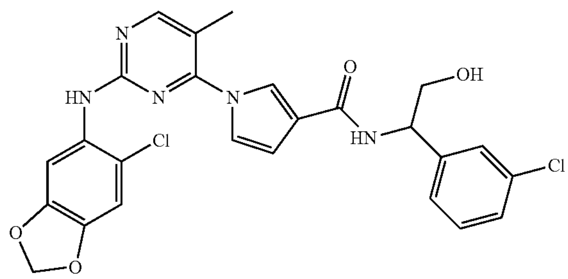 [SMILES: Cc1cnc(Nc2cc3c(cc2Cl)OCO3)nc1-n1ccc(C(=O)NC(CO)c2cccc(Cl)c2)c1] | 1-(2-((6-chloro-benzo[d][1,3]dioxol-5-yl)amino)-5-methyl-pyrimidin-4-yl)-N-(1-(3-chlorophenyl)-2-hydroxy-ethyl)-1H-pyrrole-3-carboxamide | 1HNMR (400 MHz, DMSO-d$_6$): δ 8.80 (s, 1H), 8.35 (s, 1H), 8.26 (d, J = 8 Hz, 1H), 7.94 (s, 1H), 7.41 (s, 1H), 7.37 (s, 1H), 7.33-7.30 (m, 3H), 7.21 (s, 2H), 7.10 (s, 1H), 6.75 (s, 1H), 6.06 (s, 2H), 5.05-5.01 (m, 1H), 4.92-4.91 (m, 1H), 3.67-3.63 (m, 2H), 2.27 (s, 3H) | 3 |
| 103 | 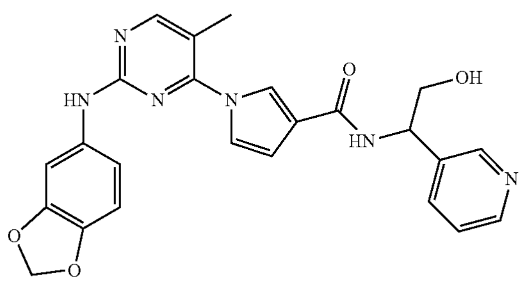 [SMILES: Cc1cnc(Nc2ccc3c(c2)OCO3)nc1-n1ccc(C(=O)NC(CO)c2cccnc2)c1] | 1-(2-(benzo[d][1,3]dioxol-5-ylamino)-5-methyl-pyrimidin-4-yl)-N-(2-hydroxy-1-(pyridin-3-yl)ethyl)-1H-pyrrole-3-carboxamide | 1HNMR (400 MHz, DMSO-d$_6$): δ 8.80 (s, 1H), 8.35 (s, 1H), 8.26 (d, J = 8 Hz, 1H), 7.94 (s, 1H), 7.41 (s, 1H), 7.37 (t, J = 2.0 Hz, 1H), 7.33-7.27 (m, 3H), 7.21 (s, 1H), 7.10 (s, 1H), 6.75 (d, J = 1.2 Hz, 1H), 6.05 (s, 2H), 5.05-4.99 (m, 1H), 4.92 (t, J = 5.6 Hz, 1H), 3.67-3.61 (m, 2H), 2.27 (s, 3H) | 3 |
| 104 | 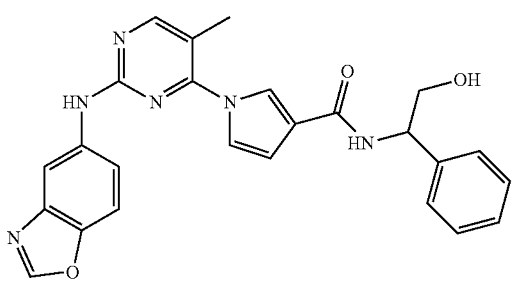 | 1-(2-(benzo[d]oxazol-5-ylamino)-5-methyl-pyrimidin-4-yl)-N-(2-hydroxy-1-phenylethyl)-1H-pyrrole-3-carboxamide | 1HNMR (400 MHz, DMSO-d$_6$): δ 11.10 (s, 1H), 9.43 (s, 1H), 8.61 (s, 1H), 8.27 (s, 1H), 8.25 (s, 1H), 8.04 (s, 1H), 7.64 (s, 1H), 7.59 (s, 1H), 7.45 (d, J = 7.2 Hz, 2H), 7.32 (d, J = 8 Hz, 1H), 7.26 (s, 1H), 6.73 (s, 1H), 6.49 (s, 1H), 5.45 (s, 1H), 4.64-4.57 (m, 1H), 4.56-4.52 (m, 1H), 1.99 (d, J = 12.0 Hz, 2H), 1.89 (s, 3H) | 3 |
| 105 | 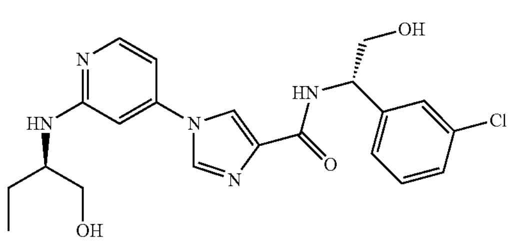 [SMILES: CC[C@H](CO)Nc1cc(-n2cnc(C(=O)N[C@H](CO)c3cccc(Cl)c3)c2)ccn1] | N-((S)-1-(3-chlorophenyl)-2-hydroxy-ethyl)-1-(2-(((R)-1-hydroxy-butan-2-yl)amino)pyridin-4-yl)-1H-imidazole-4-carboxamide | 1HNMR (400 MHz, DMSO-d$_6$): δ 8.38 (t, J = 7.2 Hz, 2H), 8.18 (s, 1H), 8.01 (d, J = 5.6 Hz, 1H), 7.42 (s, 1H), 7.32-7.26 (m, 3H), 6.84 (d, J = 5.6 Hz, 1H), 6.74 (s, 1H), 6.36 (d, J = 7.6 Hz, 1H), 5.02-4.99 (m, 2H), 4.61 (d, J = 5.6 Hz, 1H), 3.81 (s, 1H), 3.71 (t, J = 5.6 Hz, 1H), 3.47-3.44 (m, 1H), 3.34-3.27 (m, 1H), 1.67-1.65 (m, 1H), 1.63-1.61 (m, 1H), 1.07 (t, J = 7.2 Hz, 1H), 0.87 (t, J = 6.8 Hz, 3H) | 13 |

| Cmpd # | Structure | Name | NMR data | Scheme # |
|---|---|---|---|---|
| 106 | 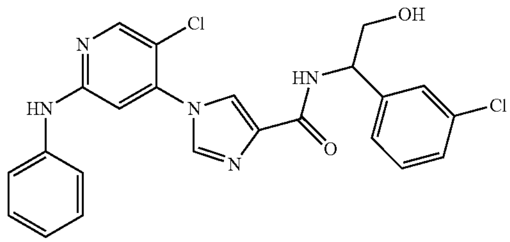 [SMILES: O=C(NC(CO)c1cccc(Cl)c1)c1cn(-c2cc(Nc3ccccc3)ncc2Cl)cn1] | 1-(5-chloro-2-(phenyl-amino)pyridin-4-yl)-N-(1-(3-chlorophenyl)-2-hydroxy-ethyl)-1H-imidazole-4-carboxamide | 1HNMR (400 MHz, DMSO-$d_6$): δ 9.44 (s, 1H), 8.41 (s, 1H), 8.38 (d, J = 4.0 Hz, 1H), 8.16 (s, 1H), 8.02 (s, 1H), 7.61 (d, J = 7.6 Hz, 2H), 7.44 (s, 1H), 7.33-7.30 (m, 2H), 7.29-7.27 (m, 3H), 6.93 (s, 2H), 5.02-5.01 (m, 2H), 3.72 (t, J = 5.6 Hz, 2H) | 10 |
| 107 | 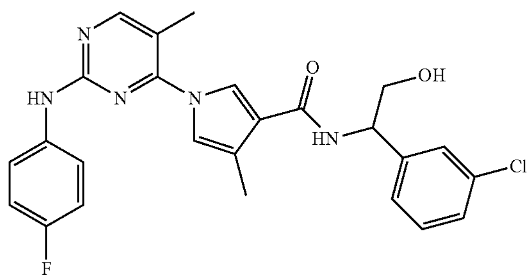 [SMILES: Cc1cn(-c2nc(Nc3ccc(F)cc3)ncc2C)cc1C(=O)NC(CO)c1cccc(Cl)c1] | N-(1-(3-chlorophenyl)-2-hydroxy-ethyl)-1-(2-((4-fluoro-phenyl)amino)-5-methyl-pyrimidin-4-yl)-4-methyl-1H-pyrrole-3-carboxamide | 1HNMR (400 MHz, DMSO-$d_6$): δ 9.67 (s, 1H), 8.43 (s, 1H), 8.14 (d, J = 7.6 Hz, 1H), 8.10 (s, 1H), 7.75-7.72 (m, 2H), 7.43 (s, 1H), 7.33 (d, J = 6.0 Hz, 2H), 7.29 (s, 1H), 7.25 (s, 1H), 7.11 (t, J = 8.8 Hz, 2H), 5.01-4.93 (m, 1H), 4.92 (t, J = 5.2 Hz, 1H), 3.64 (s, 2H), 2.33 (s, 3H), 2.19 (s, 3H) | 3 |
| 108 | 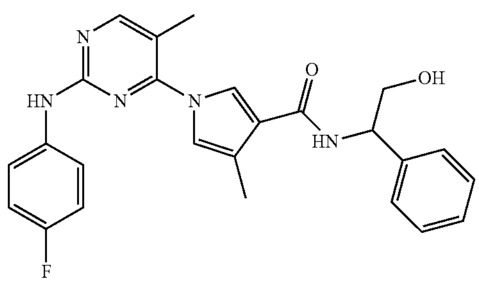 [SMILES: Cc1cn(-c2nc(Nc3ccc(F)cc3)ncc2C)cc1C(=O)NC(CO)c1ccccc1] | 1-(2-((4-fluoro-phenyl)amino)-5-methyl-pyrimidin-4-yl)-N-(2-hydroxy-1-phenylethyl)-4-methyl-1H-pyrrole-3-carboxamide | 1HNMR (400 MHz, DMSO-$d_6$): δ 9.66 (s, 1H), 8.43 (s, 1H), 8.14 (d, J = 8 Hz, 1H), 8.12 (d, J = 8.4 Hz, 1H), 7.73-7.71 (m, 2H), 7.43 (s, 2H), 7.36-7.73 (m, 2H), 7.30-7.27 (m, 1H), 7.25-7.21 (m, 1H), 7.11 (t, J = 8.8 Hz, 2H), 5.03-4.98 (m, 1H), 4.91 (t, J = 5.6 Hz, 1H), 3.66-3.63 (m, 2H), 2.33 (s, 3H), 2.19 (s, 3H). | 3 |
| 109 | 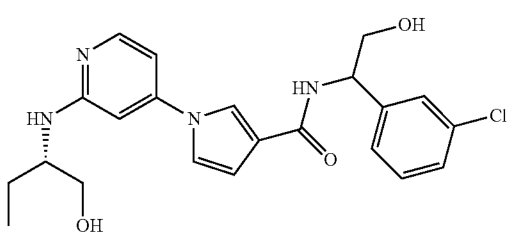 [SMILES: CC[C@@H](CO)Nc1cc(-n2ccc(C(=O)NC(CO)c3cccc(Cl)c3)c2)ccn1] | N-(1-(3-chloro-phenyl)-2-hydroxy-ethyl)-1-(2-(((S)-1-hydroxy-butan-2-yl)amino)pyridin-4-yl)-1H-pyrrole-3-carboxamide | 1HNMR (400 MHz, DMSO-$d_6$): δ 8.18 (d, J = 8.4 Hz, 1H), 7.97 (d, J = 6 Hz, 2H), 7.41 (s, 1H), 7.36 (s, 1H), 7.32 (t, J = 7.6 Hz, 2H), 7.28 (t, J = 2 Hz, 1H), 6.74-6.72 (m, 2H), 6.65 (s, 1H), 6.32 (d, J = 7.6 Hz, 1H), 5.05-5.01 (m, 1H), 4.92 (t, J = 5.2 Hz, 1H), 4.61 (s, 1H), 3.82 (d, J = 4.4 Hz, 1H), 3.65-3.63 (m, 2H), 3.48-3.43 (m, 1H), 3.37-3.27 (m, 1H), 1.69-1.65 (m, 1H), 1.47-1.41 (m, 1H), 0.87 (t, J = 7.6 Hz, 3H). | 13 |

TABLE 1-continued

| Cmpd # | Structure | Name | NMR data | Scheme # |
|---|---|---|---|---|
| 110 | 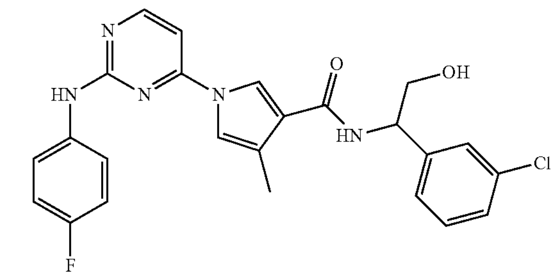 [SMILES: Cc1cn(-c2ccnc(Nc3ccc(F)cc3)n2)cc1C(=O)NC(CO)c1cccc(Cl)c1] | N-(1-(3-chloro-phenyl)-2-hydroxy-ethyl)-1-(2-((4-fluoro-phenyl)-amino)pyrimidin-4-yl)-4-methyl-1H-pyrrole-3-carboxamide | 1HNMR (400 MHz, DMSO-d$_6$): δ 9.75 (s, 1H), 8.49 (d, J = 5.6 Hz, 1H), 8.29 (s, 1H), 8.22 (d, J = 8 Hz, 1H), 7.75 (t, J = 8.8 Hz, 2H), 7.46 (d, J = 14 Hz, 2H), 7.33 (s, 2H), 7.29 (s, 1H), 7.15 (t, J = 8.8 Hz, 2H), 7.06 (d, J = 5.6 Hz, 1H), 5.00 (d, J = 6.4 Hz, 1H), 4.92 (t, J = 6 Hz, 1H), 3.64 (s, 2H), 2.18 (s, 3H). | 3 |
| 111 | 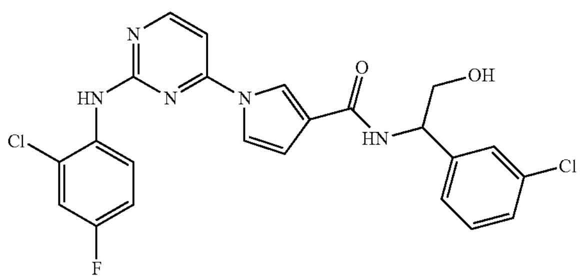 [SMILES: O=C(NC(CO)c1cccc(Cl)c1)c1ccn(-c2ccnc(Nc3ccc(F)cc3Cl)n2)c1] | 1-(2-((2-chloro-4-fluorophenyl)amino)pyrimidin-4-yl)-N-(1-(3-chlorophenyl)-2-hydroxy-ethyl)-1H-pyrrole-3-carboxamide | 1HNMR (400 MHz, DMSO-d$_6$): δ 9.12 (s, 1H), 8.42 (d, J = 5.2 Hz, 1H), 8.29 (d, J = 8 Hz, 1H), 8.19 (s, 1H), 7.68 (t, J = 8.4 Hz, 1H), 7.61 (s, 1H), 7.50 (d, J = 8.4 Hz, 1H), 7.41 (s, 1H), 7.32-7.24 (m, 4H), 7.14 (d, J = 5.2 Hz, 1H), 6.78 (s, 1H), 5.01 (d, J = 7.2 Hz, 1H), 4.92 (s, 1H), 3.65 (s, 2H). | 3 |
| 112 | 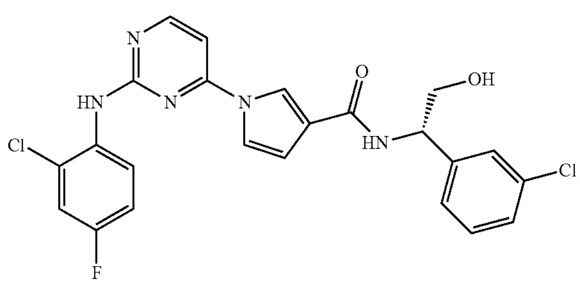 [SMILES: O=C(N[C@H](CO)c1cccc(Cl)c1)c1ccn(-c2ccnc(Nc3ccc(F)cc3Cl)n2)c1] | (S)-1-(2-((2-chloro-4-fluorophenyl)amino)pyrimidin-4-yl)-N-(1-(3-chlorophenyl)-2-hydroxy-ethyl)-1H-pyrrole-3-carboxamide | 1HNMR (400 MHz, DMSO-d$_6$): δ 9.12 (s, 1H), 8.43 (d, J = 5.2 Hz, 1H), 8.29 (d, J = 8 Hz, 1H), 8.19 (s, 1H), 7.68 (t, J = 8.4 Hz, 1H), 7.61 (s, 1H), 7.49 (d, J = 8.4 Hz, 1H), 7.41 (s, 1H), 7.32-7.24 (m, 4H), 7.14 (d, J = 5.2 Hz, 1H), 6.78 (s, 1H), 5.01 (d, J = 7.2 Hz, 1H), 4.92 (s, 1H), 3.65 (s, 2H). | 3 |
| 113 | 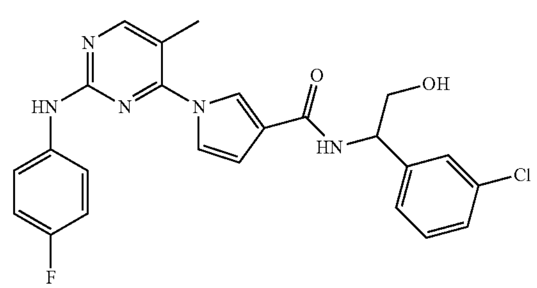 [SMILES: Cc1cnc(Nc2ccc(F)cc2)nc1-n1ccc(C(=O)NC(CO)c2cccc(Cl)c2)c1] | N-(1-(3-chloro-phenyl)-2-hydroxy-ethyl)-1-(2-((4-fluoro-phenyl)amino)-5-methyl-pyrimidin-4-yl)-1H-pyrrole-3-carboxamide | 1HNMR (400 MHz, DMSO-d$_6$): δ 9.69 (s, 1H), 8.46 (s, 1H), 8.28 (d, J = 8 Hz, 1H), 8.03 (s, 1H), 7.73-7.70 (m, 2H), 7.43 (s, 2H), 7.34 (d, J = 5.6 Hz, 2H), 7.27 (s, 1H), 7.11 (t, J = 8.8 Hz, 2H), 6.78 (s, 1H), 5.07-5.01 (m, 1H), 4.93 (t, J = 5.6 Hz, 1H), 3.68-3.62 (m, 2H), 2.31 (s, 3H). | 3 |

TABLE 1-continued

| Cmpd # | Structure | Name | NMR data | Scheme # |
|---|---|---|---|---|
| 114 | 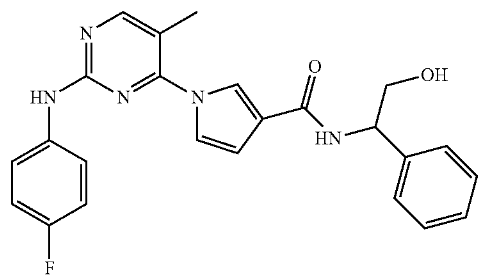 [SMILES: Cc1cnc(Nc2ccc(F)cc2)nc1-n1ccc(C(=O)NC(CO)c2ccccc2)c1] | 1-(2-((4-fluoro-phenyl)amino)-5-methyl-pyrimidin-4-yl)-N-(2-hydroxy-1-phenylethyl)-1H-pyrrole-3-carboxamide | 1HNMR (400 MHz, DMSO-d$_6$): δ 9.69 (s, 1H), 8.46 (s, 1H), 8.24 (d, J = 8.8 Hz, 1H), 8.02 (s, 1H), 7.73-7.70 (m, 2H), 7.44 (s, 1H), 7.37 (d, J = 7.6 Hz, 2H), 7.35-7.28 (m, 2H), 7.20 (d, J = 7.2 Hz, 1H), 7.11 (d, J = 8.8 Hz, 2H), 6.79 (s, 1H), 5.05 (d, J = 6.4 Hz, 1H), 4.87 (s, 1H), 3.65 (m, 2H), 2.31 (s, 3H). | 3 |
| 115 | 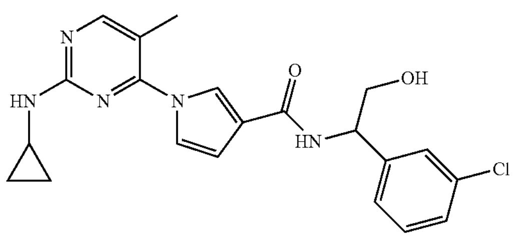 | N-(1-(3-chloro-phenyl)-2-hydroxy-ethyl)-1-(2-(cyclopropyl-amino)-5-methyl-pyrimidin-4-yl)-1H-pyrrole-3-carboxamide | 1HNMR (400 MHz, DMSO-d$_6$): δ 8.28 (s, 1H), 8.24 (d, J = 11.2 Hz, 1H), 7.96 (s, 1H), 7.41 (d, J = 6.4 Hz, 3H), 7.28-7.26 (m, 3H), 6.74 (s, 1H), 5.05-5.00 (m, 1H), 4.92 (s, 1H), 3.65 (t, J = 5.6 Hz, 2H), 2.23 (s, 3H), 0.66-0.63 (m, 2H), 0.45 (s, 3H). | 3 |
| 116 | 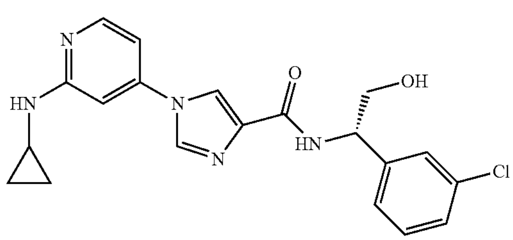 [SMILES: O=C(N[C@H](CO)c1cccc(Cl)c1)c1cn(-c2ccnc(NC3CC3)c2)cn1] | (S)-N-(1-(3-chlorophenyl)-2-hydroxy-ethyl)-1-(2-(cyclopropyl-amino)pyridin-4-yl)-1H-imidazole-4-carboxamide | 1HNMR (400 MHz, DMSO-d$_6$): δ 8.47 (s, 1H), 8.37 (d, J = 8.4 Hz, 1H), 8.28 (s, 1H), 8.07 (d, J = 5.2 Hz, 1H), 7.42 (s, 1H), 7.32 (t, J = 5.6 Hz, 3H), 7.03 (s, 1H), 6.96 (d, J = 4.0 Hz, 1H), 6.80 (s, 1H), 5.04-5.01 (m, 2H), 3.72 (t, J = 5.2 Hz, 2H), 2.56-2.48 (m, 1H), 1.33-1.22 (m, 2H), 0.43 (s, 2H). | 13 |
| 117 | 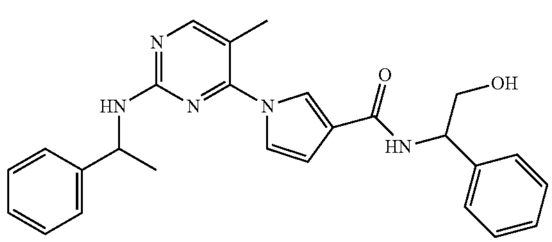 [SMILES: Cc1cnc(NC(C)c2ccccc2)nc1-n1ccc(C(=O)NC(CO)c2ccccc2)c1] | N-(2-hydroxy-1-phenyl-ethyl)-1-(5-methyl-2-((1-phenylethyl)amino)pyrimidin-4-yl)-1H-pyrrole-3-carboxamide | 1HNMR (400 MHz, DMSO-d$_6$): δ 8.21 (s, 1H), 8.19-8.16 (m, 1H), 7.91 (br s, 1H), 7.72 (d, J = 6.4 Hz, 1H), 7.47-7.34 (m, 4H), 7.31-7.01 (m, 7H), 6.72-6.71 (m, 1H), 5.04 (t, J = 6.0 Hz, 2H), 4.85 (t, J = 6.0 Hz, 1H), 3.67-3.62 (m, 2H), 3.39-3.23 (m, 1H), 2.18 (s, 3H), 1.28-1.22 (m, 1H), 1.07 (t, J = 7.2 Hz, 1H). | 3 |

TABLE 1-continued

| Cmpd # | Structure | Name | NMR data | Scheme # |
|---|---|---|---|---|
| 118 | 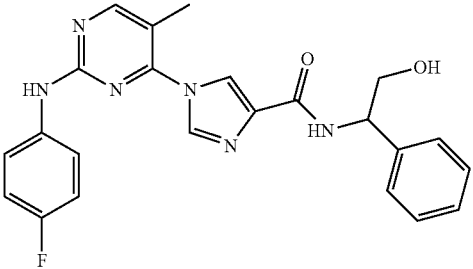 [SMILES: Cc1cnc(Nc2ccc(F)cc2)nc1-n1cnc(C(=O)NC(CO)c2ccccc2)c1] | 1-(2-((4-fluoro-phenyl)amino)-5-methyl-pyrimidin-4-yl)-N-(2-hydroxy-1-phenylethyl)-1H-imidazole-4-carboxamide | 1HNMR (400 MHz, DMSO-d$_6$): δ 9.80 (s, 1H), 8.54 (s, 1H), 8.33 (s, 1H), 8.29 (d, J = 8.4 Hz, 1H), 8.15 (s, 1H), 7.69 (t, J = 5.2 Hz, 2H), 7.36 (d, J = 7.2 Hz, 2H), 7.26 (t, J = 6.8 Hz, 2H), 7.21 (t, J = 6.8 Hz, 1H), 7.12 (t, J = 9.6 Hz, 2H), 5.04-4.97 (m, 2H), 3.71 (d, J = 4.4 Hz, 2H), 2.26 (s, 3H). | 6 |
| 119 | 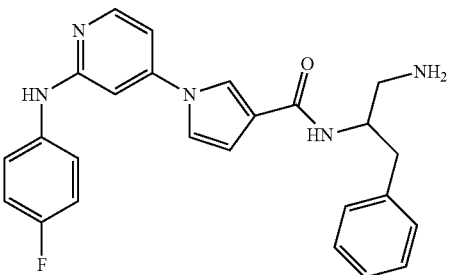 [SMILES: NCC(Cc1ccccc1)NC(=O)c1ccn(-c2ccnc(Nc3ccc(F)cc3)c2)c1] | N-(1-amino-3-phenyl-propan-2-yl)-1-(2-((4-fluoro-phenyl)amino)pyridin-4-yl)-1H-pyrrole-3-carboxamide | 1HNMR (400 MHz, DMSO-d$_6$): δ 9.15 (d, J = 9.2 Hz, 1H), 8.16 (d, J = 6 Hz, 1H), 7.90 (s, 1H), 7.66 (t, J = 4.4 Hz, 3H), 7.38 (s, 1H), 7.23 (d, J = 4 Hz, 4H), 7.14-7.12 (m, 2H), 7.01 (d, J = 4.4 Hz, 1H), 6.90 (t, J = 10 Hz, 1H), 6.71 (s, 1H), 4.02 (d, J = 5.6 Hz, 1H), 2.88-2.85 (m, 1H), 2.77-2.72 (m, 1H), 2.65-2.48 (m, 2H), 2.15 (s, 1H), 1.85 (s, 2H). | 9 |
| 120 | 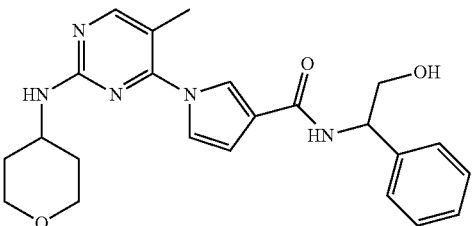 | N-(2-hydroxy-1-phenylethyl)-1-(5-methyl-2-((tetrahydro-2H-pyran-4-yl)amino)pyrimidin-4-yl)-1H-pyrrole-3-carboxamide | 1HNMR (400 MHz, DMSO-d$_6$): δ 8.25 (s, 1H), 8.19 (d, J = 8 Hz, 1H), 7.94 (s, 1H), 7.35 (d, J = 8 Hz, 3H), 7.29 (t, J = 6.8 Hz, 2H), 7.20 (t, J = 7.2 Hz, 2H), 6.74 (s, 1H), 5.06-5.00 (m, 1H), 4.85 (s, 1H), 3.86 (t, J = 14 Hz, 3H), 3.64 (s, 2H), 3.37 (t, J = 10.4 Hz, 2H), 2.21 (s, 3H), 1.81 (d, J = 12 Hz, 2H), 1.52-1.45 (m, 2H) | 3 |
| 121 | 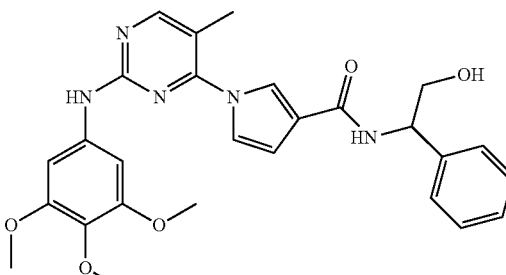 | N-(2-hydroxy-1-phenylethyl)-1-(5-methyl-2-((3,4,5-trimethoxy-phenyl)amino)pyrimidin-4-yl)-1H-pyrrole-3-carboxamide | 1HNMR (400 MHz, DMSO-d$_6$): δ 9.56 (s, 1H), 8.46 (s, 1H), 8.21 (d, J = 8.4 Hz, 1H), 8.09 (s, 1H), 7.47 (s, 1H), 7.36 (d, J = 7.2 Hz, 2H), 7.3 (t, J = 7.6 Hz, 2H), 7.21 (t, J = 7.2 Hz, 3H), 6.7 (s, 1H), 5.04 (d, J = 7.2 Hz, 1H), 4.85 (t, J = 5.6 Hz, 1H), 3.73 (s, 6H), 3.62 (s, 2H), 3.59 (s, 3H), 2.32 (s, 3H) | 3 |

| Cmpd # | Structure | Name | NMR data | Scheme # |
|---|---|---|---|---|
| 122 | 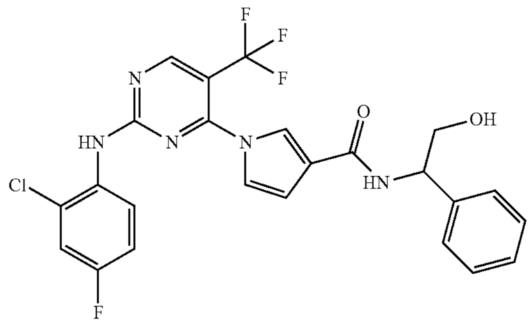 [SMILES: O=C(NC(CO)c1ccccc1)c1ccn(-c2nc(Nc3ccc(F)cc3Cl)ncc2C(F)(F)F)c1] | 1-(2-((2-chloro-4-fluorophenyl)amino)-5-(trifluoromethyl)pyrimidin-4-yl)-N-(2-hydroxy-1-phenylethyl)-1H-pyrrole-3-carboxamide | 1HNMR (400 MHz, DMSO-$d_6$): δ 9.43 (s, 1H), 8.68 (s, 1H), 8.32 (d, J = 8 Hz, 1H), 8.05 (s, 1H), 7.64-7.61 (m, 1H), 7.57-7.53 (m, 1H), 7.35-7.26 (m, 5H), 7.22-7.18 (m, 2H), 6.68 (d, J = 1.6 Hz, 1H), 5.00-4.95 (m, 1H), 4.83 (t, J = 5.6 Hz, 1H), 3.67-3.56 (m, 2H) | 3 |
| 123 | 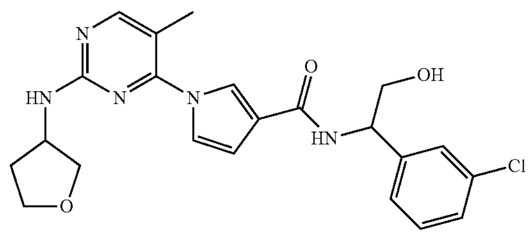 [SMILES: Cc1cnc(NC2CCOC2)nc1-n1ccc(C(=O)NC(CO)c2cccc(Cl)c2)c1] | N-(1-(3-chlorophenyl)-2-hydroxyethyl)-1-(5-methyl-2-((tetrahydrofuran-3-yl)amino)pyrimidin-4-yl)-1H-pyrrole-3-carboxamide | 1HNMR (400 MHz, DMSO-$d_6$): δ 8.27 (t, J = 4.8 Hz, 2H), 7.96 (s, 1H), 7.48 (d, J = 6.0 Hz, 1H), 7.40 (d, J = 8.8 Hz, 2H), 7.34 (t, J = 7.6 Hz, 2H), 7.28 (t, J = 8.4 Hz, 1H), 6.75 (s, 1H), 5.05-5.00 (m, 1H), 4.95 (t, J = 5.6 Hz, 1H), 4.36 (br s, 1H), 3.89-3.78 (m, 2H), 3.72-3.63 (m, 3H), 3.54-3.52 (m, 1H), 2.17 (s, 3H), 2.15-2.08 (m, 1H), 1.90-1.86 (m, 1H) | 3 |
| 124 | 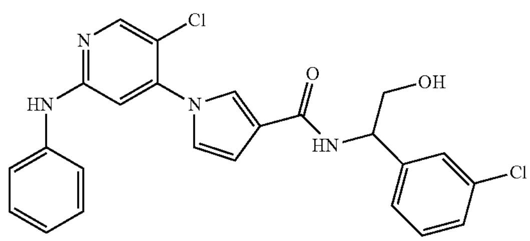 | 1-(5-chloro-2-(phenylamino)pyridin-4-yl)-N-(1-(3-chlorophenyl)-2-hydroxyethyl)-1H-pyrrole-3-carboxamide | 1HNMR (400 MHz, DMSO-$d_6$): δ 9.35 (s, 1H), 8.34 (s, 1H), 8.21 (d, J = 8 Hz, 1H), 7.76 (s, 1H), 7.61 (d, J = 7.6 Hz, 2H), 7.42 (s, 1H), 7.34-7.26 (m, 5H), 7.17 (t, J = 2.8 Hz, 1H), 6.94 (t, J = 7.6 Hz, 1H), 6.87 (s, 1H), 6.78 (s, 1H), 5.06-5.0 (m, 1H), 4.92 (t, J = 6 Hz, 1H), 3.67-3.62 (m, 2H) | 10 |
| 125 | 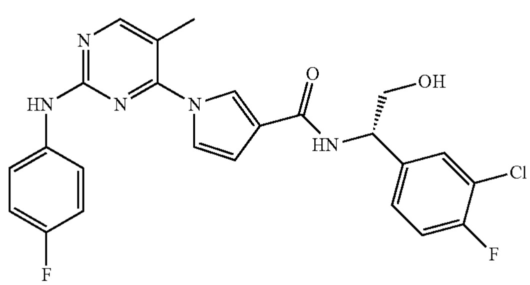 [SMILES: Cc1cnc(Nc2ccc(F)cc2)nc1-n1ccc(C(=O)N[C@H](CO)c2ccc(F)c(Cl)c2)c1] | (S)-N-(1-(3-chloro-4-fluorophenyl)-2-hydroxyethyl)-1-(2-((4-fluorophenyl)amino)-5-methylpyrimidin-4-yl)-1H-pyrrole-3-carboxamide | 1HNMR (400 MHz, DMSO-$d_6$): δ 9.7 (s, 1H), 8.46 (s, 1H), 8.27 (d, J = 7.6 Hz, 1H), 8.02 (s, 1H), 7.73-7.71 (m, 2H), 7.57 (d, J = 6 Hz, 1H), 7.44 (t, J = 2 Hz, 1H), 7.36-7.34 (m, 2H), 7.14-7.09 (m, 2H), 6.77 (s, 1H), 5.06-5.01 (m, 1H), 4.94 (t, J = 5.6 Hz, 1H), 3.68-3.61 (m, 2H), 2.31 (s, 3H) | 3 |

TABLE 1-continued

| Cmpd # | Structure | Name | NMR data | Scheme # |
|---|---|---|---|---|
| 126 | 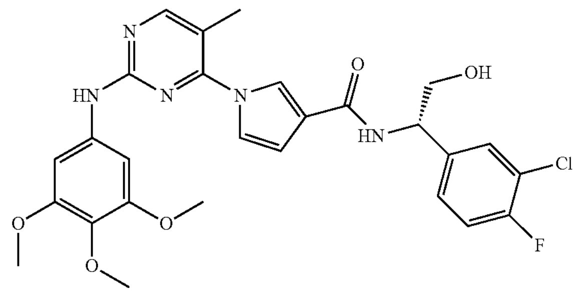 [SMILES: COc1cc(Nc2ncc(C)c(-n3ccc(C(=O)N[C@H](CO)c4ccc(F)c(Cl)c4)c3)n2)cc(OC)c1OC] | (S)-N-(1-(3-chloro-4-fluorophenyl)-2-hydroxy-ethyl)-1-(5-methyl-2-((3,4,5-trimethoxy-phenyl)amino)pyrimidin-4-yl)-1H-pyrrole-3-carboxamide | 1HNMR (400 MHz, DMSO-d$_6$): δ 9.57 (s, 1H), 8.47 (s, 1H), 8.25 (d, J = 7.6 Hz, 1H), 8.09 (s, 1H), 7.57 (d, J = 6 Hz, 1H), 7.48 (s, 1H), 7.36 (d, J = 6.8 Hz, 2H), 7.19 (s, 2H), 6.79 (s, 1H), 5.04 (d, J = 7.2 Hz, 1H), 4.93 (s, 1H), 3.73 (s, 6H), 3.64 (s, 2H), 3.60 (s, 3H), 2.32 (s, 3H) | 3 |
| 127 | 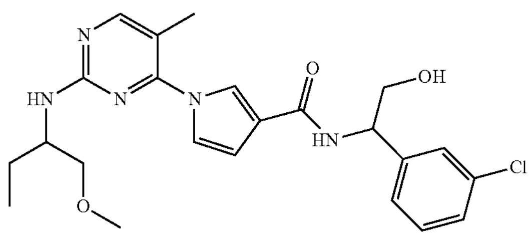 [SMILES: CCC(COC)Nc1ncc(C)c(-n2ccc(C(=O)NC(CO)c3cccc(Cl)c3)c2)n1] | N-(1-(3-chloro-phenyl)-2-hydroxy-ethyl)-1-(2-((1-methoxy-butan-2-yl)amino)-5-methyl-pyrimidin-4-yl)-1H-pyrrole-3-carboxamide | 1HNMR (400 MHz, DMSO-d$_6$): δ 8.24 (s, 2H), 7.95 (br s, 1H), 7.42 (s, 1H), 7.37 (s, 1H), 7.34 (s, 2H), 7.28 (s, 1H), 6.97 (br s, 1H), 6.74 (s, 1H), 5.03 (d, J = 7.2 Hz, 1H), 4.92 (s, 1H), 4.0 (s, 1H), 3.65 (d, J = 4.8 Hz, 2H), 3.35 (d, J = 6 Hz, 2H), 3.22 (s, 3H), 2.31 (s, 3H), 1.59 (s, 1H), 1.45-1.43 (m, 1H), 0.86 (t, J = 7.6 Hz, 3H) | 3 |
| 128 | 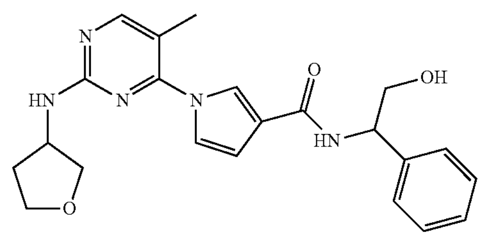 [SMILES: Cc1cnc(NC2CCOC2)nc1-n1ccc(C(=O)NC(CO)c2ccccc2)c1] | N-(2-hydroxy-1-phenylethyl)-1-(5-methyl-2-((tetrahydro-furan-3-yl)amino)pyrimidin-4-yl)-1H-pyrrole-3-carboxamide | 1HNMR (400 MHz, DMSO-d$_6$): δ 8.28 (s, 1H), 8.20 (d, J = 8.0 Hz, 1H), 7.95 (s, 1H), 7.45 (s, 1H), 7.37 (t, J = 8.4 Hz, 3H), 7.30 (t, J = 7.2 Hz, 2H), 7.21 (t, J = 6.8 Hz, 1H), 6.75 (s, 1H), 5.06-5.01 (m, 1H), 4.86 (s, 1H), 4.36 (br s, 1H), 3.89-3.78 (m, 2H), 3.72-3.63 (m, 3H), 3.54-3.52 (m, 1H), 2.17 (s, 3H), 2.15-2.08 (m, 1H), 1.90-1.86 (m, 1H) | 3 |
| 129 | 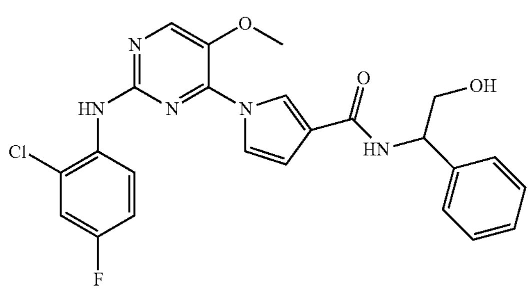 [SMILES: COc1cnc(Nc2ccc(F)cc2Cl)nc1-n1ccc(C(=O)NC(CO)c2ccccc2)c1] | 1-(2-((2-chloro-4-fluorophenyl)amino)-5-methoxy-pyrimidin-4-yl)-N-(2-hydroxy-1-phenylethyl)-1H-pyrrole-3-carboxamide | 1HNMR (400 MHz, DMSO-d$_6$): δ 8.77 (s, 1H), 8.43 (s, 1H), 8.27 (d, J = 8 Hz, 1H), 8.21 (s, 1H), 7.76-7.72 (m, 1H), 7.63 (t, J = 2.8 Hz, 1H), 7.49-7.46 (m, 1H), 7.35 (d, J = 7.6 Hz, 2H), 7.27 (t, J = 8.4 Hz, 2H), 7.24-7.19 (m, 2H), 6.79-6.78 (m, 1H), 5.05-5.0 (m, 1H), 4.85 (t, J = 5.6 Hz, 1H), 3.92 (s, 3H), 3.68-3.62 (m, 2H) | 3 |

TABLE 1-continued

| Cmpd # | Structure | Name | NMR data | Scheme # |
|---|---|---|---|---|
| 130 | 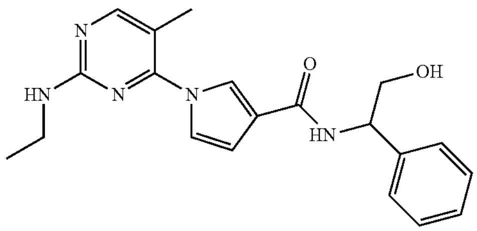 [SMILES: CCNc1ncc(C)c(-n2ccc(C(=O)NC(CO)c3ccccc3)c2)n1] | 1-(2-(ethyl-amino)-5-methyl-pyrimidin-4-yl)-N-(2-hydroxy-1-phenylethyl)-1H-pyrrole-3-carboxamide | 1HNMR (400 MHz, DMSO-$d_6$): δ 8.25 (s, 1H), 8.19 (d, J = 8.4 Hz, 1H), 7.94 (s, 1H), 7.35 (d, J = 7.6 Hz, 3H), 7.29 (t, J = 7.6 Hz, 2H), 7.22-7.16 (m, 2H), 6.74 (s, 1H), 5.06-5.01 (m, 1H), 4.86 (t, J = 6 Hz, 1H), 3.67-3.62 (m, 2H), 3.30-3.23 (m, 2H), 2.21 (s, 3H), 1.11 (t, J = 6.8 Hz, 3H) | 3 |
| 131 | 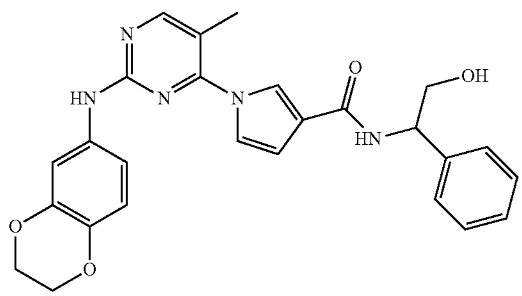 | 1-(2-((2,3-dihydro-benzo[b][1,4]dioxin-6-yl)-amino)-5-methyl-pyrimidin-4-yl)-N-(2-hydroxy-1-phenylethyl)-1H-pyrrole-3-carboxamide | 1HNMR (400 MHz, DMSO-$d_6$): δ 9.46 (s, 1H), 8.42 (s, 1H), 8.22 (d, J = 8 Hz, 1H), 8.0 (s, 1H), 7.41 (t, J = 2.8 Hz, 1H), 7.41-7.34 (m, 5H), 7.22 (d, J = 7.6 Hz, 1H), 7.11 (t, J = 2.8 Hz, 1H), 6.79 (s, 1H), 6.75 (d, J = 8.8 Hz, 1H), 5.06 (t, J = 7.2 Hz, 1H), 4.86 (t, J = 5.2 Hz, 1H), 4.20-4.16 (m, 4H), 3.66-3.64 (m, 2H), 2.29 (s, 3H) | 3 |
| 132 | 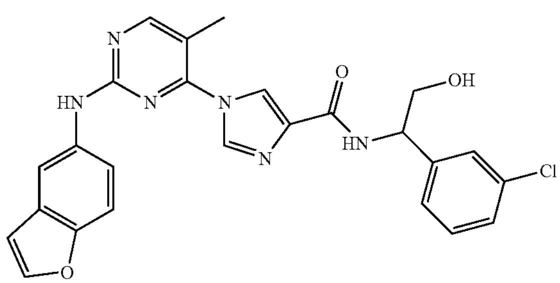 [SMILES: Cc1cnc(Nc2ccc3occc3c2)nc1-n1cnc(C(=O)NC(CO)c2cccc(Cl)c2)c1] | 1-(2-(benzo-furan-5-ylamino)-5-methyl-pyrimidin-4-yl)-N-(1-(3-chlorophenyl)-2-hydroxy-ethyl)-1H-imidazole-4-carboxamide | 1HNMR (400 MHz, DMSO-$d_6$): δ 9.77 (s, 1H), 8.54 (s, 1H), 8.42 (d, J = 8.4 Hz, 1H), 8.36 (d, J = 0.8 Hz, 1H), 8.18 (s, 1H), 8.03 (s, 1H), 7.91 (d, J = 2 Hz, 1H), 7.54-7.48 (m, 2H), 7.44 (s, 1H), 7.34 (d, J = 5.2 Hz, 2H), 7.29 (t, J = 1.6 Hz, 1H), 6.90 (d, J = 1.6 Hz, 1H), 5.02 (d, J = 8 Hz, 2H), 3.72 (d, J = 5.6 Hz, 2H), 2.27 (s, 3H) | 6 |
| 133 | 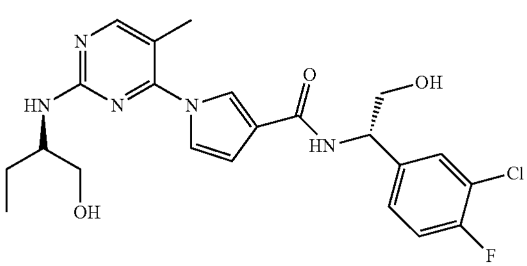 | N-((S)-1-(3-chloro-4-fluorophenyl)-2-hydroxy-ethyl)-1-(2-(((S)-1-hydroxy-butan-2-yl)amino)-5-methyl-pyrimidin-4-yl)-1H-pyrrole-3-carboxamide | 1HNMR (400 MHz, DMSO-$d_6$): 8.24 (d, J = 5.2 Hz, 2H), 7.94 (s, 1H), 7.56 (d, J = 7.2 Hz, 1H), 7.36-7.32 (m, 3H), 6.79 (d, J = 8 Hz, 1H), 6.73 (s, 1H), 5.03-4.99 (m, 1H), 4.93 (t, J = 6 Hz, 1H), 4.56 (t, J = 5.6 Hz, 1H), 3.81 (br s, 1H), 3.67-3.62 (m, 2H), 3.47-3.43 (m, 1H), 3.35-3.33 (m, 1H), 2.14 (s, 3H), 1.68-1.62 (m, 1H), 1.22 (s, 1H), 0.86 (t, J = 7.6 Hz, 3H) | 3 |

TABLE 1-continued

| Cmpd # | Structure | Name | NMR data | Scheme # |
|---|---|---|---|---|
| 134 | 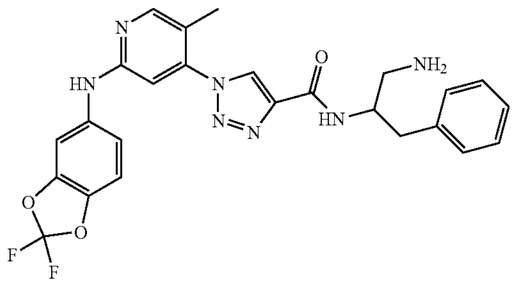 [SMILES: Cc1cnc(Nc2ccc3c(c2)OC(F)(F)O3)cc1-n1cc(C(=O)NC(CN)Cc2ccccc2)nn1] | N-(1-amino-3-phenylpropan-2-yl)-1-(2-((2,2-difluoro-benzo[d][1,3]dioxol-5-yl)amino)-5-methyl-pyridin-4-yl)-1H-1,2,3-triazole-4-carboxamide | 1HNMR (400 MHz, DMSO-d6): δ 11.29 (s, 1H), 9.49 (s, 1H), 9.04 (s, 1H), 8.59 (d, J = 8.8 Hz, 1H), 8.28 (s, 1H), 7.93 (d, J = 1.6 Hz, 1H), 7.33-7.14 (m, 8H), 6.94 (d, J = 9.6 Hz, 1H), 4.29 (s, 1H), 3.50 (s, 1H), 3.16-2.83 (m, 3H), 1.97 (s, 3H) | 12 |
| 135 | 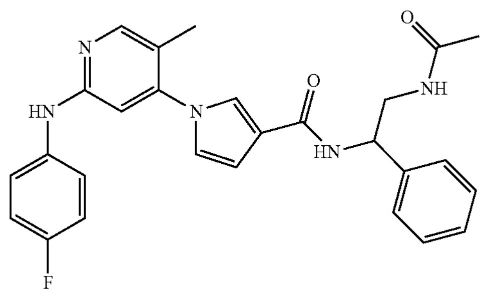 [SMILES: CC(=O)NCC(NC(=O)c1ccn(-c2cc(Nc3ccc(F)cc3)ncc2C)c1)c1ccccc1] | N-(2-acetamido-1-phenylethyl)-1-(2-((4-fluorophenyl)amino)-5-methyl-pyridin-4-yl)-1H-pyrrole-3-carboxamide | 1HNMR (400 MHz, DMSO-d6): δ 9.12 (s, 1H), 8.33 (s, 1H), 8.11 (d, J = 18.4 Hz, 2H), 7.63 (s, 3H), 7.35 (s, 5H), 7.11 (s, 3H), 6.71 (d, J = 10 Hz, 2H), 5.08 (s, 1H), 3.46 (s, 2H), 2.15 (s, 3H), 1.78 (s, 3H) | 9 |
| 136 | 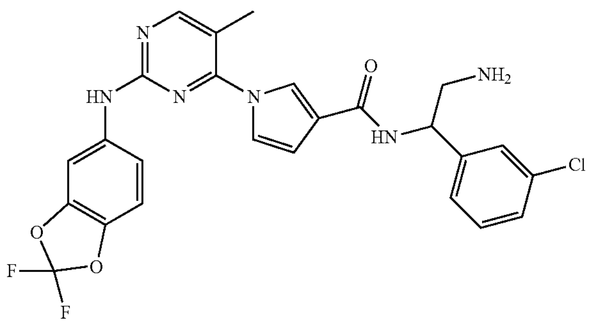 [SMILES: Cc1cnc(Nc2ccc3c(c2)OC(F)(F)O3)nc1-n1ccc(C(=O)NC(CN)c2cccc(Cl)c2)c1] | N-(2-amino-1-(3-chloro-phenyl)ethyl)-1-(2-((2,2-difluoro-benzo[d][1,3]dioxol-5-yl)amino)-5-methyl-pyrimidin-4-yl)-1H-pyrrole-3-carboxamide | 1HNMR (400 MHz, CDCl3): δ 8.34 (s, 1H), 7.95 (s, 1H), 7.69 (d, J = 1.6 Hz, 1H), 7.34 (t, J = 2.8 Hz, 1H), 7.23 (s, merged with CDCl3 peak, 1H), 7.06-6.99 (m, 2H), 6.78-6.77 (m, 1H), 3.86 (s, 3H), 2.40 (s, 3H). | 4 |
| 137 | 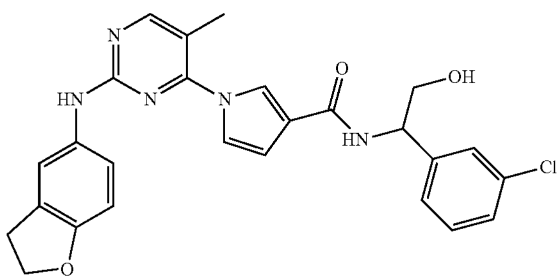 [SMILES: Cc1cnc(Nc2ccc3c(c2)CCO3)nc1-n1ccc(C(=O)NC(CO)c2cccc(Cl)c2)c1] | N-(1-(3-chloro-phenyl)-2-hydroxy-ethyl)-1-(2-((2,3-dihydro-benzofuran-5-yl)-mino)-5-methyl-pyrimidin-4-yl)-1H-pyrrole-3-carboxamide | 1HNMR (400 MHz, DMSO-d6): δ 9.41 (s, 1H), 8.4 (s, 1H), 8.27 (d, J = 8 Hz, 1H), 8.03 (s, 1H), 7.68 (d, J = 7.6 Hz, 1H), 7.43 (s, 2H), 7.34-7.27 (m, 4H), 6.76 (s, 1H), 6.67 (d, J = 8.8 Hz, 1H), 5.06-5.01 (m, 1H), 4.92 (d, J = 6 Hz, 1H), 4.47 (t, J = 8.8 Hz, 2H), 3.66 (t, J = 5.6 Hz, 2H), 3.15 (t, J = 8.8 Hz, 2H), 2.29 (s, 3H) | 3 |
| 138 | 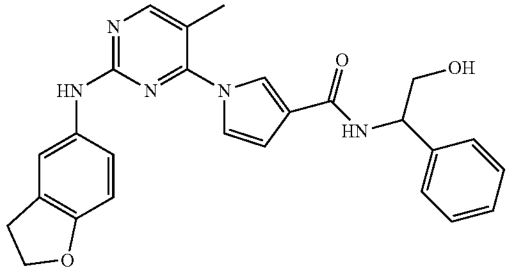 | 1-(2-((2,3-dihydro-benzofuran-5-yl)amino)-5-methyl-pyrimidin-4-yl)-N-(2-hydroxy-1-phenylethyl)-1H-pyrrole-3-carboxamide | 1HNMR (400 MHz, DMSO-d6): δ 9.4 (s, 1H), 8.39 (s, 1H), 8.23 (d, J = 8 Hz, 1H), 8.03 (s, 1H), 7.59 (s, 1H), 7.42 (s, 1H), 7.37-7.34 (m, 3H), 7.32-7.28 (m, 2H), 7.21 (t, J = 7.2 Hz, 1H), 6.77 (s, 1H), 6.67 (d, J = 8.4 Hz, 1H), 5.07-5.02 (m, 1H), 4.86 (s, 1H), 4.47 (t, J = 8.4 Hz, 2H), | 3 |

TABLE 1-continued

| Cmpd # | Structure | Name | NMR data | Scheme # |
|---|---|---|---|---|
| | | | 3.65 (t, J = 9.2 Hz, 2H), 3.15 (t, J = 8.8 Hz, 2H), 2.29 (s, 3H) | |
| 139 | 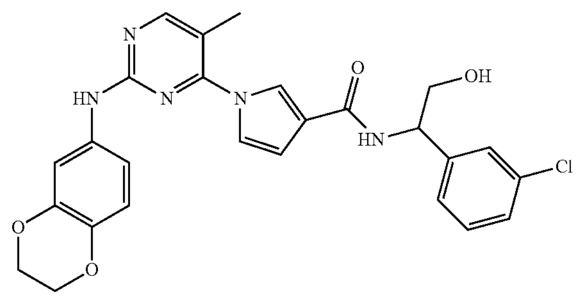 [SMILES: Cc1cnc(Nc2ccc3c(c2)OCCO3)nc1-n1ccc(C(=O)NC(CO)c2cccc(Cl)c2)c1] | N-(1-(3-chloro-phenyl)-2-hydroxy-ethyl)-1-(2-((2,3-dihydro-benzo[b][1,4]dioxin-6-yl)amino)-5-methyl-pyrimidin-4-yl)-1H-pyrrole-3-carboxamide | 1HNMR (400 MHz, DMSO-$d_6$): δ 9.47 (s, 1H), 8.42 (s, 1H), 8.27 (d, J = 8.4 Hz, 1H), 8.00 (s, 1H), 7.43 (s, 2H), 7.33 (s, 3H), 7.29 (s, 1H), 7.12-7.09 (m, 1H), 6.76 (t, J = 7.2 Hz, 2H), 5.03 (t, J = 7.6 Hz, 1H), 4.93 (s, 1H), 4.18 (t, J = 5.6 Hz, 4H), 3.66 (d, J = 4.4 Hz, 2H), 2.29 (s, 3H) | 3 |
| 140 | 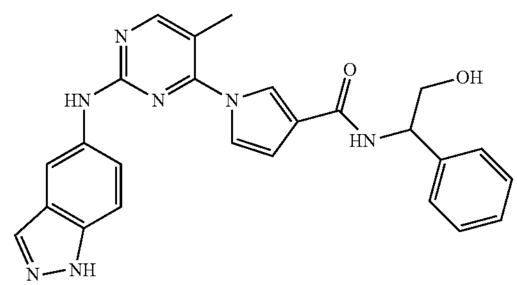 [SMILES: Cc1cnc(Nc2ccc3[nH]ncc3c2)nc1-n1ccc(C(=O)NC(CO)c2ccccc2)c1] | 1-(2-((1H-indazol-5-yl)amino)-5-methyl-pyrimidin-4-yl)-N-(2-hydroxy-1-phenylethyl)-1H-pyrrole-3-carboxamide | 1HNMR (400 MHz, DMSO-$d_6$): δ 12.87 (s, 1H), 9.61 (s, 1H), 8.45 (s, 1H), 8.26 (d, J = 8 Hz, 1H), 8.19 (s, 1H), 8.07 (s, 1H), 7.97 (s, 1H), 7.55 (d, J = 8 Hz, 1H), 7.45 (t, J = 4.4 Hz, 2H), 7.37 (d, J = 7.2 Hz, 2H), 7.30 (t, J = 7.2 Hz, 2H), 7.21 (d, J = 6.8 Hz, 1H), 6.78 (s, 1H), 5.08-505 (m, 1H), 4.87 (t, J = 5.6 Hz, 1H), 3.66 (s, 2H), 2.31 (s, 3H) | 3 |
| 141 | 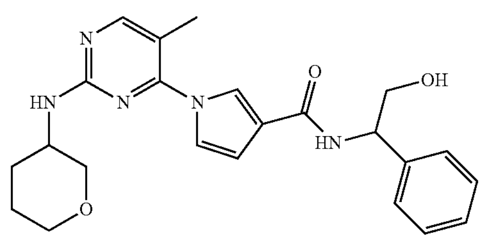 [SMILES: Cc1cnc(NC2CCCOC2)nc1-n1ccc(C(=O)NC(CO)c2ccccc2)c1] | N-(2-hydroxy-1-phenylethyl)-1-(5-methyl-2-((tetrahydro-2H-pyran-3-yl)amino)-pyrimidin-4-yl)-1H-pyrrole-3-carboxamide | 1HNMR (400 MHz, DMSO-$d_6$): δ 8.26 (s, 1H), 8.20 (d, J = 8.0 Hz, 1H), 7.94 (s, 1H), 7.36 (d, J = 12 Hz, 3H), 7.29 (t, J = 12 Hz, 3H), 7.20 (t, J = 6.8 Hz, 1H), 7.10 (s, 1H), 6.75 (s, 1H), 5.04 (d, J = 7.2 Hz, 1H), 4.86 (s, 1H), 3.84 (d, J = 8.4 Hz, 2H), 3.72 (d, J = 11.2 Hz, 1H), 3.65 (d, J = 4.0 Hz, 2H,), 3.08 (t, J = 10.8 Hz, 1H), 2.22 (s, 3H), 1.94 (br s, 1H), 1.66 (s, 1H), 1.54 (d, J = 8.0 Hz, 2H) | 3 |

TABLE 1-continued

| Cmpd # | Structure | Name | NMR data | Scheme # |
|---|---|---|---|---|
| 142 | 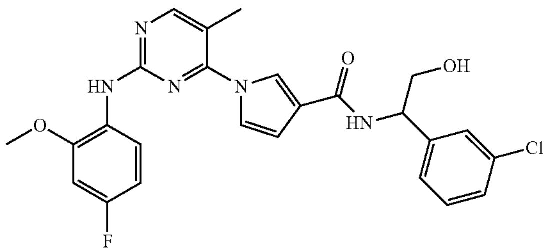 [SMILES: COc1cc(F)ccc1Nc1ncc(C)c(-n2ccc(C(=O)NC(CO)c3cccc(Cl)c3)c2)n1] | N-(1-(3-chloro-phenyl)-2-hydroxy-ethyl)-1-(2-((4-fluoro-2-methoxy-phenyl)amino)-5-methyl-pyrimidin-4-yl)-1H-pyrrole-3-carboxamide | 1HNMR (400 MHz, DMSO-d$_6$): δ 8.40 (s, 1H), 8.27 (t, J = 8.8 Hz, 2H), 8.0 (s, 1H), 7.87 (t, J = 7.6 Hz, 1H), 7.41 (s, 2H), 7.34-7.27 (m, 3H), 6.98-6.95 (m, 1H), 6.76 (s, 2H), 5.06-5.01 (m, 1H), 4.93 (t, J = 5.2 Hz, 1H), 3.82 (s, 3H), 3.68-3.64 (m, 2H), 2.30 (s, 3H) | 3 |
| 143 | 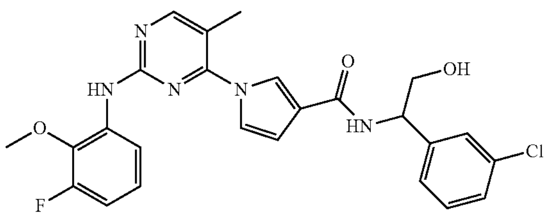 [SMILES: COc1c(F)cccc1Nc1ncc(C)c(-n2ccc(C(=O)NC(CO)c3cccc(Cl)c3)c2)n1] | N-(1-(3-chloro-phenyl)-2-hydroxy-ethyl)-1-(2-((3-fluoro-2-methoxy-phenyl)amino)-5-methyl-pyrimidin-4-yl)-1H-pyrrole-3-carboxamide | 1HNMR (400 MHz, DMSO-d$_6$): δ 9.66 (s, 1H), 8.46 (s, 1H), 8.27 (d, J = 8.4 Hz, 1H), 8.02 (s, 1H), 7.70-7.67 (m, 1H), 7.43-7.40 (m, 3H), 7.33-7.27 (m, 3H), 7.09 (t, J = 9.6 Hz, 1H), 6.79 (s, 1H), 5.27 (d, J = 7.6 Hz, 1H), 4.95-4.85 (m, 1H), 3.78 (s, 3H), 3.66 (d, J = 4.8 Hz, 2H), 2.31 (s, 3H) | 3 |
| 145 | 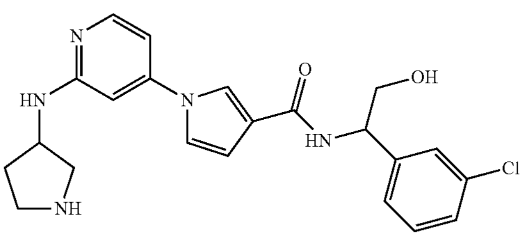 [SMILES: O=C(NC(CO)c1cccc(Cl)c1)c1ccn(-c2ccnc(NC3CCNC3)c2)c1] | N-(1-(3-chloro-phenyl)-2-hydroxy-ethyl)-1-(2-(pyrrolidin-3-ylamino)pyridin-4-yl)-1H-pyrrole-3-carboxamide | 1HNMR (400 MHz, DMSO-d$_6$): δ 8.20 (s, 1H), 8.01 (t, J = 5.6 Hz, 2H), 7.40 (d, J = 10.4 Hz, 2H), 7.30 (d, J = 15.2 Hz, 3H), 6.78-6.72 (m, 3H), 6.59 (s, 1H), 5.02 (d, J = 7.2 Hz, 1H), 4.94 (s, 1H), 4.26 (s, 1H), 3.65 (s, 2H), 3.09 (d, J = 11.2 Hz, 2H), 2.95 (s, 2H), 2.85 (s, 1H), 2.04 (t, J = 6.8 Hz, 1H), 1.62 (s, 1H) | 13 |
| 146 | 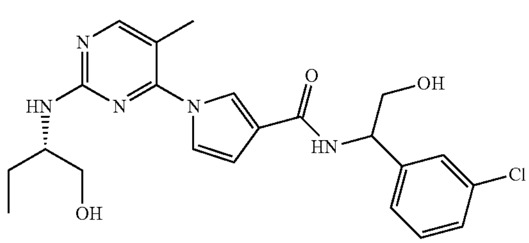 [SMILES: CC[C@@H](CO)Nc1ncc(C)c(-n2ccc(C(=O)NC(CO)c3cccc(Cl)c3)c2)n1] | N-(1-(3-chloro-phenyl)-2-hydroxy-ethyl)-1-(2-(((S)-1-hydroxy-butan-2-yl)amino)-5-methyl-pyrimidin-4-yl)-1H-pyrrole-3-carboxamide | 1HNMR (400 MHz, DMSO-d$_6$): δ 8.24 (d, J = 7.2 Hz, 2H), 7.94 (s, 1H), 7.42-7.26 (m, 5H), 6.80-6.74 (m, 2H), 5.05-5.00 (m, 1H), 4.94-4.91 (m, 1H), 4.57-4.55 (m, 1H), 3.83 (br s, 1H), 3.65 (d, J = 4.8 Hz, 2H), 3.47-3.42 (m, 1H), 3.37-3.32 (m, 1H), 2.21 (s, 3H), 1.68-1.61 (m, 1H), 1.45-1.38 (m, 1H), 0.862 (t, J = 7.2 Hz, 3H) | 3 |

TABLE 1-continued

| Cmpd # | Structure | Name | NMR data | Scheme # |
|---|---|---|---|---|
| 147 | 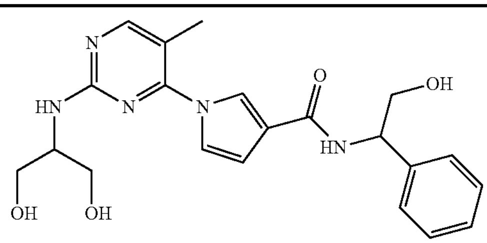 | 1-(2-((1,3-dihydroxy-propan-2-yl)amino)-5-methyl-pyrimidin-4-yl)-N-(2-hydroxy-1-phenylethyl)-1H-pyrrole-3-carboxamide | 1HNMR (400 MHz, DMSO-d<sub>6</sub>): δ 8.25 (s, 1H), 8.20 (d, J = 8 Hz, 1H), 7.95 (s, 1H), 7.39-7.28 (m, 7H), 7.22-7.18 (m, 1H), 6.75 (s, 1H), 6.59 (d, J = 8 Hz, 1H), 5.06-5.01 (m, 1H), 4.86 (t, J = 6 Hz, 1H), 4.57 (t, J = 5.2 Hz, 2H), 3.93-3.89 (m, 1H), 3.66 (t, J = 5.6 Hz, 2H), 3.51-3.48 (m, 2H), 2.22 (s, 3H) | 3 |
| 148 | 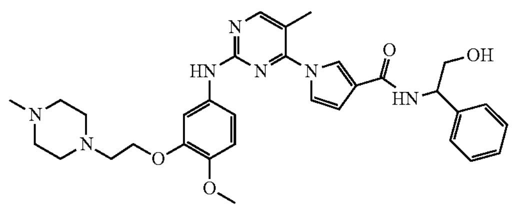 [SMILES: COc1ccc(Nc2ncc(C)c(-n3ccc(C(=O)NC(CO)c4ccccc4)c3)n2)cc1OCCN1CCN(C)CC1] | N-(2-hydroxy-1-phenylethyl)-1-(2-((4-methoxy-3-(2-(4-methyl-piperazin-1-yl)ethoxy)-phenyl)amino)-5-methyl-pyrimidin-4-yl)-1H-pyrrole-3-carboxamide | 1HNMR (400 MHz, DMSO-d<sub>6</sub>): δ 9.46 (s, 1H), 8.43 (s, 1H), 8.23 (d, J = 8.4 Hz, 1H), 8.03 (s, 1H), 7.68 (s, 1H), 7.54 (s, 1H), 7.45 (s, 1H), 7.44 (d, J = 2.4 Hz, 2H), 7.36 (d, J = 7.6 Hz, 2H), 7.30 (t, J = 6.8 Hz, 2H), 7.21 (t, J = 7.2 Hz, 1H), 7.16-7.14 (m, 1H), 6.87 (d, J = 5.2 Hz, 1H), 6.80 (s, 1H), 5.07-5.02 (m, 1H), 4.88 (s, 1H), 4.02 (s, 2H), 3.70 (s, 3H), 3.65 (s, 2H), 2.65 (s, 3H), 2.30 (s, 4H), 2.25 (s, 3H) | 3 |
| 149 | 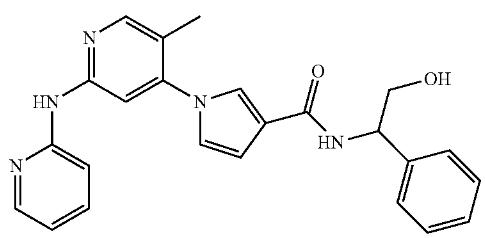 [SMILES: Cc1cnc(Nc2ccccn2)cc1-n1ccc(C(=O)NC(CO)c2ccccc2)c1] | N-(2-hydroxy-1-phenylethyl)-1-(5-methyl-2-(pyridin-2-ylamino)pyridin-4-yl)-1H-pyrrole-3-carboxamide | 1HNMR (400 MHz, DMSO-d<sub>6</sub>): δ 9.76 (s, 1H), 8.22 (s, 1H), 8.20 (d, J = 4.4 Hz, 1H), 8.12 (d, J = 8 Hz, 1H), 7.86 (s, 1H), 7.66-7.62 (m, 2H), 7.54 (d, J = 8 Hz, 1H), 7.37-7.36 (m, 2H), 7.31 (t, J = 7.2 Hz, 2H), 7.21 (t, J = 7.6 Hz, 1H), 7.09 (s, 1H), 6.84 (t, J = 6.4 Hz, 1H), 6.77 (s, 1H), 5.07-5.02 (m, 1H), 4.86 (t, J = 5.6 Hz, 1H), 3.67-3.62 (m, 2H), 2.17 (s, 3H) | 3 |
| 150 | 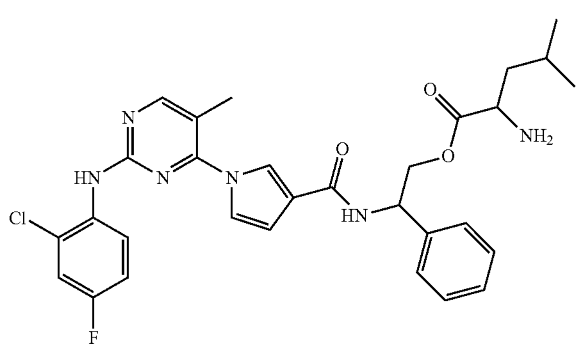 [SMILES: Cc1cnc(Nc2ccc(F)cc2Cl)nc1-n1ccc(C(=O)NC(COC(=O)C(N)CC(C)C)c2ccccc2)c1] | 2-(1-(2-((2-chloro-4-fluorophenyl)-amino)-5-methyl-pyrimidin-4-yl)-1H-pyrrole-3-carboxamido)-2-phenylethyl 2-amino-4-methyl-pentanoate | 1HNMR (400 MHz, DMSO-d<sub>6</sub>): δ 8.99 (s, 1H), 8.49-8.43 (m, 1H), 8.39 (s, 1H), 7.93 (s, 1H), 7.69-7.66 (m, 1H), 7.49-7.38 (m, 6H), 7.36-7.30 (m, 1H), 7.28-7.19 (m, 1H), 6.74 (s, 1H), 5.37-5.35 (m, 1H), 4.50-4.45 (m, 1H), 4.31-4.28 (m, 1H), 3.67 (s, 1H), 2.99 (s, 1H), 2.28 (s, 3H), 1.71 (s, 1H), 1.61-1.55 (m, 1H), 1.43-1.35 | 3, 18 |

TABLE 1-continued

| Cmpd # | Structure | Name | NMR data | Scheme # |
|---|---|---|---|---|
| | | | (m, 2H), 0.70 (t, J = 3.2 Hz, 6H) | |
| 151 | 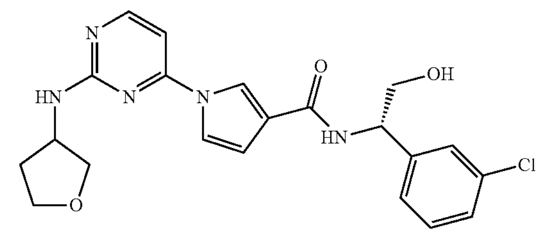 [SMILES: O=C(N[C@H](CO)c1cccc(Cl)c1)c1ccn(-c2ccnc(NC3CCOC3)n2)c1] | N-((S)-1-(3-chlorophenyl)-2-hydroxy-ethyl)-1-(5-methyl-2-((tetrahydro-furan-3-yl)amino)pyrimidin-4-yl)-1H-pyrrole-3-carboxamide | 1HNMR (400 MHz, DMSO-d$_6$): δ 8.28 (s, 1H), 8.24 (d, J = 8.0 Hz, 1H), 7.95 (s, 1H), 7.45-7.39 (m, 3H), 7.36-7.26 (m, 3H), 6.75 (s, 1H), 5.05-5.00 (m, 1H), 4.94-4.91 (t, J = 5.6 Hz, 1H), 4.35 (br s, 1H), 3.89-3.78 (m, 2H), 3.72-3.65 (m, 3H), 3.54-3.51 (m, 1H), 2.17 (s, 3H), 2.15-2.09 (m, 1H), 1.89-1.86 (m, 1H) | 3 |
| 152 | 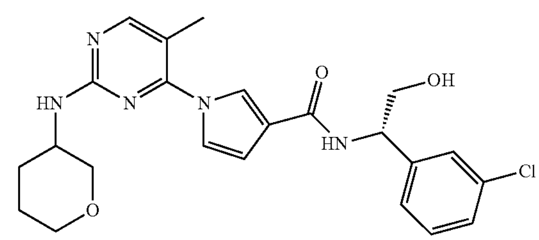 [SMILES: Cc1cnc(NC2CCCOC2)nc1-n1ccc(C(=O)N[C@H](CO)c2cccc(Cl)c2)c1] | N-((S)-1-(3-chlorophenyl)-2-hydroxy-ethyl)-1-(5-methyl-2-((tetrahydro-2H-pyran-3-yl)amino)pyrimidin-4-yl)-1H-pyrrole-3-carboxamide | 1HNMR (400 MHz, DMSO-d$_6$): δ 8.25 (d, J = 13.6 Hz, 2H), 7.95 (s, 1H), 7.42 (s, 1H), 7.37-7.28 (m, 4H), 7.11 (s, 1H), 6.74 (s, 1H), 5.03 (d, J = 6.4 Hz, 1H), 4.93 (s, 1H), 3.83 (s, 2H), 3.74-3.65 (m, 3H), 3.09 (d, J = 10 Hz, 1H), 2.22 (s, 4H), 1.94 (s, 1H), 1.66 (s, 1H), 1.55 (s, 2H) | 3 |
| 153 | 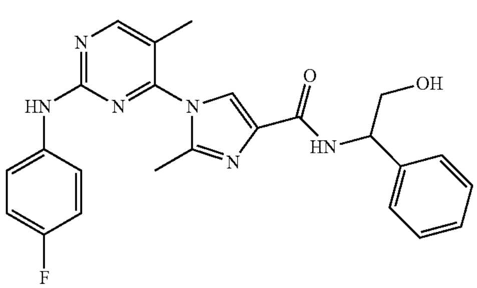 [SMILES: Cc1cnc(Nc2ccc(F)cc2)nc1-n1cc(C(=O)NC(CO)c2ccccc2)nc1C] | 1-(2-((4-fluoro-phenyl)amino)-5-methyl-pyrimidin-4-yl)-N-(2-hydroxy-1-phenylethyl)-2-methyl-1H-imidazole-4-carboxamide | 1HNMR (400 MHz, DMSO-d$_6$): δ 9.89 (s, 1H), 8.60 (s, 1H), 8.21 (d, J = 8.4 Hz, 1H), 7.92 (s, 1H), 7.70-7.67 (m, 2H), 7.37 (d, J = 7.2 Hz, 2H), 7.31 (t, J = 7.2 Hz, 2H), 7.24 (d, J = 7.2 Hz, 1H), 7.16 (t, J = 8.8 Hz, 2H), 5.02 (d, J = 4.8 Hz, 2H), 3.77-3.69 (m, 2H), 2.35 (s, 3H), 2.03 (s, 3H) | 5 |
| 154 | 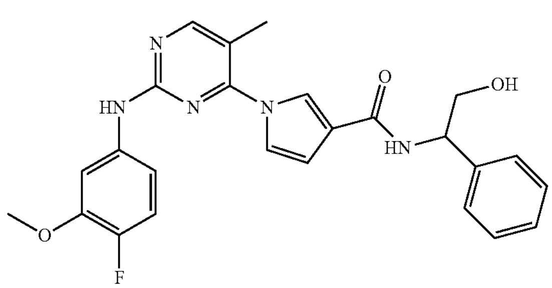 [SMILES: COc1cc(Nc2ncc(C)c(-n3ccc(C(=O)NC(CO)c4ccccc4)c3)n2)ccc1F] | 1-(2-((4-fluoro-3-methoxy-phenyl)amino)-5-methyl-pyrimidin-4-yl)-N-(2-hydroxy-1-phenylethyl)-1H-pyrrole-3-carboxamide | 1HNMR (400 MHz, DMSO-d$_6$): δ 9.75 (s, 1H), 8.49 (s, 1H), 8.28 (d, J = 8 Hz, 1H), 8.09 (s, 1H), 7.82-7.80 (m, 1H), 7.48 (s, 1H), 7.38-7.08 (m, 7H), 6.82 (s, 1H), 5.09-5.03 (m, 1H), 4.92-4.89 (m, 1H), 3.81 (s, 3H), 3.66 (s, 2H), 2.34 (s, 3H) | 3 |

TABLE 1-continued

| Cmpd # | Structure | Name | NMR data | Scheme # |
|---|---|---|---|---|
| 155 | 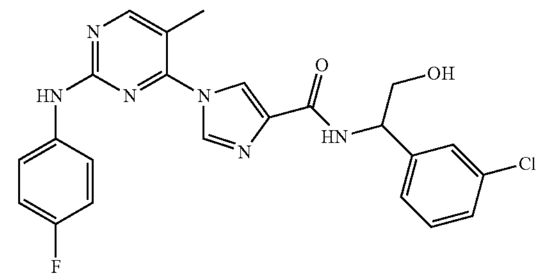 [SMILES: Cc1cnc(Nc2ccc(F)cc2)nc1-n1cnc(C(=O)NC(CO)c2cccc(Cl)c2)c1] | N-(1-(3-chlorophenyl)-2-hydroxy-ethyl)-1-(2-((4-fluoro-phenyl)amino)-5-methyl-pyrimidin-4-yl)-1H-imidazole-4-carboxamide | 1HNMR (400 MHz, DMSO-$d_6$): δ 9.81 (s, 1H), 8.54 (s, 1H), 8.42 (d, J = 8 Hz, 1H), 8.35 (s, 1H), 8.17 (s, 1H), 7.69 (m, 2H), 7.44 (s, 1H), 7.33 (s, 2H), 7.29 (s, 1H), 7.12 (t, J = 8.4 Hz, 2H), 5.04 (s, 2H), 3.73 (s, 2H), 2.27 (s, 3H) | 6 |
| 156 | 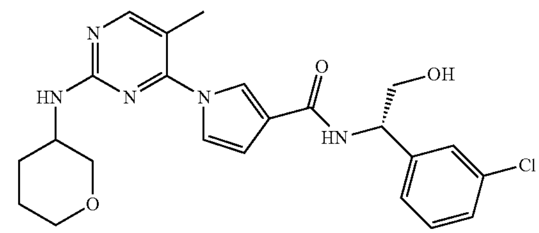 [SMILES: Cc1cnc(NC2CCCOC2)nc1-n1ccc(C(=O)N[C@H](CO)c2cccc(Cl)c2)c1] | N-((S)-1-(3-chloro-phenyl)-2-hydroxy-ethyl)-1-(5-methyl-2-((tetrahydro-2H-pyran-3-yl)amino)-pyrimidin-4-yl)-1H-pyrrole-3-carboxamide | 1HNMR (400 MHz, DMSO-$d_6$): δ 8.25 (t, J = 4.8 Hz, 2H), 7.95 (s, 1H), 7.42 (s, 1H), 7.37 (s, 1H), 7.33 (d, J = 6.4 Hz, 1H), 7.27 (d, J = 3.4 Hz, 2H), 7.10 (d, J = 7.6 Hz, 1H), 6.74 (s, 1H), 5.05-5.00 (m, 1H), 4.93 (t, J = 5.6 Hz, 1H), 3.84 (d, J = 8.0 Hz, 2H), 3.72 (d, J = 10.8 Hz, 1H), 3.67-3.63 (m, 1H), 3.08 (t, J = 10.4 Hz, 1H), 2.22 (s, 3H), 1.94 (s, 1H), 1.66 (s, 1H), 1.53 (d, J = 8.8 Hz, 2H) | 3 |
| 157 | 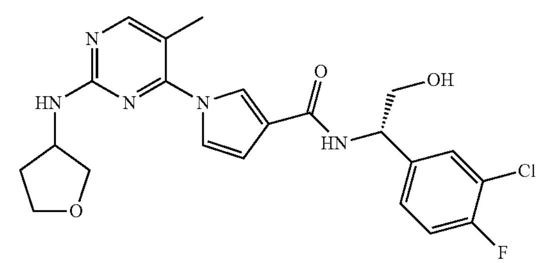 [SMILES: Cc1cnc(NC2CCOC2)nc1-n1ccc(C(=O)N[C@H](CO)c2ccc(F)c(Cl)c2)c1] | N-((S)-1-(3-chloro-4-fluorophenyl)-2-hydroxy-ethyl)-1-(5-methyl-2-((tetrahydro-furan-3-yl)amino)pyrimidin-4-yl)-1H-pyrrole-3-carboxamide | 1HNMR (400 MHz, DMSO-$d_6$): δ 8.28-8.23 (m, 2H), 7.95 (s, 1H), 7.56 (d, J = 8.4 Hz, 1H), 7.45 (d, J = 5.6 Hz, 1H), 7.39-7.32 (m, 3H), 5.05-4.99 (m, 1H), 4.94 (s, 1H), 4.36 (br s, 1H), 3.89-3.80 (m, 2H), 3.70-3.64 (m, 3H), 3.53 (s, 1H), 2.23 (s, 3H), 2.15-2.10 (m, 1H), 1.82 (d, J = 6.0 Hz, 1H) | 3 |
| 158 | 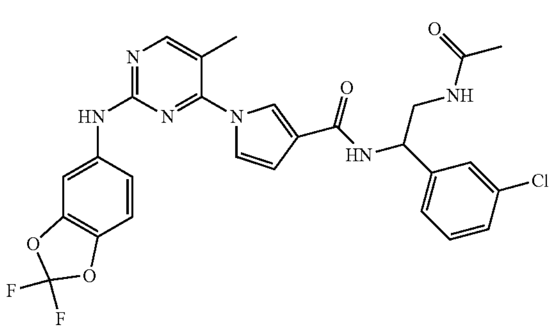 [SMILES: CC(=O)NCC(NC(=O)c1ccn(-c2nc(Nc3ccc4c(c3)OC(F)(F)O4)ncc2C)c1)c1cccc(Cl)c1] | N-(2-acetamido-1-(3-chloro-phenyl)-ethyl)-1-(2-((2,2-difluoro-benzo[d][1,3]dioxol-5-yl)amino)-5-methyl-pyrimidin-4-yl)-1H-pyrrole-3-carboxamide | 1HNMR (400 MHz, DMSO-$d_6$): δ 9.90 (s, 1H), 8.5 (s, 1H), 8.44 (d, J = 8.4 Hz, 1H), 8.03 (s, 1H), 7.98 (s, 1H), 7.91 (s, 1H), 7.46 (s, 1H), 7.41 (d, J = 11.2 Hz, 2H), 7.35-7.30 (m, 4H), 6.75 (s, 1H), 5.0 (br s, 1H), 3.47 (br s, 2H), 2.32 (s, 3H), 1.77 (s, 3H) | 4, 19 |

TABLE 1-continued

| Cmpd # | Structure | Name | NMR data | Scheme # |
|---|---|---|---|---|
| 159 | 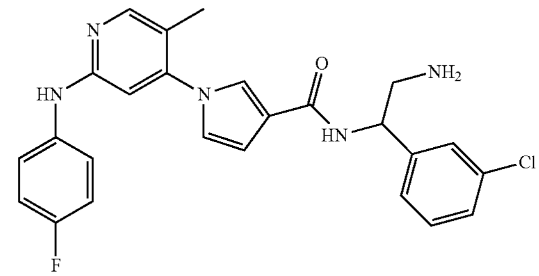 [SMILES: Cc1cnc(Nc2ccc(F)cc2)cc1-n1ccc(C(=O)NC(CN)c2cccc(Cl)c2)c1] | N-(2-amino-1-(3-chloro-phenyl)ethyl)-1-(2-((4-fluoro-phenyl)amino)-5-methyl-pyridin-4-yl)-1H-pyrrole-3-carboxamide | 1HNMR (400 MHz, DMSO-d$_6$): δ 9.07 (s, 1H), 8.15-8.12 (m, 2H), 7.67-7.61 (m, 3H), 7.39 (s, 1H), 7.36-7.26 (m, 3H), 7.09-7.06 (m, 3H), 6.75 (s, 1H), 6.69 (s, 1H), 4.90 (d, J = 6.8 Hz, 1H), 2.84 (d, J = 7.2 Hz, 2H), 1.88 (br s, 2H), 2.14 (s, 3H) | 9 |
| 160 | 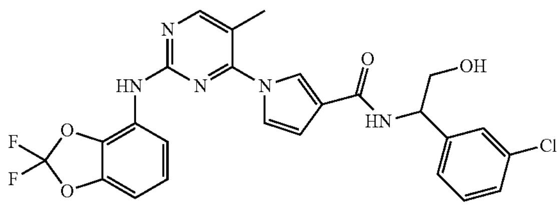 [SMILES: Cc1cnc(Nc2cccc3c2OC(F)(F)O3)nc1-n1ccc(C(=O)NC(CO)c2cccc(Cl)c2)c1] | N-(1-(3-chloro-phenyl)-2-hydroxy-ethyl)-1-(2-((2,2-difluoro-benzo[d][1,3]dioxol-4-yl)amino)-5-methyl-pyrimidin-4-yl)-1H-pyrrole-3-carboxamide | 1HNMR (400 MHz, DMSO-d$_6$): δ 9.71 (s, 1H), 8.46 (s, 1H), 8.25 (d, J = 7.6 Hz, 1H), 7.98 (s, 1H), 7.41 (s, 2H), 7.34-7.29 (m, 4H), 7.16 (t, J = 8 Hz, 2H), 6.77 (s, 1H), 5.02 (d, J = 6.8 Hz, 1H), 4.93 (s, 1H), 3.65 (s, 2H), 2.33 (s, 3H) | 3 |
| 161 | 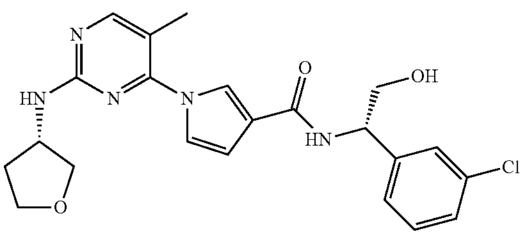 | N-((S)-1-(3-chlorophenyl)-2-hydroxy-ethyl)-1-(5-methyl-2-(((S)-tetra-hydrofuran-3-yl)amino)pyrimidin-4-yl)-1H-pyrrole-3-carboxamide | 1HNMR (400 MHz, DMSO-d$_6$): δ 8.28 (s, 1H), 8.24 (d, J = 8.4 Hz, 1H), 7.96 (s, 1H), 7.46-7.39 (m, 3H), 7.36-7.28 (m, 3H), 6.75 (s, 1H), 5.02 (t, J = 6.8 Hz, 1H), 4.93 (s, 1H), 4.37 (br s, 1H), 3.89-3.79 (m, 2H), 3.72-3.66 (m, 3H), 3.54-3.51 (m, 1H), 2.18 (s, 3H), 2.16-2.09 (m, 1H), 1.89-1.86 (m, 1H) | 3 |
| 162 | 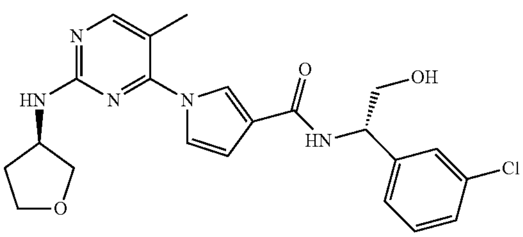 [SMILES: Cc1cnc(N[C@@H]2CCOC2)nc1-n1ccc(C(=O)N[C@H](CO)c2cccc(Cl)c2)c1] | N-((S)-1-(3-chlorophenyl)-2-hydroxy-ethyl)-1-(5-methyl-2-(((R)-tetra-hydrofuran-3-yl)amino)pyrimidin-4-yl)-1H-pyrrole-3-carboxamide | 1HNMR (400 MHz, DMSO-d$_6$): δ 8.28 (s, 1H), 8.24 (d, J = 8.0 Hz, 1H), 7.96 (s, 1H), 7.46-7.39 (m, 3H), 7.34-7.28 (m, 3H), 6.75 (s, 1H), 5.03 (d, J = 6.8 Hz, 1H), 4.93 (s, 1H), 4.37 (br s, 1H), 3.89-3.79 (m, 2H), 3.72-3.66 (m, 3H), 3.53 (t, J = 4.0 Hz, 1H), 2.15 (s, 3H), 2.16-2.09 (m, 1H), 1.87 (t, J = 6.4 Hz, 1H) | 3 |
| 163 | 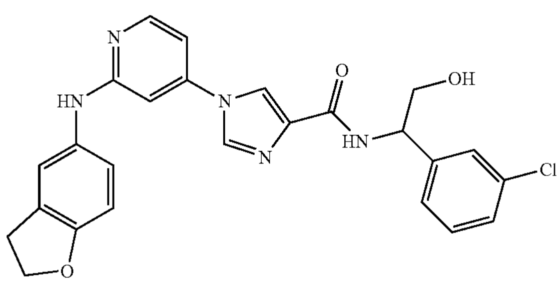 [SMILES: O=C(NC(CO)c1cccc(Cl)c1)c1cn(-c2ccnc(Nc3ccc4c(c3)CCO4)c2)cn1] | N-(1-(3-chloro-phenyl)-2-hydroxy-ethyl)-1-(2-((2,3-dihydro-benzofuran-5-yl)amino)pyridin-4-yl)-1H-imidazole-4-carboxamide | 1HNMR (400 MHz, DMSO-d$_6$): δ 8.88 (s, 1H), 8.42-8.37 (m, 2H), 8.20-8.16 (m, 2H), 7.51 (s, 1H), 7.42 (s, 1H), 7.32-7.28 (m, 4H), 7.21 (d, J = 8.4 Hz, 1H), 7.05 (d, J = 4.8 Hz, 1H), 6.88 (s, 1H), 6.8 (d, J = 8.4 Hz, 1H), 5.02 (br s, 2H), 4.47 (t, J = 8.8 Hz, 2H), | 13 |

TABLE 1-continued

| Cmpd # | Structure | Name | NMR data | Scheme # |
|---|---|---|---|---|
| | | | 3.72 (s, 2H), 3.15 (t, J = 8.4 Hz, 2H) | |
| 164 | 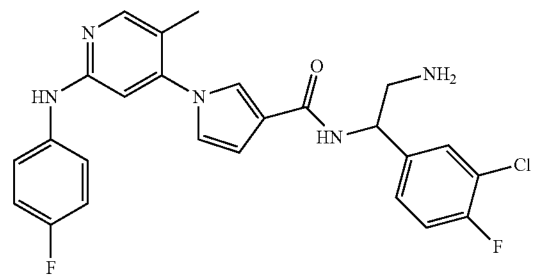 [SMILES: Cc1cnc(Nc2ccc(F)cc2)cc1-n1ccc(C(=O)NC(CN)c2ccc(F)c(Cl)c2)c1] | N-(2-amino-1-(3-chloro-4-fluoro-phenyl)ethyl)-1-(2-((4-fluorophenyl)amino)-5-methyl-pyridin-4-yl)-1H-pyrrole-3-carboxamide | 1HNMR (400 MHz, DMSO-d<sub>6</sub>): δ 9.08 (s, 1H), 8.15-8.12 (m, 2H), 7.66-7.14 (m, 3H), 7.54 (d, J = 6.8 Hz, 1H), 7.34 (d, J = 7.2 Hz, 2H), 7.09-7.06 (m, 3H), 6.74 (s, 1H), 6.68 (s, 1H), 4.89 (d, J = 7.2 Hz, 1H), 2.82 (s, 2H), 2.14 (s, 3H) | 11 |
| 165 | 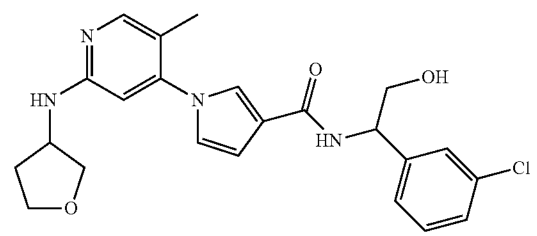 [SMILES: Cc1cnc(NC2CCOC2)cc1-n1ccc(C(=O)NC(CO)c2cccc(Cl)c2)c1] | N-(1-(3-chloro-phenyl)-2-hydroxy-ethyl)-1-(5-methyl-2-((tetra-hydrofuran-3-yl)amino)pyridin-4-yl)-1H-pyrrole-3-carboxamide | 1HNMR (400 MHz, DMSO-d<sub>6</sub>): δ 8.11 (d, J = 8 Hz, 1H), 7.96 (s, 1H), 7.58 (s, 1H), 7.42 (s, 1H), 7.35-7.26 (m, 3H), 7.02 (s, 1H), 6.76 (d, J = 6 Hz, 1H), 6.71 (s, 1H), 6.38 (s, 1H), 5.05-4.99 (m, 1H), 4.91 (t, J = 5.6 Hz, 1H), 4.35 (d, J = 5.2 Hz, 1H), 3.86-3.77 (m, 2H), 3.72-3.62 (m, 3H), 3.50-3.28 (m, 1H), 2.19-2.14 (m, 1H), 2.05 (s, 3H), 1.79-1.71 (m, 1H) | 11 |
| 166 | 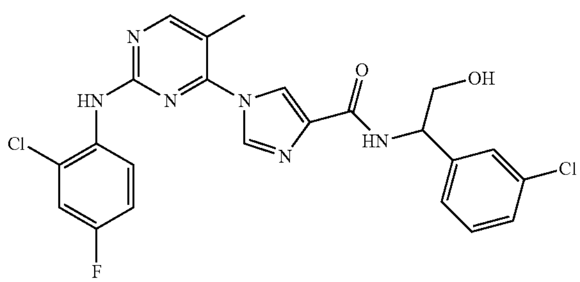 [SMILES: Cc1cnc(Nc2ccc(F)cc2Cl)nc1-n1cnc(C(=O)NC(CO)c2cccc(Cl)c2)c1] | 1-(2-((2-chloro-4-fluorophenyl)amino)-5-methyl-pyrimidin-4-yl)-N-(1-(3-chlorophenyl)-2-hydroxy-ethyl)-1H-imidazole-4-carboxamide | 1HNMR (400 MHz, DMSO-d<sub>6</sub>): δ 9.18 (s, 1H), 8.47 (s, 1H), 8.39 (d, J = 8 Hz, 1H), 8.27 (s, 1H), 8.08 (s, 1H), 7.65 (t, J = 6.4 Hz, 1H), 7.48 (d, J = 8.4 Hz, 1H), 7.42 (s, 1H), 7.28 (s, 3H), 7.22 (t, J = 8.4 Hz, 1H), 5.02 (d, J = 5.2 Hz, 2H), 3.71 (d, J = 5.2 Hz, 2H), 2.25 (s, 3H) | 6 |
| 167 | 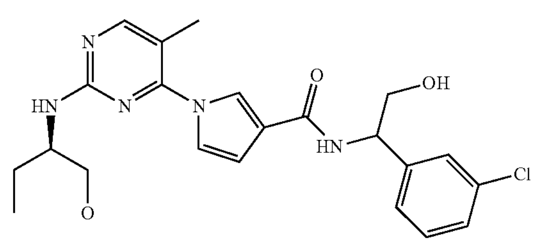 [SMILES: CC[C@H](CO)Nc1ncc(C)c(-n2ccc(C(=O)NC(CO)c3cccc(Cl)c3)c2)n1] | N-(1-(3-chloro-phenyl)-2-hydroxy-ethyl)-1-(2-(((R)-1-hydroxy-butan-2-yl)amino)-5-methyl-pyrimidin-4-yl)-1H-pyrrole-3-carboxamide | 1HNMR (400 MHz, DMSO-d<sub>6</sub>): δ 8.24 (d, J = 6.4 Hz, 1H), 7.94 (s, 1H), 7.42 (s, 1H), 7.38 (s, 1H), 7.32-7.26 (m, 3H), 6.79 (d, J = 8 Hz, 1H), 7.74 (s, 1H), 5.05-5.0 (m, 1H), 4.92 (t, J = 6 Hz, 1H), 4.56 (t, J = 5.6 Hz, 1H), 3.82 (d, J = 5.2 Hz, 2H), 3.66-6.63 (m, 1H), 3.46-3.42 (m, 1H), 3.37-3.28 (m, 1H), 2.21 (s, 3H), 1.68-1.61 (m, 1H), 1.45-1.38 (m, 1H), 0.86 (t, J = 7.6 Hz, 1H) | 3 |

TABLE 1-continued

| Cmpd # | Structure | Name | NMR data | Scheme # |
|---|---|---|---|---|
| 168 | 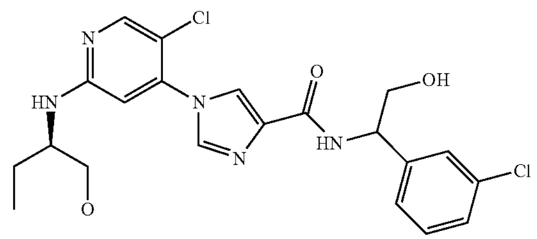 [SMILES: CC[C@H](CO)Nc1cc(-n2cnc(C(=O)NC(CO)c3cccc(Cl)c3)c2)c(Cl)cn1] | 1-(5-chloro-2-(((R)-1-hydroxy-butan-2-yl)amino)pyridin-4-yl)-N-(1-(3-chlorophenyl)-2-hydroxy-ethyl)-1H-imidazole-4-carboxamide | 1HNMR (400 MHz, DMSO-d$_6$): δ 8.37 (d, J = 8 Hz, 1H), 8.14 (t, J = 10.4 Hz, 1H), 8.07 (d, J = 8.4 Hz, 1H), 7.93 (s, 1H), 7.50 (s, 1H), 7.36-7.28 (m, 4H), 6.82 (d, J = 8 Hz, 1H), 6.65 (s, 1H), 5.01 (t, J = 5.6 Hz, 2H), 4.62 (t, J = 5.2 Hz, 1H), 3.76 (s, 1H), 3.71 (t, J = 5.2 Hz, 2H), 3.47-3.44 (m, 1H), 1.68-1.62 (m, 1H), 1.44-1.37 (m, 1H), 1.22 (s, 2H), 0.88-0.85 (m, 3H) | 10 |
| 169 | 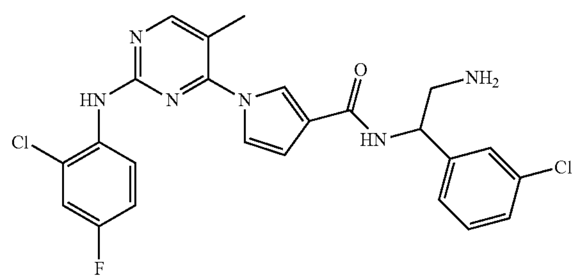 | N-(2-amino-1-(3-chloro-phenyl)ethyl)-1-(2-((2-chloro-4-fluorophenyl)amino)-5-methyl-pyrimidin-4-yl)-1H-pyrrole-3-carboxamide | 1HNMR (400 MHz, DMSO-d$_6$): δ 8.99 (s, 1H), 8.4 (s, 2H), 7.93 (s, 1H), 7.66 (t, J = 6.4 Hz, 1H), 7.45-7.36 (m, 6H), 7.23-7.20 (m, 1H), 6.75 (s, 1H), 5.22 (s, 1H), 3.18 (s, 2H), 2.96 (s, 2H), 2.28 (s, 3H) | 4 |
| 170 | 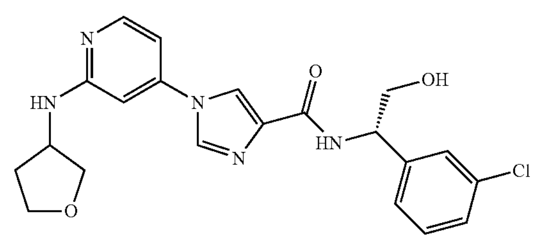 [SMILES: O=C(N[C@H](CO)c1cccc(Cl)c1)c1cn(-c2ccnc(NC3CCOC3)c2)cn1] | N-((S)-1-(3-chlorophenyl)-2-hydroxy-ethyl)-1-(2-((tetrahydro-furan-3-yl)amino)pyridin-4-yl)-1H-imidazole-4-carboxamide | 1HNMR (400 MHz, DMSO-d$_6$): δ 8.41 (s, 1H), 8.37 (d, J = 8 Hz, 1H), 8.21 (s, 1H), 8.06 (d, J = 4 Hz, 1H), 7.42 (s, 1H), 7.32-7.26 (m, 3H), 6.95-6.91 (m, 2H), 6.71 (s, 1H), 5.04-4.98 (m, 2H), 4.39 (s, 1H), 3.89-3.81 (m, 2H), 3.71 (t, J = 8 Hz, 3H), 3.55-3.50 (m, 1H), 2.21-2.14 (m, 1H), 1.81-1.79 (m, 1H) | 13 |
| 171 | 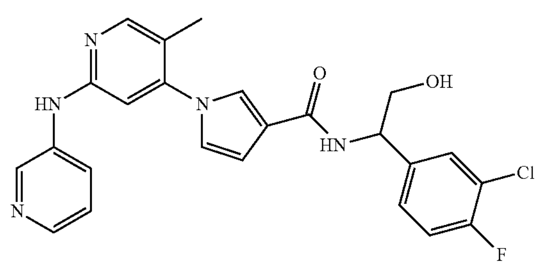 [SMILES: Cc1cnc(Nc2cccnc2)cc1-n1ccc(C(=O)NC(CO)c2ccc(F)c(Cl)c2)c1] | N-(1-(3-chloro-4-fluorophenyl)-2-hydroxy-ethyl)-1-(5-methyl-2-(pyridin-3-ylamino)pyridin-4-yl)-1H-pyrrole-3-carboxamide | 1HNMR (400 MHz, DMSO-d$_6$): δ 9.27 (s, 1H), 8.75 (s, 1H), 8.16 (d, J = 10.4 Hz, 3H), 8.09 (d, J = 4 Hz, 1H), 7.67 (s, 1H), 7.57 (d, J = 6.8 Hz, 1H), 7.34 (t, J = 8.8 Hz, 2H), 7.29-7.26 (m, 1H), 7.11 (s, 1H), 6.76 (s, 2H), 5.02 (t, J = 6.8 Hz, 1H), 4.93 (t, J = 6 Hz, 1H), 3.66-3.62 (m, 2H), 2.16 (s, 3H) | 11, 3 |

TABLE 1-continued

| Cmpd # | Structure | Name | NMR data | Scheme # |
|---|---|---|---|---|
| 172 | 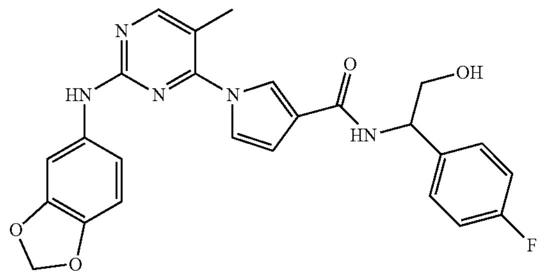 [SMILES: Cc1cnc(Nc2ccc3c(c2)OCO3)nc1-n1ccc(C(=O)NC(CO)c2ccc(F)cc2)c1] | 1-(2-(benzo[d][1,3]dioxol-5-ylamino)-5-methyl-pyrimidin-4-yl)-N-(1-(4-fluorophenyl)-2-hydroxy-ethyl)-1H-pyrrole-3-carboxamide | 1HNMR (400 MHz, DMSO-$d_6$): δ 9.54 (s, 1H), 8.43 (s, 1H), 8.23 (d, J = 8.4 Hz, 1H), 7.99 (s, 1H), 7.41 (s, 4H), 7.12 (t, J = 9.2 Hz, 3H), 6.82 (d, J = 8.4 Hz, 1H), 6.78 (d, J = 8.4 Hz, 1H), 5.94 (s, 2H), 5.04 (d, J = 7.2 Hz, 1H), 4.88 (t, J = 5.6 Hz, 1H), 3.65 (d, J = 6.4 Hz, 2H), 2.29 (s, 3H) | 3 |
| 173 | 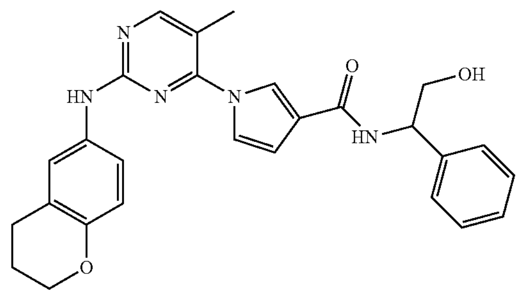 [SMILES: Cc1cnc(Nc2ccc3c(c2)CCCO3)nc1-n1ccc(C(=O)NC(CO)c2ccccc2)c1] | 1-(2-(chroman-6-ylamino)-5-methyl-pyrimidin-4-yl)-N-(2-hydroxy-1-phenylethyl)-1H-pyrrole-3-carboxamide | 1HNMR (400 MHz, DMSO-$d_6$): δ 9.37 (s, 1H), 8.39 (s, 1H), 8.23 (d, J = 8 Hz, 1H), 8.04 (s, 1H), 7.43 (d, J = 12 Hz, 2H), 7.36 (d, J = 8 Hz, 2H), 7.30 (d, J = 8 Hz, 3H), 7.20 (d, J = 8 Hz, 1H), 6.77 (s, 1H), 6.64 (d, J = 8 Hz, 1H), 5.04 (d, J = 8 Hz, 1H), 4.85 (s, 1H), 4.07-4.0 (m, 2H), 3.65 (s, 2H), 2.72 (s, 2H), 2.29 (s, 3H), 1.88 (s, 2H) | 3 |
| 174 | 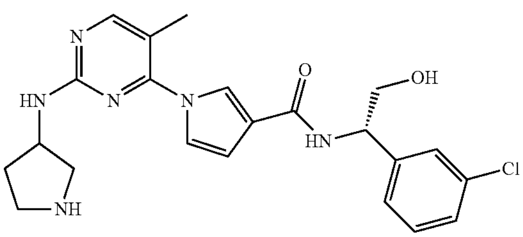 [SMILES: Cc1cnc(NC2CCNC2)nc1-n1ccc(C(=O)N[C@H](CO)c2cccc(Cl)c2)c1] | N-((S)-1-(3-chlorophenyl)-2-hydroxy-ethyl)-1-(5-methyl-2-(pyrrolidin-3-ylamino)pyrimidin-4-yl)-1H-pyrrole-3-carboxamide | 1HNMR (400 MHz, DMSO-$d_6$): δ 8.27 (s, 1H), 8.24 (d, J = 8.0 Hz, 1H), 7.95 (s, 1H), 7.41 (d, J = 11.2 Hz, 2H), 7.30 (d, J = 12 Hz, 4H), 6.75 (s, 1H), 5.02 (d, J = 6.8 Hz, 1H), 4.93 (s, 1H), 4.25 (s, 1H), 3.65 (s, 3H), 3.03-2.94 (m, 2H), 2.81-2.65 (m, 2H), 2.22 (s, 3H), 2.01-1.99 (m, 1H), 1.77-1.61 (m, 1H) | 3 |
| 175 | 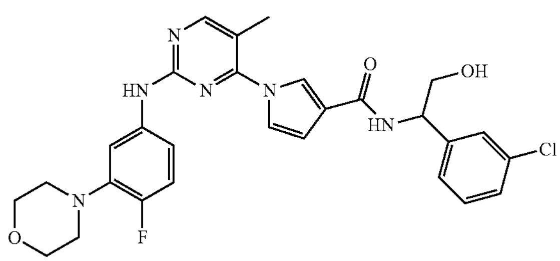 [SMILES: Cc1cnc(Nc2ccc(F)c(N3CCOCC3)c2)nc1-n1ccc(C(=O)NC(CO)c2cccc(Cl)c2)c1] | N-(1-(3-chloro-phenyl)-2-hydroxy-ethyl)-1-(2-((4-fluoro-3-morpholino-phenyl)amino)-5-methyl-pyrimidin-4-yl)-1H-pyrrole-3-carboxamide | 1HNMR (400 MHz, DMSO-$d_6$): δ 9.63 (s, 1H), 8.46 (s, 1H), 8.27 (d, J = 8.0 Hz, 1H), 8.0 (s, 1H), 7.60 (d, J = 7.2 Hz, 1H), 7.45 (d, J = 12 Hz, 2H), 7.32 (s, 2H), 7.28-7.22 (m, 2H), 7.03 (t, J = 12.4 Hz, 1H), 6.80 (s, 1H), 5.04 (d, J = 7.2 Hz, 1H), 4.93 (t, J = 5.2 Hz, 1H), 3.67 (t, J = 13.6 Hz, 6H), 2.97 (s, 4H), 2.31 (s, 3H) | 3 |

TABLE 1-continued

| Cmpd # | Structure | Name | NMR data | Scheme # |
|---|---|---|---|---|
| 176 | 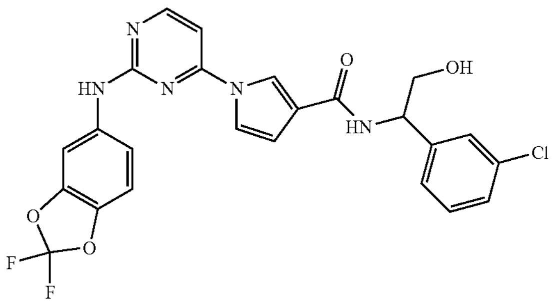 [SMILES: O=C(NC(CO)c1cccc(Cl)c1)c1ccn(-c2ccnc(Nc3ccc4c(c3)OC(F)(F)O4)n2)c1] | N-(1-(3-chloro-phenyl)-2-hydroxy-ethyl)-1-(2-((2,2-difluoro-benzo[d][1,3]dioxol-5-yl)amino)-pyrimidin-4-yl)-1H-pyrrole-3-carboxamide | 1HNMR (400 MHz, DMSO-d₆): δ 9.95 (s, 1H), 8.44 (d, J = 5.6 Hz, 1H), 8.32 (d, J = 7.6 Hz, 1H), 8.29 (s, 1H), 7.9 (s, 1H), 7.7 (s, 1H), 7.42 (br s, 2H), 7.34-7.28 (m, 4H), 7.2 (d, J = 5.6 Hz, 1H), 6.82 (s, 1H), 5.04-5.02 (m, 1H), 3.70-3.60 (m, 3H) | 3 |
| 177 | 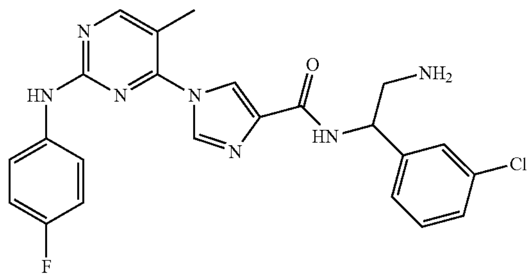 | N-(2-amino-1-(3-chlorophenyl)ethyl)-1-(2-((4-fluoro-phenyl)amino)-5-methyl-pyrimidin-4-yl)-1H-imidazole-4-carboxamide | 1HNMR (400 MHz, DMSO-d₆): δ 9.8 (s, 1H), 8.91 (d, J = 8.4 Hz, 1H), 8.54 (s, 1H), 8.34 (s, 1H), 8.15 (s, 1H), 7.84 (br s, 2H), 7.68 (s, 2H), 7.52 (s, 1H), 7.39 (s, 3H), 7.71-7.68 (m, 2H), 7.11 (t, J = 8.8 Hz, 2H), 4.93-4.92 (m, 1H), 2.91-2.87 (m, 1H), 2.26 (s, 3H) | 4 |
| 178 | 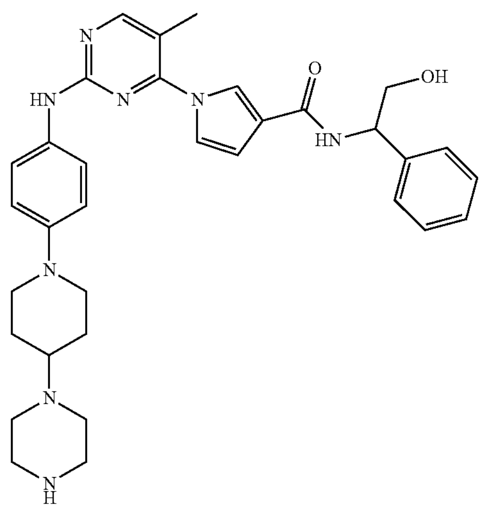 [SMILES: Cc1cnc(Nc2ccc(N3CCC(N4CCNCC4)CC3)cc2)nc1-n1ccc(C(=O)NC(CO)c2ccccc2)c1] | N-(2-hydroxy-1-phenylethyl)-1-(5-methyl-2-((4-(4-(piperazin-1-yl)-piperidin-1-yl)-phenyl)amino)pyrimidin-4-yl)-1H-pyrrole-3-carboxamide | 1HNMR (400 MHz, DMSO-d₆): δ 9.38 (s, 1H), 8.38 (s, 1H), 8.23 (d, J = 8.0 Hz, 1H), 8.00 (s, 1H), 7.51 (d, J = 8.8 Hz, 2H), 7.41 (s, 1H), 7.36 (d, J = 7.6 Hz, 2H), 7.30 (t, J = 7.6 Hz, 2H), 7.21 (d, J = 6.8 Hz, 1H), 6.87 (d, J = 8.8 Hz, 2H), 6.78 (s, 1H), 5.04 (d, J = 7.2 Hz, 1H) 4.86 (s, 1H), 3.62 (t, J = 11.6 Hz, 4H), 2.92 (s, 4H), 2.58 (s, 6H), 2.28 (s, 3H), 1.79 (d, J = 10.8 Hz 3H), 1.49 (d, J = 10 Hz, 3H) | 3 |
| 179 | 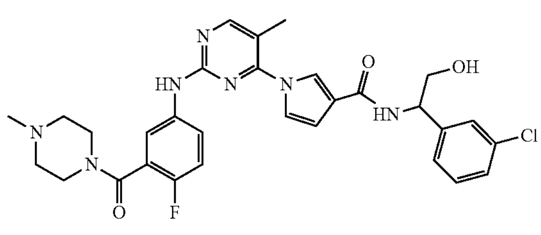 [SMILES: Cc1cnc(Nc2ccc(F)c(C(=O)N3CCN(C)CC3)c2)nc1-n1ccc(C(=O)NC(CO)c2cccc(Cl)c2)c1] | N-(1-(3-chlorophenyl)-2-hydroxy-ethyl)-1-(2-((4-fluoro-3-(4-methyl-piperazine-1-carbonyl)phenyl)amino)-5-methyl-pyrimidin-4-yl)-1H-pyrrole-3-carboxamide | 1HNMR (400 MHz, DMSO-d₆): δ 9.83 (s, 1H), 8.48 (s, 1H), 8.26 (d, J = 8 Hz, 1H), 8.01 (s, 1H), 7.74 (d, J = 6 Hz, 2H), 7.44 (d, J = 4.8 Hz, 2H), 7.32-7.28 (m, 3H), 7.19 (t, J = 9.2 Hz, 1H), 6.78 (s, 1H), 5.06-5.01 (m, 1H), 4.93 (t, J = 5.2 Hz, 1H), 3.65 (t, J = 5.2 Hz, 2H), 3.60 (br s, 2H), 3.23 (s, 2H), 2.32 (s, 5H), 2.21 (s, 2H), 2.15 (s, 3H) | 3 |

| Cmpd # | Structure | Name | NMR data | Scheme # |
|---|---|---|---|---|
| 180 | 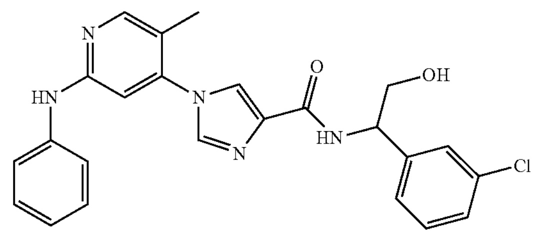 [SMILES: Cc1cnc(Nc2ccccc2)cc1-n1cnc(C(=O)NC(CO)c2cccc(Cl)c2)c1] | N-(1-(3-chloro-phenyl)-2-hydroxy-ethyl)-1-(5-methyl-2-(phenyl-amino)pyridin-4-yl)-1H-imidazole-4-carboxamide | 1HNMR (400 MHz, DMSO-$d_6$): δ 9.11 (s, 1H) 8.37 (d, J = 8 Hz, 1H), 8.17 (s, 1H), 8.09 (s, 1H), 7.99 (s, 1H), 7.61 (d, J = 8 Hz, 2H) 7.44 (s, 1H), 7.33 (s, 2H), 7.25 (t, J = 7.2 Hz, 3H), 6.88 (t, J = 6.8 Hz, 1H), 6.77 (s, 1H), 5.02 (t, J = 5.2 Hz, 2H), 3.72-3.71 (m, 2H), 2.07 (s, 3H) | 11 |
| 181 | 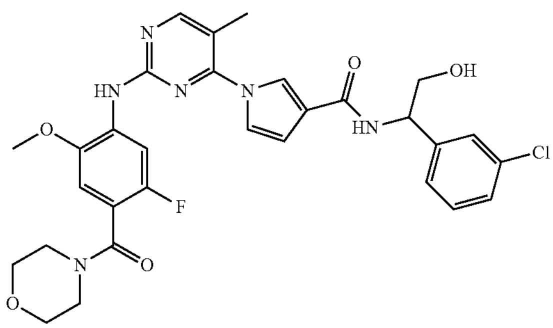 [SMILES: COc1cc(C(=O)N2CCOCC2)c(F)cc1Nc1ncc(C)c(-n2ccc(C(=O)NC(CO)c3cccc(Cl)c3)c2)n1] | N-(1-(3-chlorophenyl)-2-hydroxy-ethyl)-1-(2-((5-fluoro-2-methoxy-4-(morpholine-4-carbonyl)phenyl)amino)-5-methyl-pyrimidin-4-yl)-1H-pyrrole-3-carboxamide | 1HNMR (400 MHz, DMSO-$d_6$): δ 8.55 (s, 1H), 8.30 (d, J = 10.4 Hz, 2H), 8.23 (d, J = 12 Hz, 1H), 8.08 (s, 1H), 7.49 (s, 1H), 7.42 (s, 1H), 7.32 (s, 2H), 7.28 (s, 1H), 7.02 (d, J = 6 Hz, 1H), 6.79 (s, 1H), 5.04 (d, J = 7.2 Hz, 1H), 4.93 (t, J = 5.2 Hz, 1H), 3.88 (s, 3H), 3.71-3.62 (m, 7H), 3.53 (br s, 3H), 2.30 (s, 3H) | 3 |
| 182 | 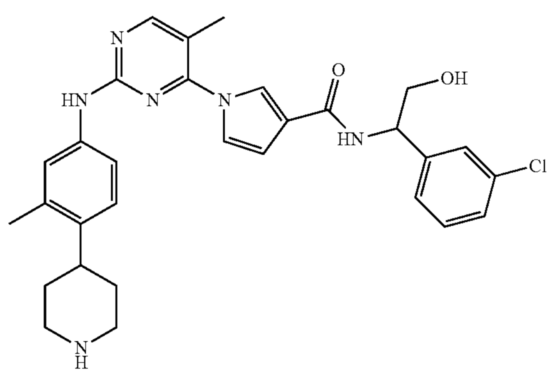 [SMILES: Cc1cc(Nc2ncc(C)c(-n3ccc(C(=O)NC(CO)c4cccc(Cl)c4)c3)n2)ccc1C1CCNCC1] | N-(1-(3-chloro-phenyl)-2-hydroxy-ethyl)-1-(5-methyl-2-((3-methyl-4-(piperidin-4-yl)phenyl)amino)pyrimidin-4-yl)-1H-pyrrole-3-carboxamide | 1HNMR (400 MHz, DMSO-$d_6$): δ 9.50 (s, 1H), 8.43 (s, 1H), 8.29 (d, J = 8 Hz, 1H), 8.06 (s, 1H), 7.51 (s, 1H), 7.5 (s, 1H), 7.47 (s, 1H), 7.43 (d, J = 5.6 Hz, 1H), 7.33 (d, J = 6 Hz, 2H), 7.28 (d, J = 6 Hz, 1H), 7.07 (d, J = 8.4 Hz, 1H), 6.78 (s, 1H), 5.06-5.01 (m, 1H), 4.93 (br s, 1H), 3.65 (br s, 2H), 3.36 (d, J = 7.2 Hz, 1H), 3.08 (d, J = 12 Hz, 2H), 2.75-2.66 (m, 3H), 2.30 (s, 3H), 2.26 (s, 3H), 1.66-1.52 (m, 4H) | 3 |
| 183 | 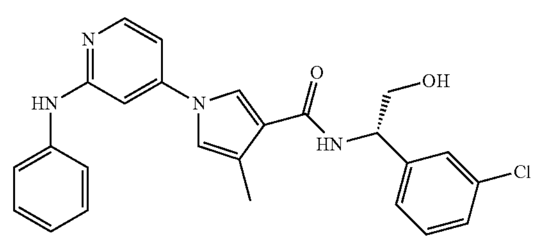 [SMILES: Cc1cn(-c2ccnc(Nc3ccccc3)c2)cc1C(=O)N[C@H](CO)c1cccc(Cl)c1] | (S)-N-(1-(3-chlorophenyl)-2-hydroxy-ethyl)-4-methyl-1-(2-(phenylamino)pyridin-4-yl)-1H-pyrrole-3-carboxamide | 1HNMR (400 MHz, DMSO-$d_6$): δ 9.14 (s, 1H), 8.18 (d, J = 5.6 Hz, 1H), 8.09 (d, J = 10 Hz, 2H), 7.65 (d, J = 8.0 Hz, 2H), 7.42 (s, 1H), 7.33 (s, 2H), 7.26 (t, J = 8.0 Hz, 3H), 7.20 (s, 1H), 6.97 (t, J = 5.2 Hz, 1H), 6.88 (s, 2H), 4.99 (d, J = 7.2 Hz, 1H), 4.93 (t, J = 5.2 Hz, 1H), 3.63 (br s, 2H), 2.18 (s, 3H) | 7 |

TABLE 1-continued

| Cmpd # | Structure | Name | NMR data | Scheme # |
|---|---|---|---|---|
| 184 | 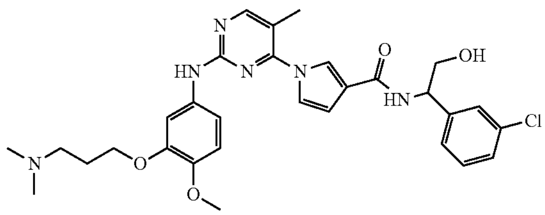 [SMILES: COc1ccc(Nc2ncc(C)c(-n3ccc(C(=O)NC(CO)c4cccc(Cl)c4)c3)n2)cc1OCCCN(C)C] | N-(1-(3-chloro-phenyl)-2-hydroxy-ethyl)-1-(2-((3-(3-(dimethyl-amino)propoxy)-4-methoxy-phenyl)amino)-5-methyl-pyrimidin-4-yl)-1H-pyrrole-3-carboxamide | 1HNMR (400 MHz, DMSO-d$_6$): δ 9.46 (s, 1H), 8.42 (s, 1H), 8.26 (d, J = 8 Hz, 1H), 8.0 (s, 1H), 7.52 (d, J = 2 Hz, 1H), 7.45-7.42 (m, 2H), 7.33 (m, 2H), 7.29-7.27 (m, 1H), 7.16-7.13 (m, 1H), 6.86 (d, J = 8.8 Hz, 1H), 6.8-6.79 (m, 1H), 5.06-5.01 (m, 1H), 4.93 (br s, 1H), 3.93 (t, J = 6.4 Hz, 2H), 3.69 (s, 3H), 3.65 (br s, 3H), 2.32-2.30 (m, 2H), 2.27 (s, 3H), 2.1 (s, 6H), 1.84-1.77 (m, 2H) | 3 |
| 185 | 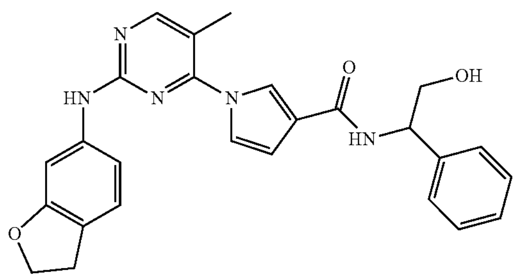 | 1-(2-((2,3-dihydrobenzo-furan-6-yl)amino)-5-methyl-pyrimidin-4-yl)-N-(2-hydroxy-1-phenylethyl)-1H-pyrrole-3-carboxamide | 1HNMR (400 MHz, DMSO-d$_6$): δ 9.57 (s, 1H), 8.44 (s, 1H), 8.22 (d, J = 8 Hz, 1H), 8.00 (s, 1H), 7.42 (s, 1H), 7.37-7.28 (m, 5H), 7.22-7.19 (m, 1H), 7.13-7.07 (m, 2H), 6.79 (s, 1H), 5.05 (m, 1H), 4.86 (t, J = 4 Hz, 1H), 4.48 (t, J = 8.4 Hz, 2H), 3.65 (m, 2H), 3.08 (t, J = 8.4 Hz, 2H), 2.30 (s, 3H) | 3 |
| 186 | 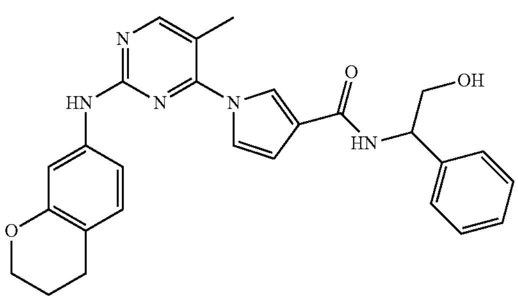 [SMILES: Cc1cnc(Nc2ccc3c(c2)OCCC3)nc1-n1ccc(C(=O)NC(CO)c2ccccc2)c1] | 1-(2-(chroman-7-ylamino)-5-methyl-pyrimidin-4-yl)-N-(2-hydroxy-1-phenylethyl)-1H-pyrrole-3-carboxamide | 1HNMR (400 MHz, DMSO-d$_6$): δ 9.51 (s, 1H), 8.44 (s, 1H), 8.22 (d, J = 8 Hz, 1H), 8.00 (s, 1H), 7.42 (t, J = 2.4 Hz, 1H), 7.37-7.35 (m, 2H), 7.30-7.28 (m, 2H), 7.22-7.21 (m, 2H), 7.14-7.12 (m, 1H), 6.91 (d, J = 8 Hz, 1H), 6.79 (br s, 1H), 5.07-5.02 (m, 1H), 4.86 (t, J = 6 Hz, 1H), 4.07 (t, J = 4.8 Hz, 2H), 3.67-3.62 (m, 2H), 2.64 (t, J = 8 Hz, 2H), 2.30 (s, 3H), 1.87 (t, J = 4 Hz, 2H), 1.21 (s, 2H) | 3 |
| 187 | 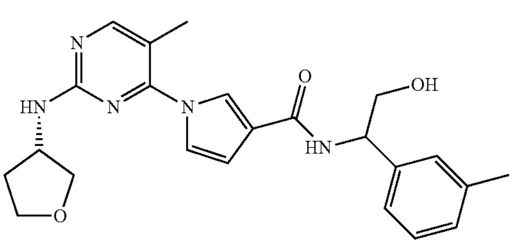 | N-(2-hydroxy-1-(m-tolyl)ethyl)-1-(5-methyl-2-(((S)-tetra-hydrofuran-3-yl)amino)pyrimidin-4-yl)-1H-pyrrole-3-carboxamide | 1HNMR (400 MHz, DMSO-d$_6$): δ 8.27 (s, 1H), 8.15 (d, J = 8 Hz, 1H), 7.94 (s, 1H), 7.43 (d, J = 4 Hz, 1H), 7.38 (s, 1H), 7.19-7.12 (m, 3H), 7.01 (d, J = 8.0 Hz, 1H), 6.74 (s, 1H), 5.02-4.97 (q, J = 8 Hz, 1H), 4.84-4.81 (t, J = 4 Hz, 1H), 4.36-4.35 (m, 1H), 3.89-3.78 (m, 2H), 3.72-3.63 (m, 3H), 3.54-3.51 | 3 |

TABLE 1-continued

| Cmpd # | Structure | Name | NMR data | Scheme # |
|---|---|---|---|---|
| | | | (m, 1H), 2.27 (s, 3H), 2.22 (s, 3H), 2.17-2.08 (m, 1H), 1.90-1.82 (m, 1H) | |
| 188 | 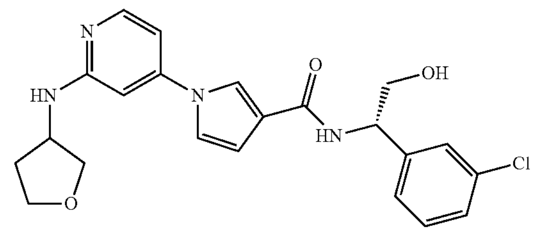 | N-((S)-1-(3-chlorophenyl)-2-hydroxy-ethyl)-1-(2-((tetrahydrofuran-3-yl)amino)pyridin-4-yl)-1H-pyrrole-3-carboxamide | 1HNMR (400 MHz, DMSO-d$_6$): δ 8.18 (d, J = 8 Hz, 1H), 8.02 (d, J = 5.6 Hz, 1H), 7.97 (s, 1H), 7.41 (s, 1H), 7.38 (s, 1H), 7.33-7.28 (m, 3H), 6.87 (d, J = 8 Hz, 1H), 6.78 (d, J = 4.4 Hz, 1H), 6.74 (s, 1H), 6.61 (s, 1H), 5.04-5.01 (m, 1H), 4.94-4.91 (m, 1H), 4.40 (br s, 1H), 3.91-3.81 (m, 2H), 3.79-3.67 (m, 3H), 3.52-3.46 (m, 1H), 2.20-2.12 (m, 1H), 1.78-1.77 (m, 1H) | 13 |
| 189 | 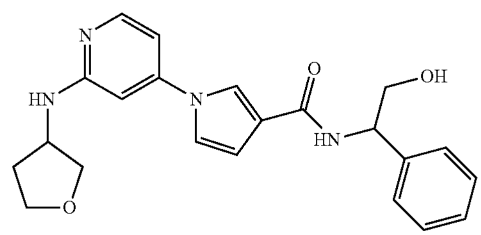 [SMILES: O=C(NC(CO)c1ccccc1)c1ccn(-c2ccnc(NC3CCOC3)c2)c1] | N-(2-hydroxy-1-phenylethyl)-1-(2-((tetrahydrofuran-3-yl)amino)pyridin-4-yl)-1H-pyrrole-3-carboxamide | 1HNMR (400 MHz, DMSO-d$_6$): δ 8.13 (d, J = 8 Hz, 1H), 8.02 (d, J = 5.6 Hz, 1H), 7.97 (s, 1H), 7.35 (d, J = 7.2 Hz, 3H), 7.29 (t, J = 6.8 Hz, 2H), 7.20 (t, J = 7.6 Hz, 1H), 6.87 (d, J = 6.8 Hz, 1H), 6.78 (d, J = 5.2 Hz, 1H), 6.74 (s, 1H), 6.60 (s, 1H), 5.05-5.02 (m, 1H), 5.0-4.85 (m, 1H), 4.38 (br s, 1H), 3.88-3.83 (m, 2H), 3.79-3.64 (m, 3H), 3.54-3.51 (m, 1H), 2.20-2.12 (m, 1H), 1.80-1.75 (m, 1H) | 13 |
| 190 | 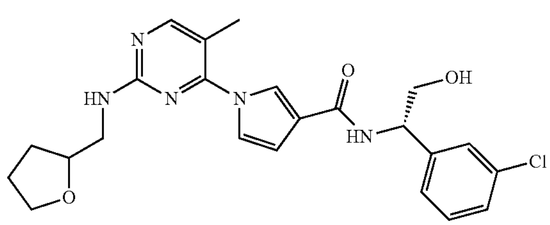 [SMILES: Cc1cnc(NCC2CCCO2)nc1-n1ccc(C(=O)N[C@H](CO)c2cccc(Cl)c2)c1] | N-((S)-1-(3-chlorophenyl)-2-hydroxy-ethyl)-1-(5-methyl-2-(((tetrahydrofuran-2-yl)methyl)amino)pyrimidin-4-yl)-1H-pyrrole-3-carboxamide | 1HNMR (400 MHz, DMSO-d$_6$): δ 8.24 (d, J = 6.4 Hz, 2H), 7.95 (s, 1H), 7.41 (s, 2H), 7.35-7.32 (m, 2H), 7.27 (d, J = 6.4 Hz, 1H), 7.14 (s, 1H), 6.65 (s, 1H), 5.05-5.03 (m, 1H), 4.92 (t, J = 6 Hz, 1H), 3.98-3.94 (m, 1H), 3.75-3.7 (m, 1H), 3.67-3.58 (m, 3H), 3.4-3.34 (m, 2H), 2.21 (s, 3H), 1.88-1.61 (m, 3H), 1.61-1.56 (m, 1H) | 3 |

TABLE 1-continued

| Cmpd # | Structure | Name | NMR data | Scheme # |
|---|---|---|---|---|
| 191 | 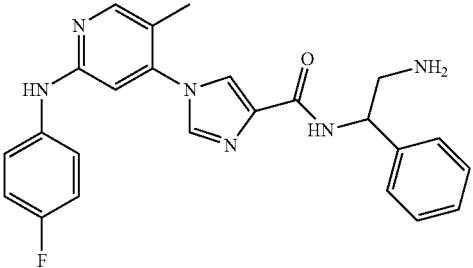 [SMILES: Cc1cnc(Nc2ccc(F)cc2)cc1-n1cnc(C(=O)NC(CN)c2ccccc2)c1] | N-(2-amino-1-phenylethyl)-1-(2-((4-fluorophenyl)amino)-5-methyl-pyridin-4-yl)-1H-imidazole-4-carboxamide | 1HNMR (400 MHz, DMSO-d$_6$): δ 9.14 (s, 1H), 8.45 (d, J = 8.4 Hz, 1H), 8.15 (s, 1H), 8.08 (s, 1H), 7.97 (s, 1H), 7.61 (t, J = 8.4 Hz, 2H), 7.37-7.29 (m, 4H), 7.24-7.22 (m, 1H), 7.11-7.06 (m, 2H), 6.72 (s, 1H), 4.98 (d, J = 5.2 Hz, 1H), 3.06-2.93 (m, 2H), 2.09 (s, 3H). | 11 |
| 192 | 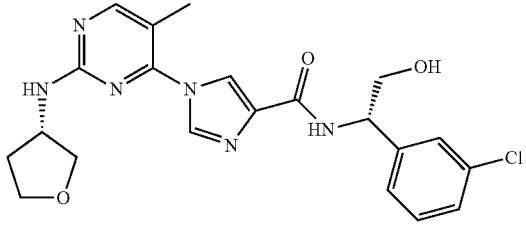 [SMILES: Cc1cnc(N[C@H]2CCOC2)nc1-n1cnc(C(=O)N[C@H](CO)c2cccc(Cl)c2)c1] | N-((S)-1-(3-chlorophenyl)-2-hydroxy-ethyl)-1-(5-methyl-2-(((S)-tetra-hydrofuran-3-yl)amino)pyrimidin-4-yl)-1H-imidazole-4-carboxamide | 1HNMR (400 MHz, DMSO-d$_6$): δ 8.38 (t, J = 8.4 Hz, 2H) 8.29 (s, 1H), 8.11 (s, 1H), 7.60 (d, J = 5.2 Hz, 1H), 7.43 (s, 1H), 7.31 (d, J = 15.6 Hz, 3H), 5.02 (d, J = 5.2 Hz, 2H), 4.34 (s, 1H), 3.87-3.78 (m, 2H), 3.72-3.67 (m, 3H), 3.55-3.28 (m, 1H), 2.19 (s, 3H), 2.19-2.08 (m, 1H), 1.89-1.85 (m, 1H) | 6 |
| 193 | 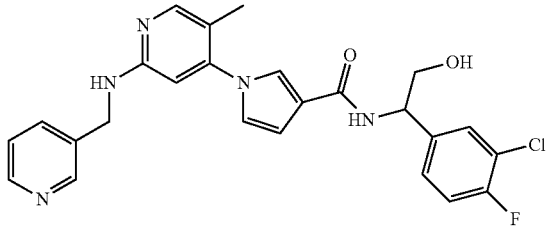 [SMILES: Cc1cnc(NCc2cccnc2)cc1-n1ccc(C(=O)NC(CO)c2ccc(F)c(Cl)c2)c1] | N-(1-(3-chloro-4-fluorophenyl)-2-hydroxy-ethyl)-1-(5-methyl-2-((pyridin-3-ylmethyl)amino)pyridin-4-yl)-1H-pyrrole-3-carboxamide | 1HNMR (400 MHz, DMSO-d$_6$): δ 8.53 (s, 1H), 8.40 (s, 1H), 8.10 (d, J = 8 Hz, 1H), 7.94 (s, 1H), 7.69 (d, J = 8 Hz, 1H), 7.56 (t, J = 8 Hz, 2H), 7.33 (t, J = 8 Hz, 3H), 7.14 (s, 1H), 7.01 (s, 1H), 6.69 (s, 1H), 6.43 (s, 1H), 5.01 (d, J = 8 Hz, 1H), 4.91 (s, 1H), 4.50 (d, J = 8 Hz, 2H), 3.63 (d, J = 4 Hz, 2H), 2.04 (s, 3H) | 11, 6 |
| 194 | 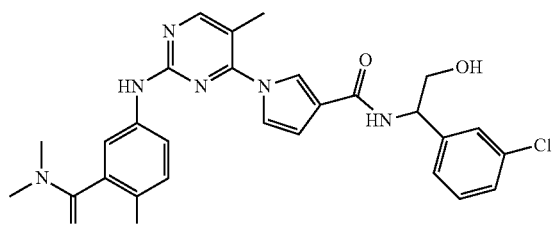 | N-(1-(3-chloro-phenyl)-2-hydroxy-ethyl)-1-(2-((3-(dimethyl-carbamoyl)-4-fluorophenyl)amino)-5-methyl-pyrimidin-4-yl)-1H-pyrrole-3-carboxamide | 1HNMR (400 MHz, DMSO-d$_6$): δ 9.82 (s, 1H), 8.48 (s, 1H), 8.26 (d, J = 8 Hz, 1H), 8.01 (s, 1H), 7.74-7.72 (m, 2H), 7.44 (d, J = 4.8 Hz, 2H), 7.34-7.29 (m, 2H), 7.28-7.27 (m, 1H), 7.20-7.18 (m, 1H), 6.79 (s, 1H), 5.06-5.01 (m, 1H), 4.93 (t, J = 5.2 Hz, 1H), 3.68-3.63 (m, 2H), 2.96 (s, 3H), 2.85 (s, 3H), 2.32 (s, 3H) | 3 |

TABLE 1-continued

| Cmpd # | Structure | Name | NMR data | Scheme # |
|---|---|---|---|---|
| 195 | 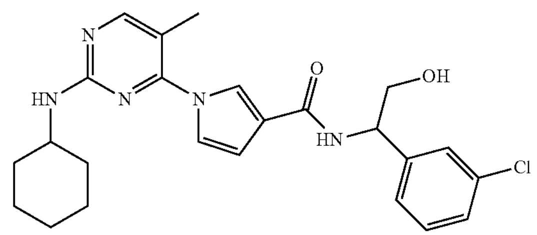 [SMILES: Cc1cnc(NC2CCCCC2)nc1-n1ccc(C(=O)NC(CO)c2cccc(Cl)c2)c1] | N-(1-(3-chlorophenyl)-2-hydroxy-ethyl)-1-(2-(cyclohexyl-amino)-5-methyl-pyrimidin-4-yl)-1H-pyrrole-3-carboxamide | 1HNMR (400 MHz, DMSO-d$_6$): δ 8.23 (s, 1H), 7.94 (s, 1H), 7.41 (s, 1H), 7.35-7.28 (m, 4H), 7.04 (d, J = 7.2 Hz, 1H), 6.73 (s, 1H), 5.05-5.01 (m, 1H), 4.91 (t, J = 5.6 Hz, 1H), 3.71-3.59 (m, 3H), 2.2 (s, 3H), 1.87-1.84 (m, 2H), 1.68-1.55 (m, 3H), 1.3-1.12 (m, 6H) | 3 |
| 196 | 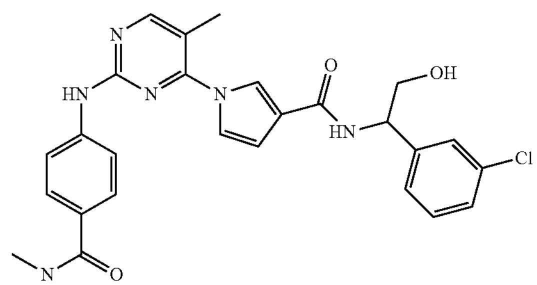 [SMILES: CNC(=O)c1ccc(Nc2ncc(C)c(-n3ccc(C(=O)NC(CO)c4cccc(Cl)c4)c3)n2)cc1] | N-(1-(3-chloro-phenyl)-2-hydroxy-ethyl)-1-(5-methyl-2-((4-(methyl-carbamoyl)phenyl)amino)pyrimidin-4-yl)-1H-pyrrole-3-carboxamide | 1HNMR (400 MHz, DMSO-d$_6$): δ 9.94 (s, 1H), 8.52 (s, 1H), 8.29 (d, J = 8.4 Hz, 1H), 8.2 (d, J = 4 Hz, 1H), 8.04 (s, 1H), 7.8-7.75 (m, 4H), 7.47 (s, 1H), 7.43 (s, 1H), 7.33-7.29 (m, 3H), 6.81 (s, 1H), 5.04 (d, J = 6.8 Hz, 1H), 4.94 (t, J = 5.6 Hz, 1H), 3.66 (d, J = 5.2 Hz, 2H), 2.74 (d, J = 4 Hz, 3H), 2.34 (s, 3H) | 3 |
| 197 | 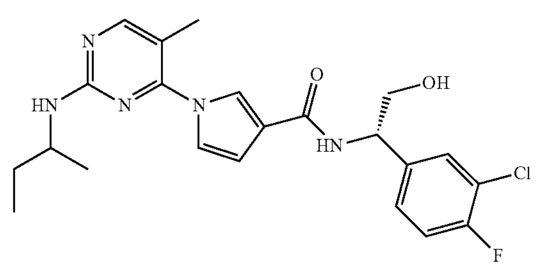 [SMILES: CCC(C)Nc1ncc(C)c(-n2ccc(C(=O)N[C@H](CO)c3ccc(F)c(Cl)c3)c2)n1] | 1-(2-(sec-butylamino)-5-methyl-pyrimidin-4-yl)-N-((S)-1-(3-chloro-4-fluoro-phenyl)-2-hydroxy-ethyl)-1H-pyrrole-3-carboxamide | 1HNMR (400 MHz, DMSO-d$_6$): δ 8.22 (d, J = 7.6 Hz, 2H), 7.93 (s, 1H), 7.55 (d, J = 7.2 Hz, 1H), 7.33 (t, J = 8.8 Hz, 3H), 6.99 (d, J = 4 Hz, 1H), 6.72 (s, 1H), 5.04-4.99 (m, 1H), 4.92 (t, J = 5.6 Hz, 1H), 3.84 (t, J = 6.8 Hz, 1H), 3.66-3.61 (m, 2H), 2.20 (s, 3H), 1.56-1.42 (m, 2H), 1.09 (d, J = 6.4 Hz, 3H), 0.84 (t, J = 7.6 Hz, 3H) | 3 |
| 198 | 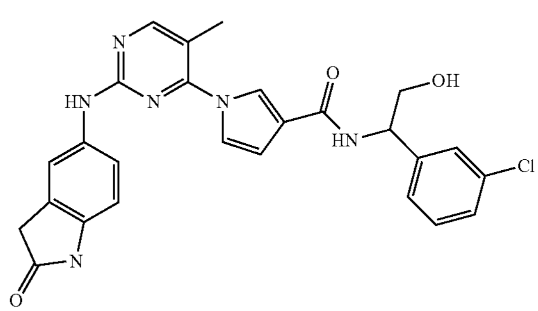 [SMILES: Cc1cnc(Nc2ccc3c(c2)CC(=O)N3)nc1-n1ccc(C(=O)NC(CO)c2cccc(Cl)c2)c1] | N-(1-(3-chloro-phenyl)-2-hydroxy-ethyl)-1-(5-methyl-2-((2-oxoindolin-5-yl)amino)pyrimidin-4-yl)-1H-pyrrole-3-carboxamide | 1HNMR (400 MHz, DMSO-d$_6$): δ 10.2 (s, 1H), 9.48 (s, 1H), 8.4 (s, 1H), 8.29 (d, J = 8 Hz, 1H), 8.04 (s, 1H), 7.6 (s, 1H), 7.46-7.42 (m, 3H), 7.34-7.26 (m, 3H), 6.77 (s, 1H), 6.72 (d, J = 12 Hz, 1H), 5.06-5.01 (m, 1H), 4.93 (t, J = 8 Hz, 1H), 3.67-3.62 (m, 2H), 3.45 (s, 2H), 2.29 (s, 3H) | 3 |

TABLE 1-continued

| Cmpd # | Structure | Name | NMR data | Scheme # |
|---|---|---|---|---|
| 199 | 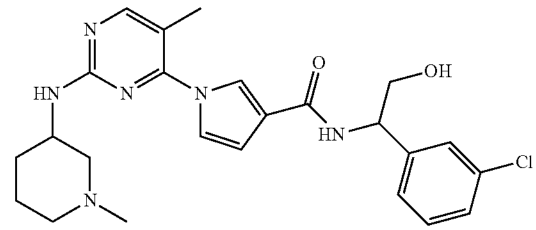 [SMILES: Cc1cnc(NC2CCCN(C)C2)nc1-n1ccc(C(=O)NC(CO)c2cccc(Cl)c2)c1] | N-(1-(3-chloro-phenyl)-2-hydroxy-ethyl)-1-(5-methyl-2-((1-methyl-piperidin-3-yl)-amino)pyrimidin-4-yl)-1H-pyrrole-3-carboxamide | 1HNMR (400 MHz, DMSO-d₆): δ 8.25 (s, 2H), 7.95 (s, 1H), 7.41 (s, 1H), 7.37-7.26 (m, 4H), 7.01 (s, 1H) 6.73 (s, 1H), 5.02 (d, J = 4 Hz, 1H), 4.94 (s, 1H), 3.87 (br s, 1H), 3.64 (d, J = 4 Hz, 2H), 2.21 (s, 3H), 2.14 (s, 3H), 1.88-1.78 (m, 4H), 1.63-1.48 (m, 4H) | 3 |
| 201 | 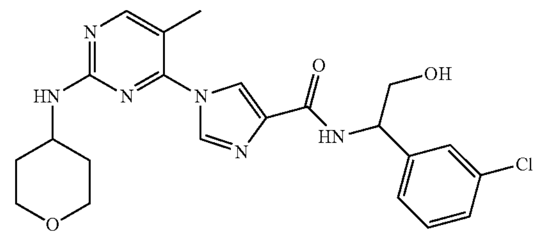 [SMILES: Cc1cnc(NC2CCOCC2)nc1-n1cnc(C(=O)NC(CO)c2cccc(Cl)c2)c1] | N-(1-(3-chloro-phenyl)-2-hydroxy-ethyl)-1-(5-methyl-2-((tetrahydro-2H-pyran-4-yl)-amino)pyrimidin-4-yl)-1H-imidazole-4-carboxamide | 1HNMR (400 MHz, DMSO-d₆): δ 8.41 (d, J = 7.8 Hz, 1H), 8.34 (s, 1H), 8.28 (s, 1H), 8.09 (s, 1H), 7.42 (s, 1H), 7.38 (d, J = 9.6 Hz, 1H), 7.32-7.27 (m, 3H), 5.05-4.98 (m, 2H), 3.85-3.77 (m, 3H), 3.71 (t, J = 4 Hz, 2H), 3.38 (t, J = 8 Hz, 2H), 2.16 (s, 3H), 1.80 (d, J = 11.2 Hz, 2H), 1.51-1.44 (m, 2H) | 6 |
| 202 | 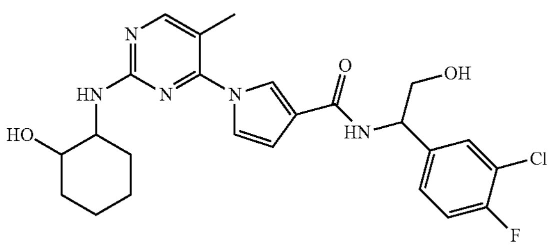 [SMILES: Cc1cnc(NC2CCCCC2O)nc1-n1ccc(C(=O)NC(CO)c2ccc(F)c(Cl)c2)c1] | N-(1-(3-chloro-4-fluorophenyl)-2-hydroxy-ethyl)-1-(2-((2-hydroxy-cyclohexyl)amino)-5-methyl-pyrimidin-4-yl)-1H-pyrrole-3-carboxamide | 1HNMR (400 MHz, DMSO-d₆): δ 8.24 (t, J = 8.4 Hz, 2H), 7.94 (s, 1H), 7.55 (d, J = 7.2 Hz, 1H), 7.35 (d, J = 7.6 Hz, 3H), 6.89 (d, J = 7.6 Hz, 1H), 6.73 (s, 1H), 5.01 (d, J = 7.2 Hz, 1H), 4.96 (m, 1H), 4.53 (d, J = 4.4 Hz, 1H), 3.64-3.55 (m, 4H), 2.20 (s, 3H), 1.93-1.85 (m, 2H), 1.60 (br s, 2H), 1.31-1.18 (m, 4H) | 3 |
| 203 | 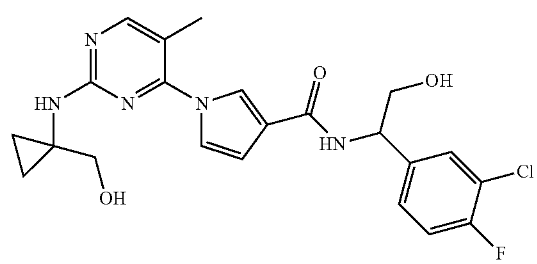 [SMILES: Cc1cnc(NC2(CO)CC2)nc1-n1ccc(C(=O)NC(CO)c2ccc(F)c(Cl)c2)c1] | N-(1-(3-chloro-4-fluorophenyl)-2-hydroxy-ethyl)-1-(2-((1-(hydroxy-methyl)cyclopropyl)amino)-5-methyl-pyrimidin-4-yl)-1H-pyrrole-3-carboxamide | 1HNMR (400 MHz, DMSO-d₆): δ 8.23 (t, J = 12.4 Hz, 2H), 7.92 (s, 1H), 7.55 (d, J = 6.4 Hz, 1H), 7.37 (t, J = 13.2 Hz, 4H), 6.74 (s, 1H), 5.00 (s, 1H), 4.93 (s, 1H), 4.62 (s, 1H), 3.63 (s, 2H), 3.52 (s, 2H), 2.24 (s, 3H), 0.75 (s, 2H), 0.62 (s, 2H) | 3 |
| 204 | 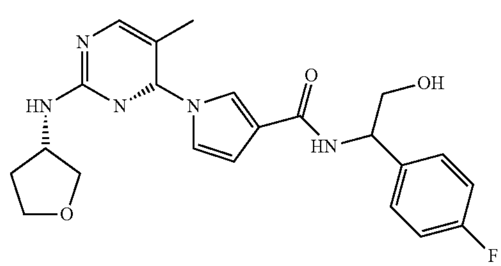 | N-(1-(4-fluoro-phenyl)-2-hydroxy-ethyl)-1-(5-methyl-2-(((S)-tetra-hydro-furan-3-yl)amino)-pyrimidin-4-yl)-1H-pyrrole-3-carboxamide | 1HNMR (400 MHz, DMSO-d₆): δ 8.27 (s, 1H), 8.19 (d, J = 8 Hz, 1H), 7.94 (s, 1H), 7.44-7.38 (m, 4H), 7.11 (t, J = 8.8 Hz, 2H), 6.74 (s, 1H), 5.02 (d, J = 7.2 Hz, 1H), 4.87 (t, J = 5.6 Hz, 1H), 4.34 (s, 1H), 3.86 (t, J = 8 Hz, 1H), | 3 |

| Cmpd # | Structure | Name | NMR data | Scheme # |
|---|---|---|---|---|
| | | | 3.80 (t, J = 7.6 Hz, 1H), 3.72-3.68 (m, 3H), 3.54-3.52 (m, 1H), 2.22 (s, 3H), 2.15-2.10 (m, 1H), 1.86 (d, J = 5.6 Hz, 1H) | |
| 205 | 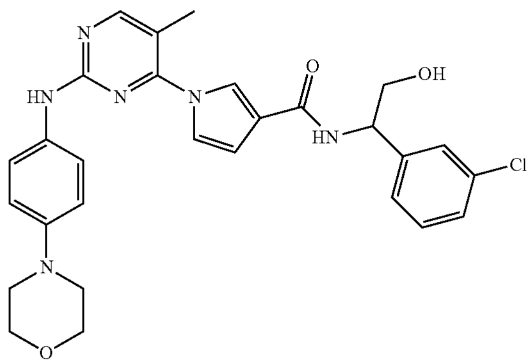 [SMILES: Cc1cnc(Nc2ccc(N3CCOCC3)cc2)nc1-n1ccc(C(=O)NC(CO)c2cccc(Cl)c2)c1] | N-(1-(3-chlorophenyl)-2-hydroxy-ethyl)-1-(5-methyl-2-((4-morpholino-phenyl)amino)pyrimidin-4-yl)-1H-pyrrole-3-carboxamide | 1HNMR (400 MHz, DMSO-d$_6$): δ 8.40 (s, 1H), 8.27 (d, J = 8.0 Hz, 1H), 8.01 (s, 1H), 7.56 (d, J = 9.2 Hz, 2H), 7.43 (s, 2H), 7.36-7.27 (m, 3H), 6.88 (d, J = 8.8 Hz, 2H), 6.78 (s, 1H), 5.04 (d, J = 6.8 Hz, 1H), 4.94 (t, J = 11.2 Hz, 1H), 3.71 (t, J = 4 Hz, 4H), 3.68-3.64 (m, 2H), 3.01 (t, J = 4.8 Hz, 4H), 2.29 (s, 3H) | 3 |
| 206 | 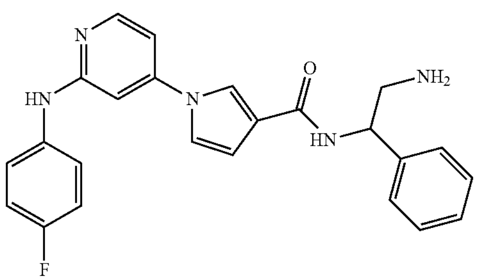 [SMILES: NCC(NC(=O)c1ccn(-c2ccnc(Nc3ccc(F)cc3)c2)c1)c1ccccc1] | N-(2-amino-1-phenylethyl)-1-(2-((4-fluorophenyl)amino)pyridin-4-yl)-1H-pyrrole-3-carboxamide | 1HNMR (400 MHz, DMSO-d$_6$): δ 9.19 (s, 1H), 8.45 (d, J = 8.4 Hz, 1H), 8.18 (d, J = 6 Hz, 1H), 7.98 (d, J = 9.6 Hz, 3H), 7.67-7.63 (m, 2H), 7.46 (s, 1H), 7.42-7.36 (m, 4H), 7.31 (d, J = 7.2 Hz, 1H), 7.11 (t, J = 8.8 Hz, 2H), 7.03 (d, J = 5.2 Hz, 1H), 6.91 (s, 1H), 6.79 (s, 1H), 5.34-5.30 (m, 1H), 3.22 (s, 2H). | 7, 4 |
| 207 | 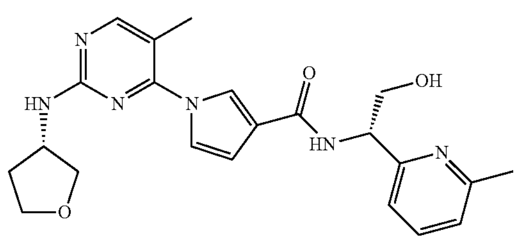 [SMILES: Cc1cccc([C@@H](CO)NC(=O)c2ccn(-c3nc(N[C@H]4CCOC4)ncc3C)c2)n1] | N-((S)-2-hydroxy-1-(6-methyl-pyridin-2-yl)ethyl)-1-(5-methyl-2-(((S)-tetra-hydrofuran-3-yl)amino)pyrimidin-4-yl)-1H-pyrrole-3-carboxamide | 1HNMR (400 MHz, DMSO-d$_6$): δ 8.28 (s, 1H), 8.17 (d, J = 7.6 Hz, 1H), 7.97 (s, 1H), 7.60 (t, J = 7.6 Hz, 1H), 7.45 (d, J = 5.2 Hz, 1H), 7.40 (s, 1H), 7.16 (d, J = 7.2 Hz, 1H), 7.09 (d, J = 8 Hz, 1H), 6.76 (s, 1H), 5.07-5.02 (m, 1H), 4.84 (t, J = 5.6 Hz, 1H), 4.36 (s, 1H), 3.89-3.79 (m, 3H), 3.75-3.69 (m, 2H), 3.67-3.51 (m, 1H), 2.45 (s, 3H), 2.24 (s, 3H), 2.18-2.09 (m, 1H), 1.90-1.85 (m, 1H) | 3 |

TABLE 1-continued

| Cmpd # | Structure | Name | NMR data | Scheme # |
|---|---|---|---|---|
| 208 | 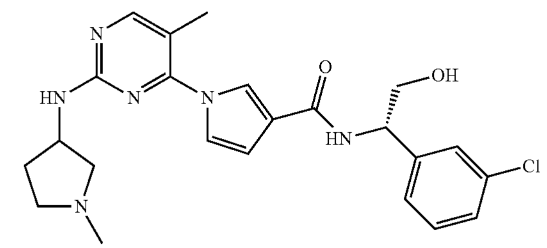 [SMILES: Cc1cnc(NC2CCN(C)C2)nc1-n1ccc(C(=O)N[C@H](CO)c2cccc(Cl)c2)c1] | N-((S)-1-(3-chlorophenyl)-2-hydroxy-ethyl)-1-(5-methyl-2-((1-methyl-pyrrolidin-3-yl)amino)pyrimidin-4-yl)-1H-pyrrole-3-carboxamide | 1HNMR (400 MHz, DMSO-d$_6$): δ 8.27 (d, J = 9.2 Hz, 2H), 7.97 (s, 1H), 7.40 (d, J = 8.8 Hz, 3H), 7.34-7.32 (m, 2H), 7.27 (d, J = 8.0 Hz, 3H), 6.76 (s, 1H), 5.05-5.00 (m, 1H), 4.94 (t, J = 6 Hz, 1H), 4.36-4.34 (m, 1H), 3.66 (d, J = 4.4 Hz, 2H), 3.00 (br s, 1H), 2.77 (s, 1H), 2.67 (d, J = 13.2 Hz, 1H), 2.58 (br s, 1H), 2.48 (s, 3H), 2.23 (s, 3H) | 3 |
| 209 | 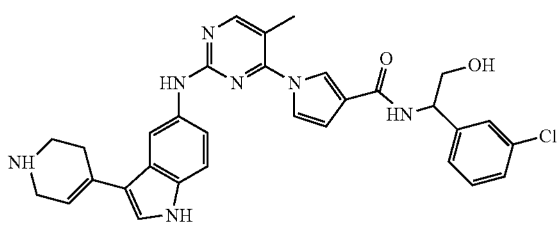 [SMILES: Cc1cnc(Nc2ccc3[nH]cc(C4=CCNCC4)c3c2)nc1-n1ccc(C(=O)NC(CO)c2cccc(Cl)c2)c1] | N-(1-(3-chlorophenyl)-2-hydroxy-ethyl)-1-(5-methyl-2-((3-(1,2,3,6-tetrahydro-pyridin-4-yl)-1H-indol-5-yl)amino)-pyrimidin-4-yl)-1H-pyrrole-3-carboxamide hydrochloride | 1HNMR (400 MHz, DMSO-d$_6$): δ 11.17 (s, 1H), 9.49 (s, 1H), 8.95 (s, 1H), 8.43-8.39 (m, 2H), 8.33 (s, 1H), 8.07 (s, 1H), 7.46-7.42 (m, 3H), 7.32-7.31 (m, 5H), 6.84 (s, 1H), 6.06 (s, 1H), 5.03 (s, 1H), 3.68-3.66 (d, J = 8 Hz, 3H), 3.3 (s, 1H), 2.70-2.65 (m, 3H), 2.31 (s, 3H) | 3 |
| 211 | 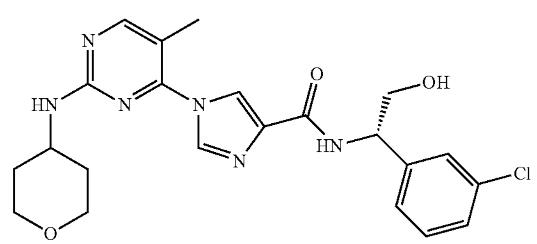 [SMILES: Cc1cnc(NC2CCOCC2)nc1-n1cnc(C(=O)N[C@H](CO)c2cccc(Cl)c2)c1] | (S)-N-(1-(3-chlorophenyl)-2-hydroxy-ethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.39 (d, J = 8 Hz, 1H), 8.34 (s, 1H), 8.28 (s, 1H), 8.09 (s, 1H), 7.43 (s, 1H), 7.37-7.32 (m, 3H), 7.29 (br s, 1H), 5.02 (d, J = 8 Hz, 2H), 3.85-3.82 (br s, 3H), 3.72 (t, J = 8 Hz, 2H), 3.39-3.26 (m, 2H), 2.17 (s, 3H), 1.81 (d, J = 8 Hz, 2H), 1.48 (d, J = 8 Hz, 2H). | 6 |
| 212 | 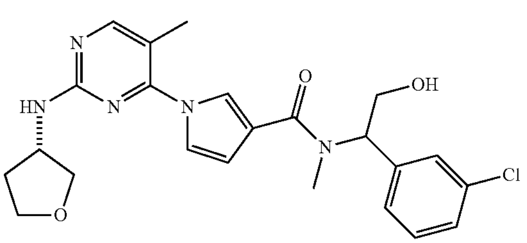 | N-(1-(3-chlorophenyl)-2-hydroxy-ethyl)-N-methyl-1-(5-methyl-2-(((S)-tetra-hydrofuran-3-yl)amino)-pyrimidin-4-yl)-1H-pyrrole-3-carboxamide | 1HNMR (400 MHz, DMSO-d$_6$): δ 8.26 (s, 1H), 7.68 (s, 1H), 7.40-7.33 (m, 5H), 7.26 (s, 1H), 6.51 (s, 1H), 5.56 (br s, 1H), 5.07 (s, 1H), 4.31 (s, 1H), 3.99-3.78 (m, 4H), 3.71-3.66 (m, 1H), 3.53-351 (m, 1H), 2.90 (br s, 3H), 2.18-2.08 (m, 4H), 1.86-1.84 (m, 1H) | 3 |

TABLE 1-continued

| Cmpd # | Structure | Name | NMR data | Scheme # |
|---|---|---|---|---|
| 213 | 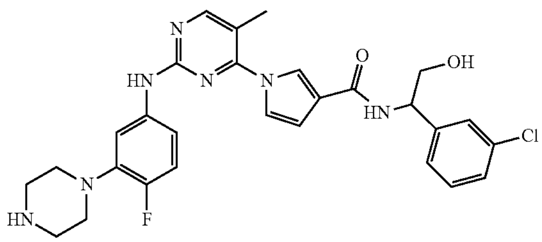 [SMILES: Cc1cnc(Nc2ccc(F)c(N3CCNCC3)c2)nc1-n1ccc(C(=O)NC(CO)c2cccc(Cl)c2)c1] | N-(1-(3-chlorophenyl)-2-hydroxy-ethyl)-1-(2-((4-fluoro-3-(piperazin-1-yl)phenyl)amino)-5-methyl-pyrimidin-4-yl)-1H-pyrrole-3-carboxamide | 1HNMR (400 MHz, DMSO-d$_6$): δ 9.63 (s, 1H), 8.46 (s, 1H), 8.29 (d, J = 8.0 Hz, 1H), 8.05 (s, 1H), 7.62 (d, J = 6.8 Hz, 1H), 7.44 (d, J = 11.2 Hz, 2H), 7.33-7.22 (m, 4H), 7.06-7.00 (t, J = 12.4 Hz, 1H,), 6.81 (s, 1H), 5.04 (d, J = 7.2 Hz, 1H), 3.70-3.60 (m, 2H), 2.97 (d, J = 12 Hz, 8H), 2.32 (s, 3H) | 3 |
| 214 | 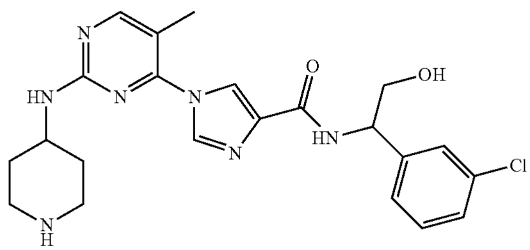 [SMILES: Cc1cnc(NC2CCNCC2)nc1-n1cnc(C(=O)NC(CO)c2cccc(Cl)c2)c1] | N-(1-(3-chlorophenyl)-2-hydroxy-ethyl)-1-(5-methyl-2-(piperidin-4-ylamino)pyrimidin-4-yl)-1H-imidazole-4-carboxamide | 1HNMR (400 MHz, DMSO-d$_6$): δ 8.38 (d, J = 8.4 Hz, 2H), 8.30 (s, 1H), 8.11 (s, 1H), 7.9 (br s, 1H), 7.54 (s, 1H), 7.42 (s, 1H), 7.32-7.29 (m, 3H), 5.03-5.02 (m, 2H), 3.96 (s, 1H), 3.72 (t, J = 5.2 Hz, 2H), 2.93 (s, 3H), 2.19 (s, 3H), 1.9 (s, 3H), 1.60 (d, J = 8 Hz, 2H) | 6 |
| 215 | 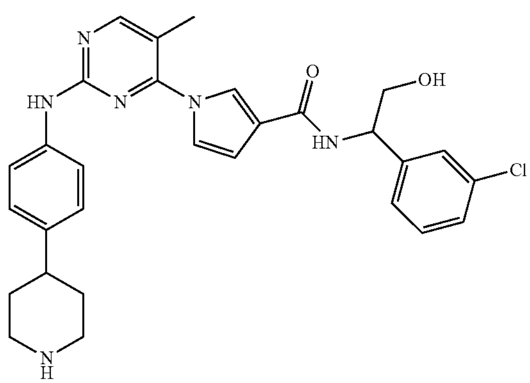 [SMILES: Cc1cnc(Nc2ccc(C3CCNCC3)cc2)nc1-n1ccc(C(=O)NC(CO)c2cccc(Cl)c2)c1] | N-(1-(3-chlorophenyl)-2-hydroxy-ethyl)-1-(5-methyl-2-((4-(piperidin-4-yl)phenyl)amino)pyrimidin-4-yl)-1H-pyrrole-3-carboxamide | 1HNMR (400 MHz, DMSO-d$_6$): δ 9.64 (s, 1H), 8.45 (s, 1H), 8.32 (d, J = 8.0 Hz, 1H), 8.04 (s, 1H), 7.67 (d, J = 8 Hz, 2H), 7.43 (s, 2H), 7.31 (d, J = 16 Hz, 3H), 7.14 (d, J = 8.4 Hz, 2H), 6.81 (s, 1H), 5.04-4.99 (m, 2H), 3.67 (s, 2H), 3.49 (s, 4H), 2.97 (t, J = 12 Hz, 2H), 2.31 (s, 3H), 1.90 (d, J = 12.8 Hz, 2H), 1.76 (d, J = 12.8 Hz, 2H) | 3 |
| 216 | 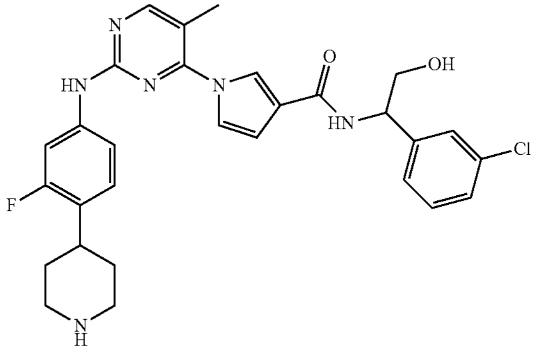 [SMILES: Cc1cnc(Nc2ccc(C3CCNCC3)c(F)c2)nc1-n1ccc(C(=O)NC(CO)c2cccc(Cl)c2)c1] | N-(1-(3-chlorophenyl)-2-hydroxy-ethyl)-1-(2-((3-fluoro-4-(piperidin-4-yl)phenyl)amino)-5-methyl-pyrimidin-4-yl)-1H-pyrrole-3-carboxamide | 1HNMR (400 MHz, DMSO-d$_6$): δ 9.87 (s, 1H), 8.49 (s, 1H), 8.30 (d, J = 8.0 Hz, 1H), 8.03 (s, 1H), 7.68 (d, J = 14 Hz, 1H), 7.44-7.42 (m, 3H), 7.32-7.28 (m, 3H), 7.15 (t, J = 8.8 Hz, 1H), 6.81 (s, 1H), 5.04-5.02 (m, 1H), 4.96-4.93 (m, 1H), 3.65 (s, 2H), 3.3-3.27 (m, 2H) 3.02-2.99 (m, 4H), 2.32 (s, 3H), 1.84-1.79 (m, 4H) | 3 |

TABLE 1-continued

| Cmpd # | Structure | Name | NMR data | Scheme # |
|---|---|---|---|---|
| 217 | 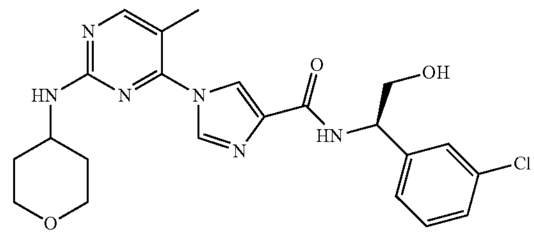 [SMILES: Cc1cnc(NC2CCOCC2)nc1-n1cnc(C(=O)N[C@@H](CO)c2cccc(Cl)c2)c1] | (R)-N-(1-(3-chlorophenyl)-2-hydroxy-ethyl)-1-(5-methyl-2-((tetrahydro-2H-pyran-4-yl)amino)-pyrimidin-4-yl)-1H-imidazole-4-carboxamide | 1HNMR (400 MHz, DMSO-d6): δ 8.37 (d, J = 12.0 Hz, 2H), 8.27 (s, 1H), 8.08 (s, 1H), 7.42 (s, 1H), 7.36-7.27 (m, 4H), 5.02-5.00 (m, 2H), 3.84-3.81 (m, 3H), 3.71 (t, J = 5.6 Hz, 2H), 3.38-3.30 (m, 2H), 2.16 (s, 3H), 1.80 (d, J = 12 Hz, 2H), 1.51-1.44 (m, 2H) | 6 |
| 218 | 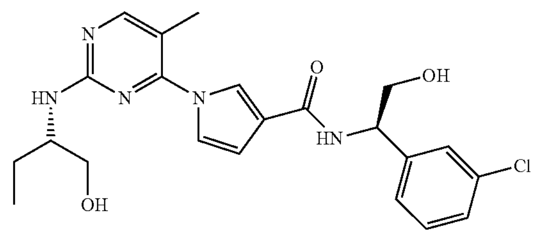 | N-((R)-1-(3-chlorophenyl)-2-hydroxy-ethyl)-1-(2-(((S)-1-hydroxy-butan-2-yl)amino)-5-methyl-pyrimidin-4-yl)-1H-pyrrole-3-carboxamide | 1HNMR (400 MHz, DMSO-d6): δ 8.23 (d, J = 6.8 Hz, 2H), 7.93 (s, 1H), 7.41 (s, 1H), 7.37 (s, 1H), 7.33-7.25 (m, 3H), 6.78 (d, J = 8 Hz, 1H), 6.73 (s, 1H), 5.04-4.99 (m, 1H), 4.91 (t, J = 5.6 Hz, 1H), 4.55 (t, J = 5.6 Hz, 1H), 3.80 (s, 1H), 3.64 (d, J = 5.2 Hz, 2H), 3.46-3.41 (m, 1H), 3.36-3.32 (m, 1H), 2.20 (s, 3H), 1.67-1.60 (m, 1H), 1.44-1.37 (m, 1H), 0.85 (t, J = 8 Hz, 3H) | 3 |
| 219 | 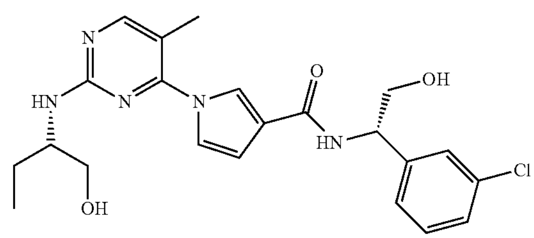 | N-((S)-1-(3-chlorophenyl)-2-hydroxy-ethyl)-1-(2-(((S)-1-hydroxy-butan-2-yl)amino)-5-methyl-pyrimidin-4-yl)-1H-pyrrole-3-carboxamide | 1HNMR (400 MHz, DMSO-d6): δ 8.24 (d, J = 6.8 Hz, 1H), 7.94 (s, 1H), 7.52 (s, 1H), 7.40-7.27 (m, 5H), 6.79-6.77 (d, J = 8 Hz, 1H), 6.73 (s, 1H), 5.02-5.01 (m, 1H), 4.92 (t, J = 5.6 Hz, 1H), 4.55 (t, J = 5.6 Hz, 1H), 3.82 (d, J = 4.8 Hz, 2H), 3.64 (d, J = 5.2 Hz, 1H), 3.42-3.27 (m, 2H), 2.2 (s, 3H), 1.64-1.62 (m, 1H), 1.42-1.40 (m, 1H), 0.85 (t, J = 8 Hz, 3H). | 3 |
| 220 | 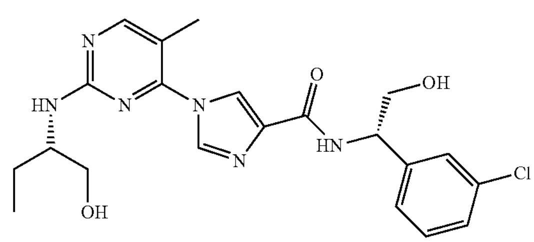 | N-((S)-1-(3-chlorophenyl)-2-hydroxy-ethyl)-1-(2-(((S)-1-hydroxy-butan-2-yl)amino)-5-methyl-pyrimidin-4-yl)-1H-imidazole-4-carboxamide | 1HNMR (400 MHz, DMSO-d6): δ 8.38 (d, J = 8.4 Hz, 1H), 8.28 (d, J = 14.8 Hz, 2H), 8.08 (s, 1H), 7.42 (s, 1H), 7.31-7.28 (m, 3H), 6.96 (d, J = 8 Hz, 1H), 5.03-4.98 (m, 2H), 4.55 (br s, 1H), 3.80 (br s, 1H), 3.72-3.70 (m, 2H), 3.45-3.41 (m, 2H), 2.17 (s, 3H), 1.65-1.60 (m, 1H), 1.44-1.40 (m, 1H), 0.851 (t, J = 8 Hz, 3H) | 6 |

TABLE 1-continued

| Cmpd # | Structure | Name | NMR data | Scheme # |
|---|---|---|---|---|
| 221 | 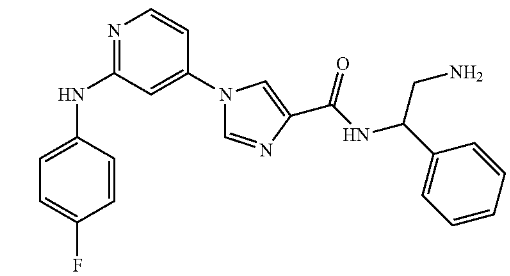 [SMILES: NCC(NC(=O)c1cn(-c2ccnc(Nc3ccc(F)cc3)c2)cn1)c1ccccc1] | N-(2-amino-1-phenylethyl)-1-(2-((4-fluorophenyl)amino)pyridin-4-yl)-1H-imidazole-4-carboxamide | 1HNMR (400 MHz, DMSO-d₆): δ 9.19 (s, 1H), 8.48 (d, J = 8.4 Hz, 1H), 8.43 (s, 1H), 8.22-8.20 (m, 2H), 7.65-7.62 (m, 2H), 7.35-7.28 (m, 4H), 7.23-7.19 (m, 1H), 7.15-7.07 (m, 3H), 6.96 (s, 1H), 4.97 (s, 1H), 3.01-3.0 (m, 1H), 2.92-2.90 (m, 1H) | 11 |
| 222 | 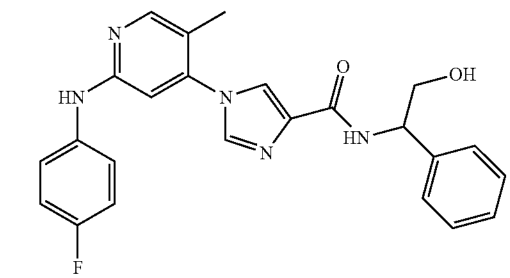 [SMILES: Cc1cnc(Nc2ccc(F)cc2)cc1-n1cnc(C(=O)NC(CO)c2ccccc2)c1] | 1-(2-((4-fluorophenyl)amino)-5-methylpyridin-4-yl)-N-(2-hydroxy-1-phenylethyl)-1H-imidazole-4-carboxamide | 1HNMR (400 MHz, DMSO-d₆): δ 9.13 (s, 1H), 8.24 (d, J = 8 Hz, 1H), 8.15 (s, 1H), 8.07 (s, 1H), 7.97 (s, 1H,) 7.67-7.59 (m, 2H) 7.36 (d, J = 7.6 Hz, 2H), 7.29 (t, J = 7.6 Hz, 2H), 7.22 (t, J = 6.8 Hz, 1H,), 7.08 (t, J = 3.2 Hz, 2H), 6.72 (s, 1H) 5.03-4.96 (m, 2H), 3.69 (br s, 2H), 2.08 (s, 3H) | 11 |
| 223 | 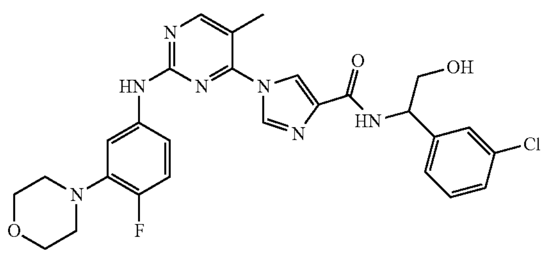 [SMILES: Cc1cnc(Nc2ccc(F)c(N3CCOCC3)c2)nc1-n1cnc(C(=O)NC(CO)c2cccc(Cl)c2)c1] | N-(1-(3-chlorophenyl)-2-hydroxy-ethyl)-1-(2-((4-fluoro-3-morpholino-phenyl)amino)-5-methyl-pyrimidin-4-yl)-1H-imidazole-4-carboxamide | 1HNMR (400 MHz, DMSO-d₆): δ 9.73 (s, 1H), 8.53 (s, 1H), 8.42 (d, J = 7.6 Hz, 1H), 8.35 (s, 1H), 8.17 (s, 1H), 7.52 (d, J = 7.6 Hz, 2H), 7.54 (d, J = 8 Hz, 1H), 7.43 (s, 1H), 7.33 (s, 1H), 7.32 (s, 1H), 7.27 (d, J = 3.2 Hz, 1H), 7.21 (d, J = 7.6 Hz, 1H), 7.06-7.01 (m, 1H), 5.02 (t, J = 4.8 Hz, 2H), 3.70 (s, 6H), 2.96 (s, 4H), 2.27 (s, 3H) | 6 |
| 225 | 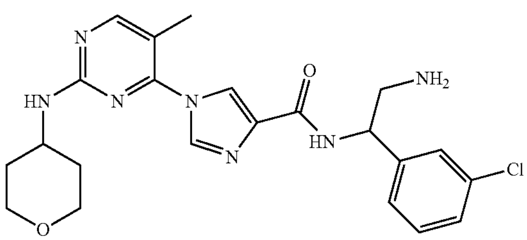 [SMILES: Cc1cnc(NC2CCOCC2)nc1-n1cnc(C(=O)NC(CN)c2cccc(Cl)c2)c1] | N-(2-amino-1-(3-chloro-phenyl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-d₆): δ 8.53 (d, J = 8 Hz, 1H), 8.32 (s, 1H), 8.25 (s, 1H), 8.06 (s, 1H), 7.40-7.27 (m, 6H), 4.91 (s, 1H), 3.83-3.81 (m, 4H), 3.47-3.26 (m, 3H), 2.95-2.88 (m, 2H), 2.16 (s, 3H), 1.79 (d, J = 8 Hz, 2H), 1.48-1.45 (m, 2H) | 4 |
| 225a | 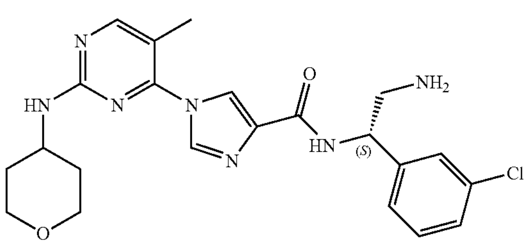 | (S)-N-(2-amino-1-(3-chlorophenyl)-ethyl)-1-(5-methyl-2-((tetrahydro-2H-pyran-4-yl)amino)-pyrimidin-4-yl)-1H-imidazole-4- | 1HNMR (400 MHz, DMSO-d₆): δ 8.58 (d, J = 6.8 Hz, 1H), 8.33 (s, 1H), 8.27 (s, 1H), 8.07 (s, 1H), 7.41 (s, 1H), 7.36-7.28 (m, 4H), 4.97 (br s, 1H), 3.84-3.82 (m, 3H), 3.38-3.33 (m, 2H), 3.01-2.94 (m, 2H), 2.16 | 4, 20 |

TABLE 1-continued

| Cmpd # | Structure | Name | NMR data | Scheme # |
|---|---|---|---|---|
| | | carboxamide, Enantiomer #1 | (s, 3H), 1.80 (d, J = 11.6 Hz, 2H), 1.52-1.44 (m, 2H). | |
| 225b | 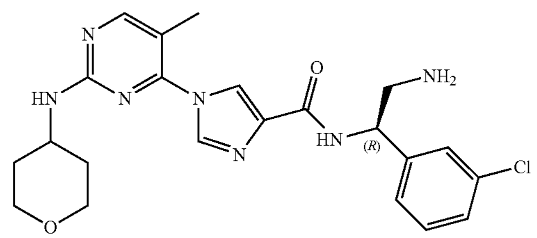 | (R)-N-(2-amino-1-(3-chlorophenyl)-ethyl)-1-(5-methyl-2-((tetrahydro-2H-pyran-4-yl)amino)-pyrimidin-4-yl)-1H-imidazole-4-carboxamide, Enantiomer #2 | 1HNMR (400 MHz, DMSO-$d_6$): δ 8.58 (d, J = 8 Hz, 1H), 8.33 (s, 1H), 8.27 (s, 1H), 8.07 (s, 1H), 7.42 (s, 1H), 7.36-7.27 (m, 4H), 5.02-4.91 (m, 1H), 3.84-3.82 (m, 3H), 3.35 (m, 2H), 3.05-2.91 (m, 2H), 2.16 (s, 3H), 1.79 (d, J = 11.6 Hz, 2H), 1.51-1.4 (m, 2H). | 4 |
| 226 | 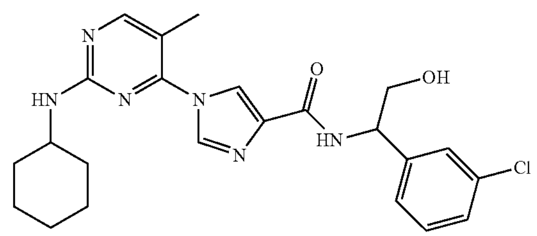 [SMILES: Cc1cnc(NC2CCCCC2)nc1-n1cnc(C(=O)NC(CO)c2cccc(Cl)c2)c1] | N-(1-(3-chloro-phenyl)-2-hydroxy-ethyl)-1-(2-(cyclohexyl-amino)-5-methyl-pyrimidin-4-yl)-1H-imidazole-4-carboxamide | 1HNMR (400 MHz, DMSO-$d_6$): δ 8.38 (d, J = 8.4 Hz, 1H), 8.30 (s, 1H), 8.25 (s, 1H), 8.07 (s, 1H), 7.42 (s, 1H), 7.34-7.27 (m, 3H), 7.21 (d, J = 7.6 Hz, 1H), 5.04-4.97 (m, 2H), 3.71 (t, J = 5.6 Hz, 2H), 2.15 (s, 3H), 1.85 (d, J = 7.2 Hz, 2H), 1.67 (s, 2H), 1.55 (d, J = 12 Hz, 1H), 1.28-1.20 (m, 6H) | 6 |
| 227 | 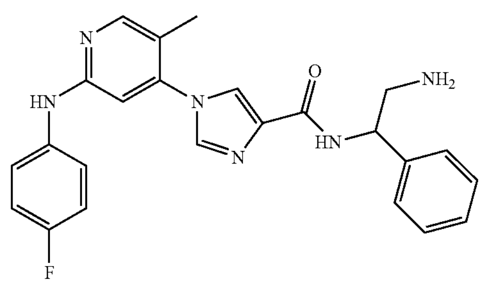 | N-(2-amino-1-phenylethyl)-1-(2-((4-fluorophenyl)-amino)-5-methyl-pyridin-4-yl)-1H-imidazole-4-carboxamide, Enantiomer #1 | 1HNMR (400 MHz, DMSO-$d_6$): δ 9.14 (s, 1H), 8.5 (d, J = 8.4 Hz, 1H), 8.15 (s, 1H), 8.08 (s, 1H), 7.97 (s, 1H), 7.63-7.59 (m, 2H), 7.37-7.30 (m, 4H), 7.23 (t, J = 6.8 Hz, 1H), 7.08 (t, J = 8.4 Hz, 2H), 6.71 (s, 1H), 5.03-5.02 (m, 1H), 4.0 (br s, 2H), 3.11-3.06 (t, J = 12.0 Hz, 1H), 2.96-2.94 (m, 1H), 2.08 (s, 3H) | 11 |
| 228 | 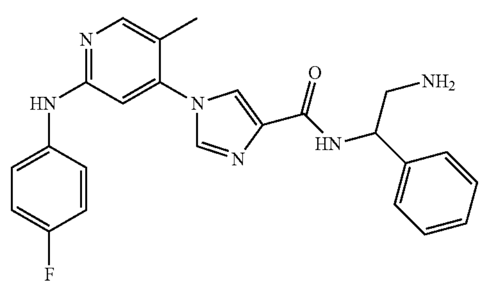 | N-(2-amino-1-phenylethyl)-1-(2-((4-fluorophenyl)-amino)-5-methyl-pyridin-4-yl)-1H-imidazole-4-carboxamide, Enantiomer #2 | 1HNMR (400 MHz, DMSO-$d_6$): δ 9.13 (s, 1H), 8.50 (d, J = 4 Hz, 1H), 8.15 (s, 1H), 8.08 (s, 1H), 7.98 (s, 1H), 7.63-7.59 (m, 2H), 7.37-7.30 (m, 4H), 7.24 (t, J = 6.8 Hz, 1H), 7.08 (t, J = 8.0 Hz, 2H), 6.71 (s, 1H), 5.02 (m, 1H), 3.11-3.06 (t, J = 12 Hz, 1H), 2.96-2.94 (m, 1H), 2.08 (s, 3H) | 11 |

TABLE 1-continued

| Cmpd # | Structure | Name | NMR data | Scheme # |
|---|---|---|---|---|
| 229 | 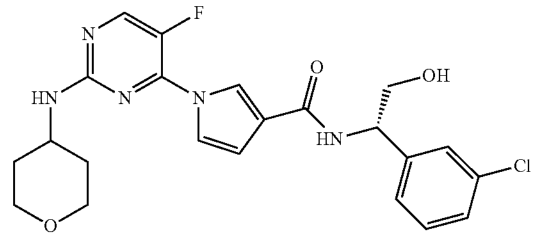 [SMILES: O=C(N[C@H](CO)c1cccc(Cl)c1)c1ccn(-c2nc(NC3CCOCC3)ncc2F)c1] | (S)-N-(1-(3-chlorophenyl)-2-hydroxy-ethyl)-1-(5-fluoro-2-((tetrahydro-2H-pyran-4-yl)amino)-pyrimidin-4-yl)-1H-pyrrole-3-carboxamide | 1HNMR (400 MHz, DMSO-d$_6$): δ 8.47 (d, J = 4 Hz, 1H), 8.39 (d, J = 8 Hz, 1H), 8.14 (s, 1H), 7.56 (s, 1H), 7.41 (s, 2H), 7.33-7.26 (m, 3H), 6.81 (s, 1H), 5.04-4.99 (m, 1H), 4.92 (t, J = 8 Hz, 1H), 3.83 (d, J = 12 Hz, 3H), 3.66-3.59 (m, 2H), 3.38 (t, J = 12 Hz, 2H), 1.83-1.80 (d, J = 12 Hz, 2H), 1.54-1.45 (m, 2H) | 3 |
| 230 | 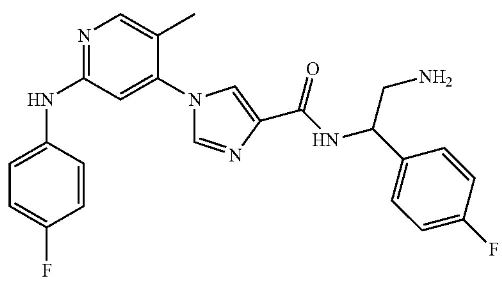 [SMILES: Cc1cnc(Nc2ccc(F)cc2)cc1-n1cnc(C(=O)NC(CN)c2ccc(F)cc2)c1] | N-(2-amino-1-(4-fluoro-phenyl)ethyl)-1-(2-((4-fluoro-phenyl)amino)-5-methyl-pyridin-4-yl)-1H-imidazole-4-carboxamide | 1HNMR (400 MHz, DMSO-d$_6$): δ 9.13 (s, 1H), 8.58 (d, J = 8 Hz, 1H), 8.15 (s, 1H), 8.08 (s, 1H), 7.98 (s, 1H), 7.63-7.59 (m, 2H), 7.41 (t, J = 8.4 Hz, 2H), 7.15 (t, J = 8.8 Hz, 2H), 7.08 (t, J = 8.8 Hz, 2H), 6.71 (s, 1H), 5.08 (s, 1H), 3.13 (s, 2H), 2.98 (d, J = 10 Hz, 2H), 2.07 (s, 3H) | 11 |
| 231 | 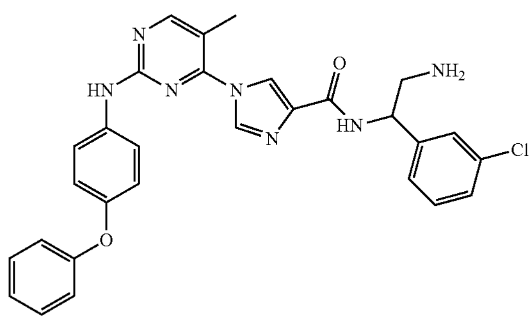 [SMILES: Cc1cnc(Nc2ccc(Oc3ccccc3)cc2)nc1-n1cnc(C(=O)NC(CN)c2cccc(Cl)c2)c1] | N-(2-amino-1-(3-chloro-phenyl)ethyl)-1-(5-methyl-2-((4-phenoxy-phenyl)amino)pyrimidin-4-yl)-1H-imidazole-4-carboxamide | 1HNMR (400 MHz, DMSO-d$_6$): δ 9.78 (s, 1H), 8.84 (d, J = 8 Hz, 1H), 5.54 (s, 1H), 8.36 (s, 1H), 8.19 (s, 1H), 7.69 (d, J = 8.8 Hz, 2H), 7.49 (s, 1H), 7.39-7.31 (m, 5H), 7.06 (t, J = 8 Hz, 1H), 6.99-6.92 (m, 4H), 5.24 (br s, 1H), 4.11 (s, 1H), 3.17 (br s, 1H), 2.25 (s, 3H), 0.85 (t, J = 8 Hz, 2 H) | 4 |
| 232 | 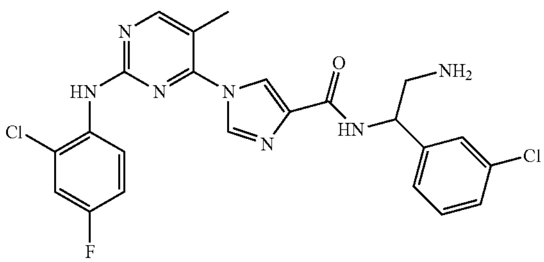 [SMILES: Cc1cnc(Nc2ccc(F)cc2Cl)nc1-n1cnc(C(=O)NC(CN)c2cccc(Cl)c2)c1] | N-(2-amino-1-(3-chloro-phenyl)ethyl)-1-(2-((2-chloro-4-fluorophenyl)amino)-5-methyl-pyrimidin-4-yl)-1H-imidazole-4-carboxamide | 1HNMR (400 MHz, DMSO-d$_6$): δ 9.17 (s, 1H), 8.89 (d, J = 4.5 Hz, 1H), 8.48 (s, 1H), 8.29 (s, 1H), 8.11 (s, 1H), 7.82 (br s, 2H), 7.66-7.62 (m, 1H), 7.50-7.47 (m, 2H), 7.40-7.36 (m, 3H), 7.21-7.18 (m, 1H), 5.30 (d, J = 2.5 Hz, 1H), 3.42-3.32 (m, 1H), 3.27-3.19 (m, 1H), 2.24 (s, 3H) | 4 |

TABLE 1-continued

| Cmpd # | Structure | Name | NMR data | Scheme # |
|---|---|---|---|---|
| 233 | 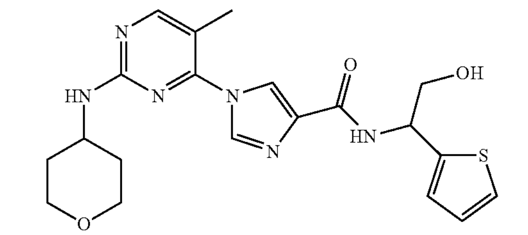 [SMILES: Cc1cnc(NC2CCOCC2)nc1-n1cnc(C(=O)NC(CO)c2cccs2)c1] | N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide | 1H NMR (400 MHz, DMSO-$d_6$): δ 8.33 (s, 1H), 8.23 (t, J = 6.0 Hz, 2H), 8.11 (s, 1H), 7.35 (t, J = 6.8 Hz, 2H), 7.02 (s, 1H), 6.94 (t, J = 4.4 Hz, 1H), 5.30-5.25 (m, 1H), 5.12 (t, J = 5.6 Hz, 1H), 3.9 (br s, 1H), 3.83 (d, J = 10.8 Hz, 2H), 3.77 (t, J = 5.2 Hz, 2H), 3.36 (t, J = 10.8 Hz, 2 H), 2.16 (s, 3H), 1.81 (d, J = 12 Hz, 2H), 1.51-1.44 (m, 2H). | 6 |
| 234 | 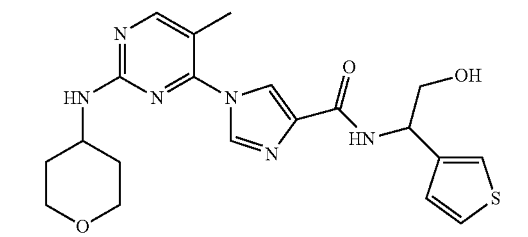 [SMILES: Cc1cnc(NC2CCOCC2)nc1-n1cnc(C(=O)NC(CO)c2ccsc2)c1] | N-(2-hydroxy-1-(thiophen-3-yl)ethyl)-1-(5-methyl-2-((tetrahydro-2H-pyran-4-yl)amino)-pyrimidin-4-yl)-1H-imidazole-4-carboxamide | 1H NMR (400 MHz, DMSO-$d_6$): δ 8.33 (s, 1H), 8.25 (s, 1H), 8.14 (d, J = 8.8 Hz, 1H), 8.09 (s, 1H), 7.43 (d, J = 3.2 Hz, 1H), 7.42-7.32 (m, 2H), 7.13 (d, J = 4.8 Hz, 1H), 5.15-5.10 (m, 1H), 4.95 (t, J = 5.6 Hz, 1H), 3.88 (br s, 1H), 3.83 (d, J = 10.8 Hz, 2H), 3.75-3.68 (m, 2H), 3.36 (t, J = 11.2 Hz, 2H), 2.16 (s, 3H), 1.81 (d, J = 11.6 Hz, 2H), 1.53-1.43 (m, 2H). | 6 |
| 235 | 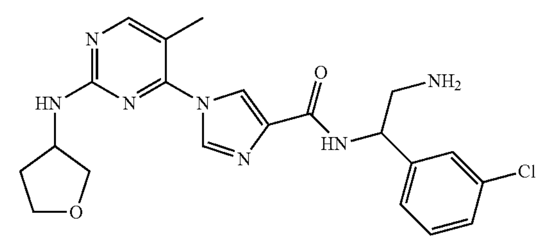 [SMILES: Cc1cnc(NC2CCOC2)nc1-n1cnc(C(=O)NC(CN)c2cccc(Cl)c2)c1] | N-(2-amino-1-(3-chloro-phenyl)ethyl)-1-(5-methyl-2-((tetra-hydrofuran-3-yl)amino)pyrimidin-4-yl)-1H-imidazole-4-carboxamide | 1HNMR (400 MHz, DMSO-$d_6$): δ 8.87 (d, J = 7.2 Hz, 1H), 8.36 (s, 1H), 8.30 (s, 1H), 8.15 (s, 1H), 7.60 (br s, 1H), 7.50 (s, 1H), 7.41-7.33 (m, 3H), 5.28 (s, 1H), 4.34 (s, 1H), 4.34-3.84 (m, 2H), 3.81-3.71 (m, 1H), 3.68-3.53 (m, 1H), 3.36-3.27 (m, 1H), 3.33-3.19 (m, 1H), 2.99-2.93 (m, 1H), 2.18 (s, 3H), 1.90-1.82 (m, 1H). | 4 |
| 236 | 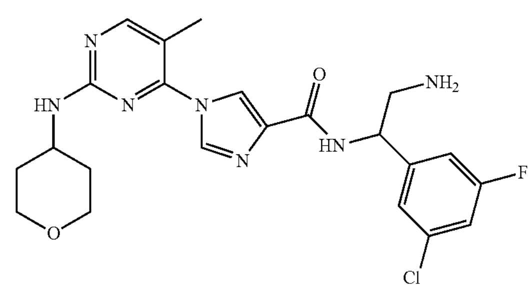 [SMILES: Cc1cnc(NC2CCOCC2)nc1-n1cnc(C(=O)NC(CN)c2cc(F)cc(Cl)c2)c1] | N-(2-amino-1-(3-chloro-5-fluoro-phenyl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 8.57 (d, J = 7.2 Hz, 1H), 8.33 (s, 1H), 8.27 (s, 1H), 8.08 (s, 1H), 7.34 (br s, 1H), 7.27 (br s, 1H), 7.18 (d, J = 10 Hz, 1H), 4.91 (s, 1H), 3.84-3.81 (m, 3H), 3.38-3.27 (m, 2H), 2.93 (s, 1H), 2.87 (s, 1H), 2.30 (s, 3H), 1.83-1.78 (m, 2H), 1.49 (br s, 2H) | 4 |

TABLE 1-continued

| Cmpd # | Structure | Name | NMR data | Scheme # |
|---|---|---|---|---|
| 237 | 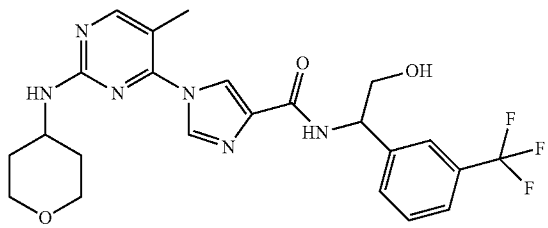 [SMILES: Cc1cnc(NC2CCOCC2)nc1-n1cnc(C(=O)NC(CO)c2cccc(C(F)(F)F)c2)c1] | N-(2-hydroxy-1-(3-(trifluoromethyl)-phenyl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-d₆): δ 8.49 (d, J = 8.0 Hz, 1H), 8.33 (s, 1H), 8.27 (s, 1H), 8.08 (s, 1H), 7.73 (s, 1H), 7.66 (d, J = 12 Hz, 1H), 7.59-7.51 (m, 2H), 7.35 (d, J = 7.6 Hz, 1H), 5.12-5.03 (m, 2H), 3.89 (br s, 1H), 3.83 (d, J = 11.6 Hz, 2H), 3.74 (t, J = 5.6 Hz, 2H), 3.35 (t, J = 10.4 Hz, 2H), 2.16 (s, 3H), 1.80 (d, J = 11.2 Hz, 2H), 1.52-1.42 (m, 2H) | 3 |
| 238 | 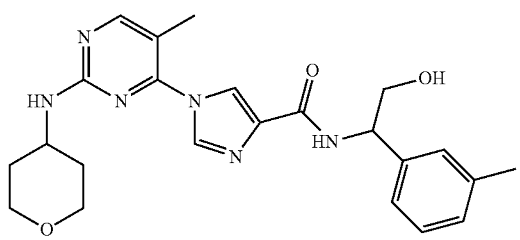 [SMILES: Cc1cccc(C(CO)NC(=O)c2cn(-c3nc(NC4CCOCC4)ncc3C)cn2)c1] | N-(2-hydroxy-1-(m-tolyl)ethyl)-1-(5-methyl-2-((tetrahydro-2H-pyran-4-yl)amino)pyrimidin-4-yl)-1H-imidazole-4-carboxamide | 1HNMR (400 MHz, DMSO-d₆): δ 8.39 (s, 1H), 8.26 (s, 1H), 8.20 (d, J = 8.4 Hz, 1H), 8.07 (s, 1H), 7.35 (d, J = 7.2 Hz, 1H), 7.19-7.12 (m, 3H), 7.02 (d, J = 7.2 Hz, 1H), 4.93-4.96 (m, 2H), 3.83 (d, J = 10.8 Hz, 3H), 3.67 (d, J = 4.8 Hz, 2H), 3.35 (t, 2H), 2.30 (s, 3H), 2.16 (s, 3H), 1.81 (d, J = 12.8 Hz, 2H)), 1.52-1.43 (m, 2H). | 3 |
| 239 | 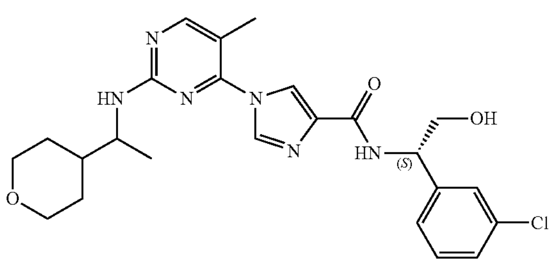 | 1-{5-Methyl-2-[1-(tetrahydro-pyran-4-yl)-ethyl-amino]-pyrimidin-4-yl}-1H-pyrrole-3-carboxylic acid [(S)-1-(3-chloro-phenyl)-2-hydroxy-ethyl]-amide | 1HNMR (400 MHz, DMSO-d₆): δ 8.38 (d, J = 8.0 Hz, 2H), 8.30 (s, 1H), 8.26 (s, 1H), 8.07 (s, 1H), 7.42 (s, 1H), 7.31-7.23 (m, 2H), 5.02 (s, 2H), 3.83 (d, J = 5.2 Hz, 2H), 3.71 (t, J = 5.2 Hz, 3H), 3.32-3.16 (m, 2H), 2.16 (s, 3H), 1.58 (t, J = 10.4 Hz, 3H), 1.07 (d, J = 6.8 Hz, 3H) | 17, 6 |
| 240 | 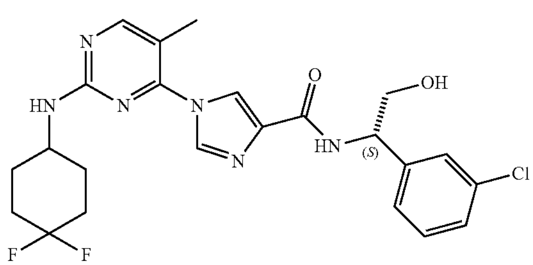 | (S)-N-(1-(3-chlorophenyl)-2-hydroxyethyl)-1-(2-((4,4-difluorocyclohexyl)amino)-5-methyl-pyrimidin-4-yl)-1H-imidazole-4-carboxamide | 1HNMR (400 MHz, DMSO-d₆): δ 8.38 (d, J = 7.6 Hz, 1H), 8.34 (s, 1H), 8.28 (s, 1H), 8.09 (s, 1H), 7.42 (br s, 2H), 7.31 (s, 2H), 7.28 (s, 1H), 5.01 (d, J = 4.8 Hz, 2H), 3.91 (br s, 1H), 3.71 (t, J = 5.6 Hz, 2H), 2.04-1.98 (m, 2H), 1.89 (d, J = 10.8 Hz, 2H), 1.58-1.55 (m, 2H | 4, 6 |

TABLE 1-continued

| Cmpd # | Structure | Name | NMR data | Scheme # |
|---|---|---|---|---|
| 241 | 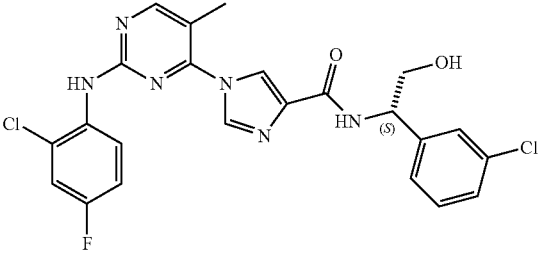 | (S)-1-(2-((2-chloro-4-fluorophenyl)-amino)-5-methyl-pyrimidin-4-yl)-N-(1-(3-chlorophenyl)-2-hydroxy-ethyl)-1H-imidazole-4-carboxamide | 1HNMR (400 MHz, DMSO-d$_6$): δ 9.14 (s, 1H), 8.46 (s, 1H), 8.39 (d, J = 8.4 Hz, 1H), 8.26 (s, 1H), 8.07 (s, 1H), 7.67-7.63 (m, 1H), 7.49-7.46 (m, 1H), 7.42 (s, 1H), 7.34-7.31 (s, 2H), 7.27-7.21 (m, 1H), 7.20-7.18 (m, 1H), 5.03-4.97 (m, 2H), 3.71 (t, J = 5.6 Hz, 2H), 2.30 (s, 3H). | 6 |
| 242 | 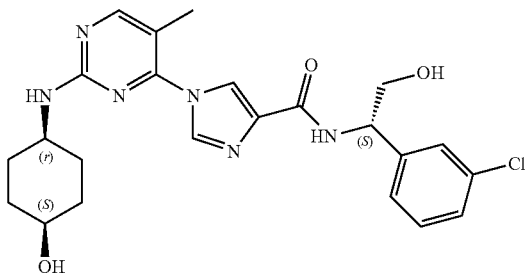 | N-((S)-1-(3-chlorophenyl)-2-hydroxy-ethyl)-1-(2-(((1r,4S)-4-hydroxy-cyclohexyl)amino)-5-methyl-pyrimidin-4-yl)-1H-imidazole-4-carboxamide | 1HNMR (400 MHz, DMSO-d$_6$): δ 8.38 (d, J = 8 Hz, 1H), 8.31 (s, 1H), 8.26 (s, 1H), 7.42 (s, 1H), 7.31-7.28 (m, 3H), 7.19 (d, J = 7.2 Hz, 1H), 5.02-4.99 (m, 2H), 4.479-4.471 (m, 1H), 3.72-3.71 (m, 2H), 3.70 (br, 1H), 3.37-3.36 (m, 1H), 2.15 (s, 3H), 1.87-1.79 (m, 4H), 1.27-1.19 (m, 4H). | 3, 6 |
| 243 | 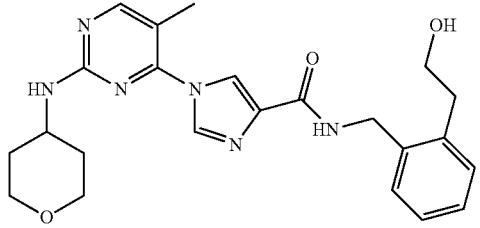 [SMILES: Cc1cnc(NC2CCOCC2)nc1-n1cnc(C(=O)NCc2ccccc2CCO)c1] | N-(2-(2-hydroxy-ethyl)benzyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.46 (t, J = 6 Hz, 1H), 8.33 (s, 1H), 8.24 (s, 1H), 8.09 (s, 1H), 7.35 (d, J = 7.2 Hz, 1H), 7.25 (d, J = 5.2 Hz, 1H), 7.16-7.13 (m, 3H), 4.67 (t, J = 5.2 Hz, 1H), 4.48 (d, J = 6 Hz, 2H), 3.89 (br s, 1H), 3.83 (d, J = 11.2 Hz, 2H), 3.62-3.57 (m, 2H), 3.39-3.32 (m, 2H), 2.82 (t, J = 6.8 Hz, 2 H), 2.17 (s, 3H), 1.80 (d, J = 11.2 Hz, 2H), 1.52-1.44 (m, 2H). | 3 |
| 245 | 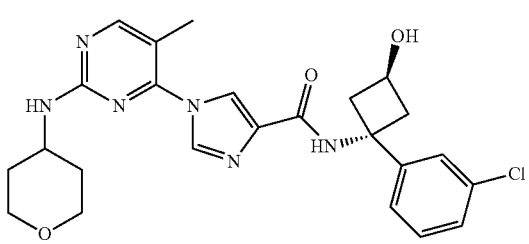 [SMILES: Cc1cnc(NC2CCOCC2)nc1-n1cnc(C(=O)N[C@]2(c3cccc(Cl)c3)C[C@@H](O)C2)c1] | N-((1s,3s)-1-(3-chloro-phenyl)-3-hydroxy-cyclobutyl)-1-(5-methyl-2-((tetrahydro-2H-4-yl)amino)pyrimidin-4-yl)-1H-imidazole-4-carboxamide | 1HNMR (400 MHz, DMSO-d$_6$) δ 8.87 (s, 1H), 8.32 (s, 1H), 8.23 (s, 1H), 7.99 (s, 1H), 7.48 (s, 1H), 7.44 (d, J = 8 Hz, 1H), 7.32 (t, J = 8 Hz, 2H), 7.23 (d, J = 8 Hz, 1H), 5.12 (d, J = 6 Hz, 1H), 3.98-3.81 (m, 4H), 3.35 (t, J = 11.2 Hz, 2H), 2.92 (b, 2H), 2.38 (b, 2H), 2.15 (s, 3H), 1.79 (d, J = 11.6 Hz, 2H), 1.52-1.43 (m, 2H). | 6 |

TABLE 1-continued

| Cmpd # | Structure | Name | NMR data | Scheme # |
|---|---|---|---|---|
| 246 | 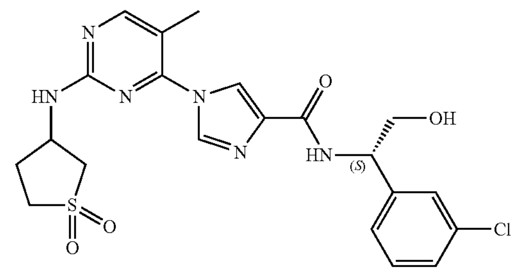 | N-((S)-1-(3-chlorophenyl)-2-hydroxy-ethyl)-1-(2-((1,1-dioxido-tetrahydro-thiophen-3-yl)amino)-5-methyl-pyrimidin-4-yl)-1H-imidazole-4-carboxamide | 1HNMR (400 MHz, DMSO-d₆): δ 8.40-8.39 (m, 2H), 8.29 (s, 1H), 8.13 (s, 1H), 7.79 (d, J = 6.8 Hz, 1H), 7.42 (s, 1H), 7.31 (bs, 2H), 7.28-7.27 (m, 1H), 5.00 (q, J₁ = 5.6 Hz, J₂ = 7.6 Hz, 2H), 3.71 (d, J = 6.0 Hz, 1H), 3.54-3.49 (m, 1H), 3.36-3.27 (m, 1H), 3.19-3.14 (m, 1H), 2.98-2.95 (m, 1H), 2.47-2.39 (m, 1H), 2.20-2.12 (m, 4H), | 4, 6 |
| 247 | 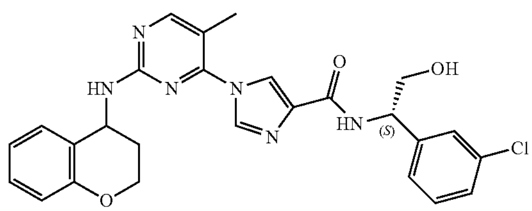 | N-((S)-1-(3-chlorophenyl)-2-hydroxy-ethyl)-1-(2-(chroman-4-ylamino)-5-methyl-pyrimidin-4-yl)-1H-imidazole-4-carboxamide | 1HNMR (400 MHz, DMSO-d₆): δ 8.39-8.37 (m, 2H), 8.29 (s, 1H), 8.11 (s, 1H), 7.81 (d, J = 8 Hz, 1H), 7.41 (s, 1H), 7.31 (bs, 2H), 7.27-7.26 (m, 1H), 7.17 (d, J = 7.6 Hz, 1H), 6.80 (t, J = 7.6 Hz, 1H), 6.74 (d, J = 8.0 Hz, 1H), 5.00 (bs, 1H), 5.0 (q, J₁ = 6.0 Hz, J₂ = 7.6 Hz, 1H), 4.28-4.18 (m, 2H), 3.71 (d, J = 5.2 Hz, 2H), 2.21 (s, 3H), 2.07-2.03 (m, 2H). | 6 |
| 248 | 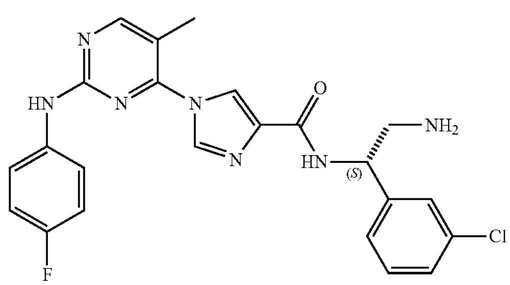 | (S)-N-(2-amino-1-(3-chlorophenyl)-ethyl)-1-(2-((4-fluoro-phenyl)amino)-5-methyl-pyrimidin-4-yl)-1H-imidazole-4-carboxamide | 1HNMR (400 MHz, DMSO-d₆): δ 8.56 (d, J = 8.4 Hz, 1H), 8.53 (s, 1H), 8.14 (s, 1H), 7.70-7.67 (m, 2H), 7.41 (s, 1H), 7.35-7.26 (m, 3H), 7.11 (t, J = 8.8 Hz, 2H), 4.94-4.88 (m, 1H), 2.98-2.93 (m, 1H), 2.89-2.86 (m, 1H), 2.26 (s, 3H) | 4 |
| 249 | 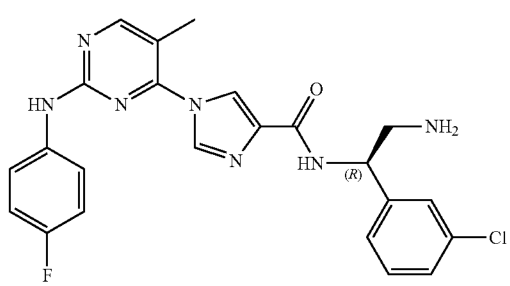 | (R)-N-(2-amino-1-(3-chlorophenyl)-ethyl)-1-(2-((4-fluoro-phenyl)-amino)-5-methyl-pyrimidin-4-yl)-1H-imidazole-4-carboxamide | 1HNMR (400 MHz, DMSO-d₆): δ 9.79 (s, 1H), 8.55 (d, J = 8.4 Hz, 1H), 8.53 (s, 1H), 8.33 (s, 1H), 8.15 (s, 1H), 7.70-7.67 (m, 2H), 7.41 (s, 1H), 7.35-7.32 (m, 2H), 7.30-7.26 (m, 1H), 7.11 (t, J = 8.4 Hz, 2H), 4.95-4.90 (m, 1H), 3.00-2.95 (m, 1H), 2.90-2.86 (m, 1H), 2.26 (s, 3H) | 4 |

TABLE 1-continued

| Cmpd # | Structure | Name | NMR data | Scheme # |
|---|---|---|---|---|
| 250 | 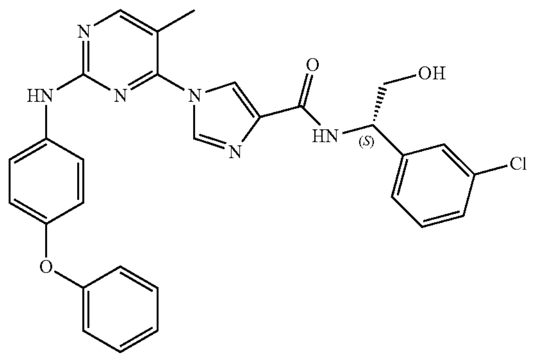 | N-(1-(3-chlorophenyl)-2-hydroxy-ethyl)-1-(5-methyl-2-((4-phenoxy-phenyl)amino)pyrimidin-4-yl)-1H-imidazole-4-carboxamide | 1HNMR (400 MHz, DMSO-d$_6$): δ 9.79 (s, 1H), 8.53 (s, 1H), 8.40 (d, J = 8.0 Hz, 1H), 8.34 (s, 1H), 8.16 (s, 1H), 7.70 (d, J = 8.8 Hz, 2H), 7.33 (s, 1H), 7.35-7.27 (m, 5H), 7.07-7.045 (m, 1H), 6.99-6.92 (m, 4H), 5.03-4.98 (m, 2H), 3.73-3.70 (m, 2H), 2.30 (s, 3H) | 6 |
| 251 | 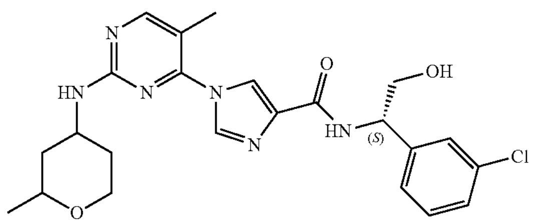 | N-((S)-1-(3-chlorophenyl)-2-hydroxy-ethyl)-1-(5-methyl-2-((2-methyl-tetrahydro-2H-pyran-4-yl)amino)pyrimidin-4-yl)-1H-imidazole-4-carboxamide | 1HNMR (400 MHz, DMSO-d$_6$): δ 8.34-8.32 (m, 1H), 8.22-8.21 (m, 1H), 8.15-8.14 (d, J = 7.6 Hz, 1H), 8.06-8.04 (m, 1H), 7.42 (s, 1H), 7.33-7.30 (m, 2H), 7.269-7.260 (m, 1H), 6.984 (br, 1H), 5.052-5.00 (m, 1H), 4.82 (s, 1H), 3.81-3.77 (m, 1H), 3.75-3.66 (m, 2H), 3.45-3.37 (m, 2H), 2.24-2.18 (m, 3H), 1.92-1.89 (m, 1H), 1.80-1.75 (m, 2H), 1.51-1.39 (m, 1H), 1.21 (m, 2H), 1.18-1.15 (m, 1H), 1.07-1.05 (m, 1H). | 6 |
| 252 | 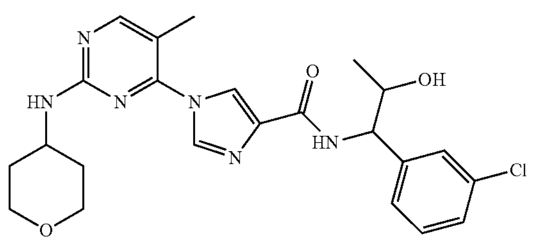 [SMILES: Cc1cnc(NC2CCOCC2)nc1-n1cnc(C(=O)NC(c2cccc(Cl)c2)C(C)O)c1] | N-(1-(3-chlorophenyl)-2-hydroxy-propyl)-1-(5-methyl-2-((tetrahydro-2H-pyran-4-yl)amino)-pyrimidin-4-yl)-1H-imidazole-4-carboxamide (isomer #2) | 1HNMR (400 MHz, DMSO-d$_6$): δ 8.43-8.41 (d, J = 8.8 Hz, 1H), 8.33 (s, 1H), 8.25 (s, 1H), 8.05 (s, 1H), 7.43 (s, 1H), 7.36-7.27 (m, 4H), 4.98-4.97 (m, 1H), 4.80-4.76 (m, 1H), 4.06-4.01 (m, 1H), 3.84-3.81 (m, 3H), 3.38-3.27 (m, 2H), 2.15 (m, 3H), 1.81-1.78 (m, 2H), 1.51-1.43 (m, 2H), 1.02 (m, 3H). | 3 |
| 253 | 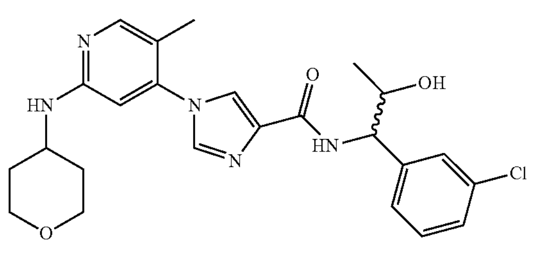 [SMILES: Cc1cnc(NC2CCOCC2)cc1-n1cnc(C(=O)NC(c2cccc(Cl)c2)C(C)O)c1] | N-(1-(3-chlorophenyl)-2-hydroxy-propyl)-1-(5-methyl-2-((tetrahydro-2H-pyran-4-yl)amino)-pyrimidin-4-yl)-1H-imidazole-4-carboxamide (isomer #1) | 1HNMR (400 MHz, DMSO-d$_6$): δ 8.42 (d, J = 9.2 Hz, 1H), 8.33 (s, 1H), 8.25 (s, 1H), 8.05 (s, 1H), 7.43 (s, 1H), 7.35-7.27 (m, 4H), 4.98-4.97 (m, 1H), 4.80-4.76 (m, 1H), 4.06-4.0 (m, 1H), 3.84-3.81 (m, 3H), 3.38-3.26 (m, 2H), 2.15 (s, 3H), 1.81-1.78 (m, 2H), 1.51-1.43 (m, 2H), 1.07-1.01 (m, 3H). | 3 |

TABLE 1-continued

| Cmpd # | Structure | Name | NMR data | Scheme # |
|---|---|---|---|---|
| 254 | 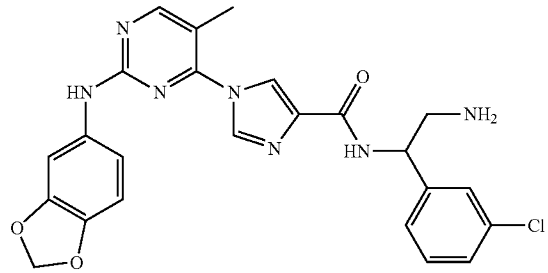 [SMILES: Cc1cnc(Nc2ccc3c(c2)OCO3)nc1-n1cnc(C(=O)NC(CN)c2cccc(Cl)c2)c1] | N-(2-amino-1-(3-chloro-5-fluoro-phenyl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 9.64 (s, 1H), 8.60 (s, 1H), 8.50 (s, 1H), 8.32 (s, 1H), 8.13 (s, 1H), 7.41-7.31 (m, 4H), 7.05 (s, 1H), 6.83 (s, 1H), 5.94 (s, 2H), 4.9 (s, 1H), 3.3-2.80 (m, 2H), 2.25 (s, 3H) | 3 |
| 255 | 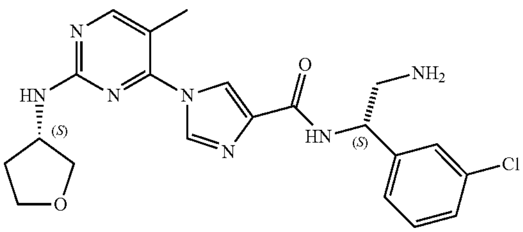 | N-((S)-2-amino-1-(3-chlorophenyl)ethyl)-1-(5-methyl-2-(((S)-tetrahydro-furan-3-yl)amino)-pyrimidin-4-yl)-1H-imidazole-4-carboxamide | 1HNMR (400 MHz, DMSO-$d_6$): δ 8.53 (d, J = 2.8 Hz, 1H), 8.35 (s, 1H), 8.28 (s, 1H), 8.09 (s, 1H), 7.58 (s, 1H), 7.40 (s, 1H), 7.34-7.25 (m, 3H), 4.93-4.85 (m, 1H), 4.34 (s, 1H), 3.86-3.81 (m, 2H), 3.71-3.67 (m, 1H), 3.52-3.27 (m, 1H), 2.97-2.92 (m, 1H), 2.89-2.84 (m, 1H), 2.18 (s, 3H), 2.07-1.94 (m, 1H), 1.84-1.75 (m, 1H), 1.86 (br s, 2H) | 20 |
| 256 | 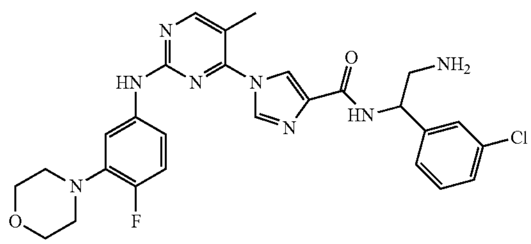 [SMILES: Cc1cnc(Nc2ccc(F)c(N3CCOCC3)c2)nc1-n1cnc(C(=O)NC(CN)c2cccc(Cl)c2)c1] | N-(2-amino-1-(3-chloro-phenyl)ethyl)-1-(2-((4-fluoro-3-morpholino-phenyl)amino)-5-methyl-pyrimidin-4-yl)-1H-imidazole-4-carboxamide | 1HNMR (400 MHz, DMSO-$d_6$) δ 9.73 (s, 1H), 8.57 (d, J = 8.4 Hz, 1H), 8.54 (s, 1H), 8.35 (s, 1H), 8.16 (s, 1H), 7.54 (d, J = 6.4 Hz, 1H), 7.41 (s, 1H), 7.35-7.20 (m, 4H), 7.06-7.01 (m, 1H), 4.94-4.89 (m, 1H), 3.70 (s, 4H), 2.97 (s, 5H), 2.90-2.85 (m, 1H), 2.27 (s, 3H) | 3 |
| 257 | 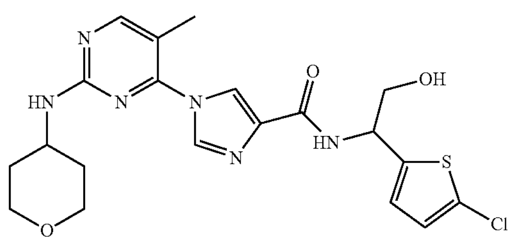 | N-(1-(5-chlorothio-phen-2-yl)-2-hydroxy-ethyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 8.33 (s, 1H), 8.31 (s, 1H), 8.25 (s, 1H), 8.12 (s, 1H), 7.36 (d, J = 7.2 Hz, 1H), 6.93-6.87 (m, 2H), 5.24-5.17 (m, 2H), 3.84-3.75 (m, 5H), 3.38-3.27 (m, 2H), 2.16 (s, 3H), 1.88-1.79 (m, 2H), 1.51-1.44 (m, 2H). | 3 |
| 258 | 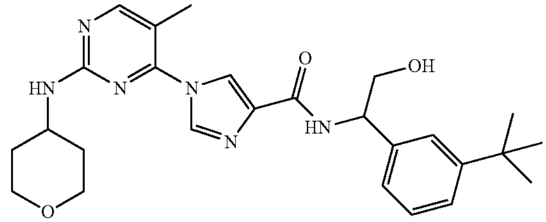 [SMILES: Cc1cnc(NC2CCOCC2)nc1-n1cnc(C(=O)NC(CO)c2cccc(C(C)(C)C)c2)c1] | N-(1-(3-(tert-butyl)phenyl)-2-hydroxy-ethyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 8.33 (s, 1H), 8.25 (d, J = 8 Hz, 2H), 8.07 (s, 1H), 7.39-7.34 (m, 2H), 7.23-7.19 (m, 2H), 7.14 (d, J = 7.2 Hz, 1H), 5.01 (d, J = 7.6 Hz, 1H), 4.93 (t, 1H), 3.84-3.81 (m, 3H), 3.70 (s, 2H), 3.38-3.27 (m, 2H), 2.16 (s, 3H), 1.80 (d, J = 12 Hz, 2H), 1.49-1.44 (m, 2H), 1.35 (s, 9H) | 3 |

TABLE 1-continued

| Cmpd # | Structure | Name | NMR data | Scheme # |
|---|---|---|---|---|
| 259 | 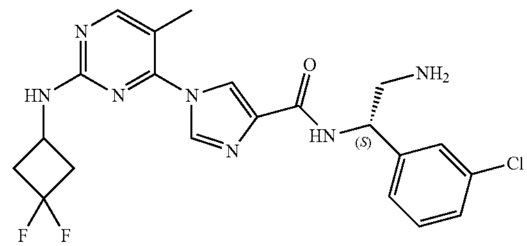 | (S)-N-(2-amino-1-(3-chlorophenyl)-ethyl)-1-(2-((3,3-difluoro-cyclobutyl)amino)-5-methyl-pyrimidin-4-yl)-1H-imidazole-4-carboxamide | 1HNMR (400 MHz, DMSO-d$_6$): δ 8.54 (d, J = 8.0 Hz, 1H), 8.38 (s, 1H), 8.29 (s, 1H), 8.10 (s, 1H), 7.86 (d, J = 5.6 Hz, 1H), 7.40 (s, 1H), 7.35-7.25 (m, 3H), 4.93-4.88 (m, 1H), 4.17 (d, J = 6.0 Hz, 1H), 2.90-2.84 (m, 4H), 2.68-2.55 (m, 2H), 2.20 (s, 3H), 1.54 (br s, 2H). | 20 |
| 260 | 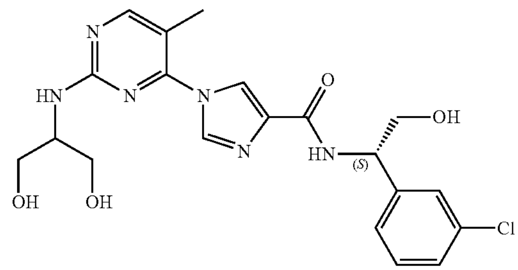 | (S)-N-(1-(3-chlorophenyl)-2-hydroxy-ethyl)-1-(2-((1,3-dihydroxy-propan-2-yl)amino)-5-methyl-pyrimidin-4-yl)-1H-imidazole-4-carboxamide | 1HNMR (400 MHz, DMSO-d$_6$): δ 8.39 (d, J = 8.0 Hz, 1H), 8.31 (d, J = 15.6 Hz, 2H), 8.10 (s, 1H), 7.42 (s, 1H), 7.31-7.28 (m, 3H), 6.77 (d, J = 8.0 Hz, 1H), 5.02 (s, 2H), 4.56 (s, 2H), 3.89 (br, 1H), 3.71 (s, 2H), 3.49-3.47 (m, 4H), 2.18 (s, 3H). | 6 |
| 261 | 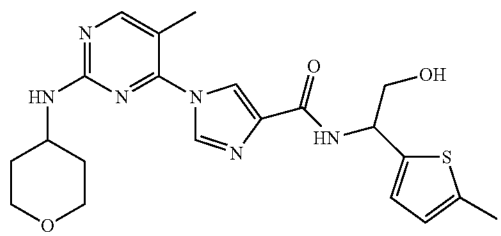 [SMILES: Cc1ccc(C(CO)NC(=O)c2cn(-c3nc(NC4CCOCC4)ncc3C)cn2)s1] | N-(2-hydroxy-1-(5-methyl-thiophen-2-yl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.33 (s, 1H), 8.24 (s, 1H), 8.14-8.10 (m, 2H), 7.36 (d, J = 8.0 Hz, 1H), 6.77 (d, J = 4.0 Hz, 1H), 6.60 (d, J = 4.0 Hz, 1H), 5.19-5.07 (m, 2H), 3.89-3.82 (m, 3H), 3.74-3.71 (m, 2H), 3.38-3.33 (m, 2H), 2.30 (s, 3H), 2.16 (m, 3H), 1.81 (d, J = 12.0 Hz, 2H), 1.52-1.43 (m, 2H) | 3 |
| 262 | 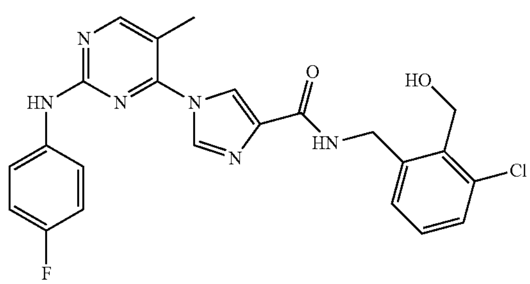 [SMILES: Cc1cnc(Nc2ccc(F)cc2)nc1-n1cnc(C(=O)NCc2cccc(Cl)c2CO)c1] | N-(3-chloro-2-(hydroxy-methyl)benzyl)-1-(2-((4-fluoro-phenyl)-amino)-5-methyl-pyrimidin-4-yl)-1H-imidazole-4-carboxamide | 1HNMR (400 MHz, DMSO-d$_6$): δ 8.64 (d, J = 6 Hz, 1H), 8.53 (s, 1H), 8.31 (s, 1H), 8.16 (s, 1H), 7.70-7.66 (m, 2H), 7.33-7.25 (m, 3H), 7.11 (t, J = 8.8 Hz 2H), 5.24 (t, J = 5.2 Hz 1H), 4.76 (d, J = 4.8 Hz, 2H), 4.61 (d, J = 6 Hz, 2H), 2.25 (s, 3H). | 3 |
| 264 | 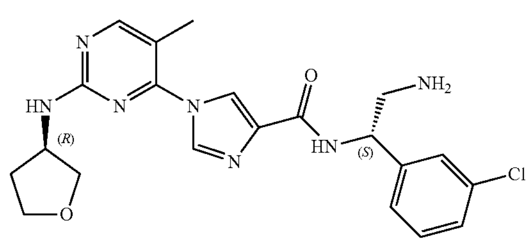 | N-((S)-2-amino-1-(3-chlorophenyl)-ethyl)-1-(5-methyl-2-(((R)-tetra-hydrofuran-3-yl)amino)pyrimidin-4-yl)-1H-imidazole-4-carboxamide | 1HNMR (400 MHz, DMSO-d$_6$): δ 8.53 (d, J = 8.0 Hz, 1H), 8.35 (s, 1H), 8.28 (s, 1H), 8.09 (s, 1H), 7.58 (d, J = 5.6 Hz, 1H), 7.40 (s, 1H), 7.35-7.25 (m, 3H), 4.94-4.89 (m, 1H), 4.34 (s, 1H), 3.86-3.77 (m, 2H), 3.71-3.66 (m, 1H), 3.54-3.51 (m, 1H), 2.97-2.92 (m, 1H), 2.89-2.85 (m, 1H), 2.18 (s, 3H), 2.16-2.07 | 20 |

TABLE 1-continued

| Cmpd # | Structure | Name | NMR data | Scheme # |
|---|---|---|---|---|
| | | | (m, 1H), 1.88-1.82 (m, 1H), 1.54 (br s, 2H). | |
| 265 | 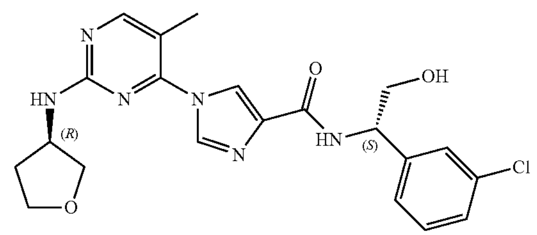 | N-((S)-1-(3-chlorophenyl)-2-hydroxy-ethyl)-1-(5-methyl-2-(((R)-tetrahydrofuran-3-yl)amino)pyrimidin-4-yl)-1H-imidazole-4-carboxamide | 1HNMR (400 MHz, DMSO-d$_6$): δ 8.39 (d, J = 8.4 Hz, 1H), 8.35 (s, 1H), 8.28 (s, 1H), 8.10 (s, 1H), 7.60 (d, J = 5.2 Hz, 1H), 7.42 (s, 1H), 7.31 (s, 2H), 7.28 (s, 1H), 5.03-4.99 (m, 2H), 4.41 (s, 1H), 3.86-3.79 (m, 2H), 3.72-3.68 (m, 3H), 3.54-3.51 (m, 1H), 2.18 (s, 3H), 2.11 (s, 1H), 1.89 (s, 1H). | 3 |
| 266 | 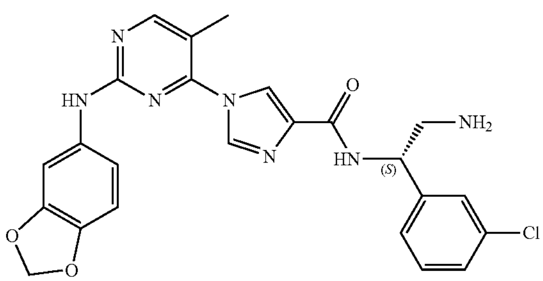 | (S)-N-(2-amino-1-(3-chlorophenyl)-ethyl)-1-(2-(benzo[d][1,3]dioxol-5-ylamino)-5-methyl-pyrimidin-4-yl)-1H-imidazole-4-carboxamide | 1HNMR (400 MHz, DMSO-d$_6$): δ 8.55 (d, J = 8.4 Hz, 1H), 8.50 (s, 1H), 8.32 (s, 1H), 8.13 (s, 1H), 7.41-7.35 (m, 2H), 7.33-7.25 (m, 3H), 7.07-7.05 (m, 2H), 6.82 (d, J = 8.4 Hz, 1H), 5.94 (s, 2H), 4.93-4.88 (m, 1H), 2.97-2.85 (m, 2H), 2.25 (s, 3H) | 20 |
| 267 | 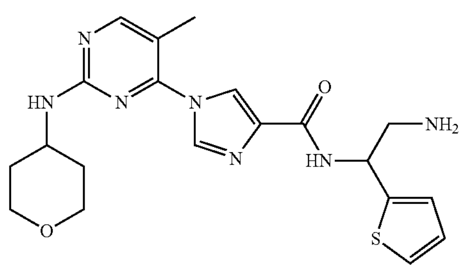 [SMILES: Cc1cnc(NC2CCOCC2)nc1-n1cnc(C(=O)NC(CN)c2cccs2)c1] | N-(2-amino-1-(thiophen-2-yl)ethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.37 (d, J = 8.4 Hz, 1H), 8.33 (s, 1H), 8.24 (s, 1H), 8.10 (s, 1H), 7.36-7.33 (m, 2H), 6.99 (s, 1H), 6.96-6.94 (m, 1H), 5.18-5.16 (m, 1H), 3.84 (s, 1H), 3.82 (m, 2H), 3.38-3.27 (m, 2H), 3.02-2.95 (m, 2H), 2.17 (s, 3H), 1.82-1.79 (m, 2H), 1.54-1.46 (m, 4H). | 3 |
| 268 | 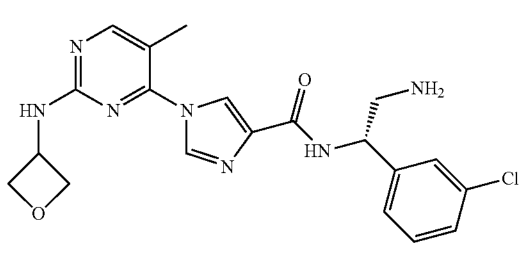 [SMILES: Cc1cnc(NC2COC2)nc1-n1cnc(C(=O)N[C@H](CN)c2cccc(Cl)c2)c1] | (S)-N-(2-amino-1-(3-chlorophenyl)-ethyl)-1-(5-methyl-2-(oxetan-3-ylamino)pyrimidin-4-yl)-1H-imidazole-4-carboxamide | 1HNMR (400 MHz, DMSO-d$_6$): δ 8.53 (d, J = 8 Hz, 1H), 8.36 (s, 1H), 8.27 (s, 1H), 8.09-8.08 (b, 2H), 7.40 (s, 1H), 7.35-7.25 (m, 3H), 4.92-4.87 (m, 2H), 4.74 (t, J = 6.8 Hz, 2H), 4.50 (t, J = 6 Hz, 2H), 2.97-2.94 (m, 1H) 2.89-2.84 (m, 1H), 2.19 (s, 3H), 1.54 (bs, 2H). | 20 |

TABLE 1-continued

| Cmpd # | Structure | Name | NMR data | Scheme # |
|---|---|---|---|---|
| 269 | 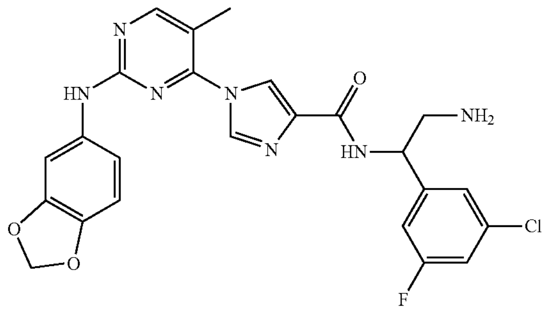 [SMILES: Cc1cnc(Nc2ccc3c(c2)OCO3)nc1-n1cnc(C(=O)NC(CN)c2cc(F)cc(Cl)c2)c1] | N-(2-amino-1-(3-chloro-5-fluoro-phenyl)ethyl)-1-(2-(benzo[d][1,3]dioxol-5-ylamino)-5-methyl-pyrimidin-4-yl)-1H-imidazole-4-carboxamide | 1HNMR (400 MHz, DMSO-d$_6$): δ 9.64 (s, 1H), 8.60 (d, J = 8.0 Hz, 1H), 8.50 (s, 1H), 8.33 (s, 1H), 8.14 (s, 1H), 7.38 (s, 1H), 7.27 (d, J = 7.6 Hz, 2H), 7.19 (d, J = 9.6 Hz, 1H), 7.07-7.05 (m, 1H), 6.82 (d, J = 8.4 Hz, 1H), 5.94 (s, 2H), 4.91 (d, J = 6.8 Hz, 1H), 2.97-2.85 (m, 2H), 2.21 (s, 3H). | 9 |
| 270 | 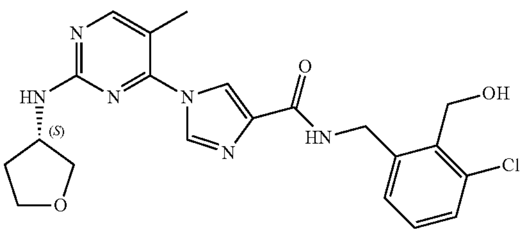 | (S)-N-(3-chloro-2-(hydroxy-methyl)benzyl)-1-(5-methyl-2-(tetrahydro-furan-3-yl)amino)-pyrimidin-4-yl)-1H-imidazole-4-carboxamide | 1HNMR (400 MHz, DMSO-d$_6$): δ 8.63 (t, J = 6.0 Hz, 1H), 8.35 (s, 1H), 8.26 (s, 1H), 8.11 (s, 1H), 7.59 (d, J = 5.2 Hz, 1H), 7.32-7.22 (m, 3H), 5.23 (t, J = 4.8 Hz, 1H), 4.76 (d, J = 4.8 Hz, 2H), 4.61 (d, J = 6.0 Hz, 2H), 4.34 (s, 1H), 3.87-3.77 (m, 2H), 3.71-3.66 (m, 1H), 3.54-3.51 (m, 1H), 2.19 (s, 3H), 2.18-2.09 (m, 1H), 1.88-1.85 (m, 1H). | 3 |
| 271 | 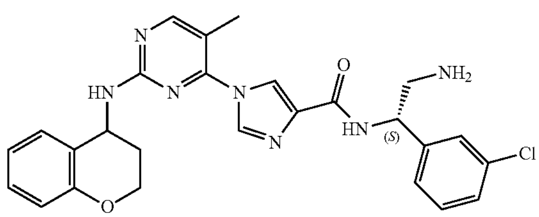 | N-((S)-2-amino-1-(3-chlorophenyl)ethyl)-1-(2-(chroman-4-ylamino)-5-methyl-pyrimidin-4-yl)-1H-imidazole-4-carboxamide | 1HNMR (400 MHz, DMSO-d$_6$): δ 8.53 (d, J = 8.0 Hz, 1H), 8.39 (s, 1H), 8.28 (s, 1H), 8.10 (s, 1H), 7.80 (d, J = 8.0 Hz, 1H), 7.40 (s, 1H), 7.34-7.25 (m, 3H), 7.17-7.16 (m, 1H), 7.12-7.09 (m, 1H), 6.80 (t, J = 7.2 Hz, 1H), 6.74 (d, J = 8.4 Hz, 1H), 5.22 (br s, 1H), 4.93-4.88 (m, 1H), 4.26-4.20 (br s, 2H), 2.98-2.94 (m, 1H), 2.93-2.87 (m, 1H), 2.30 (s, 3H), 2.21 (br s, 1H), 1.88 (br s, 2H). | 4 |
| 272 | 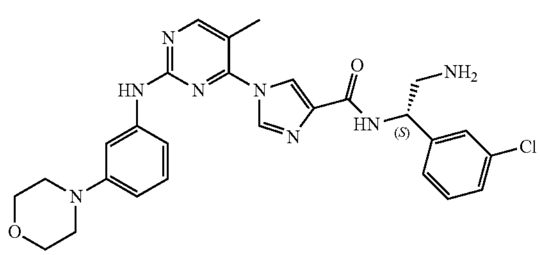 | (S)-N-(2-amino-1-(3-chlorophenyl)ethyl)-1-(5-methyl-2-((3-morpholino-phenyl)amino)pyrimidin-4-yl)-1H-imidazole-4-carboxamide | 1HNMR (400 MHz, DMSO-d$_6$): δ 9.73 (s, 1H), 8.57-8.53 (m, 2H), 8.34 (s, 1H), 8.16 (s, 1H), 7.54-7.53 (m, 1H), 7.41 (s, 1H), 7.31-7.22 (m, 4H), 7.03 (t, J = 12 Hz, 1H), 4.92-4.91 (m, 1H), 3.70 (s, 4H), 2.96-2.88 (m, 6H), 2.27 (s, 3H), (NH2 peak merged with solvent) | 4 |

TABLE 1-continued

| Cmpd # | Structure | Name | NMR data | Scheme # |
|---|---|---|---|---|
| 273 | 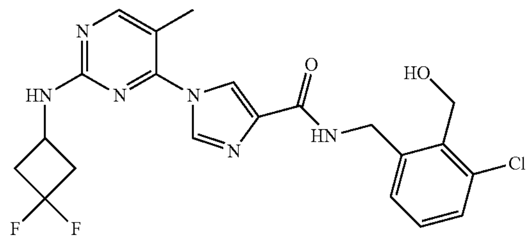 [SMILES: Cc1cnc(NC2CC(F)(F)C2)nc1-n1cnc(C(=O)NCc2cccc(Cl)c2CO)c1] | N-(3-chloro-2-(hydroxymethyl)benzyl)-1-(2-((3,3-difluorocyclobutyl)amino)-5-methylpyrimidin-4-yl)-1H-imidazole-4-carboxamide | 1HNMR (400 MHz, DMSO-d$_6$): δ 8.63 (t, J = 5.6 Hz, 1H), 8.38 (s, 1H), 8.27 (s, 1H), 8.12 (s, 1H), 7.85 (d, J = 5.6 Hz, 1H), 7.32-7.22 (m, 2H), 5.25-5.22 (m, 1H), 4.75 (d, J = 4.8 Hz, 2H), 4.60 (d, J = 6 Hz, 2H), 4.18-4.15 (m, 1H), 2.95-2.19 (m, 2H), 2.68-2.60 (m, 2H), 2.19 (s, 3H). | 3 |
| 274 | 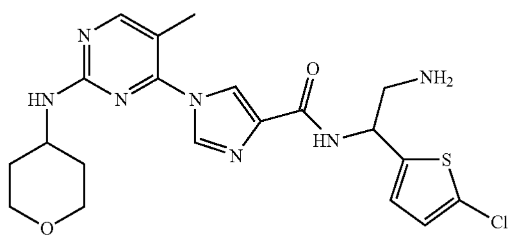 [SMILES: Cc1cnc(NC2CCOCC2)nc1-n1cnc(C(=O)NC(CN)c2ccc(Cl)s2)c1] | N-(2-amino-1-(5-chlorothiophen-2-yl)ethyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.45 (d, J = 8.4 Hz, 1H), 8.34 (s, 1H), 8.25 (s, 1H), 8.11 (s, 1H), 7.35 (d, J = 7.2 Hz, 1H), 6.92 (d, J = 3.6 Hz, 1H), 6.84 (d, J = 4.0 Hz, 1H), 5.09-5.05 (m, 1H), 3.85-3.82 (m, 3H), 3.39-3.27 (m, 2H), 3.026-2.92 (m, 2H), 2.17 (s, 3H), 1.80 (d, J = 11.6 Hz, 2H), 1.52-1.44 (m, 2H). | 4 |
| 275 | 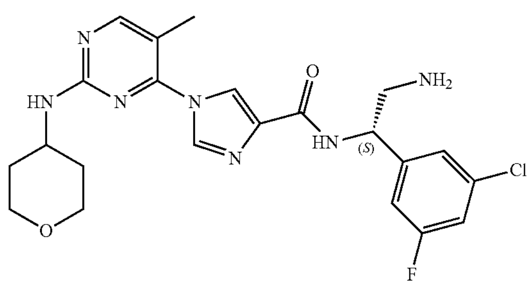 | (S)-N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.72 (d, J = 8.0 Hz, 1H), 8.33 (s, 1H), 8.26 (s, 1H), 8.07 (s, 1H), 7.35 (d, J = 7.2 Hz, 1H), 7.27-7.24 (m, 2H), 7.17 (d, J = 9.2 Hz, 1H), 7.0 (bs, 1H), 5.15-5.05 (m, 1H), 3.95-3.81 (m, 3H), 3.38-3.35 (m, 4H), 2.16 (s, 3H), 1.81-1.78 (m, 2H), 1.51-1.41 (m, 2H), 1.30 (s, 9H). | 20 |
| 276 | 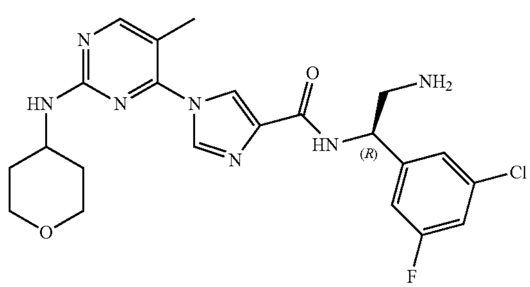 | (R)-N-(2-amino-1-(3-chloro-5-fluoro-phenyl)ethyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.72 (d, J = 8.0 Hz, 1H), 8.33 (s, 1H), 8.26 (s, 1H), 8.07 (s, 1H), 7.35 (d, J = 7.2 Hz, 1H), 7.27-7.24 (m, 2H), 7.17 (d, J = 9.2 Hz, 1H), 7.0 (bs, 1H), 5.15-5.05 (m, 1H), 3.95-3.81 (m, 3H), 3.38-3.35 (m, 4H), 2.16 (s, 3H), 1.81-1.78 (m, 2H), 1.51-1.41 (m, 2H), 1.30 (s, 9H). | 4 |

TABLE 1-continued

| Cmpd # | Structure | Name | NMR data | Scheme # |
|---|---|---|---|---|
| 277 | 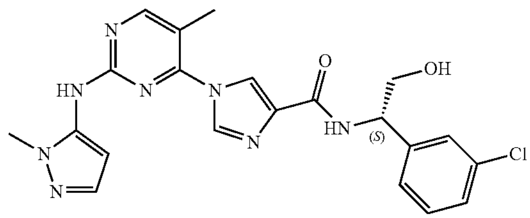 | (S)-N-(1-(3-chlorophenyl)-2-hydroxyethyl)-1-(5-methyl-2-((1-methyl-1H-pyrazol-5-yl)amino)-pyrimidin-4-yl)-1H-imidazole-4-carboxamide | 1HNMR (400 MHz, DMSO-d$_6$): δ 9.59 (s, 1H), 8.52 (s. 1H), 8.41-8.39 (d, J = 8.0 Hz, 1H), 8.29 (s, 1H), 8.10 (s, 1H), 7.42 (s, 1H), 7.31-7.28 (m, 4H), 6.21-6.22 (s, 1H), 5.03-4.98 (m, 2H), 3.72-3.70 (m, 2H), 3.6 (s, 3H), 2.26 (s, 3H). | 6 |
| 278 | 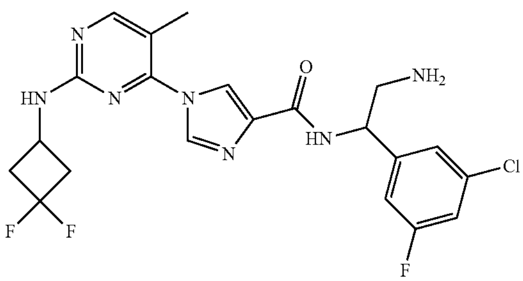 [SMILES: Cc1cnc(NC2CC(F)(F)C2)nc1-n1cnc(C(=O)NC(CN)c2cc(F)cc(Cl)c2)c1] | N-(2-amino-1-(3-chloro-5-fluoro-phenyl)ethyl)-1-(2-((3,3-difluoro-cyclobutyl)amino)-5-methyl-pyrimidin-4-yl)-1H-imidazole-4-carboxamide | 1HNMR (400 MHz, DMSO-d$_6$): δ 8.58 (d, J = 8.0 Hz, 1H), 8.38 (s, 1H), 8.29 (s, 1H), 8.10 (s, 1H), 7.86 (d, J = 6.0 Hz, 1H), 7.27-7.17 (m, 3H), 4.91 (d, J = 7.2 Hz, 1H), 4.17 (s, 1H), 2.94-2.85 (m, 5H), 2.20 (s, 3H), | 4 |
| 279 | 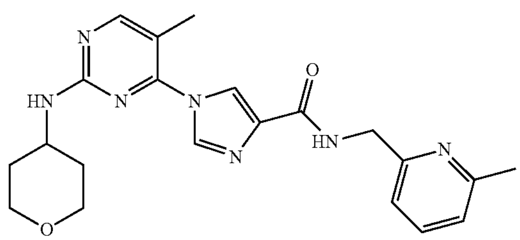 [SMILES: Cc1cccc(CNC(=O)c2cn(-c3nc(NC4CCOCC4)ncc3C)cn2)n1] | 1-(5-methyl-2-((tetrahydro-2H-pyran-4-yl)amino)-pyrimidin-4-yl)-N-((6-methyl-pyridin-2-yl)methyl)-1H-imidazole-4-carboxamide | 1HNMR (400 MHz, DMSO-d$_6$): δ 8.65 (t, J = 5.6 Hz, 1H), 8.34 (s, 1H), 8.27 (s, 1H), 8.11 (s, 1H), 7.61 (t, J = 7.2 Hz, 1 H), 7.35 (d, J = 6.8 Hz, 1H), 7.10-7.07 (m, 2H), 4.49-4.48 (m, 2H), 3.89 (s, 1H), 3.85-3.82 (m, 2H), 3.39-3.26 (m, 2H), 2.44 (s, 3H), 2.18 (s, 3H), 1.82-1.79 (m, 2H), 1.53-1.43 (m, 2H). | 3 |
| 280 | 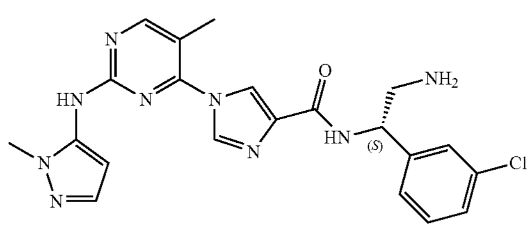 | (S)-N-(2-amino-1-(3-chlorophenyl)-ethyl)-1-(5-methyl-2-((1-methyl-1H-pyrazol-5-yl)amino)-pyrimidin-4-yl)-1H-imidazole-4-carboxamide | 1HNMR (400 MHz, DMSO-d$_6$): δ 9.58 (s, 1H), 8.55 (d, J = 8.4 Hz, 1H), 8.51 (s, 1H), 8.28 (s, 1H), 8.02 (s, 1H), 7.40 (s, 1H), 7.35-7.25 (m, 4H), 6.21 (s, 1H), 4.94-4.88 (m, 1H), 3.65 (s, 3H), 2.98-2.85 (m, 2H), 2.30 (s, 3H), 2.04 (bs, 2 H). | 20 |
| 281 | 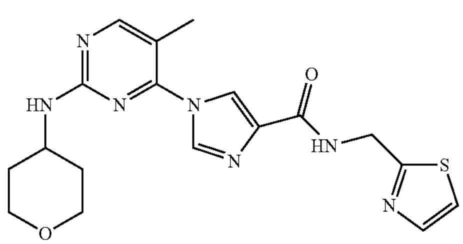 [SMILES: Cc1cnc(NC2CCOCC2)nc1-n1cnc(C(=O)NCc2nccs2)c1] | 1-(5-methyl-2-((tetrahydro-2H-pyran-4-yl)amino)-pyrimidin-4-yl)-N-(thiazol-2-ylmethyl)-1H-imidazole-4-carboxamide | 1HNMR (400 MHz, DMSO-d$_6$): δ 8.96 (t, J = 6.0 Hz, 1H), 8.34 (s, 1H), 8.27 (s, 1H), 8.15 (s, 1H), 7.70 (d, J = 3.2 Hz, 1H), 7.57 (d, J = 3.2 Hz, 1H), 7.35 (d, J = 7.6 Hz, 1H), 4.70 (d, J = 6 Hz, 2H), 3.89 (bs, 1H), 3.83 (d, J = 11.6 Hz, 2H), 3.39-3.27 (m, 2H), 2.18 (s, 3H), 1.81 (d, J = 12.4 Hz, 2H), 1.52-1.43 (m, 2H); | 3 |

TABLE 1-continued

| Cmpd # | Structure | Name | NMR data | Scheme # |
|---|---|---|---|---|
| 282 | 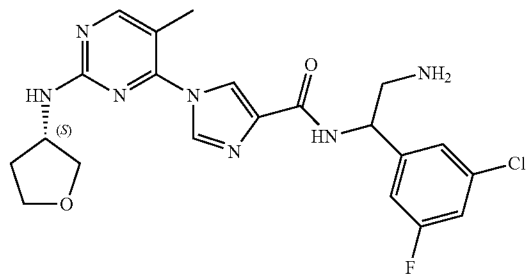 | N-(2-amino-1-(3-chloro-5-fluorophenyl)ethyl)-1-(5-methyl-2-(((S)-tetrahydrofuran-3-yl)amino)pyrimidin-4-yl)-1H-imidazole-4-carboxamide | 1HNMR (400 MHz, DMSO-d$_6$): δ 8.59 (d, J = 8.4 Hz, 1H), 8.35 (s, 1H), 8.28 (s, 1H), 8.10 (s, 1H), 7.60-7.58 (m, 1H), 7.28-7.24 (m, 2H), 7.19 (d, J = 9.6 Hz, 1H), 4.94-4.91 (m, 1H), 4.38-4.31 (m, 1H), 3.86-3.77 (m, 2H), 3.71-3.66 (m, 1H), 3.54-3.51 (m, 1H), 2.99-2.94 (m, 1H), 2.91-2.86 (m, 1H), 2.18 (s, 3H), 2.14-2.04 (m, 1H), 1.88-1.85 (m, 1H). | 4 |
| 283 | 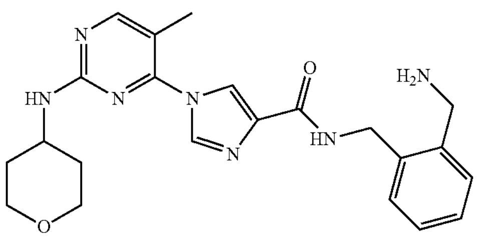 [SMILES: Cc1cnc(NC2CCOCC2)nc1-n1cnc(C(=O)NCc2ccccc2CN)c1] | N-(2-(aminomethyl)benzyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.78 (t, J = 6.0 Hz, 1H), 8.33 (s, 1H), 8.22 (s, 1H), 8.08 (s, 1H), 7.35-7.31 (m, 2H), 7.28-7.26 (m, 1H), 7.20-7.15 (m, 2H), 4.49 (d, J = 6.0 Hz, 2H), 3.84-3.82 (m, 4H), 3.36 (t, J = 10.0 Hz, 2H), 2.16 (s, 3H), 1.80 (d, J = 11.2 Hz, 2H), 1.52-1.43 (m, 2H). | 3 |
| 284 | 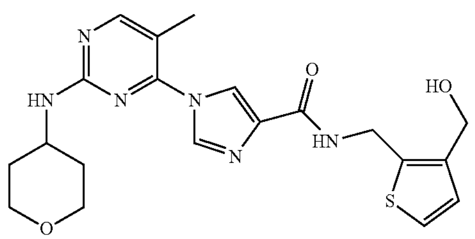 [SMILES: Cc1cnc(NC2CCOCC2)nc1-n1cnc(C(=O)NCc2sccc2CO)c1] | N-((3-(hydroxymethyl)thiophen-2-yl)methyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.59 (s, 1H), 8.33 (s, 1H), 8.23 (s, 1H), 8.10 (s, 1H), 7.34 (d, J = 7.2 Hz, 1H), 7.25 (d, J = 5.2 Hz, 1H), 6.93 (d, J = 5.2 Hz, 1H), 5.02 (t, J = 5.2 Hz, 1H), 4.57-4.56 (m, 2H), 4.51-4.49 (m, 2H), 3.88 (br s, 1H), 3.88-3.81 (m, 3H), 3.39-3.27 (m, 2H), 2.16 (s, 3H), 1.80 (d, J = 11.2 Hz, 2H), 1.51-1.43 (m, 2H). | 3 |
| 285 | 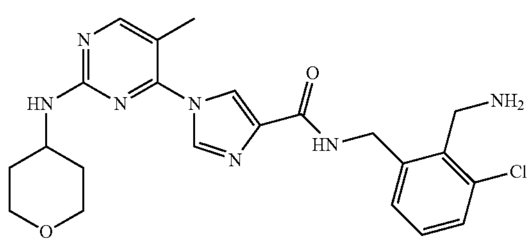 [SMILES: Cc1cnc(NC2CCOCC2)nc1-n1cnc(C(=O)NCc2cccc(Cl)c2CN)c1] | N-(2-(aminomethyl)-3-chlorobenzyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.83 (s, 1H), 8.33 (s, 1H), 8.23 (s, 1H), 8.09 (s, 1H), 7.35-7.22 (m, 3H), 7.20 (d, J = 7.6 Hz, 1H), 4.56 (d, J = 6.0 Hz, 2H), 3.91-3.84 (m, 4H), 3.88-3.26 (m, 2H), 2.16 (s, 3H), 1.97 (d, J = 7.6 Hz, 1H), 1.80 (d, J = 11.2 Hz, 2H), 1.48 (t, J = 11.2 Hz, 2H). | 4 |

TABLE 1-continued

| Cmpd # | Structure | Name | NMR data | Scheme # |
|---|---|---|---|---|
| 286 | 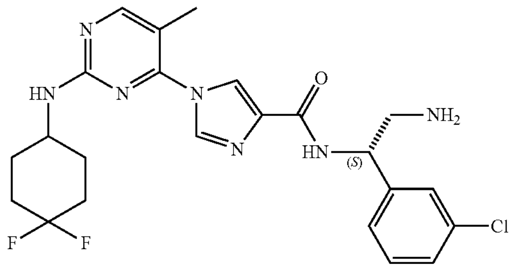 | (S)-N-(2-amino-1-(3-chlorophenyl)-ethyl)-1-(2-((4,4-difluoro-cyclo-hexyl)amino)-5-methyl-pyrmidin-4-yl)-1H-imidazole-4-carboxamide | 1HNMR (400 MHz, DMSO-d$_6$): δ 8.63 (d, J = 8.4 Hz, 1H), 8.35 (s, 1H), 8.28 (s, 1H), 8.09 (s, 1H), 7.43-7.27 (m, 5H), 5.02-5.0 (m, 1H), 3.9 (bs, 1H), 3.09-3.04 (m, 1H), 2.98-2.93 (m, 1H), 2.17 (s, 3H), 2.04-1.97 (m, 2H), 1.91-1.88 (m, 4H), 1.58-1.55 (m, 2H). | 20 |
| 287 | 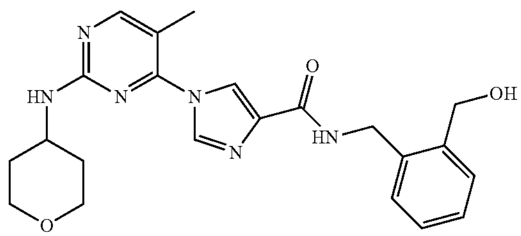 [SMILES: Cc1cnc(NC2CCOCC2)nc1-n1cnc(C(=O)NCc2ccccc2CO)c1] | N-(2-(hydroxy-methyl)benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.48 (t, J = 6.0 Hz, 1H), 8.33 (s, 1H), 8.23 (s, 1H), 8.09 (s, 1H), 7.35-7.33 (m, 1H), 7.28-7.26 (m, 1H), 7.21-7.19 (m, 1H), 5.21-5.18 (m, 1H), 4.59 (d, J = 5.2 Hz, 2H), 4.47 (d, J = 6.0 Hz, 2H), 3.94-3.88 (m, 1H), 3.84-3.81 (m, 2H), 3.39-3.33 (m, 2H), 2.16 (s, 3H), 1.83-1.79 (m, 2H), 1.51-1.43 (m, 2H). | 3 |
| 288 | 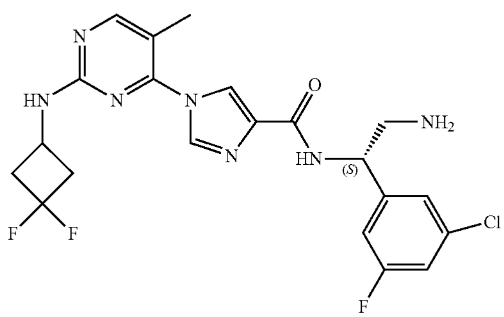 | (S)-N-(2-amino-1-(3-chloro-5-fluoro-phenyl)ethyl)-1-(2-((3,3-difluoro-cyclobutyl)amino)-5-methyl-pyrimidin-4-yl)-1H-imidazole-4-carboxamide | 1HNMR (400 MHz, DMSO-d$_6$): δ 8.60 (d, J = 8.4 Hz 1H), 8.38 (s, 1H), 8.29 (s, 1H), 8.11 (s, 1H), 7.87 (d, J = 8.4 Hz 1H), 7.24 (m, 3H), 4.93 (d, J = 8 Hz 1H), 4.16 (s, 1H), 2.93 (m, 5H), 2.2 (s, 3H), 1.96 (s, 2H). | 4 |
| 289 | 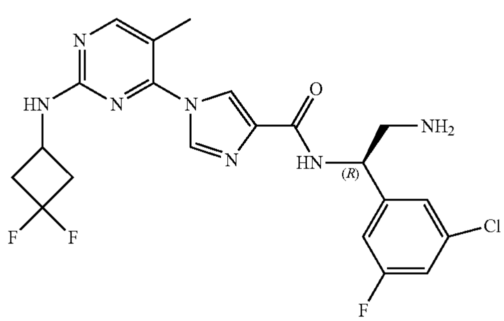 | (R)-N-(2-amino-1-(3-chloro-5-fluoro-phenyl)ethyl)-1-(2-((3,3-difluoro-cyclobutyl)amino)-5-methyl-pyrimidin-4-yl)-1H-imidazole-4-carboxamide | 1HNMR (400 MHz, DMSO-d$_6$): δ 8.60 (d, J = 8.4 Hz, 1H), 8.38 (s, 1H), 8.29 (s, 1H), 8.11 (s, 1H), 7.87 (d J = 8.4 Hz, 1H), 7.25 (m, 3H), 4.93 (d, J = 8 Hz, 1H), 4.16 (s, 1H), 2.95-2.9 (m, 5H), 2.2 (s, 3H). | 4 |

TABLE 1-continued

| Cmpd # | Structure | Name | NMR data | Scheme # |
|---|---|---|---|---|
| 290 | Enantiomer-1 | N-(2-amino-1-(5-chloro-thiophen-2-yl)ethyl)-1-(5-methyl-2-((tetrahydro-2H-pyran-4-yl)amino)-pyrimidin-4-yl)-1H-imidazole-4-carboxamide (enantiomer #1) | 1HNMR (400 MHz, DMSO-d$_6$): δ 8.58 (d, J = 8.4 Hz, 1H), 8.34 (s, 1H), 8.26 (s, 1H), 8.12 (s, 1H), 7.35 (d, J = 7.2 Hz, 1H), 6.95 (d, J = 3.6 Hz, 1H), 6.87 (d, J = 3.6 Hz, 1H), 5.18 (d, J = 6.4 Hz, 1H), 3.85-3.82 (m, 3H), 3.38-3.27 (m, 2H), 3.13-3.06 (m, 2H), 2.16 (s, 3H), 1.80 (d, J = 11.6 Hz, 2H), 1.52-1.44 (m, 2H). | 4 |
| 291 | Enantiomer-2 | N-(2-amino-1-(5-chloro-thiophen-2-yl)ethyl)-1-(5-methyl-2-((tetrahydro-2H-pyran-4-yl)amino)-pyrimidin-4-yl)-1H-imidazole-4-carboxamide (enantiomer #2) | 1HNMR (400 MHz, DMSO-d$_6$): δ 8.49 (d, J = 8.4 Hz, 1H), 8.34 (s, 1H), 8.25 (s, 1H), 8.12 (s, 1H), 7.35 (d, J = 7.2 Hz, 1H), 6.95 (d, J = 3.6 Hz, 1H), 6.87 (d, J = 3.6 Hz, 1H), 5.18 (d, J = 6.4 Hz, 1H), 3.85-3.82 (m, 3H), 3.38-3.27 (m, 2H), 3.13-3.06 (m, 2H), 2.16 (s, 3H), 1.80 (d, J = 11.6 Hz, 2H), 1.52-1.44 (m, 2H). | 4 |
| 292 | 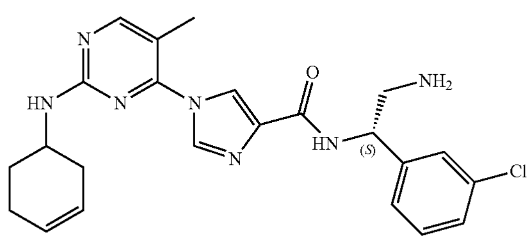 | N-((S)-2-amino-1-(3-chlorophenyl)-ethyl)-1-(2-(cyclohex-3-en-1-ylamino)-5-methyl-pyrimidin-4-yl)-1H-imidazole-4-carboxamide | 1HNMR (400 MHz, DMSO-d$_6$): δ 8.53 (d, J = 8.4 Hz, 1H), 8.33 (s, 1H), 8.26 (s, 1H), 8.07 (s, 1H), 7.04 (s, 1H), 7.34-7.26 (m, 4H), 5.62 (bs, 2H), 4.91-4.89 (m, 1H), 3.9 (bs, 1H), 2.94-2.92 (m, 1H), 2.89-2.87 (m, 1H), 2.28 (s, 1H), 2.17 (s, 3H), 2.09 (bs, 2H), 1.89-1.87 (m, 5H). | 20 |
| 293 | 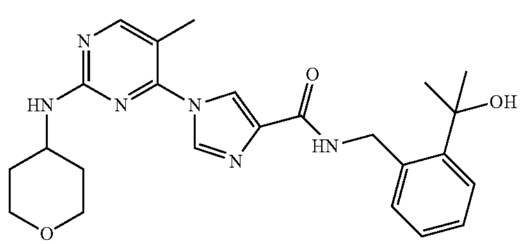 [SMILES: Cc1cnc(NC2CCOCC2)nc1-n1cnc(C(=O)NCc2ccccc2C(C)(C)O)c1] | N-(2-(2-hydroxy-propan-2-yl)benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.37 (s, 1H), 8.34 (d, J = 10.4 Hz, 1H), 8.22 (s, 1H), 8.06 (s, 1H), 7.35-7.29 (m, 3H), 7.15 (t, J = 3.6 Hz, 2H), 4.76 (d, J = 6.4 Hz, 2H), 3.91 (bs, 1H), 3.8 (d, 11.2 Hz, 2H), 3.37 (d, J = 11.2 Hz, 2H), 2.16 (s, 3H), 1.80 (d, J = 12 Hz, 2H), 1.55 (s, 6H), 1.47 (d, J = 12.0 Hz, 2H) | 3 |

TABLE 1-continued

| Cmpd # | Structure | Name | NMR data | Scheme # |
|---|---|---|---|---|
| 294 | 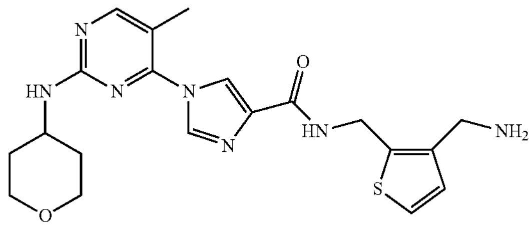 [SMILES: Cc1cnc(NC2CCOCC2)nc1-n1cnc(C(=O)NCc2sccc2CN)c1] | N-((3-(aminomethyl)thiophen-2-yl)methyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.71 (t, J = 6.0 Hz, 1H), 8.33 (s, 1H), 8.23 (s, 1H), 8.09 (s, 1H), 7.34 (d, J = 6.8 Hz, 1H), 7.24 (d, J = 4.8 Hz, 1H), 6.97 (d, J = 4.8 Hz, 1H), 4.55 (d, J = 6.0 Hz, 2H), 3.90 (br s, 1H), 3.84-3.81 (m, 2H), 3.72 (s, 2H), 3.36 (t, J = 11.2 Hz, 2H), 2.16 (s, 3H), 1.81 (d, J = 12.0 Hz, 2H), 1.48 (d, J = 8.8 Hz, 2H). | 4 |
| 295 | 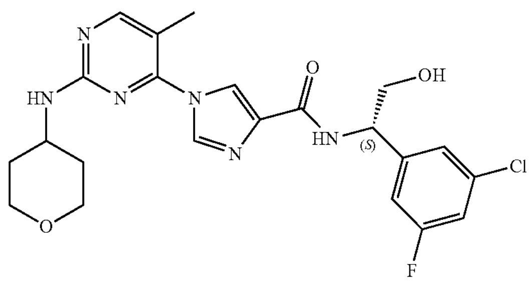 | (S)-N-(1-(3-chloro-5-fluorophenyl)-2-hydroxyethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.43 (d, J = 8.0 Hz, 1H), 8.33 (s, 1H), 8.27 (s, 1H), 8.09 (s, 1H), 7.35 (d, J = 6.8 Hz, 1H), 7.29-7.25 (m, 2H), 7.20 (d, J = 9.6 Hz, 1H), 5.07-5.0 (m, 2H), 3.88-3.82 (m, 3H), 3.71 (t, J = 8.0, 2H), 3.36 (t, J = 10.8 Hz, 2H), 2.17 (3H), 1.80 (d, J = 11.6 Hz, 2H), 1.48 (d, J = 8.8 Hz, 2H). | 3 |
| 296 | 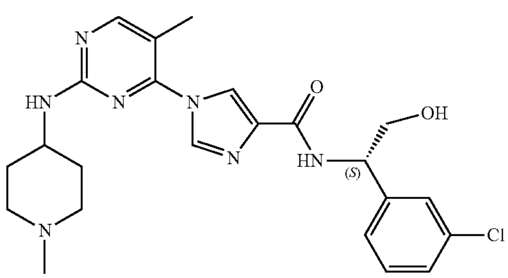 | (S)-N-(1-(3-chlorophenyl)-2-hydroxyethyl)-1-(5-methyl-2-((1-methyl-piperidin-4-yl)amino)-pyrimidin-4-yl)-1H-imidazole-4-carboxamide | 1HNMR (400 MHz, DMSO-d$_6$): δ 8.45 (d, J = 8.0 Hz, 1H), 8.32 (s, 1H), 8.26 (s, 1H), 8.08 (s, 1H), 7.42 (s, 1H), 7.31 (m, 4H), 5.03 (m, 2H), 3.71 (t, J = 5.2 Hz, 2H), 3.63 (s, 1H), 2.73 (d, J = 10.0 Hz, 2H), 2.16-2.14 (m, 5H), 1.95 (s, 2H), 1.81 (d, J = 11.2 Hz, 2H), 1.52-1.44 (m, 2H) | 6 |
| 297 | 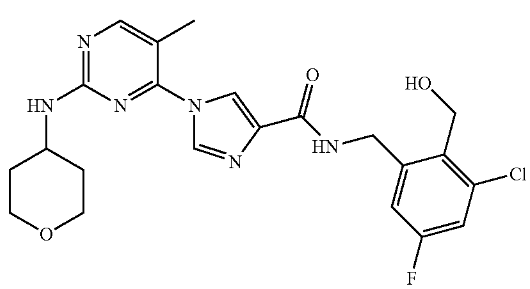 [SMILES: Cc1cnc(NC2CCOCC2)nc1-n1cnc(C(=O)NCc2cc(F)cc(Cl)c2CO)c1] | N-(3-chloro-5-fluoro-2-(hydroxymethyl)-benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.73 (t, 1H), 8.33 (s, 1H), 8.26 (s, 1H), 8.11 (s, 1H), 7.35 (d, J = 7.6 Hz, 1H), 7.30-7.28 (m, 1H), 7.10-7.07 (m, 1H), 5.22 (t, J = 5.6 Hz, 1H), 4.71 (d, J = 5.2 Hz, 2H), 4.60 (d, J = 6 Hz, 2H), 3.89 (s, 1H), 3.83 (d, J = 10.8 Hz, 2H), 3.39-3.32 (m, 2H), 2.17 (s, 3H), 1.82 (t, 2H), 1.53-1.44 (m, 2H). | 3 |

TABLE 1-continued

| Cmpd # | Structure | Name | NMR data | Scheme # |
|---|---|---|---|---|
| 298 | 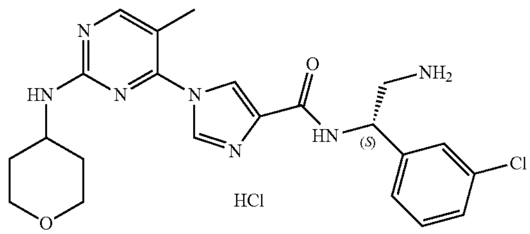 | (S)-N-(2-amino-1-(3-chlorophenyl)-ethyl)-1-(5-methyl-2-((tetrahydro-2H-pyran-4-yl)amino)-pyrimidin-4-yl)-1H-imidazole-4-carboxamide hydrochloride salt | 1HNMR (400 MHz, DMSO-d$_6$): δ 8.90 (d, J = 9.2 Hz, 1H), 8.35 (s, 1H), 8.29 (s, 1H), 8.14 (s, 1H), 7.97 (br s, 3H), 7.51 (s, 1H), 7.42-7.37 (m, 4H), 5.32 (d, J = 4.4 Hz, 1H), 3.83 (d, J = 11.6 Hz, 3H), 3.38-3.35 (m, 2H), 3.31-3.23 (m, 2H), 2.16 (s, 3H), 1.80 (d, J = 12.8 Hz, 2H), 1.52-1.42 (m, 2H). | 20 |
| 299 | 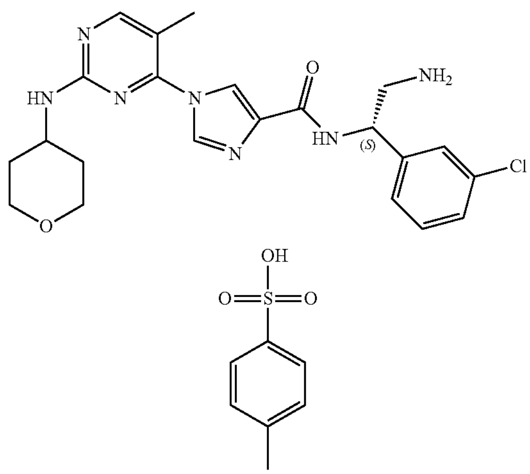 | (S)-N-(2-amino-1-(3-chlorophenyl)-ethyl)-1-(5-methyl-2-((tetrahydro-2H-pyran-4-yl)amino)-pyrimidin-4-yl)-1H-imidazole-4-carboxamide p-toluene-sulfonic acid salt | 1HNMR (400 MHz, DMSO-d$_6$): δ 8.81 (d, J = 8.8 Hz, 1H), 8.35 (s, 1H), 8.29 (s, 1H), 8.11 (s, 1H), 7.49-7.44 (m, 2H), 7.41-7.35 (m, 4H), 7.09-7.07 (br s, 3H), 5.24 (d, J = 4 Hz, 1H), 3.85-3.82 (m, 3H), 3.38-3.27 (m, 3H), 3.18-3.13 (m, 1H), 2.30 (s, 3H), 2.16 (s, 2H), 1.80 (d, J = 11.6 Hz, 2H), 1.52-1.44 (m, 2H). | 20 |
| 300 | 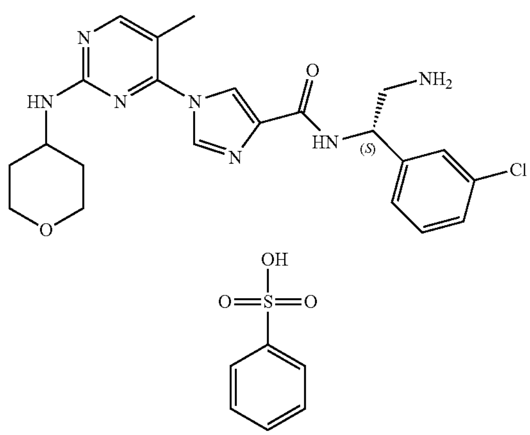 | (S)-N-(2-amino-1-(3-chlorophenyl)-ethyl)-1-(5-methyl-2-((tetrahydro-2H-pyran-4-yl)amino)-pyrimidin-4-yl)-1H-imidazole-4-carboxamide benzenesulfonic acid salt | 1HNMR (400 MHz, DMSO-d$_6$): δ 8.89 (d, J = 9.2 Hz, 1H), 8.35 (s, 1H), 8.29 (s, 1H), 8.12 (s, 1H), 7.91 (br s, 3H), 7.58 (d, J = 5.6 Hz, 2H), 7.51 (s, 1H), 7.42-7.35 (m, 4H), 7.28 (d, J = 6 Hz, 3H), 5.34-5.31 (m, 1H), 3.85-3.82 (m, 3H), 3.41-3.32 (m, 3H), 3.28 (s, 1H), 2.16 (s, 3H), 1.80 (d, J = 11.6 Hz, 2H), 1.52-1.54 (m, 2H). | 20 |
| 301 | 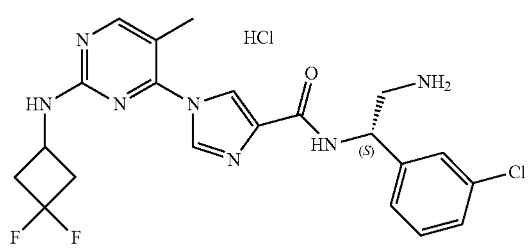 | (S)-N-(2-amino-1-(3-chlorophenyl)-ethyl)-1-(2-((3,3-difluoro-cyclobutyl)amino)-5-methyl-pyrimidin-4-yl)-1H-imidazole-4-carboxamide hydrochloride salt | 1HNMR (400 MHz, DMSO-d$_6$): δ 8.90 (d, J = 8.8 Hz, 1H), 8.39 (s, 1H), 8.31 (s, 1H), 8.18 (s, 1H), 7.88 (d, J = 4.8 Hz, 1H), 7.62 (br s, 3H), 7.50 (s, 1H), 7.38-7.35 (m, 3H), 5.29 (d, J = 4 Hz, 1H), 4.16 (s, 1H), 3.39-3.28 (m, 1H), 3.18-3.14 (m, 1H), 2.92 (t, 2H), 2.61 (t, 2H), 2.19 (s, 3H) | 20 |

TABLE 1-continued

| Cmpd # | Structure | Name | NMR data | Scheme # |
|---|---|---|---|---|
| 302 | 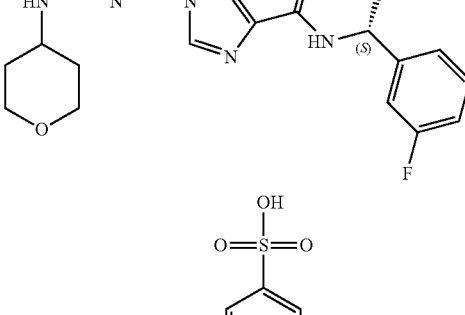 | (S)-N-(2-amino-2-(3-chloro-5-fluoro-phenyl)ethyl)-1-(5-methyl-2-((tetrahydro-2H-pyran-4-yl)amino)-pyrimidin-4-yl)-1H-imidazole-4-carboxamide benzenesulfonic acid salt | 1HNMR (400 MHz, DMSO-$d_6$): δ 8.92 (d, J = 8.8 Hz, 1H), 8.35 (s, 1H), 8.30 (s, 1H), 8.13 (s, 1H), 7.83 (br s, 3H), 7.57 (d, J = 6.4 Hz, 2H), 7.37 (s, 3H), 7.28 (d, J = 6.4 Hz, 4H), 5.32 (d, J = 4.4 Hz, 1H), 3.83 (d, J = 11.6 Hz, 3H), 3.41-3.27 (m, 3H), 3.18-3.14 (m, 1H), 2.16 (s, 3H), 1.80 (d, J = 12 Hz, 2H), 1.52-1.44 (m, 2H). | 20 |
| 303 | 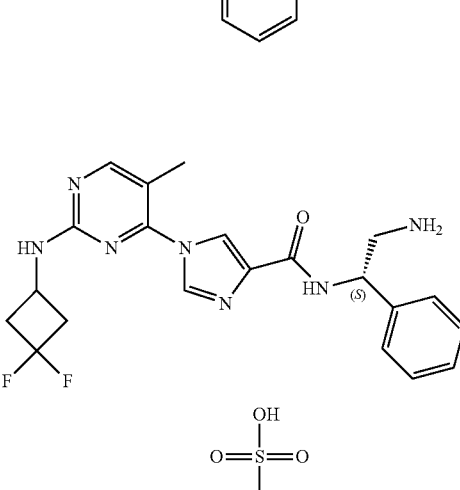 | (S)-N-(2-amino-1-(3-chlorophenyl)-ethyl)-1-(2-((3,3-difluoro-cyclo-butyl)amino)-5-methyl-pyrimidin-4-yl)-1H-imidazole-4-carboxamide p-toluene-sulfonic acid salt | 1HNMR (400 MHz, DMSO-$d_6$): δ 8.88 (d, J = 9.2 Hz, 1H), 8.39 (s, 1H), 8.32 (s, 1H), 8.14 (s, 1H), 7.87 (d, J = 5.2 Hz, 2H), 7.75 (br s, 3H), 7.51 (s, 1H), 7.46-7.42 (m, 2H), 7.40-7.35 (m, 3H), 7.08 (d, J = 7.6 Hz, 2H), 5.31 (d, J = 4.4 Hz, 1H), 4.16 (s, 1H), 3.40-3.27 (m, 1H), 3.24-3.19 (m, 1H), 2.94-2.91 (m, 2H), 2.64-2.61 (t, 2H), 2.26 (s, 3H), 2.19 (s, 3H). | 20 |
| 304 | 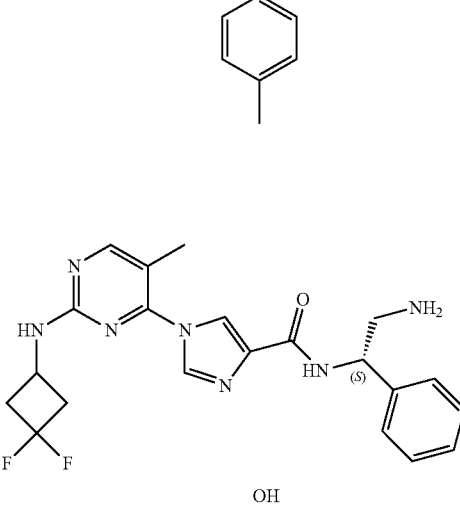 | (S)-N-(2-amino-1-(3-chlorophenyl)-ethyl)-1-(2-((3,3-difluoro-cyclobutyl)amino)-5-methyl-pyrimidin-4-yl)-1H-imidazole-4-carboxamide benzene-sulfonic acid salt | 1HNMR (400 MHz, DMSO-$d_6$): δ 8.88 (d, J = 8.8 Hz, 1H), 8.39 (s, 1H), 8.32 (s, 1H), 8.14 (s, 1H), 7.87 (d, J = 4.8 Hz, 1H), 7.72 (br s, 3H), 7.57 (d, J = 6 Hz, 2H), 7.51 (s, 1H), 7.42-7.37 (m, 3H), 7.28 (d, J = 6.4 Hz, 3H), 5.31 (d, J = 4.4 Hz, 1H), 4.16 (s, 1H), 3.39-3.27 (m, 1H), 3.23 (d, J = 4.8 Hz, 1H), 2.94-2.91 (m, 2H), 2.63 (d, J = 12 Hz, 2H), 2.19 (s, 3H) | 20 |

TABLE 1-continued

| Cmpd # | Structure | Name | NMR data | Scheme # |
|---|---|---|---|---|
| 305 | 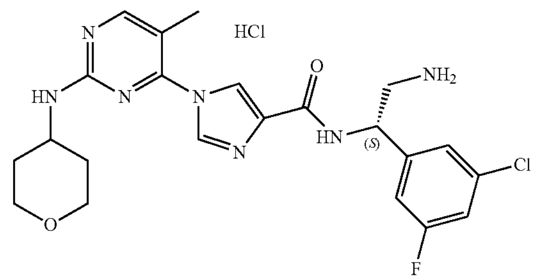 | (S)-N-(2-amino-1-(3-chloro-5-fluoro-phenyl)ethyl)-1-(5-methyl-2-((tetrahydro-2H-pyran-4-yl)amino)pyrimidin-4-yl)-1H-imidazole-4-carboxamide hydrochloride salt | 1HNMR (400 MHz, DMSO-d$_6$): δ 8.95 (d, J = 8.8 Hz, 1H), 8.35 (s, 1H), 8.30 (s, 1H), 8.15 (s, 1H), 8.00 (br s, 3H), 7.37 (br s, 3H), 7.28 (d, J = 9.6 Hz, 1H), 5.34-5.31 (m, 1H), 3.85-3.82 (m, 3H), 3.37-3.33 (m, 3H), 3.26-3.23 (m, 1H), 2.16 (s, 3H), 1.80 (d, J = 11.6 Hz, 2H), 1.52-1.44 (m, 2H) | 20 |
| 306 | 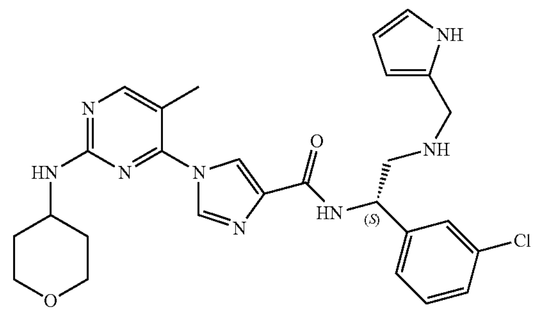 | (S)-N-(2-(((1H-pyrrol-2-yl)-methyl)amino)-1-(3-chlorophenyl)-ethyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 10.50 (s, 1H), 8.50 (d, J = 8.0 Hz, 1H), 8.33 (s, 1H), 8.27 (s, 1H), 8.07 (s, 1H), 7.41 (s, 1H), 7.36-7.25 (m, 4H), 6.58 (s, 1H), 5.86 (s, 1H), 5.82 (s, 1H), 5.06 (d, J = 5.6 Hz, 1H), 3.85-3.82 (m, 3H), 3.65 (s, 2H), 3.36 (t, J = 11.2 Hz, 2H), 2.95-2.90 (m, 1H), 2.82-2.79 (m, 1H), 2.17 (s, 3H), 1.81 (d, J = 11.6 Hz, 2H), 1.52-1.47 (m, 2H). | 20 |
| 307 | 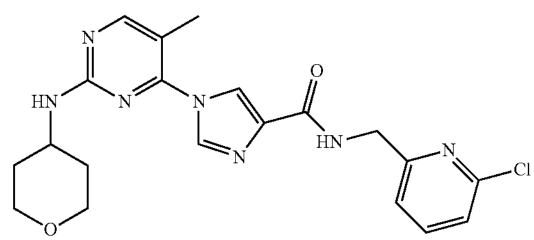 [SMILES: Cc1cnc(NC2CCOCC2)nc1-n1cnc(C(=O)NCc2cccc(Cl)n2)c1] | N-((6-chloropyridin-2-yl)methyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.75 (bs, 1H), 8.34 (s, 1H), 8.28 (s, 1H), 8.12 (s, 1H), 80 (t, J = 7.6 Hz, 1H), 7.37-7.35 (m, 2H), 7.29 (d, J = 7.6 Hz, 1H), 4.50 (d, J = 6.4 Hz, 2H), 3.89 (b, 1H), 3.84 (d, J = 10.8 Hz, 2H), 3.37 (t, J = 10.8 Hz, 2H), 2.18 (s, 3H), 1.81 (d, J = 11.6 Hz, 2H), 1.50-1.47 (m, 2H). | 3 |
| 308 | 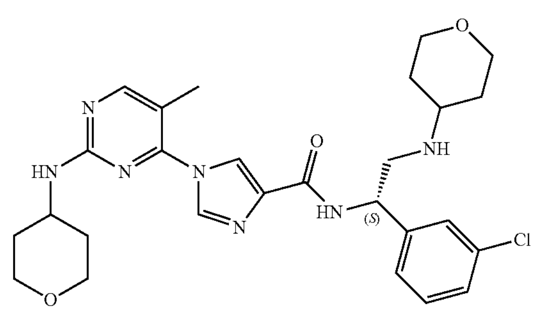 | (S)-N-(1-(3-chlorophenyl)-2-((tetrahydro-2H-pyran-4-yl)amino)-ethyl)-1-(5-methyl-2-((tetrahydro-2H-pyran-4-yl)amino)pyrimidin-4-yl)-1H-imidazole-4-carboxamide | 1HNMR (400 MHz, DMSO-d$_6$): δ 8.49 (d, J = 6.8 Hz, 1H), 8.33 (s, 1H), 8.27 (s, 1H), 8.07 (s, 1H), 7.43 (s, 1H), 7.32-7.27 (m, 4H), 5.01 (bs, 1H), 3.85-3.76 (m, 4H), 3.36 (t, J = 11.6 Hz, 2H) 3.27 (s, 2H), 2.98 (bs, 1H), 2.90 (bs, 1H), 2.48 (s, 1H), 2.17 (s, 3H), 1.85 (bs, 25.6 Hz, 2H), 1.74 (t, J = 18.8 Hz, 2H), 1.52-1.47 (m, 2H), 1.27 (bs, 3H). | 20 |

TABLE 1-continued

| Cmpd # | Structure | Name | NMR data | Scheme # |
|---|---|---|---|---|
| 309 | 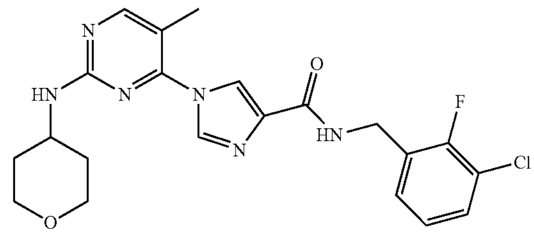 [SMILES: Cc1cnc(NC2CCOCC2)nc1-n1cnc(C(=O)NCc2cccc(Cl)c2F)c1] | N-(3-chloro-2-fluoro-benzyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 8.72 (t, J = 6.0 Hz, 1H), 8.34 (s, 1H), 8.26 (s, 1H), 8.11 (s, 1H), 7.45 (t, J = 7.6 Hz, 1H), 7.36-7.28 (m, 2H), 7.17 (t, J = 8 Hz, 1H), 4.50 (d, J = 6.0 Hz, 2H), 3.92-3.82 (m, 3H), 3.36 (t, J = 11.2 Hz, 2H), 2.17 (s, 3H), 1.81 (d, J = 12.0 Hz, 2H), 1.56-1.43 (m, 2H). | 3 |
| 310 | 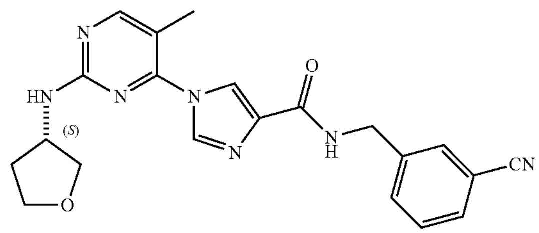 | (S)-N-(3-cyano-benzyl)-1-(5-methyl-2-((tetrahydro-furan-3-yl)amino)-pyrimidin-4-yl)-1H-imidazole-4-carboxamide | 1HNMR (400 MHz, DMSO-$d_6$): δ 8.82 (bs, 1H), 8.36 (s, 1H), 8.28 (s, 1H), 8.12 (s, 1H), 7.71-7.68 (m, 2H), 7.64 (d, J = 8.0 Hz, 1H), 7.60 (bs, 1H), 7.54-7.50 (m, 1H), 4.47 (d, J = 5.6 Hz, 2H), 4.35 (bs, 1H), 3.87-3.81 (m, 2H), 3.72-3.70 (d, J = 8.0 Hz, 1H), 3.54-3.53 (m, 1H), 2.19 (s, 3H), 2.15-2.10 (m, 1H), 1.87-1.85 (m, 1H). | 3 |
| 311 | 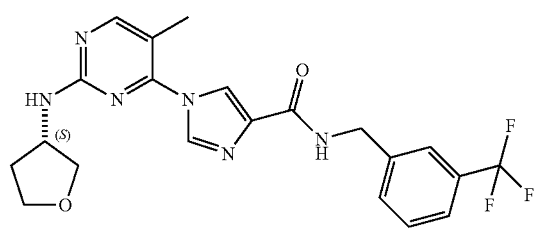 | (S)-1-(5-methyl-2-((tetrahydro-furan-3-yl)amino)-pyrimidin-4-yl)-N-(3-(trifluoro-methyl)benzyl)-1H-imidazole-4-carboxamide | 1HNMR (400 MHz, DMSO-$d_6$): δ 8.84 (t, J = 6.4 Hz, 1H), 8.36 (s, 1H), 8.28 (s, 1H), 8.12 (s, 1H), 7.65 (s, 1H), 7.62-7.52 (m, 4H), 4.50 (d, J = 6.4 Hz, 2H), 4.36 (bs, 1H), 3.87-3.80 (m, 2H), 3.70-3.68 (m, 1H), 3.55-3.27 (m, 1H), 2.19 (s, 3H), 2.13-2.12 (m, 1H), 1.86 (bs, 1H). | 3 |
| 312 | 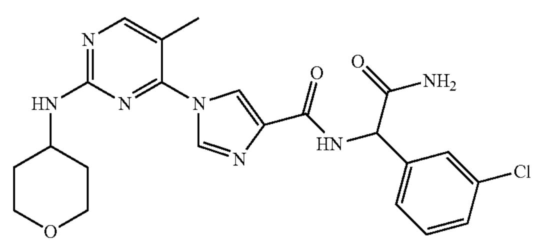 [SMILES: Cc1cnc(NC2CCOCC2)nc1-n1cnc(C(=O)NC(C(N)=O)c2cccc(Cl)c2)c1] | N-(2-amino-1-(3-chloro-phenyl)-2-oxoethyl)-1-(5-methyl-2-((tetrahydro-2H-pyran-4-yl)amino)-pyrimidin-4-yl)-1H-imidazole-4-carboxamide | 1HNMR (400 MHz, DMSO-$d_6$): δ 8.34-8.28 (m, 3H), 8.12 (s, 1H), 7.86 (s, 1H), 7.48 (s, 1H), 7.42-7.36 (m, 5H), 5.51 (d, J = 7.6 Hz, 1H), 3.88 (s, 1H), 3.84 (d, J = 11.6 Hz, 2H), 3.36 (t, J = 11.8 Hz, 2H), 2.16 (s, 3H), 1.81 (d, J = 11.6 Hz, 2H), 1.52-1.44 (m, 2H), | 3 |

TABLE 1-continued

| Cmpd # | Structure | Name | NMR data | Scheme # |
|---|---|---|---|---|
| 313 | 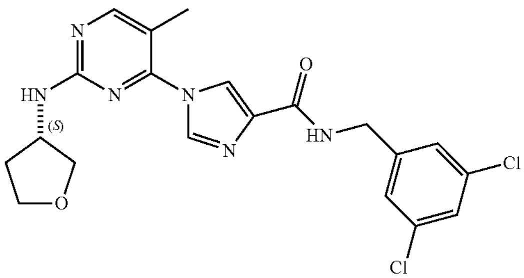 | (S)-N-(3,5-dichlorobenzyl)-1-(5-methyl-2-((tetrahydrofuran-3-yl)amino)pyrimidin-4-yl)-1H-imidazole-4-carboxamide | 1HNMR (400 MHz, DMSO-d$_6$): δ 8.80 (bs, 1H), 8.36 (s, 1H), 8.28 (s, 1H), 8.12 (s, 1H), 7.57-7.53 (m, 3H), 7.29 (d, J = 8.0 Hz, 1H), 4.40 (d, J = 6.4 Hz, 2H), 4.36 (bs, 1H), 3.87-3.78 (m, 2H), 3.72-3.68 (m, 1H), 3.55-3.52 (m, 1H), 2.19 (s, 3H), 2.15-2.10 (m, 1H), 1.87-1.85 (m, 1H). | 3 |
| 314 | 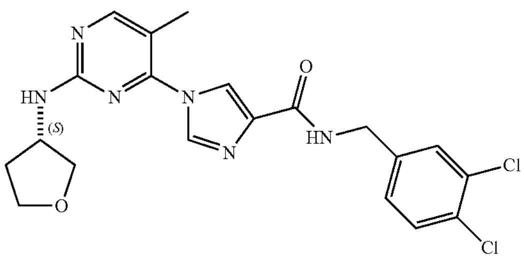 | (S)-N-(3,4-dichlorobenzyl)-1-(5-methyl-2-((tetrahydrofuran-3-yl)amino)pyrimidin-4-yl)-1H-imidazole-4-carboxamide | 1H NMR (400 MHz, DMSO-d$_6$): δ 8.81 (t, J = 5.6 Hz, 1H), 8.36 (s, 1H), 8.28 (s, 1H), 8.12 (s, 1H), 7.58-7.53 (m, 3H), 7.29 (d, J = 8.0 Hz, 2H), 4.41-4.36 (m, 3H), 3.87-3.78 (m, 2H), 3.72-3.66 (m, 1H), 3.55-3.52 (m, 1H), 2.19 (s, 3H), 2.15-2.08 (m, 1H), 1.88-1.85 (m, 1H). | 3 |
| 315 | 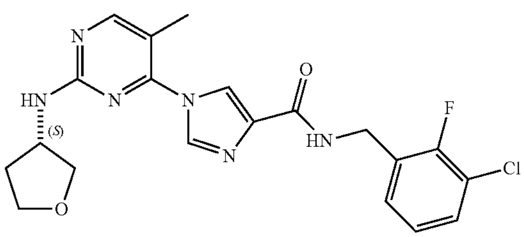 | (S)-N-(3-chloro-2-fluorobenzyl)-1-(5-methyl-2-((tetrahydrofuran-3-yl)amino)pyrimidin-4-yl)-1H-imidazole-4-carboxamide | 1H NMR (400 MHz, DMSO-d$_6$): δ 8.73 (t, J = 6 Hz, 1H), 8.36 (s, 1H), 8.28 (s, 1H), 8.13 (s, 1H), 7.59 (d, J = 5.2 Hz, 1H), 7.46-7.28 (m, 1H), 7.32-7.28 (m, 1H), 7.17 (t, J = 8 Hz, 1H), 4.50 (d, J = 4 Hz, 2H), 4.35 (bs, 1H), 3.87-3.78 (m, 2H), 3.72-3.68 (m, 1H), 3.55-3.52 (m, 1H), 2.19 (s, 3H), 2.15-2.08 (m, 1H), 1.89-1.6 (m, 1H). | 3 |
| 316 | 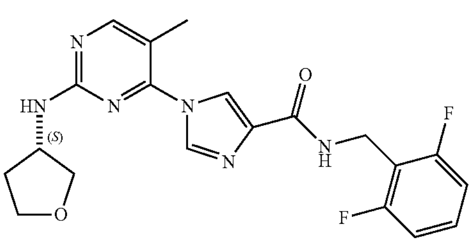 | (S)-N-(2,6-difluorobenzyl)-1-(5-methyl-2-((tetrahydrofuran-3-yl)amino)pyrimidin-4-yl)-1H-imidazole-4-carboxamide | 1H NMR (400 MHz, DMSO-d$_6$): δ 8.38 (bs, 2H), 8.27 (s, 1H), 8.13 (s, 1H), 7.63 (bs, 1H), 7.38 (m, 1H), 7.08 (m, 2H), 4.55 (d, J = 5.6 Hz, 2H), 4.38 (bs, 1H), 3.88-3.83 (m, 2H), 3.73-3.71 (m, 1H), 3.57 (bs, 1H), 2.21 (s, 3H), 2.16-2.13 (m, 1H), 1.90 (bs, 1H). | 3 |
| 317 | 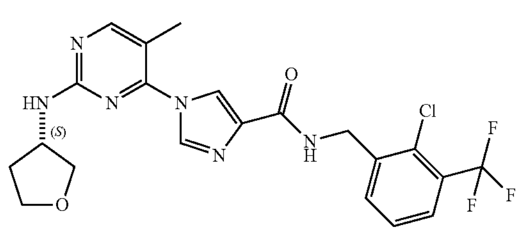 | (S)-N-(2-chloro-3-(trifluoromethyl)benzyl)-1-(5-methyl-2-((tetrahydrofuran-3-yl)amino)pyrimidin-4-yl)-1H- | 1H NMR (400 MHz, DMSO-d$_6$): δ 8.82 (bs, 1H), 8.37 (s, 1H), 8.31 (s, 1H), 8.16 (s, 1H), 7.76 (d, J = 7.6 Hz 1H), 7.61 (d, J = 6.4 Hz, 2H), 7.54-7.51 (m, 1H), 4.57 (d, J = 6.0 Hz, 2H), 4.36 (bs, 1H), 3.88-3.79 | 3 |

TABLE 1-continued

| Cmpd # | Structure | Name | NMR data | Scheme # |
|---|---|---|---|---|
| | | imidazole-4-carboxamide | (m, 2H), 3.73-3.69 (m, 1H), 3.56-3.54 (m, 1H), 2.21 (s, 3H), 2.16-2.11 (m, 1H), 1.90-1.87 (m, 1H). | |
| 318 | 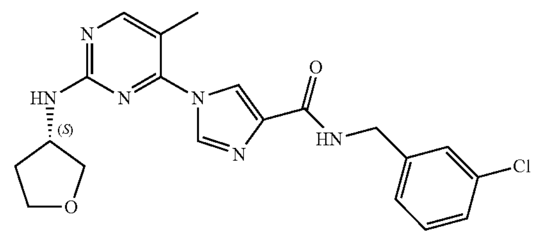 | (S)-N-(3-chloro-benzyl)-1-(5-methyl-2-((tetrahydro-furan-3-yl)amino)-pyrimidin-4-yl)-1H-imidazole-4-carboxamide | 1H NMR (400 MHz, DMSO-d$_6$): δ 8.77 (t, J = 6.0 Hz, 1H), 8.36 (s, 1H), 8.28 (s, 1H), 8.12 (s, 1H), 7.59 (d, J = 5.2 Hz, 1H), 7.34-7.25 (m, 4H), 4.42 (d, J = 6.4 Hz, 2H), 4.35 (bs, 1H), 3.88-3.78 (m, 2H), 3.72-3.66 (m, 2H), 3.55-3.52 (m, 1H), 2.20 (s, 3H), 2.17-2.08 (m, 1H), 1.90-1.83 (m, 1H). | 3 |
| 319 | 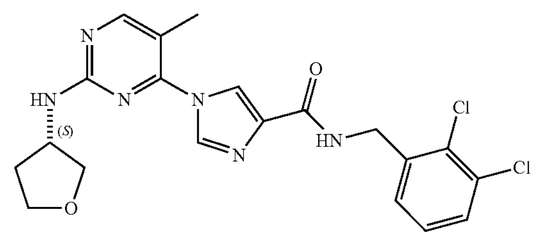 | (S)-N-(2,3-dichloro-benzyl)-1-(5-methyl-2-((tetrahydro-furan-3-yl)amino)-pyrimidin-4-yl)-1H-imidazole-4-carboxamide | 1H NMR (400 MHz, DMSO-d$_6$): δ 8.82 (bs, 1H), 8.42 (s, 1H), 8.36 (s, 1H), 8.21 (s, 1H), 7.67 (bs, 1H), 7.59 (d, J = 8.0 Hz, 1H), 7.39 (t, J = 7.6 Hz, 1H), 7.33 (d, J = 7.2 Hz, 1H), 4.58 (d, J = 6.4 Hz, 2H), 4.42 (bs, 1H), 3.94-3.84 (m, 2H), 3.78-3.73 (m, 1H), 3.61-3.33 (m, 1H), 2.26 (s, 3H), 2.21-2.15 (m, 1H), 1.93-1.92 (m, 1H). | 3 |
| 320 | 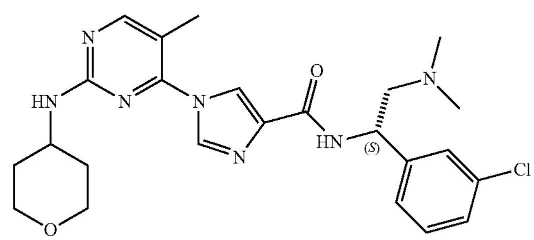 | (S)-N-(1-(3-chlorophenyl)-2-(dimethyl-amino)-ethyl)-1-(5-methyl-2-((tetrahydro-2H-pyran-4-yl)amino)-pyrimidin-4-yl)-1H-imidazole-4-carboxamide | 1H NMR (400 MHz, DMSO-d$_6$): δ 8.41-8.39 (d, J = 8 Hz, 1H), 8.3 (s, 1H), 8.26 (s, 1H), 7.47 (s, 1H), 7.36-7.30 (q, J = 6 Hz, 3H), 7.26 (d, J = 4 Hz, 1H), 5.04 (t, J = 6 Hz, 1H), 3.89 (bs, 1H), 3.85 (d, J = 16 Hz, 2H), 3.36 (t, J = 12 Hz, 2H), 2.78 (t, J = 12 Hz, 1H), 2.42 (s, 1H), 2.18 (s, 10 H), 1.80 (d, J = 12 Hz, 2H), 1.52-1.44 (m, 2H). | 20 |
| 321 | 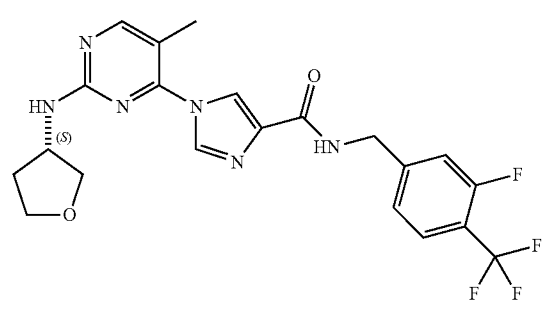 | (S)-N-(3-fluoro-4-(trifluoro-methyl)benzyl)-1-(5-methyl-2-((tetrahydro-furan-3-yl)amino)-pyrimidin-4-yl)-1H-imidazole-4-carboxamide | 1H NMR (400 MHz, DMSO-d$_6$): δ 8.89-8.86 (m, 1H), 8.36 (s, 1H), 8.29 (s, 1H), 8.13 (s, 1H), 7.72 (t, J = 8.0 Hz, 1H), 7.60 (bs, J = 8.0 Hz, 1H), 7.39-7.32 (m, 2H), 4.50 (d, J = 4 Hz, 2H), 4.36 (s, 1H) 3.88-3.78 (m, 2H), 3.72-3.67 (m, 1H), 3.55-3.52 (q, 1H), 2.20 (s, 1H), 2.15-2.08 (m, 1H), 1.86 (t, 1H), 1.22 (s, 1H). | 3 |

TABLE 1-continued

| Cmpd # | Structure | Name | NMR data | Scheme # |
|---|---|---|---|---|
| 322 | 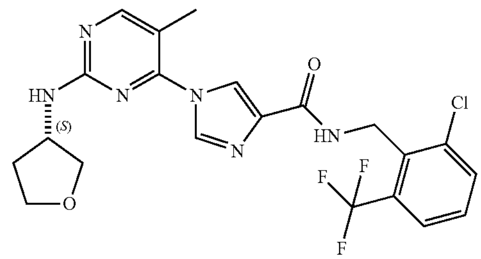 | (S)-N-(2-chloro-6-(trifluoro-methyl)-benzyl)-1-(5-methyl-2-((tetrahydrofuran-3-yl)amino)-pyrimidin-4-yl)-1H-imidazole-4-carboxamide | 1H NMR (400 MHz, DMSO-d$_6$): δ 8.35 (s, 1H), 8.22 (s, 1H), 8.16 (s, 1H), 7.88 (s, 1H), 7.84 (d, J = 8 Hz, 1H), 7.77-7.75 (d, J = 8 Hz, 1H), 7.60-7.56 (m, 2H), 4.70 (d, J = 4 Hz, 2H), 4.36 (s, 1H), 3.87-3.78 (m, 2H), 3.71-3.66 (m, 1H), 3.54-3.52 (m, 1H), 2.15 (s, 3H), 2.13-2.08 (m, 1H), 1.88-1.85 (m, 1H). | 3 |
| 323 | 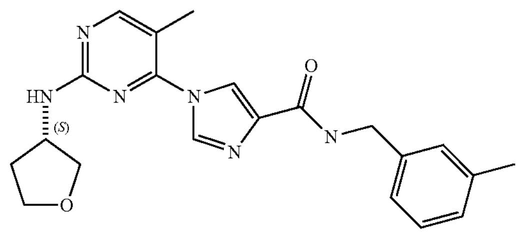 | (S)-1-(5-methyl-2-((tetrahydrofuran-3-yl)amino)-pyrimidin-4-yl)-N-(3-methylbenzyl)-1H-imidazole-4-carboxamide | 1H NMR (400 MHz, DMSO-d$_6$): δ 8.59 (s, 1H), 8.36 (s, 1H), 8.27 (s, 1H), 8.11 (s, 1H), 7.59 (d, J = 8 Hz, 1H), 7.17 (t, J = 12 Hz, 1H), 7.11-7.09 (m, 2H), 7.02 (d, J = 7.6 Hz, 1H), 4.39 (d, J = 8 Hz, 3H), 3.88-3.78 (m, 2H) 3.72-3.69 (m, 1H), 3.55-3.52 (m, 1H), 2.26 (s, 3H), 2.20 (s, 3H), 2.15-2.08 (m, 1H) 1.89-1.76 (m, 1H). | 3 |
| 324 | 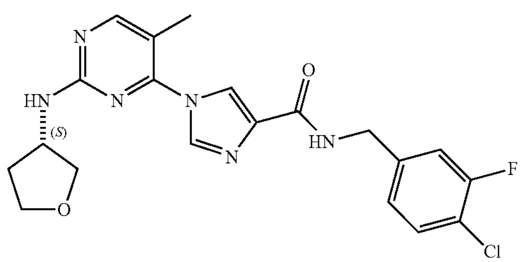 | (S)-N-(4-chloro-3-fluorobenzyl)-1-(5-methyl-2-((tetrahydrofuran-3-yl)amino)-pyrimidin-4-yl)-1H-imidazole-4-carboxamide | 1H NMR (400 MHz, DMSO-d$_6$): δ 8.79 (t, J = 6.0 Hz, 1H), 8.36 (s, 1H), 8.28 (s, 1H), 8.12 (s, 1H), 7.59 (d, J = 2.0 Hz, 1H), 7.51 (t, J = 8.2 Hz, 1H), 7.30 (d, J = 5.4 Hz, 1H), 7.16 (d, J = 4.2 Hz, 1H), 4.42 (d, J = 3.4 Hz, 2H), 4.36 (s, 1H), 3.88-3.78 (m, 2H), 3.72-3.66 (m, 1H), 3.55-3.52 (m, 1H), 2.19 (s, 3H), 2.15-2.09 (m, 1H), 1.89-1.86 (m, 1H) | 3 |
| 325 | 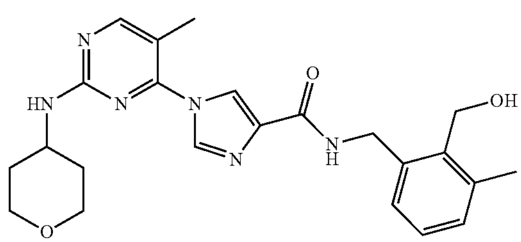 [SMILES: Cc1cnc(NC2CCOCC2)nc1-n1cnc(C(=O)NCc2cccc(C)c2CO)c1] | N-(2-(hydroxymethyl)-3-methylbenzyl)-1-(5-methyl-2-((tetrahydro-2H-pyran-4-yl)amino)-pyrimidin-4-yl)-1H-imidazole-4-carboxamide | 1H NMR (400 MHz, DMSO-d$_6$) δ 8.47-8.44 (m, 1H), 8.33 (s, 1H), 8.23 (s, 1H), 8.08 (s, 1H), 7.34 (d, J = 7.6 Hz, 1H), 7.15 (d, 1H), 7.11 (t, J = 7.6 Hz, 1H), 7.05 (d, J = 6.4 Hz, 1H), 4.99 (t, J = 5.6 Hz, 1H), 4.60 (d, J = 5.2 Hz, 2H), 4.56 (m, 2H), 3.85 (m, J = 14.8 Hz, 3H), 3.36 (t, J = 10.8 Hz, 2H), 2.30 (s, 3H), 2.16 (s, 3H), 2.05 (s, 1H), 1.81 (d, J = 11.6 Hz, 2H), 1.53-1.44 (m, 2H), 1.22 (s, 1H). | 3 |

TABLE 1-continued

| Cmpd # | Structure | Name | NMR data | Scheme # |
|---|---|---|---|---|
| 326 | 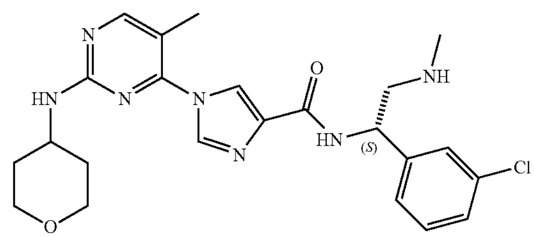 | (S)-N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide | 1H NMR (400 MHz, DMSO-d$_6$) δ 8.51 (d, J = 8.0 Hz, 1H), 8.34 (s, 1H), 8.27 (s, 1H), 8.07 (s, 1H), 7.43 (s, 1H), 7.36-7.27 (m, H), 5.11-5.06 (m, 1H), 3.85-3.82 (m, 3H), 3.39-3.27 (m, 2H), 3.00-2.95 (m, 1H), 2.85-2.80 (m, 1H), 2.29 (s, 3H), 2.17 (s, 3H), 1.81 (d, J = 11.2 Hz, 2H), 1.53-1.43 (q, 2H), 1.22 (s, 1H). | 20 |
| 327 | 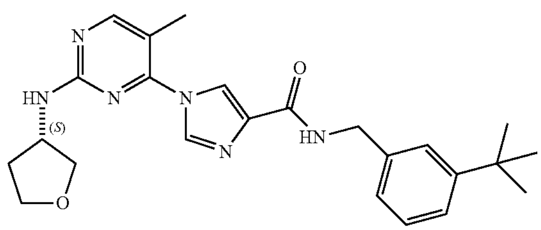 | (S)-1-(5-methyl-2-((tetrahydrofuran-3-yl)amino)pyrimidin-4-yl)-N-(3-tert-butylbenzyl)-1H-imidazole-4-carboxamide | 1H NMR (400 MHz, DMSO-d$_6$) δ 8.607 (t, J = 6.0 Hz, 1H), 8.35 (s 1H), 8.27 (s 1H), δ 8.12 (s 1H), 7.59 (d, J = 2.6 Hz, 1H), 7.35 (s 1H), 7.25-7.19 (m, 2H), 7.10 (d, J = 3.2 Hz, 1H), 4.42 (d, J = 3.2 Hz, 2H), 3.86-3.80 (m, 2H), δ (m, 1H), δ (m, 1H), 2.197 (s, 3H), δ (q, 1H), δ (q, 1H), 1.25 (s, 9H), | 3 |
| 328 | 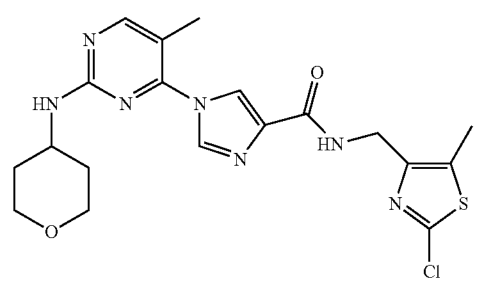 [SMILES: Cc1cnc(NC2CCOCC2)nc1-n1cnc(C(=O)NCc2nc(Cl)sc2C)c1] | N-((2-chloro-5-methyl-thiazol-4-yl)methyl)-1-(5-methyl-2-((tetrahydro-2H-pyran-4-yl)amino)pyrimidin-4-yl)-1H-imidazole-4-carboxamide | 1H NMR (400 MHz, DMSO-d$_6$) δ 8.43 (t, J = 5.2 Hz, 1H), 8.33 (s, 1H), 8.24 (s, 1H), 8.09 (s, 1H), 7.35 (d, J = 7.6 Hz, 1H), 4.38 (d, J = 6.0 Hz, 2H), 3.89-3.82 (m, 3H), 3.36 (t, J = 11.6 Hz, 2H), 2.42 (s, 3H), 2.16 (s, 3H), 1.81 (d, J = 12.0 Hz, 2H), 1.52-1.44 (m, 2H). | 3 |
| 329 | 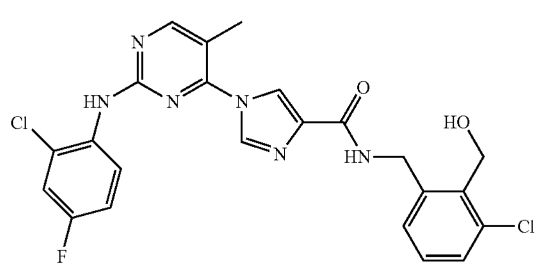 [SMILES: Cc1cnc(Nc2ccc(F)cc2Cl)nc1-n1cnc(C(=O)NCc2cccc(Cl)c2CO)c1] | N-(3-chloro-2-(hydroxymethyl)benzyl)-1-(2-((2-chloro-4-fluoro-phenyl)amino)-5-methyl-pyrimidin-4-yl)-1H-imidazole-4-carboxamide | 1H NMR (400 MHz, DMSO-d$_6$) δ 9.17 (s, 1H), 8.63 (t, J = 6 Hz, 1H), 8.46 (s, 1H), 8.24 (s, 1H), 8.09 (s, 1H), 7.67-7.63 (m, 1H), 7.50-7.47 (dd, J = 8.8 Hz, 1H), 7.32-7.20 (m, 4H), 5.24 (t, J = 4.8 Hz, 1H), 4.75 (d, J = 4.8 Hz, 2H), 4.6 (d, J = 6, 2H), 2.25 (s, 3H). | 3 |

TABLE 1-continued

| Cmpd # | Structure | Name | NMR data | Scheme # |
|---|---|---|---|---|
| 330 | 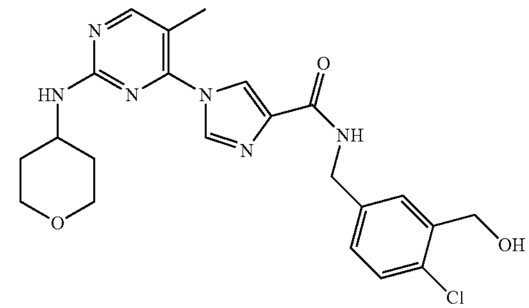 [SMILES: Cc1cnc(NC2CCOCC2)nc1-n1cnc(C(=O)NCc2ccc(Cl)c(CO)c2)c1] | N-(4-chloro-3-(hydroxy-methyl)-benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$) δ 8.70 (t, J = 6 Hz, 1H), 8.34 (s, 1H), 8.25 (s, 1H), 8.09 (s, 1H), 7.51 (s, 1H), 7.36-7.30 (m, 2H), 7.19 (d, J = 8 Hz, 1H), 5.34 (t, J = 4 Hz, 1H), 4.51 (d, J = 4 Hz, 2H), 4.21 (d, J = 4 Hz, 2H), 3.90 (bs, 1H), 3.84 (d, J = 12 Hz, 2H), 3.39-303 (m, 2H), 2.17 (s, 3H), 1.84-1.79 (m, 2H), 1.52-1044 (m, 2H). | 3 |
| 331 | 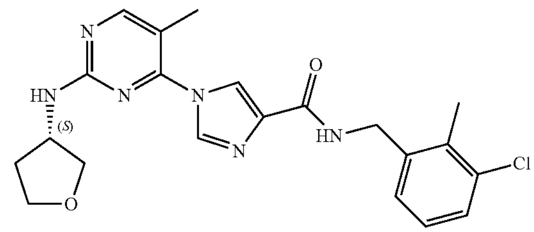 | (S)-N-(3-chloro-2-methylbenzyl)-1-(5-methyl-2-((tetrahydro-furan-3-yl)amino)pyrimidin-4-yl)-1H-imidazole-4-carboxamide | 1H NMR (400 MHz, DMSO-d$_6$) δ 8.60 (t, J = 6.4 Hz, 1H), 8.36 (s 1H), 8.28 (s 1H), 8.13 (s 1H), 7.60-7.58 (d, J = 4 Hz, 1H), 7.31-7.29 (d, J = 4 Hz 1H), 7.21 (d, J = 4 Hz, 1H), 7.136 (t, J = 15.2 Hz, 1H), 4.45 (d, J = 2 Hz, 2H), 4.36 (d, J = 2 Hz, 1H), 3.88-3.78 (m, J = 19.2 Hz, 2H), 3.72-3.68 (m, 1H), 3.55-3.52 (m, 1H), 2.30 (s, J = 1.4 Hz, 3H), 2.17 (s, 3H), 2.13-2.08 (m, 1H), 1.90-1.83 (m, 1H). | 3 |
| 332 | 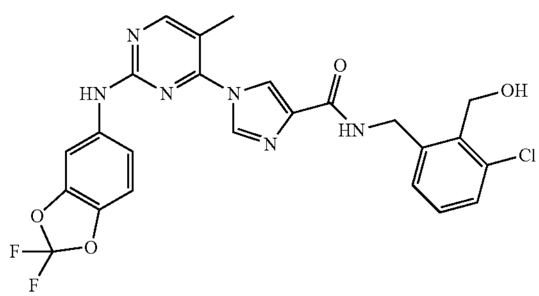 [SMILES: Cc1cnc(Nc2ccc3c(c2)OC(F)(F)O3)nc1-n1cnc(C(=O)NCc2cccc(Cl)c2CO)c1] | N-(3-chloro-2-(hydroxy-methyl)-benzyl)-1-(2-((2,2-difluoro-benzo[d][1,3]dioxol-5-yl)amino)-5-methyl-pyrimidin-4-yl)-1H-imidazole-4-carboxamide | 1H NMR (400 MHz, DMSO-d$_6$) δ 8.68-8.65 (t, J = 6.4 Hz, 1H), 8.57 (s, 1H), 8.34 (d, J = 0.8 Hz, 1H), 8.19 (s, 1H), 7.88 (d, J = 8 Hz, 1H), 7.38-7.23 (m, 5H), 5.25 (t, J = 5.2 Hz, 1H), 4.76 (d, J = 5.2 Hz, 2H), 4.62 (d, J = 6.4 Hz, 2H), 2.30 (s, 3H), 1.21 (s, 1H). | 3 |
| 333 | 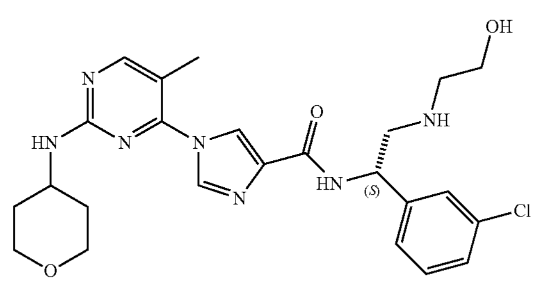 | (S)-N-(1-(3-chlorophenyl)-2-((2-hydroxy-ethyl)amino)ethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$) δ 8.50 (d, J = 8.0 Hz, 1H), 8.34 (s, 1H), 8.27 (s, 1H), 8.07 (s, 1H), 7.43 (s, 1H), 7.36-7.27 (m, 4H), 5.07-5.04 (m, 1H), 4.41 (t, J = 5.6 Hz, 1H), 3.85-3.82 (m, 3H), 3.42-3.27 (m, 4H), 3.07.2.99 (m, 1H), 2.92-2.86 (m, 1H), 2.57 (br s, 2H), 2.17 (s, 3H), 1.81 (d, J = 11.2 Hz, 2H), 1.66 (br s, 1H), 1.52-1.44 (m, 2H). | 20 |

TABLE 1-continued

| Cmpd # | Structure | Name | NMR data | Scheme # |
|---|---|---|---|---|
| 334 | 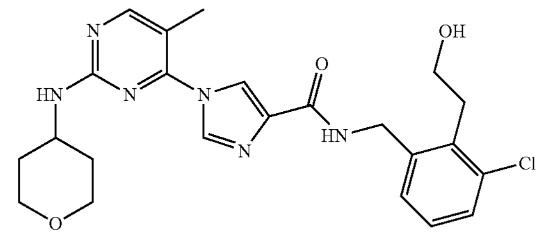 [SMILES: Cc1cnc(NC2CCOCC2)nc1-n1cnc(C(=O)NCc2cccc(Cl)c2CCO)c1] | N-(3-chloro-2-hydroxy-ethylbenzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$) 8.64-8.63 (t, J = 6.0 Hz, 1H), 8.34 (s, 1H), 8.25 (s, 1H), 8.10 (d, J = 0.8 Hz, 1H), 7.35 (d, J = 8.0 Hz, 1H), 7.20 (d, J = 8 Hz, 1H), 7.24 (d, J = 7.2 Hz, 1H), 7.17 (t, J = 8.0 Hz, 1H), 4.83 (t, J = 5.6 Hz, 1H), 4.54 (d, J = 6 Hz, 2H), 3.85-3.82 (m, 2H), 3.58 (q, 2H), 3.39-3.34 (m, 2H), 3.03 (t, J = 6.8 Hz, 2H), 2.17 (s, 3H), 1.81 (d, J = 10.8 Hz, 2H), 1.53-1.43 (m, 2H), 1.21 (s, 1H). | 3 |
| 335 | 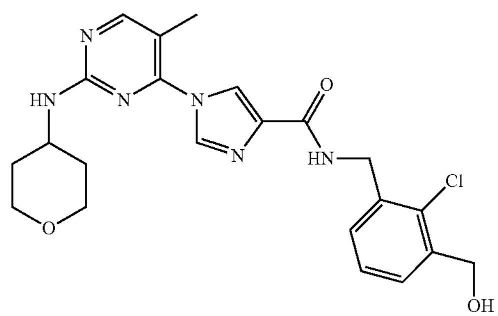 [SMILES: Cc1cnc(NC2CCOCC2)nc1-n1cnc(C(=O)NCc2cccc(CO)c2Cl)c1] | N-(2-chloro-3-(hydroxy-methyl)-benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$) δ 8.63-8.61 (t, J = 6 Hz, 1H), 8.34 (s, 1H), 8.28 (s, 1H), 8.12 (s, 1H), 7.43 (d, J = 6.8 Hz, 1H), 7.35 (d, J = 6.8 Hz, 1H), 7.29 (t, J = 7.6 Hz, 1H), 7.20-7.19 (d, J = 7.6 Hz, 1H), 5.34 (t, J = 5.6 Hz, 1H), 4.57 (d, J = 5.6 Hz, 2H), 4.51 (d, J = 5.6 Hz, 2H), 3.90 (br s, 1H), 3.85-3.82 (d, J = 11.6 Hz, 2H), 3.37 (t, J = 10.8 Hz, 2H), 2.18 (s, 3H), 1.81 (d, J = 11.6 Hz, 1H), 1.52-1.45 (m, 2H). | 3 |
| 336 | 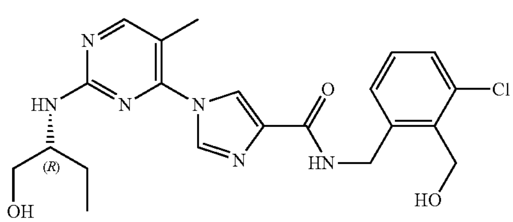 | (R)-N-(3-chloro-2-(hydroxy-methyl)-benzyl)-1-(2-((1-hydroxy-butan-2-yl)amino)-5-methyl-pyrimidin-4-yl)-1H-imidazole-4-carboxamide | 1HNMR (400 MHz, DMSO-d$_6$) δ 8.63-8.61 (m, 1H), 8.30 (s, 1H), 8.24 (s, 1H), 8.10 (s, 1H), 7.33-7.23 (m, 3H), 6.97-6.95 (d, J = 8 Hz, 1H), 5.24 (t, J = 5.2 Hz, 1H), 4.76 (d, J = 5.6 Hz, 2H), 4.61-4.54 (m, 3H), 3.81 (br s, 1H), 3.45-3.41 (m, 1H), 3.36-3.27 (m, 1H), 2.17 (s, 3H), 1.66-1.61 (m, 1H), 1.44-1.37 (m, 1H), 0.85 (t, J = 6.8 Hz, 3H). | 3 |

TABLE 1-continued

| Cmpd # | Structure | Name | NMR data | Scheme # |
|---|---|---|---|---|
| 337 | 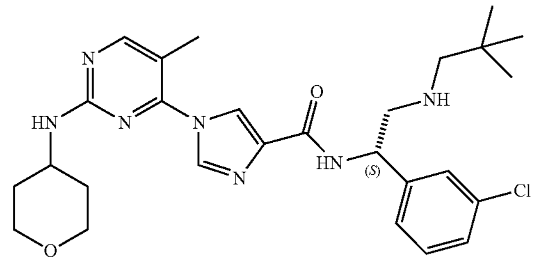 | (S)-N-(1-(3-chlorophenyl)-2-(neopentyl-amino)-ethyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$) δ 8.52 (d, J = 11.2 Hz, 1H), 8.33 (s, 1H), 8.27 (s, 1H), 8.07 (s, 1H), 7.43 (s, 1H), 7.35-7.26 (m, 4H), 5.05 (q, 1H), 3.89-3.82 (m, 3H), 3.36 (t, J = 10.8 Hz, 2H), 2.99-2.83 (m, 2H), 2.30-2.24 (m, 2H), 2.17 (s, 3H), 1.80 (d, J = 11.2 Hz, 2H), 1.53-1.43 (m, 3H), 0.80 (s, 9H). | 20 |
| 338 | 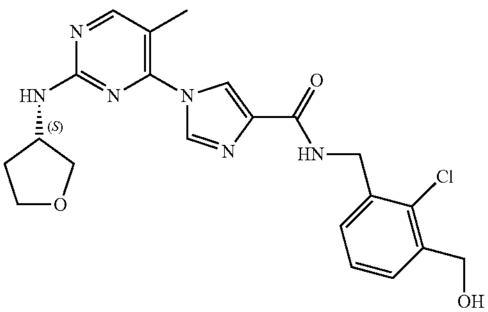 | (S)-N-(2-chloro-3-(hydroxy-methyl)-benzyl)-1-(5-methyl-2-((tetrahydro-furan-3-yl)amino)-pyrimidin-4-yl)-1H-imidazole-4-carboxamide | 1HNMR (400 MHz, DMSO-d$_6$) δ 8.64-8.62 (t, J = 5.6 Hz, 1H), 8.36 (s, 1H), 8.29 (s, 1H), 8.14 (s, 1H), 7.60 (d, J = 5.2 Hz, 1H), 7.43 (d, J = 7.6 Hz, 1H), 7.29 (t, J = 7.6 Hz, 1H), 7.19 (d, J = 7.2 Hz, 1H), 5.34 (t, J = 5.2 Hz, 1H), 4.58-4.50 (m, 4H), 4.35 (br s, 1H), 3.88-3.80 (m, 2H), 3.69 (q, 1H), 3.55-3.27 (m, 1H), 2.20 (s, 3H), 2.14-2.12 (m, 1H), 1.89-1.86 (m, 1H). | 3 |
| 339 | 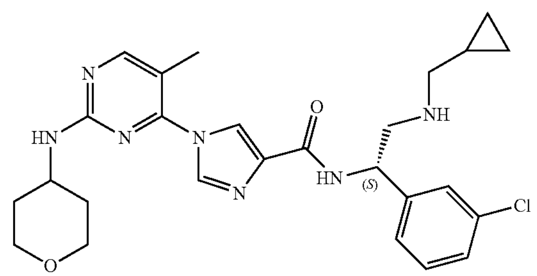 | 1-[5-Methyl-2-(tetrahydro-pyran-4-ylamino)-pyrimidin-4-yl]-1H-imidazole-4-carboxylic acid [(S)-1-(3-chloro-phenyl)-2-(cyclopropyl-methyl-amino)-ethyl]-amide | 1HNMR (400 MHz, DMSO-d$_6$) δ 8.48 (d, J = 7.6 Hz, 1H), 8.34 (s, 1H), 8.27 (s, 1H), 8.07 (s, 1H), 7.42 (s, 1H), 7.36-7.27 (m, 4H), 5.05-5.02 (m, 1H), 3.85-3.82 (m, 3H), 3.36 (t, J = 11.6 Hz, 2H), 3.01-2.86 (m, 2H), 2.38-2.37 (m, 2H), 2.17 (s, 3H), 1.80 (d, J = 11.6 Hz, 2H), 1.52-1.44 (m, 2H), 1.21 (br s, 1H), 0.93-0.83 (m, 1H), 0.35 (d, J = 8.0 Hz, 2H), 0.03 (d, J = 4.0, 2 Hz). | 20 |
| 340 | 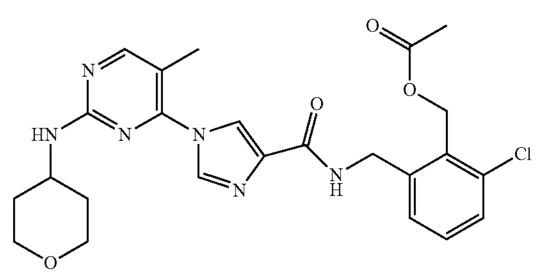 [SMILES: CC(=O)OCc1c(Cl)cccc1CNC(=O)c1cn(-c2nc(NC3CCOCC3)ncc2C)cn1] | 2-chloro-6-((1-(5-methyl-2-((tetrahydro-2H-pyran-4-yl)amino)-pyrimidin-4-yl)-1H-imidazole-4-carboxamido)-methyl)benzyl acetate | 1HNMR (400 MHz, DMSO-d$_6$) δ 8.63-8.62 (t, J = 5.6 Hz, 1H), 8.34 (s, 1H), 8.25 (s, 1H), 8.1 (s, 1H), 7.42-7.35 (m, 4H), 5.32 (s, 2H), 4.48 (d, J = 6.4 Hz, 2H), 3.85-3.82 (m, 3H), 3.36 (t, J = 10.8 Hz, 1H), 2.17 (s, 3H), 1.98 (s, 3H), 1.80 (d, J = 10.8 Hz, 2H), 1.49-1.47 (m, 2H). | 3 |

TABLE 1-continued

| Cmpd # | Structure | Name | NMR data | Scheme # |
|---|---|---|---|---|
| 341 | 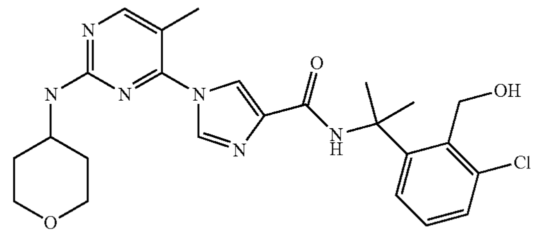 [SMILES: Cc1cnc(NC2CCOCC2)nc1-n1cnc(C(=O)NC(C)(C)c2cccc(Cl)c2CO)c1] | N-(2-(3-chloro-2-(hydroxymethyl)-phenyl)propan-2-yl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.33 (br s, 1H), 8.23 (br s, 1H), 7.98 (d, J = 11.6 Hz, 2H), 7.42 (d, J = 7.6 Hz, 1H), 7.34-7.32 (m, 2H), 7.27-7.23 (m, 1H), 4.84 (s, 3H), 3.84-3.82 (m, 3H) 3.39-3.33 (m, 2H), 2.16 (s, 1H), 1.80 (s, 7H), 1.49-1.44 (m, 2H). | 3 |
| 342 | 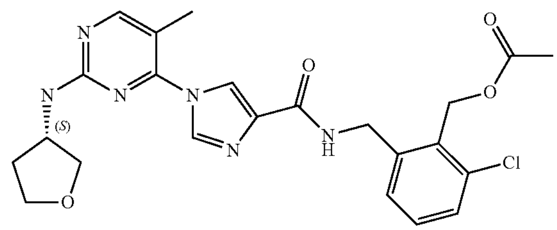 | (S)-2-chloro-6-((1-(5-methyl-2-((tetrahydrofuran-3-yl)amino)pyrimidin-4-yl)-1H-imidazole-4-carboxamido)methyl)benzyl acetate | 1HNMR (400 MHz, DMSO-d$_6$): δ 8.64-8.61 (m, 1H), 8.35 (s, 1H), 8.27 (s, 1H), 8.11 (s, 1H), 7.59 (d, J = 5.2 Hz, 1H), 7.42-7.35 (m, 3H), 5.32 (s, 2H), 4.55-4.54 (m, 2H), 4.34 (br s, 1H), 3.87-3.78 (m, 2H), 3.72-3.66 (m, 1H), 3.55-3.51 (m, 1H), 2.18 (s, 3H), 2.15-2.10 (m, 1H), 1.98 (s, 3H), 1.88-1.85 (m, 1H). | 3 |
| 343 | 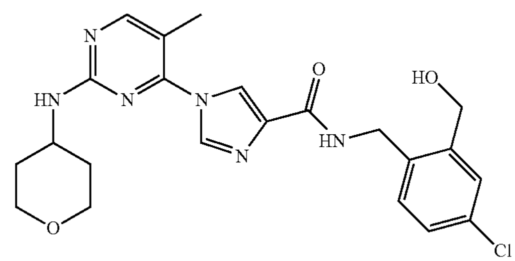 [SMILES: Cc1cnc(NC2CCOCC2)nc1-n1cnc(C(=O)NCc2ccc(Cl)cc2CO)c1] | N-(4-chloro-2-hydroxymethyl-benzyl)-1-(5-methyl-2-((tetrahydro-2H-pyran-4-yl)amino)-pyrimidin-4-yl)-1H-imidazole-4-carboxamide | 1HNMR (400 MHz, DMSO-d$_6$): δ 8.57 (t, J = 8.0 Hz, 1H), 8.34 (s, 1H), 8.25 (s, 1H), 8.09 (s, 1H), 7.40 (s, 1H), 7.35 (d, J = 7.6 Hz, 1H), 7.28 (d, J = 8.4 Hz, 2H), 5.33 (t, J = 5.2 Hz, 1H), 4.60 (d, J = 5.6 Hz, 2H), 4.41 (d, J = 5.6 Hz, 2H), 3.89 (br s, 1H), 3.84 (d, J = 11.6 Hz, 2H), 3.39-3.34 (m, 2H), 2.71 (s, 3H), 1.81 (d, J = 9.2 Hz, 2H), 1.52-1.44 (m, 2H), 1.21 (s, 1H). | 3 |
| 344 | 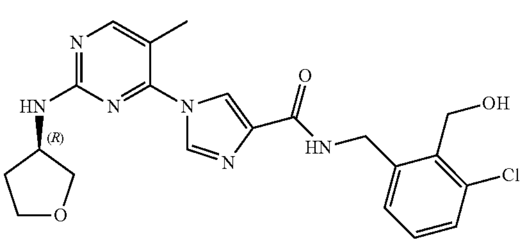 | (R)-N-(3-chloro-2-(hydroxymethyl)-benzyl)-1-(5-methyl-2-((tetrahydrofuran-3-yl)amino)-pyrimidin-4-yl)-1H-imidazole-4-carboxamide | 1HNMR (400 MHz, DMSO-d$_6$): δ 8.63 (t, J = 6.4 Hz, 1H), 8.35 (s, 1H), 8.26 (s, 1H), 8.12 (s, 1H), 7.59 (d, J = 5.2 Hz, 1H), 7.33-7.23 (m, 3H), 5.24-5.22 (m, 1H), 4.76 (d, J = 5.6 Hz, 2H), 4.61 (d, J = 6.4 Hz, 2H), 4.34 (br s, 1H), 3.87-3.78 (m, 2 H), 3.72-3.66 (m, 1H), 3.55-3.52 (m, 1H), 2.19 (s, 3H), 2.15-2.08 (m, 1H), 1.88-1.84 (m, 1H) | 3 |

TABLE 1-continued

| Cmpd # | Structure | Name | NMR data | Scheme # |
|---|---|---|---|---|
| 345 | 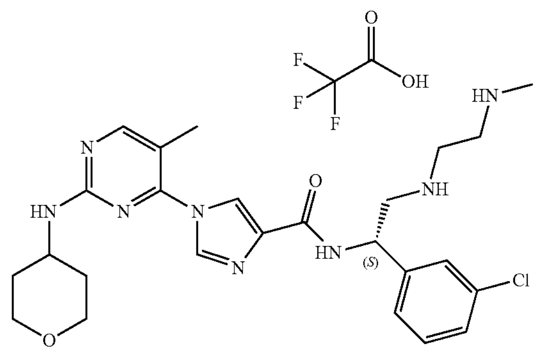 | ((S)-N-(1-(3-chlorophenyl)-2-((2-(methyl-amino)ethyl)amino)ethyl)-1-(5-methyl-2-((tetrahydro-2H-pyran-4-yl)amino)-pyrimidin-4-yl)-1H-imidazole-4-carboxamide 2,2,2-trifluoroacetate | 1HNMR (400 MHz, DMSO-d$_6$): δ 8.93 (d, J = 8.0 Hz, 1H), 8.62 (br s, 1H), 8.56 (br s, 1H), 8.36 (s, 1H), 8.31 (s, 1H), 8.13 (s, 1H), 7.54-7.40 (m, 4H), 5.41 (s, 1H), 3.90 (br s, 9H), 3.86-3.83 (m, 4H), 3.60-3.44 (m, 2H), 3.38-3.25 (m, 6H), 2.61 (s, 3H), 2.16 (s, 3H), 1.80 (d, J = 11.2 Hz, 2H), 1.50-1.49 (m, 2H) | 20 |
| 346 | 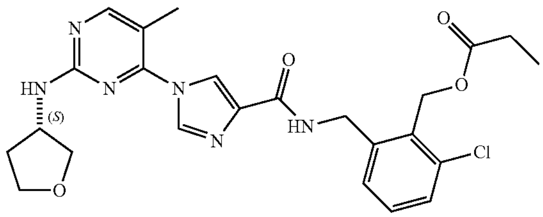 | (S)-2-chloro-6-((1-(5-methyl-2-((tetrahydro-furan-3-yl)amino)pyrimidin-4-yl)-1H-imidazole-4-carboxamido)-methyl)benzyl-propionate | 1HNMR (400 MHz, DMSO-d$_6$): δ 8.64-8.61 (m, 1H), 8.35 (s, 1H), 8.26 (s, 1H), 8.11 (s, 1H), 7.59 (d, J = 5.2 Hz, 1H), 7.41-7.35 (m, 3H), 5.33 (s, 2H), 4.54 (d, J = 6.4 Hz, 2H), 4.36 (br s, 1H) 3.87-3.78 (m, 2H), 3.72-3.66 (m, 1H), 3.55-3.51 (m, 1H), 2.30-2.24 (m, 2H), 2.18 (s, 3H), 2.15-2.08 (m, 1H), 1.90-1.82 (m, 1H), 1.00-0.99 (m, 3H). | 3 |
| 347 | 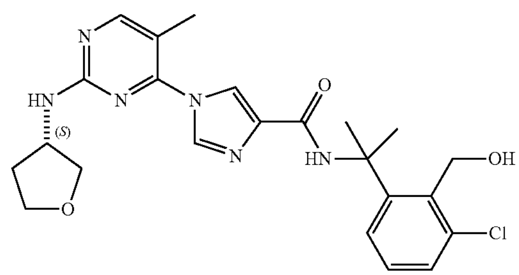 | (S)-N-(2-(3-chloro-2-(hydroxy-methyl)-phenyl)propan-2-yl)-1-(5-methyl-2-((tetrahydro-furan-3-yl)amino)pyrimidin-4-yl)-1H-imidazole-4-carboxamide | 1HNMR (400 MHz, DMSO-d$_6$): δ 8.35 (br s, 1H), 8.24 (br s, 1H), 8.0 (d, J = 8.4 Hz, 2H), 7.58 (br s, 1H), 7.42 (d, J = 8.0 Hz, 1H), 7.33 (d, J = 8.0 Hz, 1H), 7.27-7.23 (m, 1H), 4.83 (s, 3H), 4.33 (br s, 1H), 3.86-3.79 (m, 2H), 3.7-3.67 (m, 1H), 3.53-3.52 (m, 1H), 2.17 (s, 3H), 2.17-2.11 (m, 1H), 1.9-1.85 (m, 1H), 1.80 (s, 6H). | 3 |
| 348 | 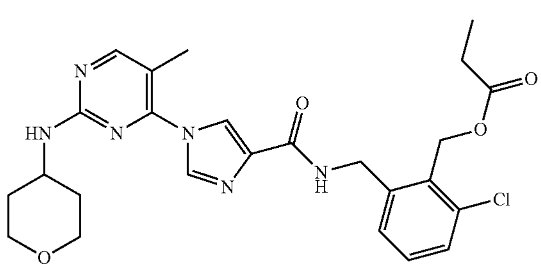 [SMILES: CCC(=O)OCc1c(Cl)cccc1CNC(=O)c1cn(-c2nc(NC3CCOCC3)ncc2C)cn1] | 2-chloro-6-((1-(5-methyl-2-((tetrahydro-2H-pyran-4-yl)amino)-pyrimidin-4-yl)-1H-imidazole-4-carboxamido)-methyl)benzyl-propionate | 1HNMR (400 MHz, DMSO-d$_6$): δ 8.62 (t, J = 5.6 Hz, 1H), 8.34 (s, 1H), 8.25 (s, 1H), 8.09 (s, 1H), 7.40-7.35 (m, 4H), 5.33 (s, 2H), 4.54 (d, J = 6 Hz, 2H), 3.85-3.82 (m, 3H), 3.36 (t, J = 11.6 Hz, 2H), 2.48-2.24 (m, 2H), 2.16 (s, 3H), 1.80 (d, J = 11.6 Hz, 2H), 1.52-1.44 (m, 2H), 0.99 (t, J = 7.6 Hz, 3H). | 3 |

Example 34. Biological Assays

ERK1 and ERK2 HTRF (Biochemical) Assays

These assays employed a homogeneous time resolved fluorescence (HTRF) technique. The compounds were serially diluted by half-log with concentrations ranging from 0.0005 to 10 uM in the assay buffer (50 mM Tris pH=7.5, 1 mM EGTA, 2 mM DTT, 10 mM $MgCl_2$, 0.100 Tween-20) and 20 uL of substrate-ATP mix [1 uM Biotin-LC-Myelin Basic Protein (MBP) derivatized Peptide (Anaspec)-24 uM ATP (Sigma)] was added to each well of the assay plate. Then 10 uL of enzyme mix [25 nM ERK1 or ERK2 (Jubilant Biosys) in assay buffer] was added to each well. The plate was incubated at room temperature for 60 min with shaking. The HTRF mix [625 nM LANCER Ultra Europium-anti-phospho-MBP (Perkin Elmer) and 2 nM Phycolink® Streptavidin-Allophycocyanin (SA-APC) (Prozyme) in HTRF buffer (50 mM Tris-HCl pH=7.5, 100 mM NaCl, 0.1% BSA, 0.05% Tween20, 0.5 mM EDTA)] was prepared and 75 uL of this mix was added to the HTRF plate. After incubation for 60 min at room temperature, 10 uL of the reaction mixture was transferred to the HTRF assay plate and incubated for 45 min at room temperature with shaking. Plate was read using Pherastar in HTRF mode (excitation 337 nm, emission 665 & 620 nm). The $IC_{50}$ values (half maximal inhibitory concentration values) were subsequently determined using a sigmoidal dose-response curve (variable slope) in GraphPad Prism® 5 software. Compounds of the invention caused inhibition of ERK1 and ERK2 as determined in these assays. Representative data are provided in Table 2.

Cell Proliferation (Alamar Blue) Assay

HT-29 (colorectal carcinoma, B-RafV600E), HCT116 (colorectal carcinoma, K Ras G13D), A375 (melanoma, B-RafV600E) and SK-Mel2 (melanoma, NRAS Q61R) cells (obtained from ATCC, USA) were seeded (5000 cells/well) in 96-well tissue culture plate and incubated at 37° C./5% $CO_2$ for 16-24 hours. The cells were then treated with compounds, at concentrations typically from 0.0005 to 10 uM prepared in 3-fold serial dilutions. The plates were then incubated for 72 h at 37° C./5% $CO_2$ in a moist environment. Then Alamar Blue™ reagent (final concentration 1×) was added to each well and incubated for 1-3 h at 37° C./5% $CO_2$. The plates were read on fluorescence reader at 540 nm excitation and 590 nm emission wavelengths. The $IC_{50}$ values were subsequently determined using a sigmoidal dose-response curve (variable slope) using GraphPad Prism® 5 software. Compounds of the invention caused inhibition of HT-29, HCT116, A375 and SK-Mel2 cell proliferation as determined in these assays. Representative data for the HT-29 and HCT116 cell proliferation assays are provided in Table 2.

Phospho-RSK1(S380) ELISA Assay

HT-29 cells (colorectal carcinoma, B-RafV600E); obtained from ATCC, USA) were seeded (60,000 cells/well) in a 96-well plate and incubated at 37° C./5% $CO_2$ overnight and then treated with desired compound dilutions for 2 h. Medium was removed and cells were rinsed once with ice-cold 1×PBS, then 0.070 mL ice-cold 1× cell lysis buffer containing 1 mM PMSF was added to each well and the plate was incubated on a shaker for 2 h and 30 min at 4° C. The plate was then centrifuged for 20 min (×4000 rpm) at 4° C. and the supernatant was transferred to a new plate. Cell lysates were diluted with sample diluent at a ratio of 1:1. The ELISA was then carried out following the manufacturer's protocol (PathScan® phospho-RSK1(Ser380) Sandwich ELISA Kit, Cell Signaling Technologies). The plate was read at 450 nm within 30 min after adding STOP solution. The $IC_{50}$ values were subsequently determined using a sigmoidal dose-response curve (variable slope) in GraphPad Prism® 5 software. Compounds of the invention inhibited phosphorylation of RSK1(S380) (the downstream target of ERK1/2) as determined in this assay. Representative data are provided in Table 2.

In vivo Studies in Tumor Xenograft Models

Tumor Cell Implantation and Randomization of Animals

Foxn1 nu/nu strain of female mice (obtained from Charles River Laboratories, USA), 8-10 weeks of age, body weight range 23-25 g, were used for the tumor xenograft efficacy studies. Human cancer cell lines (such as melanoma A375, colorectal HT29, pancreatic BxPC3, colorectal HCT116, and lung A549) were first grown in vitro, and then about five million ($5 \times 10^6$) of these cells in 100 µL of serum free medium were mixed with an equal amount of matrigel, and the entire mixture was injected subcutaneously at the right flank region of mice. The tumors were measured with Vernier calipers periodically after the first week of injection. When the tumor volume reached 120-150 $mm^3$ (about 3-4 weeks after injection) the animals were randomized into different groups so that their tumor volume was approximately the same in all groups.

Determination of In Vivo Efficacy of Tumor Growth Inhibition

For PO dosing, the compounds were prepared in a formulation containing 0.5% Methyl cellulose and 0.01% Tween 80. For IV, SC, or IP dosing, the compounds were prepared in 6% solutol-ethanol (1:1), 6% DMSO and 88% saline. Animals were dosed with compounds prepared in specific formulations via PO, IP or SC route either QD or BID at the required doses. Tumors size and body weights were measured twice or thrice in a week. Tumors were harvested at the end of the study after euthanizing the animals according to approved protocols. From the harvested tumor one part was snap frozen and submitted for PK studies, and the other part was homogenized and the lysates were tested for target inhibition using western blotting. Before the tumor was harvested, blood (~200 µL) was collected by ocular bleeding for PK studies.

Changes in tumor volume (Δ volumes) for each treated (T) and control (C) group were calculated by subtracting the mean tumor volume on the first day of treatment (starting day) from the mean tumor volume on the specified observation day. These values were used to calculate a percentage growth (% T/C) using the formula:

% $T/C=(\Delta T/\Delta C) \times 100$, where $\Delta T>0$, or

% $T/C=(\Delta T/\Delta Ti) \times 100$, where $\Delta T<0$ and $Ti$ is the mean tumor volume at the start of the experiment.

Percentage tumor growth inhibition was calculated as [100−% T/C]. Percentage body weight change was calculated as [(Body weight on specified observation day−Body weight on starting day)/Body weight on starting day]×100.

Results

Compounds of the invention were active in these in vivo tumor xenograft studies. For example, in a human melanoma xenograft model (A375) harboring B-RAF V600E mutation, compounds of Example 201 and Example 211 caused approximately 70 to 76% tumor growth inhibition when dosed orally at 50 mg/kg BID for 17 days. There was no significant body weight loss observed at this dose for either compound. In a pharmacodynamic assay, compounds of Example 201 and Example 211 caused inhibition of phospho-RSK (the downstream target of ERK1/2) by about 66 and 84%, respectively, as measured in A375 tumor samples harvested at 1 h after dosing at 50 mg/kg PO, when compared to the vehicle control. Also, in this same model (A375), compounds of Example 255, Example 225a, and Example 259 caused approximately 70 to 90% tumor growth inhibition when dosed orally at 50 mg/kg BID for 19 days. There was no significant body weight loss observed at this dose for either compound.

In a human colon cancer xenograft model (HT-29) harboring B-RAF V600E mutation, the compound of Example 201 caused approximately 50% tumor growth inhibition when dosed orally at 50 mg/kg BID for 20 days. There was no significant body weight loss observed at this dose in this study.

In a human pancreatic carcinoma xenograft model, BxPC3 (wild type KRAS), the compound of Example 201 caused about 63% tumor growth inhibition when dosed orally at 50 mg/kg BID for 25 days. There was no significant body weight loss observed at this dose in this study.

In a human colon cancer xenograft model (HCT116; harboring KRAS mutation), the compounds of Example 259, Example 225a, and Example 275 caused approximately 90-100% tumor growth inhibition when dosed orally at 50 mg/kg BID for 24 days. There was no significant body weight loss observed at this dose in this study.

In a human lung carcinoma xenograft model (A549; harboring KRAS mutation), the compound of Example 304, Example 302 and Example 300 caused about 65 to 82% tumor growth inhibition when dosed orally at 50 mg/kg BID for 20 days. There was no significant body weight loss observed at this dose in this study.

TABLE 2

Biochemical, Mechanistic and Proliferation Cell-based Assay Results

| Cmpd # | Biochemical Assay[1] | | Mechanistic Cell Assay[2] | Cell Proliferation Assay[2] | |
|---|---|---|---|---|---|
| | ERK1 | ERK2 | RSK1 Phos HT29 | HT29 | HCT116 |
| 1 | A | A | NA | NA | E |
| 2 | A | B | NA | E | E |
| 3 | B | B | NA | E | E |
| 4 | E | E | NA | E | E |
| 5 | C | NA | NA | NA | NA |
| 6 | A | A | E | E | E |
| 7 | B | B | NA | E | E |
| 9 | NA | E | NA | NA | NA |
| 10 | NA | E | NA | NA | NA |
| 11 | NA | E | NA | NA | NA |
| 12 | A | A | E | E | E |
| 13 | C | C | NA | NA | NA |
| 14 | C | C | NA | NA | E |
| 15 | B | NA | NA | NA | E |
| 16 | C | B | NA | NA | E |
| 18 | A | C | E | E | E |
| 20 | A | A | NA | NA | E |
| 21 | A | A | E | E | E |
| 22 | C | B | NA | E | E |
| 23 | A | A | E | D | E |
| 24 | A | A | E | E | E |
| 25 | A | NA | NA | NA | NA |
| 26 | A | NA | NA | NA | NA |
| 27 | NA | NA | NA | NA | NA |
| 28 | B | B | NA | NA | NA |
| 29 | A | A | C | C | D |
| 30 | A | A | NA | E | E |
| 31 | A | A | D | C | D |
| 32 | A | A | D | E | E |
| 33 | A | A | E | NA | E |
| 34 | A | A | E | NA | E |
| 35 | A | A | NA | NA | E |
| 36 | C | A | NA | NA | E |
| 37 | C | A | NA | E | D |
| 38 | A | A | E | E | E |
| 39 | B | A | NA | E | E |
| 40 | B | B | NA | E | E |
| 41 | C | A | NA | E | E |
| 42 | A | A | D | C | C |
| 43 | E | E | NA | NA | NA |
| 44 | B | A | NA | E | E |
| 45 | A | A | NA | E | E |
| 46 | A | A | NA | E | E |
| 47 | A | A | C | B | C |
| 48 | A | A | C | C | D |
| 49 | B | A | NA | E | E |
| 50 | NA | A | NA | E | E |
| 51 | C | B | NA | E | E |
| 52 | NA | C | NA | NA | NA |
| 53 | C | C | NA | NA | NA |
| 54 | B | A | NA | E | E |
| 55 | B | B | NA | E | E |
| 56 | NA | C | NA | NA | NA |
| 57 | A | A | NA | E | E |
| 58 | A | A | D | D | E |
| 59 | B | A | C | C | C |
| 60 | A | A | A | A | B |
| 61 | NA | D | NA | NA | NA |
| 62 | A | A | D | D | D |
| 63 | A | A | C | D | D |
| 64 | A | A | D | C | D |
| 65 | NA | A | A | B | B |
| 66 | A | A | B | C | D |
| 67 | A | A | D | E | E |
| 68 | A | A | A | B | B |
| 69 | A | A | D | D | D |
| 70 | A | A | C | E | D |
| 71 | A | A | C | D | E |
| 72 | A | A | A | D | E |
| 73 | A | A | E | D | D |
| 74 | A | A | D | D | E |
| 75 | A | A | D | D | E |
| 76 | A | A | C | D | E |
| 77 | A | A | B | D | E |
| 78 | A | A | NA | E | E |
| 79 | C | A | NA | E | E |
| 80 | A | A | E | E | E |
| 81 | A | A | NA | E | E |
| 82 | B | A | NA | E | E |
| 83 | C | A | NA | E | E |
| 84 | A | A | NA | E | E |
| 85 | C | C | NA | E | E |
| 86 | B | B | NA | E | E |
| 87 | A | A | B | C | D |
| 88 | A | A | NA | E | E |
| 89 | C | A | NA | E | E |
| 90 | C | A | NA | E | E |
| 91 | A | A | D | D | E |
| 92 | A | A | NA | D | E |
| 93 | A | A | A | A | A |
| 94 | A | A | D | NA | D |
| 95 | B | A | C | C | D |
| 96 | A | A | C | C | D |
| 97 | NA | C | NA | E | E |
| 98 | A | A | NA | NA | NA |
| 99 | C | C | NA | E | E |
| 100 | B | A | C | E | E |
| 101 | A | A | NA | D | E |
| 103 | C | A | NA | E | E |
| 104 | NA | C | NA | E | E |
| 105 | A | A | B | E | E |
| 106 | A | A | B | D | E |
| 107 | A | A | D | D | D |

TABLE 2-continued

Biochemical, Mechanistic and Proliferation Cell-based Assay Results

| Cmpd # | Biochemical Assay[1] ERK1 | ERK2 | Mechanistic Cell Assay[2] RSK1 Phos HT29 | Cell Proliferation Assay[2] HT29 | HCT116 |
|---|---|---|---|---|---|
| 108 | A | A | NA | E | E |
| 109 | A | A | C | E | E |
| 110 | B | A | E | E | E |
| 111 | B | A | NA | E | E |
| 112 | A | A | NA | NA | E |
| 113 | B | A | B | B | B |
| 114 | A | A | B | D | C |
| 115 | A | A | C | E | E |
| 116 | A | A | D | E | E |
| 117 | C | B | D | E | E |
| 118 | B | A | C | B | D |
| 119 | NA | C | NA | E | E |
| 120 | NA | C | NA | E | E |
| 121 | A | A | C | C | C |
| 122 | NA | E | NA | NA | NA |
| 123 | A | A | B | C | D |
| 124 | A | A | D | D | E |
| 125 | A | A | B | C | C |
| 126 | A | A | B | B | A |
| 127 | A | A | D | E | E |
| 128 | A | A | D | D | E |
| 129 | A | A | D | E | E |
| 130 | C | C | D | E | E |
| 131 | A | A | C | C | C |
| 132 | A | A | D | D | D |
| 133 | A | A | C | C | D |
| 134 | NA | D | NA | NA | NA |
| 135 | A | A | D | NA | NA |
| 136 | B | A | E | D | D |
| 137 | A | A | B | C | B |
| 138 | A | A | B | B | B |
| 139 | A | A | A | C | B |
| 140 | A | A | E | D | D |
| 141 | A | A | E | E | E |
| 142 | A | A | C | D | D |
| 143 | A | A | C | D | C |
| 145 | E | D | E | NA | NA |
| 146 | A | A | B | D | D |
| 147 | B | A | E | E | E |
| 148 | A | A | D | D | D |
| 149 | B | A | E | E | E |
| 150 | C | A | D | E | E |
| 151 | A | A | B | A | D |
| 152 | A | A | B | B | D |
| 153 | C | C | E | E | E |
| 154 | A | A | C | D | B |
| 155 | A | A | B | C | D |
| 156 | A | A | C | C | D |
| 157 | A | A | C | C | D |
| 158 | C | B | E | D | D |
| 159 | B | A | D | D | D |
| 160 | A | A | D | E | E |
| 161 | A | A | A | A | C |
| 162 | A | A | A | B | D |
| 163 | A | A | B | D | E |
| 164 | A | A | D | D | E |
| 165 | A | A | D | E | E |
| 166 | A | A | C | D | E |
| 167 | A | A | D | D | E |
| 168 | A | B | D | E | E |
| 169 | B | B | D | C | D |
| 170 | A | A | E | D | E |
| 171 | A | A | E | D | E |
| 172 | A | A | B | D | C |
| 173 | A | A | B | B | B |
| 174 | A | A | E | E | E |
| 175 | A | A | B | A | C |
| 176 | A | A | D | D | E |
| 177 | A | A | B | A | B |
| 178 | C | C | C | E | D |
| 179 | A | A | D | D | D |
| 180 | A | A | C | D | E |
| 181 | A | A | D | E | E |
| 182 | A | A | D | D | C |
| 183 | B | A | D | E | E |
| 184 | A | A | D | D | C |
| 185 | A | A | C | C | C |
| 186 | A | A | D | D | C |
| 187 | A | A | C | C | D |
| 188 | C | C | E | E | E |
| 189 | C | D | NA | NA | NA |
| 190 | A | B | C | E | E |
| 191 | A | B | B | C | D |
| 192 | A | A | C | C | E |
| 193 | C | C | D | E | E |
| 194 | A | A | C | C | D |
| 195 | A | A | B | B | D |
| 196 | A | A | D | D | D |
| 197 | A | A | C | D | E |
| 198 | A | A | D | D | D |
| 199 | A | A | D | D | E |
| 201 | A | A | B | A | D |
| 202 | B | B | E | D | E |
| 203 | C | C | NA | E | E |
| 204 | B | B | D | D | E |
| 205 | A | A | B | B | C |
| 206 | A | A | D | D | E |
| 207 | A | A | D | C | E |
| 208 | A | A | NA | D | E |
| 209 | A | A | NA | E | E |
| 211 | A | A | A | A | B |
| 212 | A | A | D | D | E |
| 213 | A | A | C | B | C |
| 214 | A | A | E | E | E |
| 215 | B | A | D | C | E |
| 216 | A | A | D | C | D |
| 217 | C | C | NA | E | E |
| 218 | C | D | NA | E | E |
| 219 | A | A | C | B | D |
| 220 | A | A | C | B | D |
| 221 | A | A | NA | C | D |
| 222 | C | B | NA | E | E |
| 223 | A | A | NA | C | C |
| 225 | A | A | A | A | A |
| 225a | A | A | A | A | A |
| 225b | A | A | B | A | D |
| 226 | A | A | NA | C | E |
| 227 | A | A | NA | B | E |
| 228 | C | C | NA | NA | NA |
| 229 | A | A | NA | A | D |
| 230 | A | A | NA | D | E |
| 231 | A | A | NA | NA | NA |
| 232 | A | A | NA | NA | NA |
| 233 | A | A | A | NA | E |
| 234 | A | A | D | NA | NA |
| 235 | A | A | B | NA | B |
| 236 | A | A | A | A | A |
| 237 | A | A | C | NA | E |
| 238 | A | A | C | NA | D |
| 239 | A | A | D | NA | E |
| 240 | A | A | B | NA | C |
| 241 | A | A | C | NA | E |
| 242 | A | A | C | NA | D |
| 243 | A | A | D | NA | E |
| 245 | A | A | C | NA | D |
| 246 | A | A | E | NA | E |
| 247 | A | A | A | NA | E |
| 248 | A | A | B | NA | A |
| 249 | D | C | D | NA | D |
| 250 | D | C | D | NA | E |
| 251 | A | A | A | NA | C |
| 252 | A | A | B | NA | C |
| 253 | A | A | D | NA | E |
| 254 | A | A | B | NA | A |

TABLE 2-continued

Biochemical, Mechanistic and Proliferation Cell-based Assay Results

| Cmpd # | Biochemical Assay[1] ERK1 | ERK2 | Mechanistic Cell Assay[2] RSK1 Phos HT29 | Cell Proliferation Assay[2] HT29 | HCT116 |
|---|---|---|---|---|---|
| 255 | A | A | A | A | A |
| 256 | A | A | A | NA | A |
| 257 | A | A | C | NA | E |
| 258 | A | A | C | NA | D |
| 259 | A | A | B | B | A |
| 260 | A | A | E | NA | E |
| 261 | A | A | D | NA | E |
| 262 | A | A | A | NA | D |
| 264 | A | A | A | NA | B |
| 265 | A | A | C | NA | B |
| 266 | A | A | A | NA | A |
| 267 | A | A | B | NA | B |
| 268 | A | A | A | NA | A |
| 269 | A | A | A | NA | A |
| 270 | A | A | B | A | A |
| 271 | A | A | A | NA | A |
| 272 | A | A | C | NA | B |
| 273 | A | A | B | NA | A |
| 274 | A | A | B | NA | A |
| 275 | A | A | A | A | A |
| 276 | A | A | B | C | D |
| 277 | A | A | D | C | C |
| 278 | A | A | A | NA | A |
| 279 | A | A | B | NA | D |
| 280 | A | A | A | A | A |
| 281 | A | A | B | D | E |
| 282 | A | A | A | A | A |
| 283 | A | A | D | D | E |
| 284 | A | A | D | C | D |
| 285 | A | A | A | A | B |
| 286 | A | A | A | A | A |
| 287 | A | A | D | A | C |
| 288 | A | A | B | A | A |
| 289 | C | B | D | NA | E |
| 290 | A | A | A | A | A |
| 291 | A | A | C | C | D |
| 292 | A | A | A | NA | A |
| 293 | A | A | D | NA | D |
| 294 | A | A | E | NA | NA |
| 295 | A | A | A | NA | NA |
| 296 | A | A | D | NA | NA |
| 297 | A | A | C | A | B |
| 298 | A | A | NA | NA | NA |
| 299 | A | A | NA | NA | NA |
| 300 | A | A | NA | NA | NA |
| 301 | NA | NA | NA | NA | NA |
| 302 | A | A | NA | NA | NA |
| 303 | A | A | NA | NA | NA |
| 304 | A | A | NA | NA | NA |
| 305 | A | A | NA | NA | NA |
| 306 | A | A | B | A | A |
| 307 | A | A | D | D | NA |
| 308 | A | A | D | E | C |
| 309 | A | A | D | C | D |
| 310 | C | A | E | E | E |
| 311 | B | A | D | NA | E |
| 312 | A | A | D | NA | E |
| 313 | A | A | C | NA | E |
| 314 | A | A | C | NA | E |
| 315 | A | A | E | E | E |
| 316 | D | C | E | E | E |
| 317 | B | A | E | E | E |
| 318 | A | A | D | D | E |
| 319 | A | A | D | E | E |
| 320 | A | A | C | C | D |
| 321 | B | A | D | E | E |
| 322 | D | D | E | E | E |
| 323 | A | A | C | E | E |
| 324 | A | A | D | E | E |
| 325 | NA | NA | NA | NA | NA |
| 326 | A | A | A | A | A |
| 327 | A | A | B | D | E |
| 328 | A | A | C | C | E |
| 329 | A | A | A | A | C |
| 330 | A | A | C | D | E |
| 331 | A | A | A | D | D |
| 332 | A | A | A | D | C |
| 333 | A | A | A | A | A |
| 334 | A | A | A | A | A |
| 335 | A | A | B | C | E |
| 336 | A | A | A | A | B |
| 337 | A | A | B | B | D |
| 338 | A | A | D | E | D |
| 339 | A | A | A | A | A |
| 340 | A | A | A | A | A |
| 341 | A | A | C | D | D |
| 342 | A | A | B | A | A |
| 343 | A | A | B | C | C |
| 344 | A | A | NA | NA | NA |
| 345 | A | A | E | D | D |
| 346 | B | A | NA | NA | NA |
| 347 | C | B | NA | NA | NA |
| 348 | A | A | NA | NA | NA |

[1]Biochemical Assay: IC$_{50}$ values; A: ≤50 nM, B: >50 to 100 nM, C: >100 to 500 nM, D: >500 nM to 2.5 uM, E: >2.5 uM, NA: Data not available
[2]Mechanistic Cell Assay and Cell Proliferation Assays: IC$_{50}$ values; A: ≤100 nM, B: >100-250 nM, C: >250-500 nM, D: >500 nM-2.5 uM, E: >2.5 uM; NA: Data not available.

In one embodiment, the compound selected from the group consisting of:

(S)-1-(2-(benzo[d][1,3]dioxol-5-ylamino)-5-methylpyrimidin-4-yl)-N-(2-hydroxy-1-phenylethyl)-1H-pyrrole-3-carboxamide;

1-(2-(benzofuran-5-ylamino)-5-methylpyrimidin-4-yl)-N-(2-hydroxy-1-phenylethyl)-1H-pyrrole-3-carboxamide;

1-(2-(benzo furan-5-ylamino)-5-methylpyrimidin-4-yl)-N-(1-(3-chlorophenyl)-2-hydroxyethyl)-1H-pyrrole-3-carboxamide;

N-(3-chloro-2-(hydroxymethyl)benzyl)-1-(5-methyl-2-((tetrahydro-2H-pyran-4-yl)amino)-pyrimidin-4-yl)-1H-imidazole-4-carboxamide;

(S)—N-(1-(3-chloro-4-fluorophenyl)-2-hydroxyethyl)-1-(5-methyl-2-((3,4,5-trimethoxyphenyl)amino)pyrimidin-4-yl)-1H-pyrrole-3-carboxamide;

1-(2-((2,3-dihydrobenzofuran-5-yl)amino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((2,3-dihydrobenzo[b][1,4]dioxin-6-yl)amino)-5-methylpyrimidin-4-yl)-1H-pyrrole-3-carboxamide;

N—((S)-1-(3-chlorophenyl)-2-hydroxyethyl)-1-(5-methyl-2-((tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((S)-tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((R)-tetrahydrofuran-3-yl)amino)pyrimidin-4-yl)-1H-pyrrole-3-carboxamide;

1-(2-(chroman-6-ylamino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((4-fluoro-3-morpholinophenyl)amino)-5-methyl-pyrimidin-4-yl)-1H-pyrrole-3-carboxamide;

N-(2-amino-1-(3-chlorophenyl)ethyl)-1-(2-((4-fluorophenyl)amino)-5-methylpyrimidin-4-yl)-1H-imidazole-4-carboxamide;

N-(1-(3-chlorophenyl)-2-hydroxyethyl)-1-(5-methyl-2-((tetrahydro-2H-pyran-4-yl)-amino)pyrimidin-4-yl)-1H-imidazole-4-carboxamide;

N-(1-(3-chlorophenyl)-2-hydroxyethyl)-1-(5-methyl-2-((4-morpholinophenyl)amino)pyrimidin-4-yl)-1H-pyrrole-3-carboxamide;

(S)—N-(1-(3-chlorophenyl)-2-hydroxyethyl)-1-(5-methyl-2-((tetrahydro-2H-pyran-4-yl)amino)-pyrimidin-4-yl)-1H-imidazole-4-carboxamide;

(R)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;

(S)—N-(1-(3-chlorophenyl)-2-hydroxyethyl)-1-(5-fluoro-2-((tetrahydro-2H-pyran-4-yl)amino)-pyrimidin-4-yl)-1H-pyrrole-3-carboxamide;

N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(2-((3,3-difluorocyclobutyl)amino)-5-methylpyrimidin-4-yl)-1H-imidazole-4-carboxamide;

(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide;

(S)—N-(2-(((1H-pyrrol-2-yl)methyl)amino)-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(3-chloro-2-(hydroxymethyl)benzyl)-1-(5-methyl-2-(tetrahydrofuran-3-yl)amino)-pyrimidin-4-yl)-1H-imidazole-4-carboxamide;

(S)—N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-((2-hydroxyethyl)amino)ethyl)-1-(5-methyl-2-((tetrahydro-2H-pyran-4-yl)amino)pyrimidin-4-yl)-1H-imidazole-4-carboxamide; and N-(3-chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide, or a pharmaceutically acceptable salt, prodrug, solvate, hydrate, or stereoisomer thereof.

In one embodiment, the compound of formula (I) defined in each of the previous embodiments being a substantially pure stereoisomer.

In one embodiment, a composition comprising at least one compound of formula (I) defined in each of the previous embodiments or a pharmaceutically acceptable salt, prodrug, solvate, hydrate, or stereoisomer thereof, and a pharmaceutically acceptable carrier.

In one embodiment, a composition comprising at least one compound selected from the group consisting of:

(S)-1-(2-(benzo[d][1,3]dioxol-5-ylamino)-5-methylpyrimidin-4-yl)-N-(2-hydroxy-1-phenylethyl)-1H-pyrrole-3-carboxamide;

1-(2-(benzofuran-5-ylamino)-5-methylpyrimidin-4-yl)-N-(2-hydroxy-1-phenylethyl)-1H-pyrrole-3-carboxamide;

1-(2-(benzofuran-5-ylamino)-5-methylpyrimidin-4-yl)-N-(1-(3-chlorophenyl)-2-hydroxyethyl)-1H-pyrrole-3-carboxamide;

N-(3-chloro-2-(hydroxymethyl)benzyl)-1-(5-methyl-2-((tetrahydro-2H-pyran-4-yl)amino)-pyrimidin-4-yl)-1H-imidazole-4-carboxamide;

(S)—N-(1-(3-chloro-4-fluorophenyl)-2-hydroxyethyl)-1-(5-methyl-2-((3,4,5-trimethoxyphenyl)amino)pyrimidin-4-yl)-1H-pyrrole-3-carboxamide;

1-(2-((2,3-dihydrobenzofuran-5-yl)amino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((2,3-dihydrobenzo[b][1,4]dioxin-6-yl)amino)-5-methylpyrimidin-4-yl)-1H-pyrrole-3-carboxamide;

N—((S)-1-(3-chlorophenyl)-2-hydroxyethyl)-1-(5-methyl-2-((tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((S)-tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((R)-tetrahydrofuran-3-yl)amino)pyrimidin-4-yl)-1H-pyrrole-3-carboxamide;

1-(2-(chroman-6-ylamino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((4-fluoro-3-morpholinophenyl)amino)-5-methyl-pyrimidin-4-yl)-1H-pyrrole-3-carboxamide;

N-(2-amino-1-(3-chlorophenyl)ethyl)-1-(2-((4-fluorophenyl)amino)-5-methylpyrimidin-4-yl)-1H-imidazole-4-carboxamide;

N-(1-(3-chlorophenyl)-2-hydroxyethyl)-1-(5-methyl-2-((tetrahydro-2H-pyran-4-yl)-amino)pyrimidin-4-yl)-1H-imidazole-4-carboxamide;

N-(1-(3-chlorophenyl)-2-hydroxyethyl)-1-(5-methyl-2-((4-morpholinophenyl)amino)pyrimidin-4-yl)-1H-pyrrole-3-carboxamide;

(S)—N-(1-(3-chlorophenyl)-2-hydroxyethyl)-1-(5-methyl-2-((tetrahydro-2H-pyran-4-yl)amino)-pyrimidin-4-yl)-1H-imidazole-4-carboxamide;

(R)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(5-methyl-2-((tetrahydro-2H-pyran-4-yl)amino)-pyrimidin-4-yl)-1H-imidazole-4-carboxamide;

(S)—N-(1-(3-chlorophenyl)-2-hydroxyethyl)-1-(5-fluoro-2-((tetrahydro-2H-pyran-4-yl)amino)-pyrimidin-4-yl)-1H-pyrrole-3-carboxamide;

N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(2-((3,3-difluorocyclobutyl)amino)-5-methylpyrimidin-4-yl)-1H-imidazole-4-carboxamide;

(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide;

(S)—N-(2-(((1H-pyrrol-2-yl)methyl)amino)-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(3-chloro-2-(hydroxymethyl)benzyl)-1-(5-methyl-2-(tetrahydrofuran-3-yl)amino)-pyrimidin-4-yl)-1H-imidazole-4-carboxamide;

(S)—N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-((2-hydroxyethyl)amino) ethyl)-1-(5-methyl-2-((tetrahydro-2H-pyran-4-yl)amino) pyrimidin-4-yl)-1H-imidazole-4-carboxamide; and N-(3-chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide, or a pharmaceutically acceptable salt, prodrug, solvate, hydrate, or stereoisomer thereof, and a pharmaceutically acceptable carrier.

In one embodiment, a composition of each of above, further comprising an additional therapeutic agent.

In one embodiment, a method of treating a condition treatable by inhibiting ERK1/2 comprising administration to an individual in need a composition comprising a therapeutically effective amount of at least one compound of formula (I) defined in each of the previous embodiments as to at least slow the progression of the condition.

In one further embodiment, the condition is cancer of prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, skin or a leukemia or lymphoma.

In one embodiment, a method of treating a condition treatable by inhibiting ERK1/2 comprising administration to an individual in need a composition comprising a therapeutically effective amount of at least one compound selected from the group consisting of:

(S)-1-(2-(benzol[d][1,3]dioxol-5-ylamino)-5-methylpyrimidin-4-yl)-N-(2-hydroxy-1-phenylethyl)-1H-pyrrole-3-carboxamide;

1-(2-(benzofuran-5-ylamino)-5-methylpyrimidin-4-yl)-N-(2-hydroxy-1-phenylethyl)-1H-pyrrole-3-carboxamide;

1-(2-(benzofuran-5-ylamino)-5-methylpyrimidin-4-yl)-N-(1-(3-chlorophenyl)-2-hydroxyethyl)-1H-pyrrole-3-carboxamide;

N-(3-chloro-2-(hydroxymethyl)benzyl)-1-(5-methyl-2-((tetrahydro-2H-pyran-4-yl)amino)pyrimidin-4-yl)-1H-imidazole-4-carboxamide;

(S)—N-(1-(3-chloro-4-fluorophenyl)-2-hydroxyethyl)-1-(5-methyl-2-((3,4,5-trimethoxyphenyl)amino)pyrimidin-4-yl)-1H-pyrrole-3-carboxamide;

1-(2-((2,3-dihydrobenzofuran-5-yl)amino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((2,3-dihydrobenzo[b][1,4]dioxin-6-yl)amino)-5-methylpyrimidin-4-yl)-1H-pyrrole-3-carboxamide;

N—((S)-1-(3-chlorophenyl)-2-hydroxyethyl)-1-(5-methyl-2-((tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((S)-tetrahydrofuran-3-yl)amino)pyrimidin-4-yl)-1H-pyrrole-3-carboxamide;

N—((S)-1-(3-chlorophenyl)-2-hydroxyethyl)-1-(5-methyl-2-(((R)-tetrahydrofuran-3-yl)amino)pyrimidin-4-yl)-1H-pyrrole-3-carboxamide;

1-(2-(chroman-6-ylamino)-5-methylpyrimidin-4-yl)-N-(2-hydroxy-1-phenylethyl)-1H-pyrrole-3-carboxamide;

N-(1-(3-chlorophenyl)-2-hydroxyethyl)-1-(2-((4-fluoro-3-morpholinophenyl)amino)-5-methylpyrimidin-4-yl)-1H-pyrrole-3-carboxamide;

N-(2-amino-1-(3-chlorophenyl)ethyl)-1-(2-((4-fluorophenyl)amino)-5-methylpyrimidin-4-yl)-1H-imidazole-4-carboxamide;

N-(1-(3-chlorophenyl)-2-hydroxyethyl)-1-(5-methyl-2-((tetrahydro-2H-pyran-4-yl)-amino)pyrimidin-4-yl)-1H-imidazole-4-carboxamide;

N-(1-(3-chlorophenyl)-2-hydroxyethyl)-1-(5-methyl-2-((4-morpholinophenyl)-amino)pyrimidin-4-yl)-1H-pyrrole-3-carboxamide;

(S)—N-(1-(3-chlorophenyl)-2-hydroxyethyl)-1-(5-methyl-2-((tetrahydro-2H-pyran-4-yl)amino)pyrimidin-4-yl)-1H-imidazole-4-carboxamide;

(R)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(2-amino-1-(3-chlorophenyl)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-hydroxyethyl)-1-(5-fluoro-2-((tetrahydro-2H-pyran-4-yl)amino)pyrimidin-4-yl)-1H-pyrrole-3-carboxamide;

N-(2-hydroxy-1-(thiophen-2-yl)ethyl)-1-(5-methyl-2-((tetrahydro-2H-pyran-4-yl)amino)-pyrimidin-4-yl)-1H-imidazole-4-carboxamide;

(S)—N-(2-amino-1-(3-chlorophenyl)ethyl)-1-(2-((3,3-difluorocyclobutyl)amino)-5-methylpyrimidin-4-yl)-1H-imidazole-4-carboxamide;

(S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide;

(S)—N-(2-(((1H-pyrrol-2-yl)methyl)amino)-1-(3-chlorophenyl)ethyl)-1-(5-methyl-2-((tetrahydro-2H-pyran-4-yl) amino)pyrimidin-4-yl)-1H-imidazole-4-carboxamide;

(S)—N-(3-chloro-2-(hydroxymethyl)benzyl)-1-(5-methyl-2-(tetrahydrofuran-3-yl)amino)-pyrimidin-4-yl)-1H-imidazole-4-carboxamide;

(S)—N-(1-(3-chlorophenyl)-2-(methylamino)ethyl)-1-(5-methyl-2-((tetrahydro-2H-pyran-4-yl)amino)pyrimidin-4-yl)-1H-imidazole-4-carboxamide;

(S)—N-(1-(3-chlorophenyl)-2-((2-hydroxyethyl)amino) ethyl)-1-(5-methyl-2-((tetrahydro-2H-pyran-4-yl)amino) pyrimidin-4-yl)-1H-imidazole-4-carboxamide; and N-(3-chloro-5-fluoro-2-(hydroxymethyl)benzyl)-1-(5-methyl-2-((tetrahydro-2H-pyran-4-yl)amino)pyrimidin-4-yl)-1H-imidazole-4-carboxamide, or a pharmaceutically acceptable salt, prodrug, solvate, hydrate, or stereoisomer thereof.

While the present invention has been described in conjunction with the specific embodiments set forth above, many alternatives, modifications and variations thereof will be apparent to those of ordinary skill in the art. All such alternative, modifications and variations are intended to fall within the spirit and scope of the present invention.

What is claimed is:

1. A method of inhibiting ERK1/2, the method comprising contacting ERK1/2 with a compound that is N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

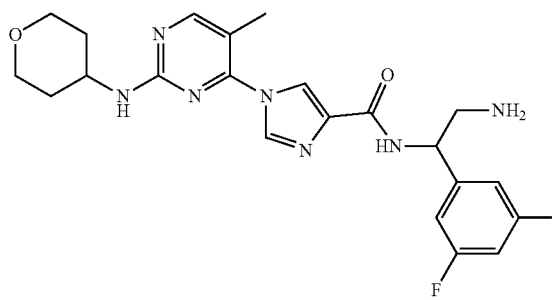

or a pharmaceutically acceptable salt or stereoisomer thereof.

2. The method of claim 1, wherein the contacting step is in vitro.

3. The method of claim 1, wherein the contacting step is in vivo.

4. The method of claim 1, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

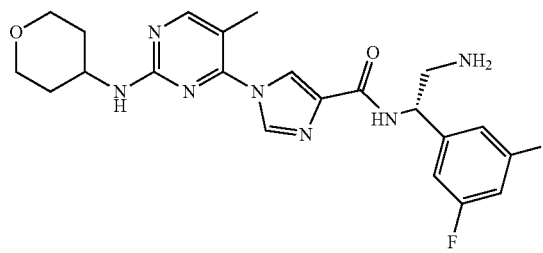

or a pharmaceutically acceptable salt thereof.

5. The method of claim 4, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

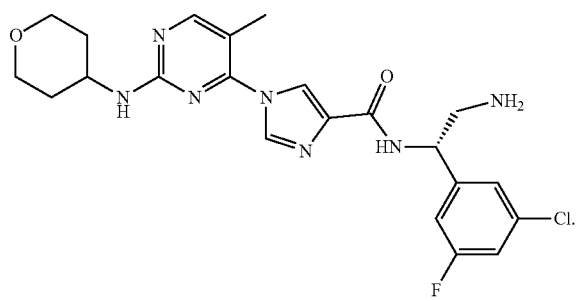 [SMILES: Cc1cnc(NC2CCOCC2)nc1-n1cnc(C(=O)N[C@H](CN)c2cc(F)cc(Cl)c2)c1]

6. The method of claim 4, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

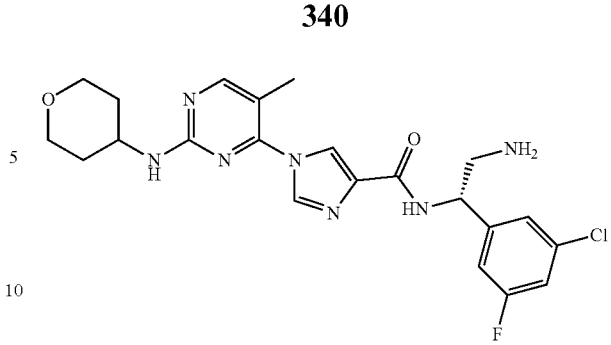

mandelic acid salt.

7. The method of claim 4, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

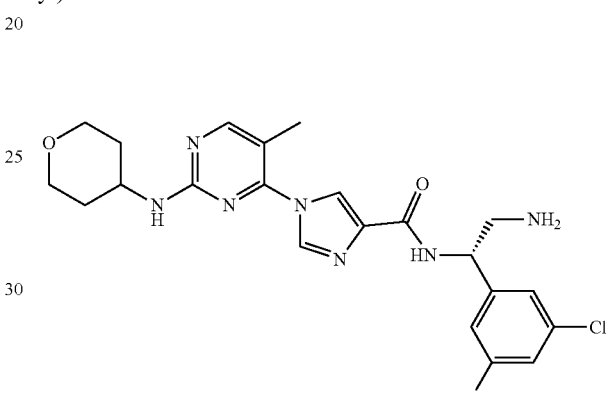

hydrochloric acid salt.

8. The method of claim 4, wherein the compound is S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

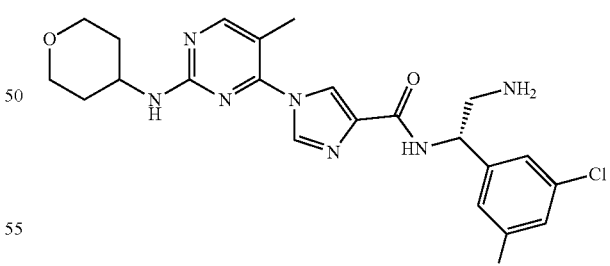

benzenesulfonic acid salt.

9. A method of treating colorectal cancer, colon cancer, pancreatic cancer, thyroid cancer, lung cancer, or melanoma, in a subject, the method comprising administrating a compound that is N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

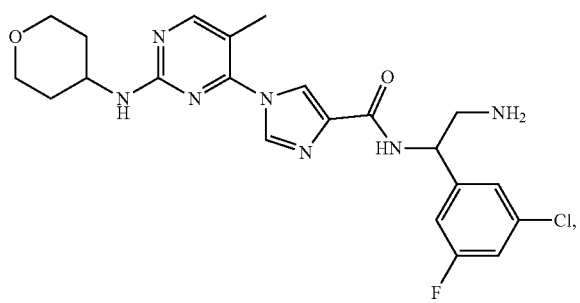 [SMILES: Cc1cnc(NC2CCOCC2)nc1-n1cnc(C(=O)NC(CN)c2cc(F)cc(Cl)c2)c1]

or a pharmaceutically acceptable salt or stereoisomer thereof.

10. The method of claim 9, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

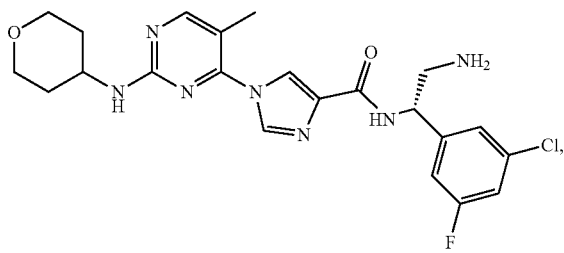 [SMILES: Cc1cnc(NC2CCOCC2)nc1-n1cnc(C(=O)N[C@H](CN)c2cc(F)cc(Cl)c2)c1]

or a pharmaceutically acceptable salt thereof.

11. The method of claim 9, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

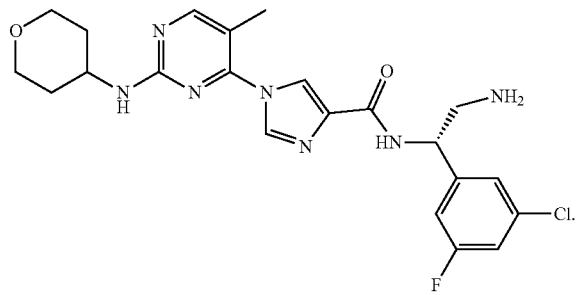 [SMILES: Cc1cnc(NC2CCOCC2)nc1-n1cnc(C(=O)N[C@H](CN)c2cc(F)cc(Cl)c2)c1]

12. The method of claim 9, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

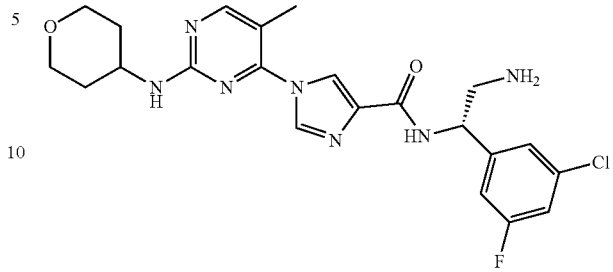

mandelic acid salt.

13. The compound of claim 9, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

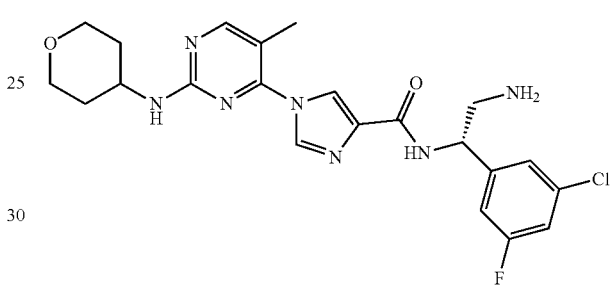

hydrochloric acid salt.

14. The method of claim 9, wherein the compound is (S)—N-(2-amino-1-(3-chloro-5-fluorophenyl)ethyl)-1-(5-methyl-2-((tetrahydro-2H-pyran-4-yl)amino)pyrimidin-4-yl)-1H-imidazole-4-carboxamide:

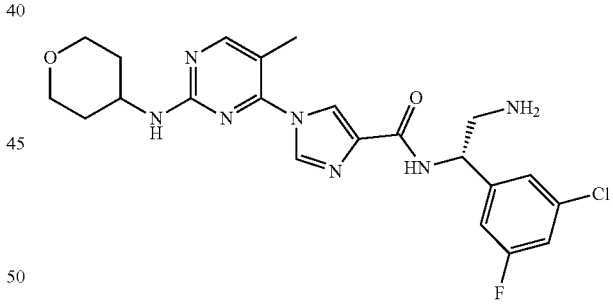

benzenesulfonic acid salt.

* * * * *

UNITED STATES PATENT AND TRADEMARK OFFICE
CERTIFICATE OF CORRECTION

| | | |
|---|---|---|
| PATENT NO. | : 11,925,629 B2 | Page 1 of 1 |
| APPLICATION NO. | : 17/368559 | |
| DATED | : March 12, 2024 | |
| INVENTOR(S) | : Venkatesan et al. | |

It is certified that error appears in the above-identified patent and that said Letters Patent is hereby corrected as shown below:

On the Title Page

In item (71) Applicant, replace:
"Asana Biosciences, LLC, Bridgeville, NJ (US)"
With:
--Asana Biosciences, LLC, Bridgewater, NJ (US)--

Signed and Sealed this
Ninth Day of April, 2024

Katherine Kelly Vidal
*Director of the United States Patent and Trademark Office*